(12) United States Patent
Kim et al.

(10) Patent No.: US 12,312,342 B2
(45) Date of Patent: May 27, 2025

(54) COMPOUND AND ORGANIC LIGHT EMITTING DEVICE COMPRISING SAME

(71) Applicant: LG CHEM, LTD., Seoul (KR)

(72) Inventors: Minjun Kim, Daejeon (KR); Dong Hoon Lee, Daejeon (KR); Sang Duk Suh, Daejeon (KR); Donghee Kim, Daejeon (KR); Seoyeon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 796 days.

(21) Appl. No.: 17/420,977

(22) PCT Filed: Jan. 21, 2020

(86) PCT No.: PCT/KR2020/001014
§ 371 (c)(1),
(2) Date: Jul. 6, 2021

(87) PCT Pub. No.: WO2020/153713
PCT Pub. Date: Jul. 30, 2020

(65) Prior Publication Data
US 2022/0102646 A1 Mar. 31, 2022

(30) Foreign Application Priority Data
Jan. 21, 2019 (KR) ................. 10-2019-0007477

(51) Int. Cl.
*H01L 51/00* (2006.01)
*C07D 405/14* (2006.01)
(Continued)

(52) U.S. Cl.
CPC ......... *C07D 405/14* (2013.01); *C07D 409/14* (2013.01); *H10K 85/636* (2023.02);
(Continued)

(58) Field of Classification Search
None
See application file for complete search history.

(56) References Cited

U.S. PATENT DOCUMENTS

2004/0251816 A1 12/2004 Leo et al.
2014/0071530 A1 3/2014 Park et al.
(Continued)

FOREIGN PATENT DOCUMENTS

CN 103429570 A * 12/2012
CN 107428701 A 12/2017
(Continued)

*Primary Examiner* — Tae H Yoon
(74) *Attorney, Agent, or Firm* — Bryan Cave Leighton Paisner LLP

(57) ABSTRACT

A compound of Formula 1 and an organic light emitting device including the same, and the compound providing low driving voltage, high light emitting efficiency, and a long service life of the organic light emitting device.

(Continued)

[Formula 1]

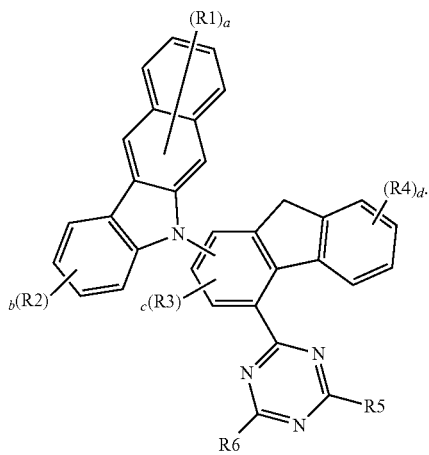

14 Claims, 1 Drawing Sheet

(51) Int. Cl.
*C07D 409/14* (2006.01)
*H10K 85/60* (2023.01)
*H10K 50/11* (2023.01)
*H10K 50/15* (2023.01)
*H10K 50/16* (2023.01)
*H10K 50/17* (2023.01)
*H10K 101/00* (2023.01)

(52) U.S. Cl.
CPC ....... *H10K 85/654* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/17* (2023.02); *H10K 50/171* (2023.02); *H10K 2101/90* (2023.02)

(56) References Cited

U.S. PATENT DOCUMENTS

| | | |
|---|---|---|
| 2018/0037546 A1 | 2/2018 | Sugino et al. |
| 2018/0051007 A1 | 2/2018 | Jung et al. |
| 2019/0288222 A1 | 9/2019 | Moon et al. |
| 2020/0111969 A1 | 4/2020 | No et al. |
| 2020/0123133 A1 | 4/2020 | No et al. |
| 2022/0259187 A1* | 8/2022 | Lee ................. C07D 405/14 |

FOREIGN PATENT DOCUMENTS

| | | |
|---|---|---|
| CN | 107635978 A | 1/2018 |
| CN | 107827807 A | 3/2018 |
| CN | 107973786 A | 5/2018 |
| EP | 3432688 A1 * | 1/2019 |
| KR | 10-2011-0107681 A | 10/2011 |
| KR | 10-2012-0081539 A | 7/2012 |
| KR | 10-2017-0086329 A | 7/2017 |
| KR | 10-2017-0102000 A | 9/2017 |
| KR | 10-2017-0111387 A | 10/2017 |
| KR | 10-2018-0045798 A | 5/2018 |
| KR | 10-2018-0066818 A | 6/2018 |
| KR | 10-2018-0108426 A | 10/2018 |
| WO | 2003/012890 A2 | 2/2003 |
| WO | WO 2016/068458 A1 * | 5/2016 |
| WO | WO 2017/183625 A1 * | 10/2017 |

* cited by examiner

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2020/001014 filed on Jan. 21, 2020, which claims priority to Korean Patent Application No. 10-2019-0007477 filed on Jan. 21, 2019, disclosures of which are incorporated herein by reference in their entireties.

FIELD OF DISCLOSURE

The present application relates to a compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a first electrode, a second electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between the two electrodes, holes are injected from the first electrode into the organic material layer and electrons are injected from the second electrode into the organic material layer, and when the injected holes and electrons meet each other, an exciton is formed, and light is emitted when the exciton falls down again to a ground state.

There is a continuous need for developing a new material for the aforementioned organic light emitting device.

SUMMARY

The present application has been made in an effort to provide a compound and an organic light emitting device including the same.

The present application provides a compound of the following Formula 1.

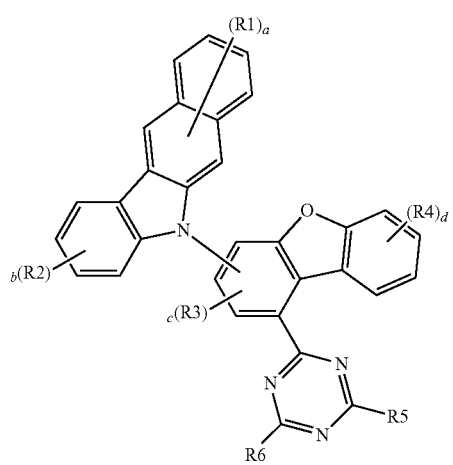

[Formula 1]

In Formula 1,
R1 to R4 are each independently hydrogen or deuterium,
R5 and R6 are each independently a substituted or unsubstituted aryl group; or a substituted or unsubstituted heterocyclic group,
a is an integer from 0 to 6,
b and d are each independently an integer from 0 to 4, c is an integer from 0 to 2,
when a to d are each independently an integer of 2 or higher, substituents in the parentheses are the same as or different from each other, and
when b to d are each independently 2 or higher, two or more adjacent R2's, R3's, and R4's can be bonded to each other respectively to form a ring.

Further, the present application provides an organic light emitting device including: a first electrode; a second electrode provided to face the first electrode; and an organic material layer having one or more layers provided between the first electrode and the second electrode, in which one or more layers of the organic material layer include the above-described compound.

Advantageous Effects

An organic light emitting device using the compound according to an exemplary embodiment of the present application can have a low driving voltage, high light emitting efficiency, or a long service life.

DESCRIPTION OF REFERENCE NUMERALS

Figure 1:
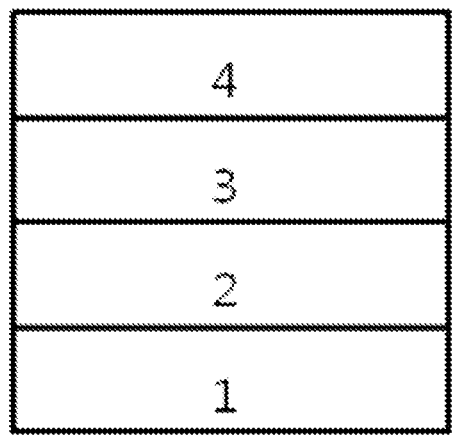
FIG. 1 illustrates an example of an organic light emitting device in which a substrate 1, a first electrode 2, a light emitting layer 3, and a second electrode 4 are sequentially stacked.

1: Substrate
2: First electrode
3: Light emitting layer
4: Second electrode
5: Hole injection layer
6: Hole transport layer
7: Electron blocking layer
8: Hole blocking layer
9: Electron injection and transport layer

DETAILED DESCRIPTION

Hereinafter, the present specification will be described in more detail.

The present specification provides the compound of Formula 1.

According to an exemplary embodiment of the present application, the compound of Formula 1 has an advantage capable of adjusting the triplet energy by having a core structure as described above, and can exhibit long service life and high efficiency characteristics.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of hydrogen; a halogen group; a nitrile group; a nitro group; a hydroxy group; a substituted or unsubstituted alkyl group; a substituted or unsubstituted cycloalkyl group; a substituted or unsubstituted alkenyl group; a substituted or unsubstituted amine group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification, examples of a halogen group include fluorine, chlorine, bromine or iodine.

In the present specification, the alkyl group can be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, a cycloalkyl group is not particularly limited, but has preferably 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkenyl group can be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, it can be

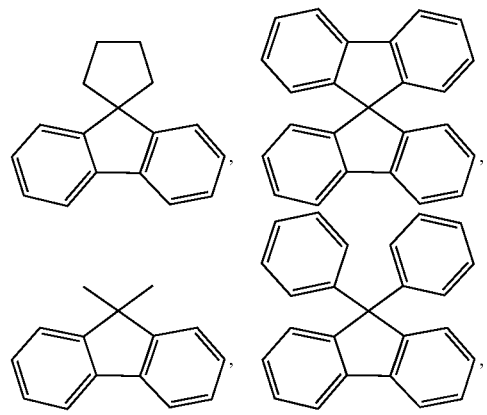

and the like, but is not limited thereto.

In the present specification, a heterocyclic group includes one or more atoms other than carbon, that is, one or more heteroatoms, and specifically, the heteroatom can include one or more atoms selected from the group consisting of O, N, Se, and S, and the like. The number of carbon atoms of the heterocyclic group is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, an amine group can be selected from the group consisting of —NH$_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenyl terphenylamine group, an N-phenanthrenylfluorenylamine group, an N-biphenylfluorenylamine group, and the like, but are not limited thereto.

In the present specification, an N-alkylarylamine group means an amine group in which an alkyl group and an aryl group are substituted with N of the amine group.

In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the above-described description on the alkyl group, the aryl group, and the heteroaryl group can be each applied to an alkyl group, an aryl group, and a heteroaryl group in an alkylamine group; an N-alkylarylamine group; an arylamine group; an N-arylheteroarylamine group; an N-alkylheteroarylamine group, and a heteroarylamine group.

In the present specification, the "adjacent" group can mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the case where adjacent groups are bonded to each other to form a ring means that adjacent groups are bonded to each other to form a substituted or unsubstituted hydrocarbon ring or a substituted or unsubstituted hetero ring as described above, a monocyclic ring or polycyclic ring can be formed, and the ring can be an aliphatic ring, an aromatic ring, or a fused form thereof, and is not limited thereto.

In the present specification, being bonded to an adjacent group to form a ring means being bonded to an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a combined form thereof.

In the present specification, the aliphatic hydrocarbon ring means a ring composed of only carbon and hydrogen atoms which is a ring that is not aromatic.

In the present specification, the above-described description on the aryl group can be applied to an aromatic hydrocarbon ring except for a divalent aromatic hydrocarbon ring. Examples of the aromatic hydrocarbon ring include a benzene ring, a naphthalene ring, an anthracenene ring, and the like, but are not limited thereto.

In the present specification, the above-described description on the heterocyclic group can be applied to a hetero ring except for a divalent hetero ring.

In the present specification, an aliphatic hetero ring means an aliphatic ring including one or more of hetero atoms.

In the present specification, an aromatic hetero ring means an aromatic ring including one or more of hetero atoms.

The compound of Formula 1 is any one selected from the following Formulae 2 to 4.

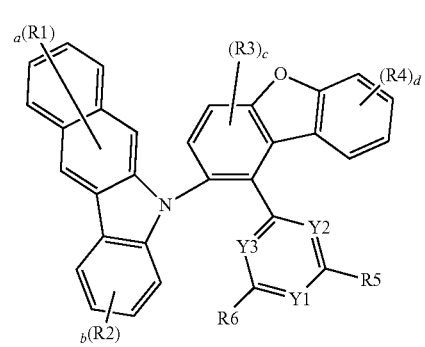

[Formula 2]

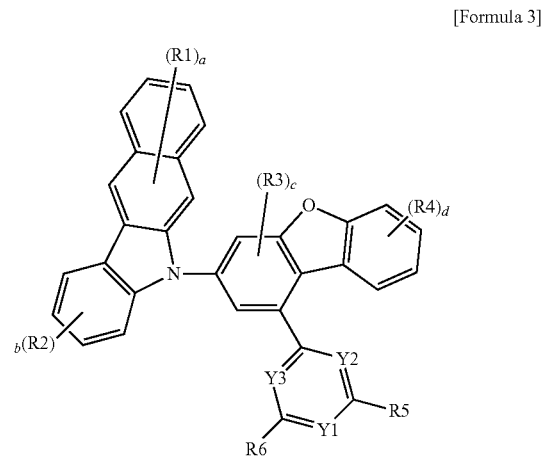

[Formula 3]

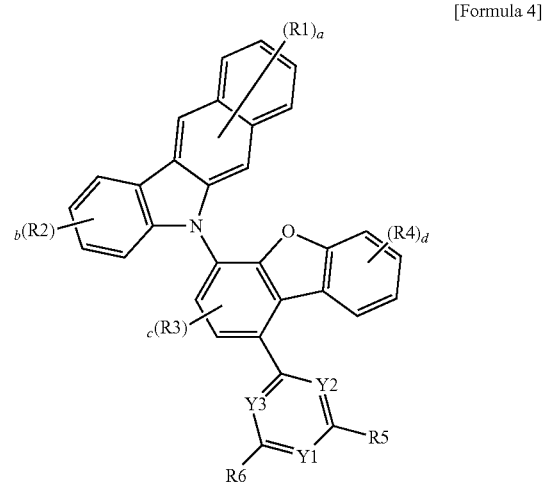

[Formula 4]

In Formulae 2 to 4, R1 to R6 and a to d are the same as those defined in Formula 1.

According to an exemplary embodiment of the present application, R1 to R4 are each independently hydrogen or deuterium.

According to an exemplary embodiment of the present application, R1 to R4 are hydrogen.

According to an exemplary embodiment of the present application, when b to d are each independently 2 or higher, two or more adjacent R2's, R3's, and R4's can be bonded to each other respectively to form a ring.

According to an exemplary embodiment of the present application, when b is 2 or higher, two or more adjacent R2's can be bonded to each other to form a ring.

According to an exemplary embodiment of the present application, when b is 2 or higher, two or more adjacent R2's can be bonded to each other to form a benzene ring.

According to an exemplary embodiment of the present application, when c is 2, two adjacent R3's can be bonded to each other to form a ring.

According to an exemplary embodiment of the present application, when c is 2, two adjacent R3's can be bonded to each other to form a benzene ring.

According to an exemplary embodiment of the present application, when d is 2 or higher, two or more adjacent R4's can be bonded to each other to form a ring.

According to an exemplary embodiment of the present application, when d is 2 or higher, two or more adjacent R4's can be bonded to each other to form a benzene ring.

The compound of Formula 1 is any one selected from the following Formulae 2-1 to 2-8, 3-1 to 3-8, and 4-1 to 4-8.

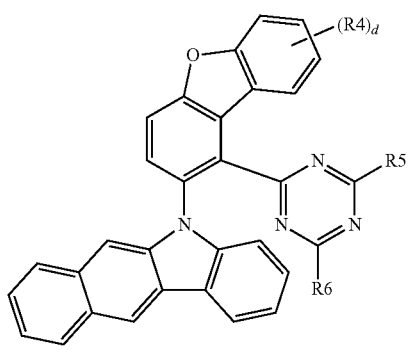

[Formula 2-1]

[Formula 2-2]

[Formula 2-3]

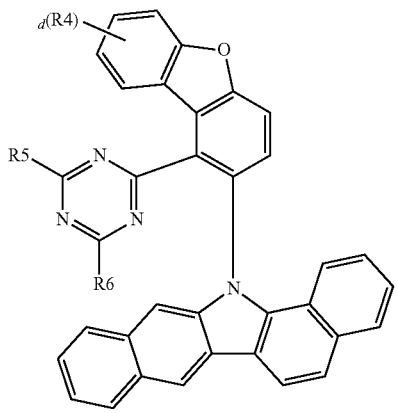

[Formula 2-4]

[Formula 2-5]

[Formula 2-6]

[Formula 2-7]
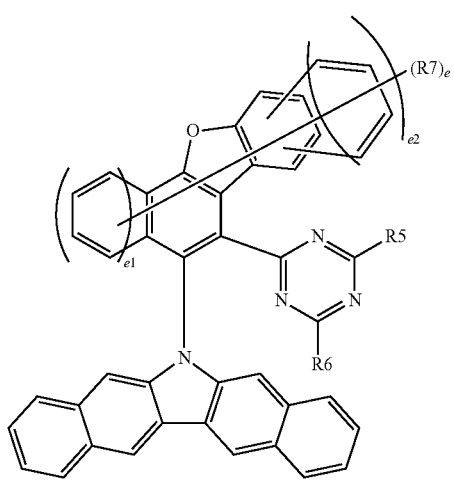
[Formula 2-8]
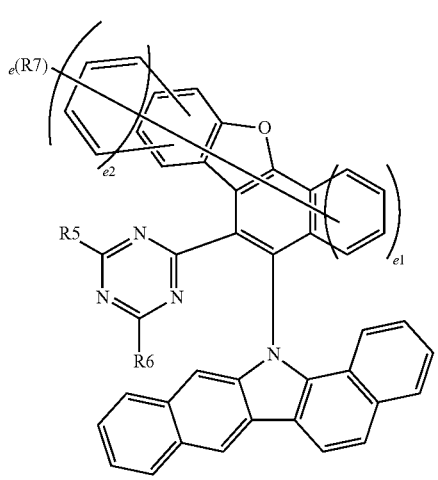
[Formula 3-1]
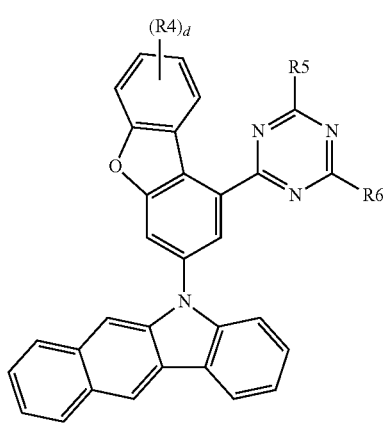
[Formula 3-2]
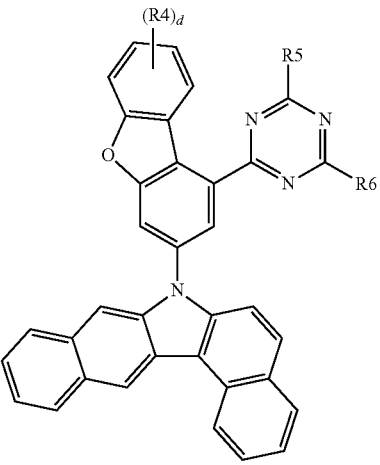
[Formula 3-3]
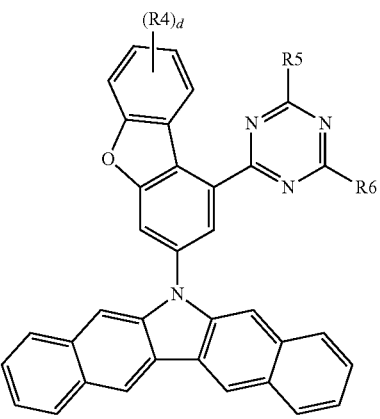
[Formula 3-4]
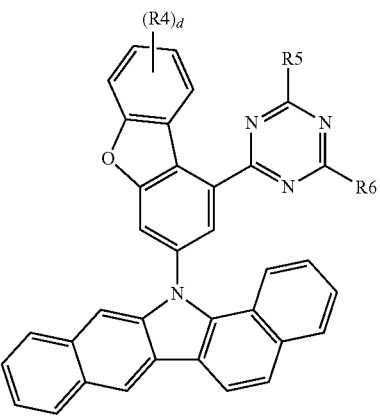

[Formula 3-5]
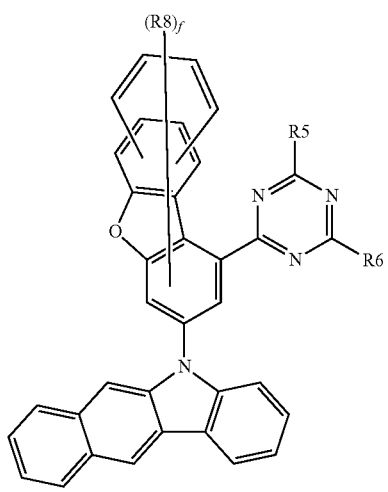
[Formula 3-6]
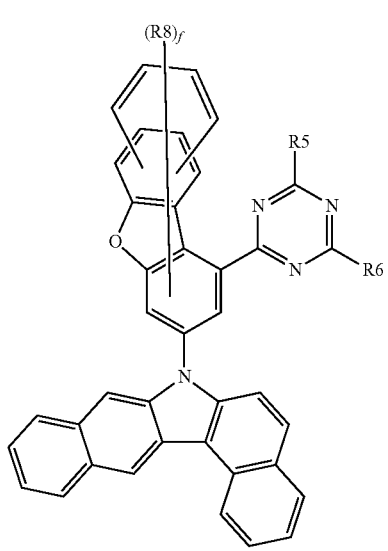
[Formula 3-7]
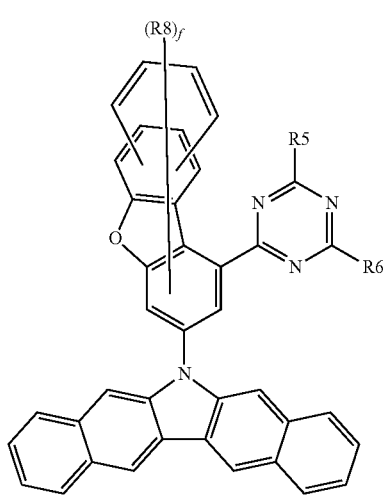
[Formula 3-8]
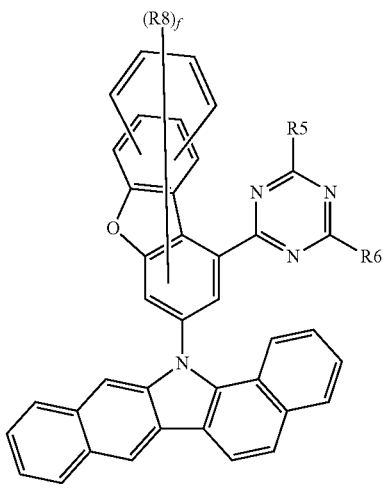
[Formula 4-1]
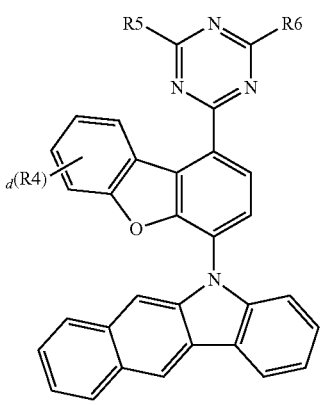
[Formula 4-2]
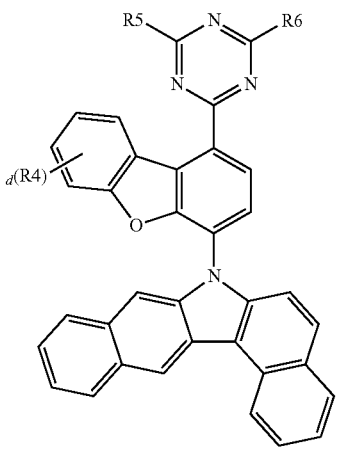

[Formula 4-3]

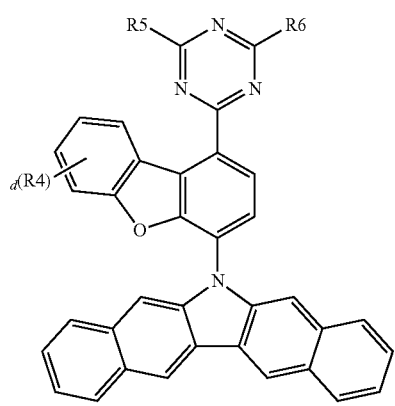

[Formula 4-4]

[Formula 4-5]

[Formula 4-6]

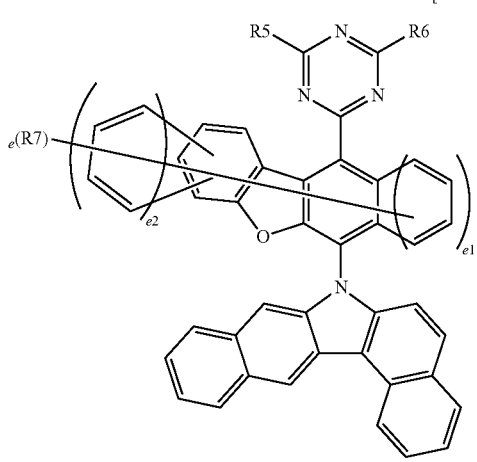

[Formula 4-7]

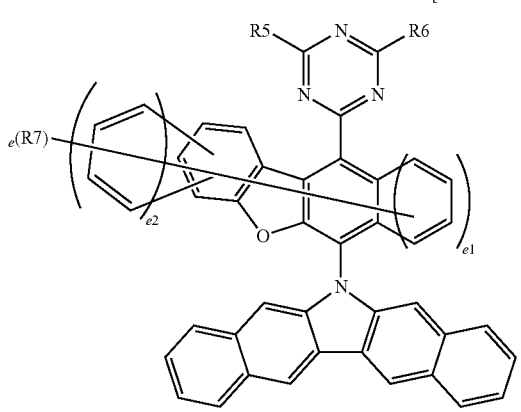

[Formula 4-8]

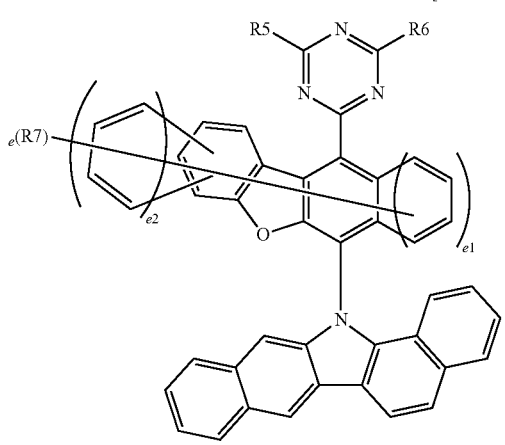

In Formulae 2-1 to 2-8, 3-1 to 3-8, and 4-1 to 4-8, R4 to R6 and d are the same as those defined in Formula 1, R7 and R8 are each independently hydrogen or deuterium, e1 and e2 are each 0 or 1, and a sum of e1 and e2 is 1 or 2, e is an integer from 0 to 10, and f is an integer from 0 to 8, when e is 2 or higher, a plurality of R7's are the same as or different from each other, and when f is 2 or higher, a plurality of R8's are the same as or different from each other.

According to an exemplary embodiment of the present application, R5 and R6 are each independently a substituted or unsubstituted aryl group having 6 to 60 carbon atoms; or a substituted or unsubstituted heterocyclic group having 2 to 60 carbon atoms.

According to an exemplary embodiment of the present application, R5 and R6 are each independently a substituted or unsubstituted aryl group having 6 to 30 carbon atoms; or a substituted or unsubstituted heterocyclic group having 2 to 30 carbon atoms.

According to an exemplary embodiment of the present application, R5 and R6 are each independently a substituted or unsubstituted aryl group having 6 to 15 carbon atoms; or a substituted or unsubstituted heterocyclic group having 2 to 15 carbon atoms.

According to an exemplary embodiment of the present application, R5 and R6 are each independently a substituted or unsubstituted phenyl group; a substituted or unsubstituted naphthyl group; a substituted or unsubstituted biphenyl group; a substituted or unsubstituted phenanthrene group; a substituted or unsubstituted carbazole group; a substituted or unsubstituted dibenzothiophene group; or a substituted or unsubstituted dibenzofuran group.

According to an exemplary embodiment of the present application, R5 and R6 are each independently a phenyl group; a naphthyl group; a biphenyl group; a phenanthrene group; a carbazole group which is unsubstituted or substituted with a phenyl group; a dibenzothiophene group; or a dibenzofuran group.

Furthermore, according to an exemplary embodiment of the present application, the compound of Formula 1 is any one selected from the following structural formulae.

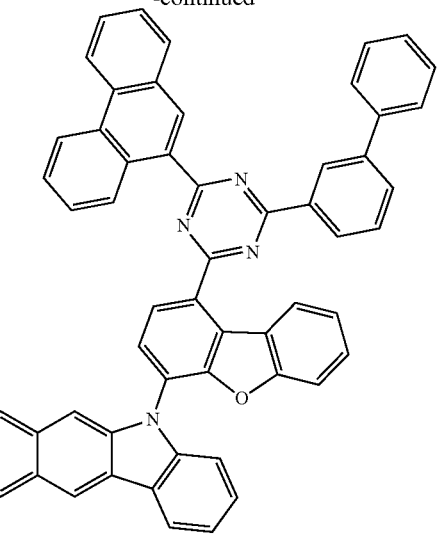

-continued

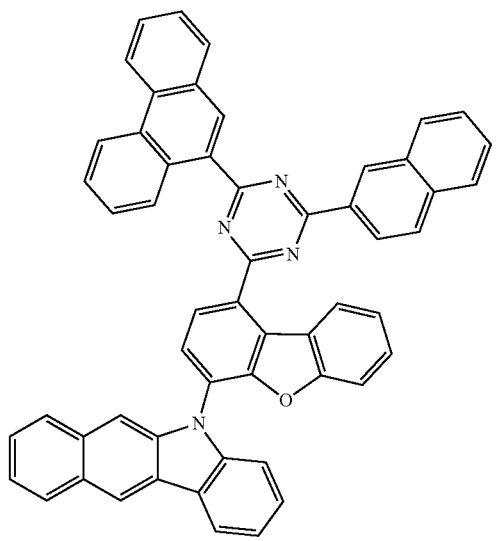

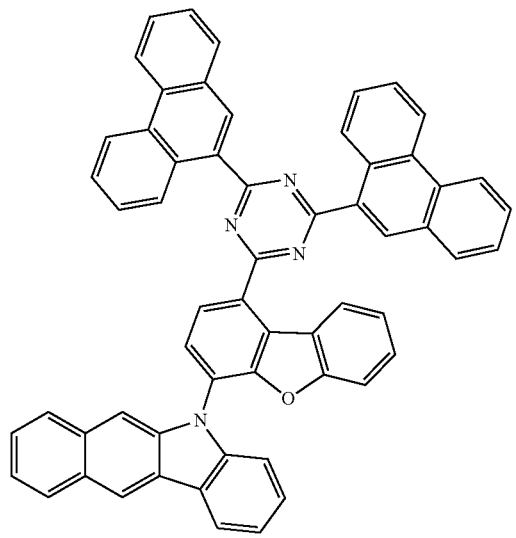

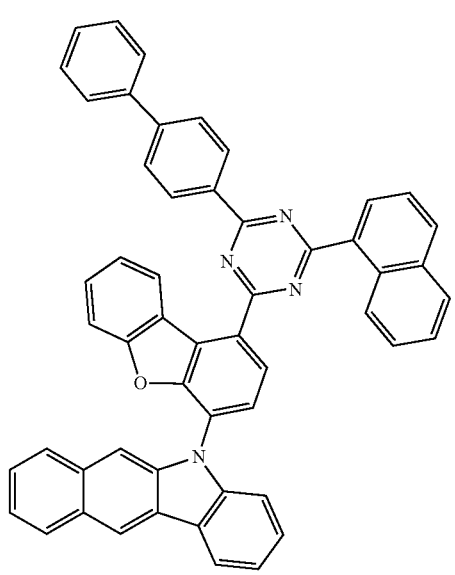

17
-continued
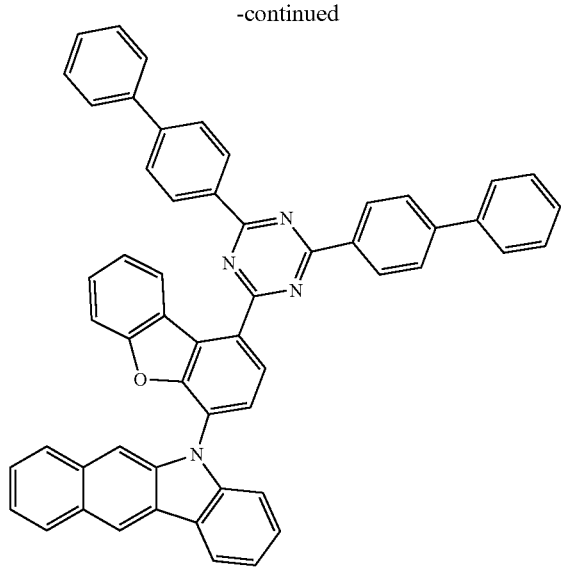
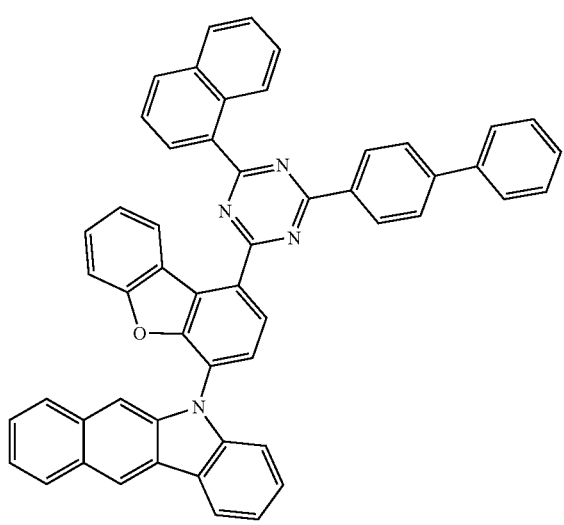
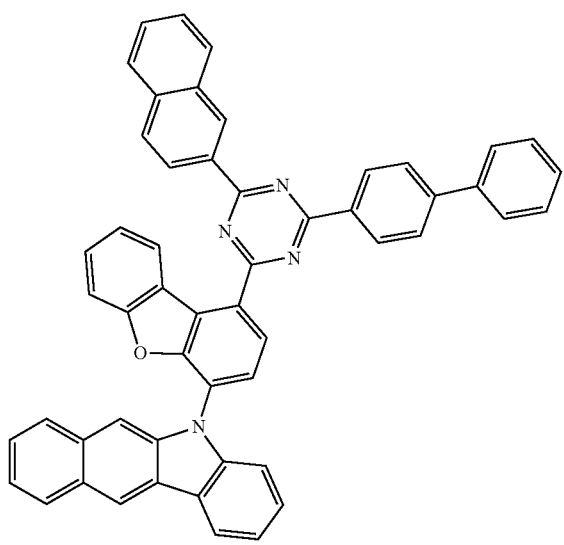
18
-continued
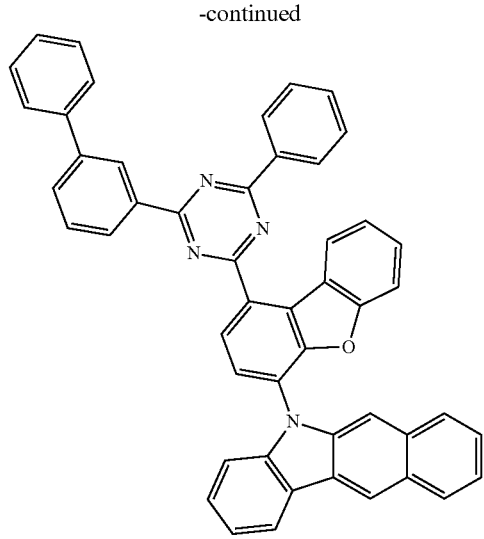
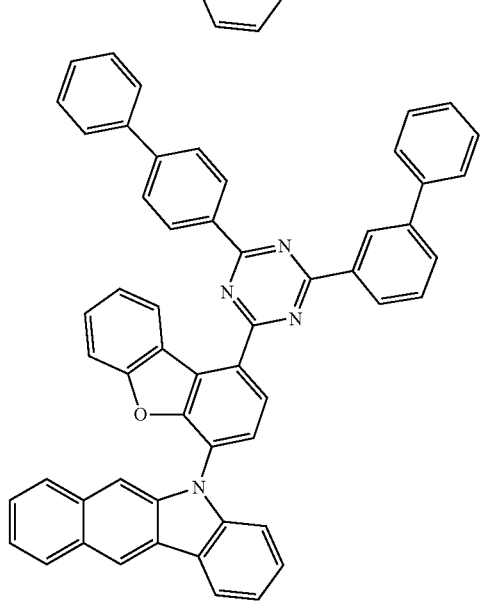

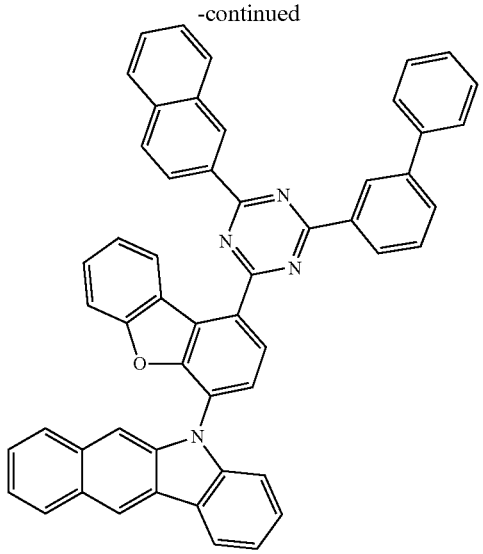
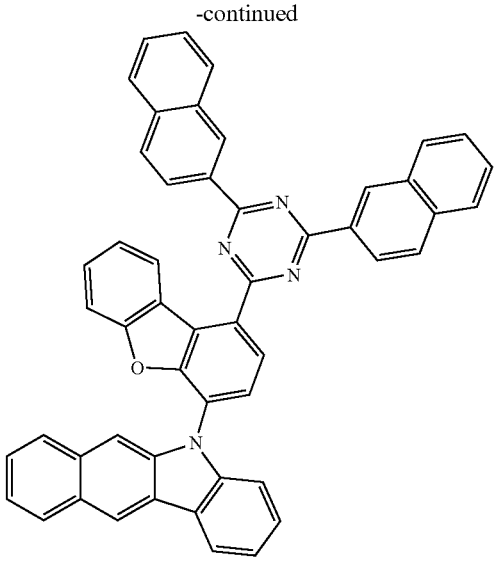
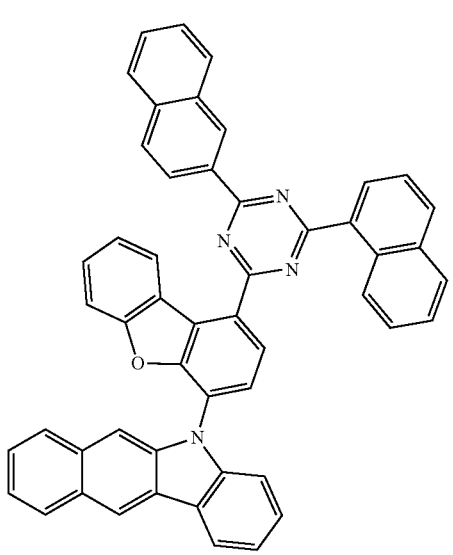
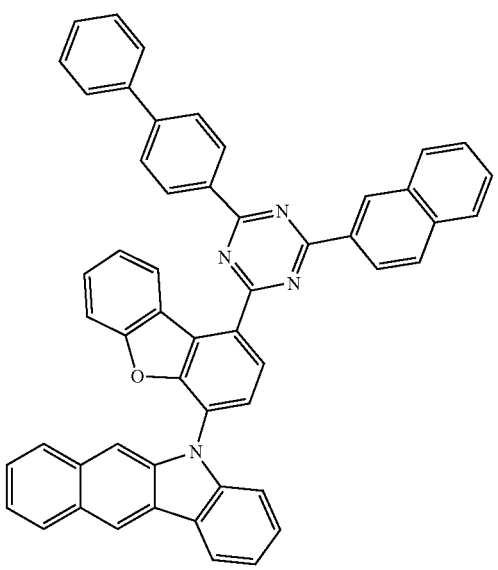
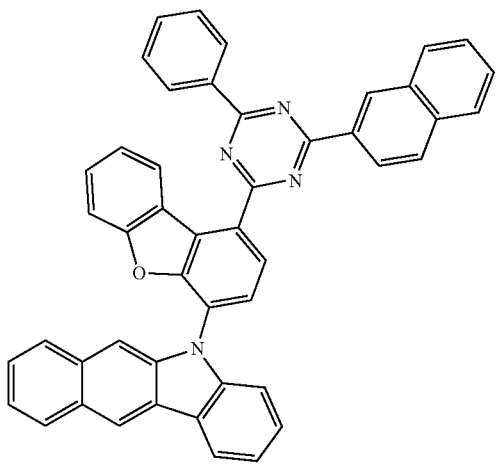
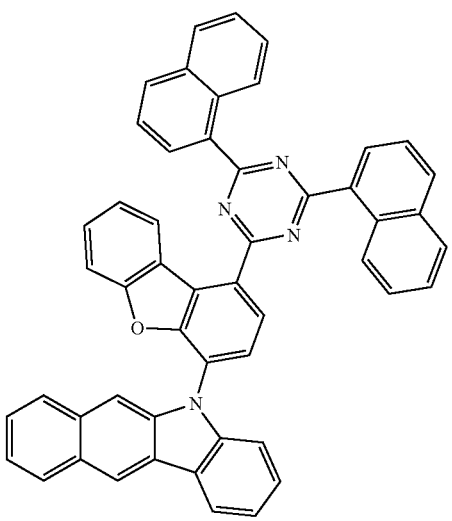

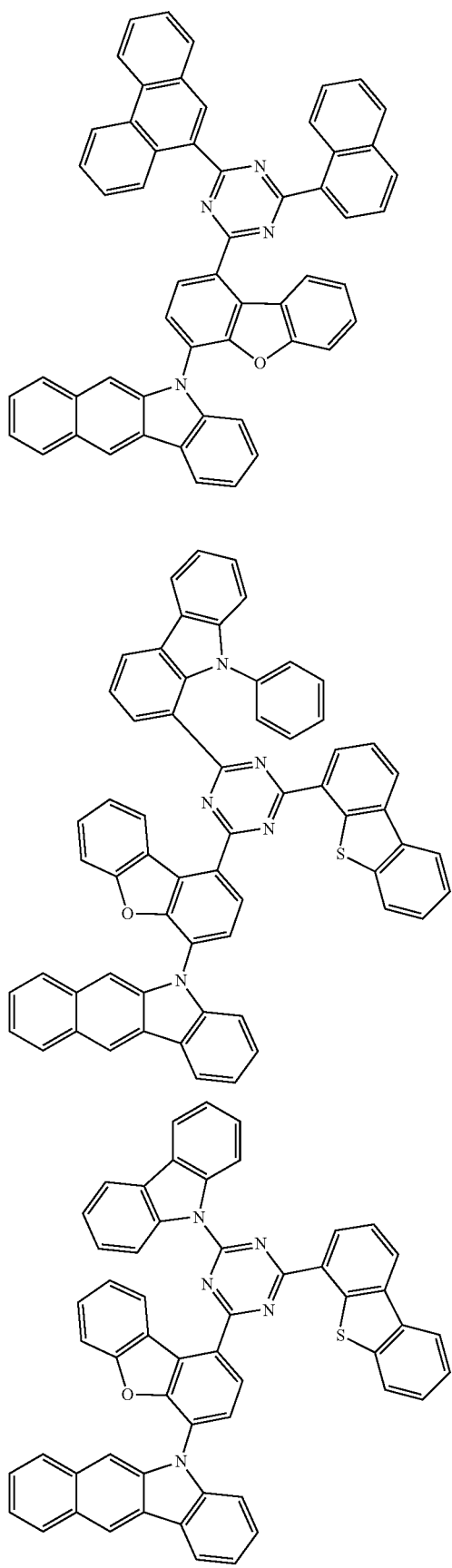

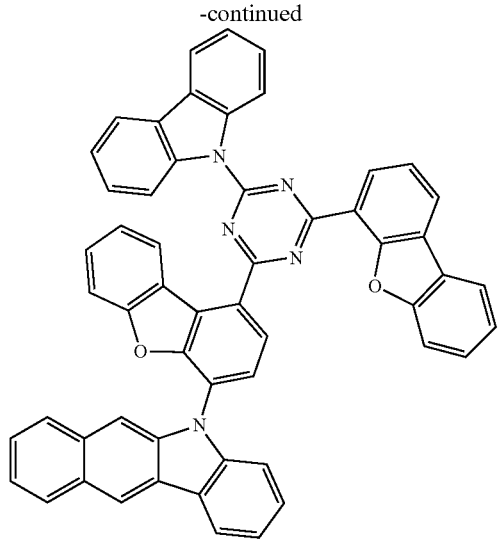
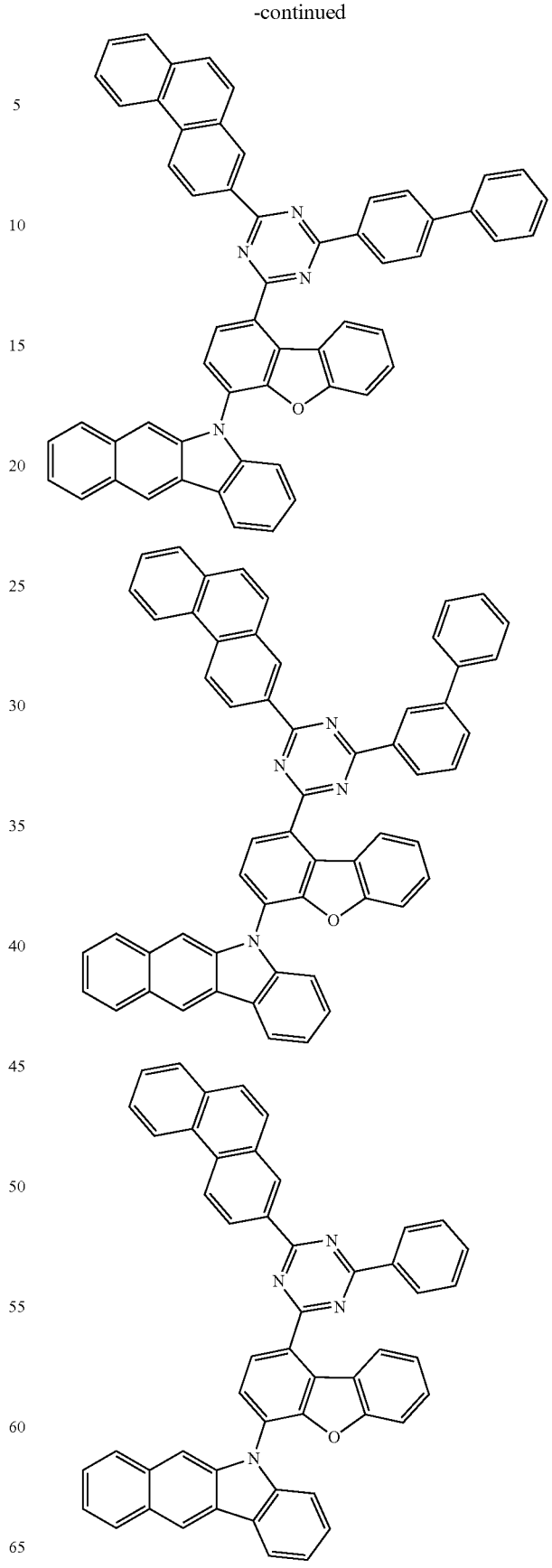

-continued
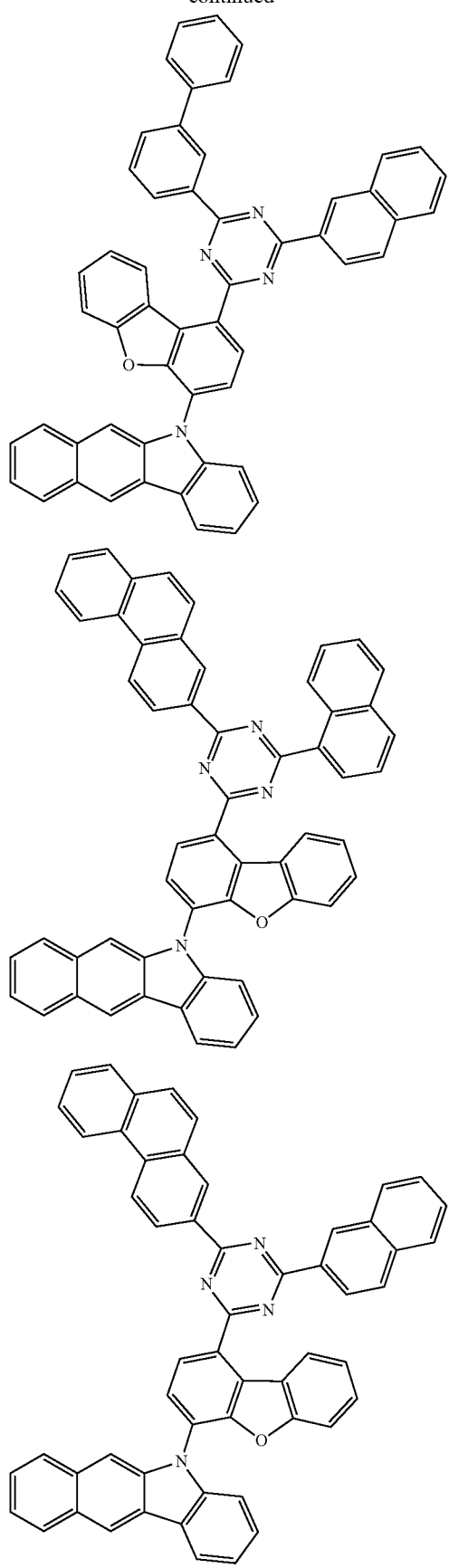
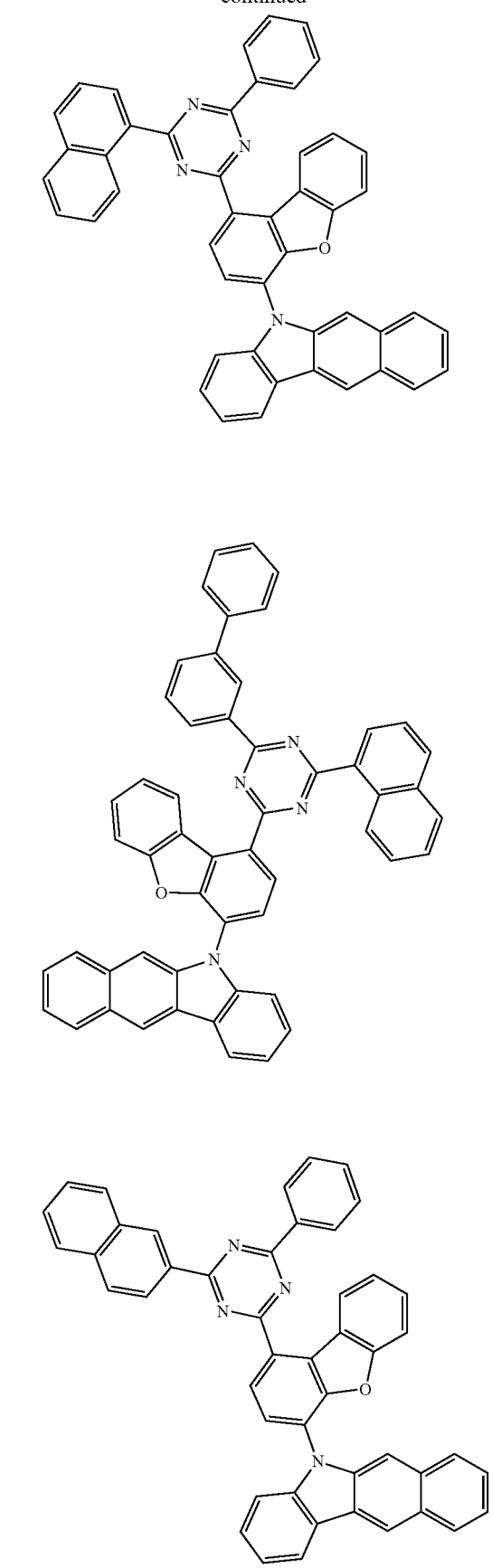

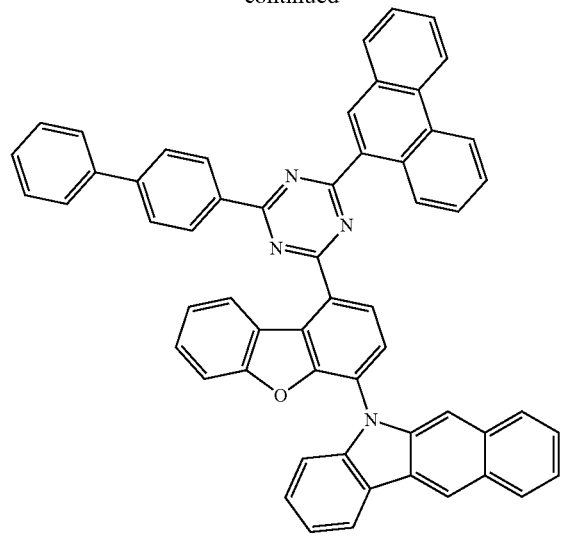
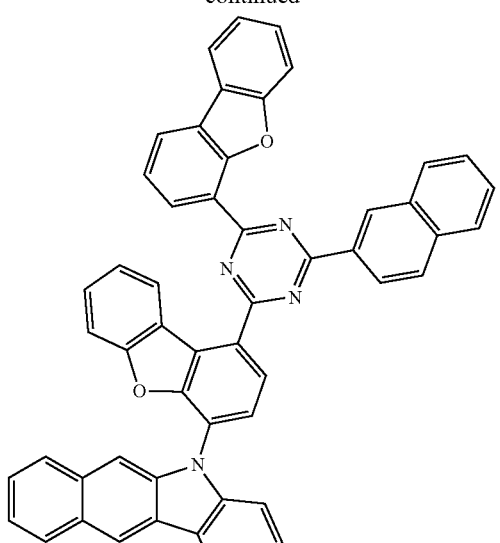
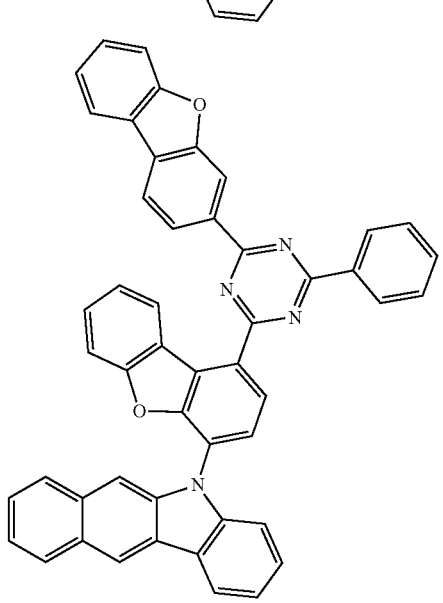

-continued
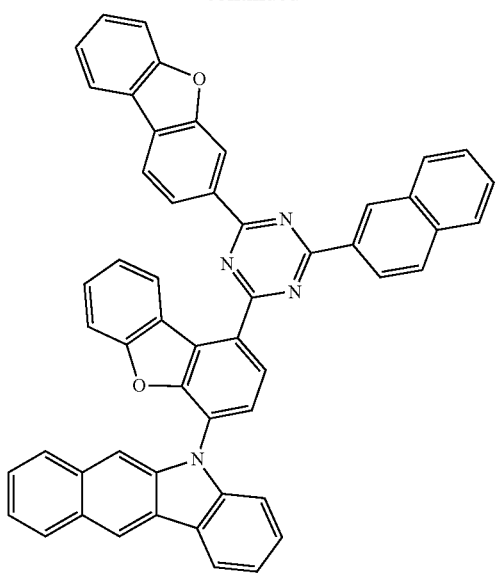
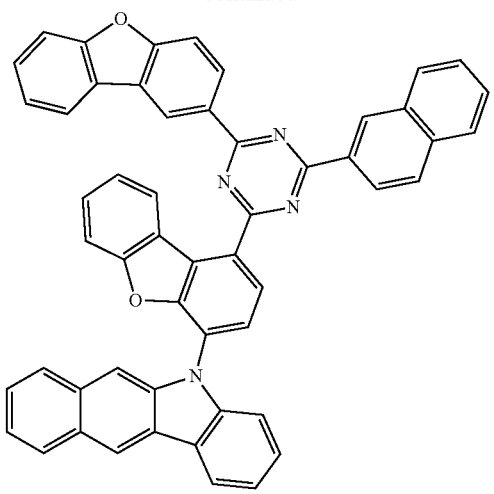
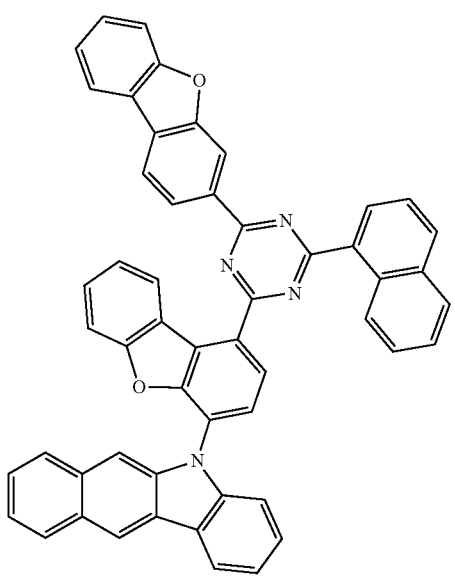
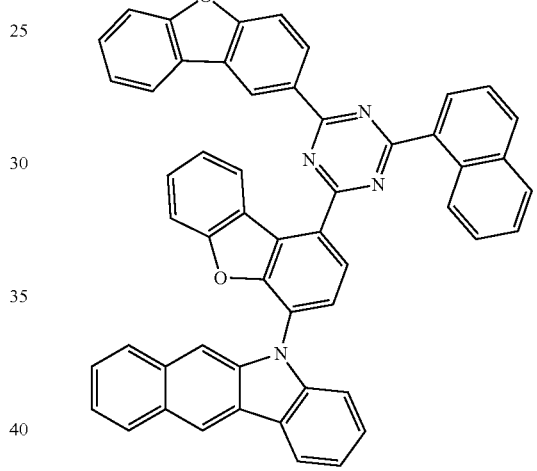
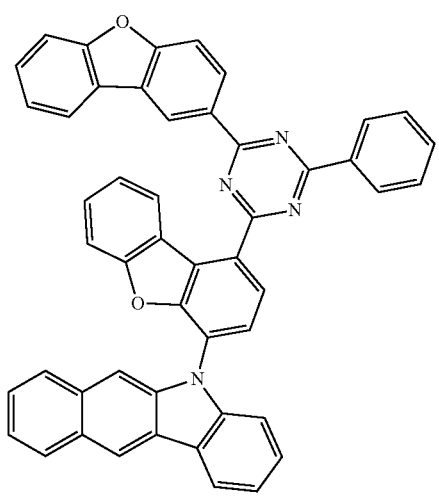
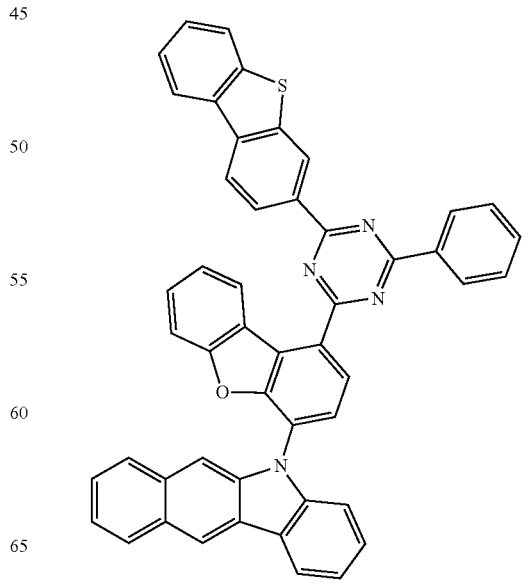

31
-continued
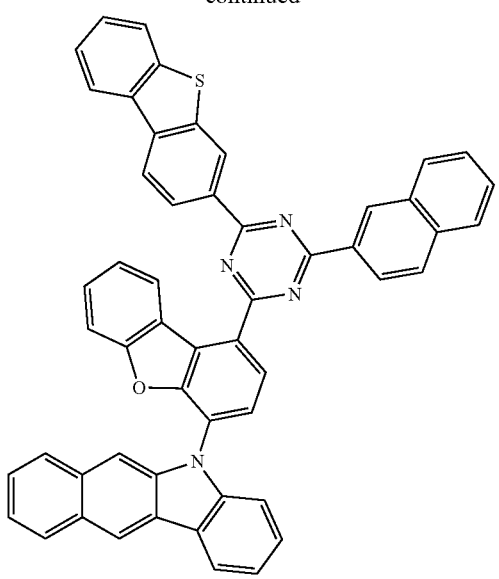
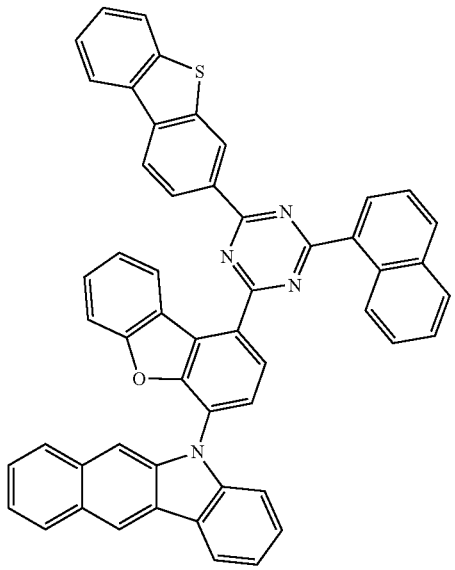
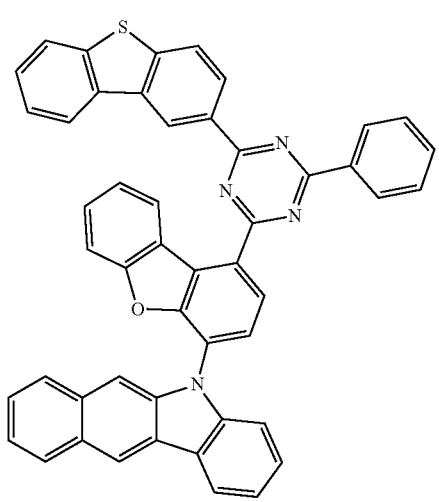
32
-continued
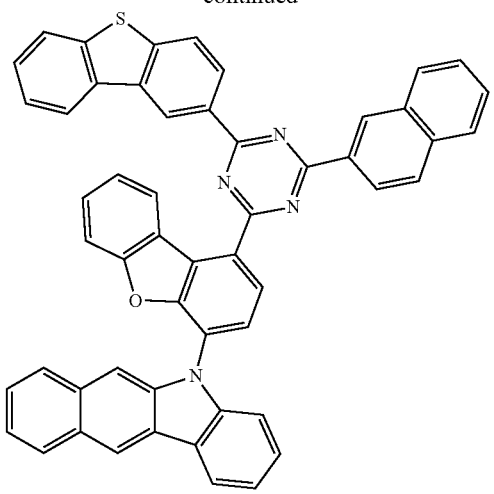
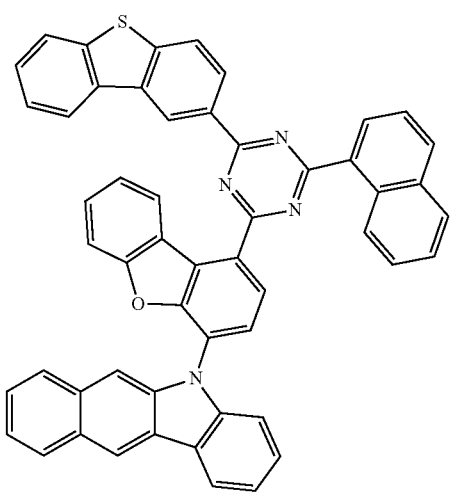
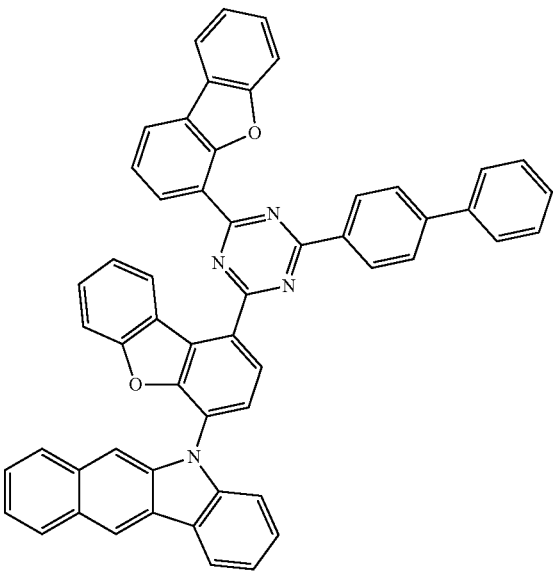

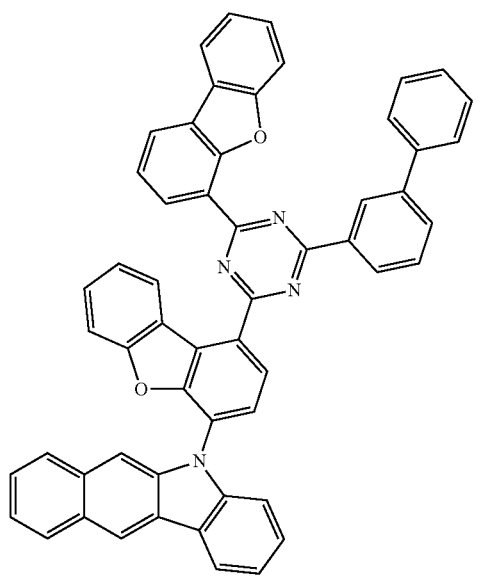
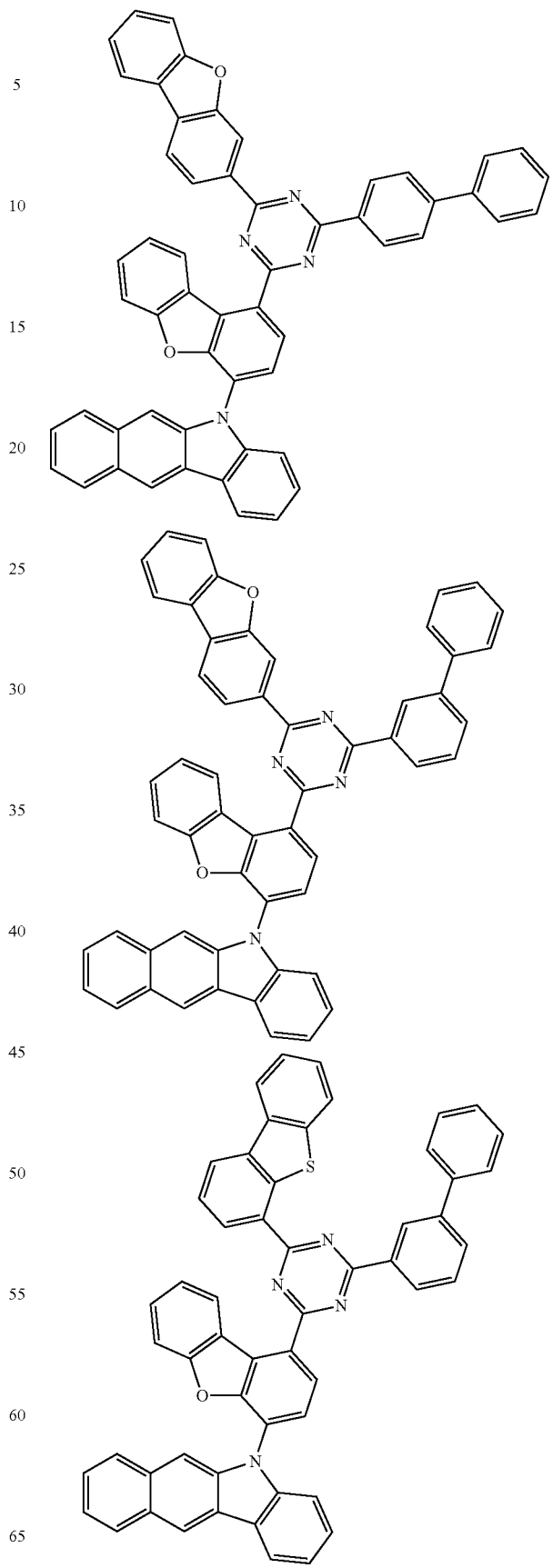

-continued
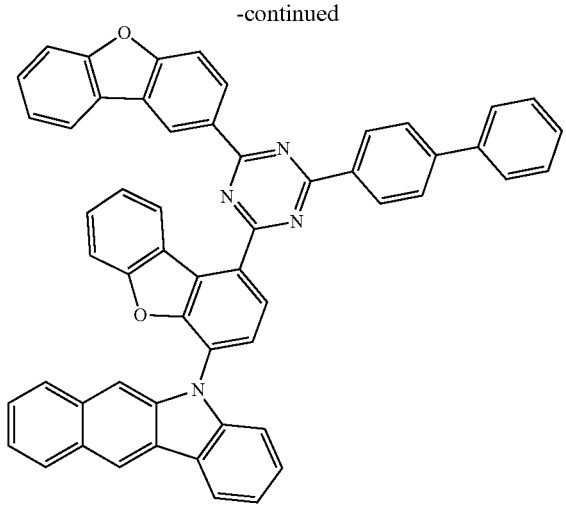
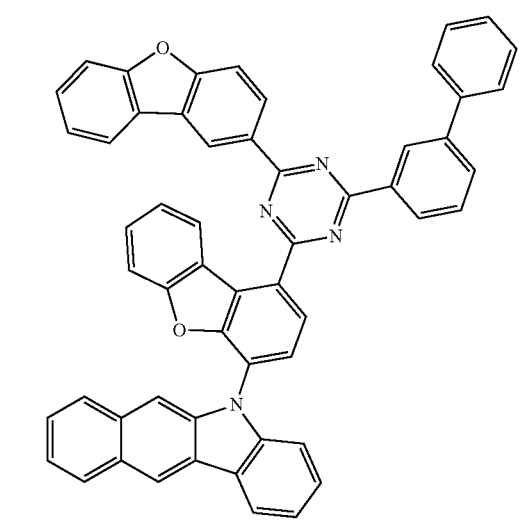
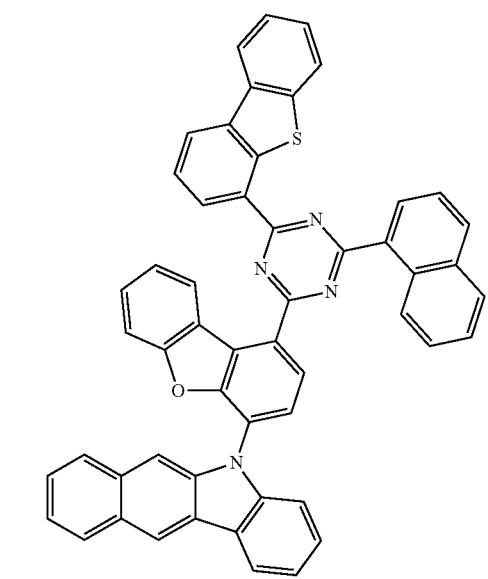
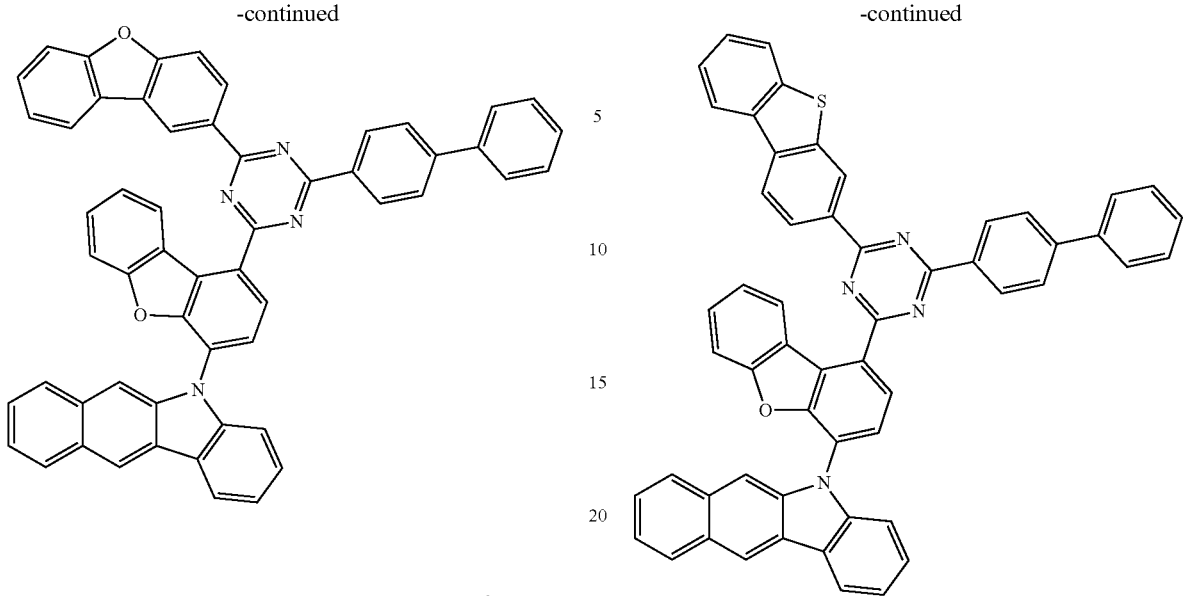
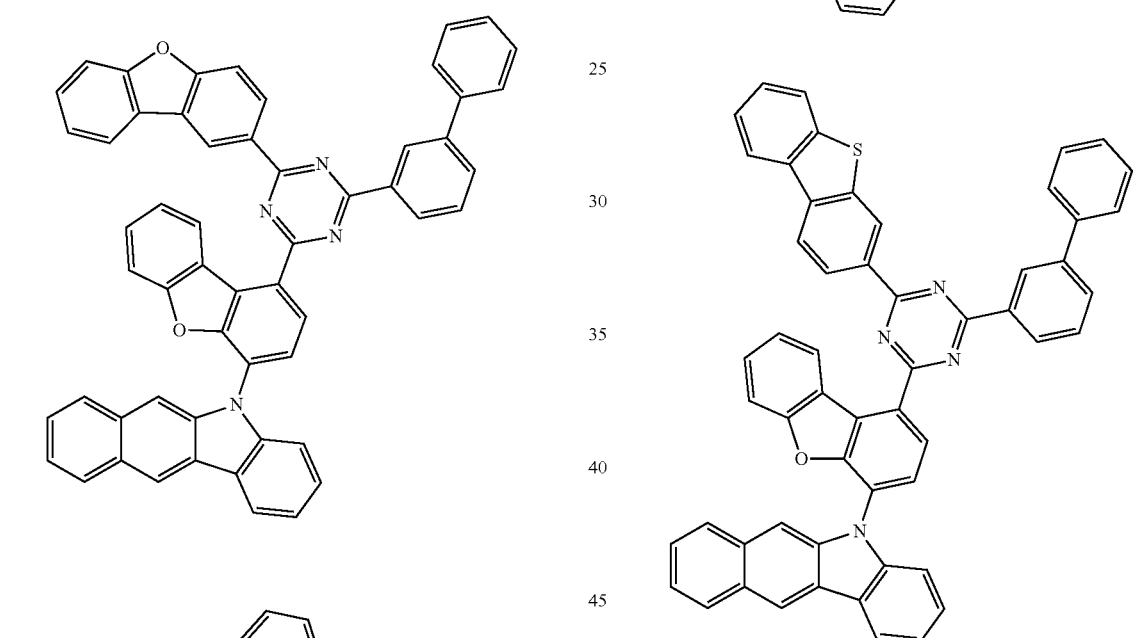
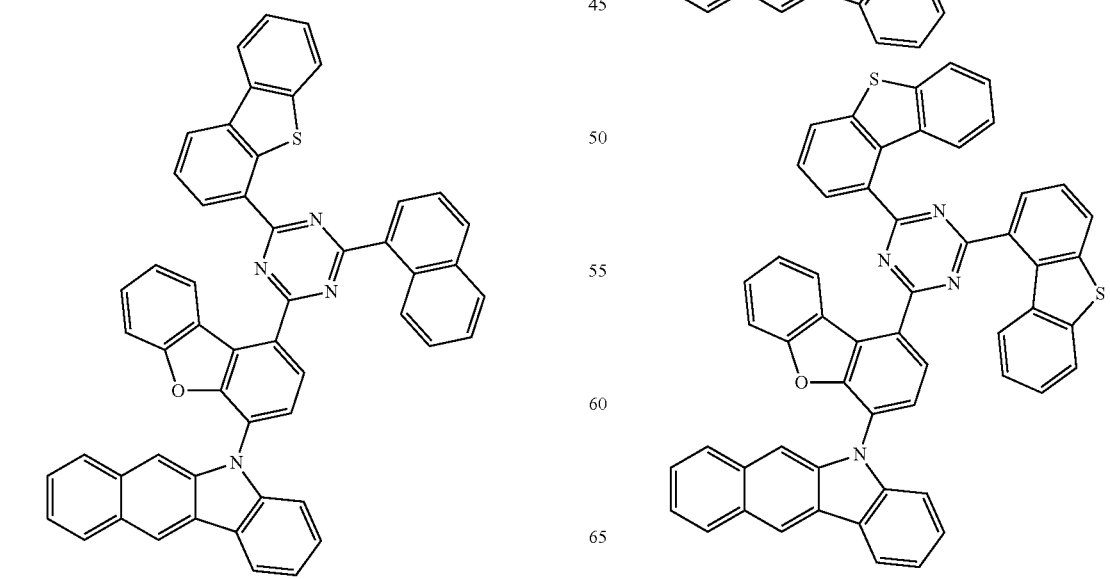

37
-continued
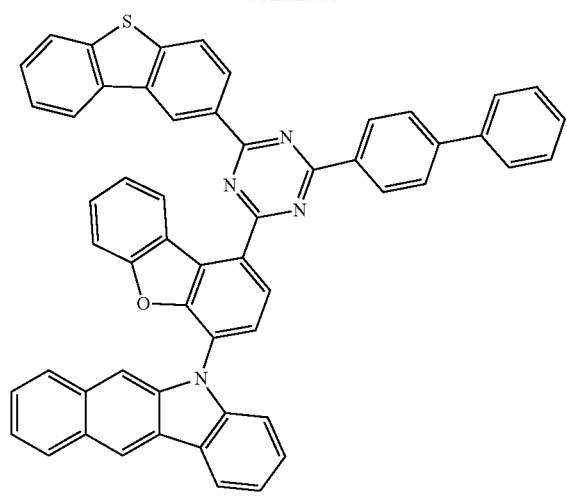
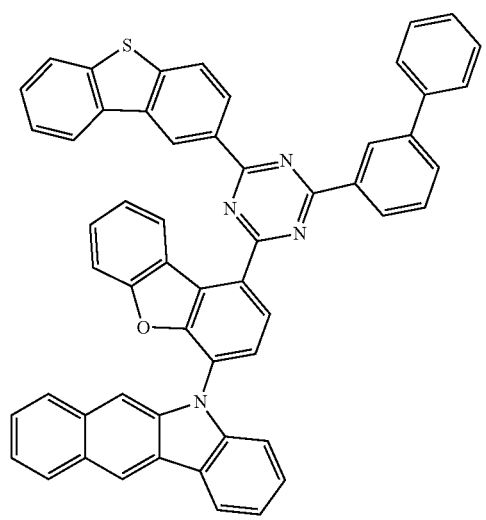
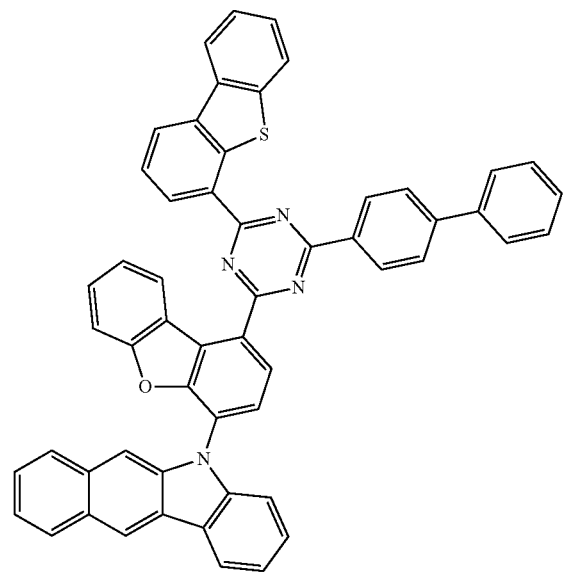
38
-continued
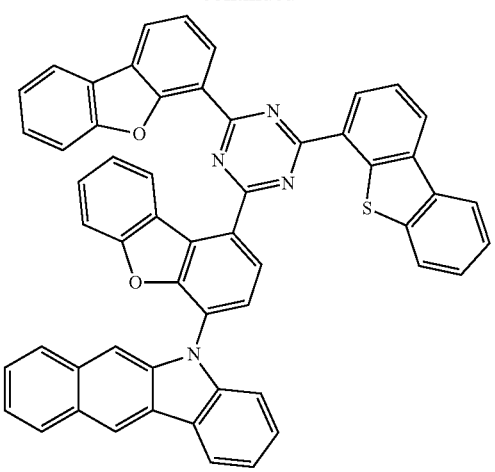
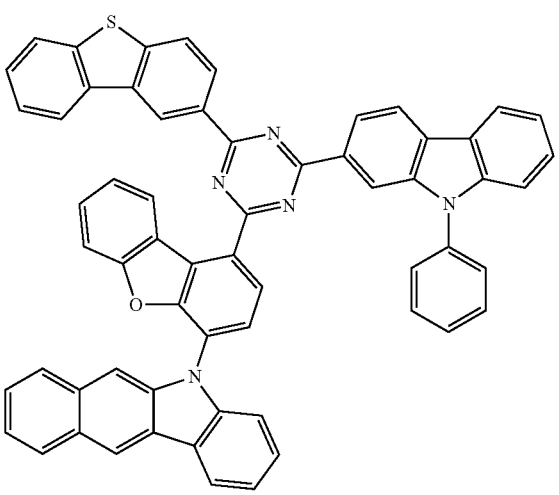

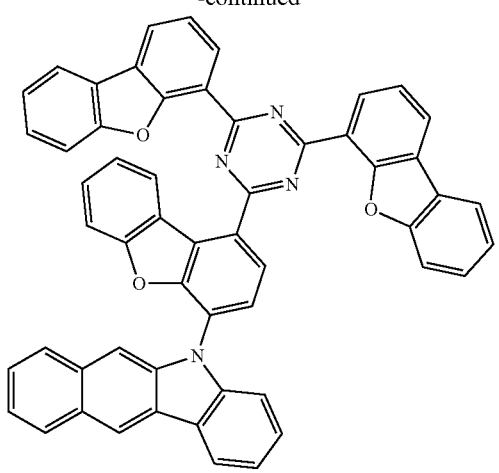
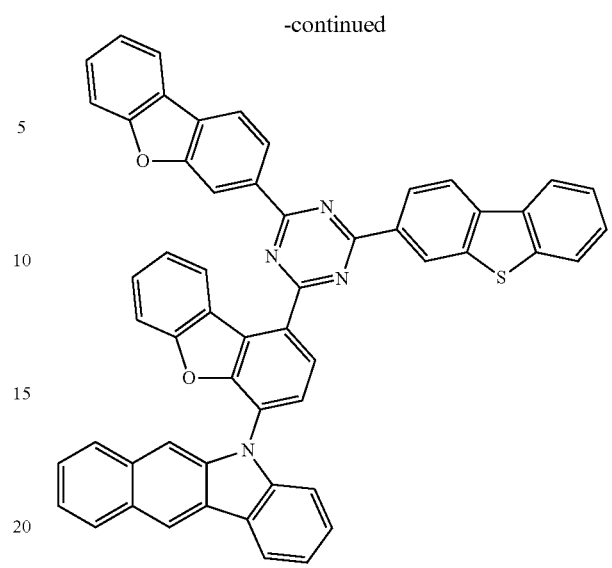
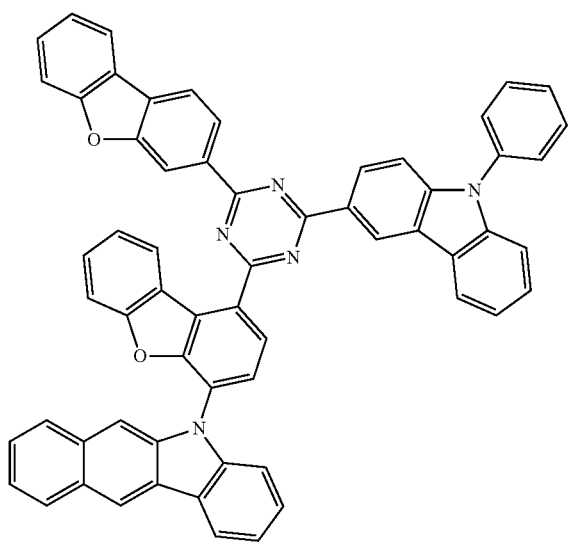
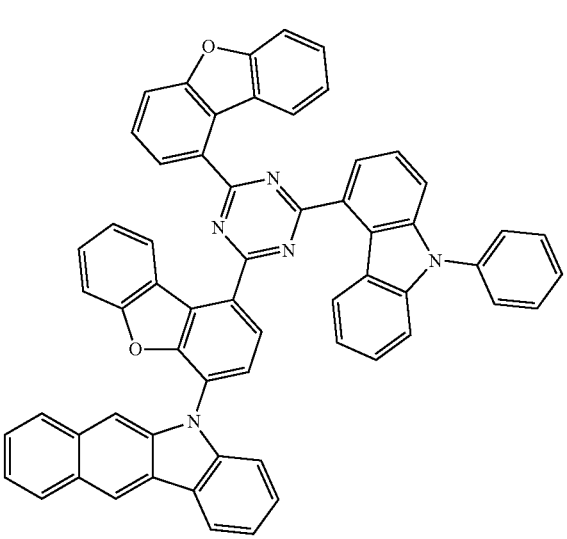
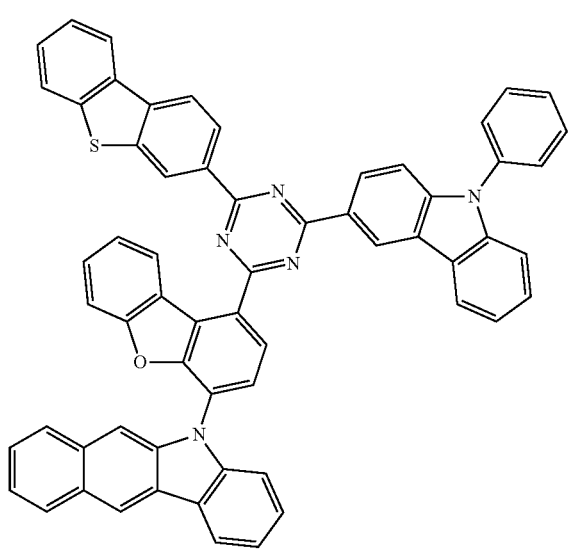
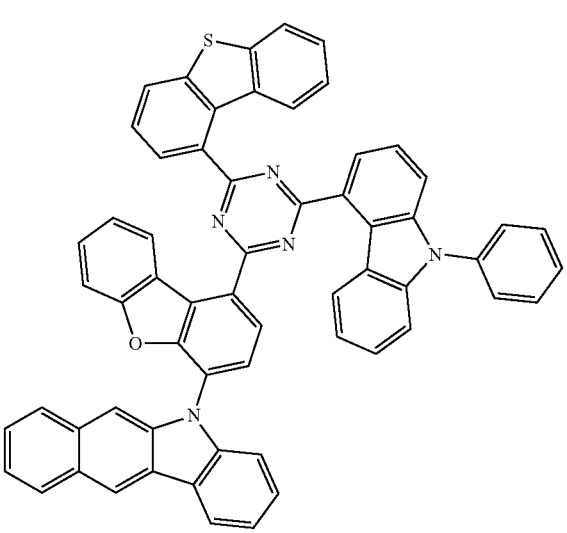

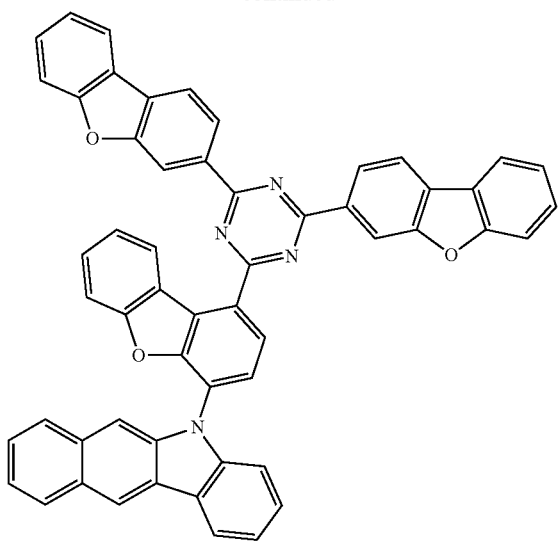
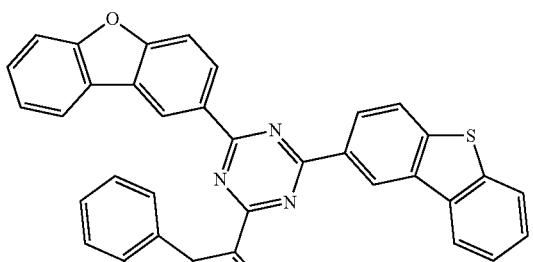
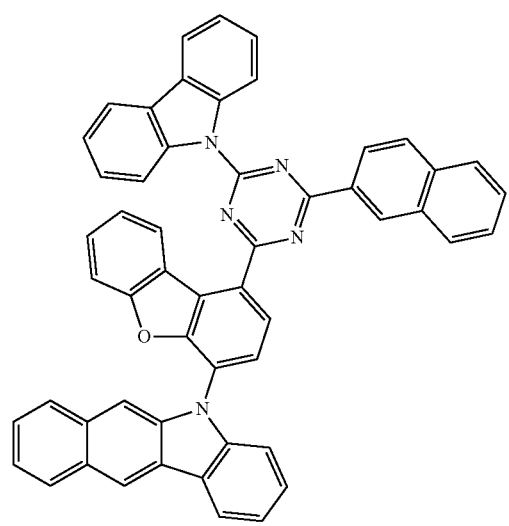
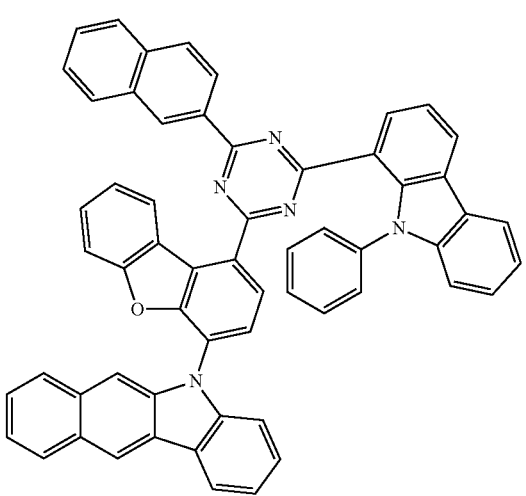

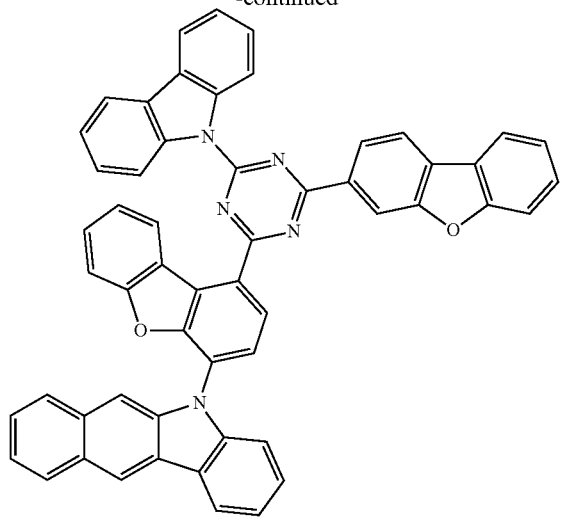
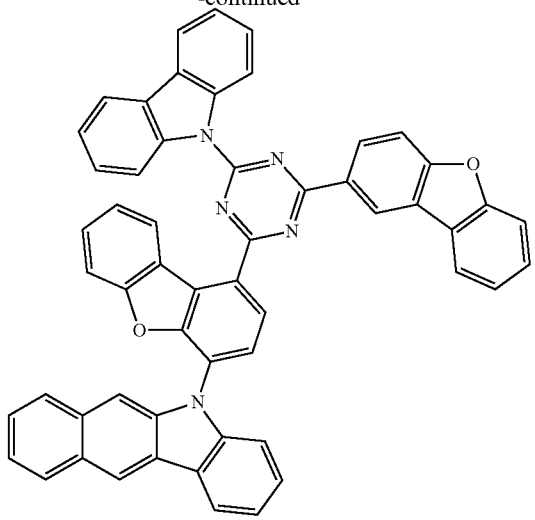
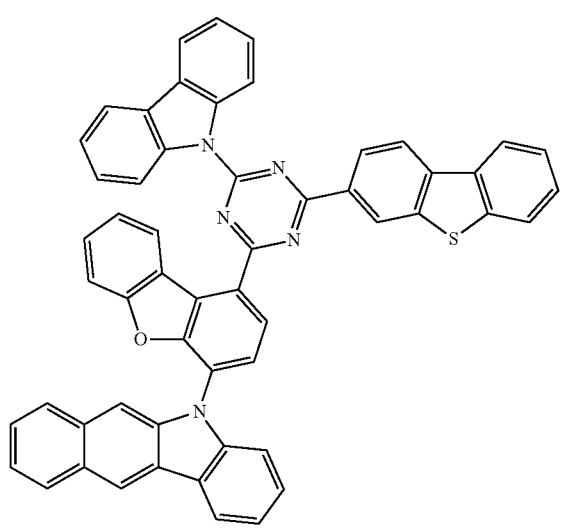
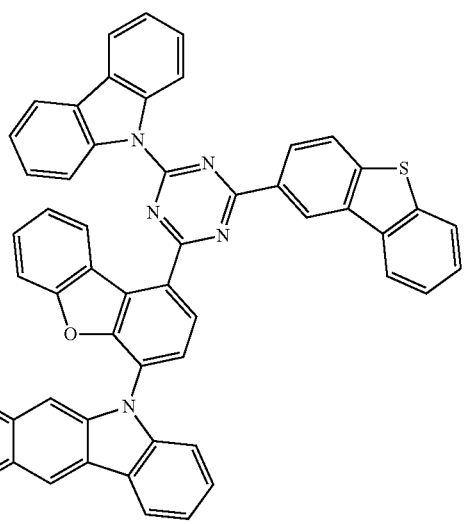
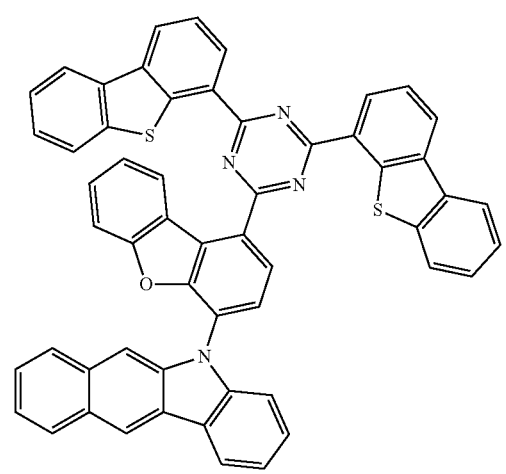
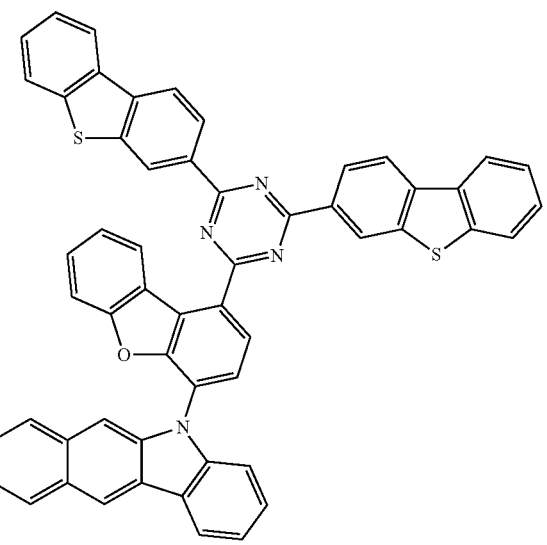

-continued
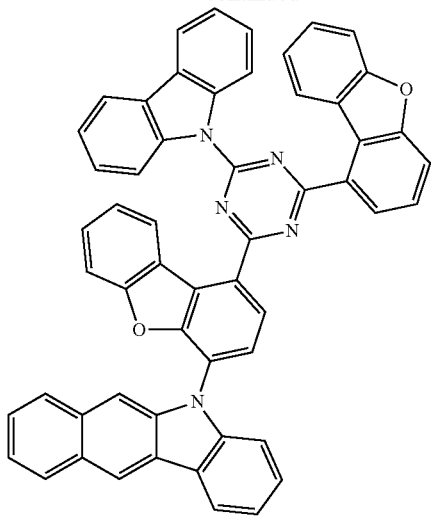
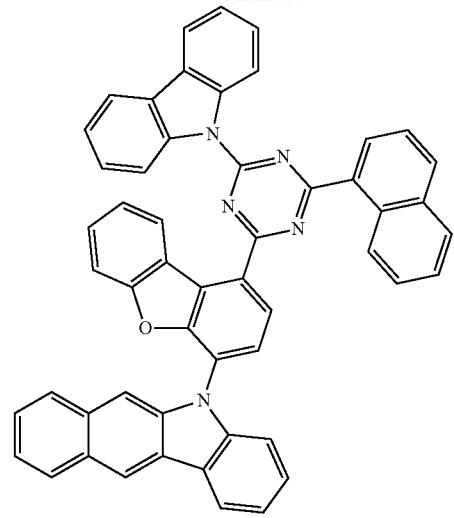
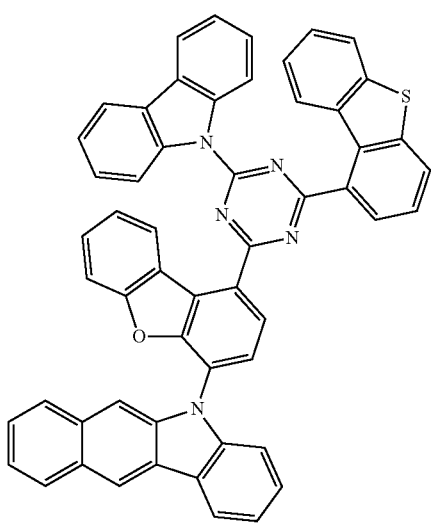
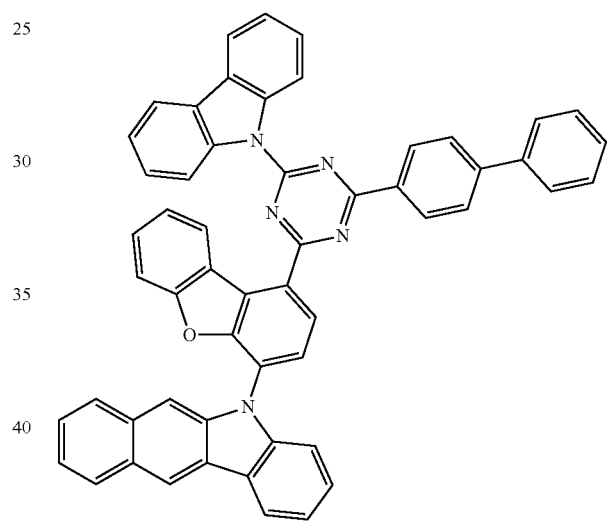
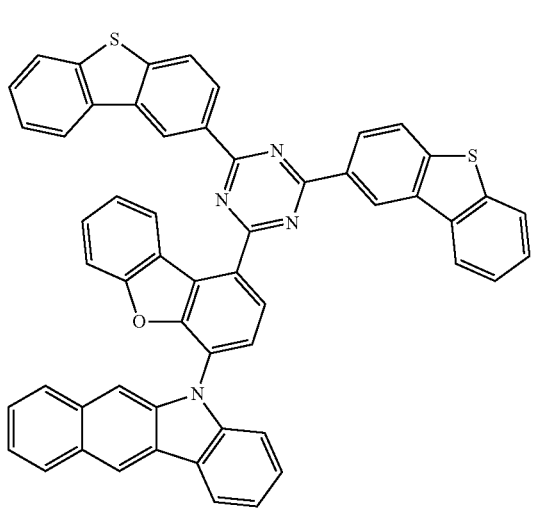
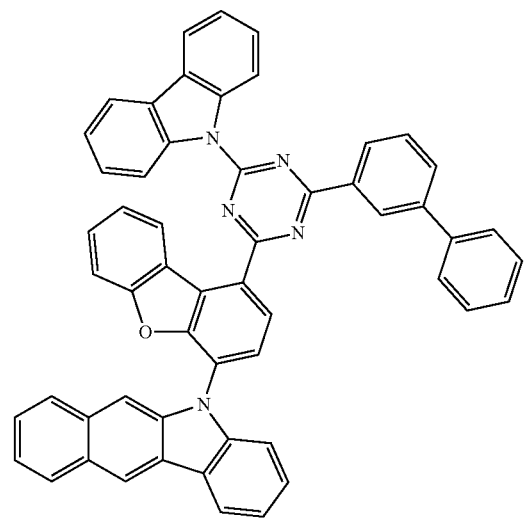

-continued
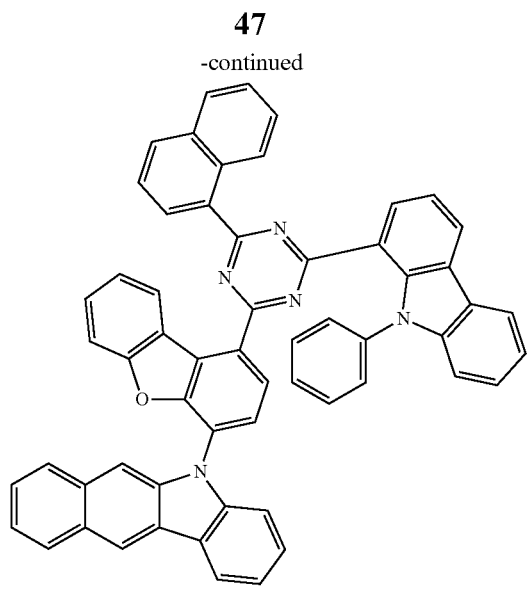
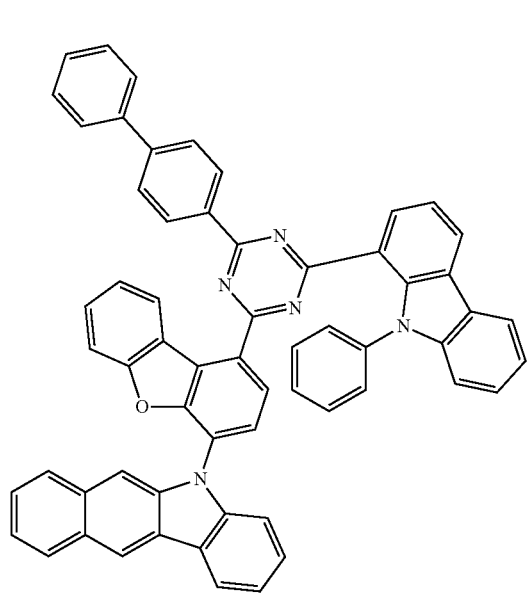
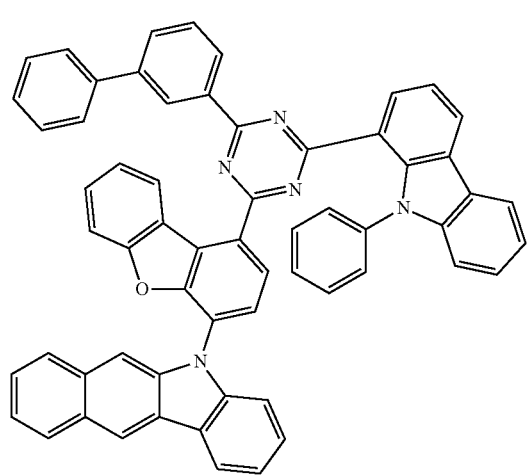
-continued
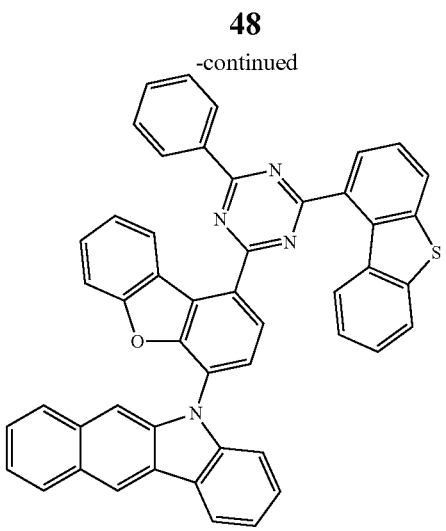
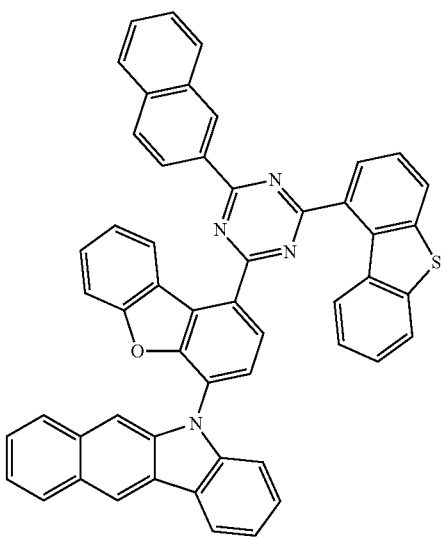
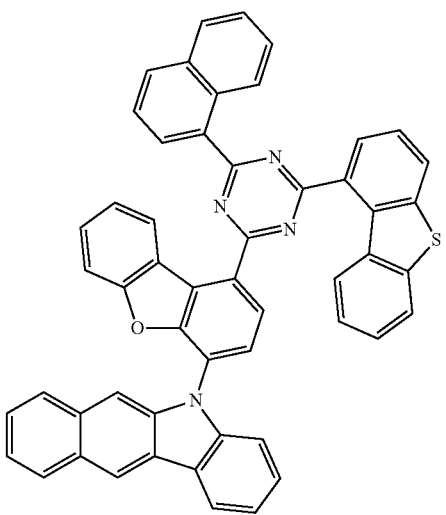

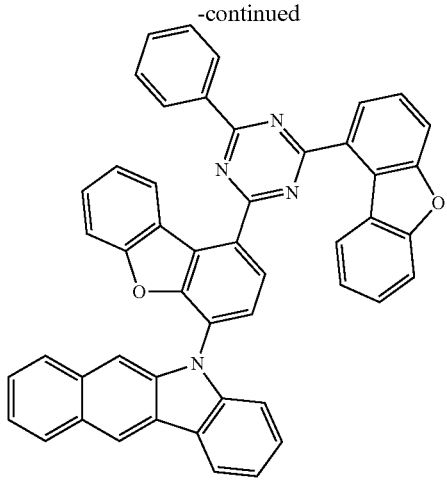
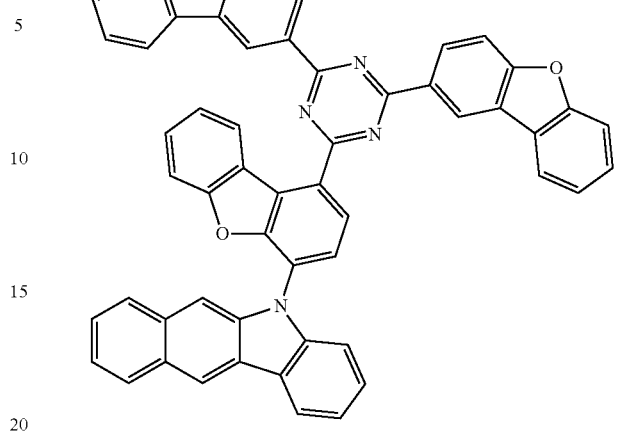
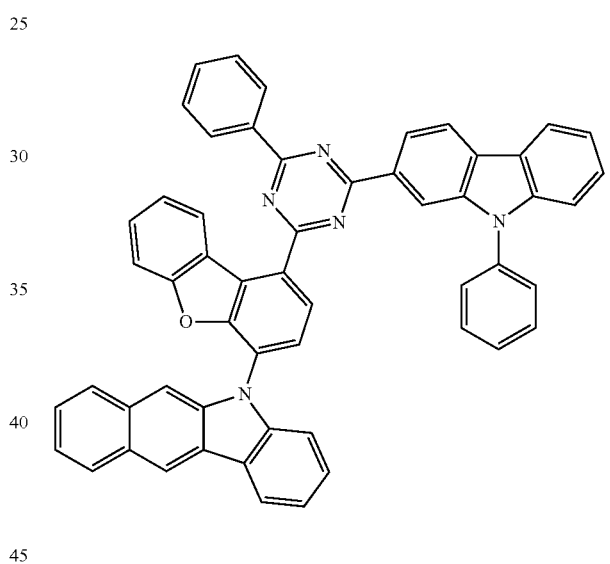
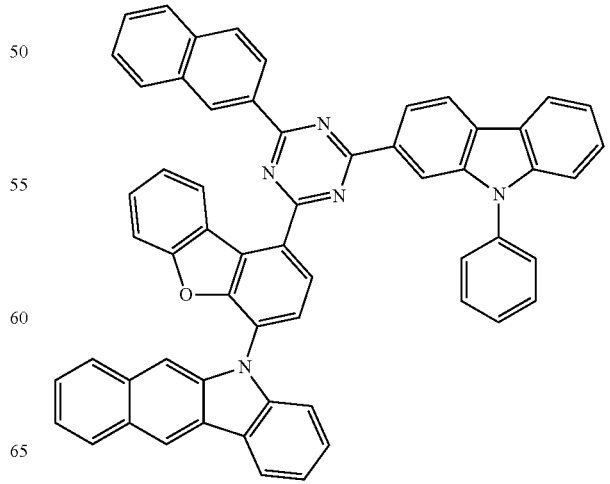

-continued
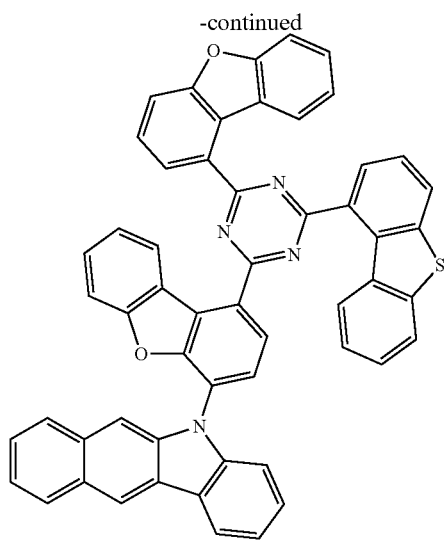
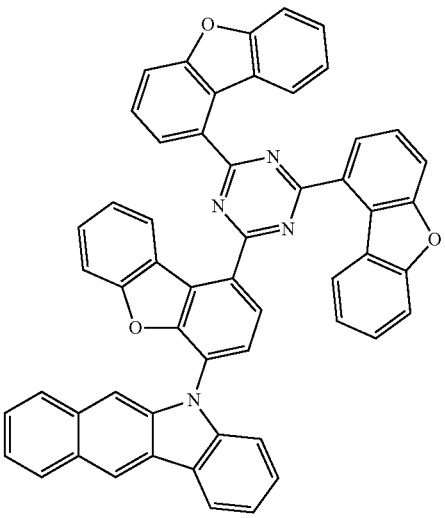
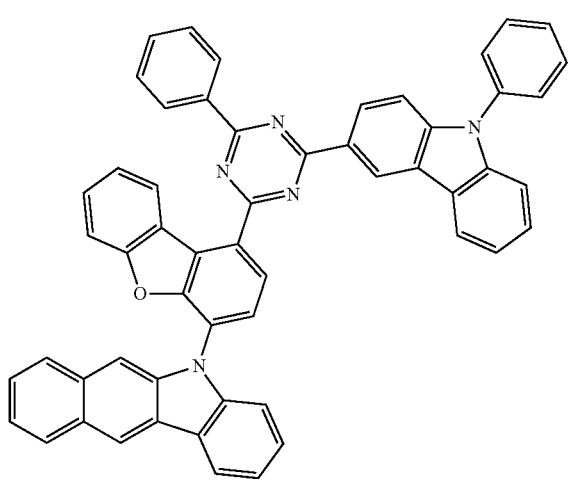
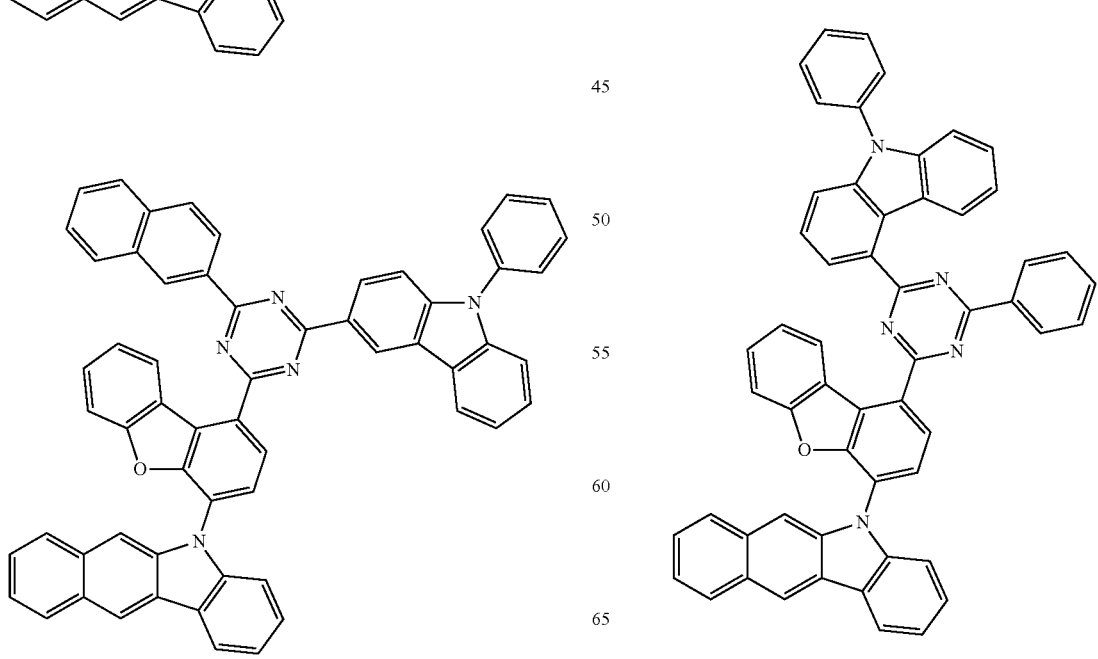

53
-continued
54
-continued
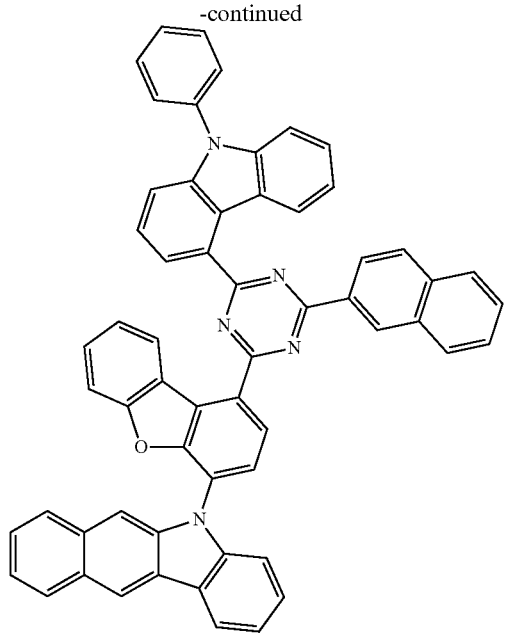
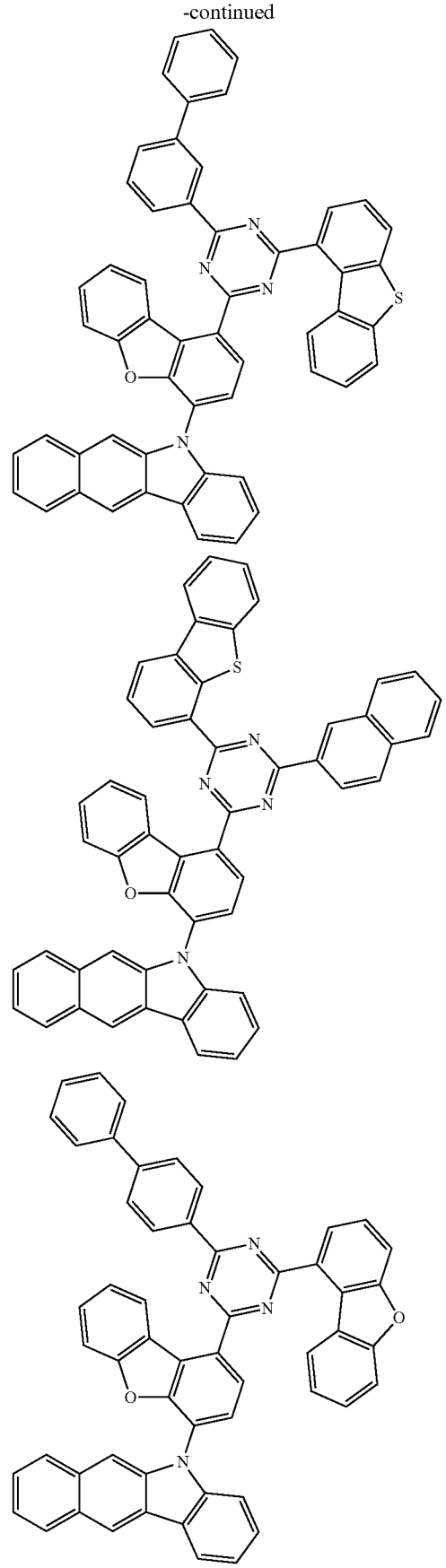

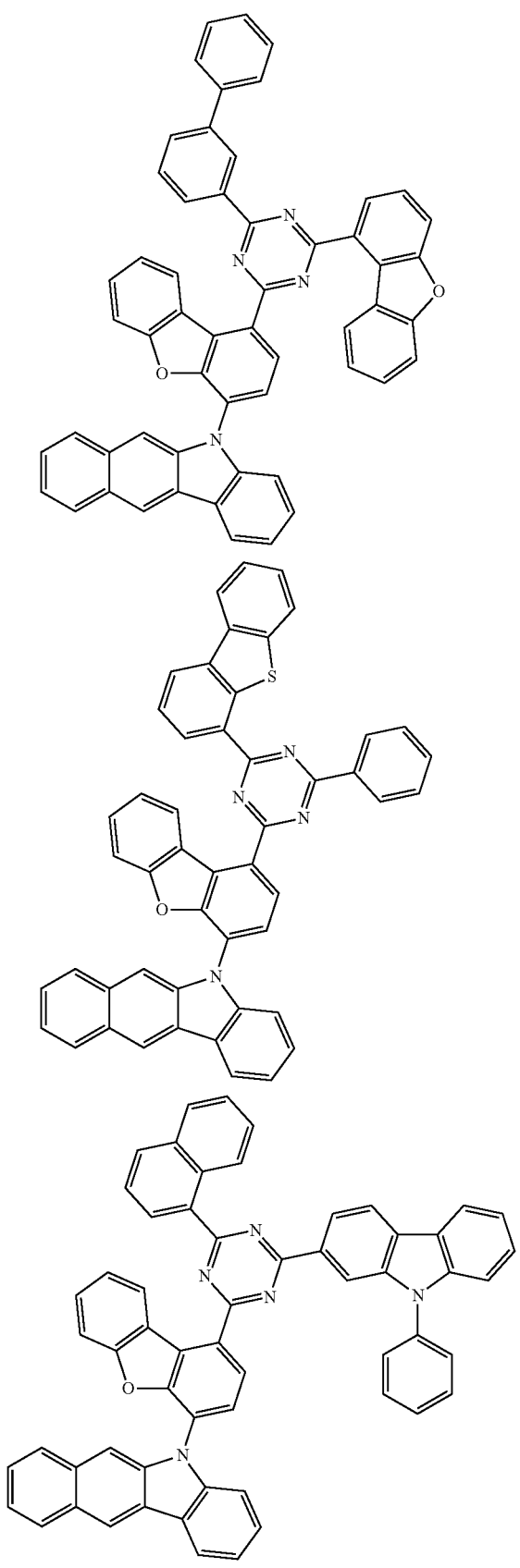
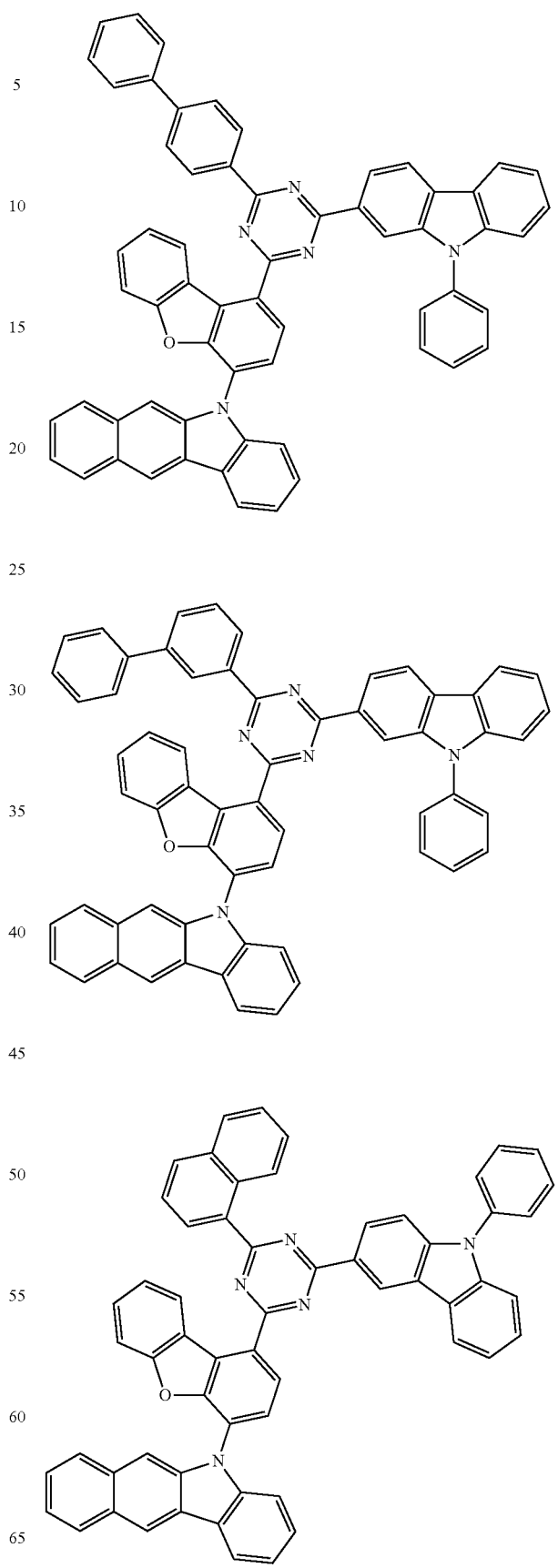

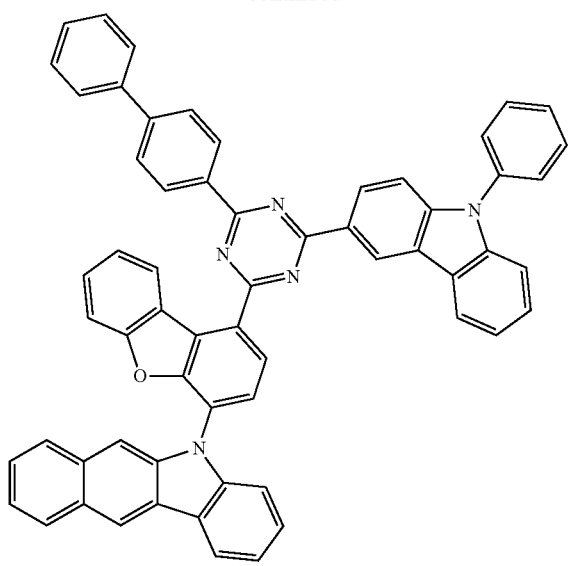
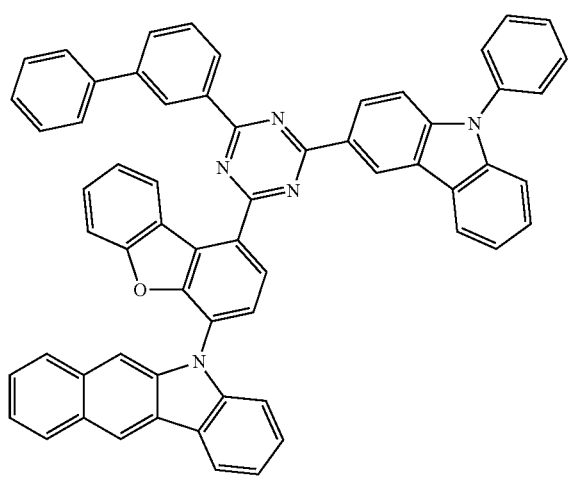
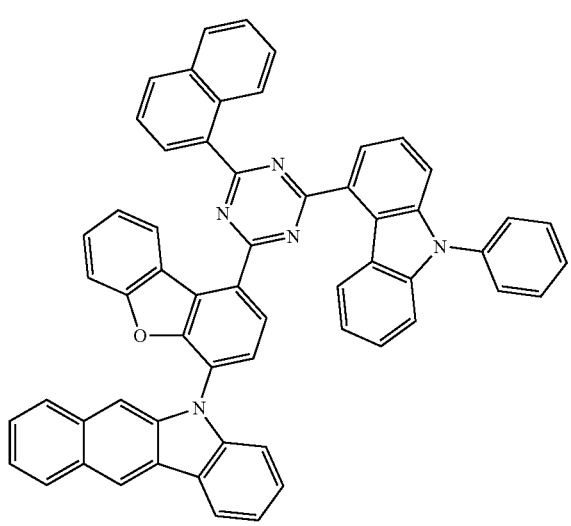
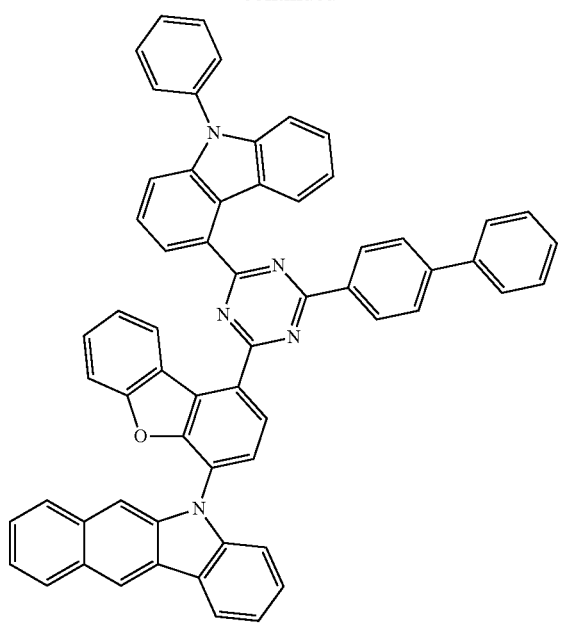
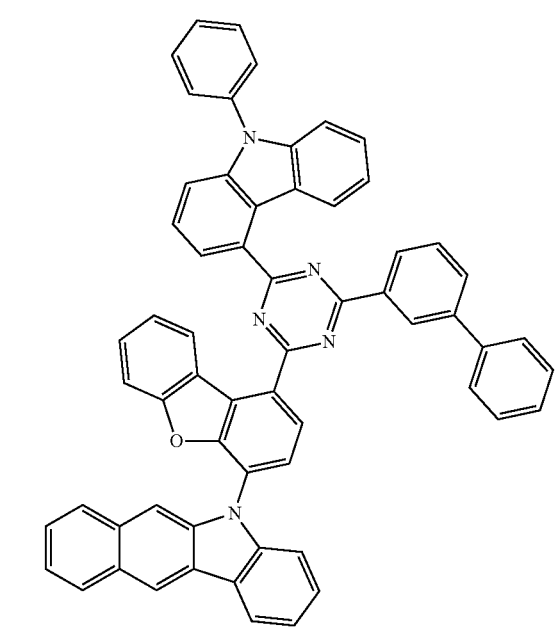

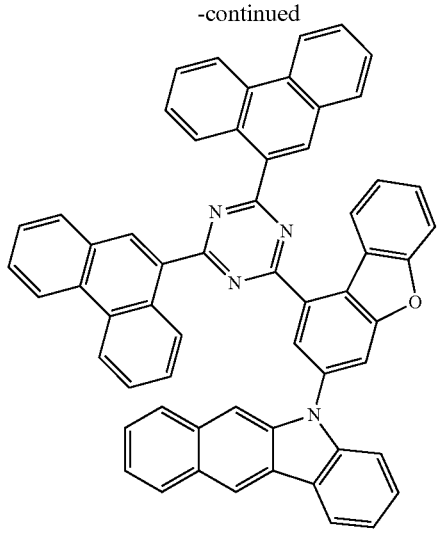
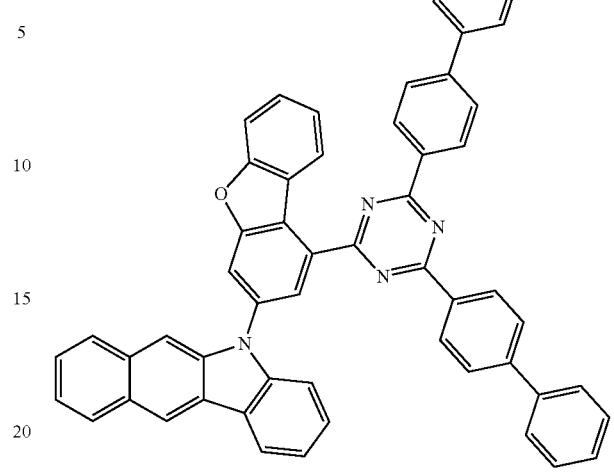
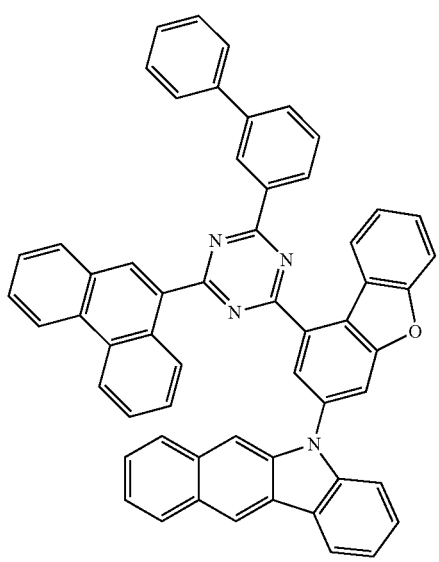
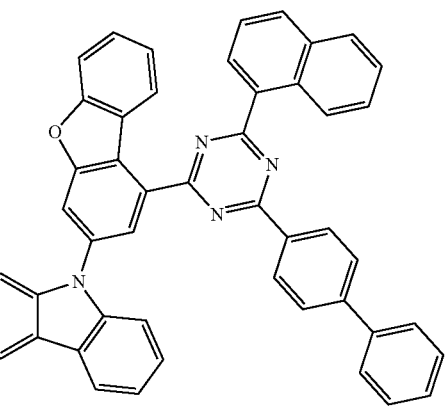
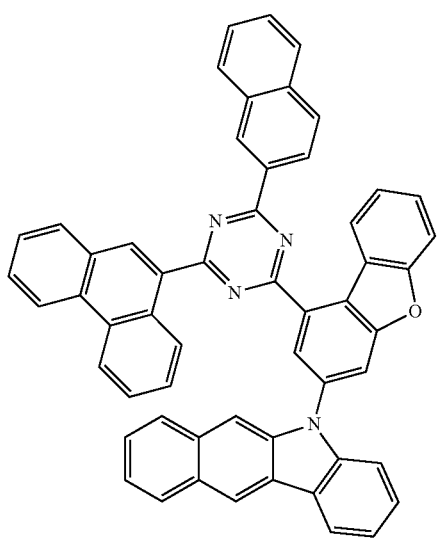
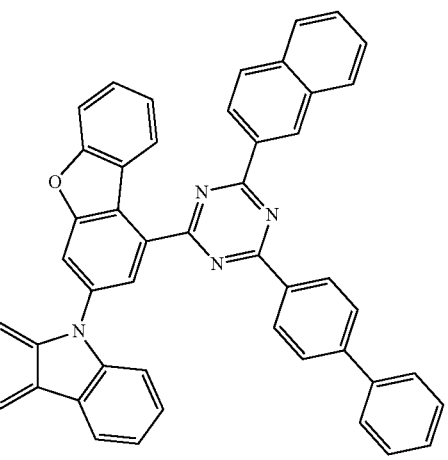

-continued
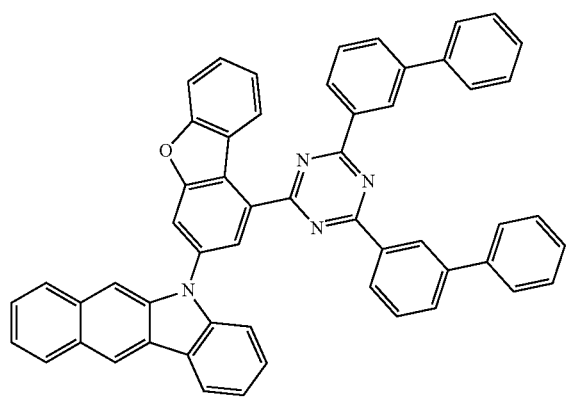
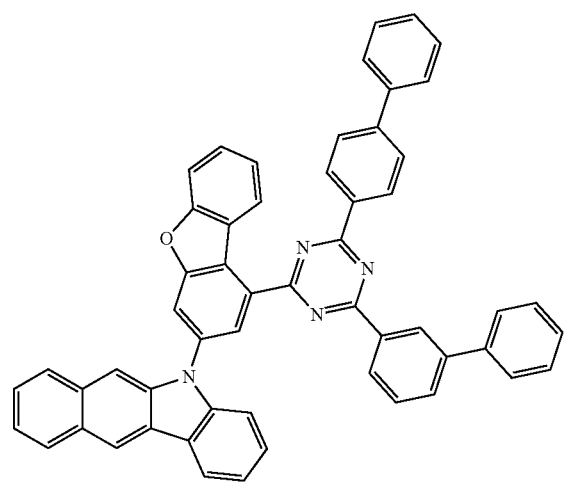
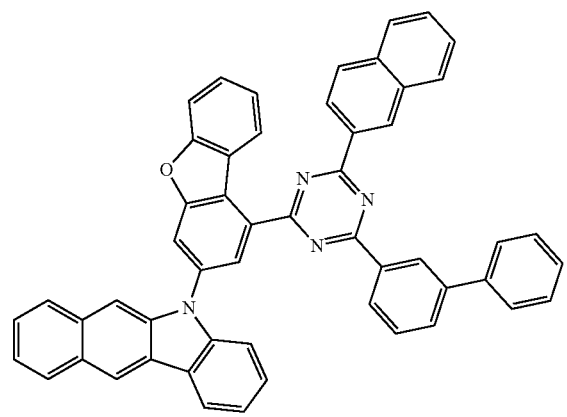
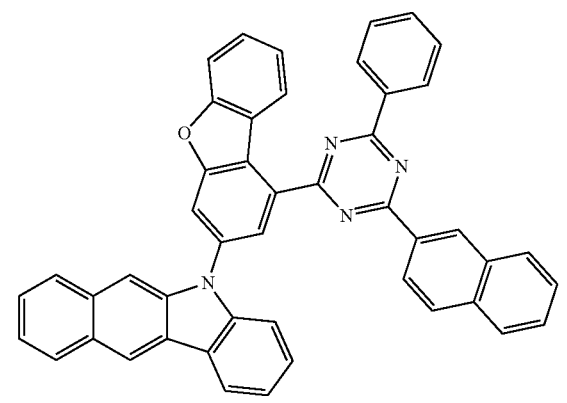
-continued
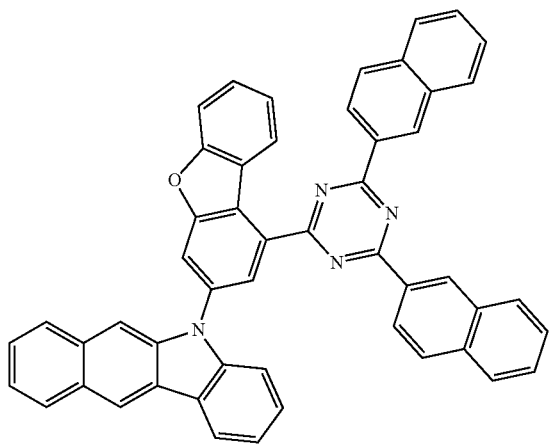
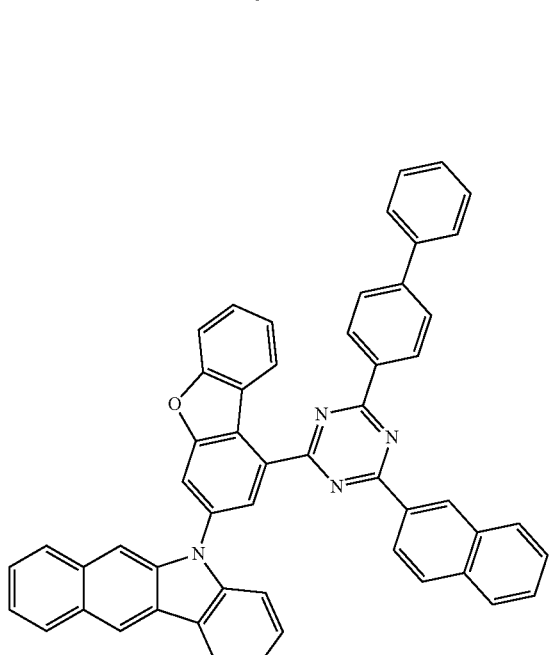
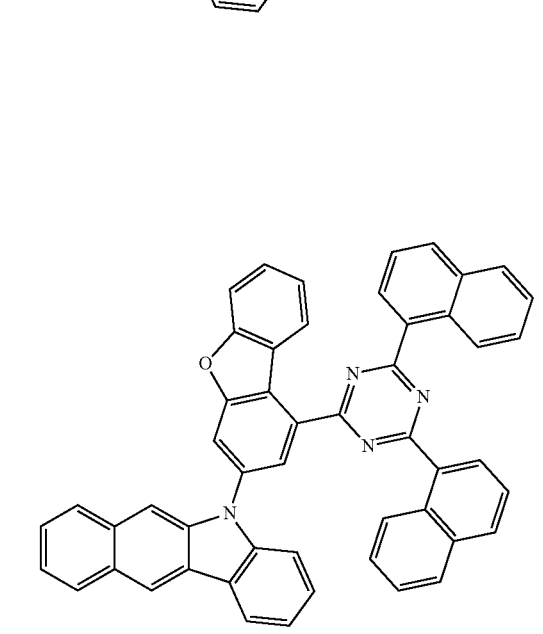

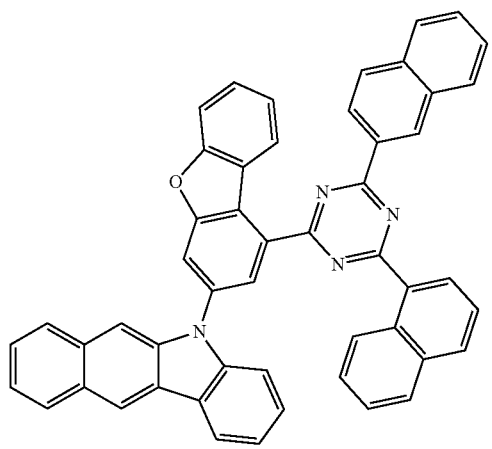
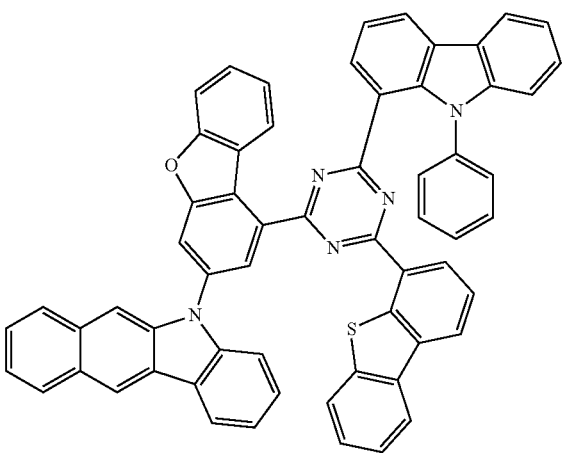
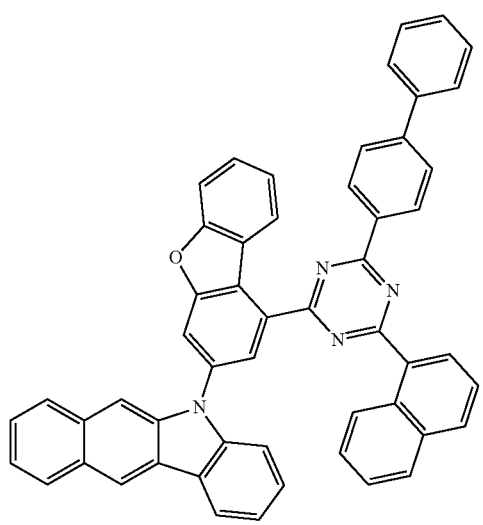
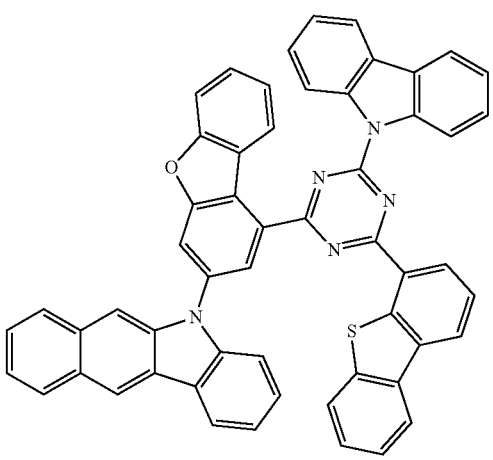
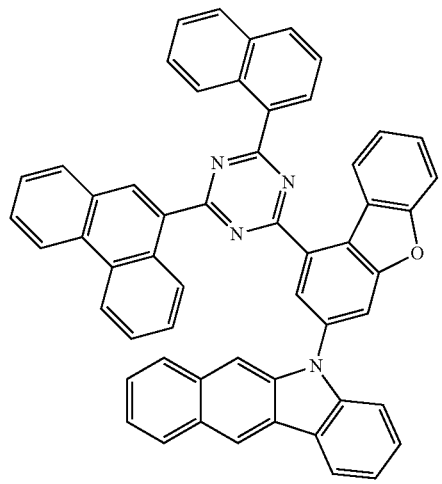
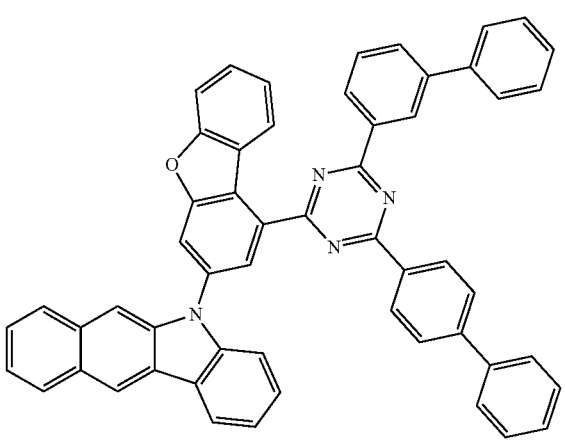

65
66
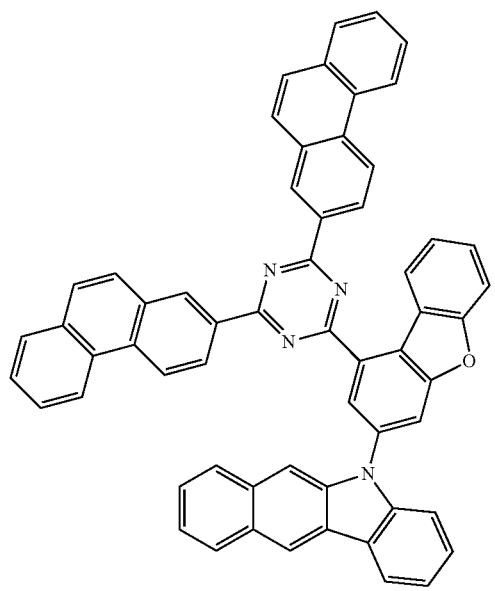
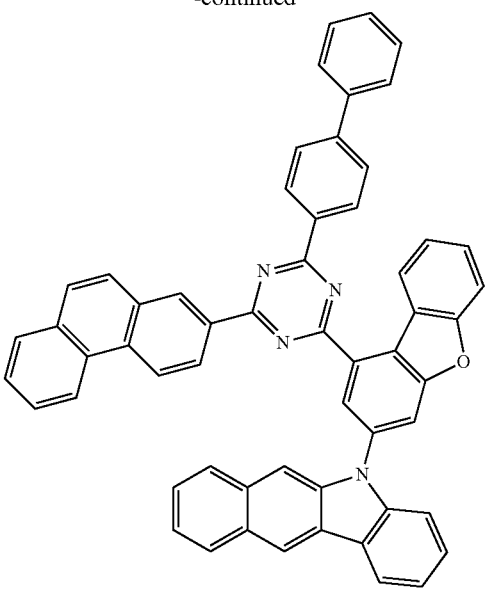
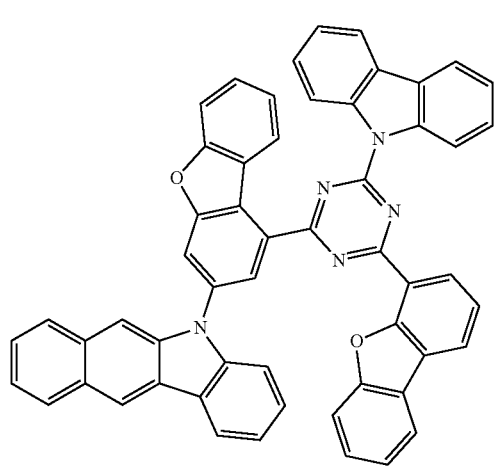
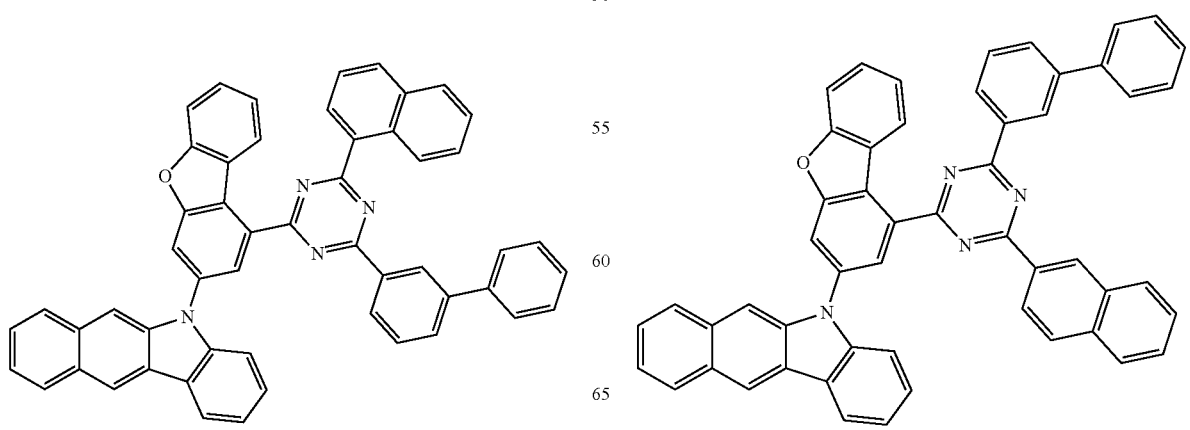

67
-continued
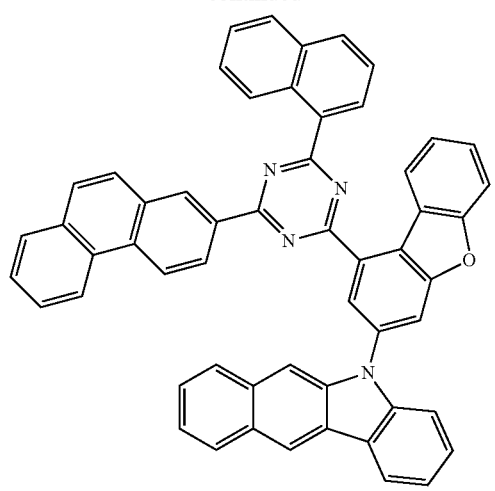
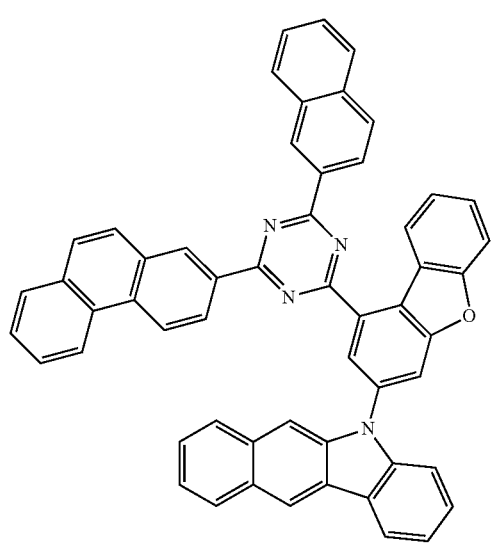
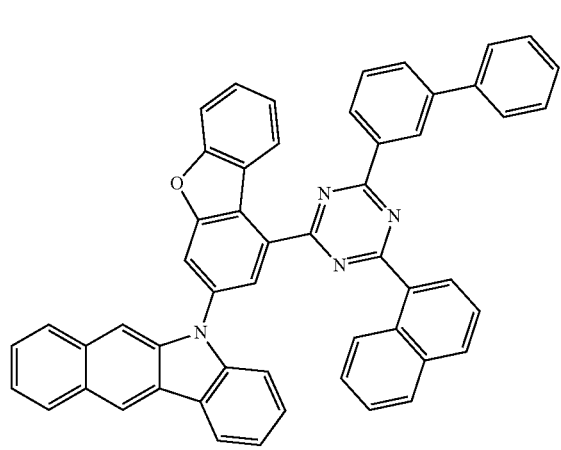
68
-continued
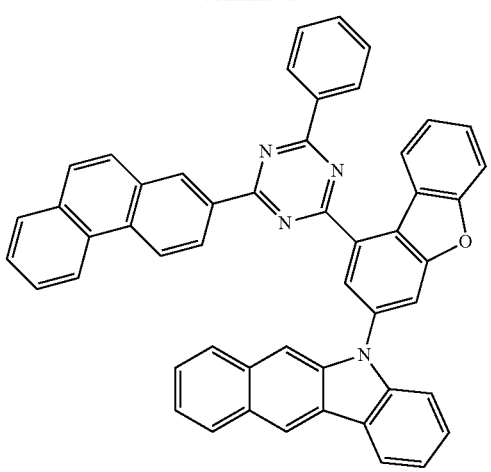
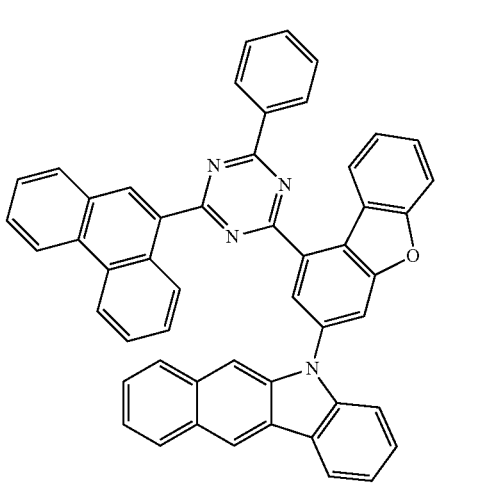
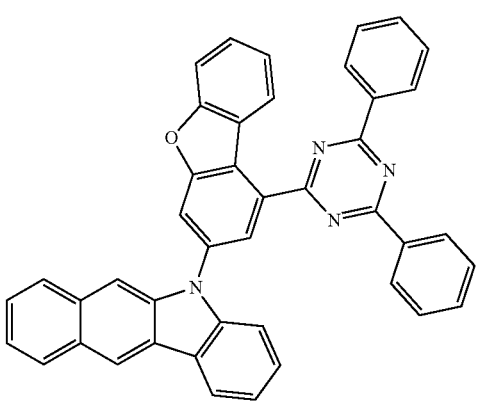

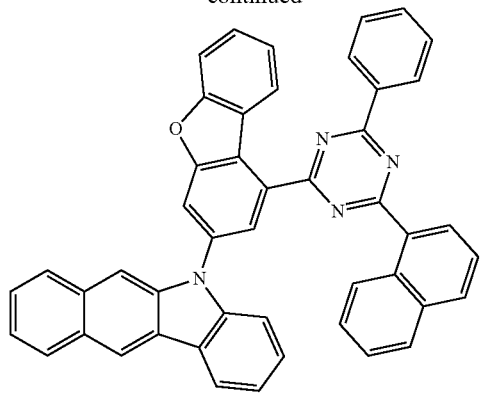
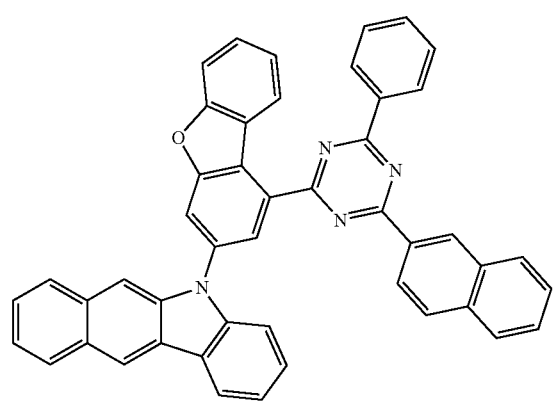
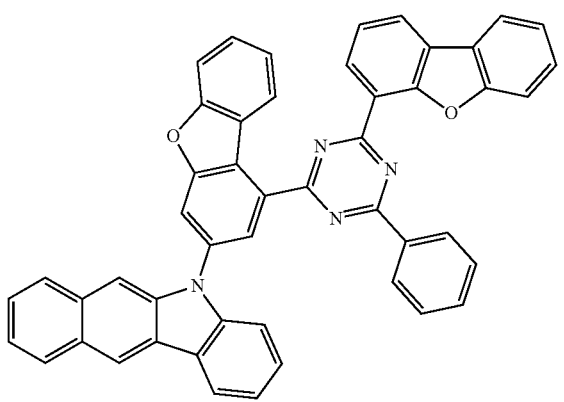
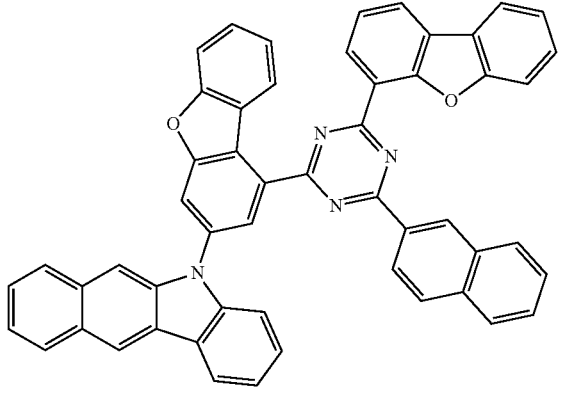
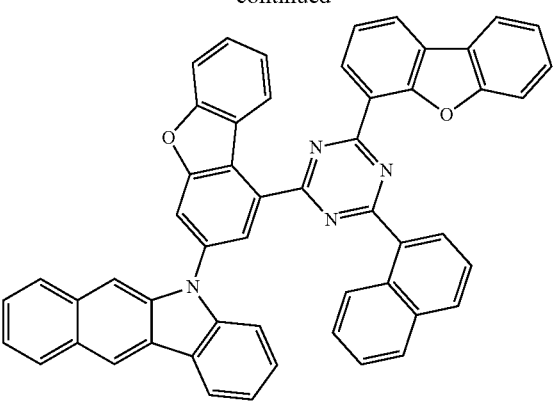
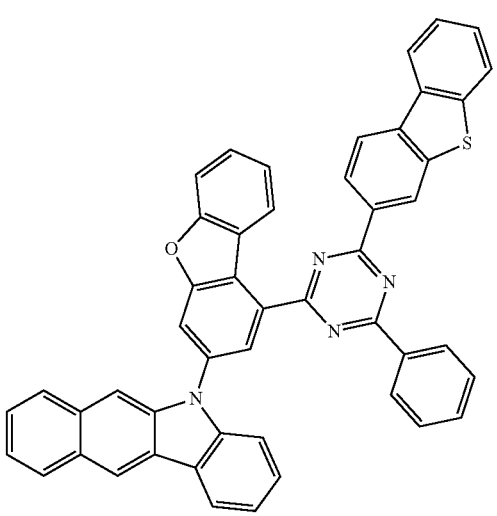
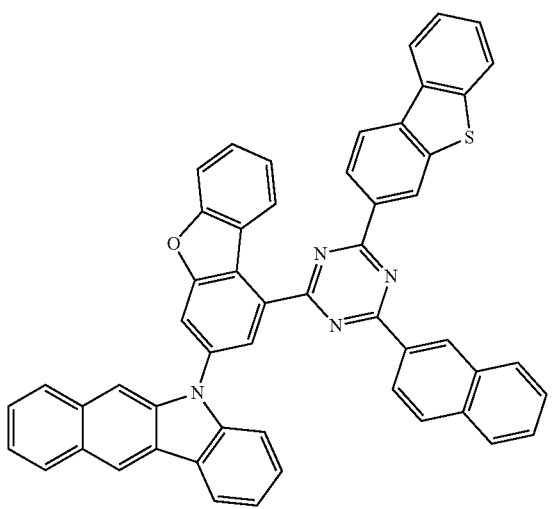

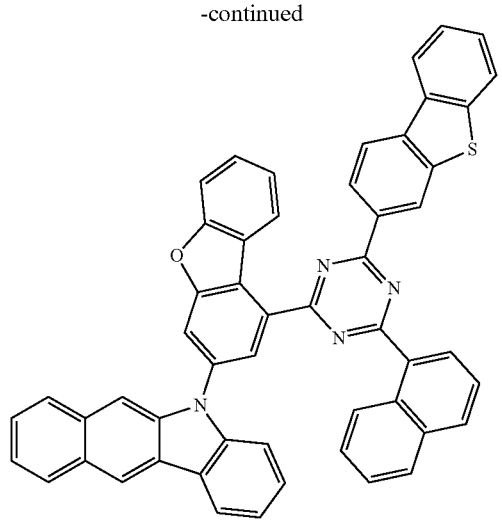
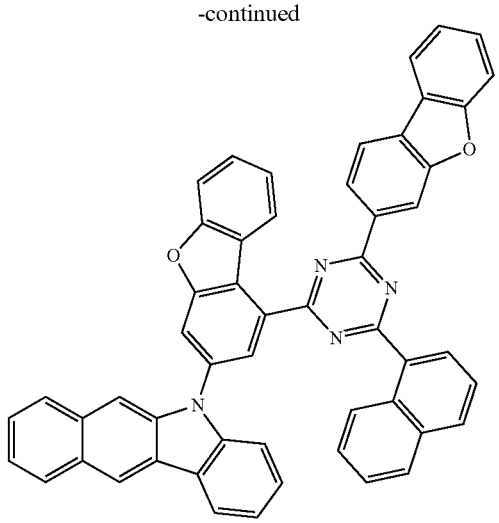
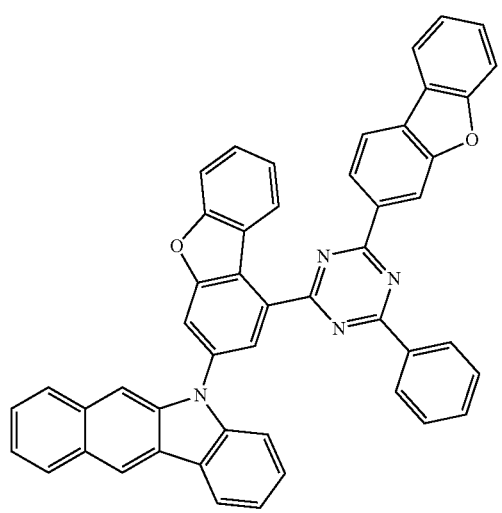
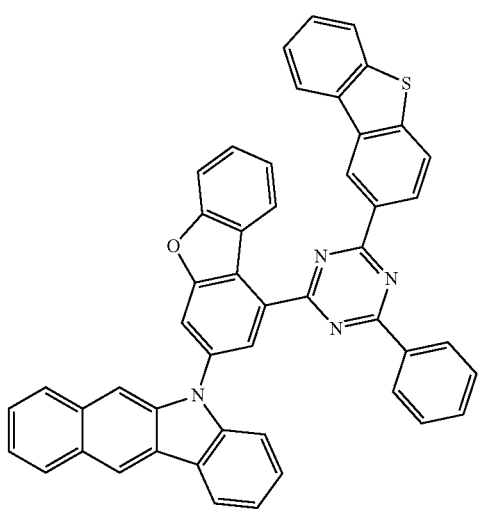
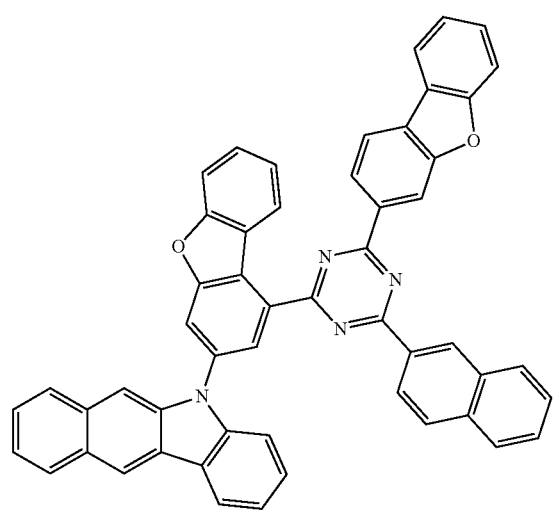
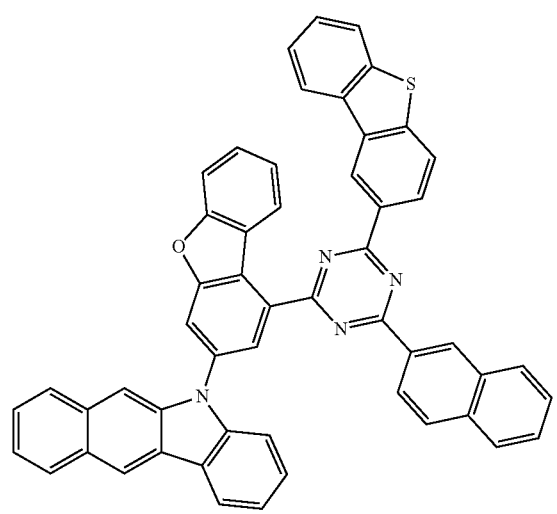

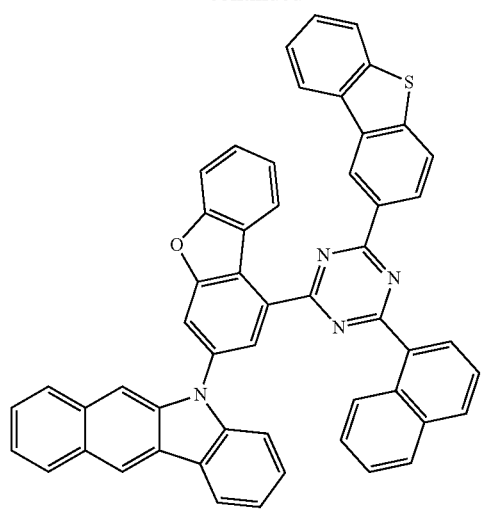
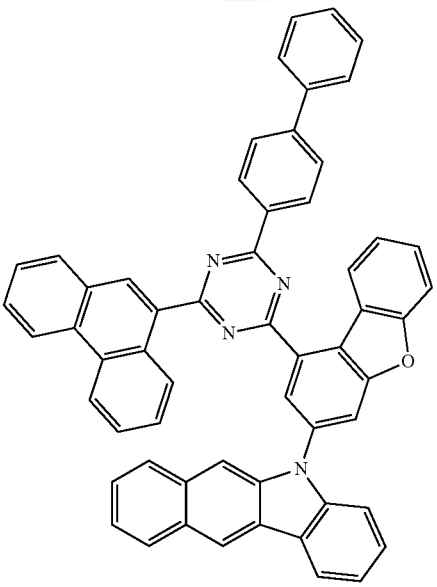
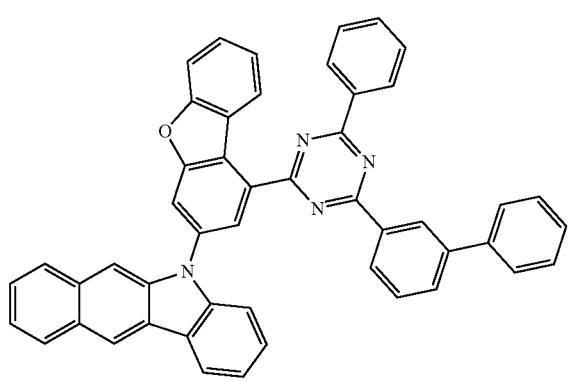
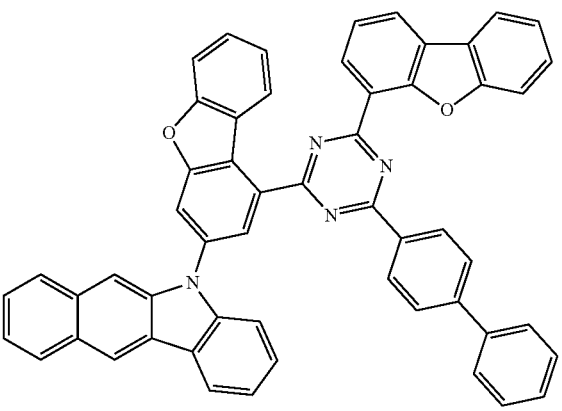
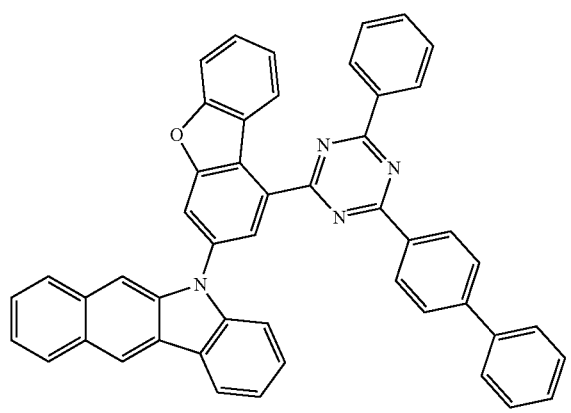
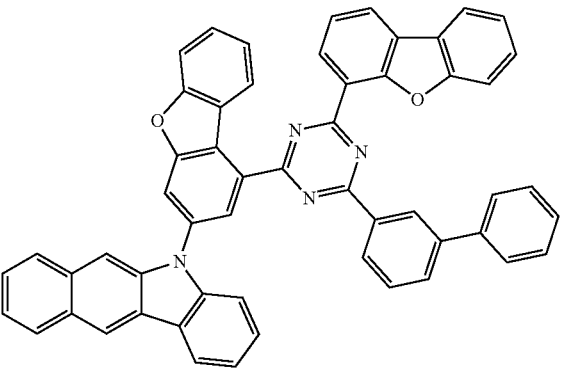

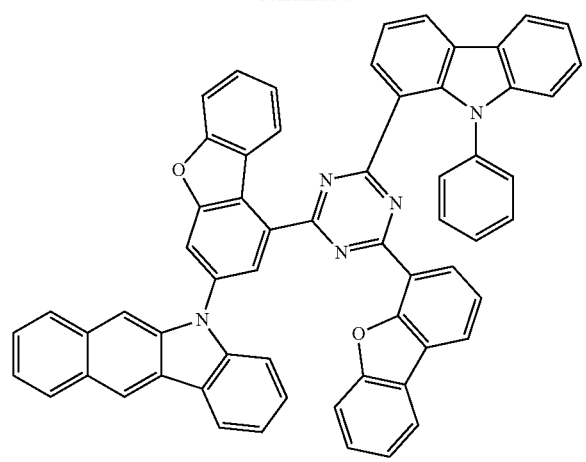
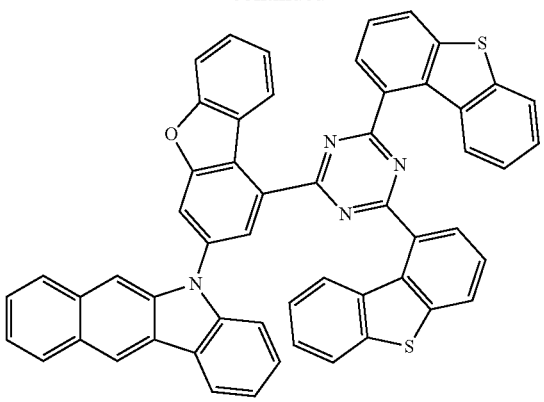
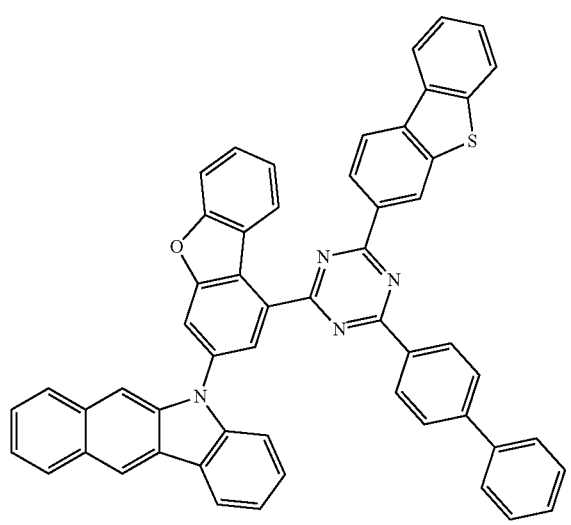
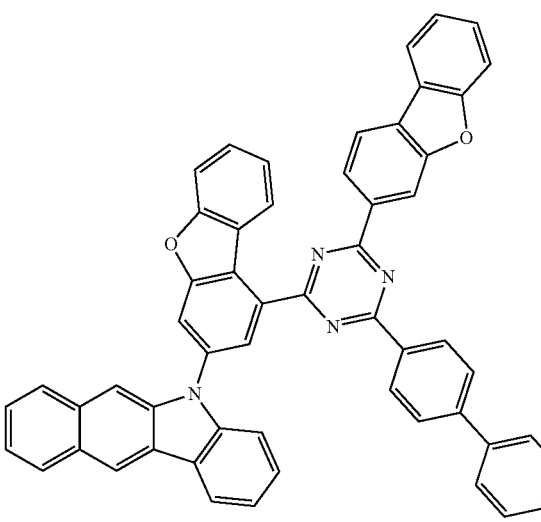
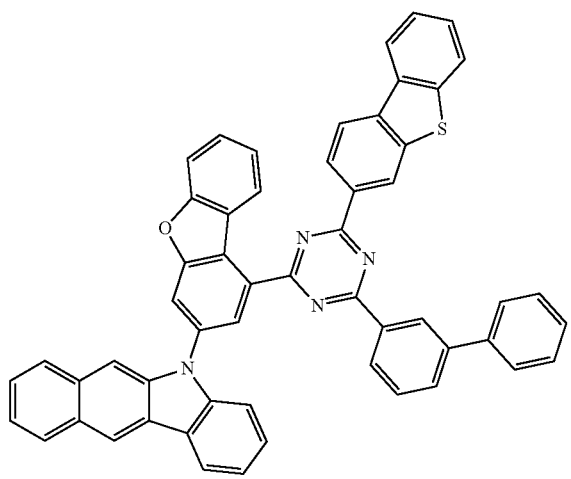
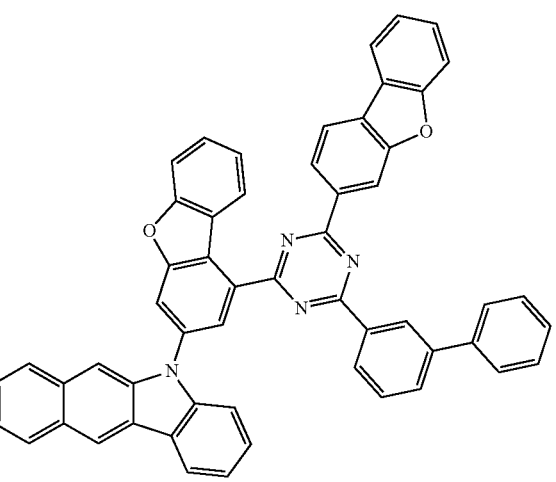

77
-continued
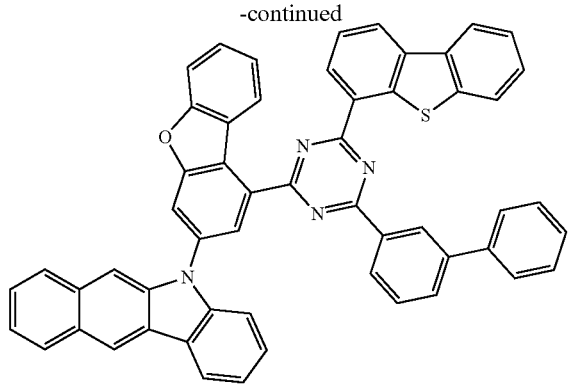
78
-continued
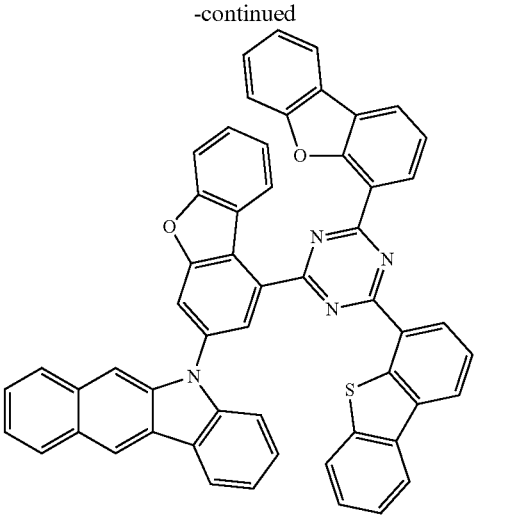
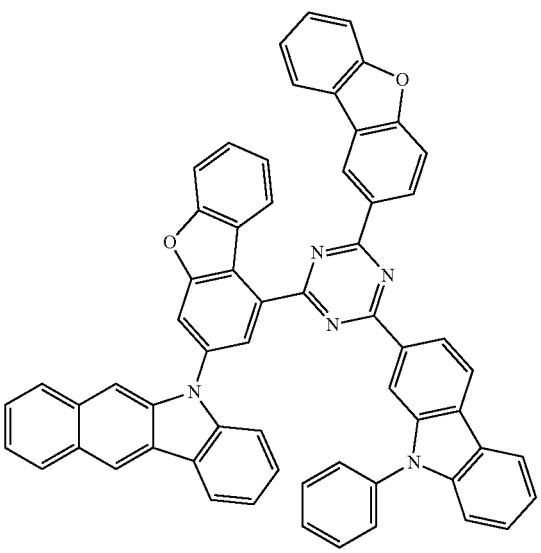
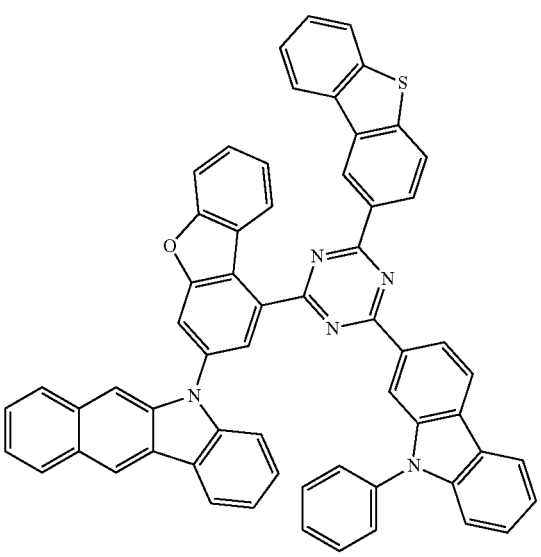

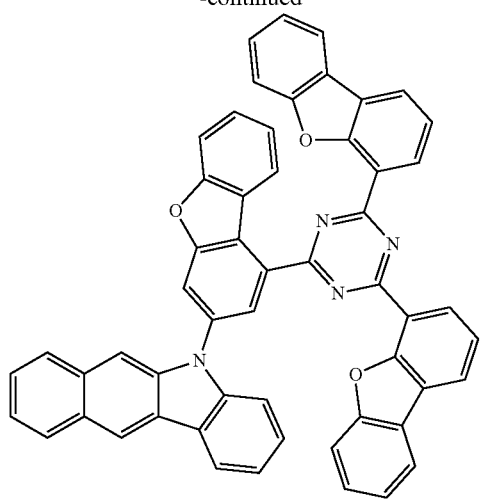
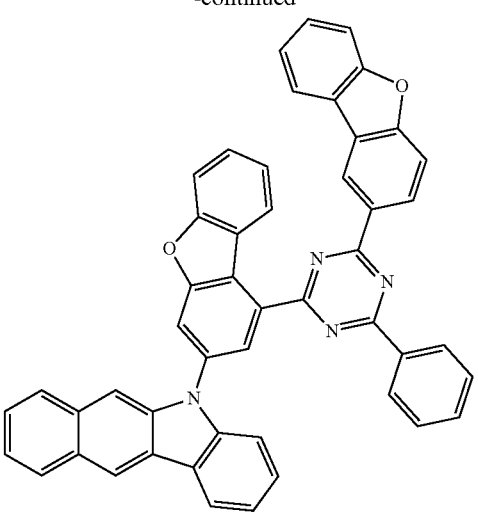
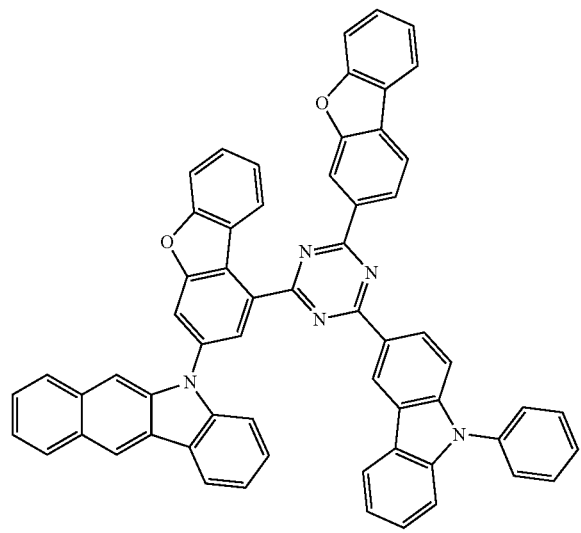
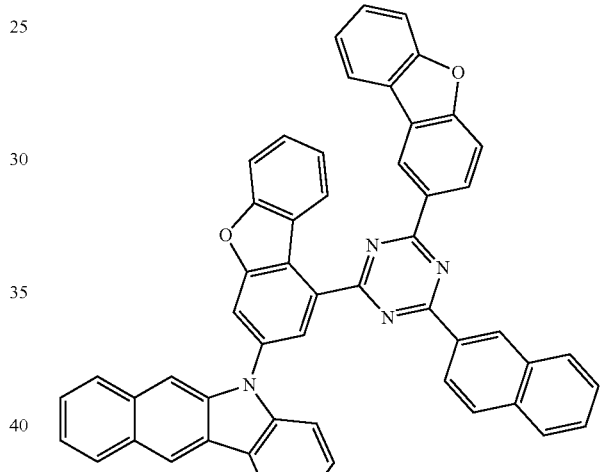
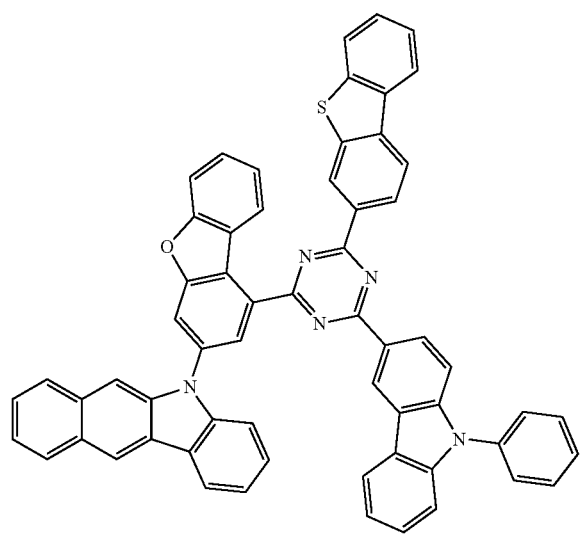
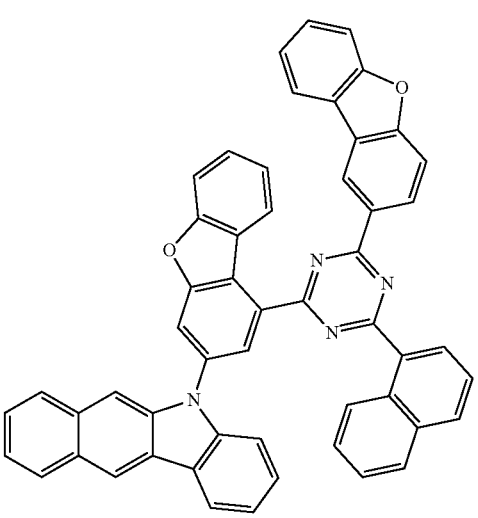

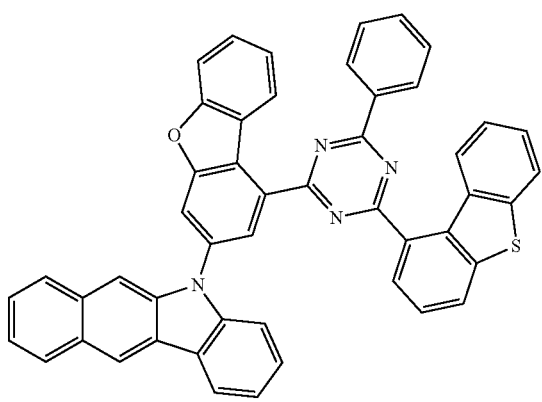
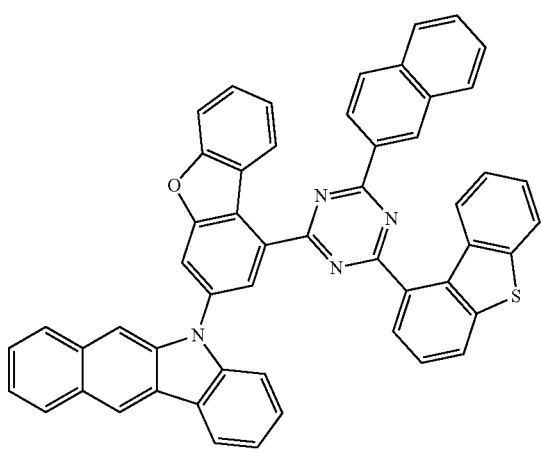
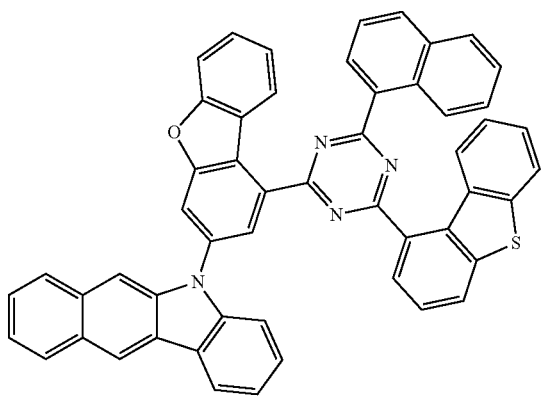
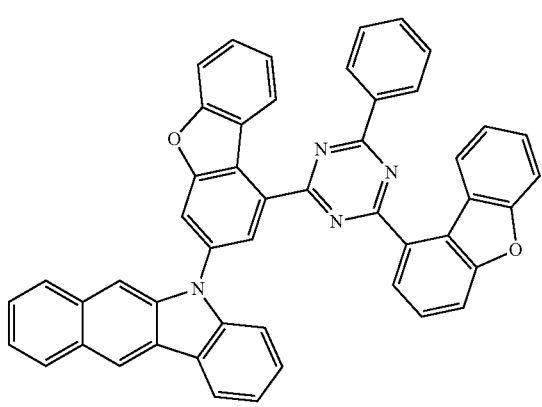
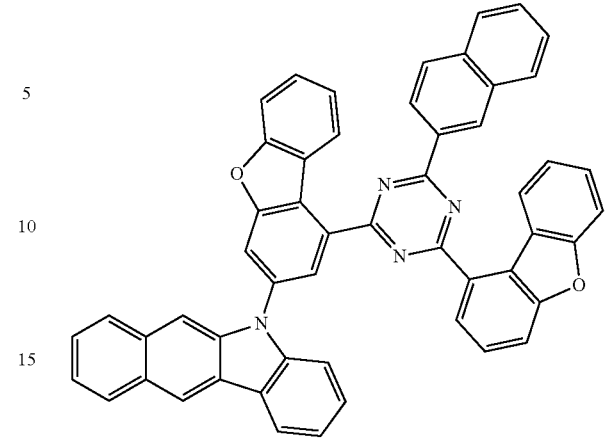
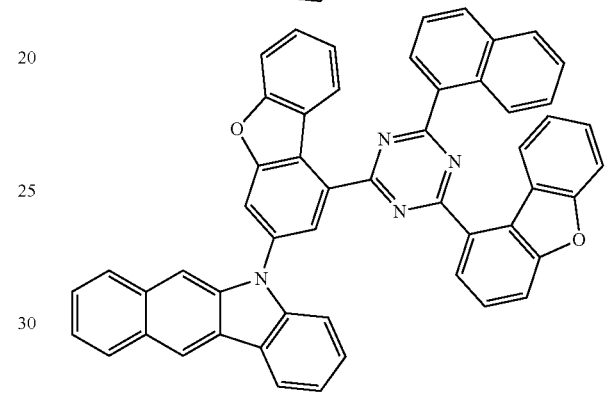
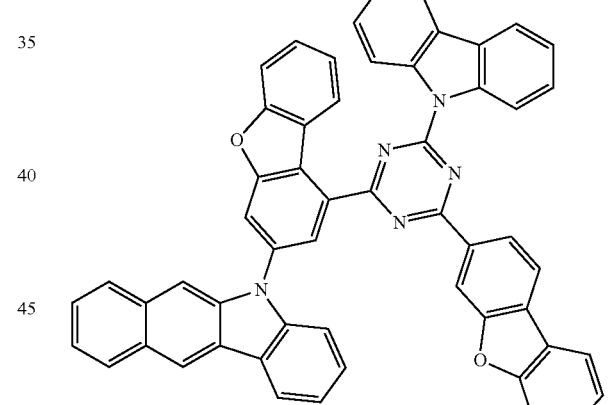
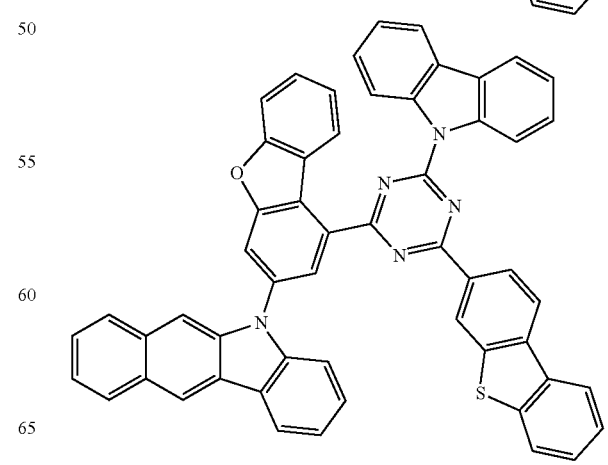

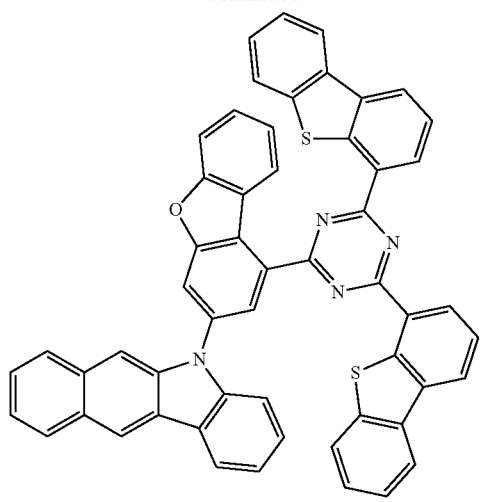
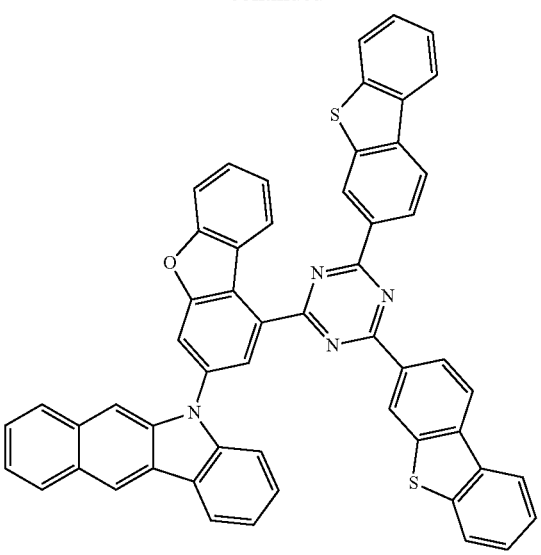
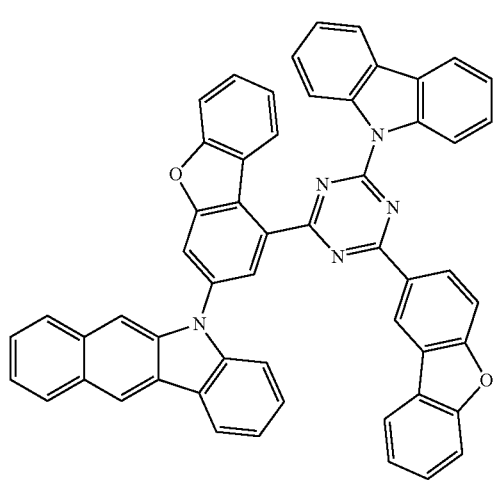
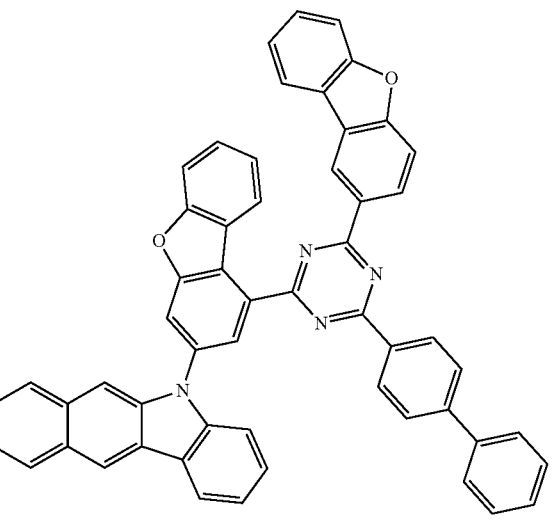
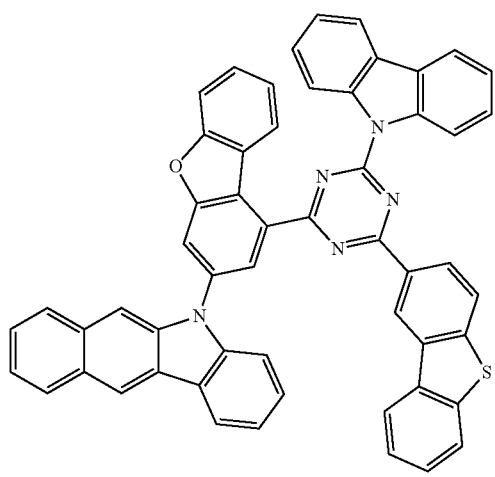
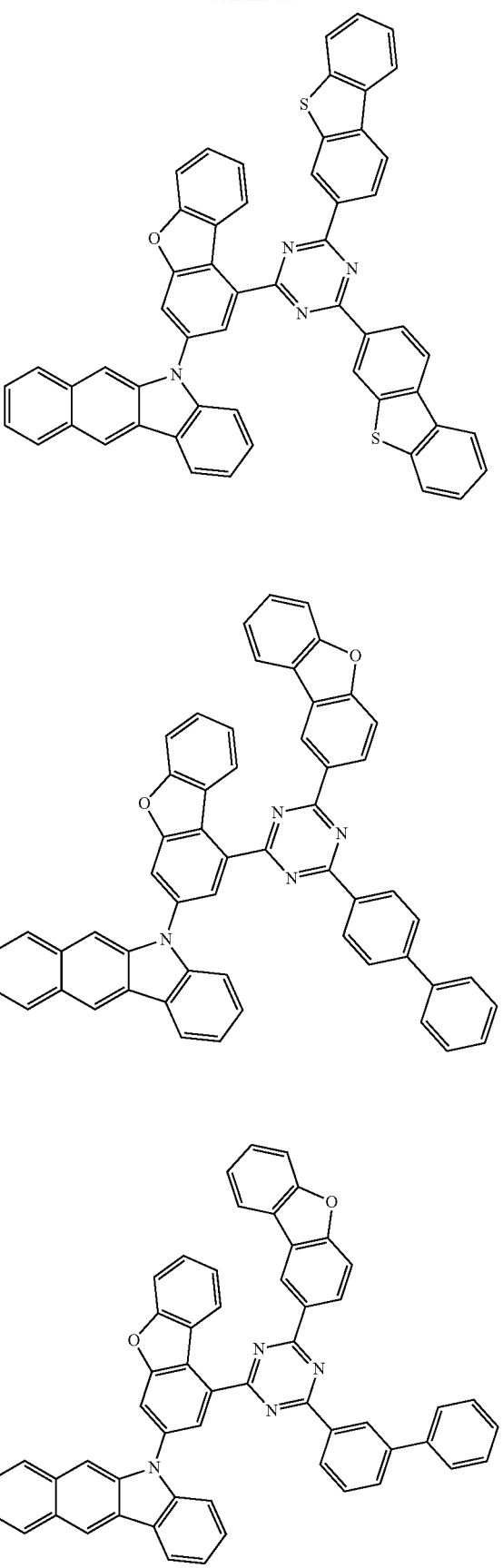

85
-continued
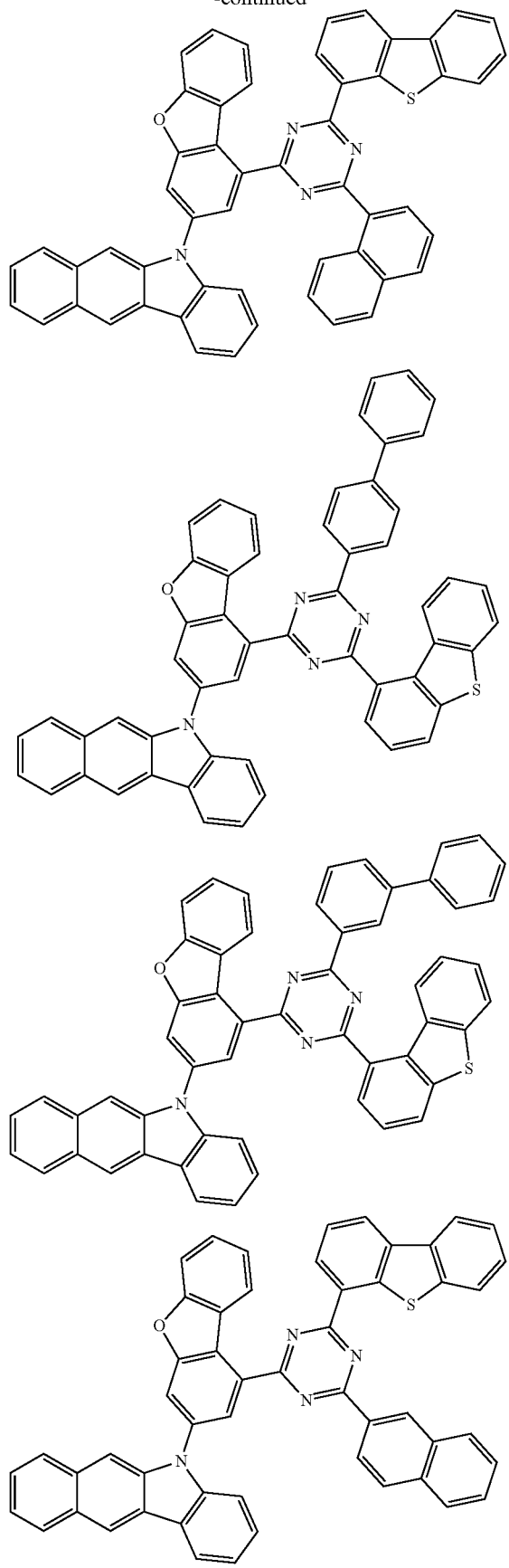
86
-continued
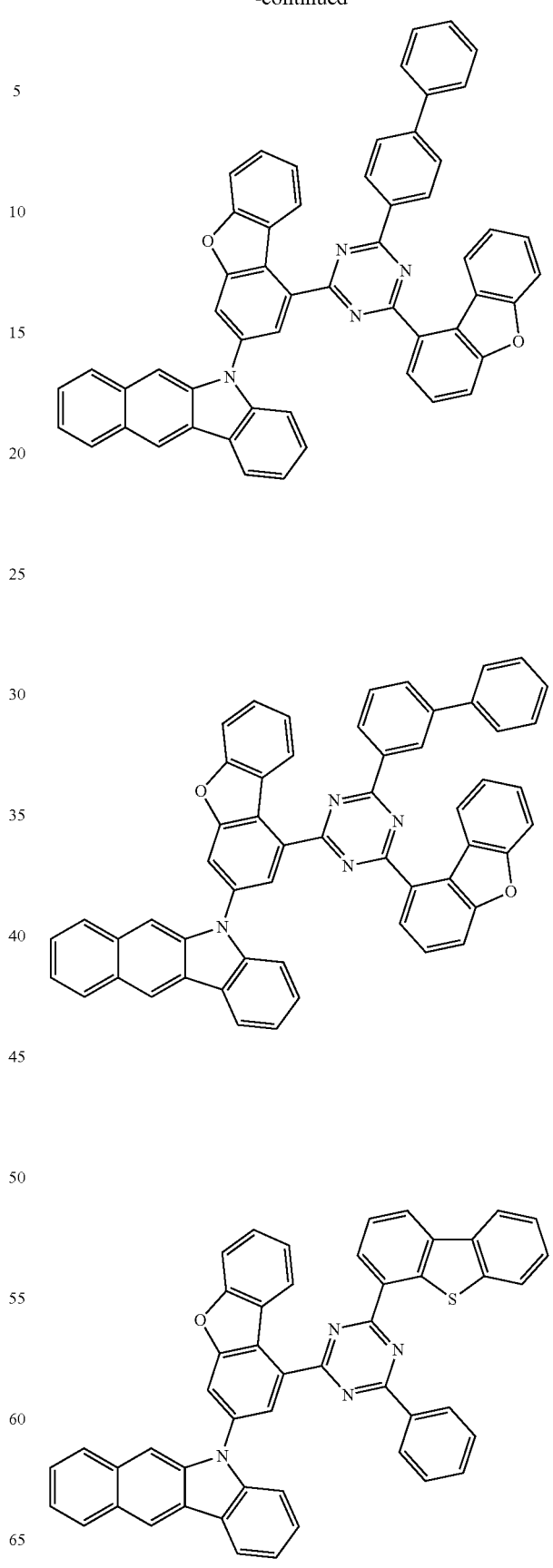

87
-continued
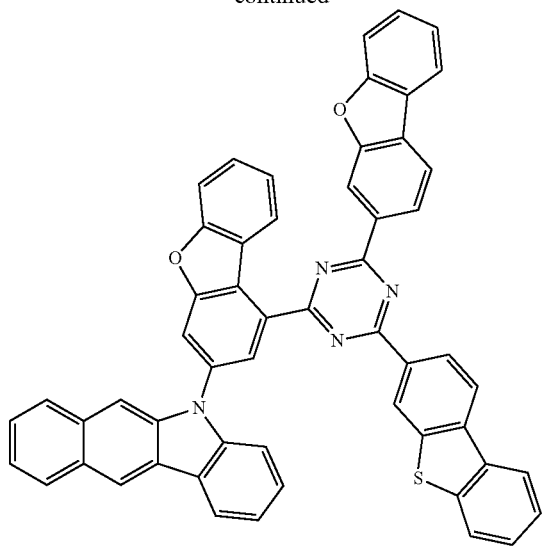
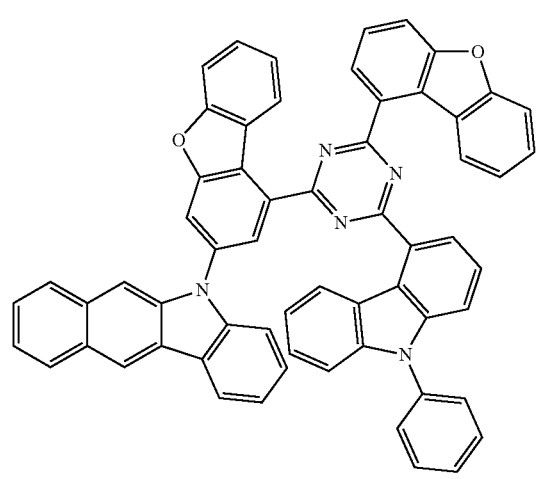
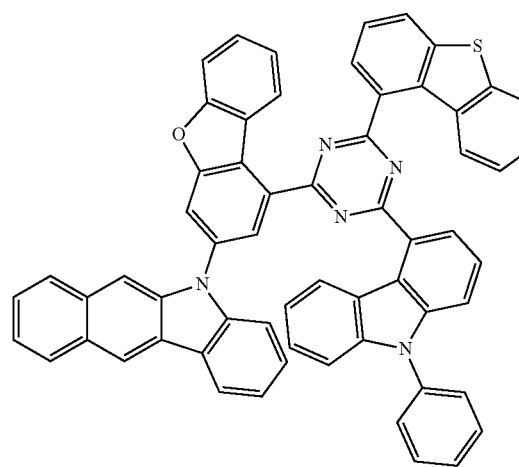
88
-continued
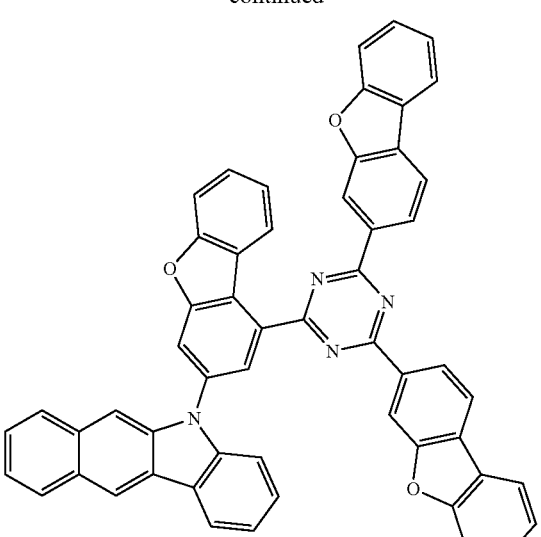
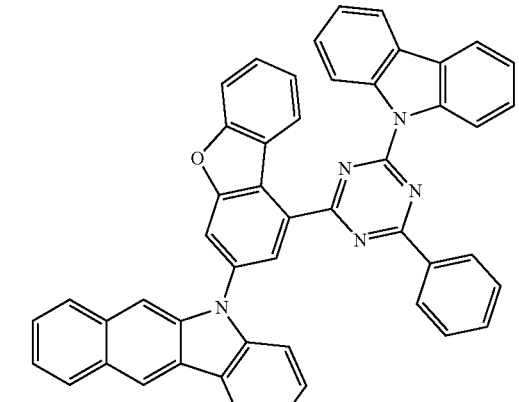
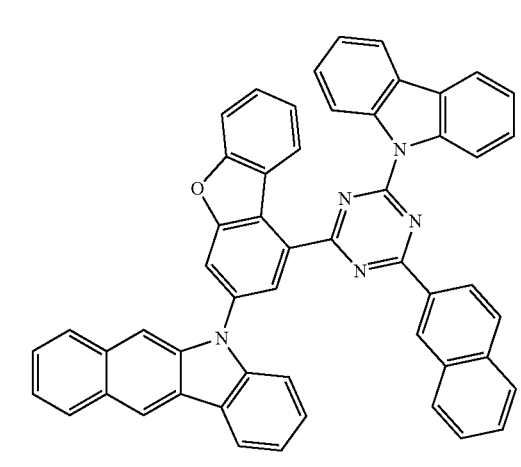

-continued
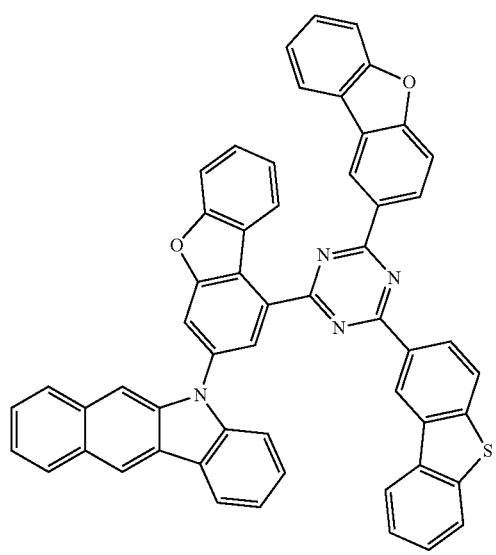
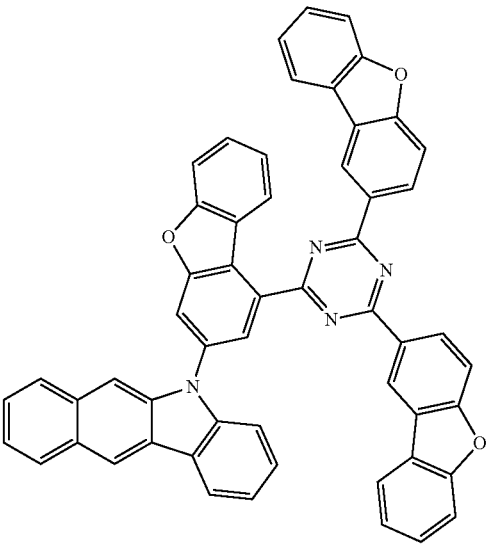
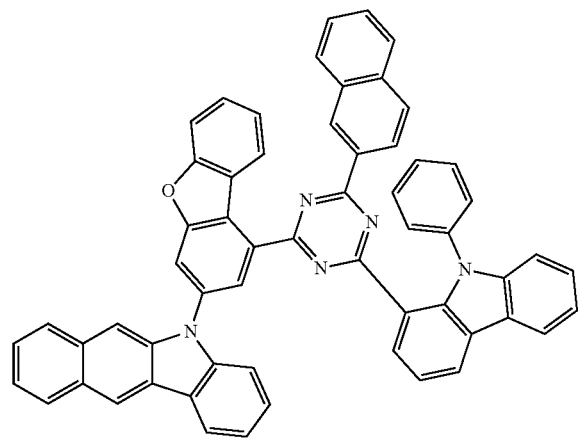
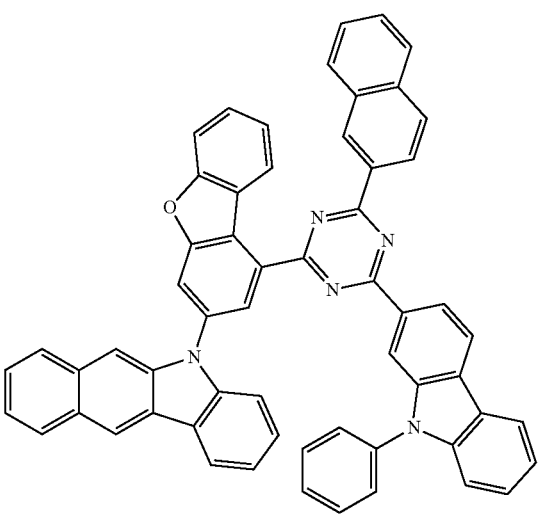

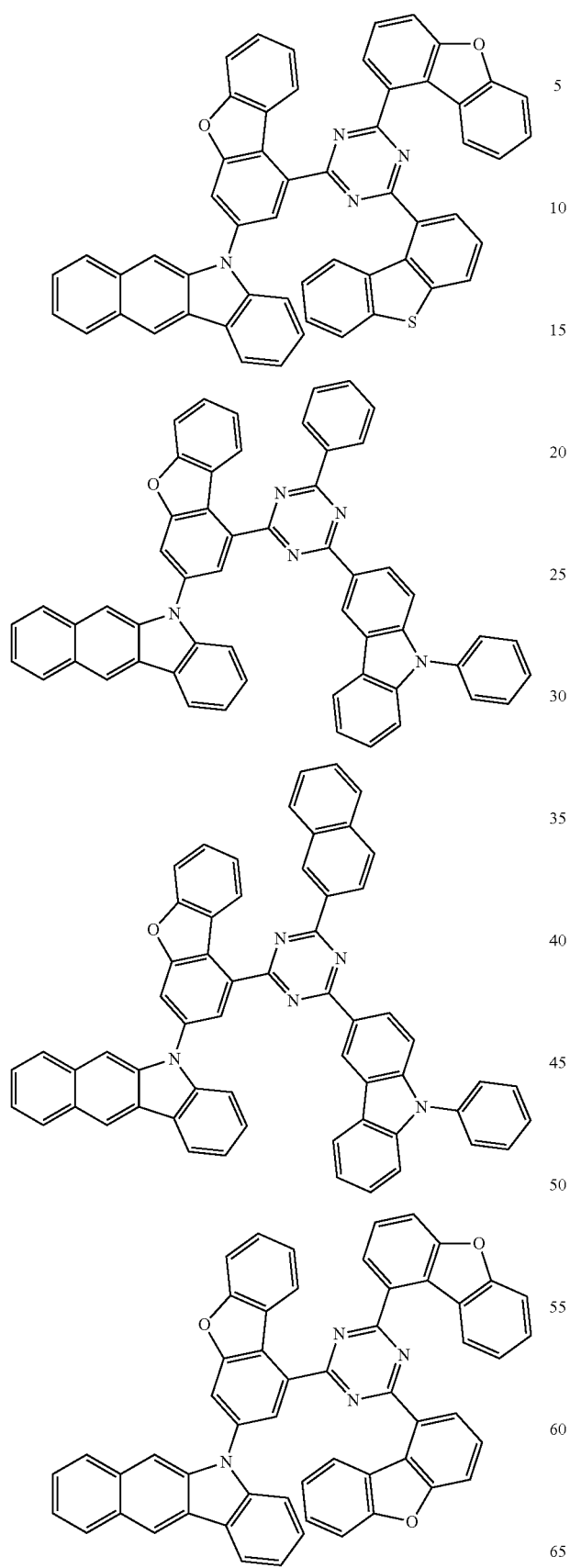
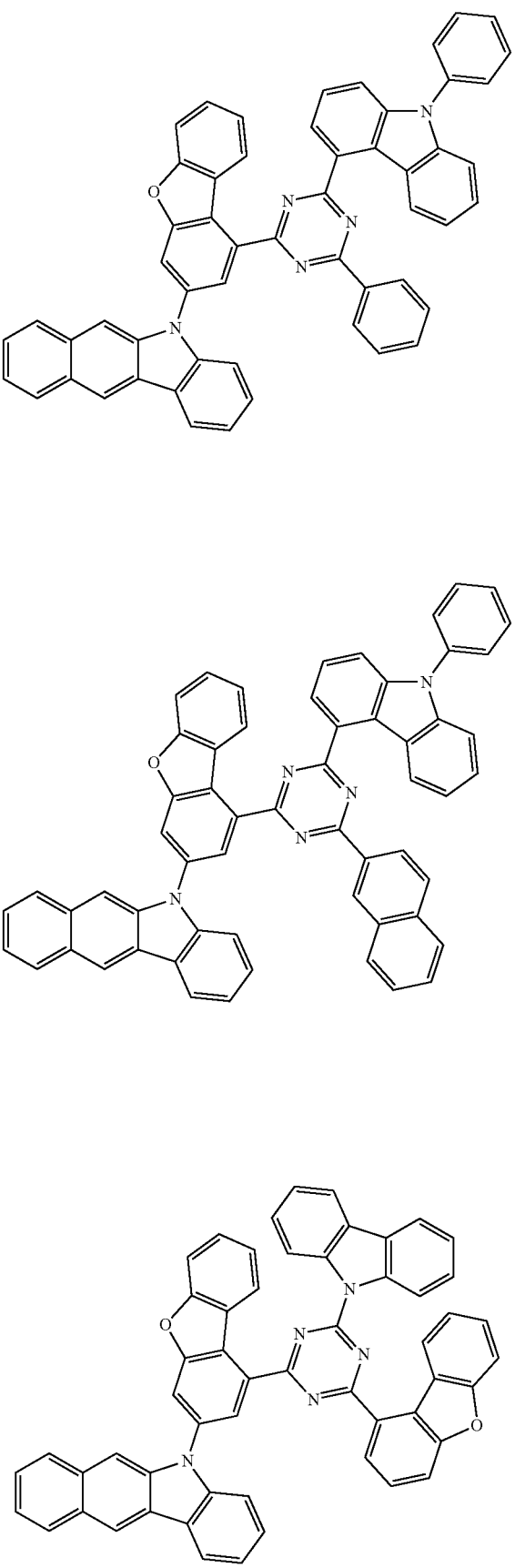

93
-continued
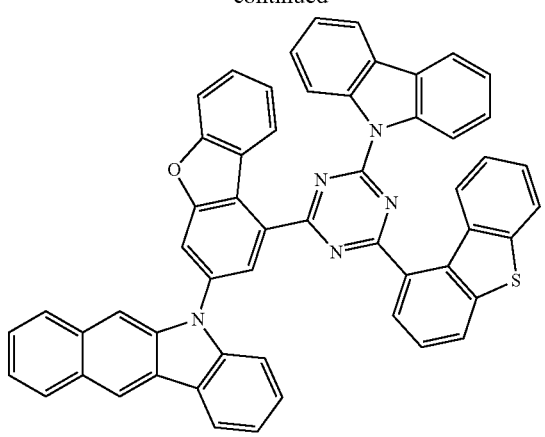
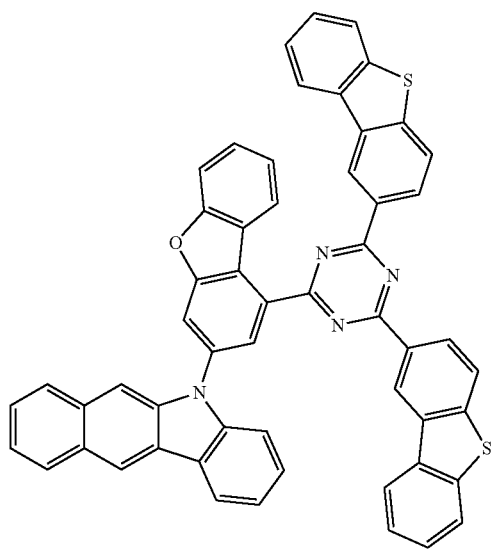
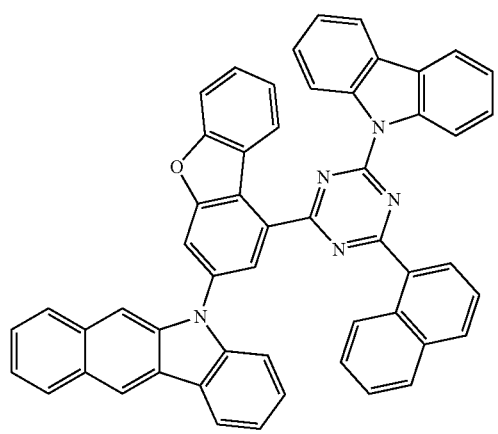
94
-continued
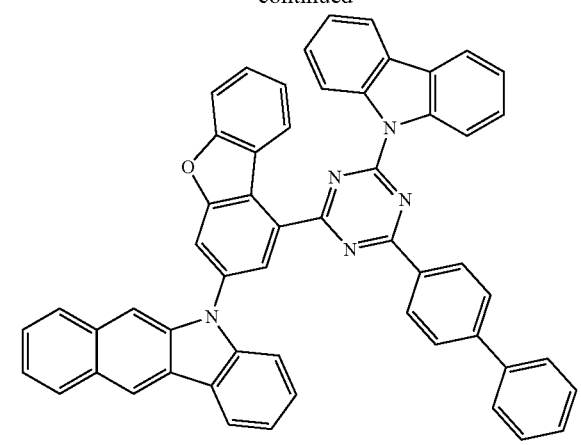
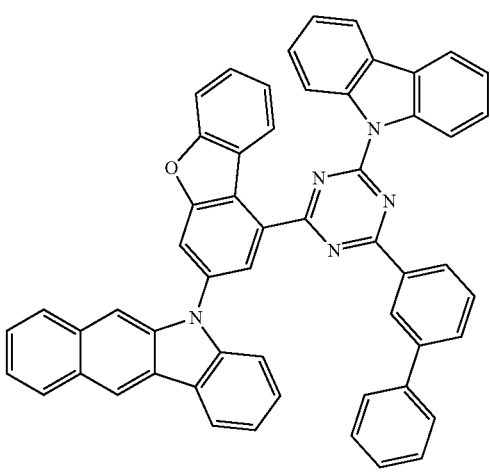
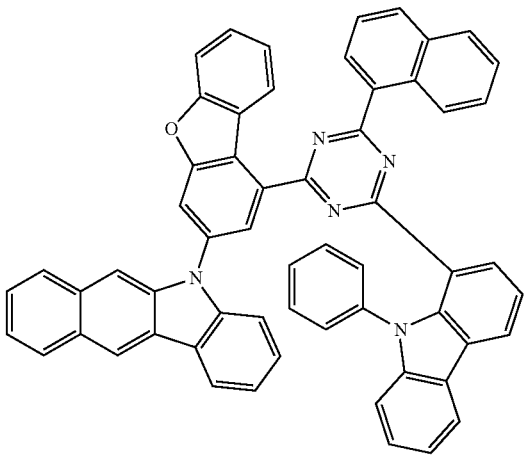

95
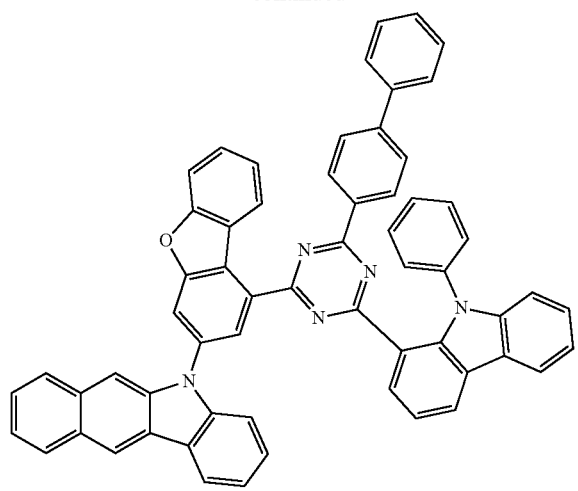
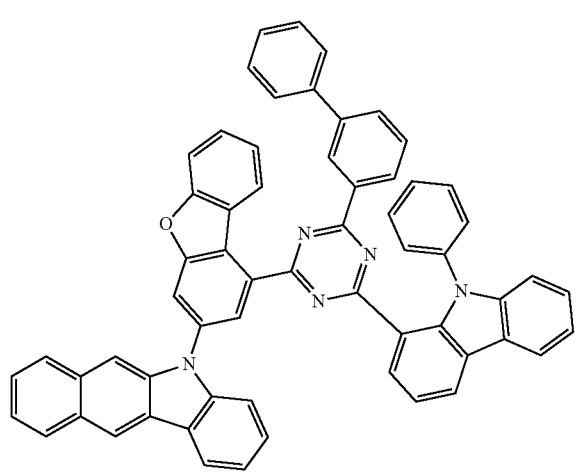
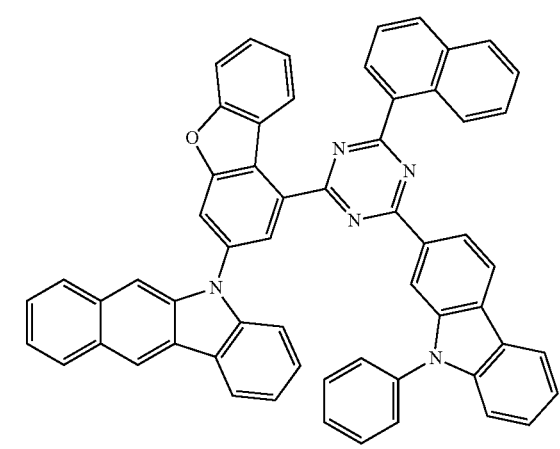
96
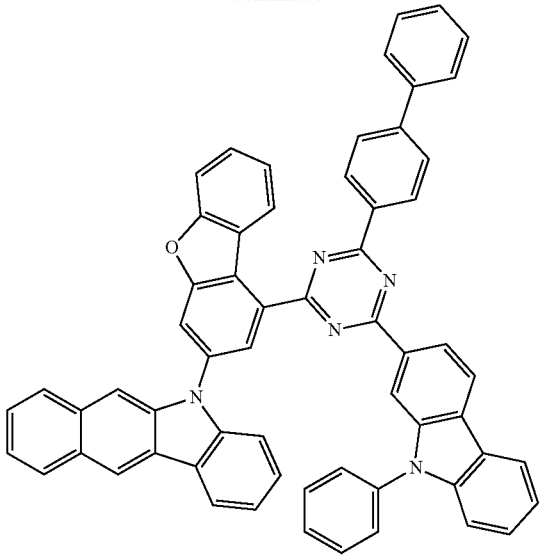
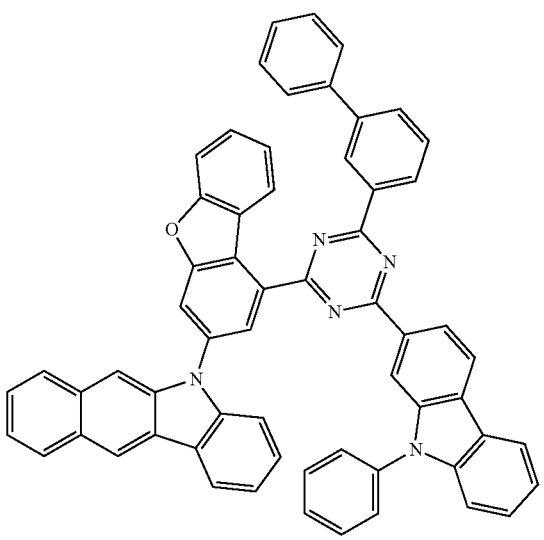
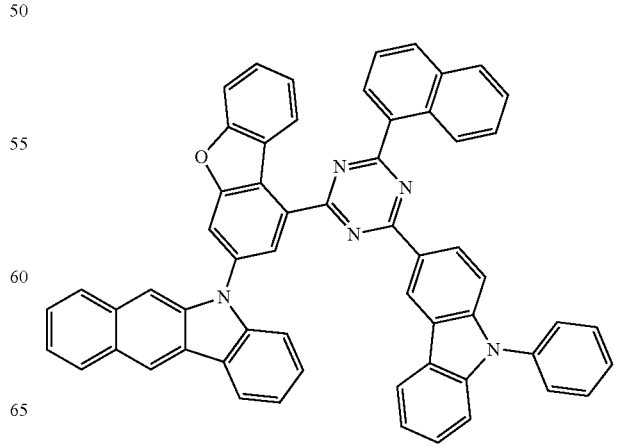

97
-continued
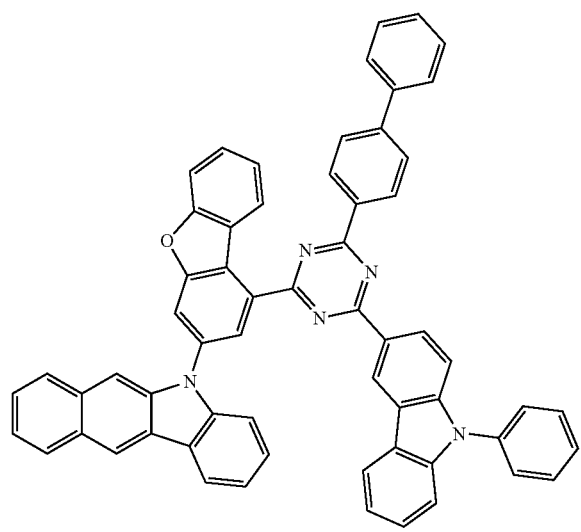
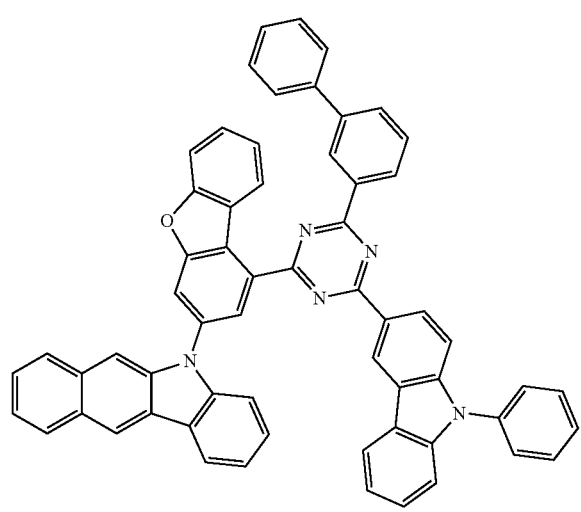
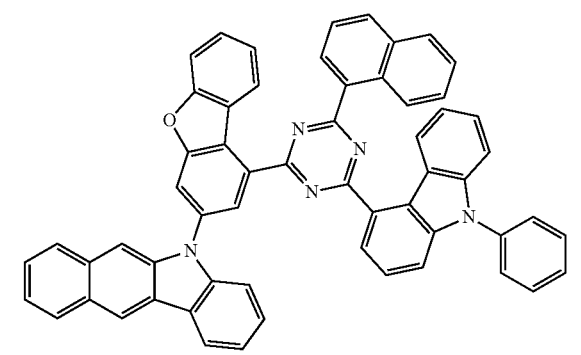
98
-continued
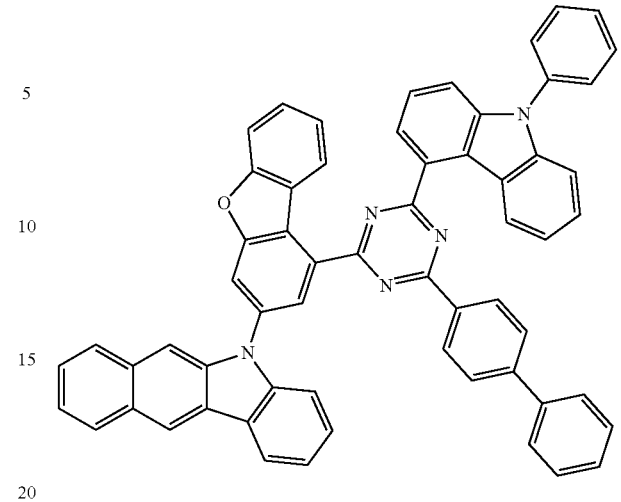
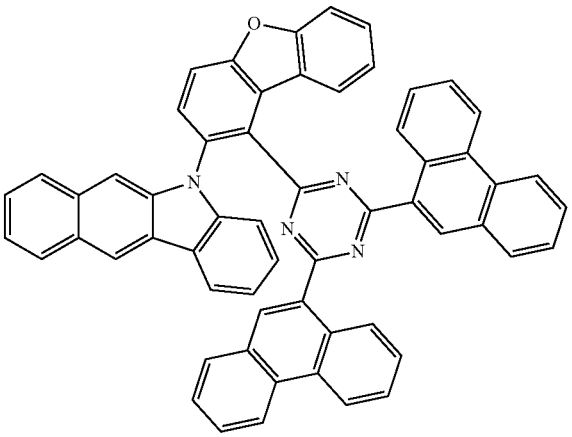

99
-continued
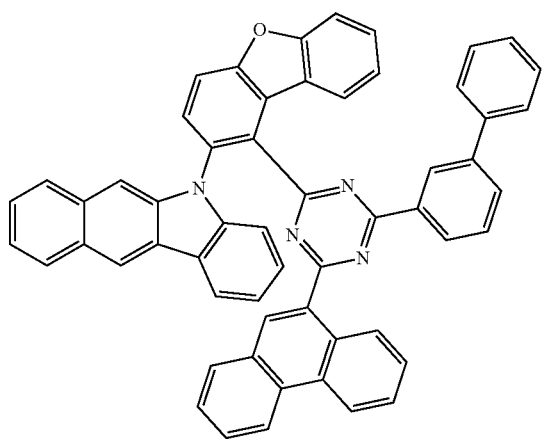
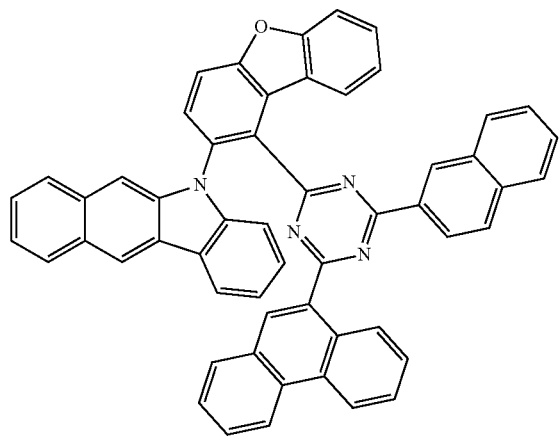
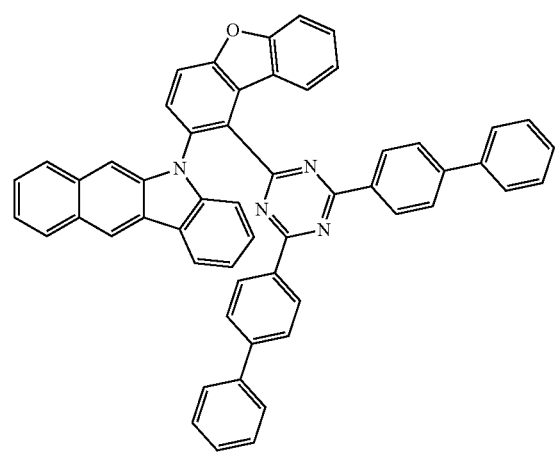
100
-continued
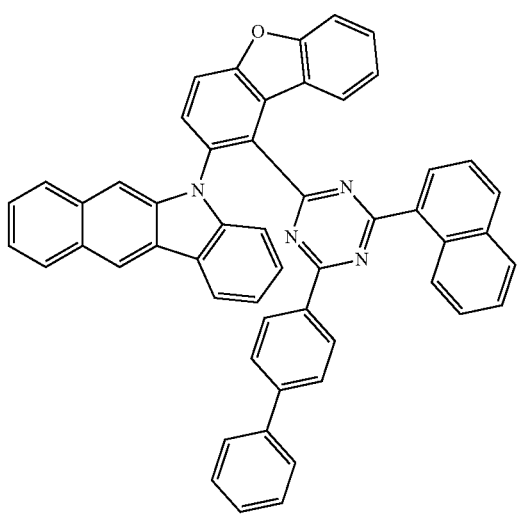
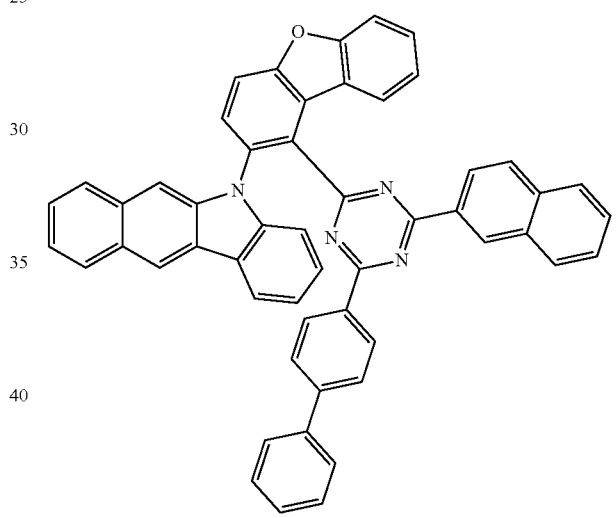
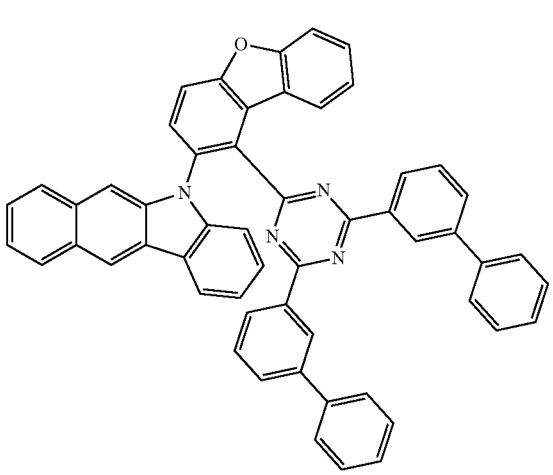

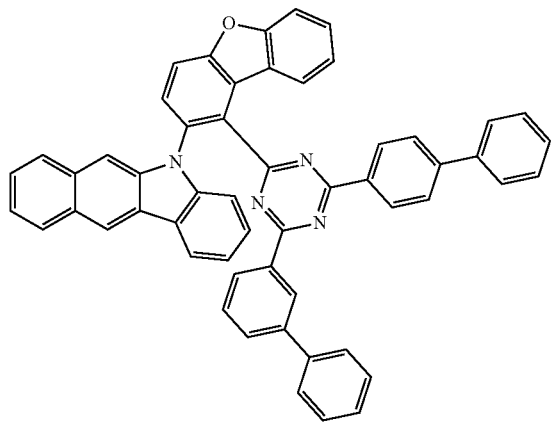
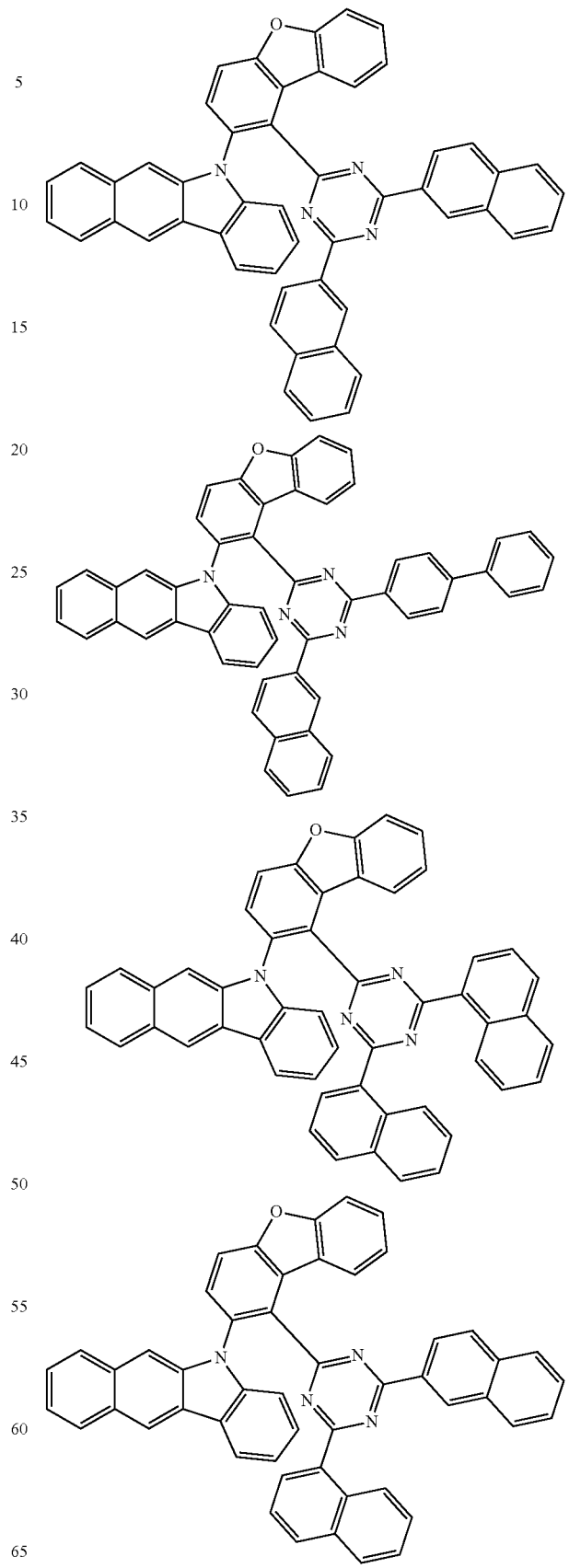

103
-continued
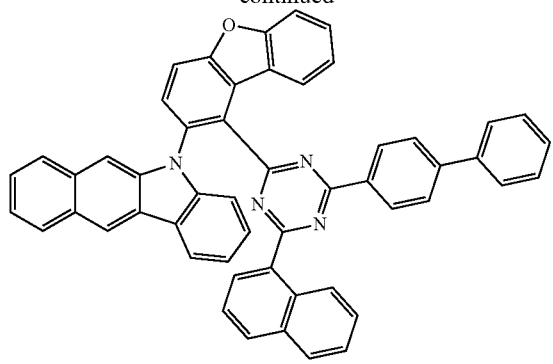
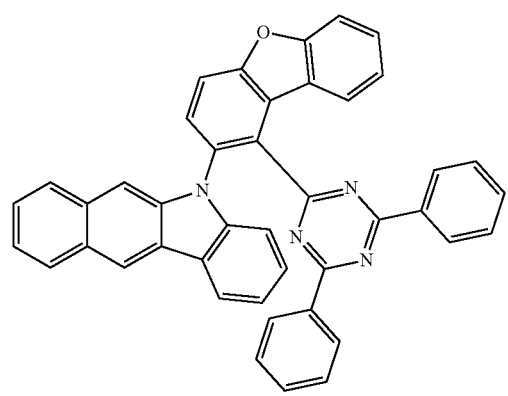
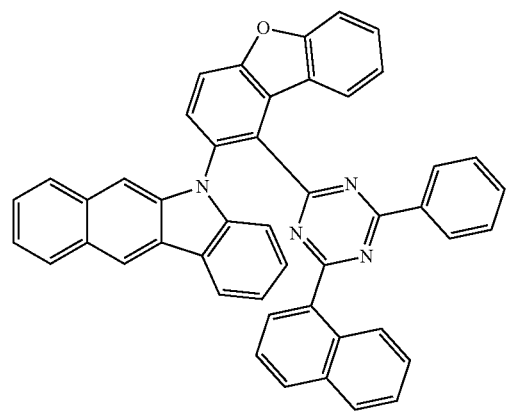
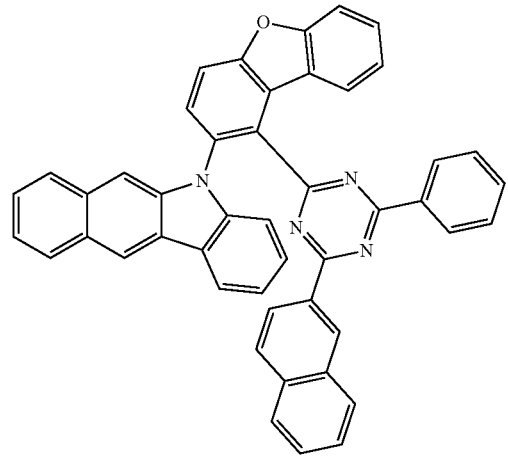
104
-continued
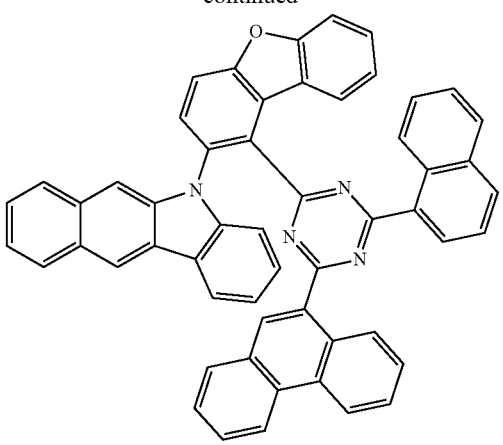
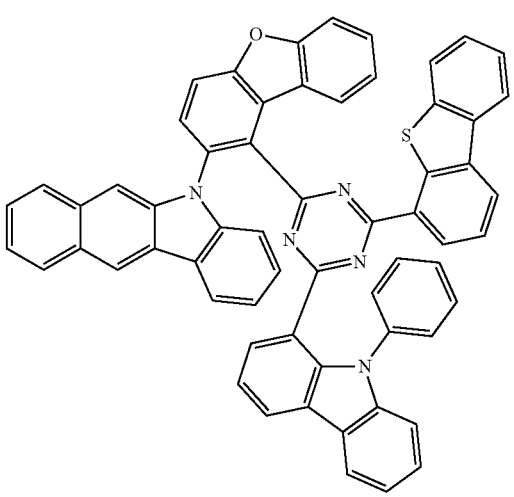
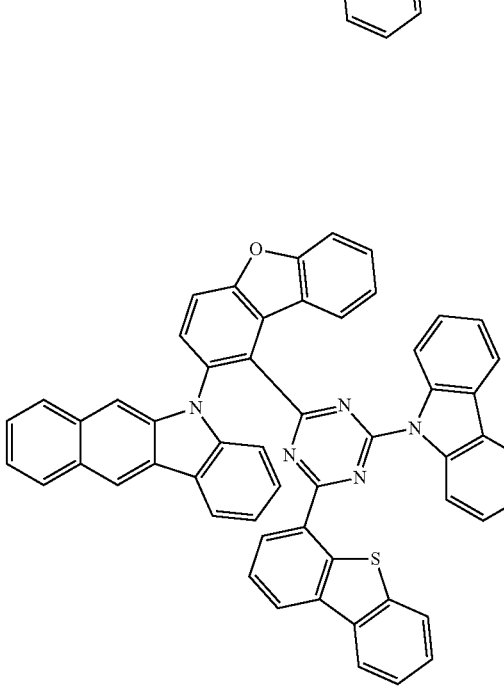

105
-continued
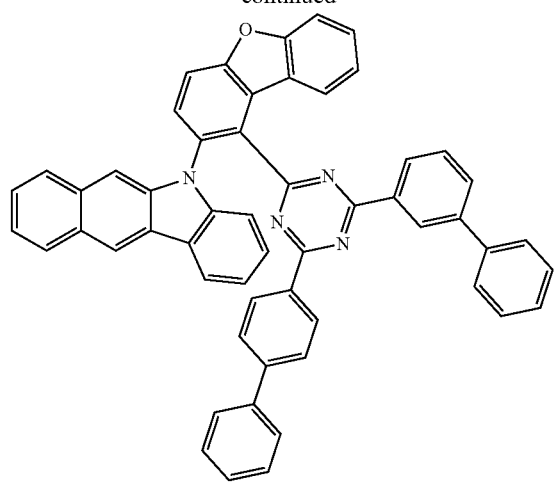
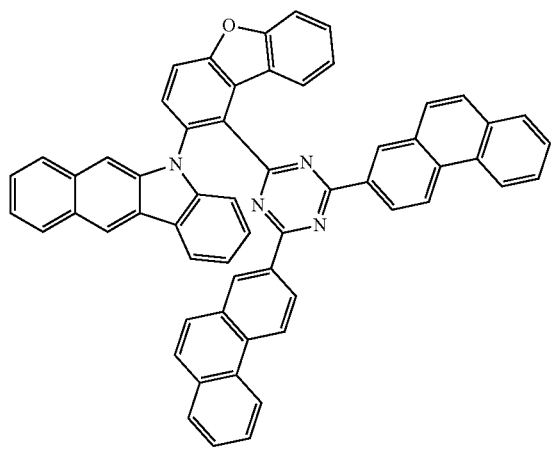
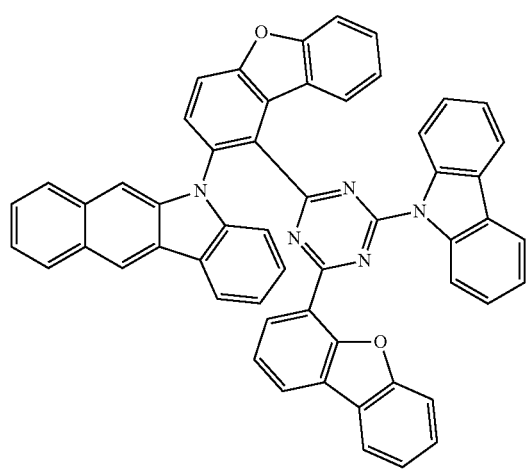
106
-continued
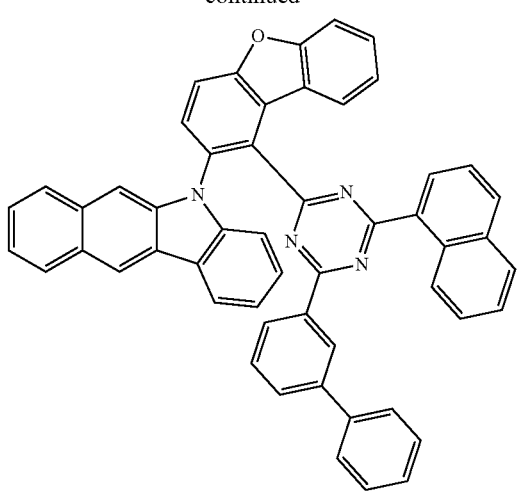
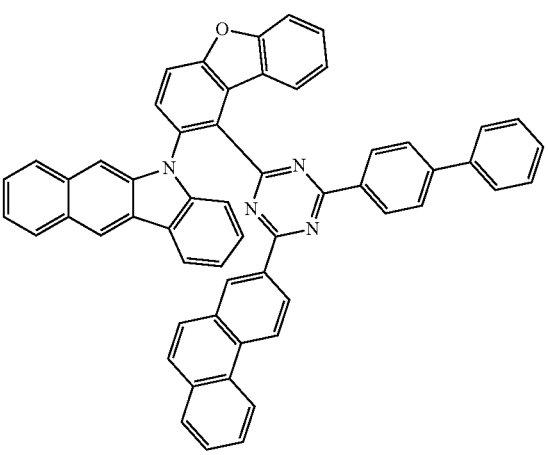
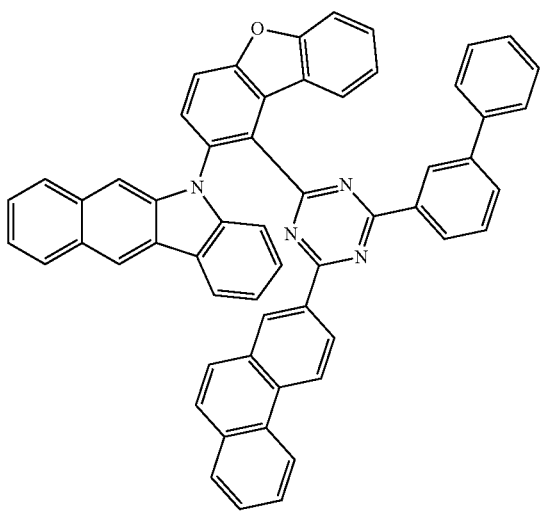

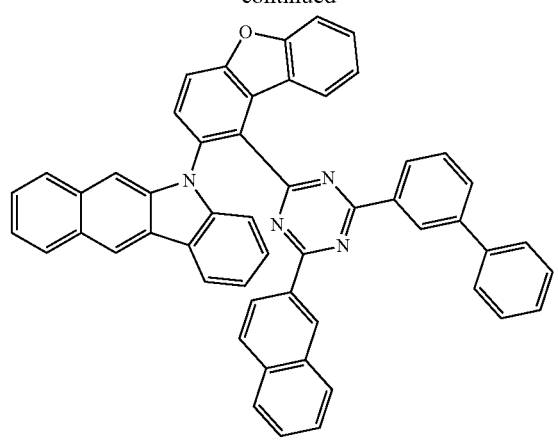
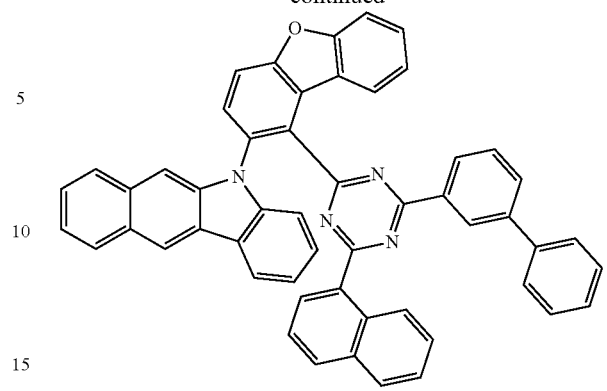
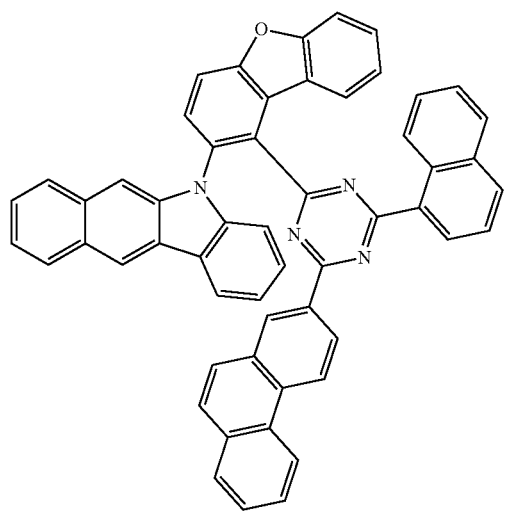
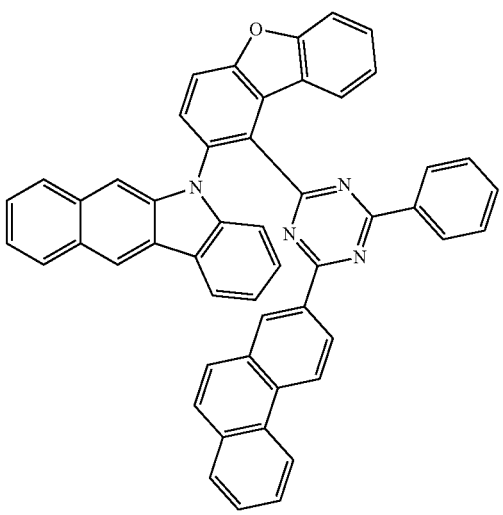
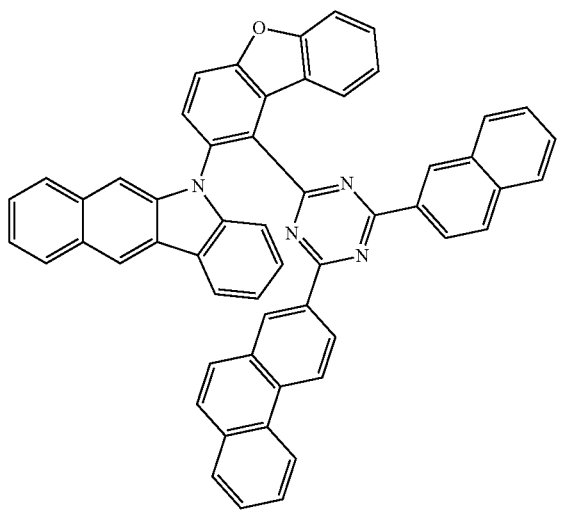
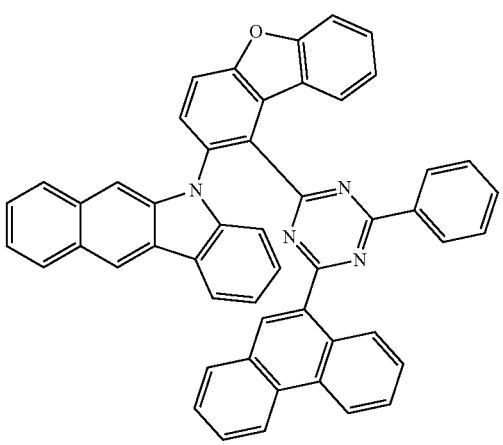

109
-continued
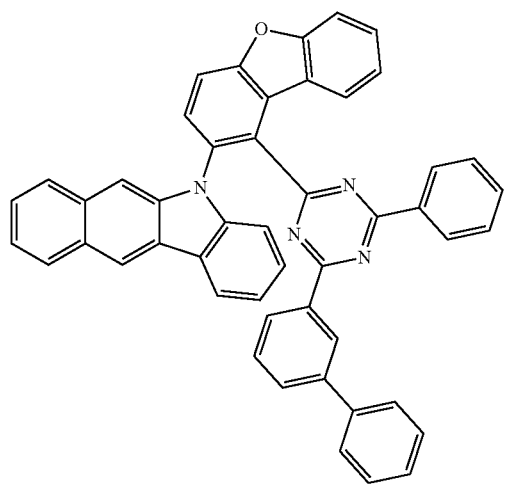
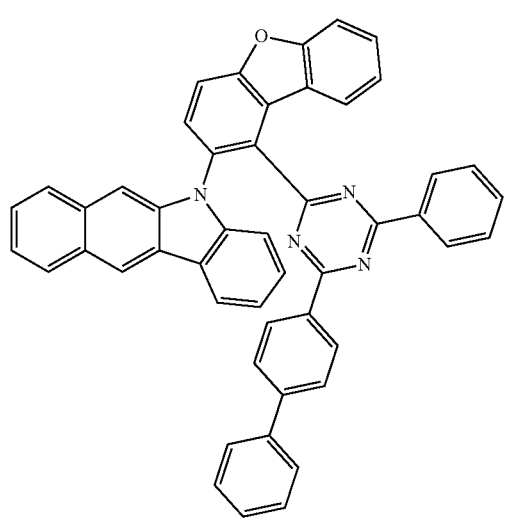
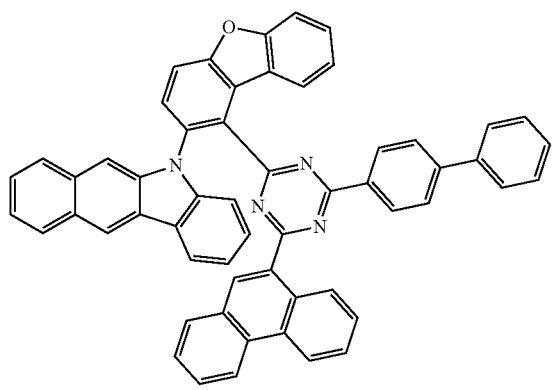
110
-continued
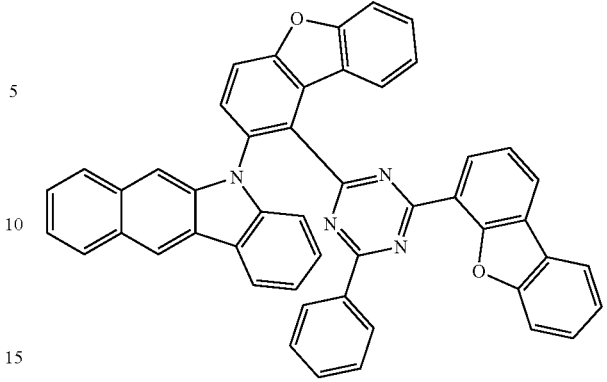
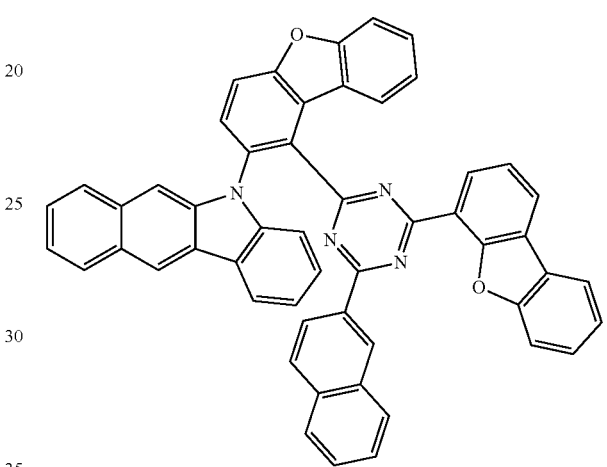
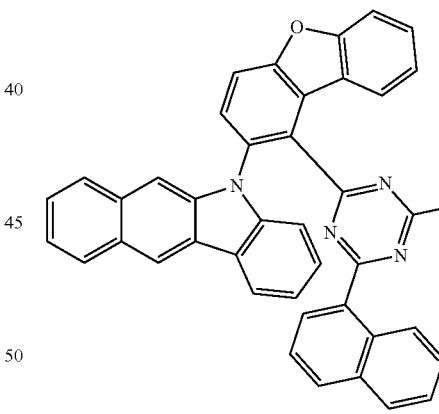
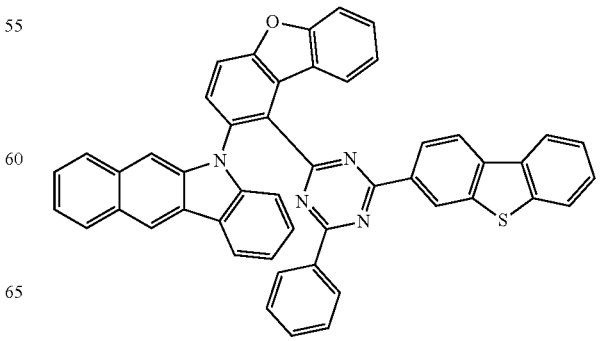

| 111 | 112 |
|---|---|
| -continued | -continued |
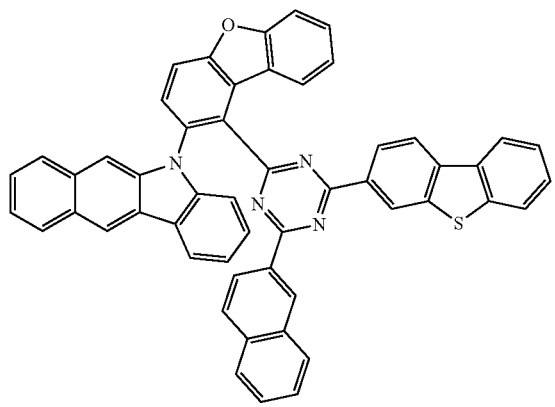
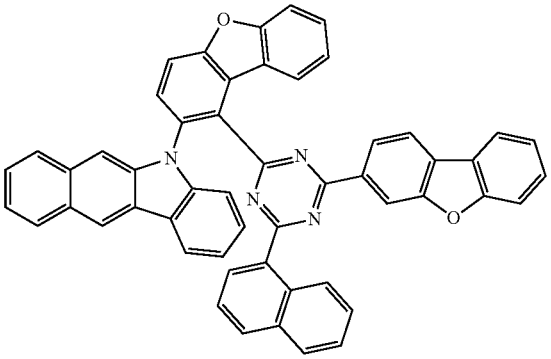
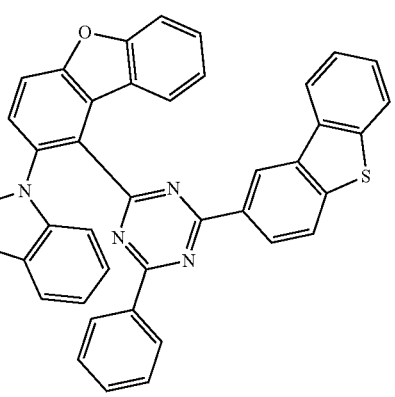
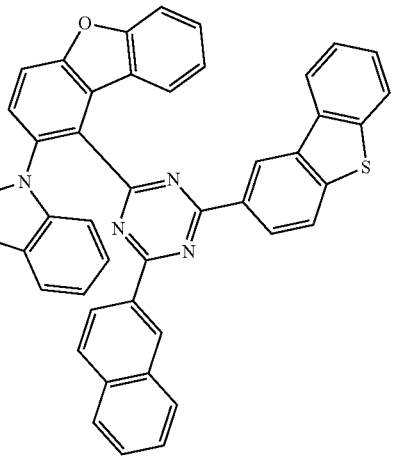
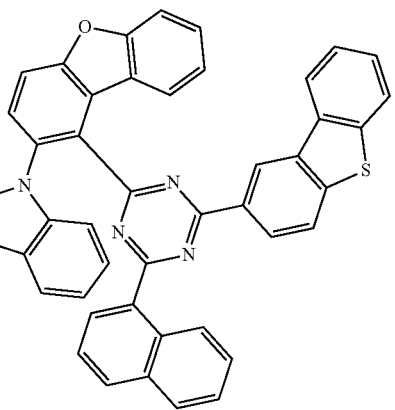

-continued
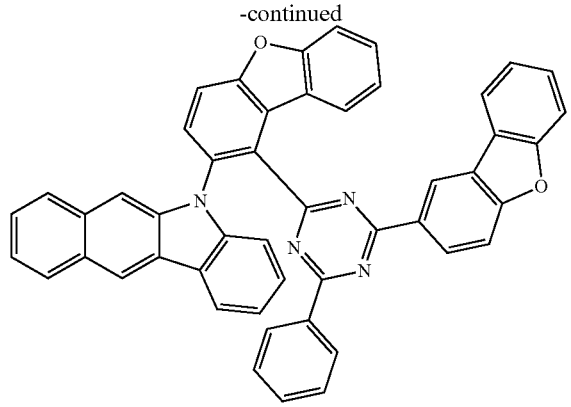
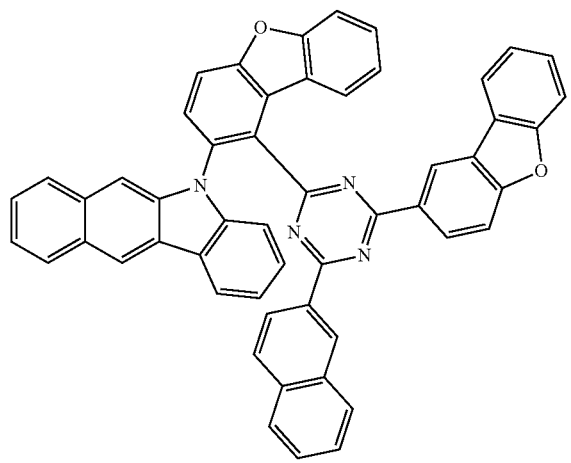
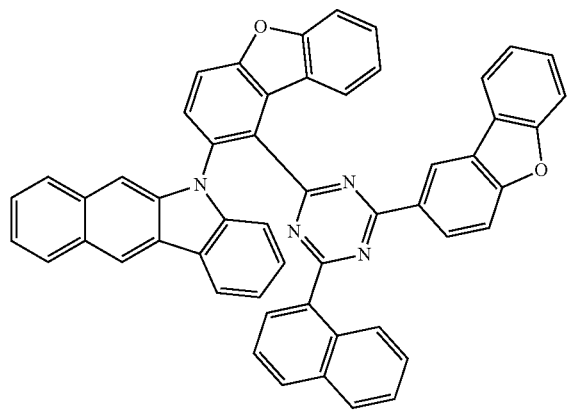
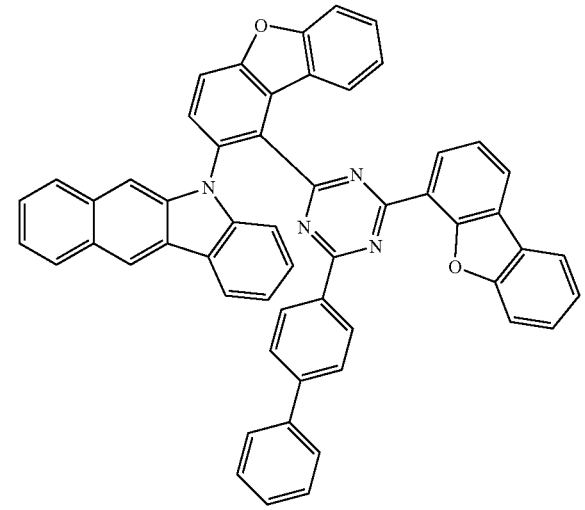
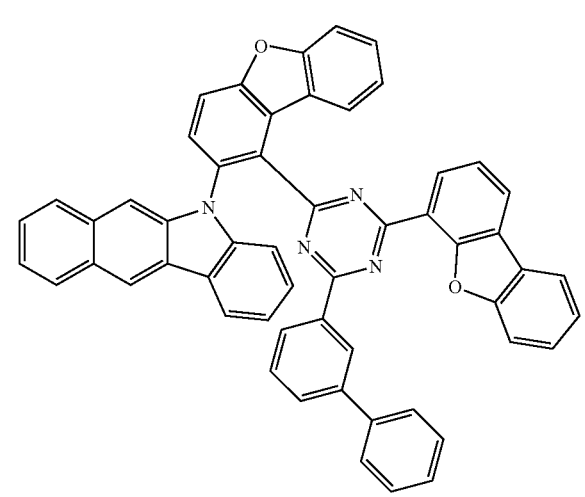
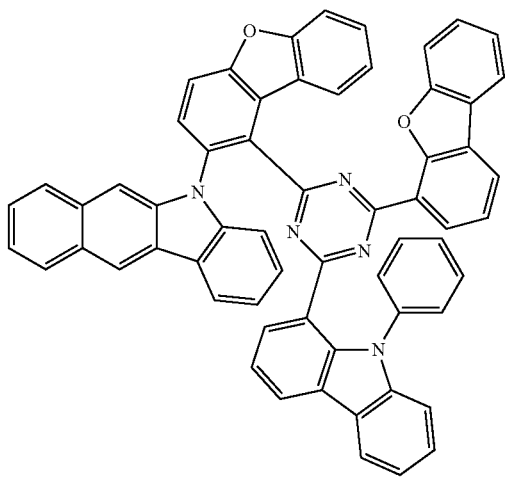

115
-continued
116
-continued
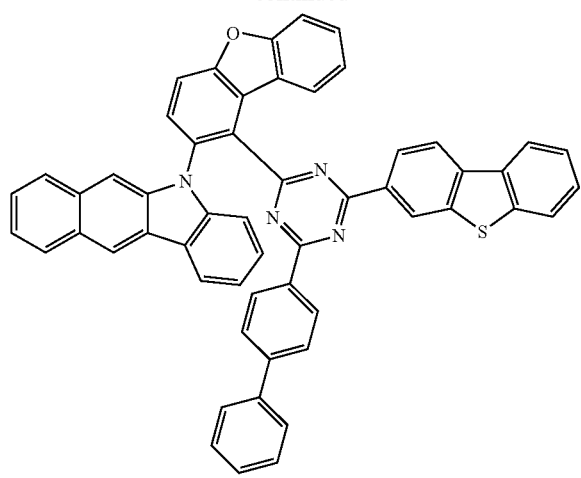
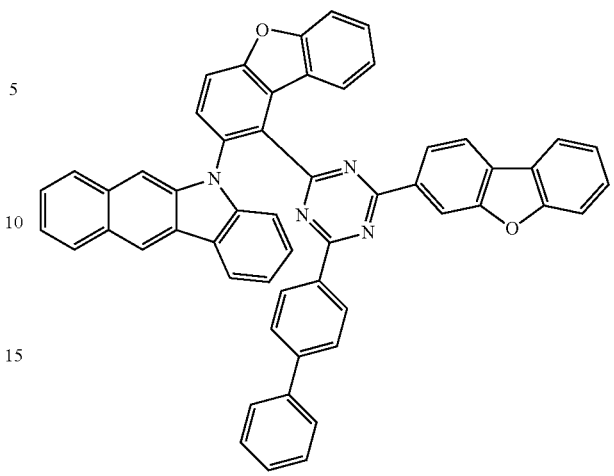
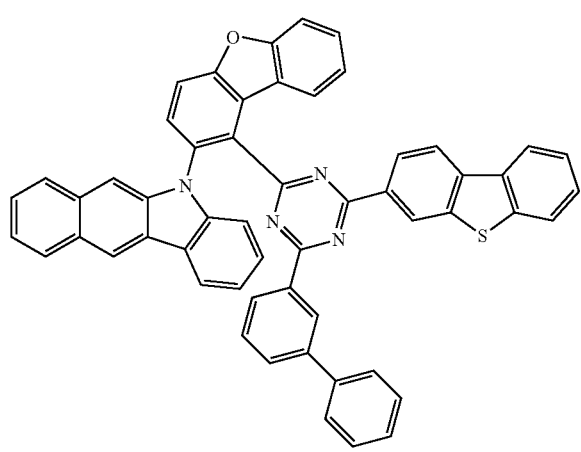
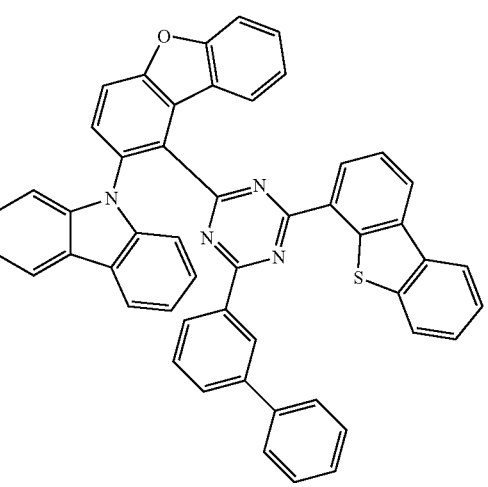

117
-continued
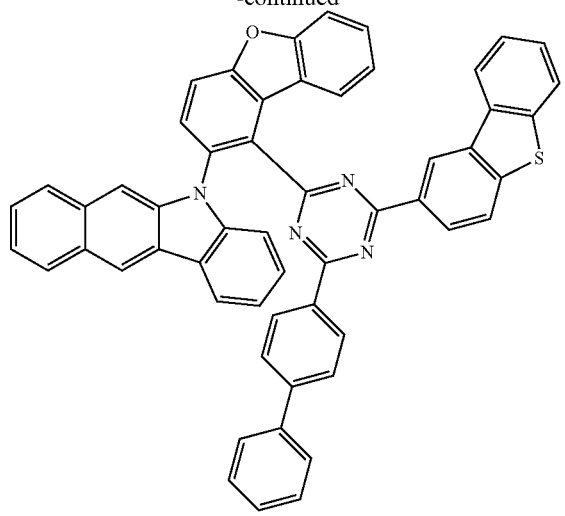
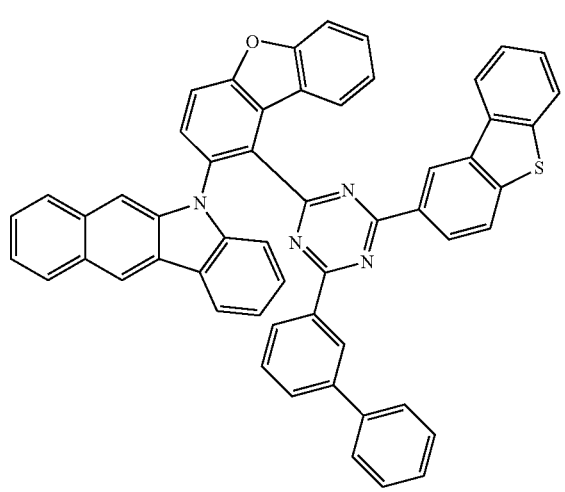
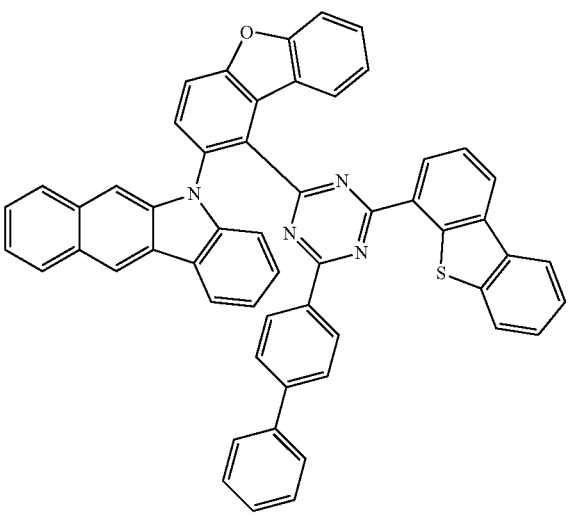
118
-continued
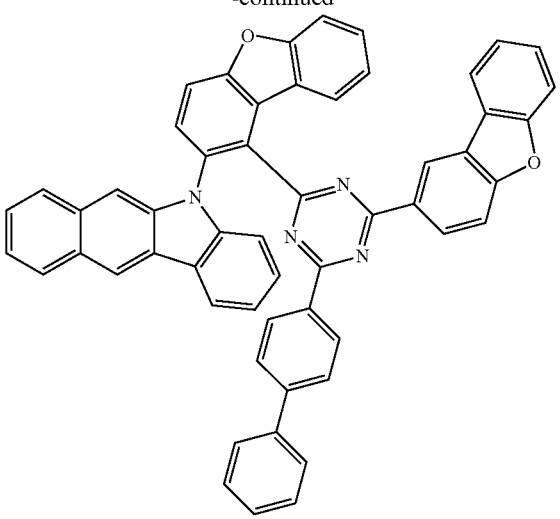
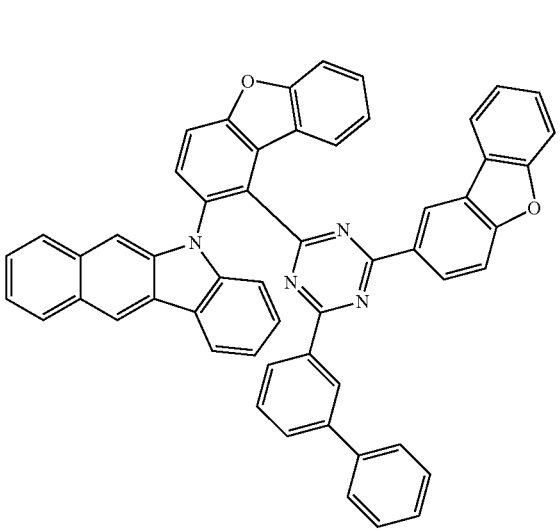
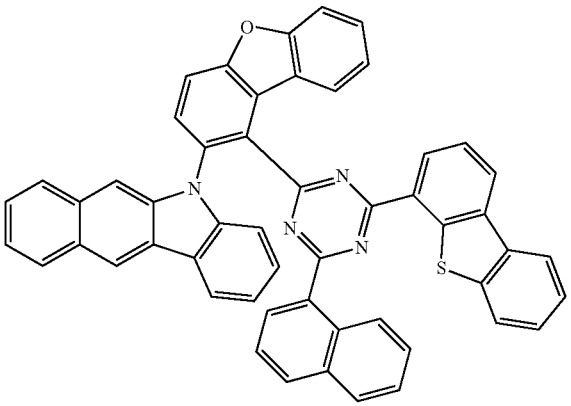

119
-continued
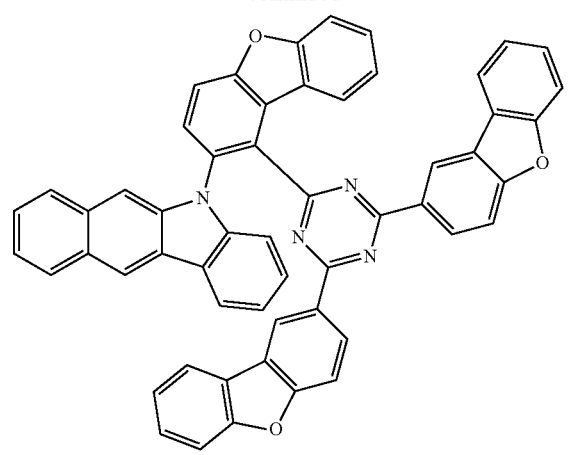
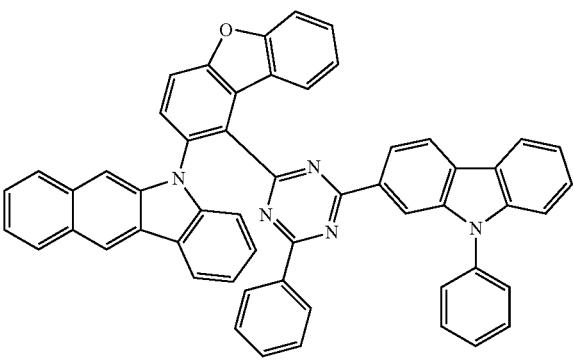
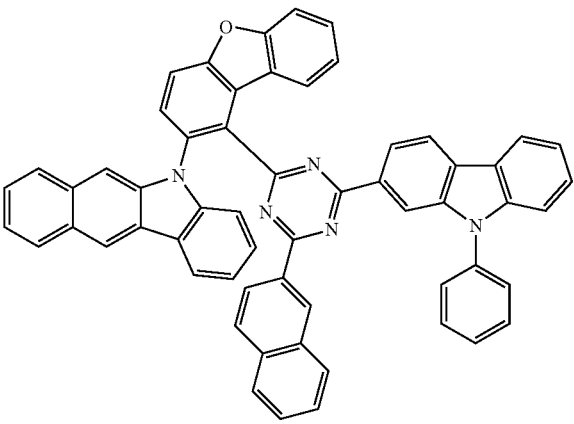
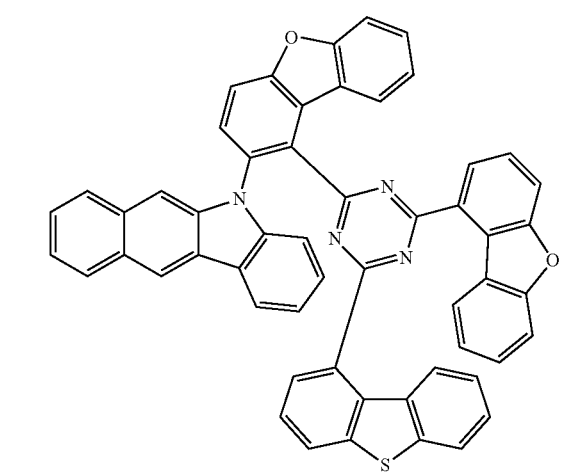
120
-continued
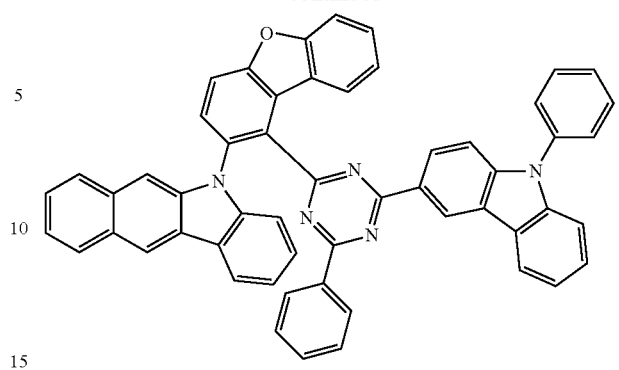
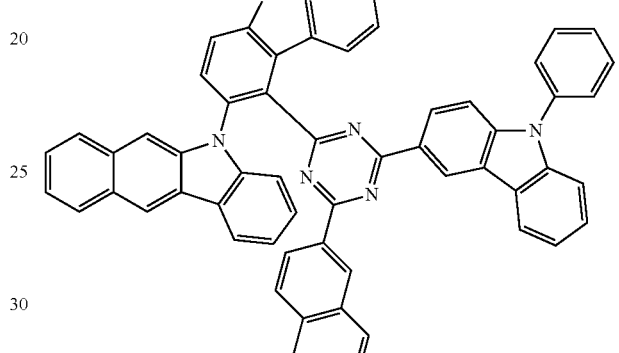
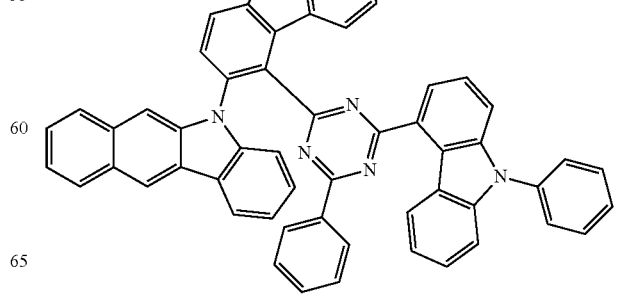

121
-continued
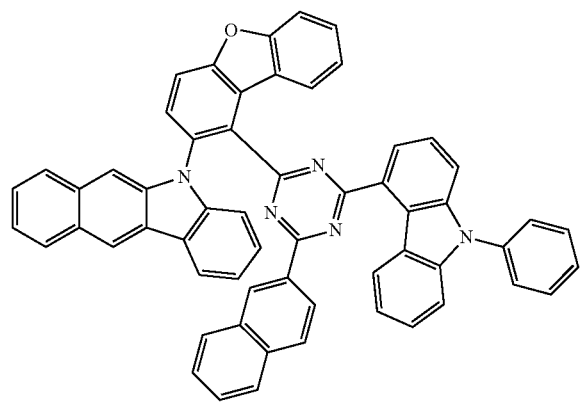
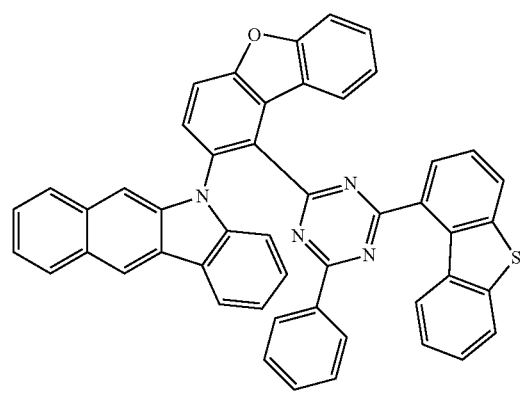
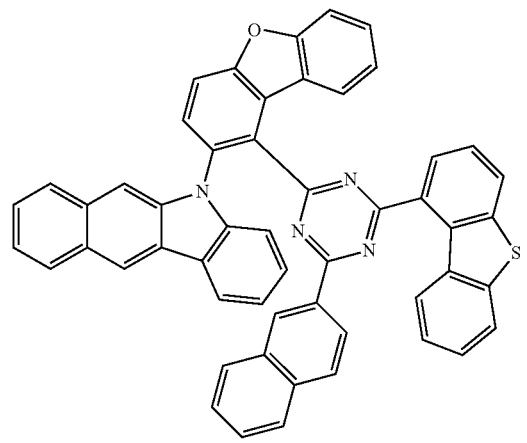
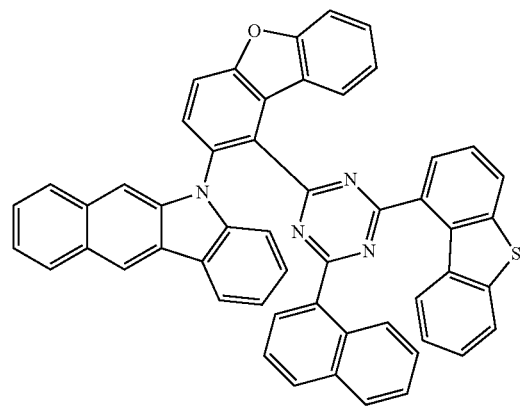
122
-continued
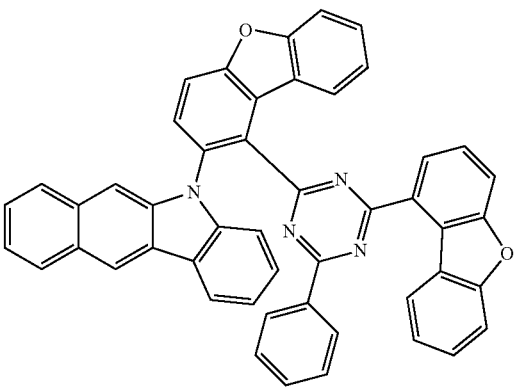
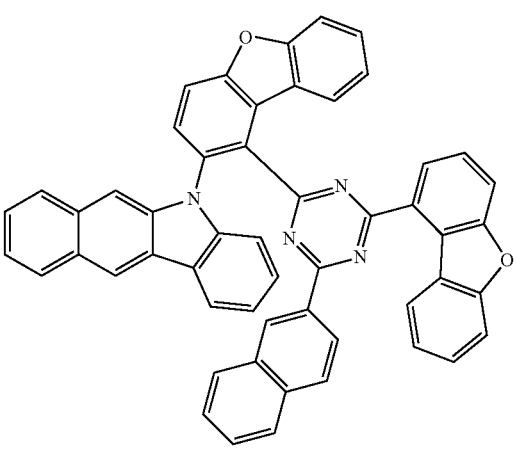
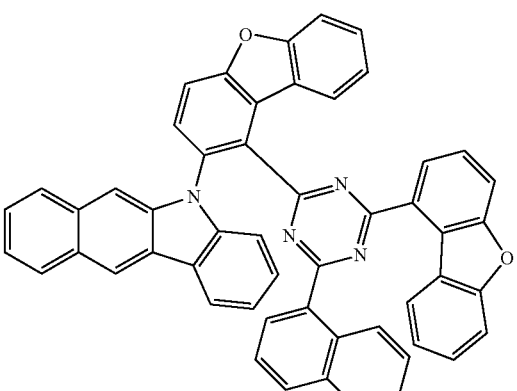
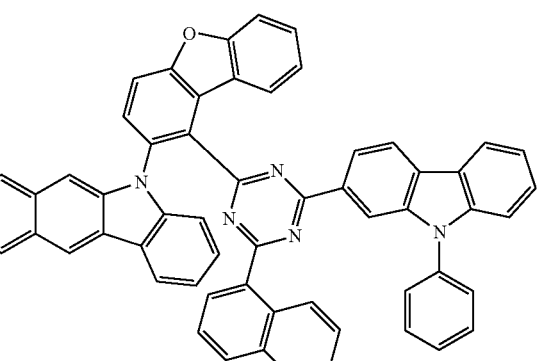

123
-continued
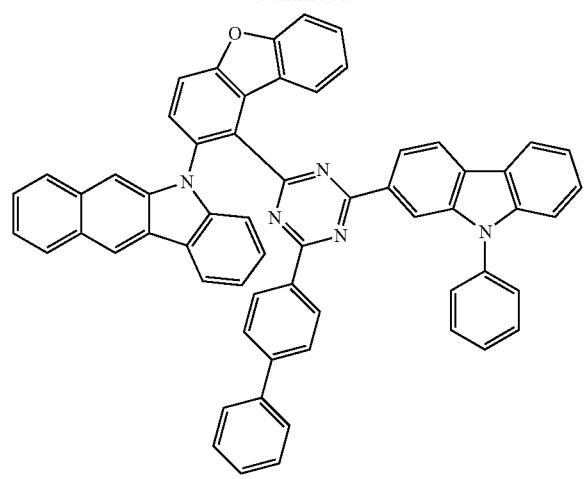
124
-continued
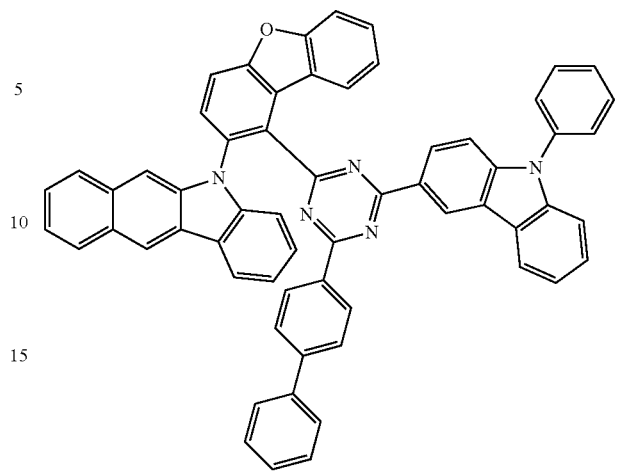
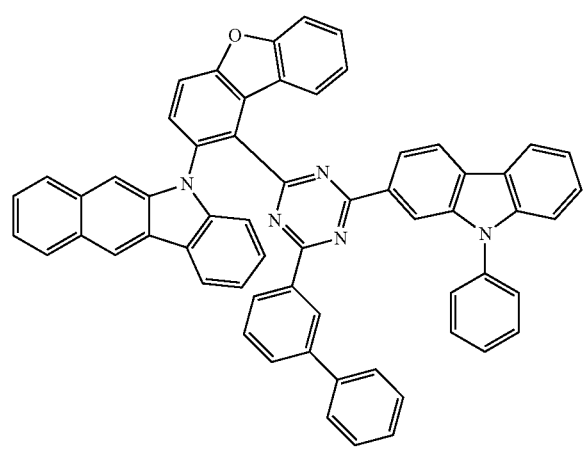
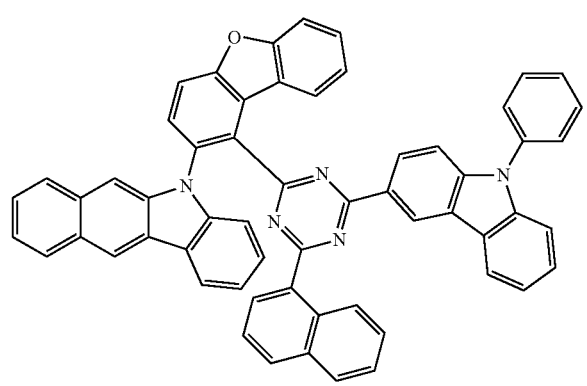
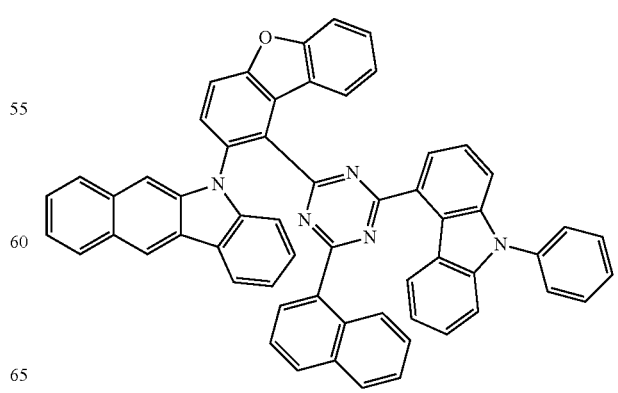

125
-continued
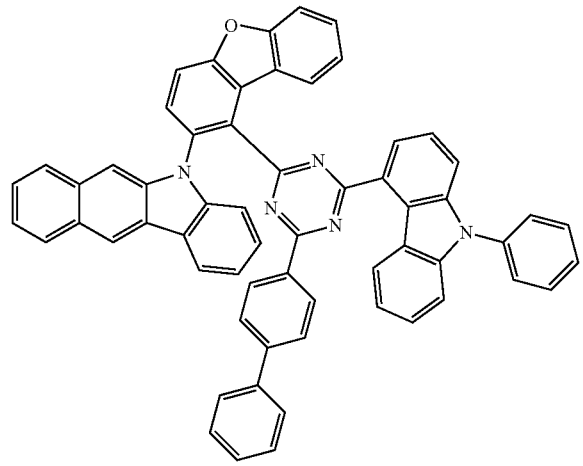
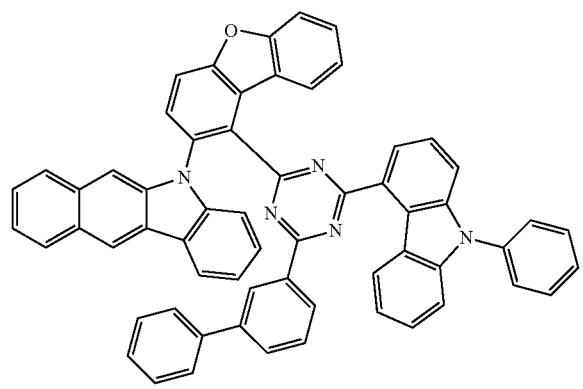
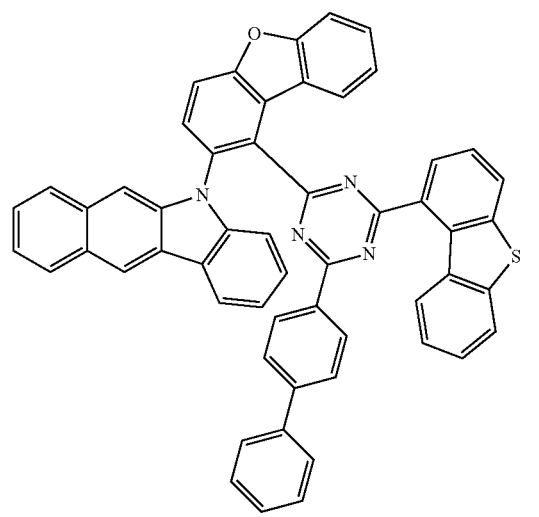
126
-continued
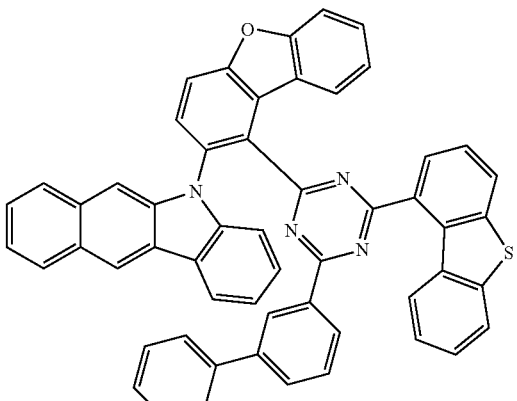
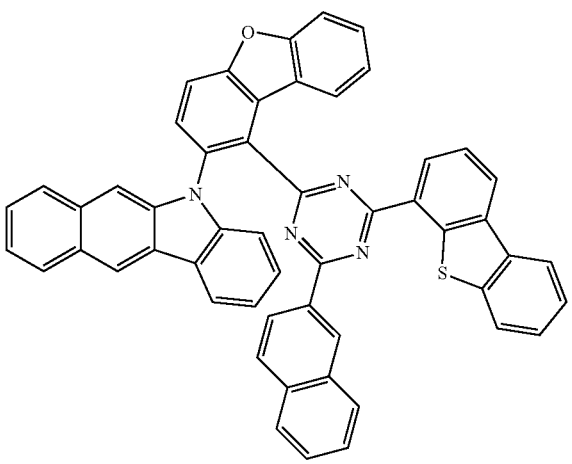
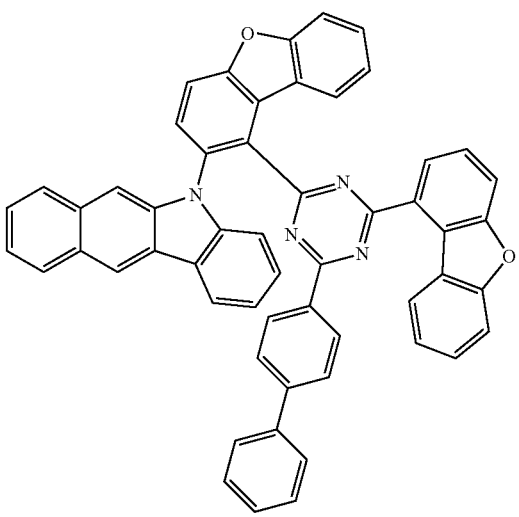

127
-continued
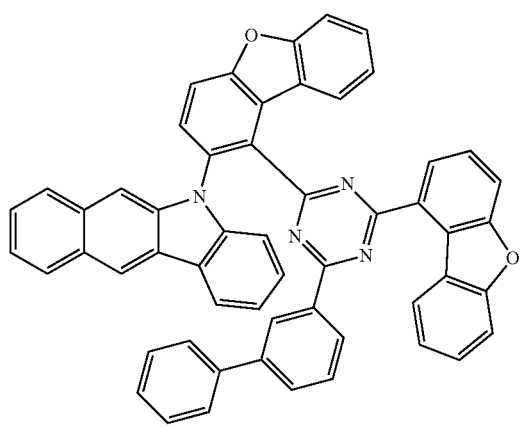
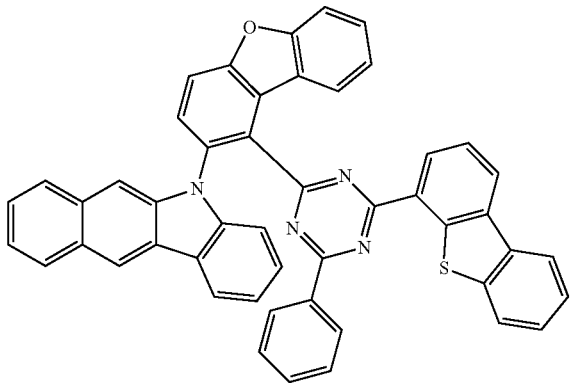
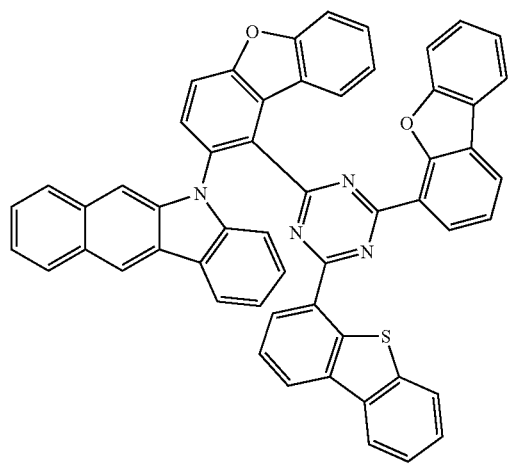
128
-continued
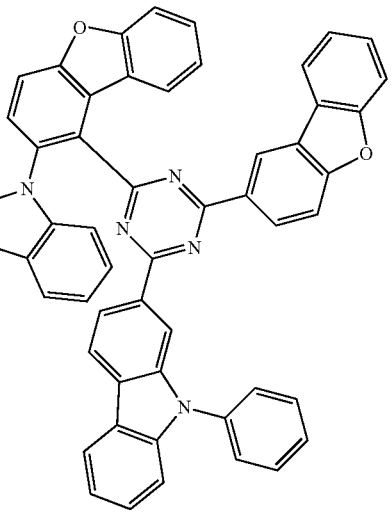
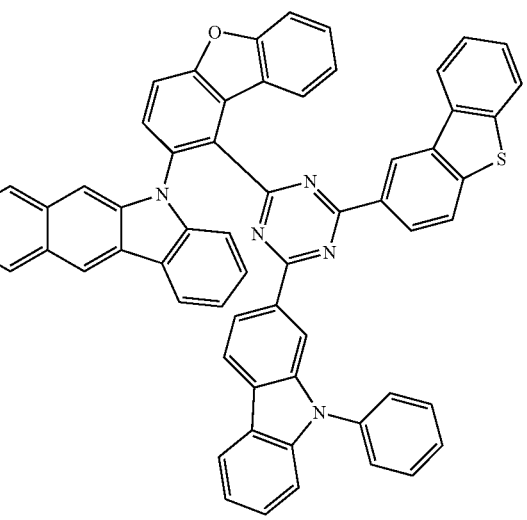
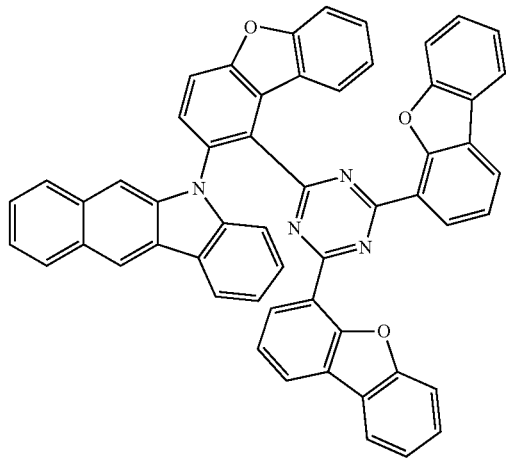

129
-continued
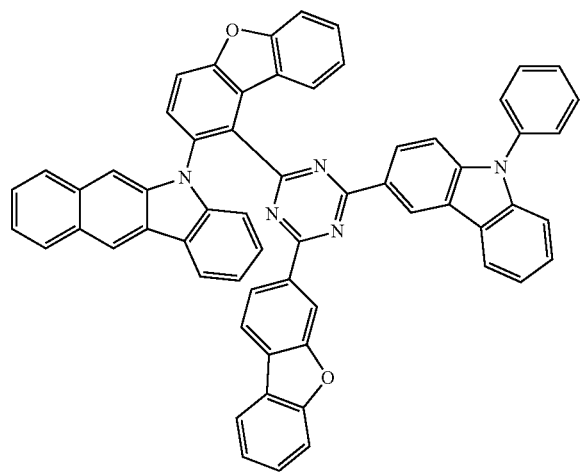
130
-continued
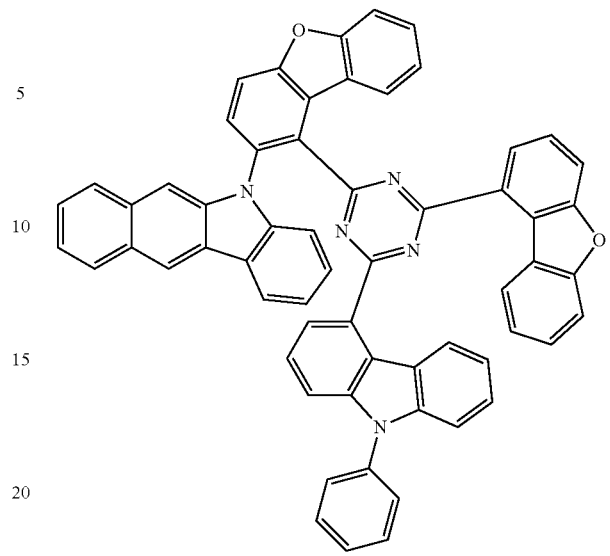
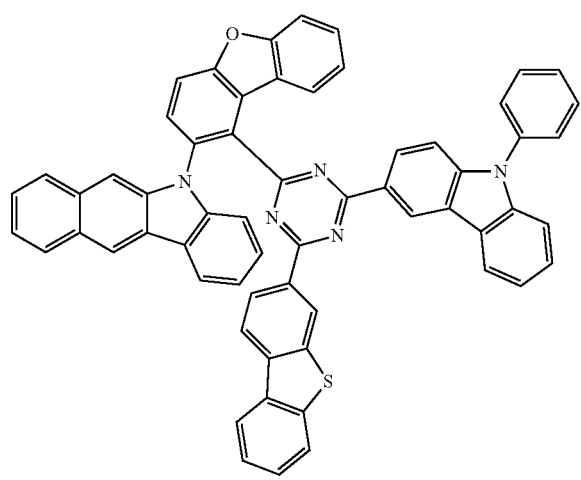
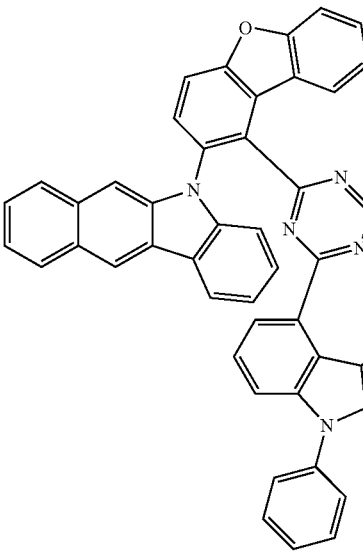
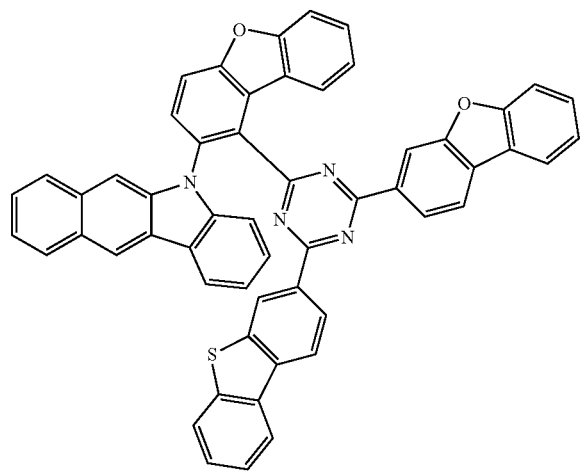
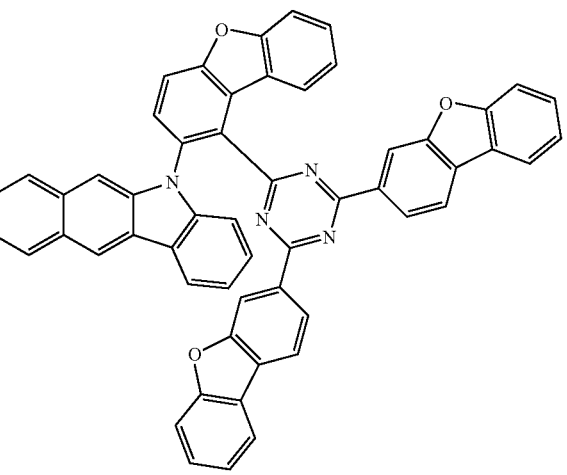

131
-continued
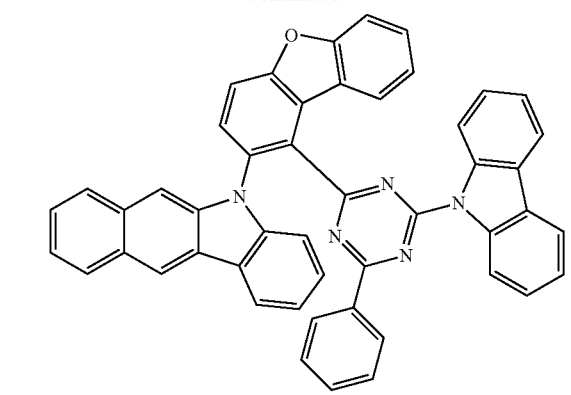
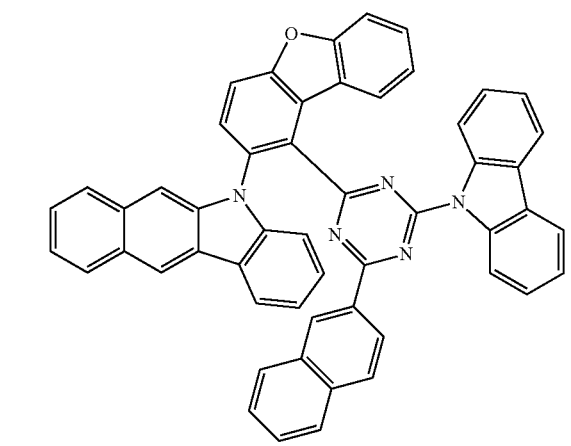
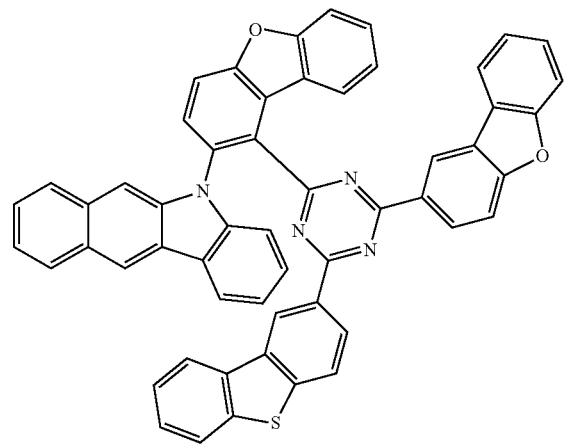
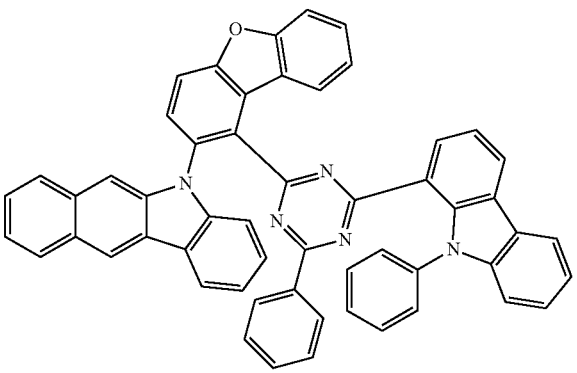
132
-continued
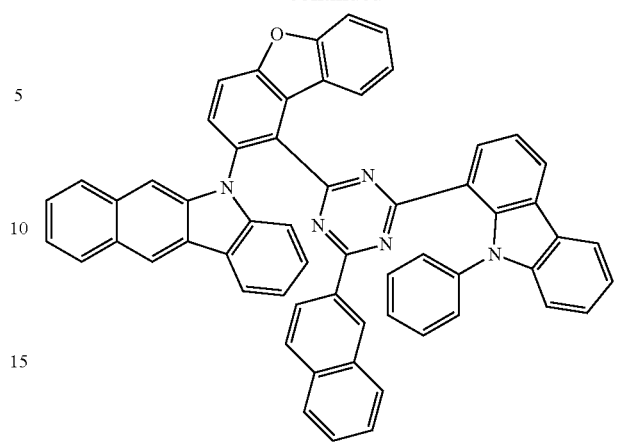
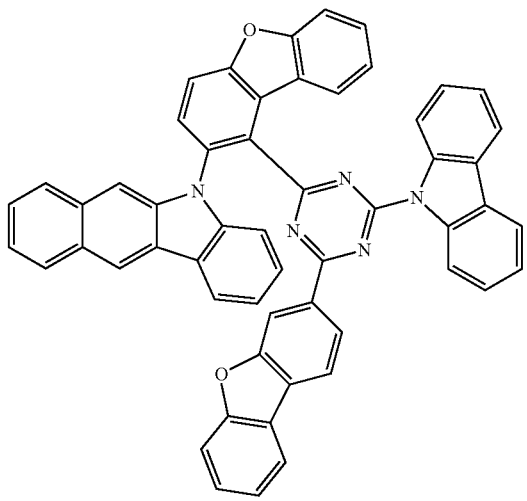
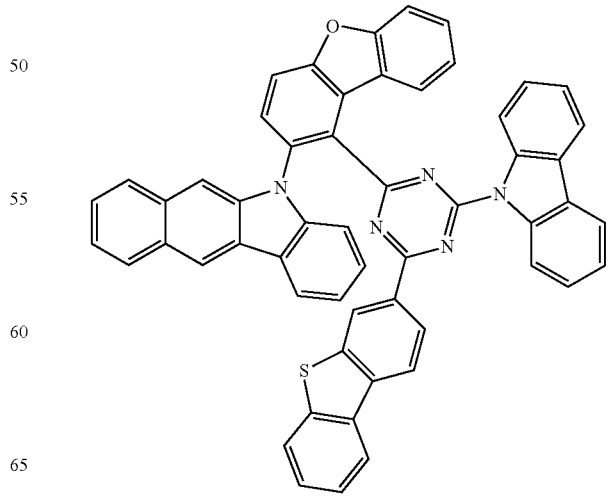

133
-continued
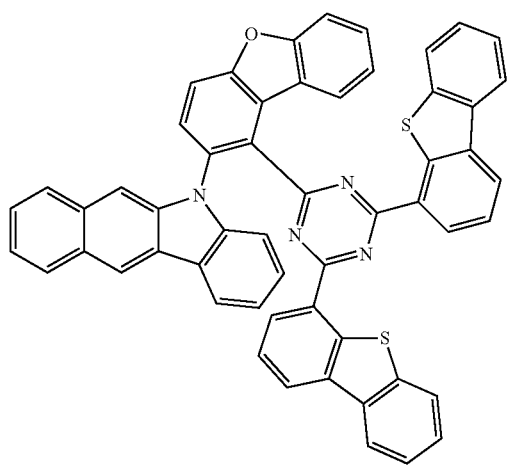
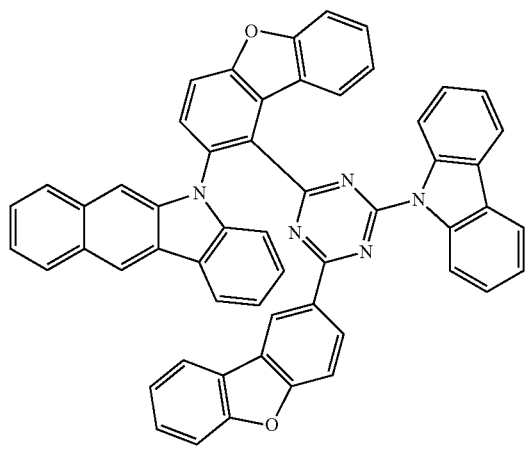
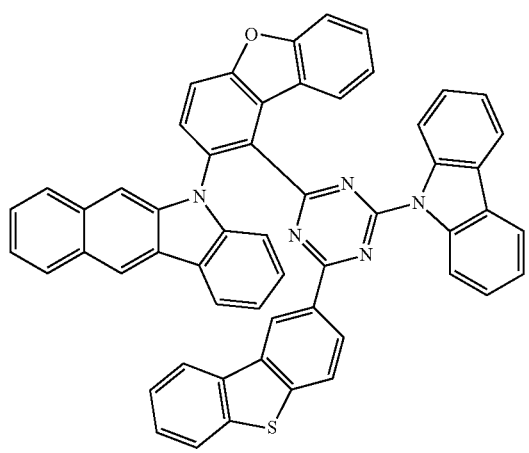
134
-continued
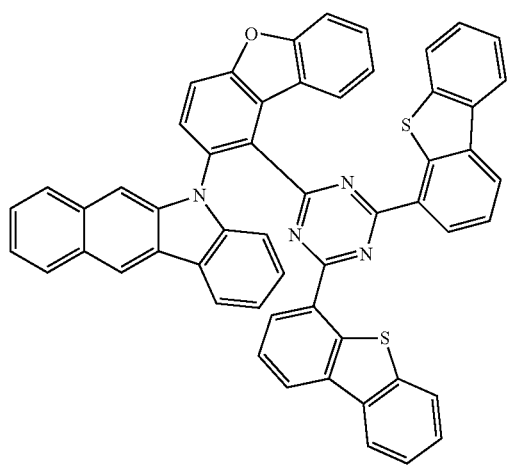
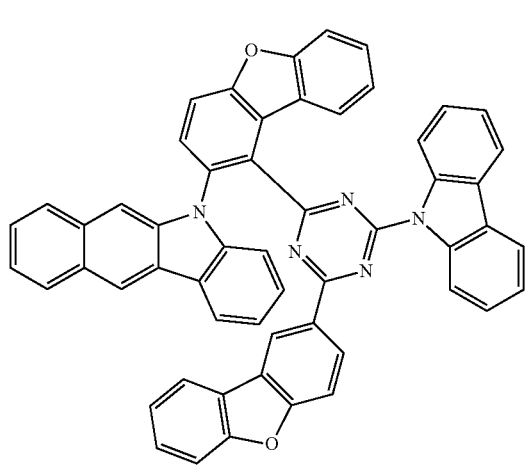
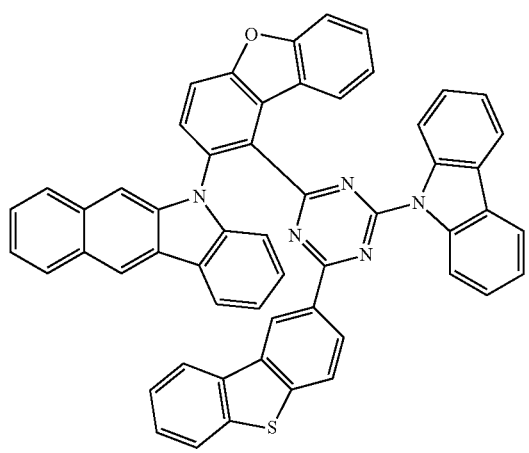

135
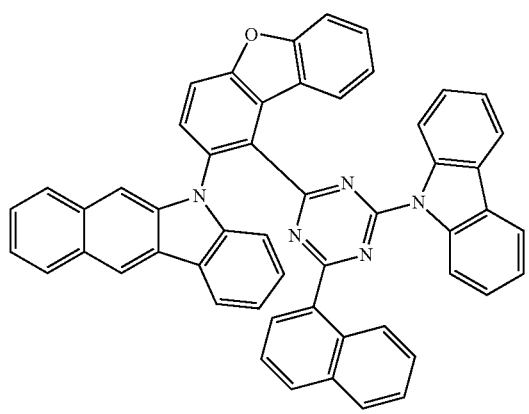
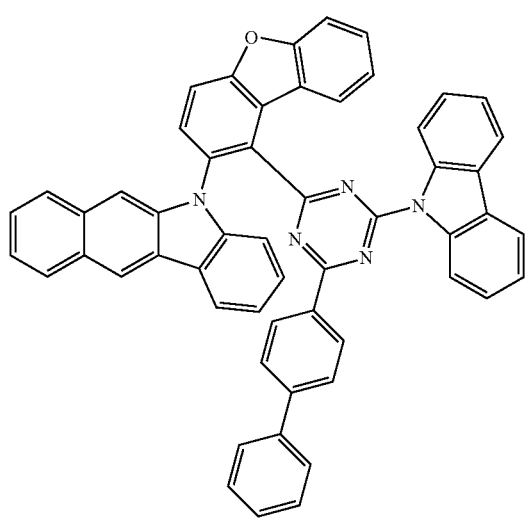
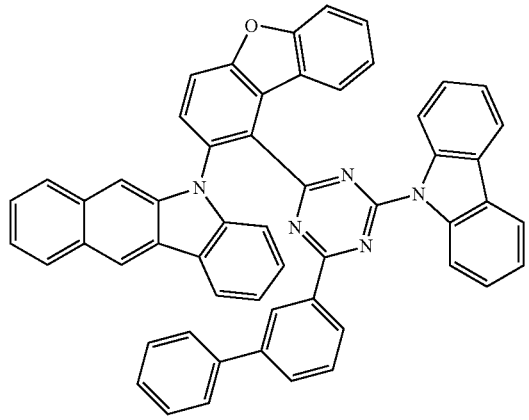
136
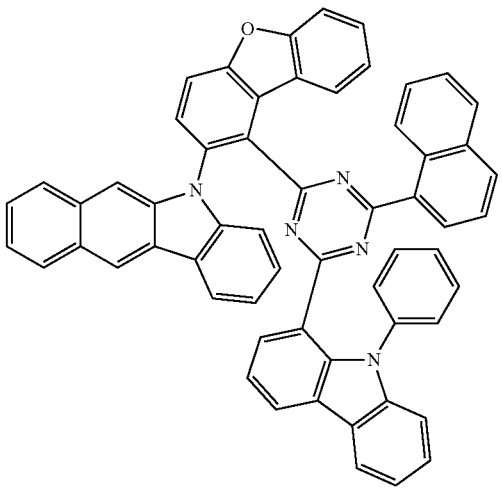
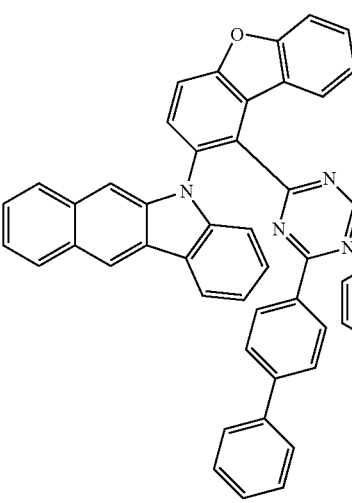
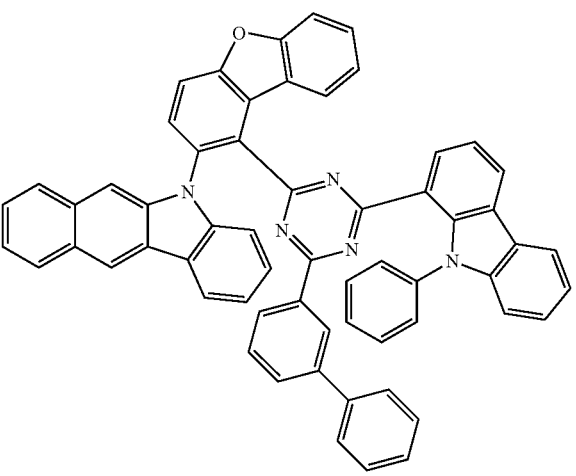

137
-continued
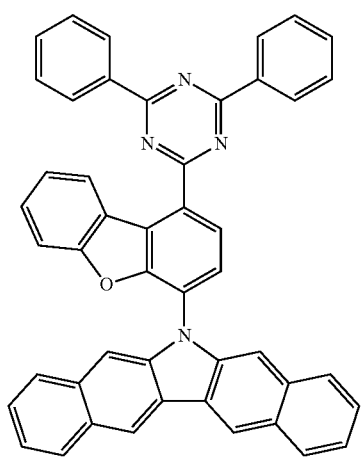
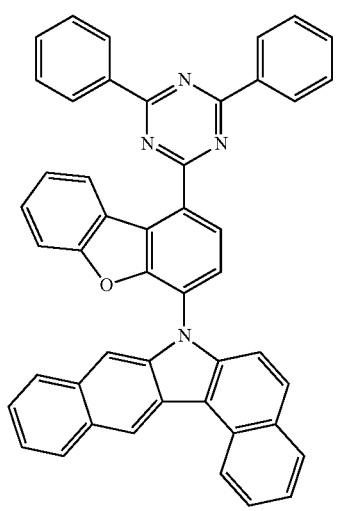
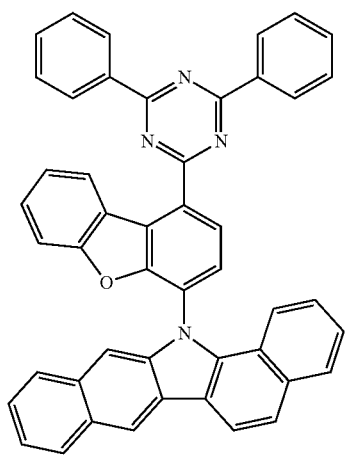
138
-continued
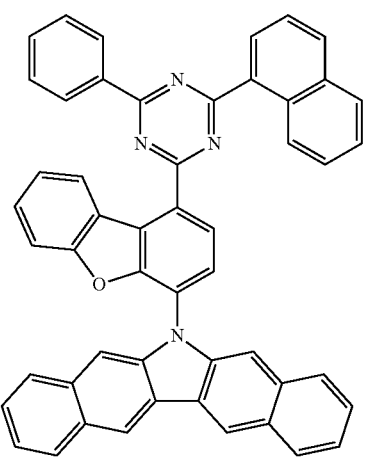
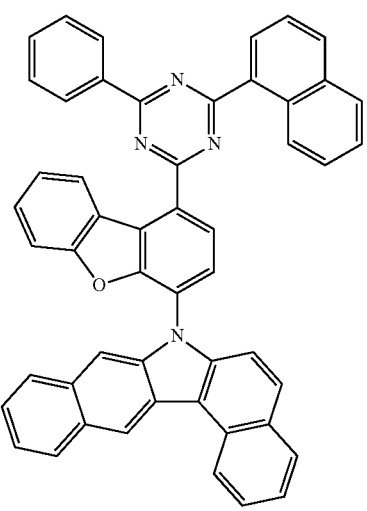
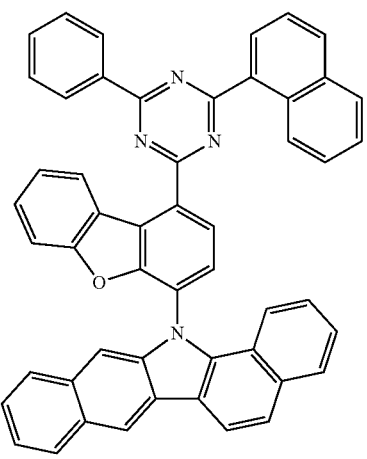

139
-continued
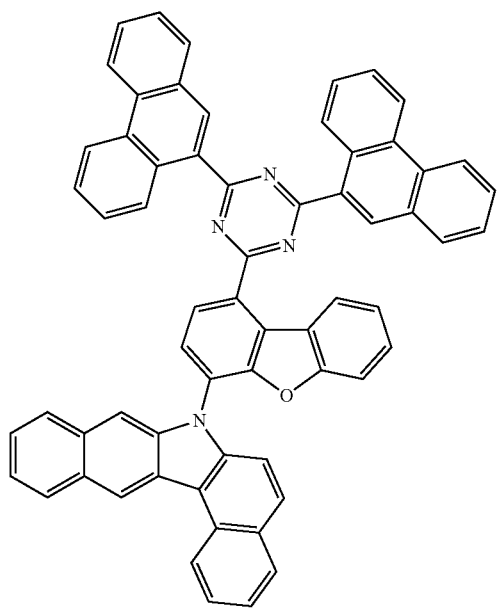
140
-continued
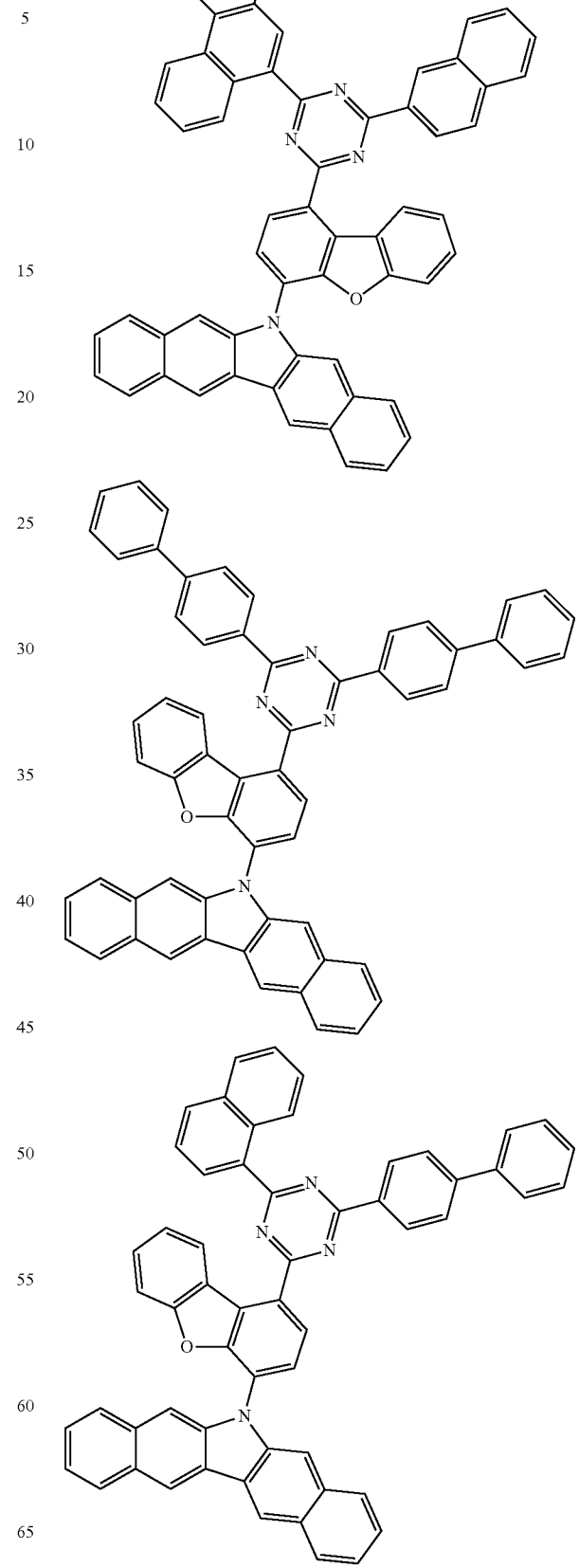

141
-continued
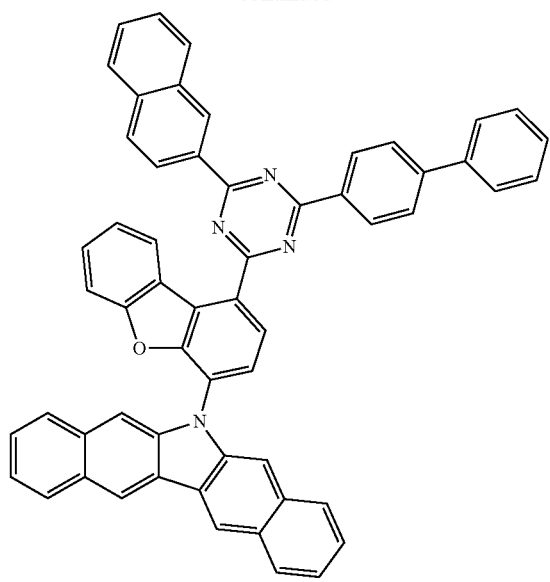
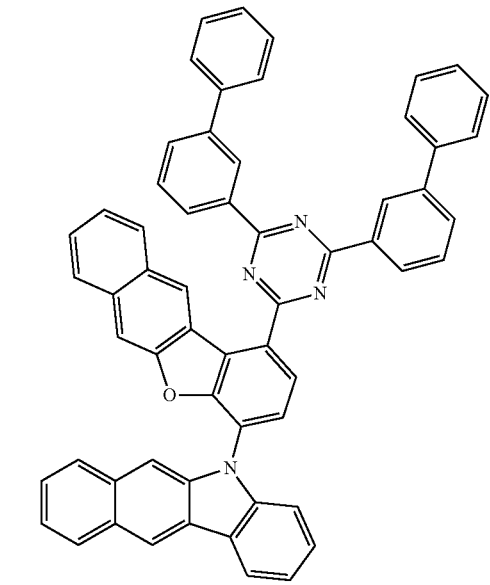
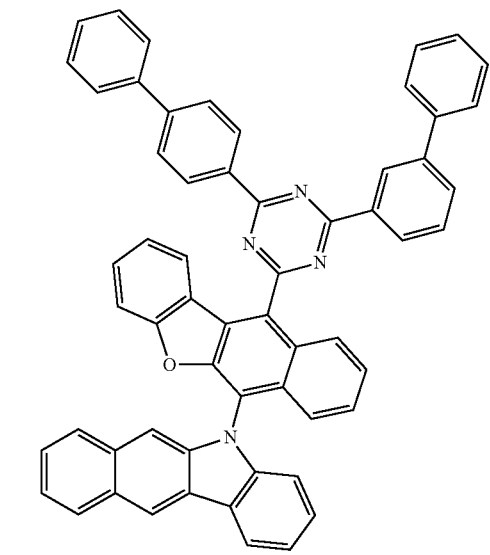
142
-continued
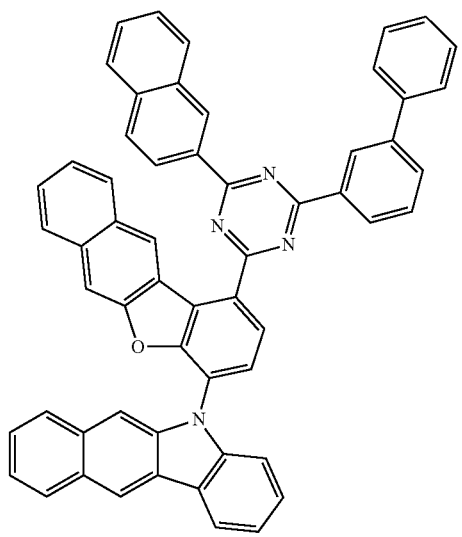
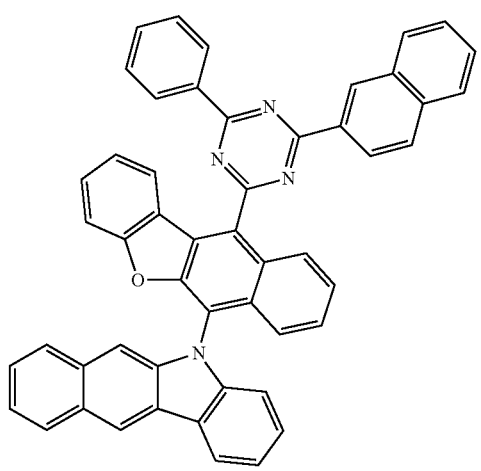
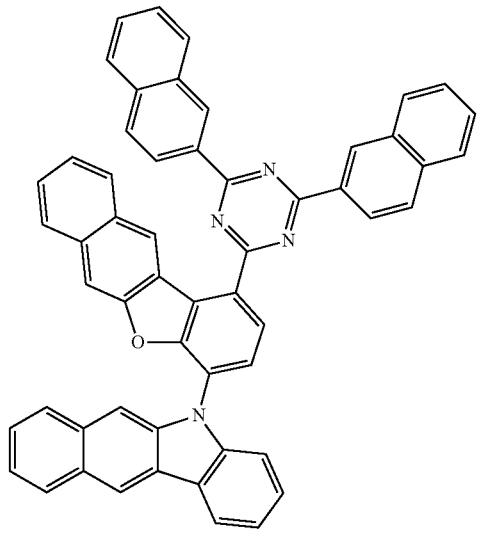

143
-continued
144
-continued
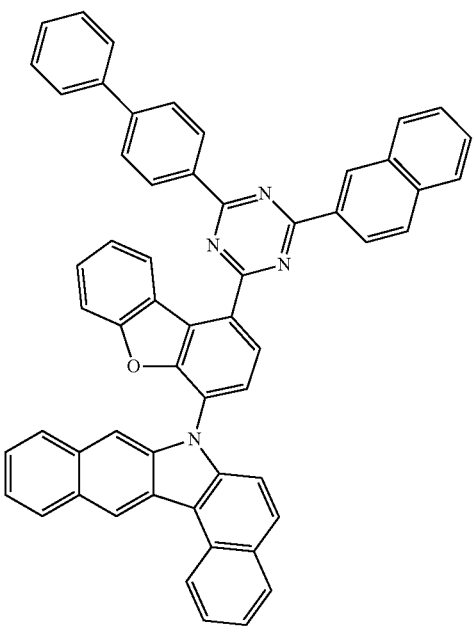
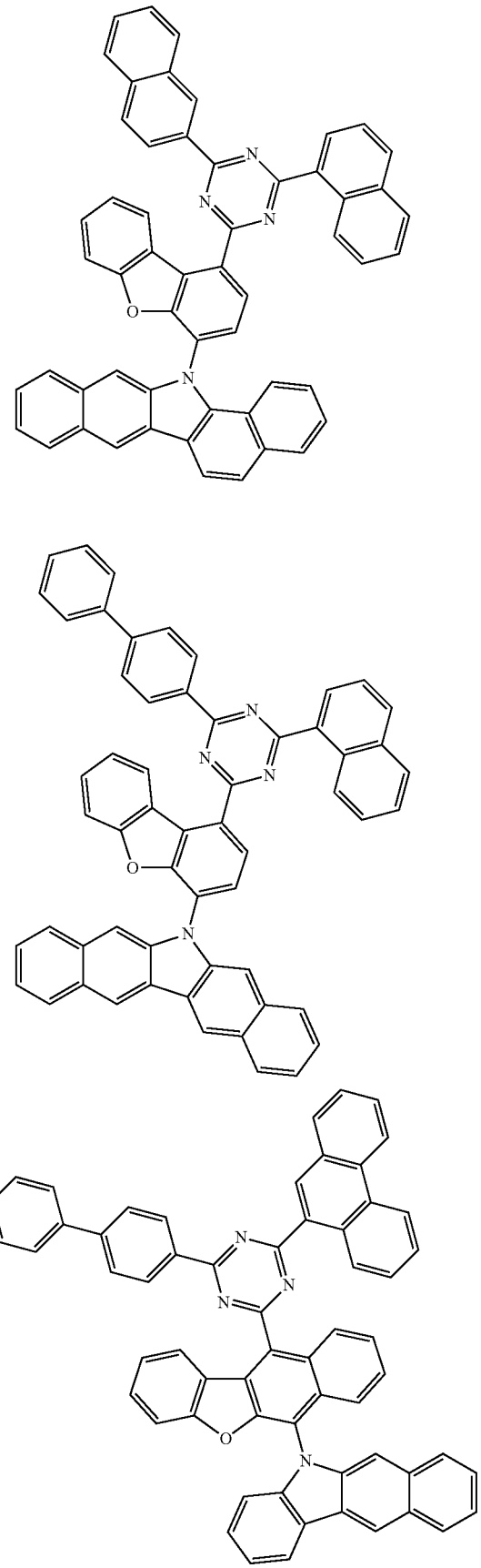

145
-continued
146
-continued
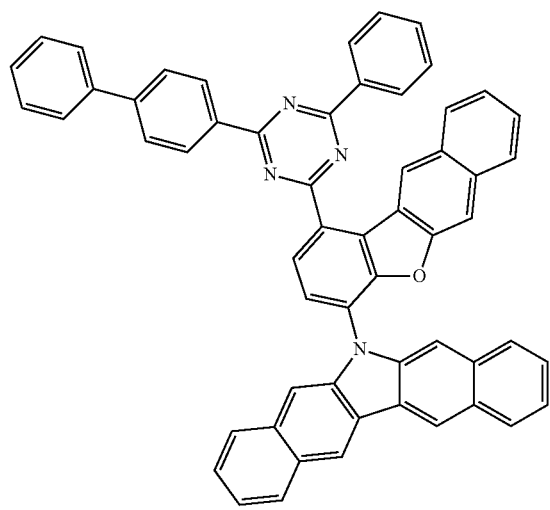
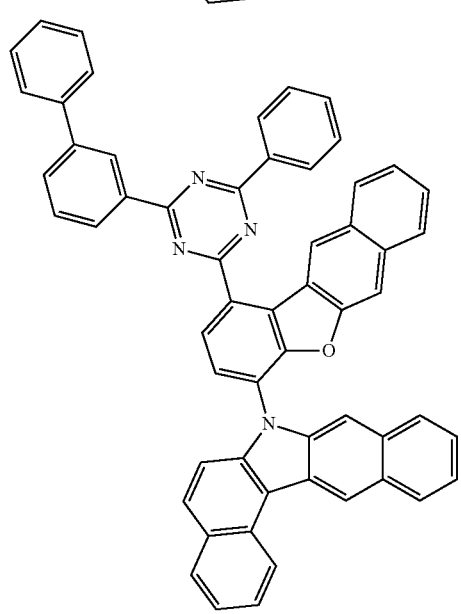
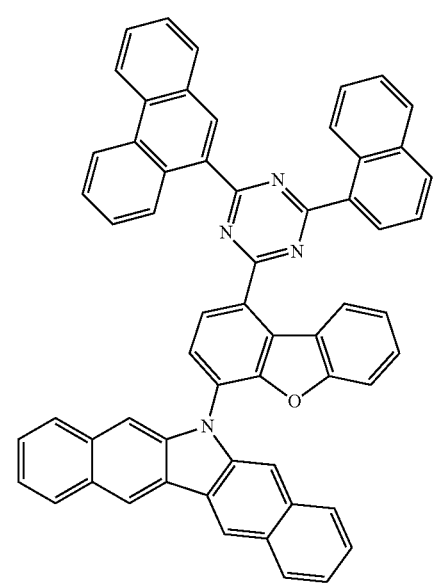
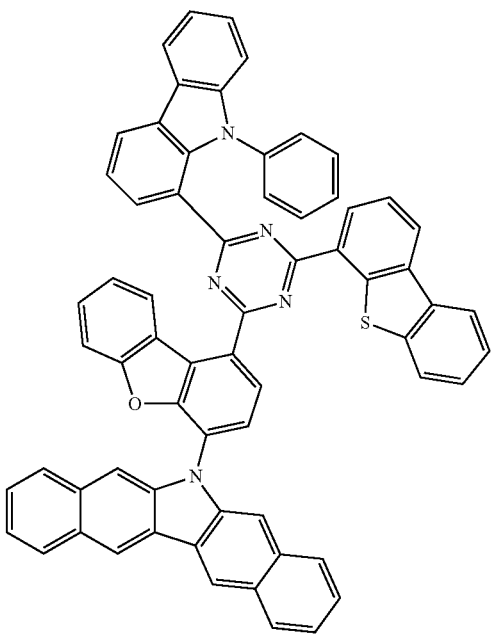

147
-continued
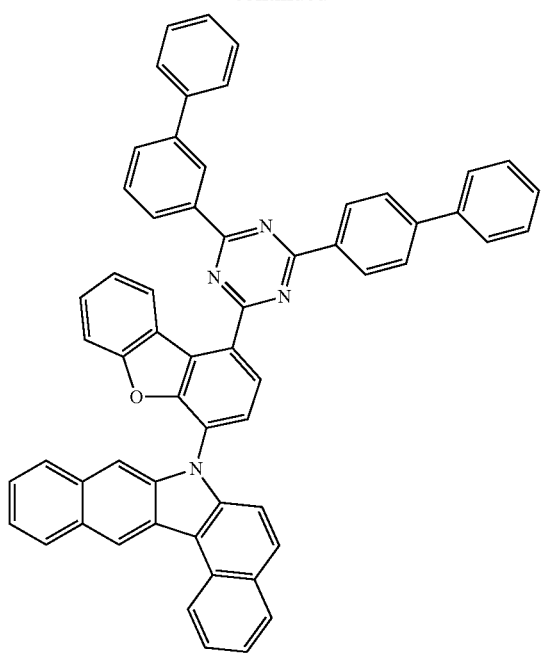
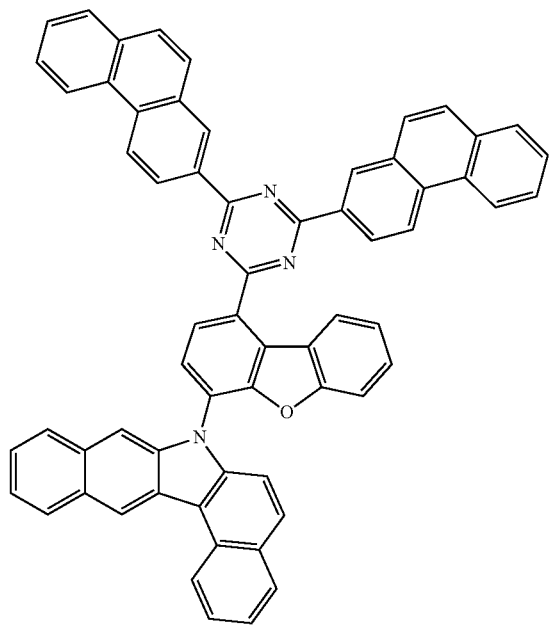
148
-continued
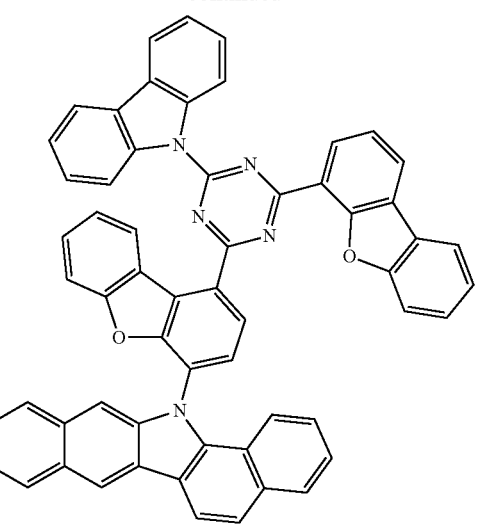
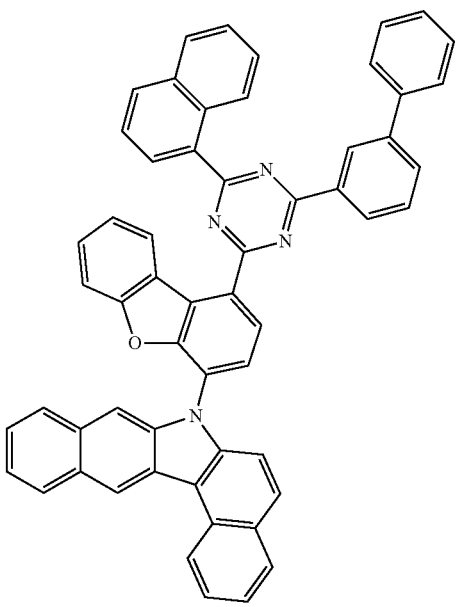

149
-continued
150
-continued
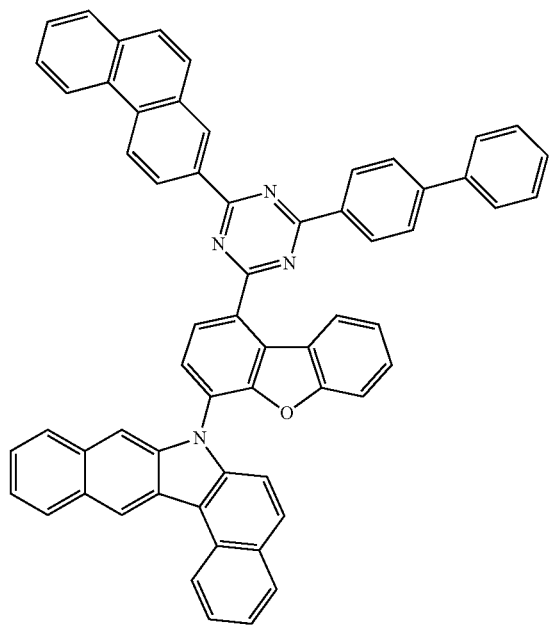
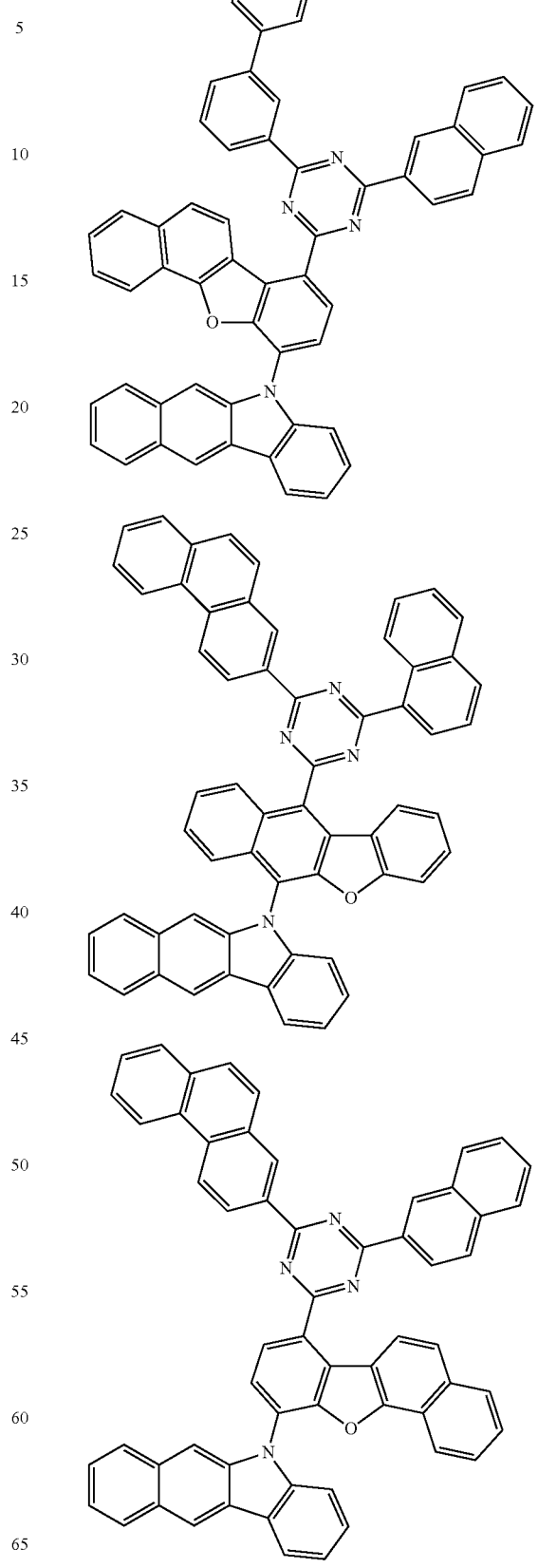

151
-continued
152
-continued
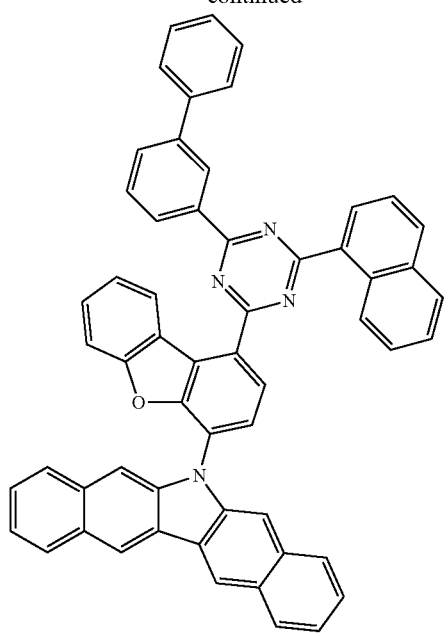
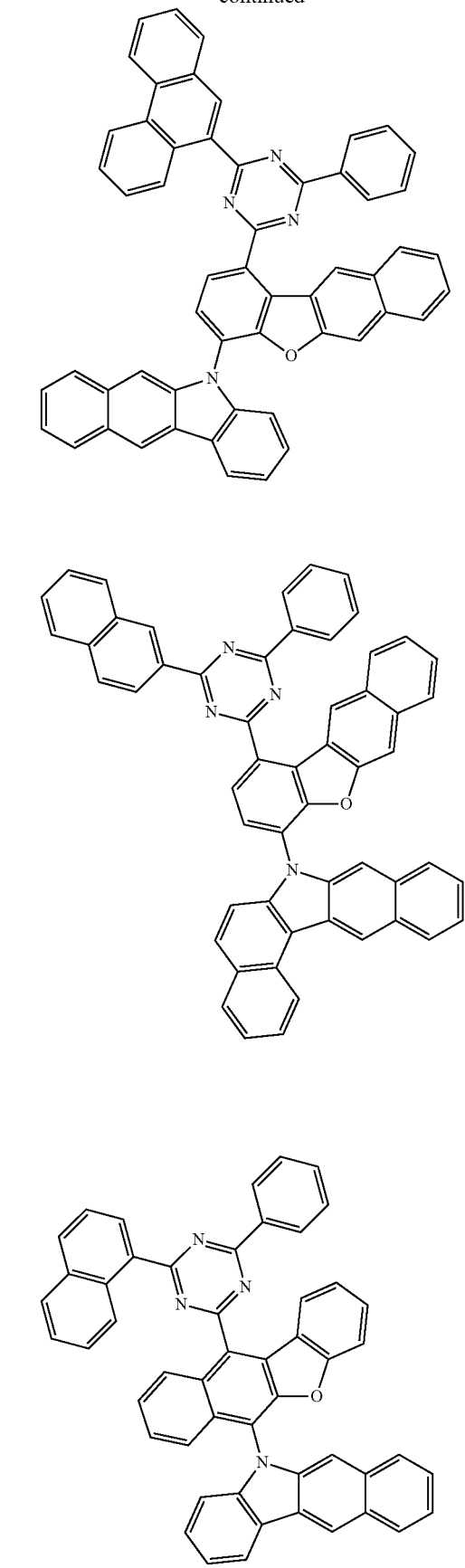

153
-continued
154
-continued
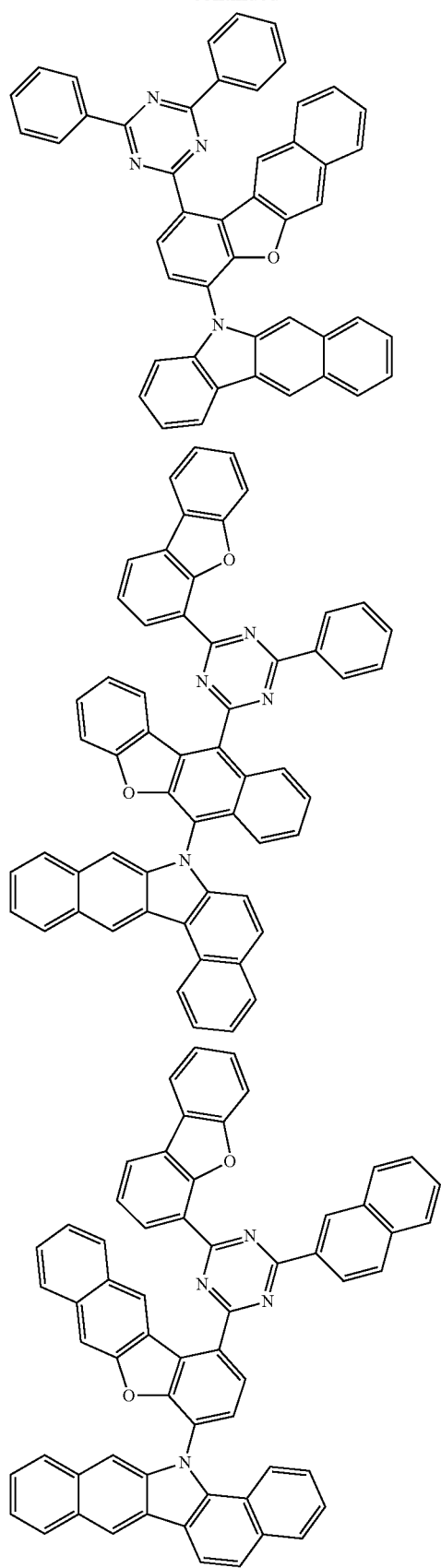
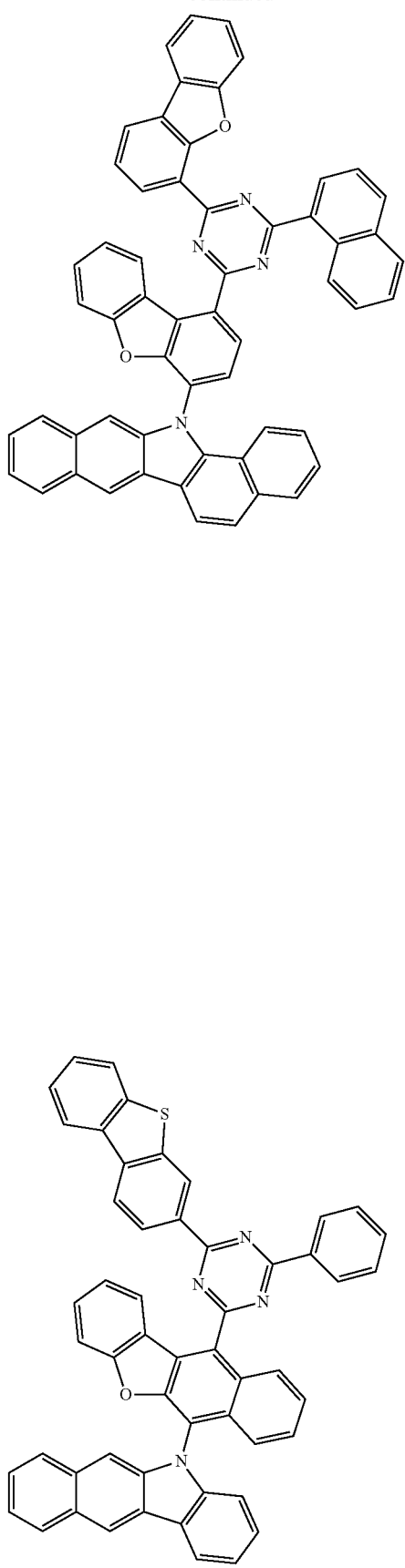

155
-continued
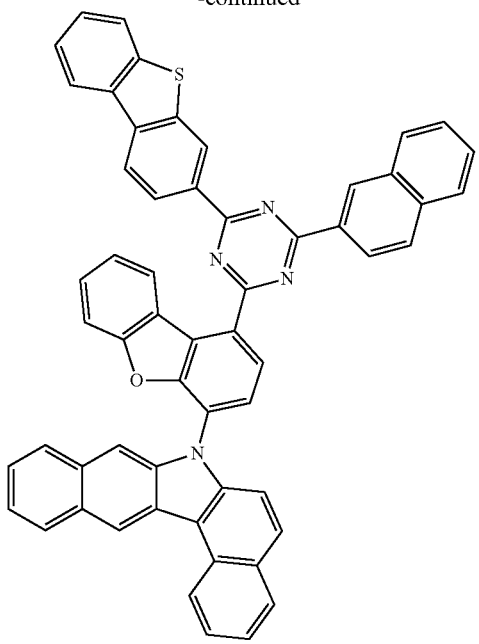
156
-continued
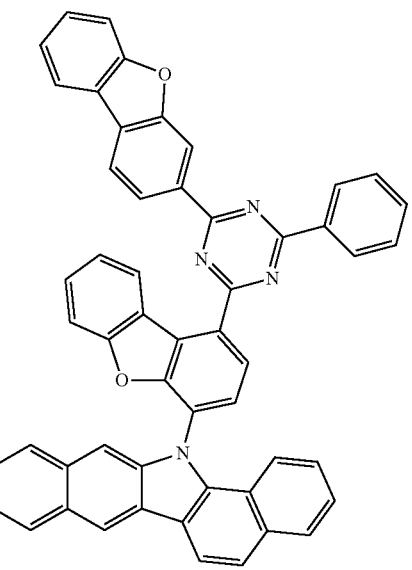
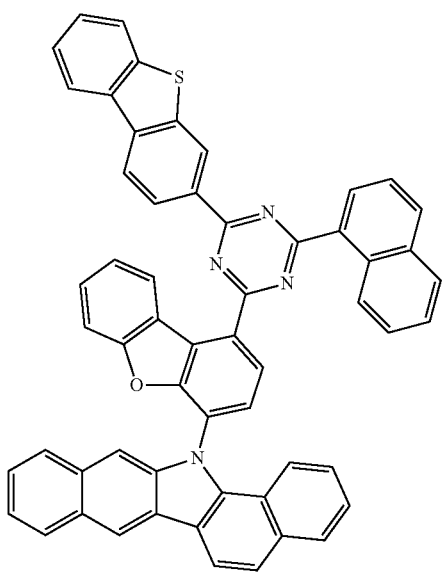
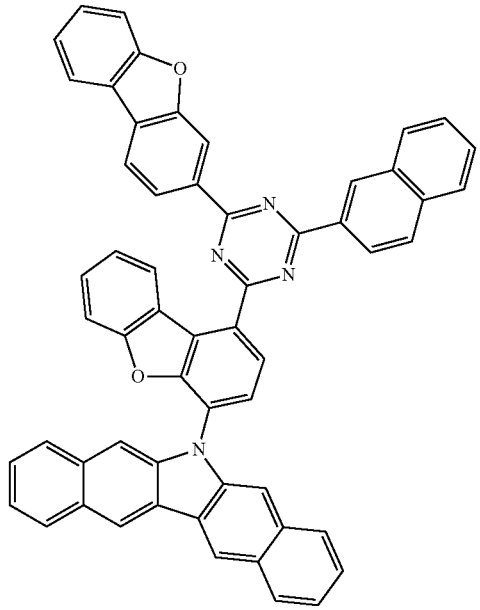

157
-continued
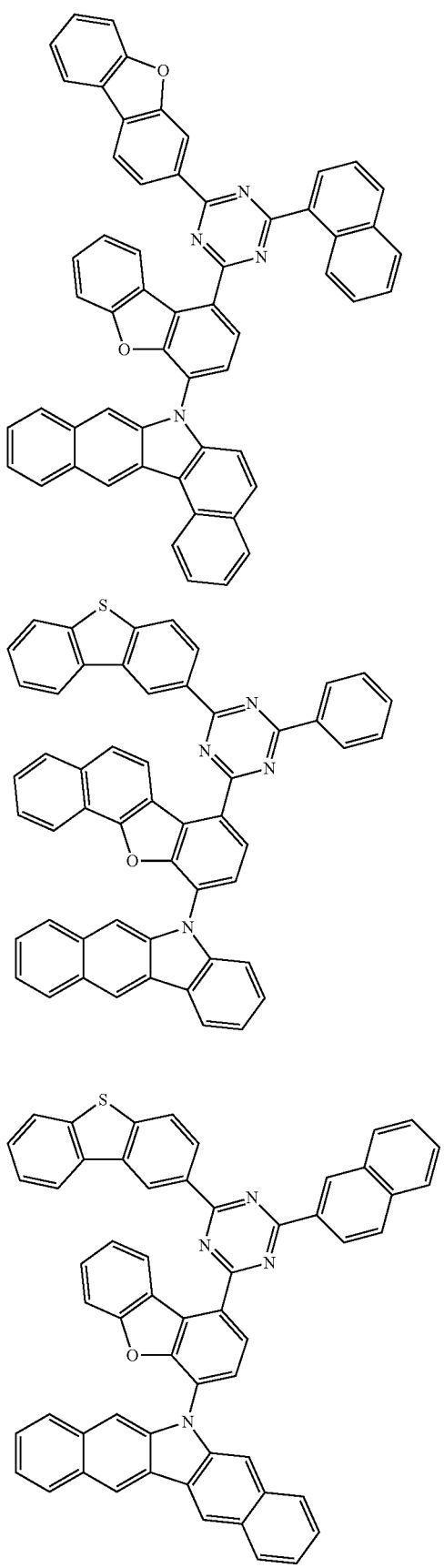
158
-continued
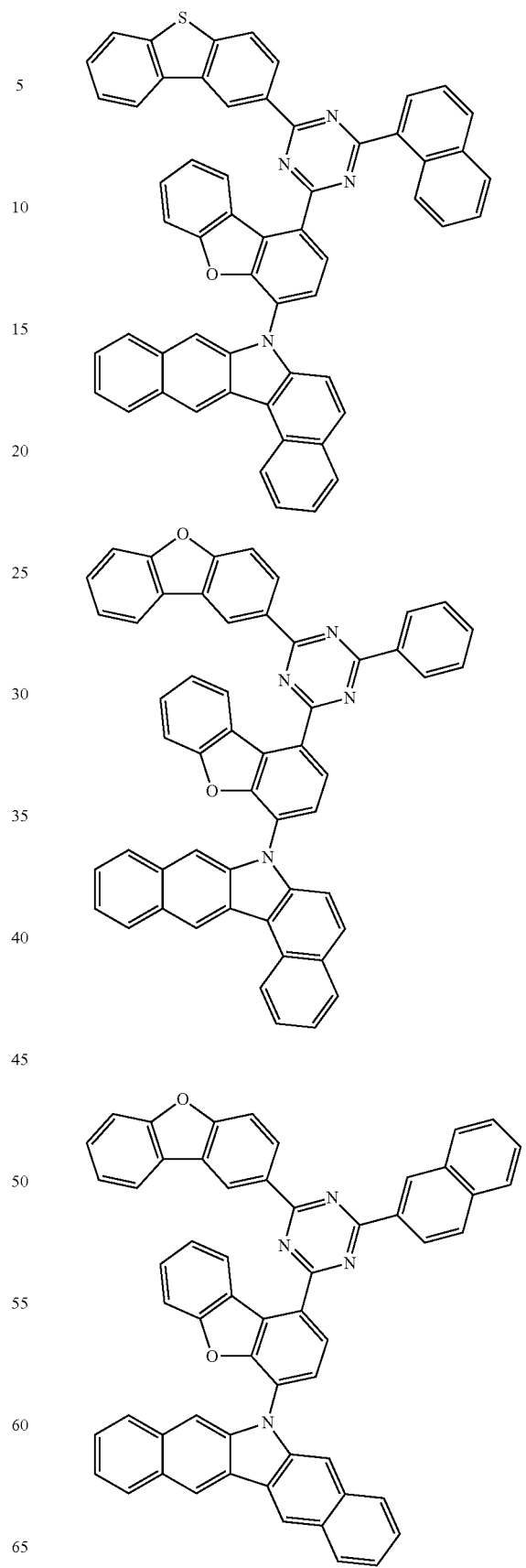

159
-continued
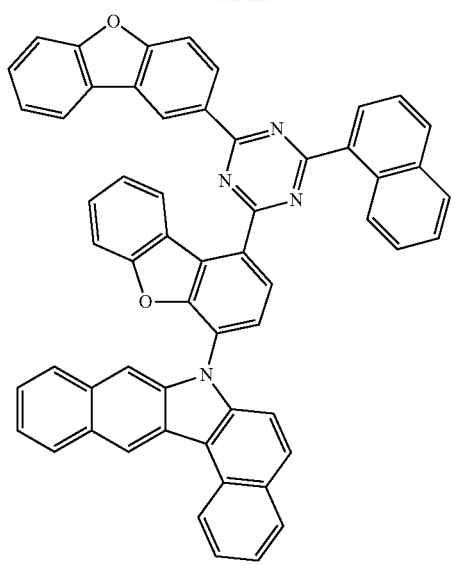
160
-continued
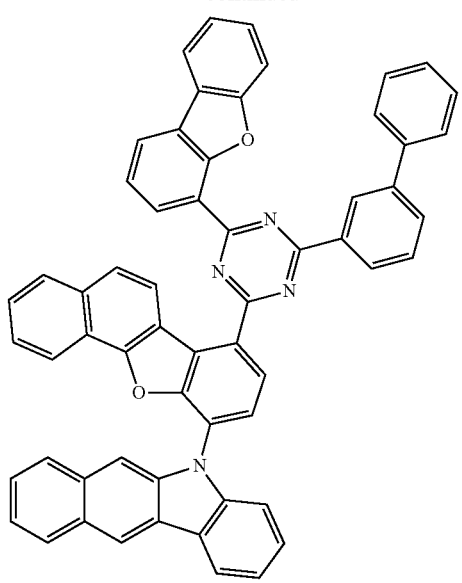
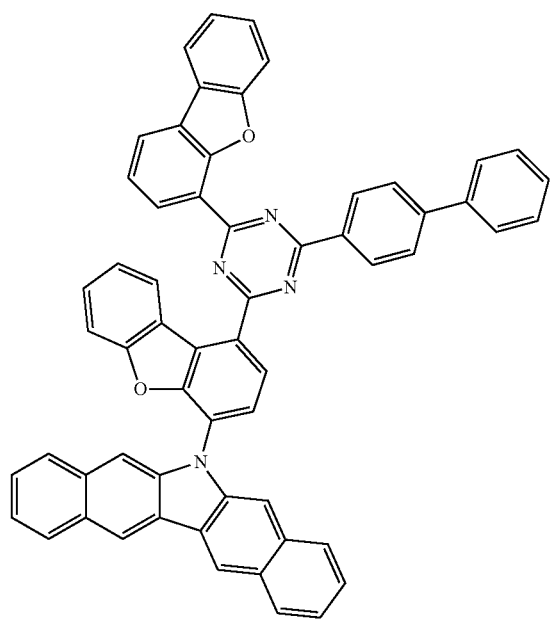
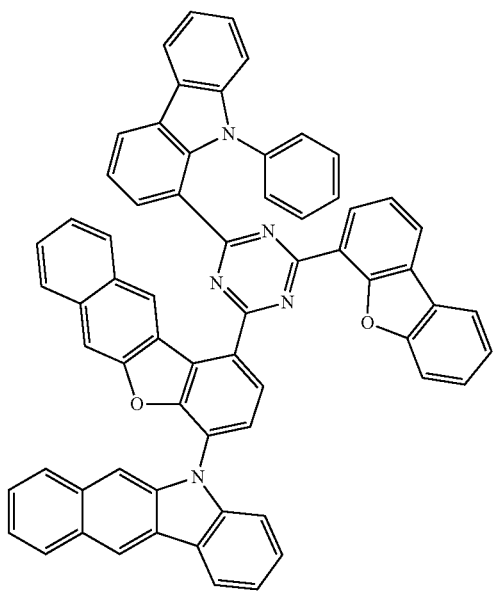

161
-continued
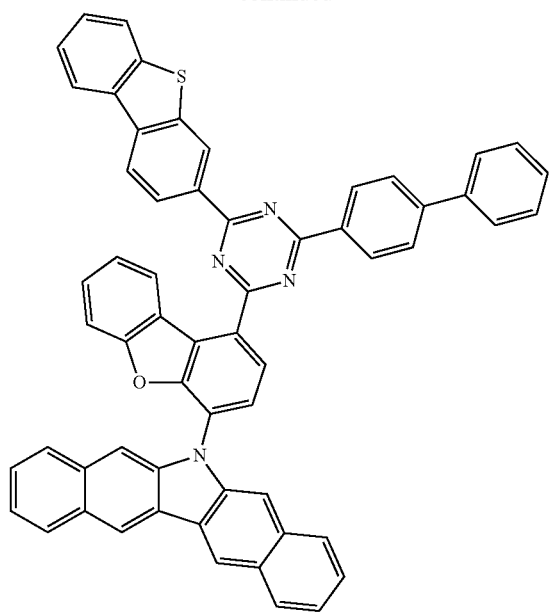
162
-continued
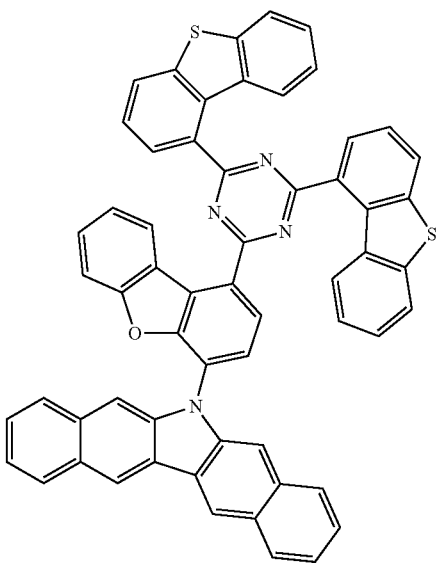
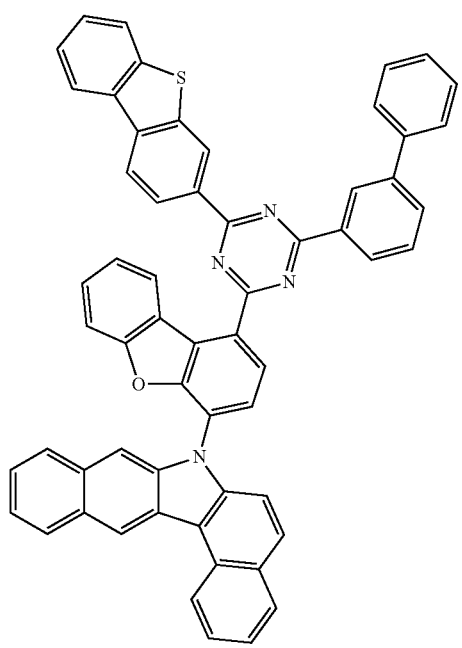
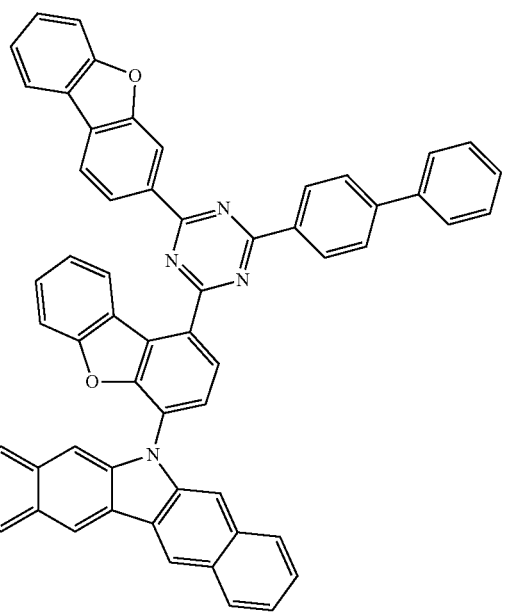

163
-continued
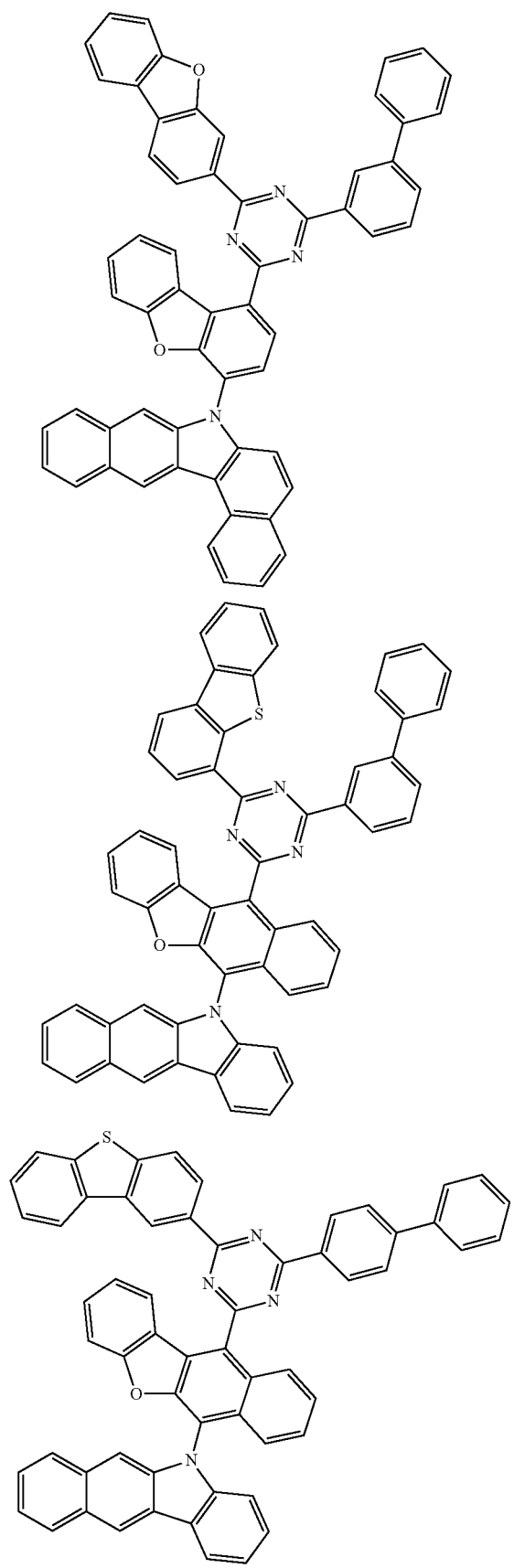
164
-continued
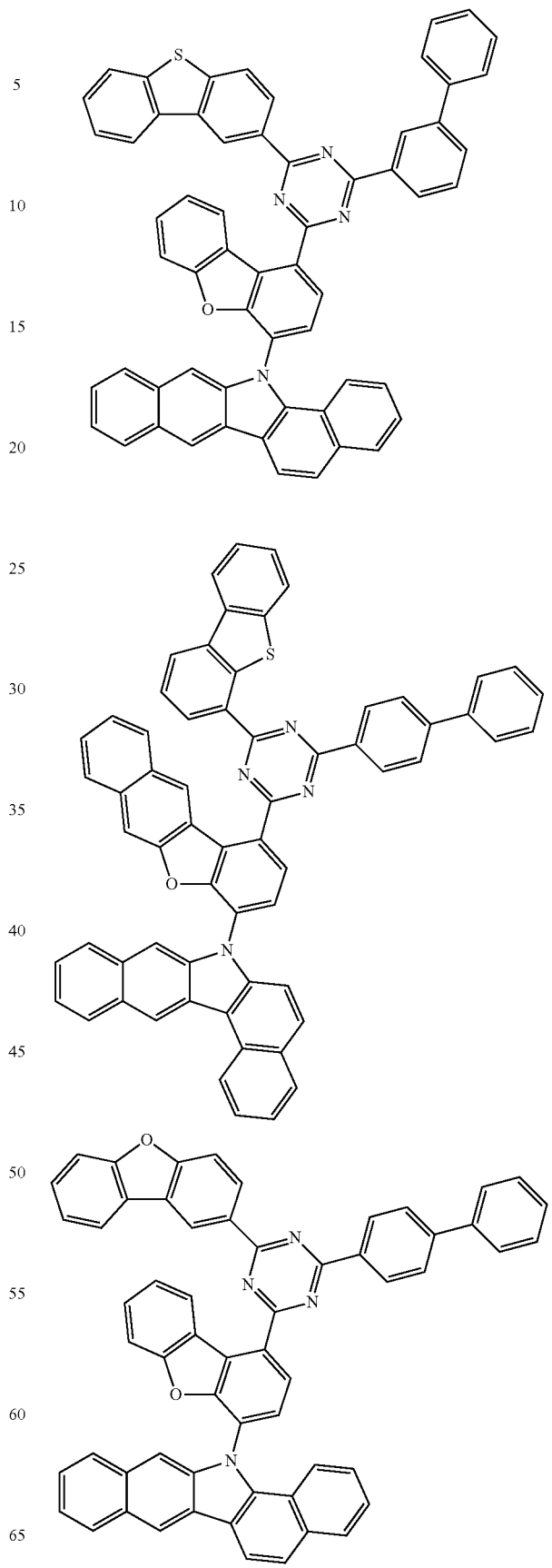

-continued
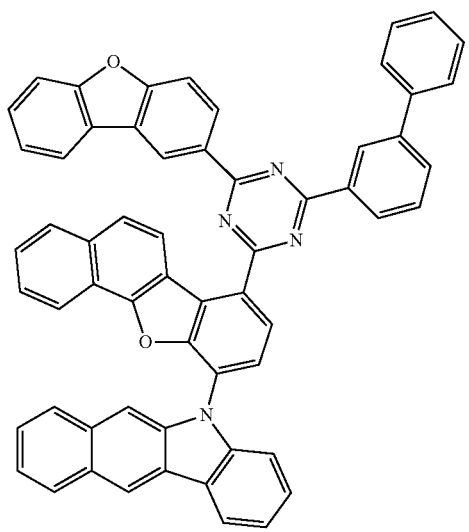
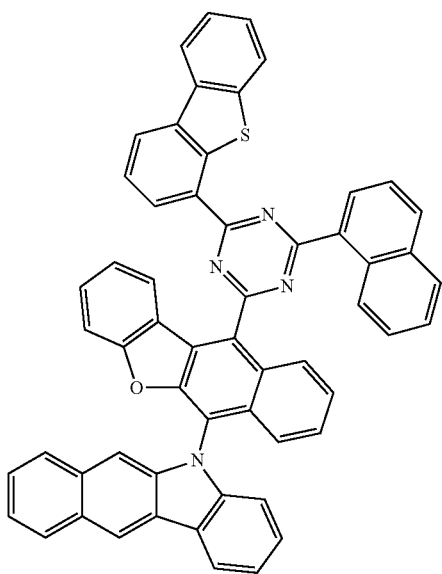
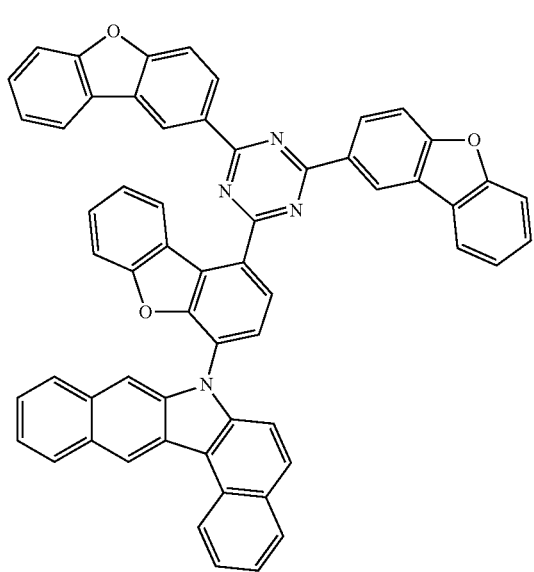
-continued
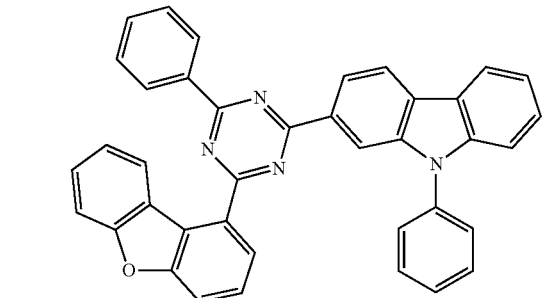
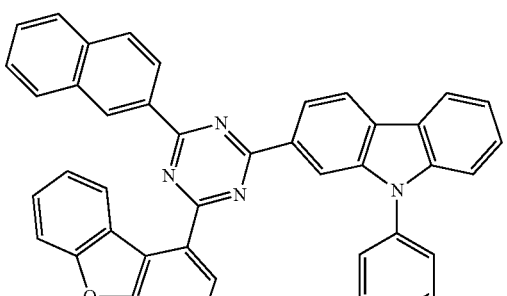
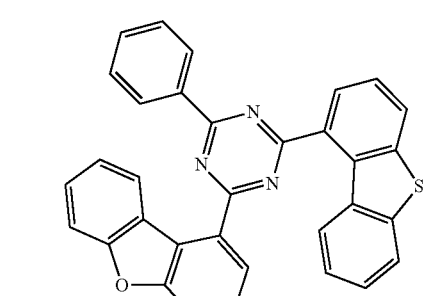

167
-continued
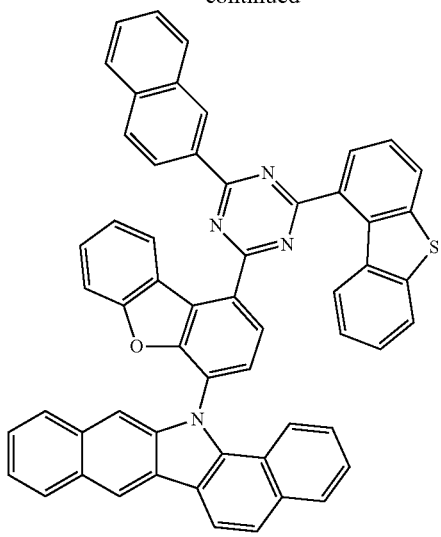
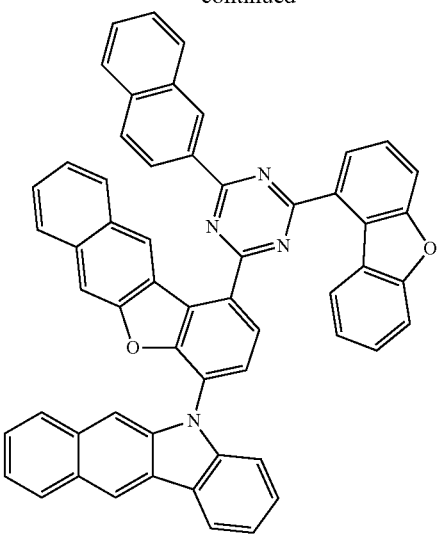
168
-continued
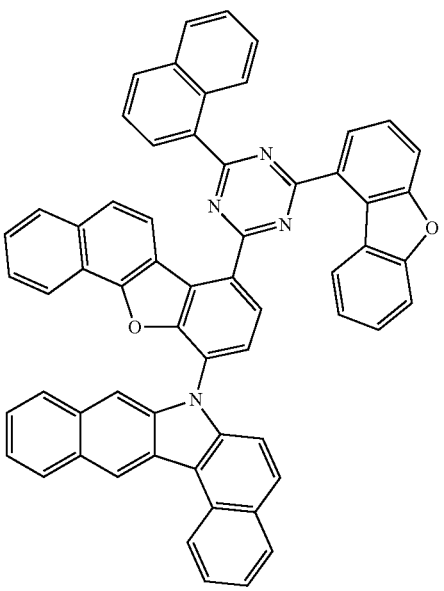
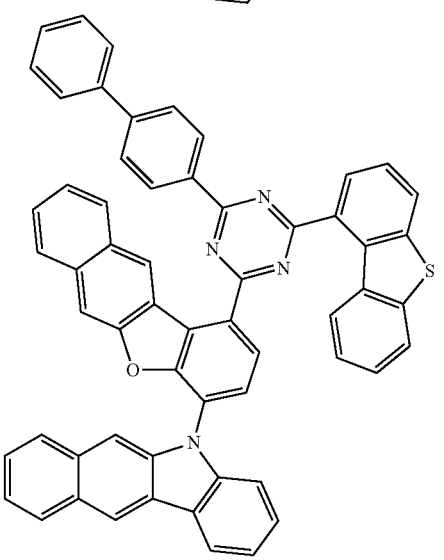

169
-continued
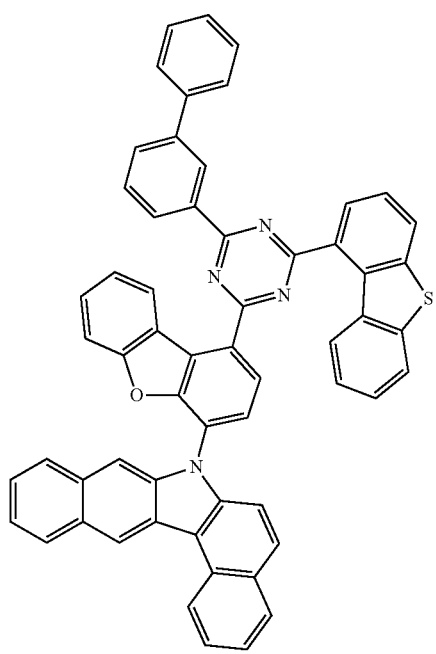
170
-continued
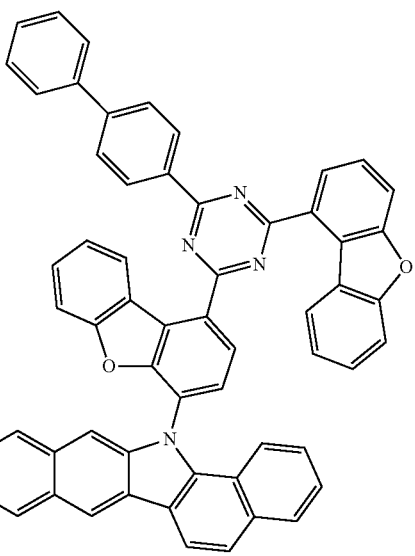
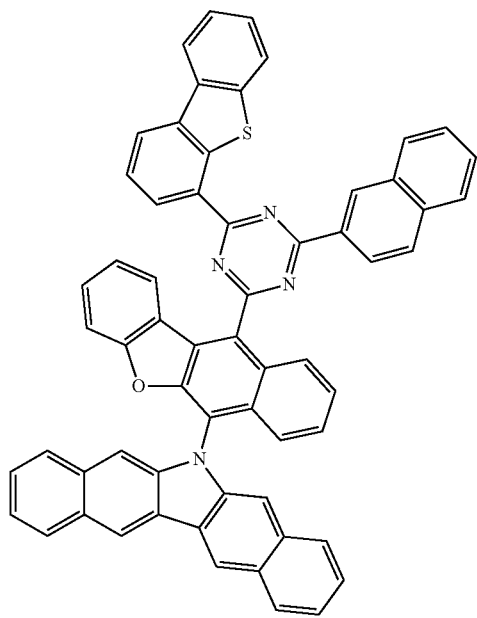
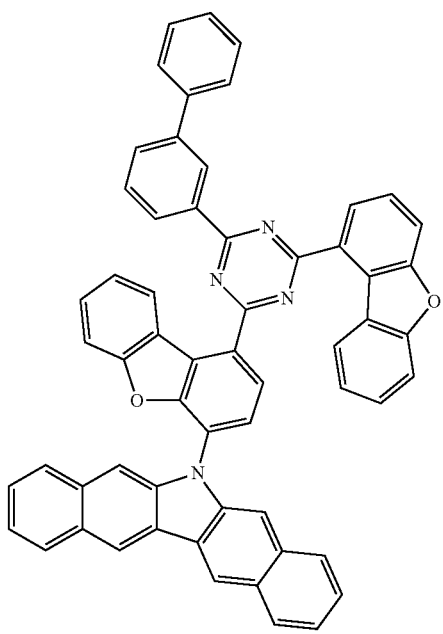

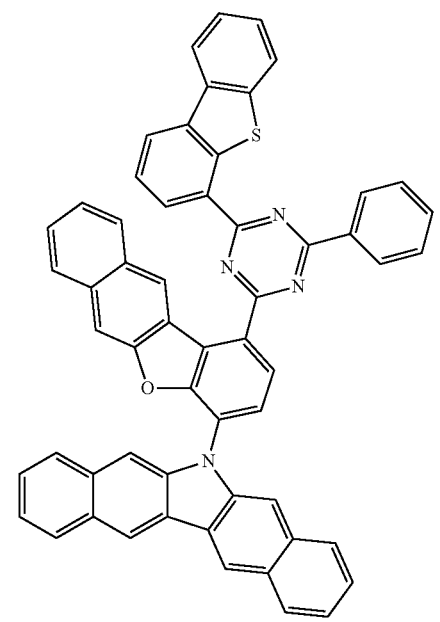 [SMILES: c1ccc(-c2nc(-c3cccc4c3sc3ccccc34)nc(-c3ccc(-n4c5cc6ccccc6cc5c5cc6ccccc6cc54)c4oc5cc6ccccc6cc5c34)n2)cc1]
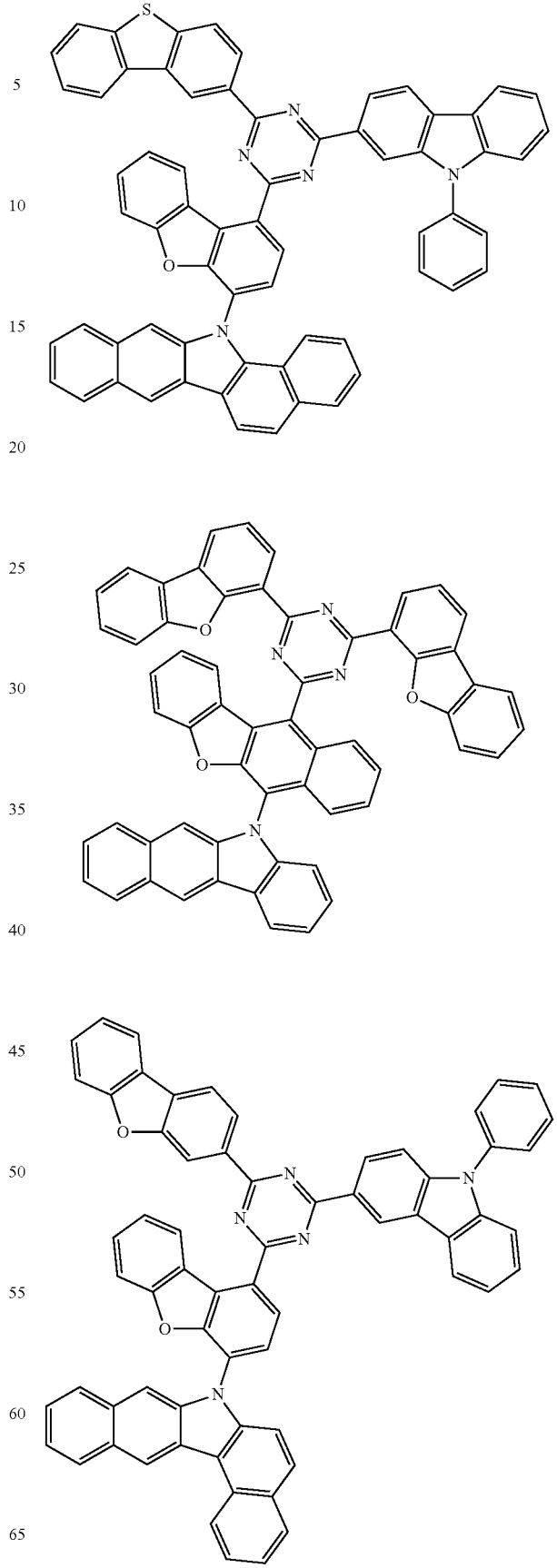

173
-continued
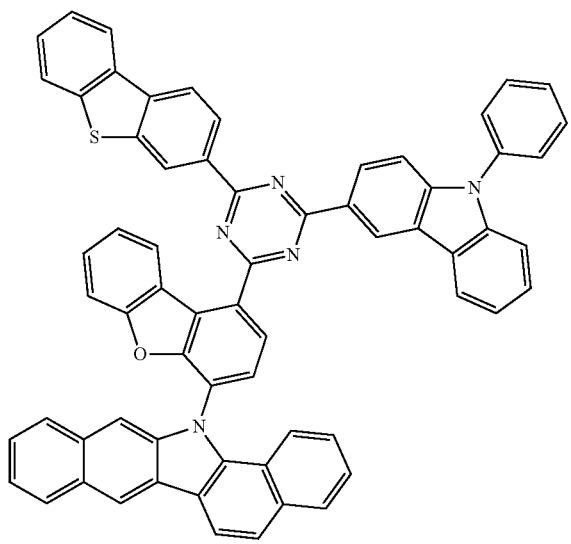
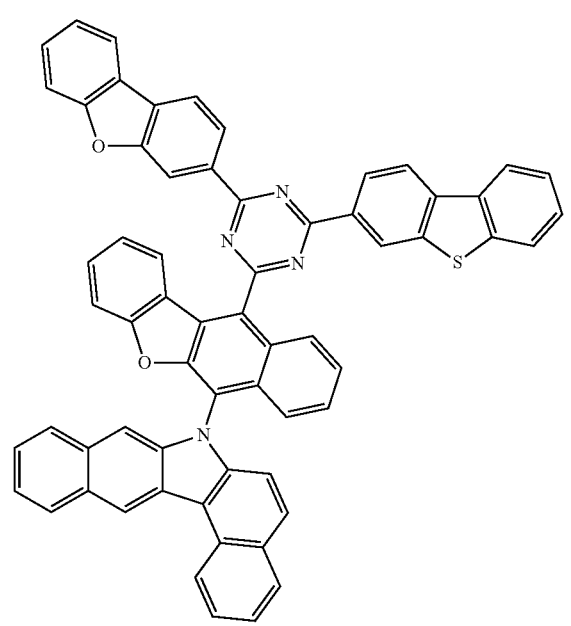
174
-continued
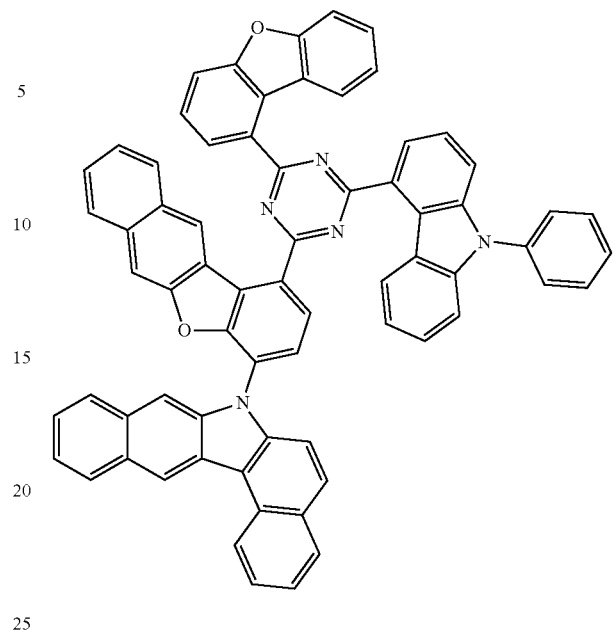
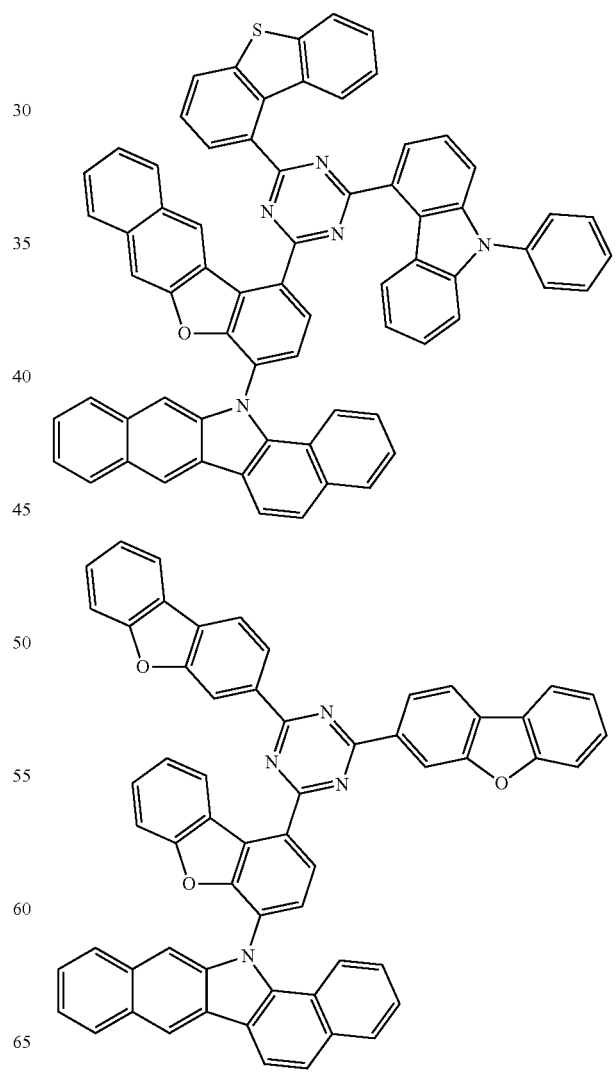

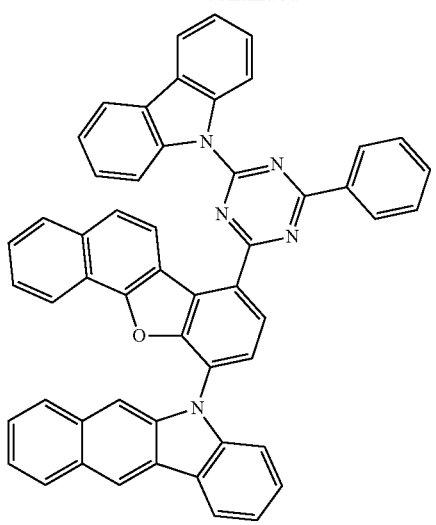
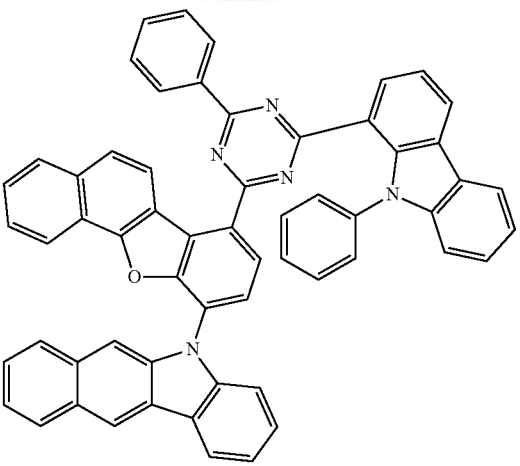
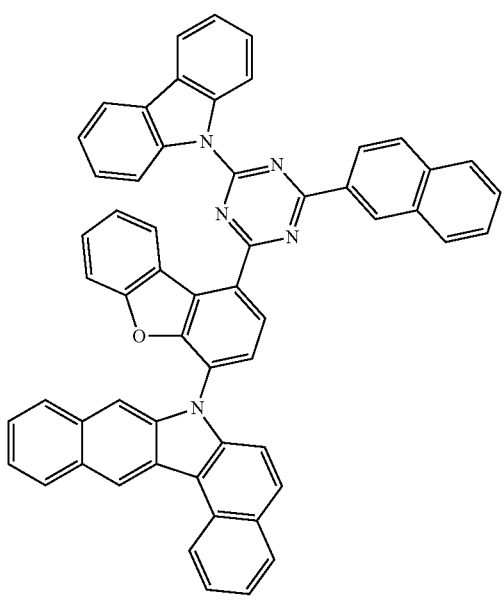
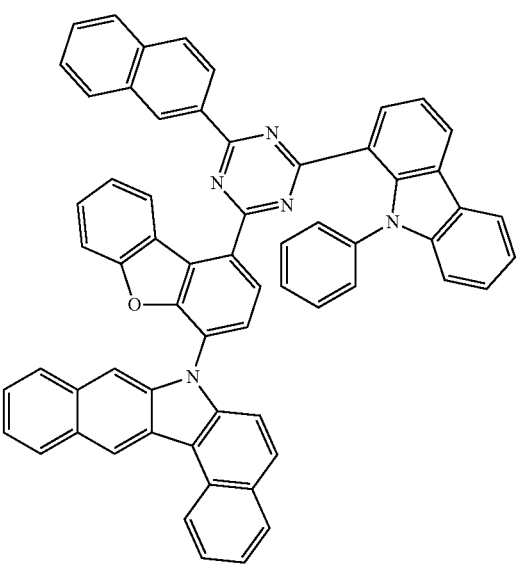
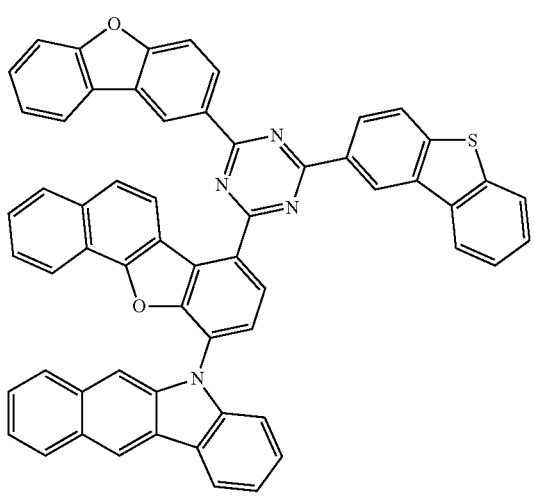
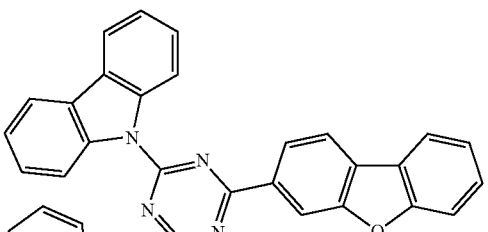

177
-continued
178
-continued
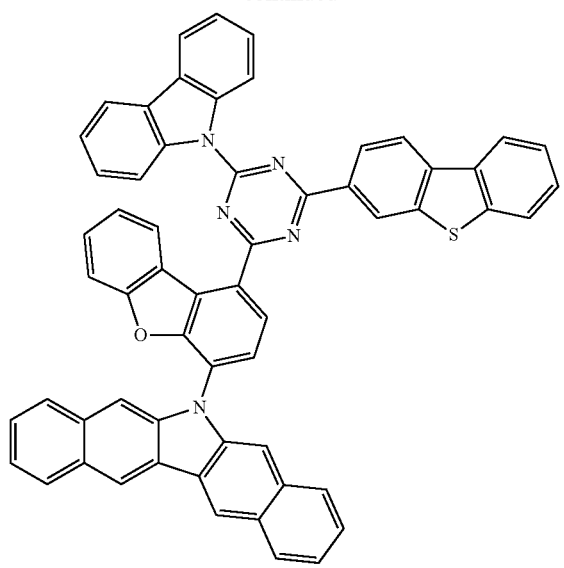
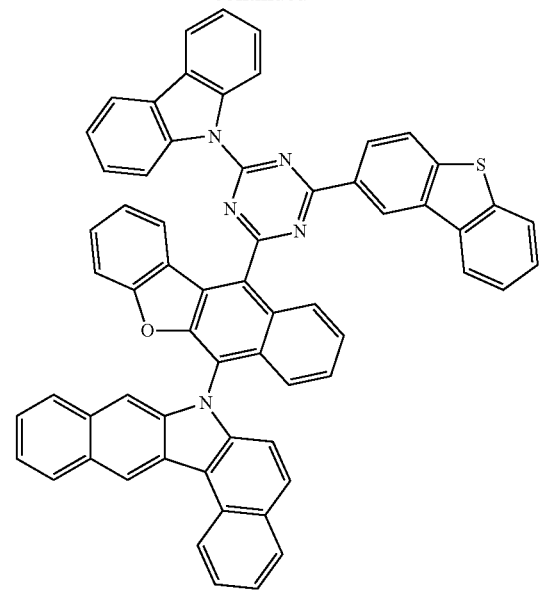
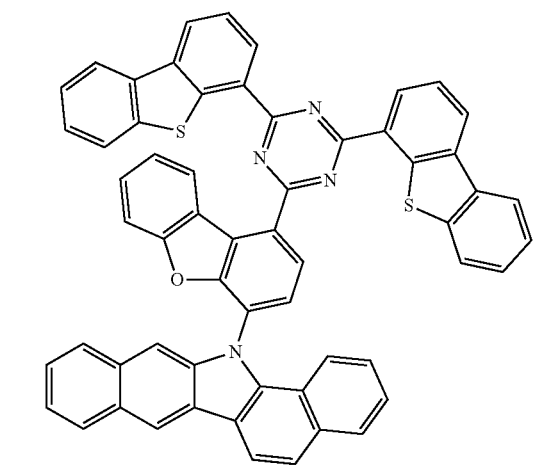
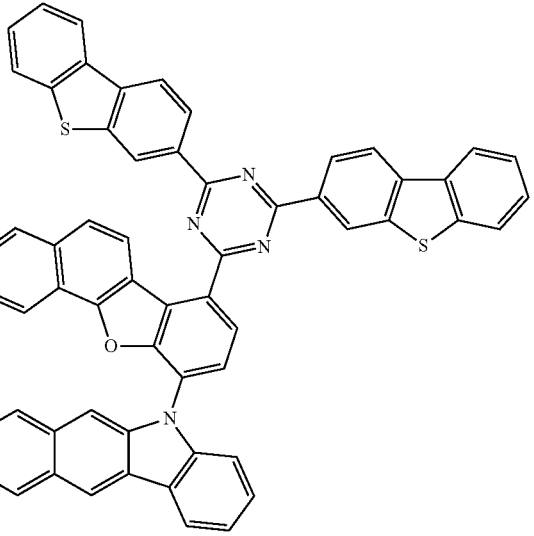
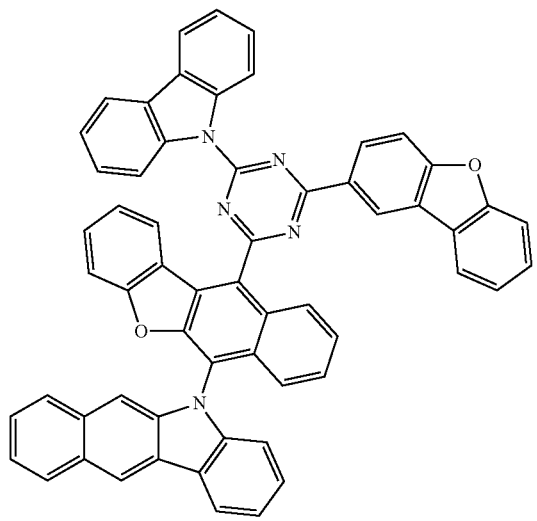
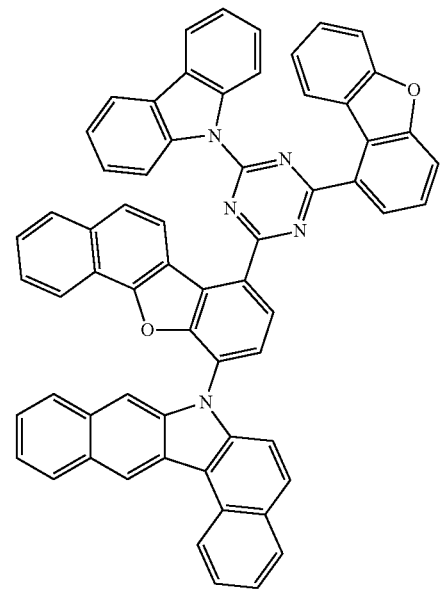

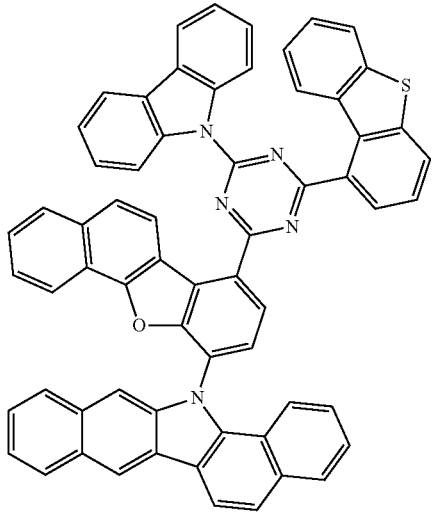
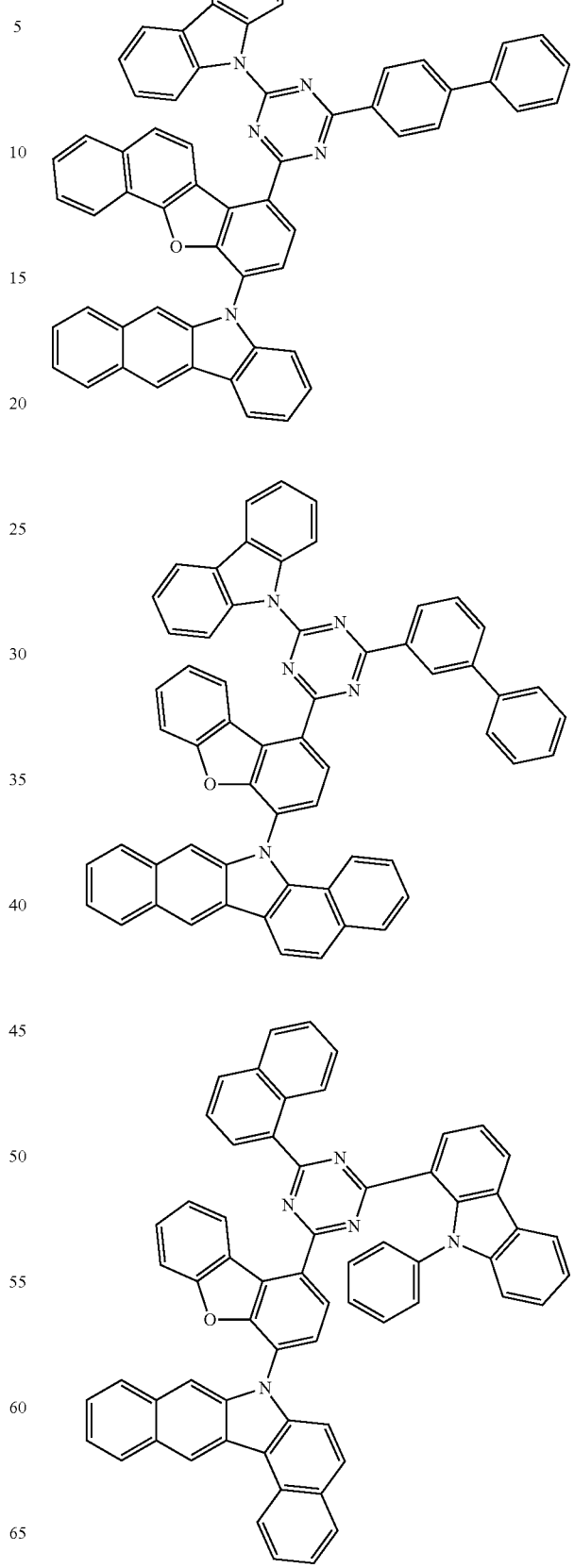

181
-continued
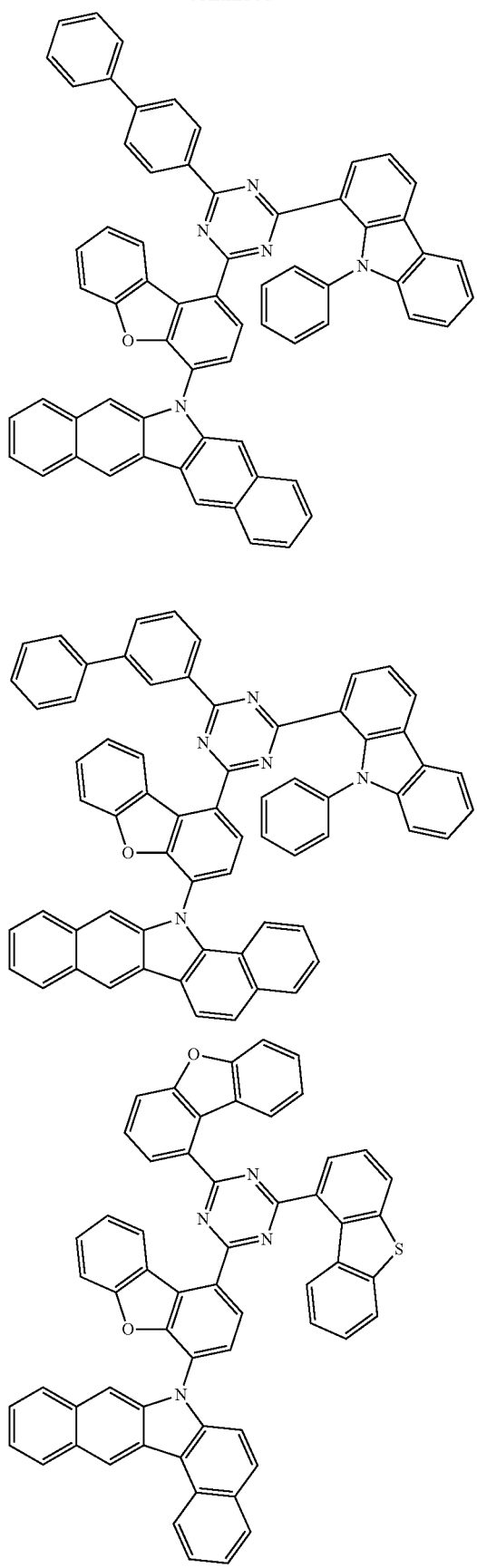
182
-continued
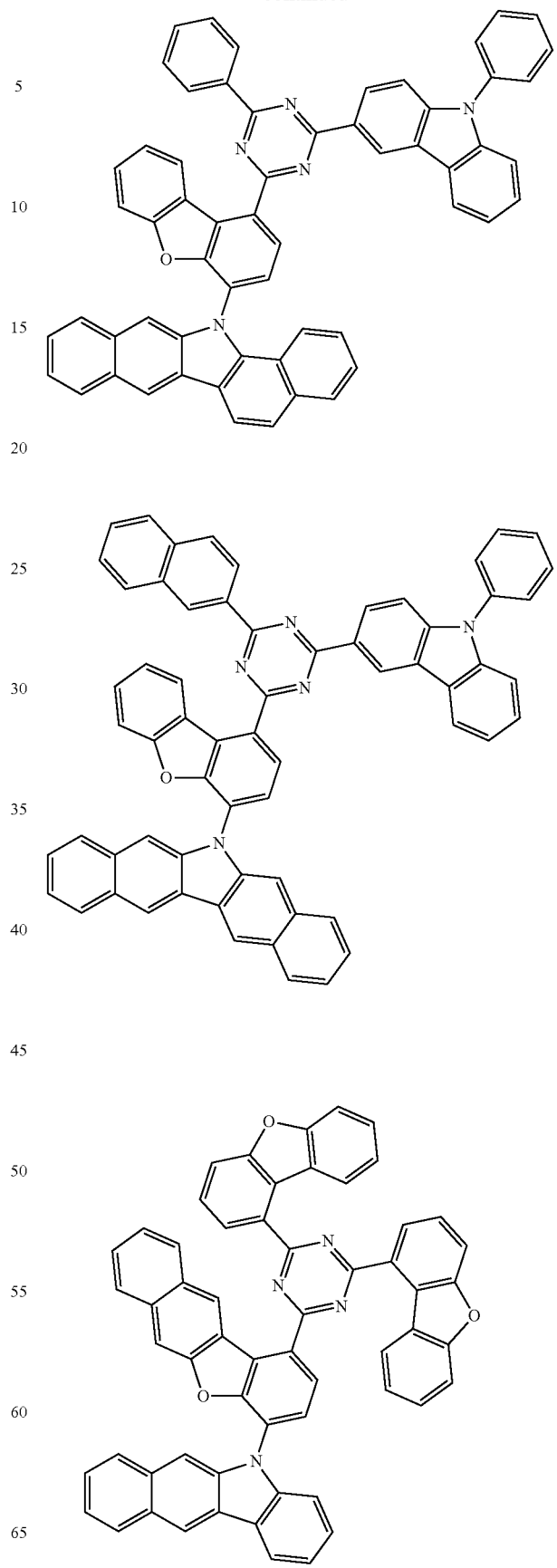

183
-continued
184
-continued
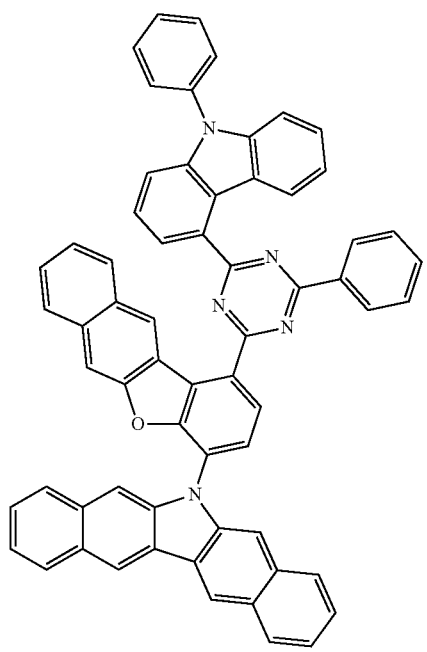
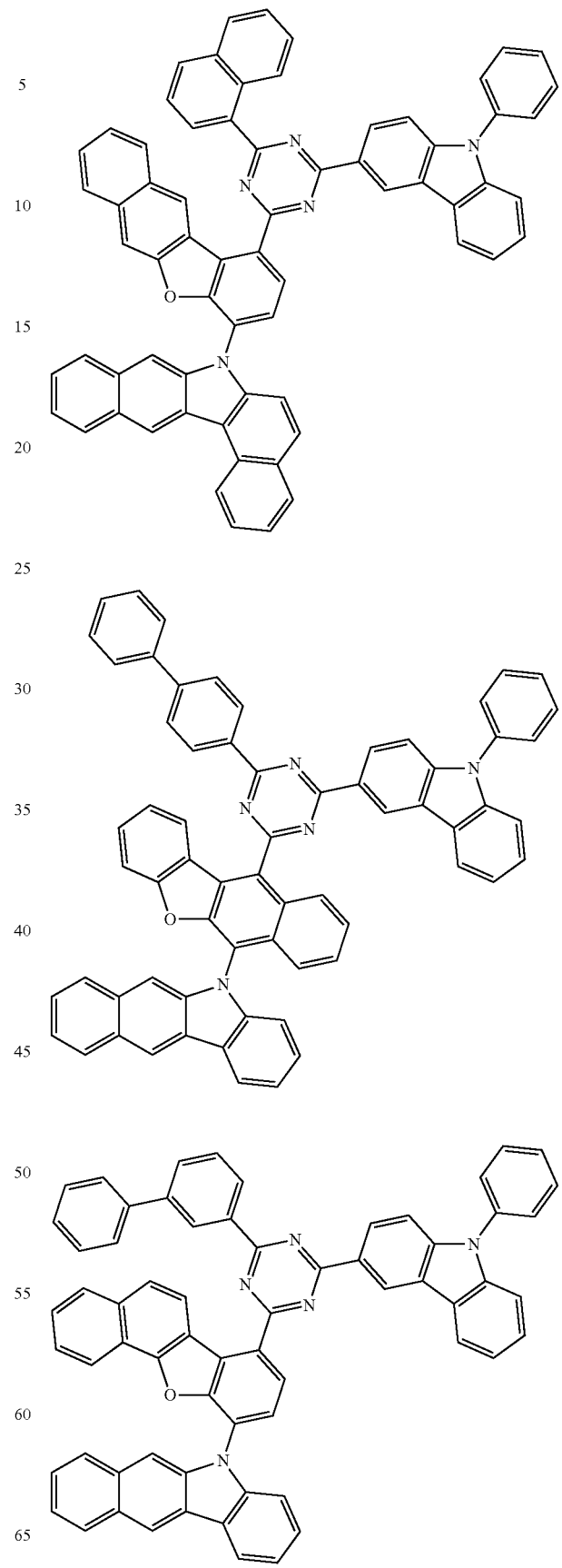

185
-continued
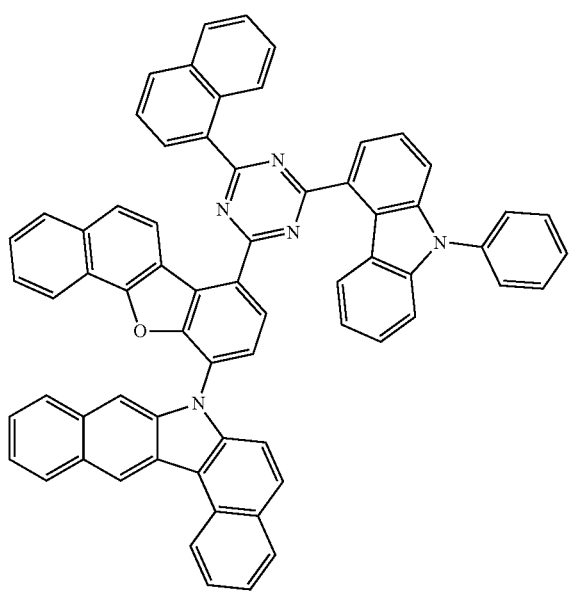
186
-continued
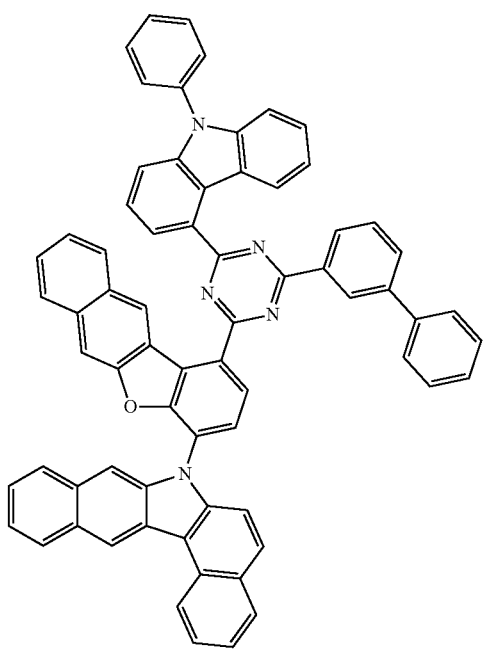
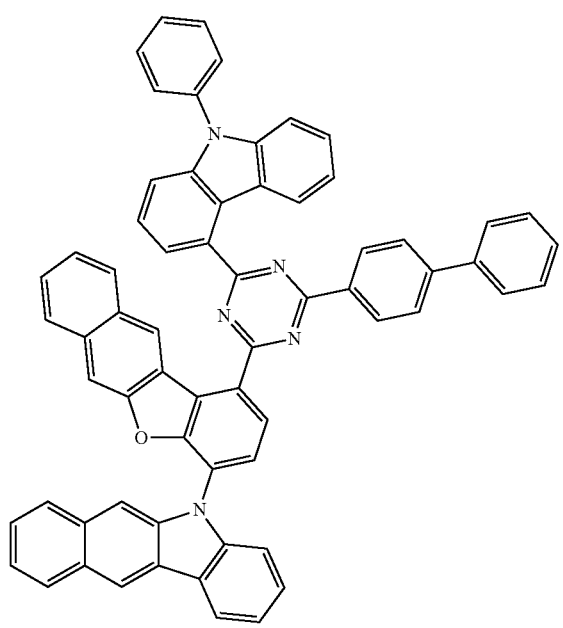
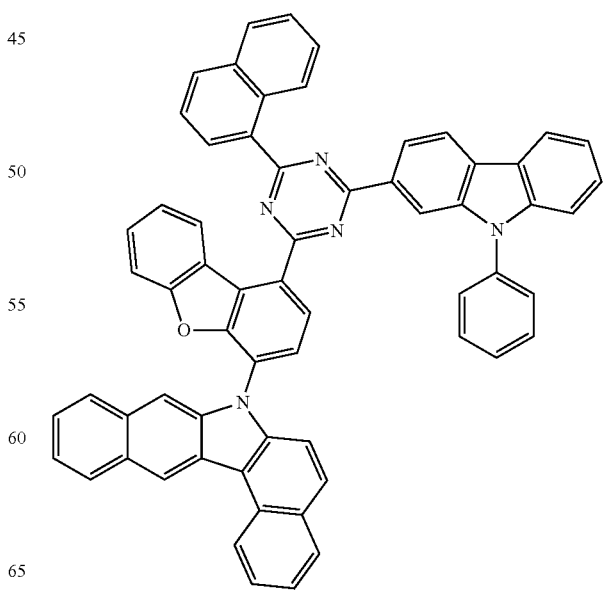

187
-continued
188
-continued
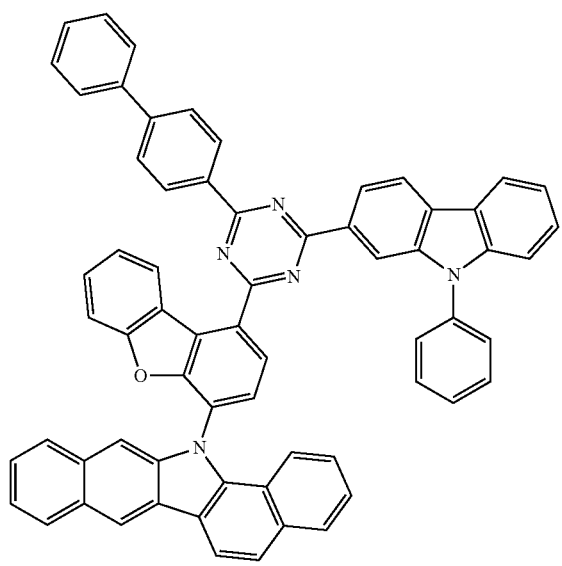
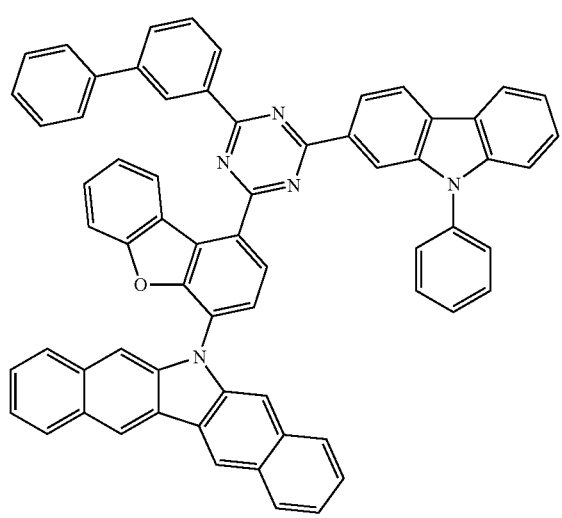
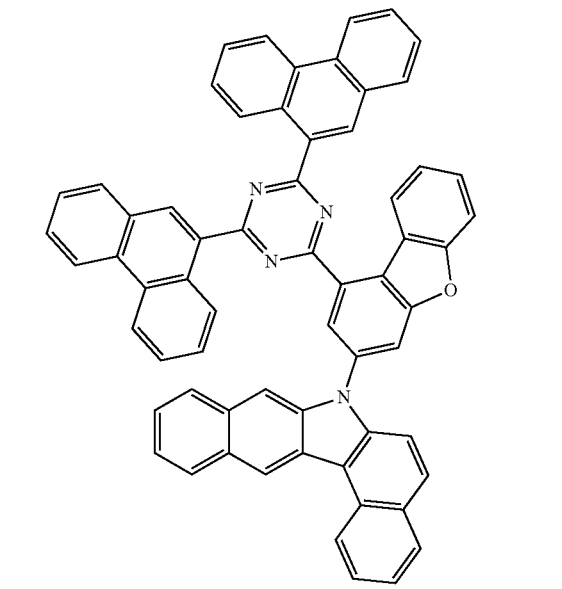
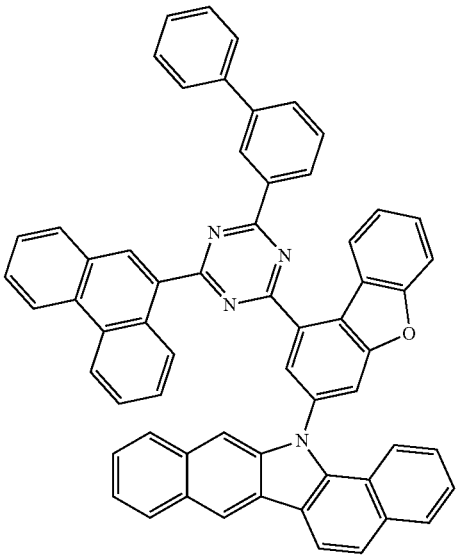

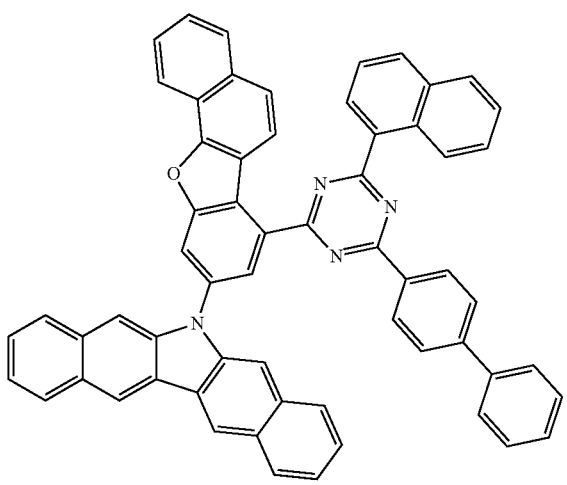
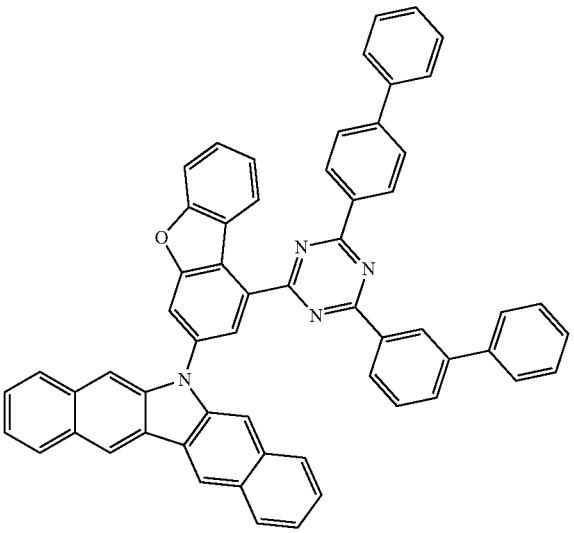
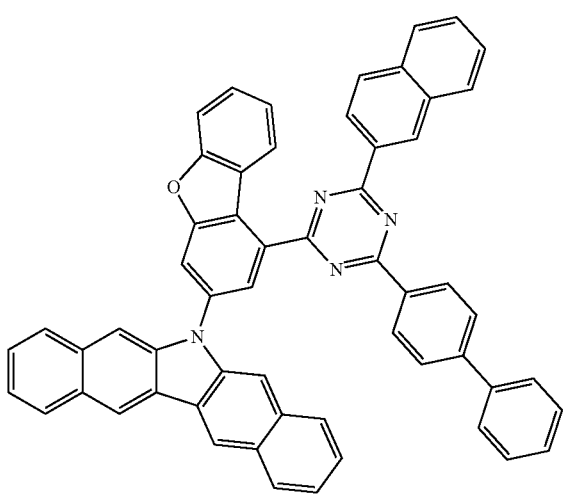
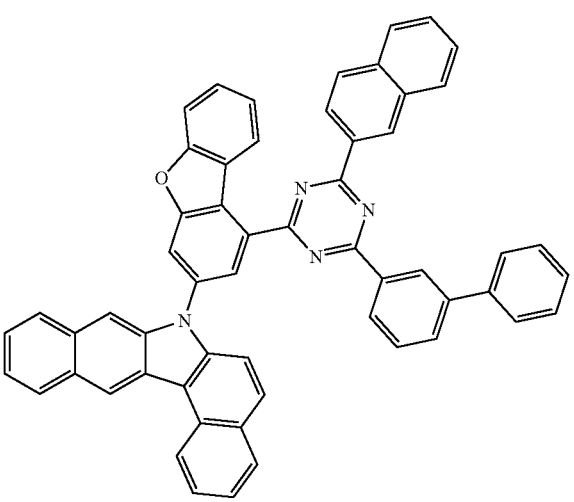
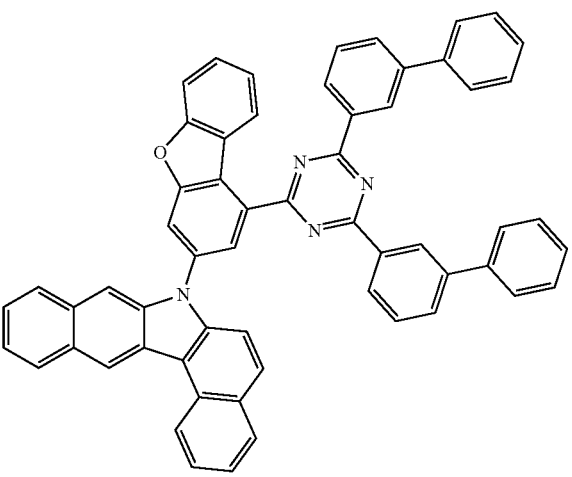
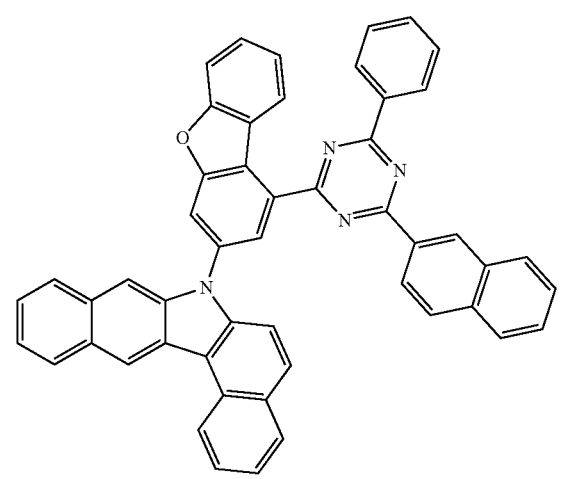

191
-continued
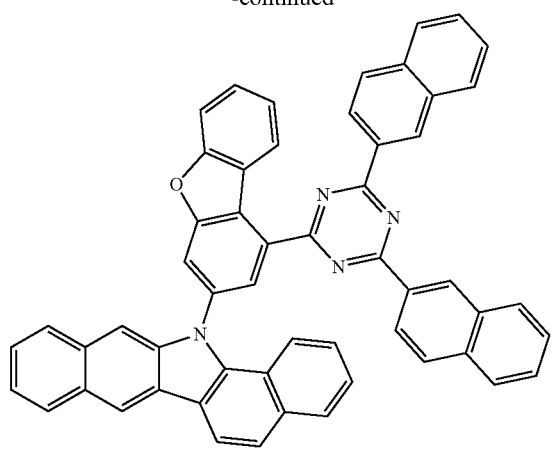
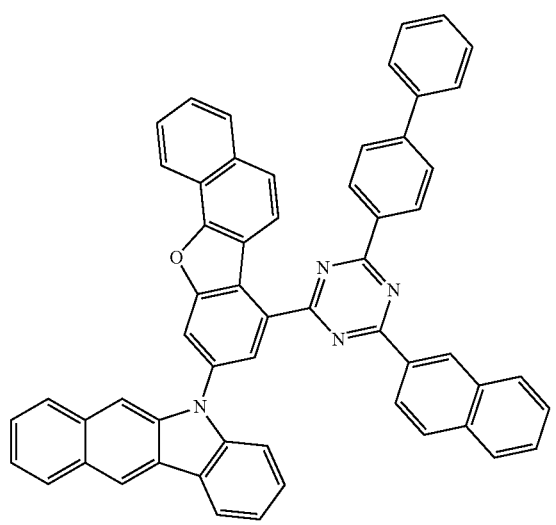
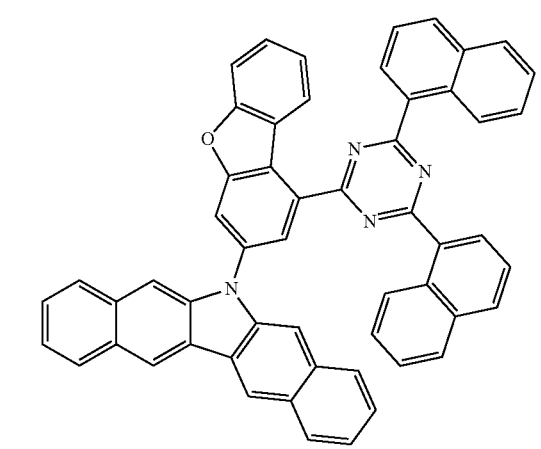
192
-continued
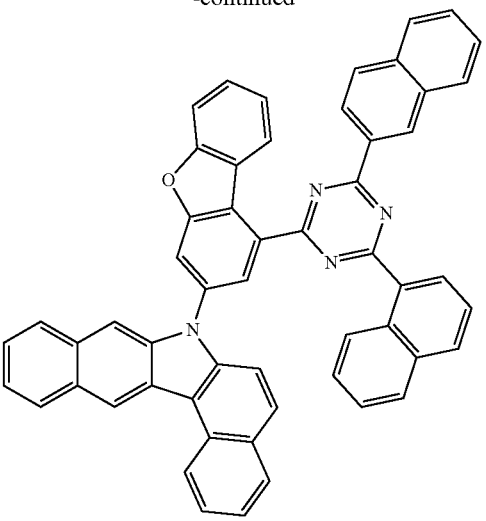
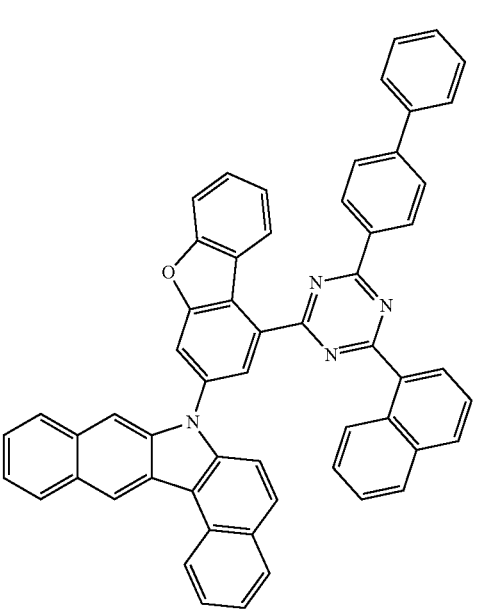
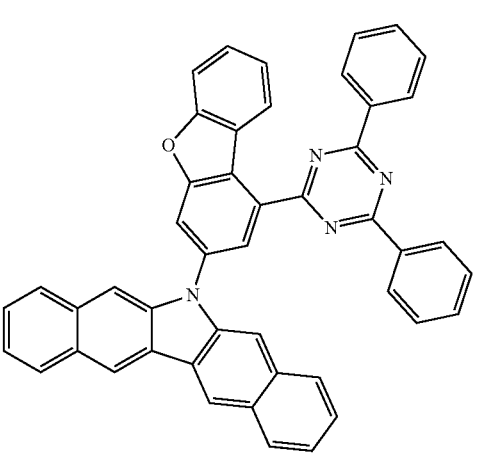

193
-continued
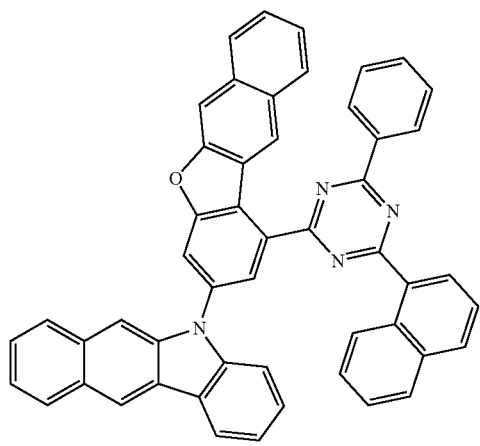
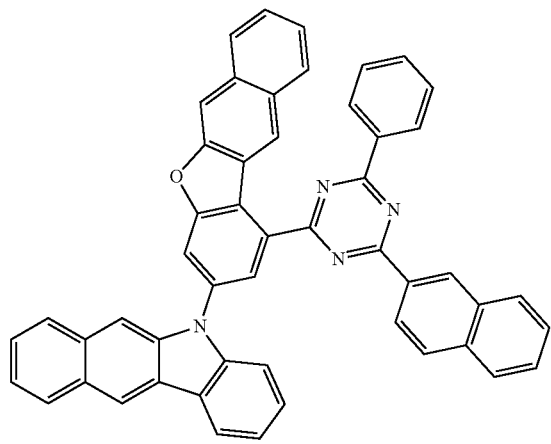
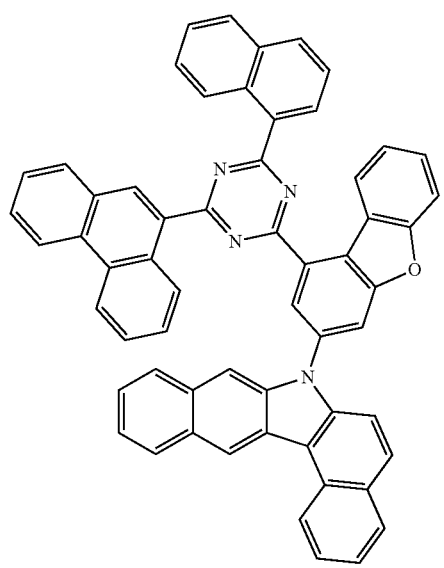
194
-continued
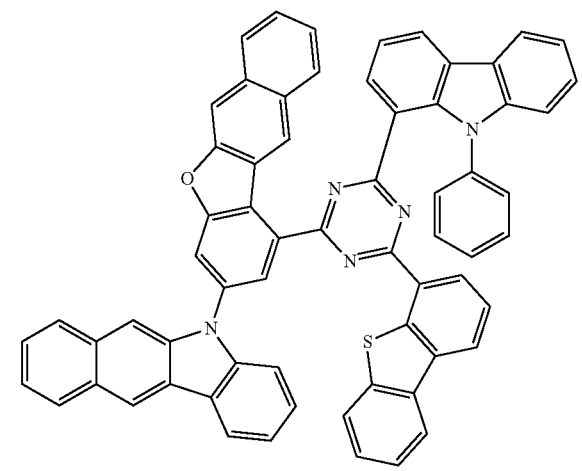
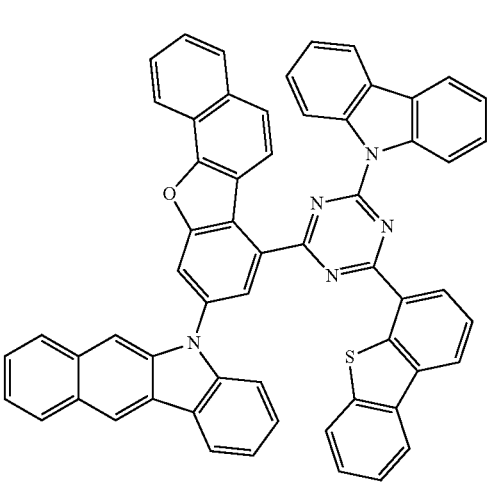
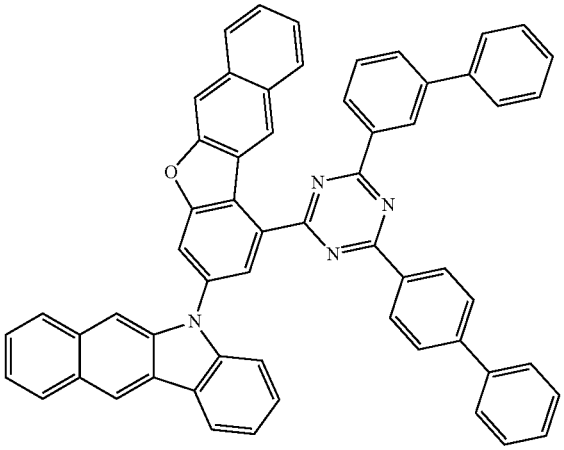

195
-continued
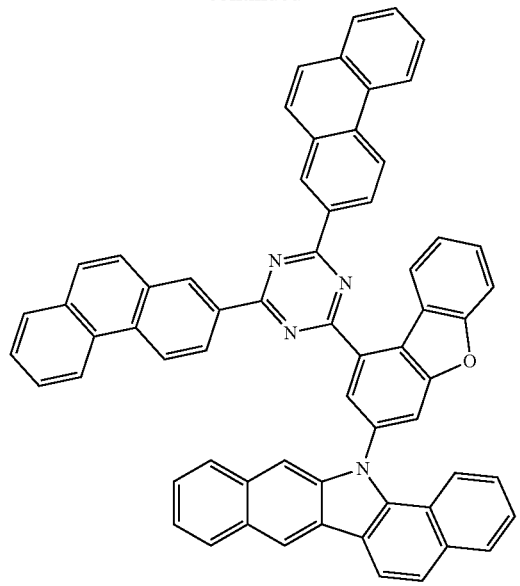
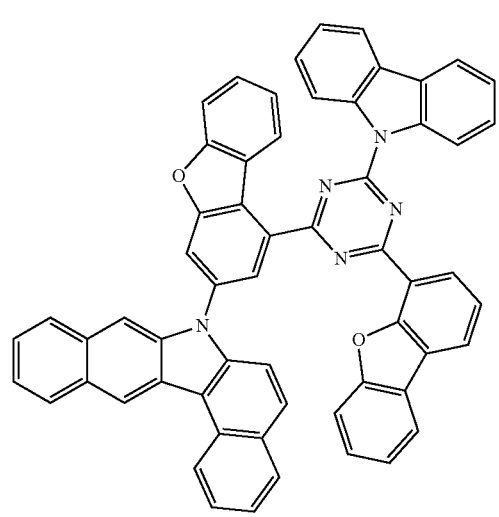
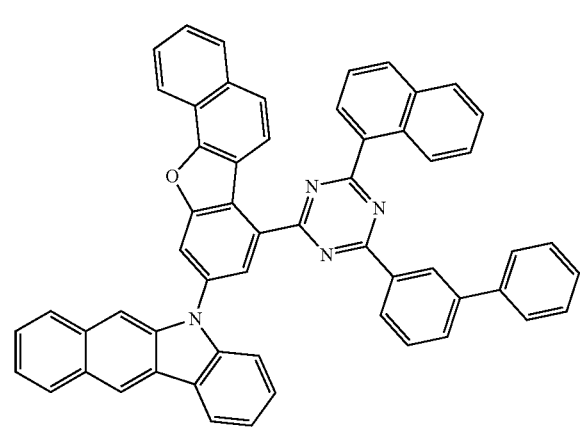
196
-continued
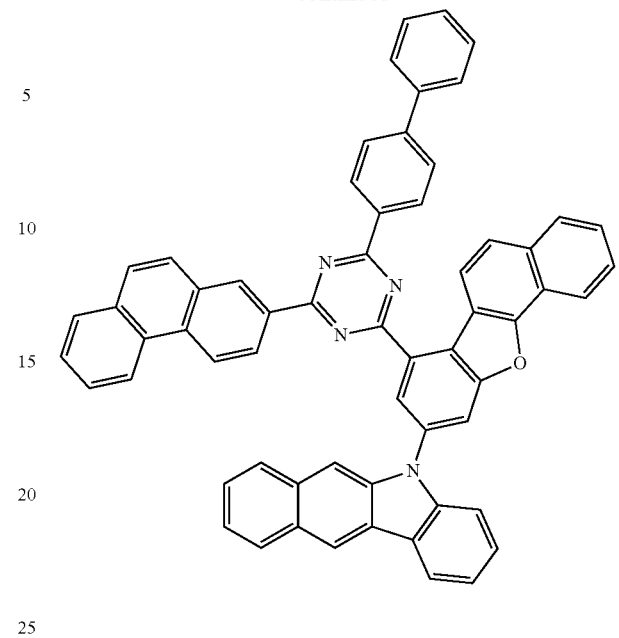
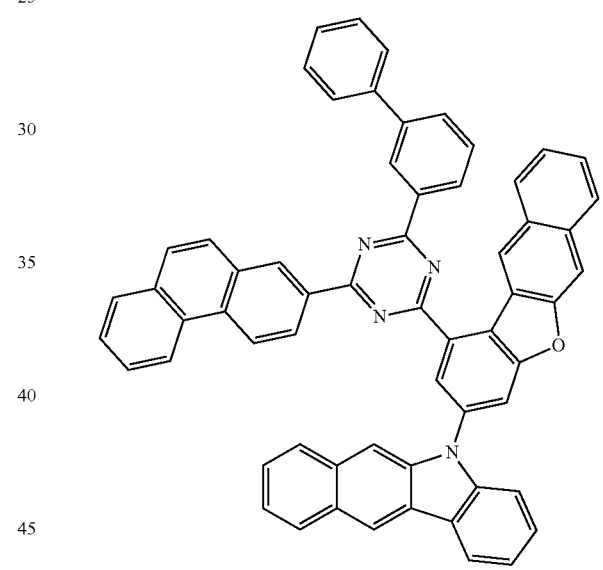
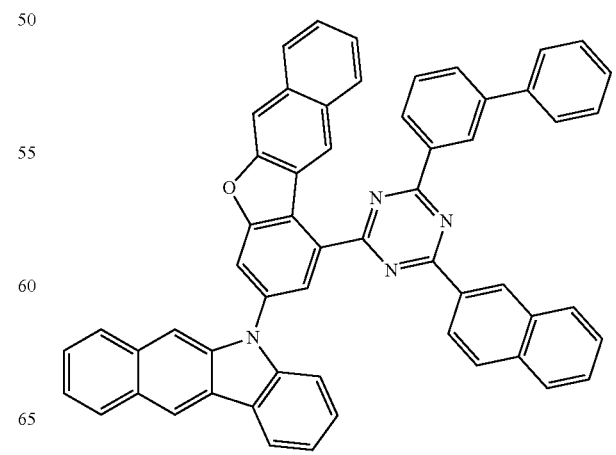

197
-continued
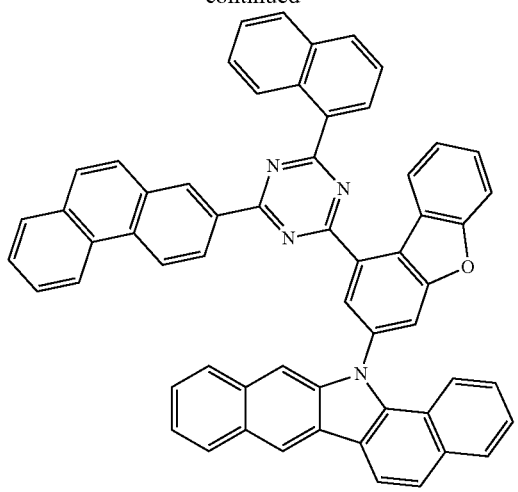
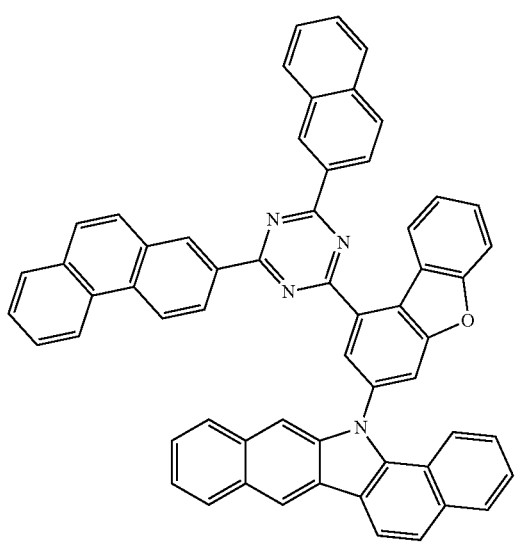
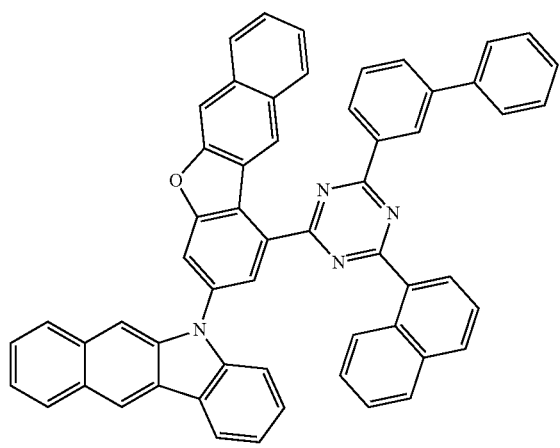
198
-continued
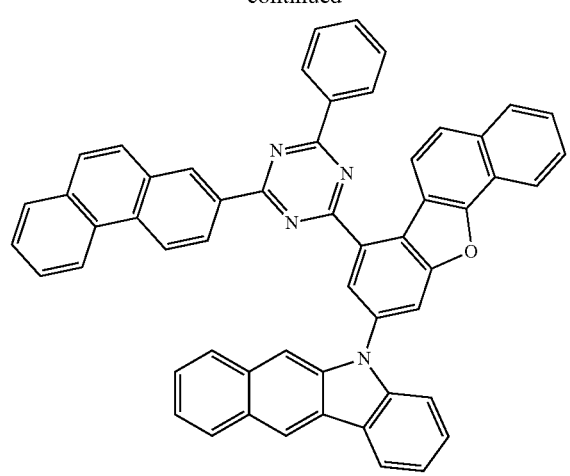
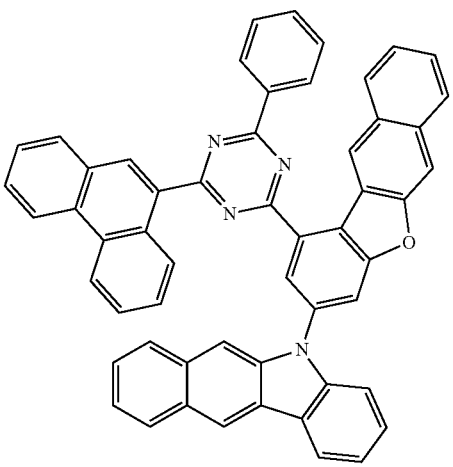
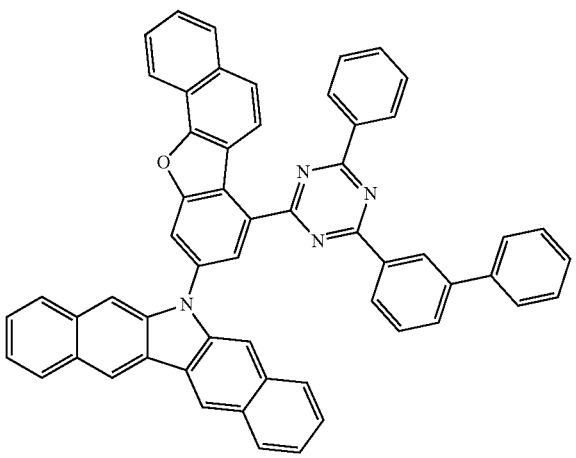

199
-continued
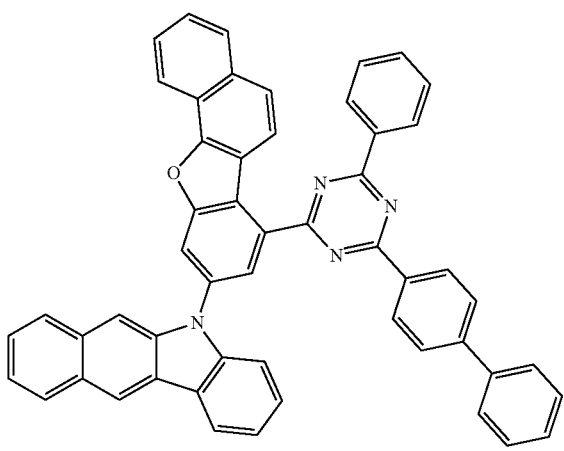
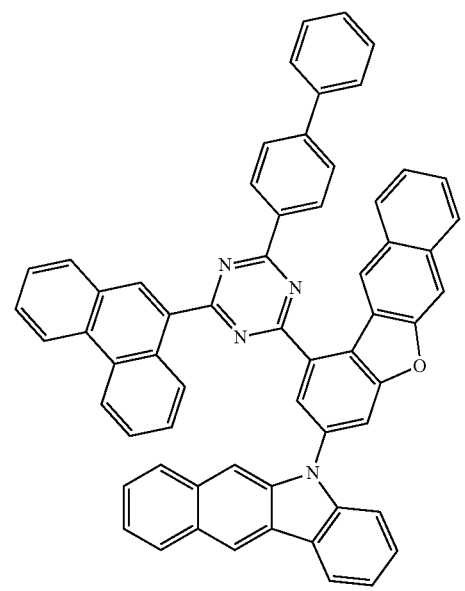
200
-continued
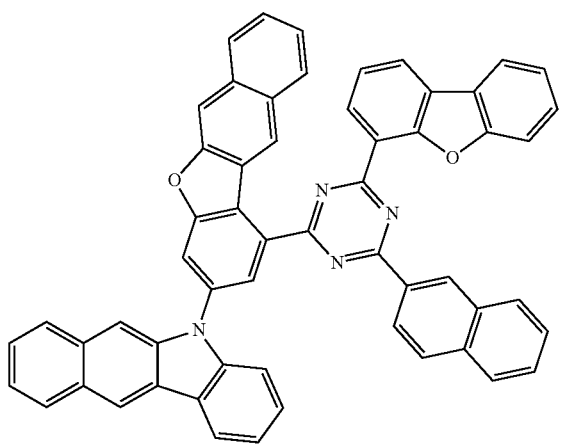
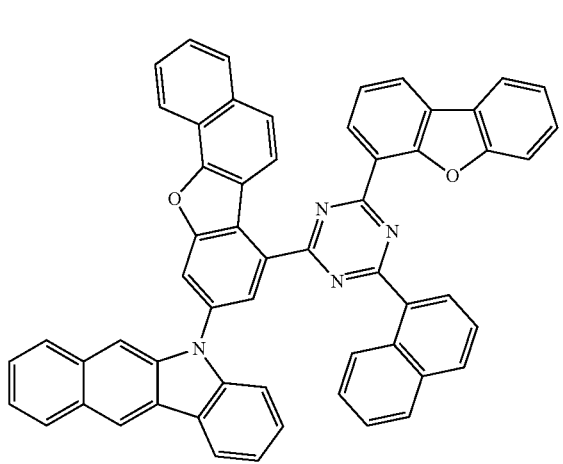
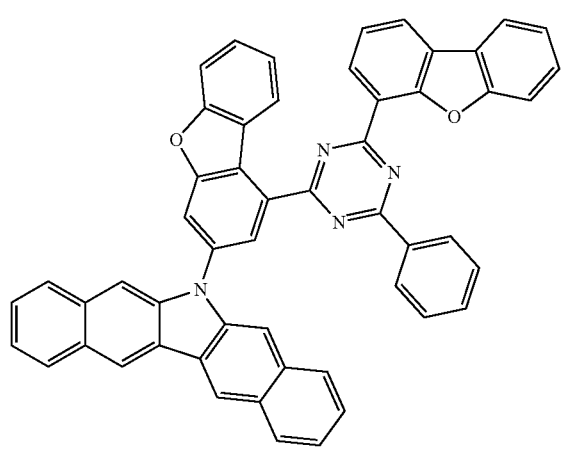
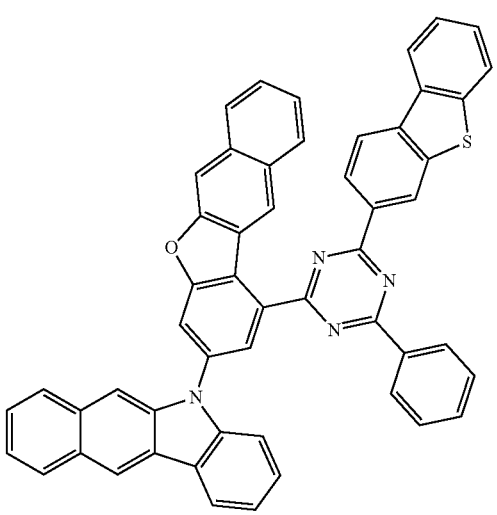

201
-continued
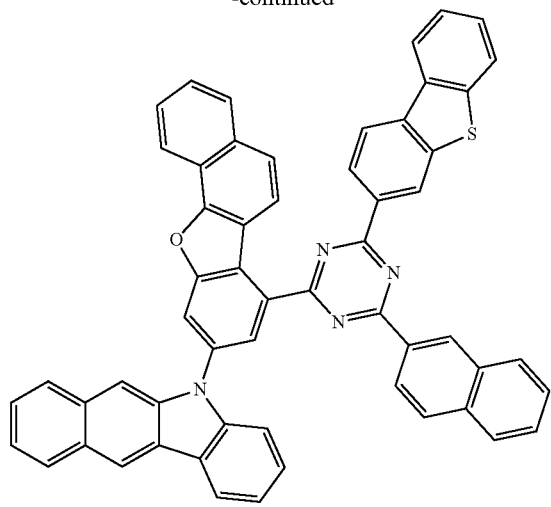
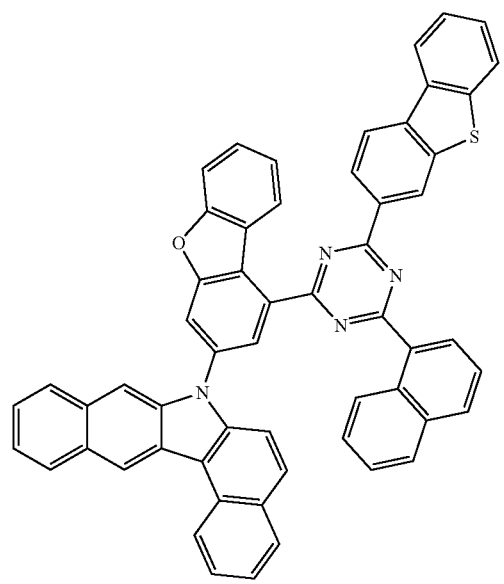
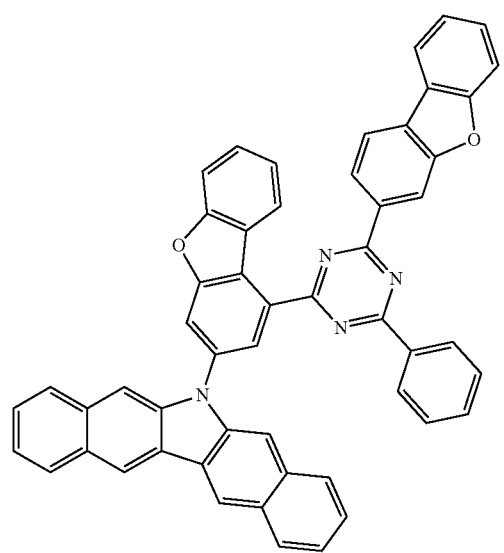
202
-continued
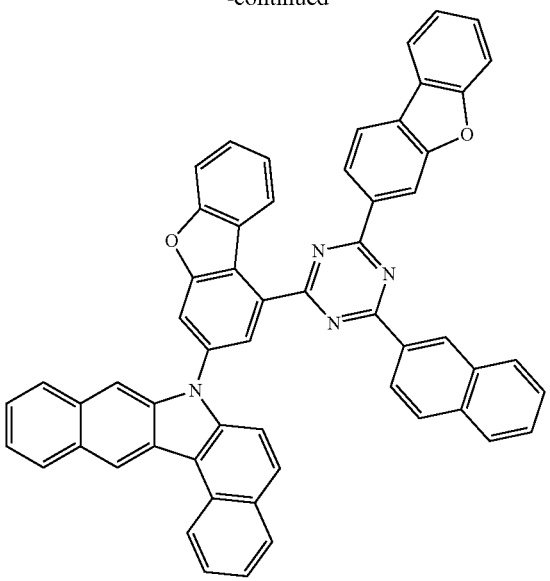
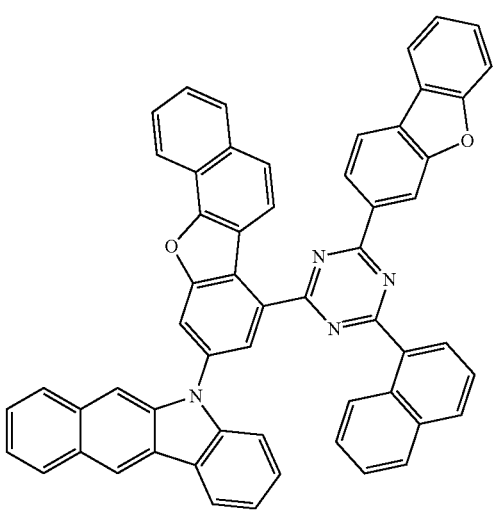
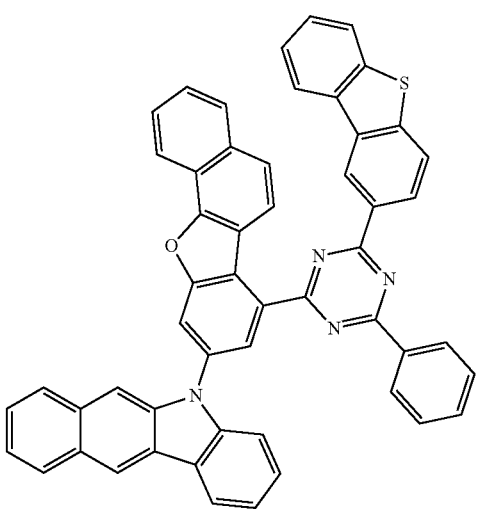

203
-continued
204
-continued
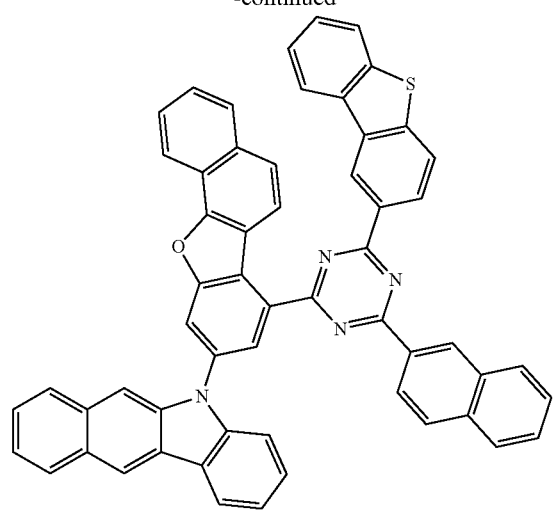
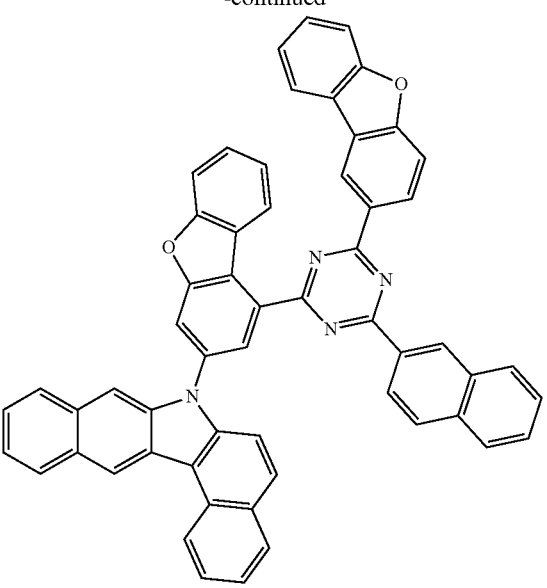
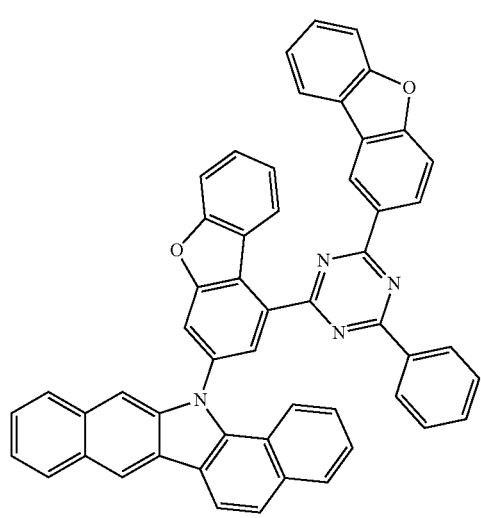
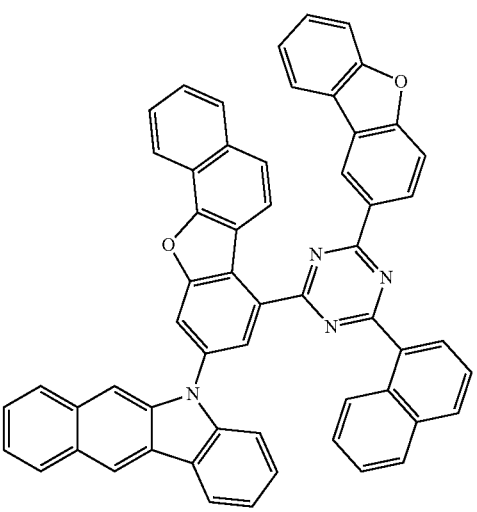

205
-continued
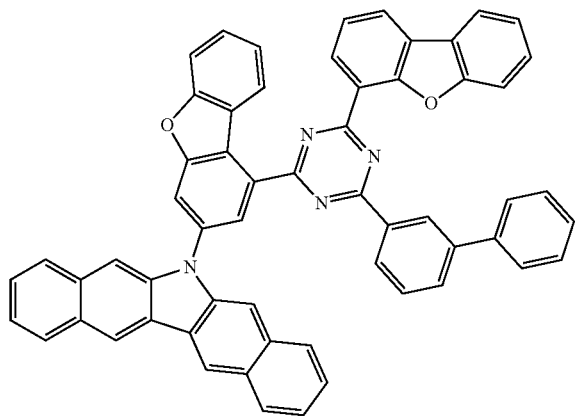
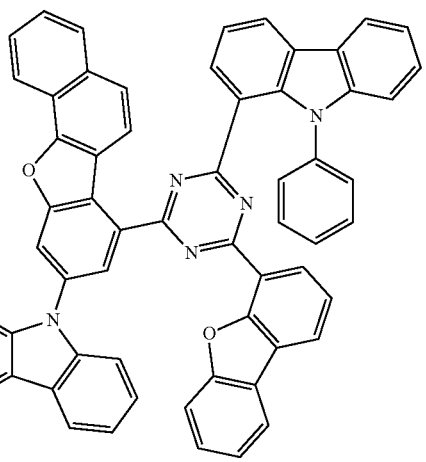
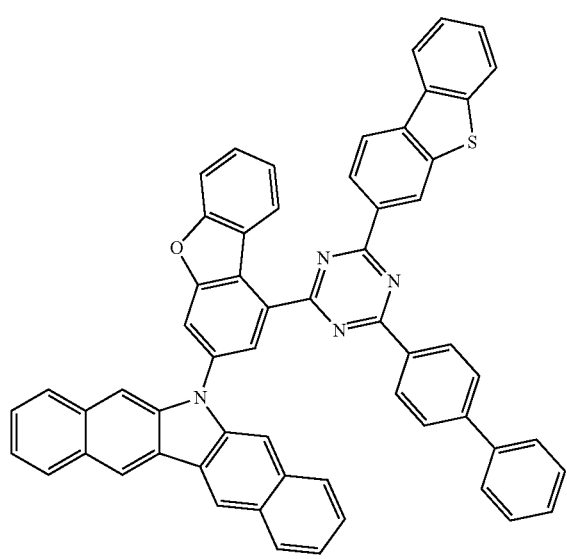
206
-continued
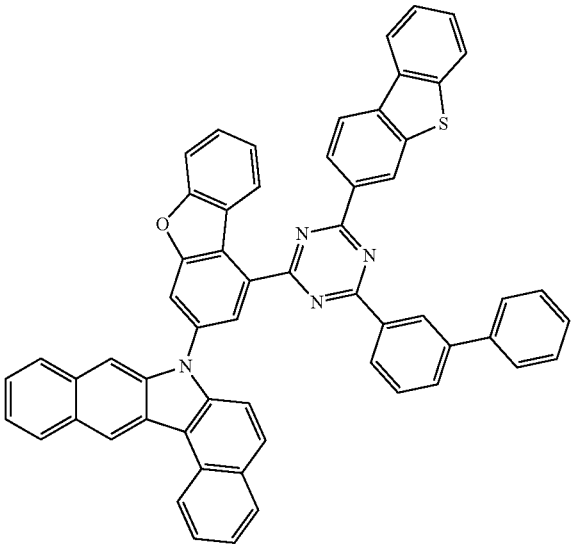
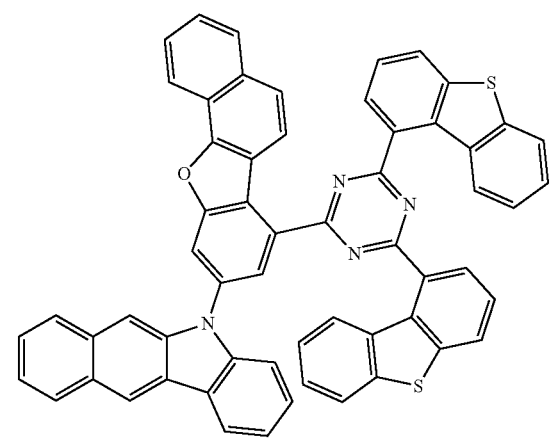
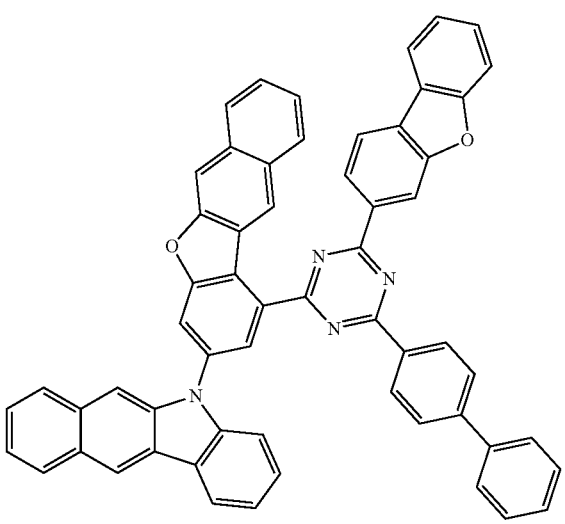

207
-continued
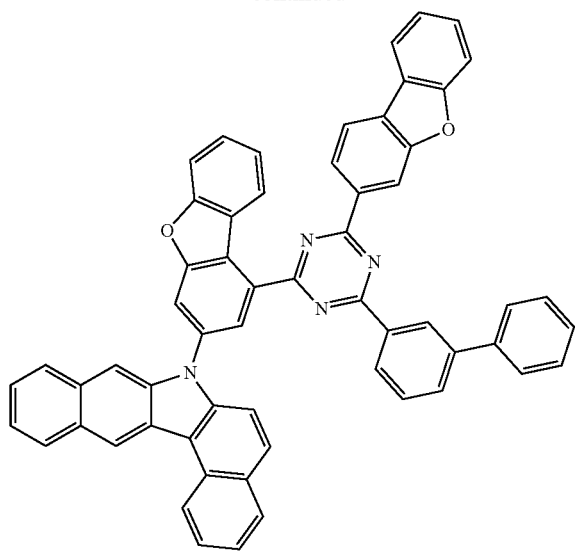
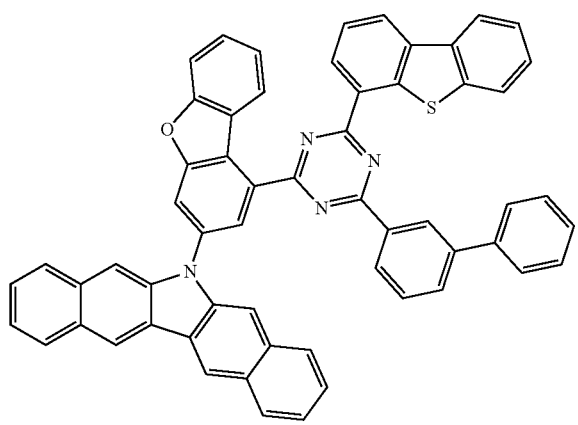
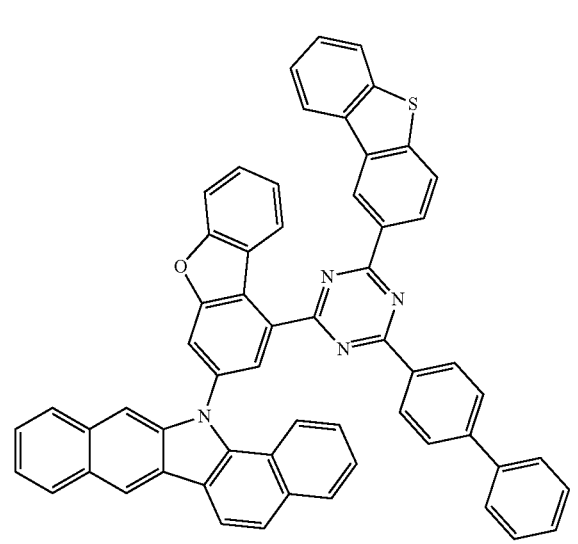
208
-continued
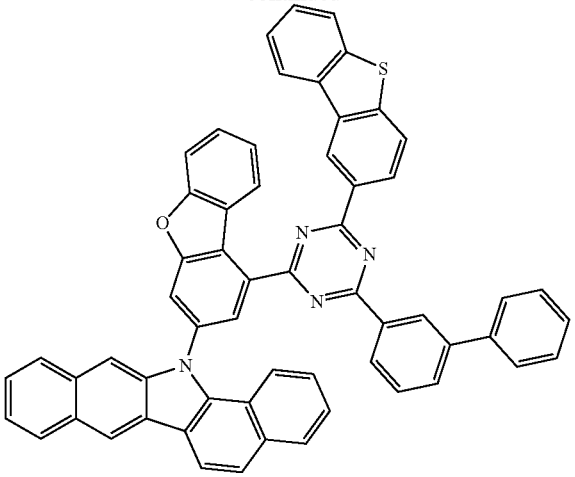
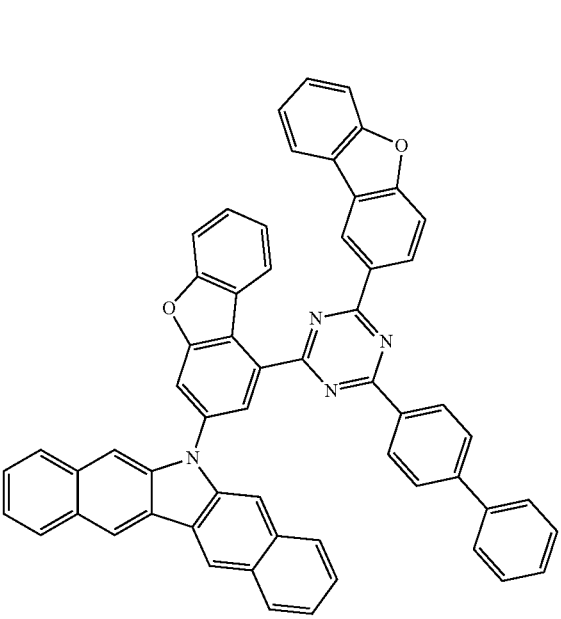

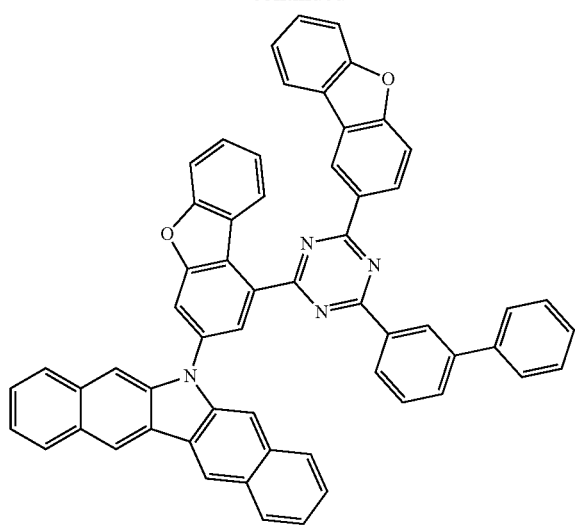
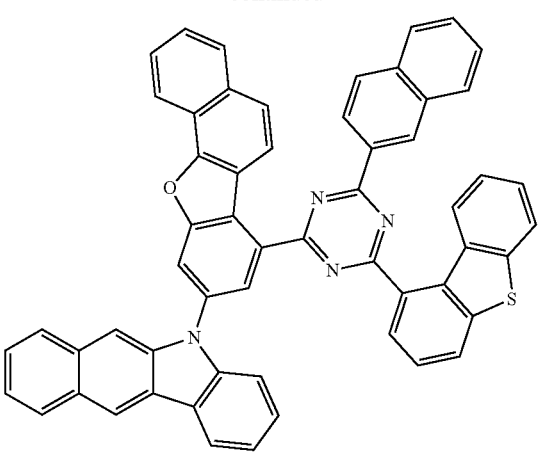
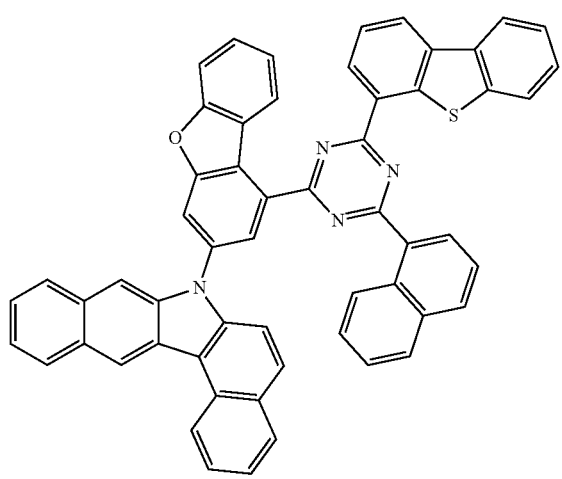
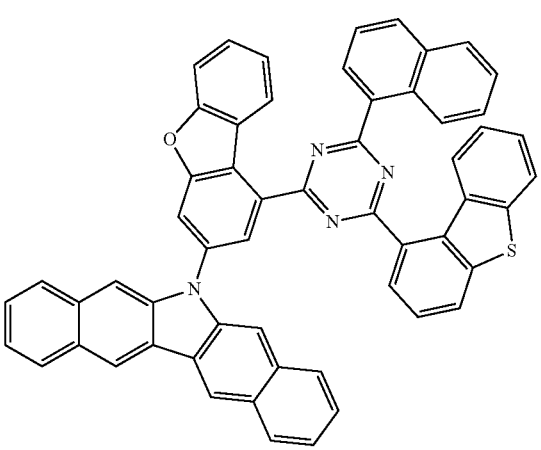
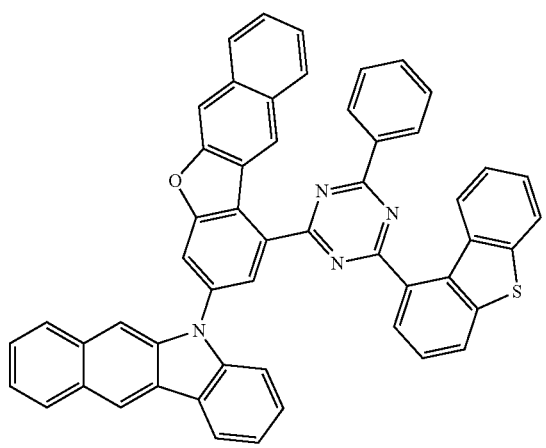
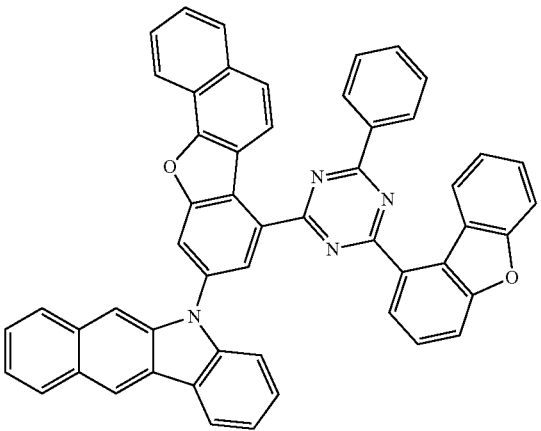

211
-continued
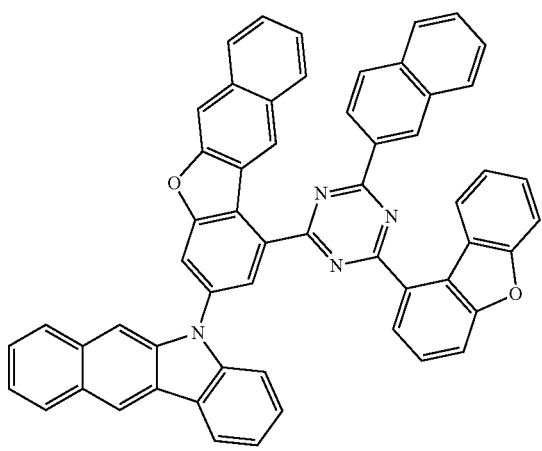
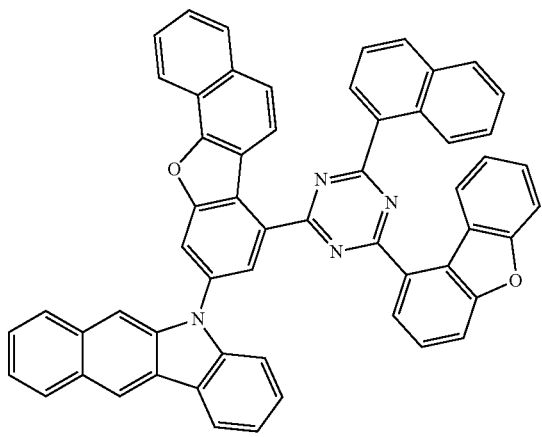
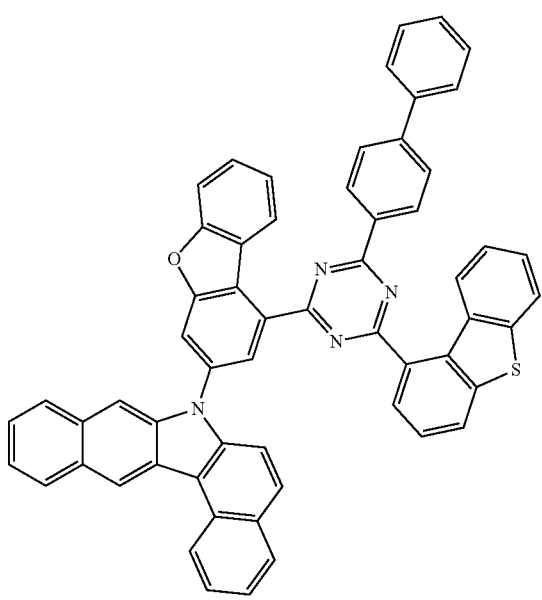
212
-continued
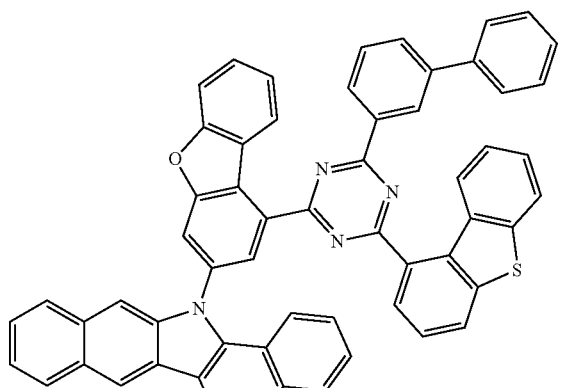
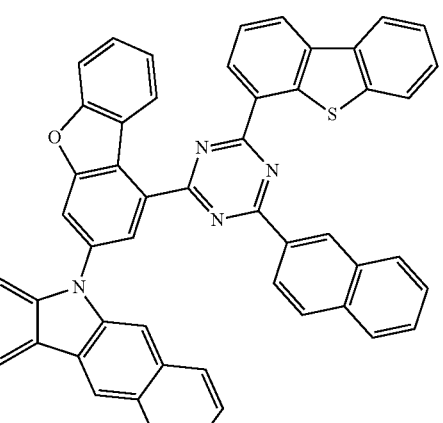
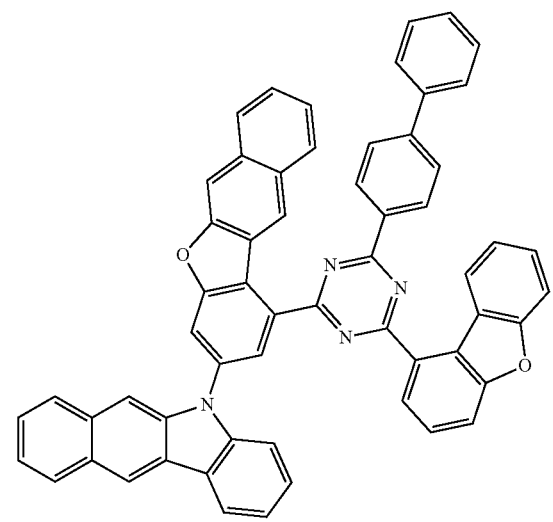

213
-continued
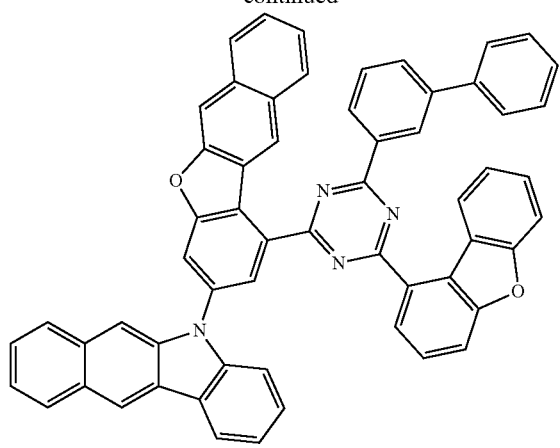
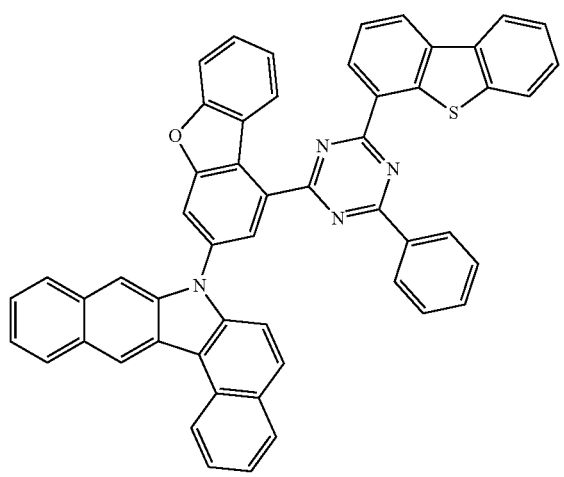
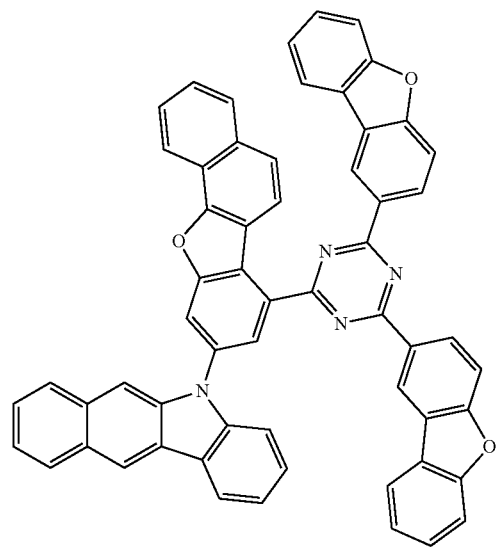
214
-continued
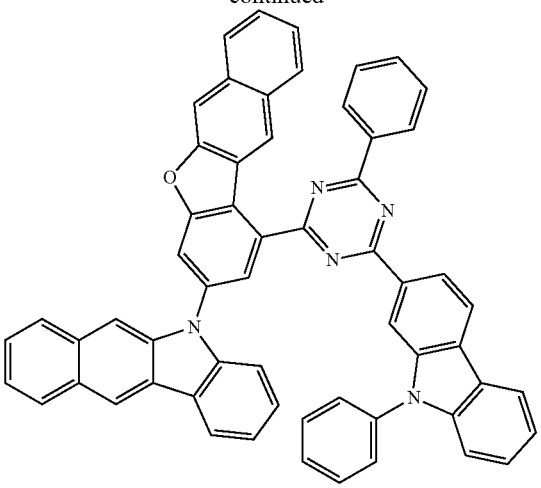
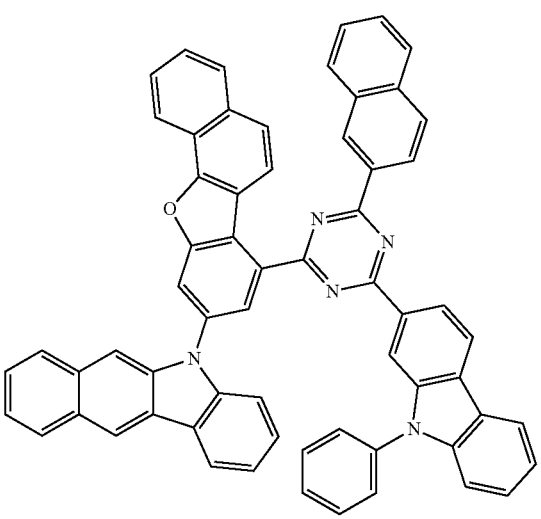
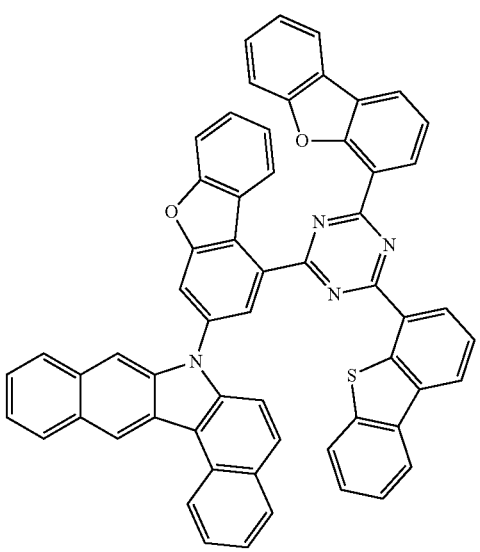

215
-continued
216
-continued
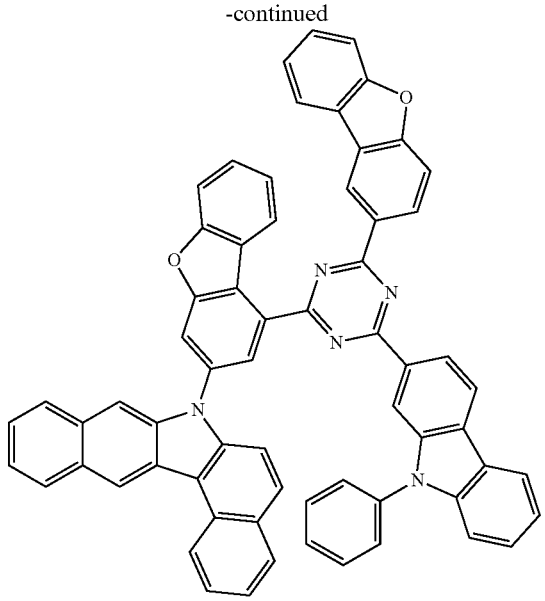
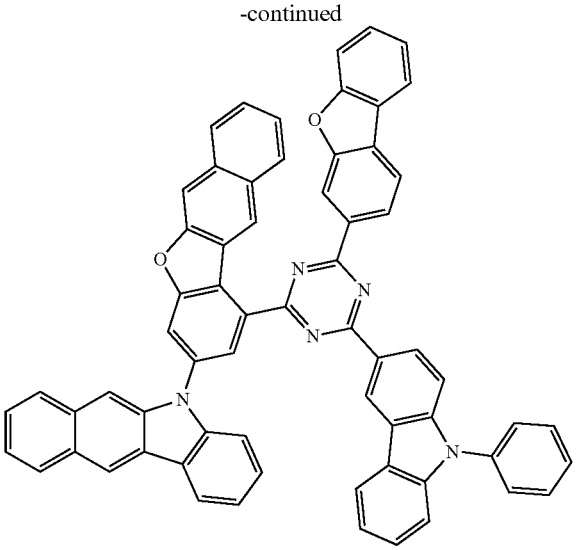
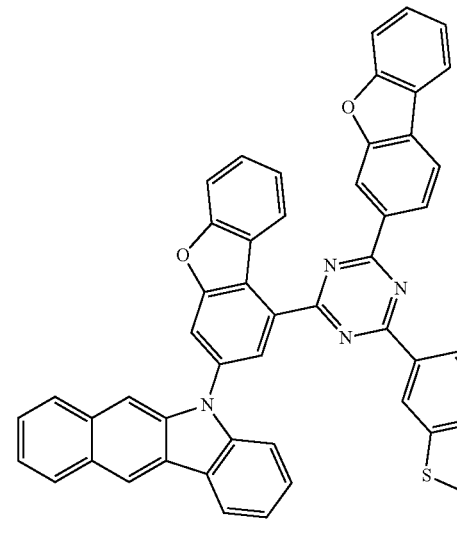

217
-continued
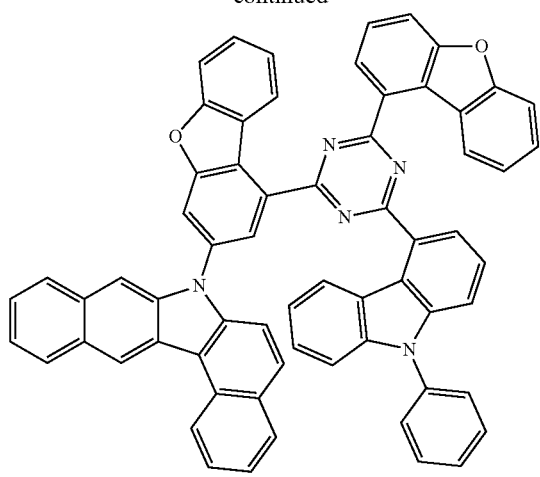
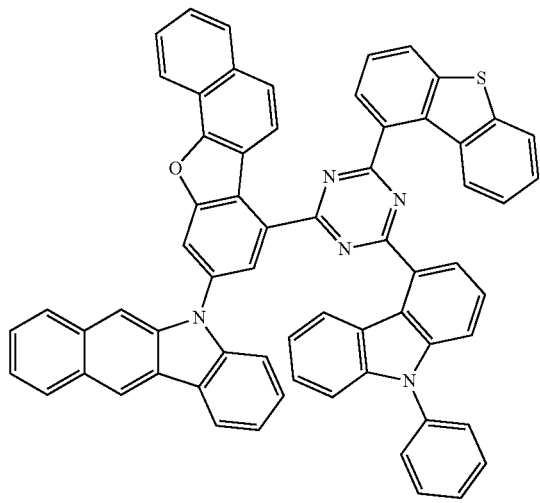
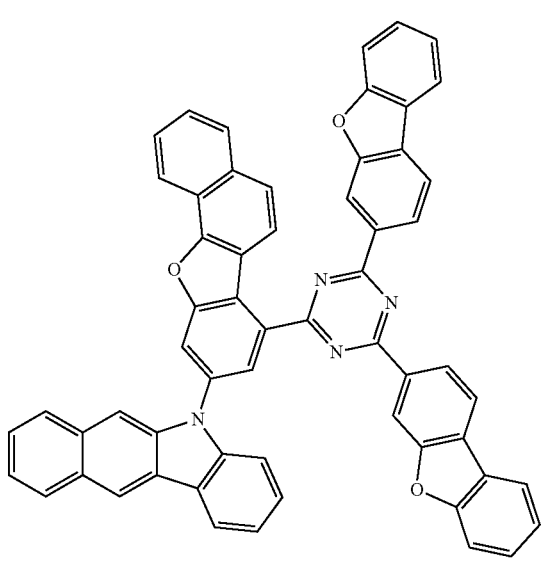
218
-continued
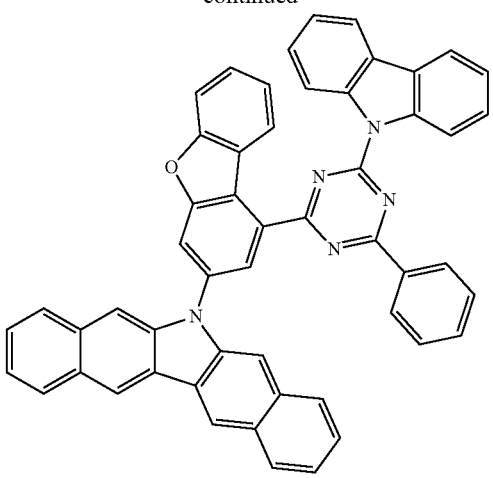
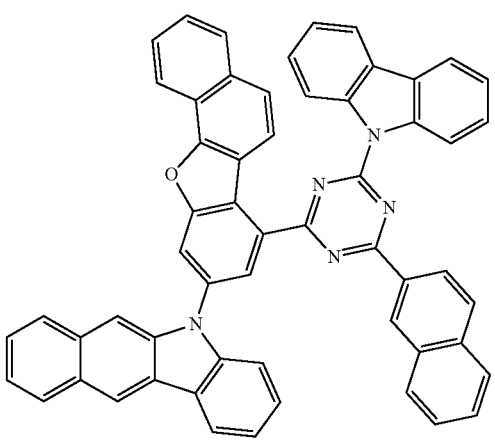
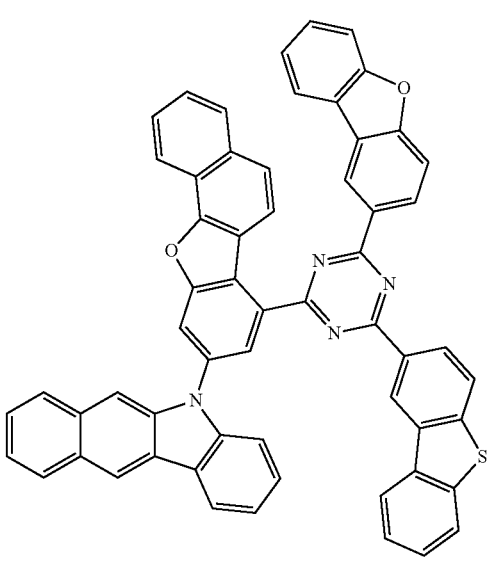

219
-continued
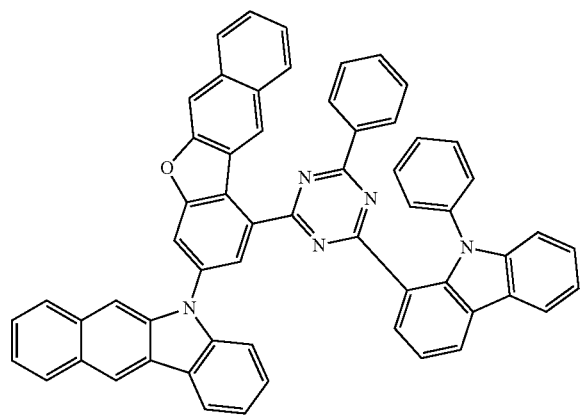
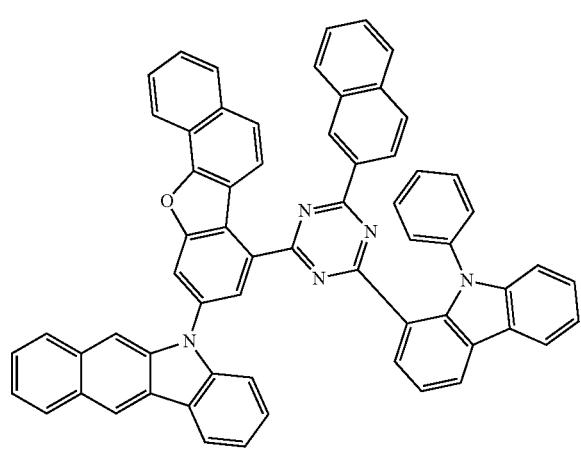
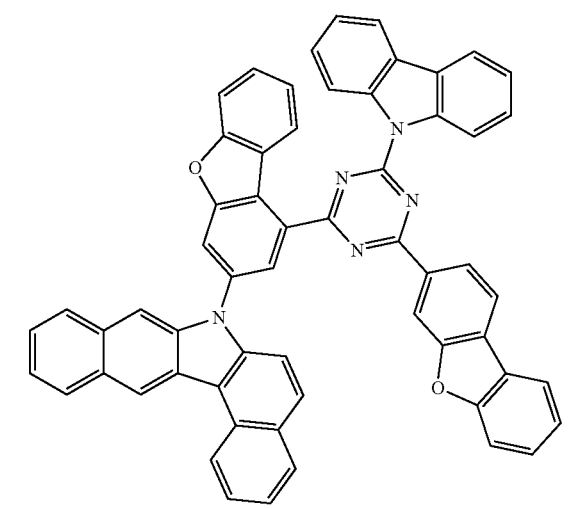
220
-continued
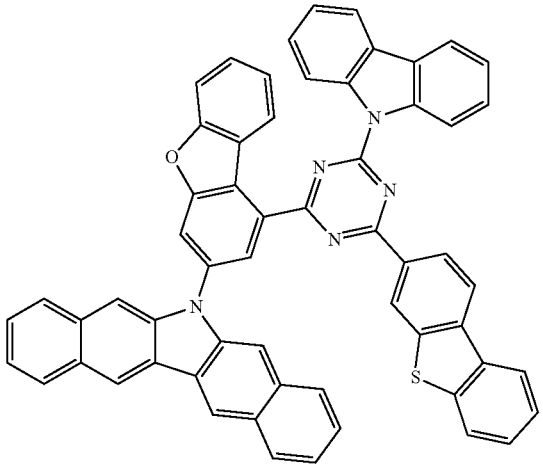
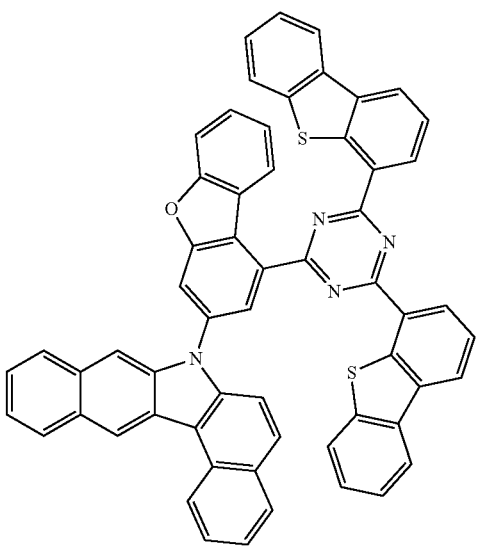
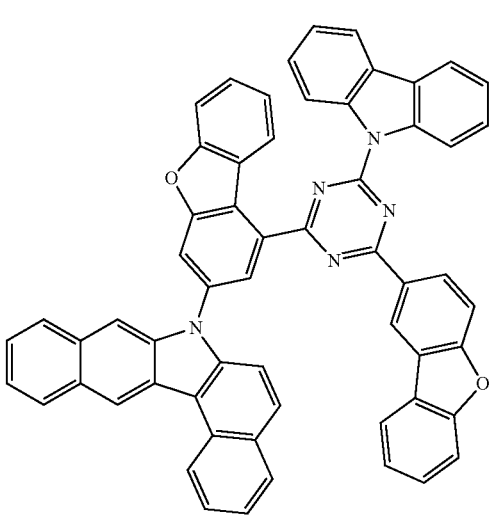

221
-continued
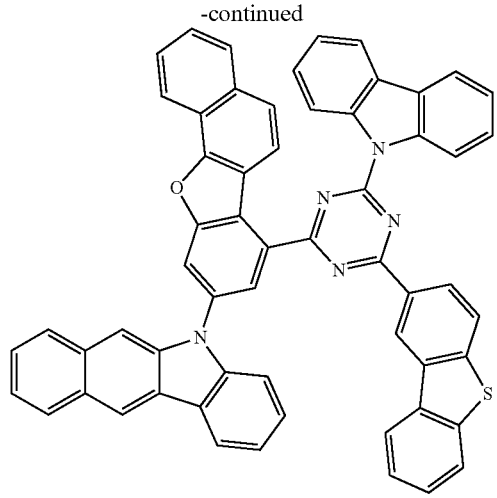
222
-continued
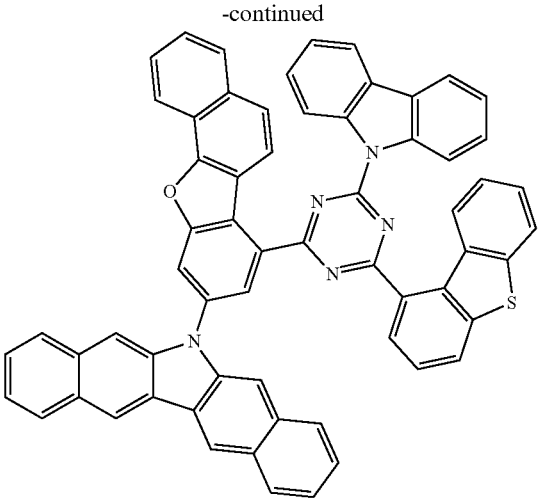
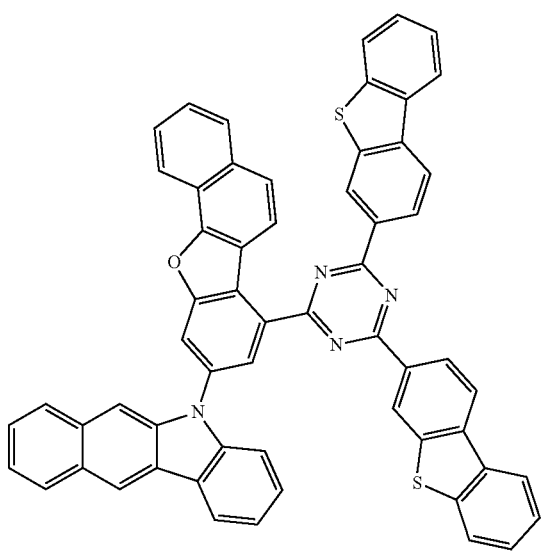
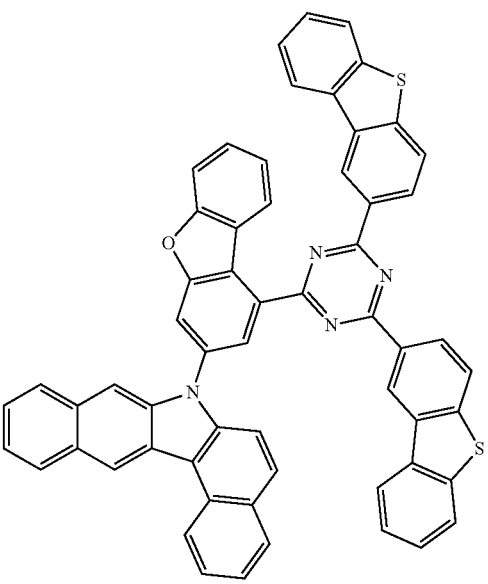
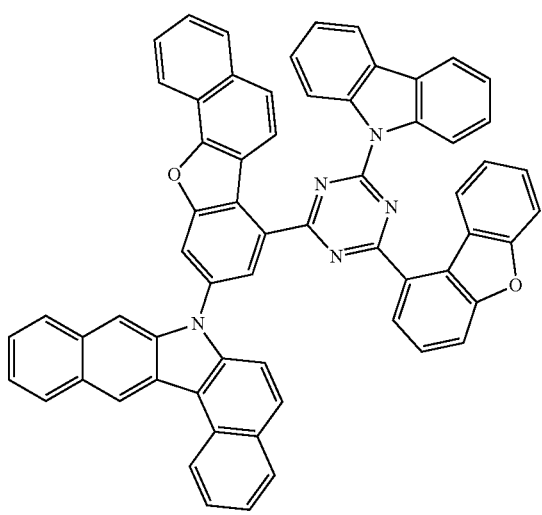
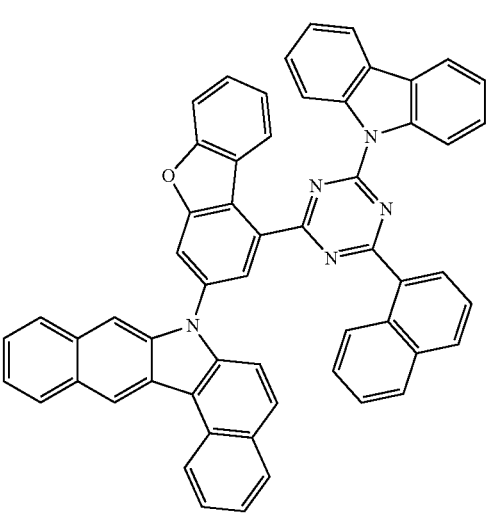

223
-continued
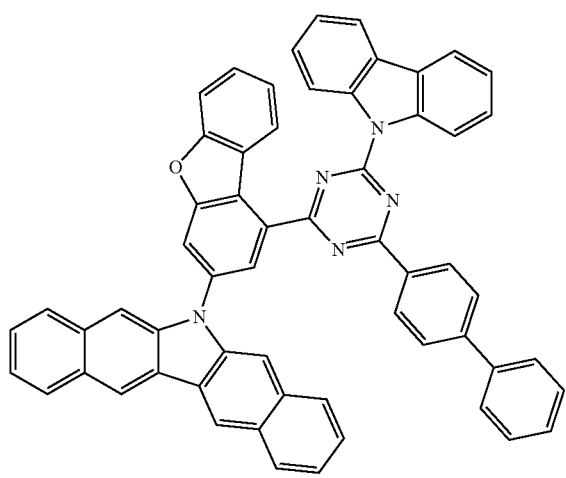
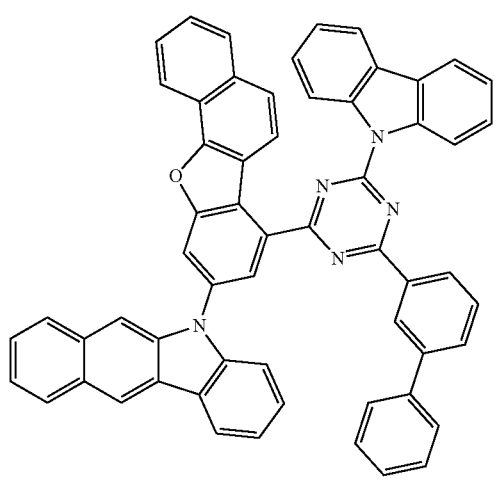
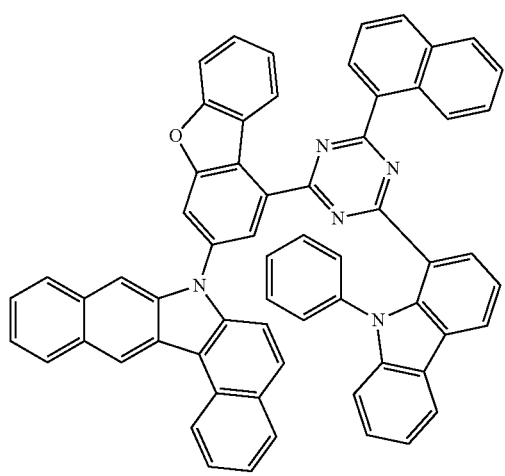
224
-continued
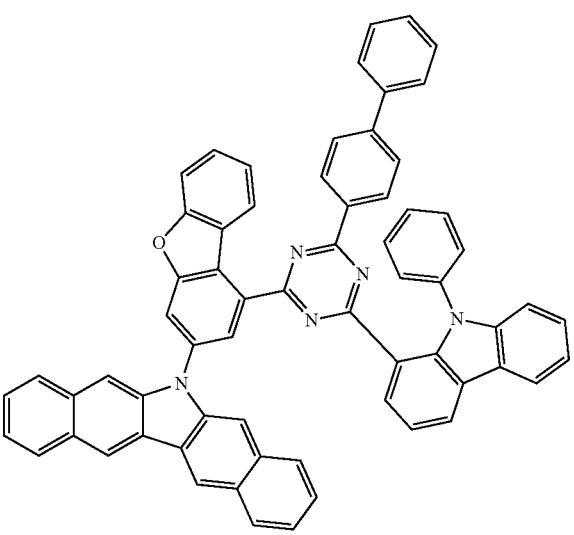
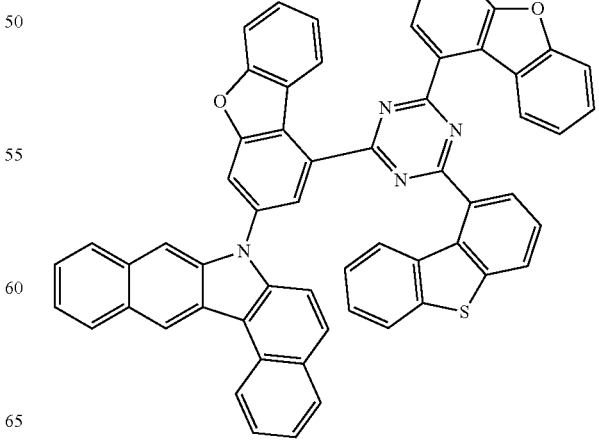

225
-continued
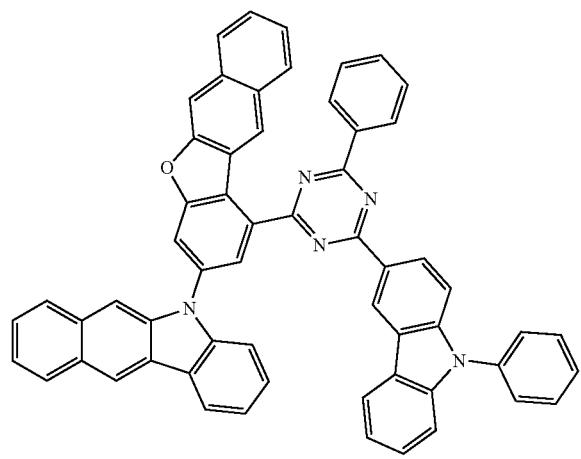
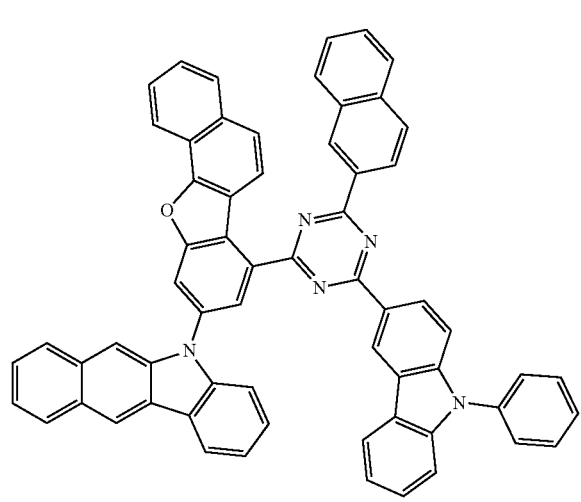
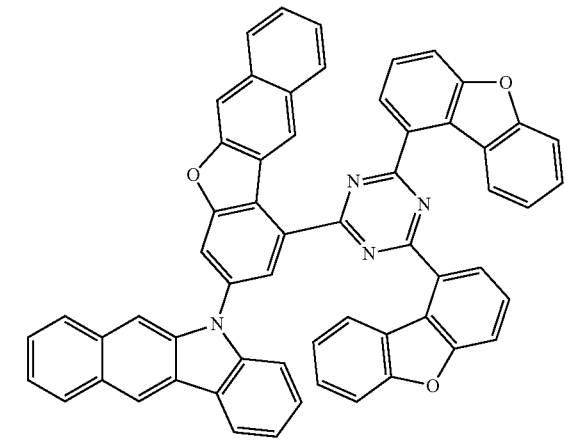
226
-continued
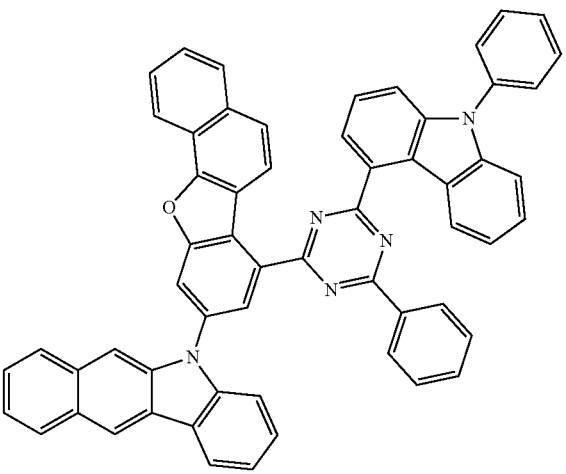
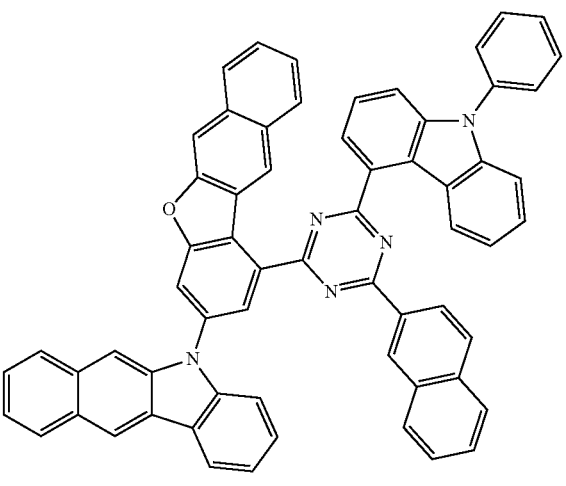
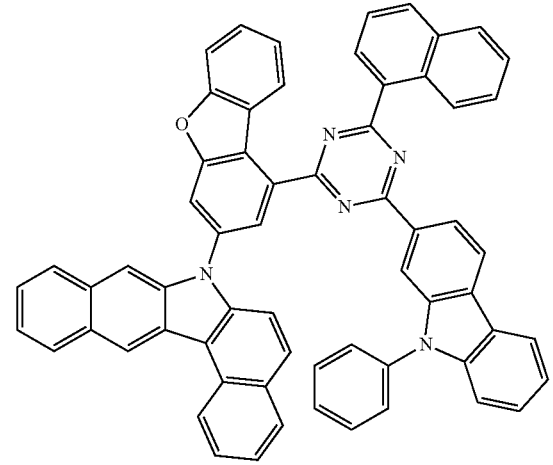

227
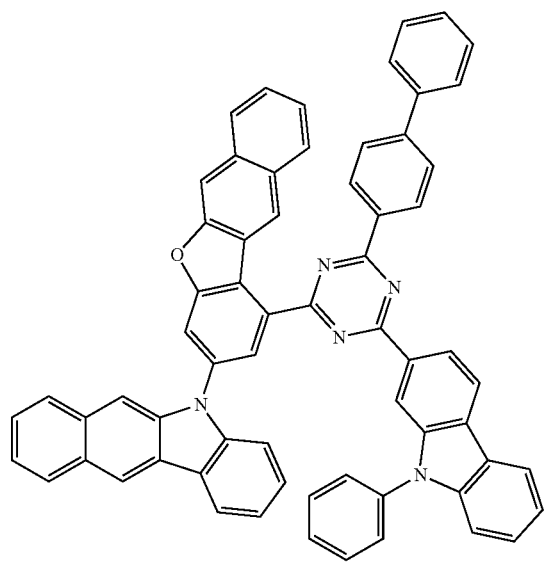
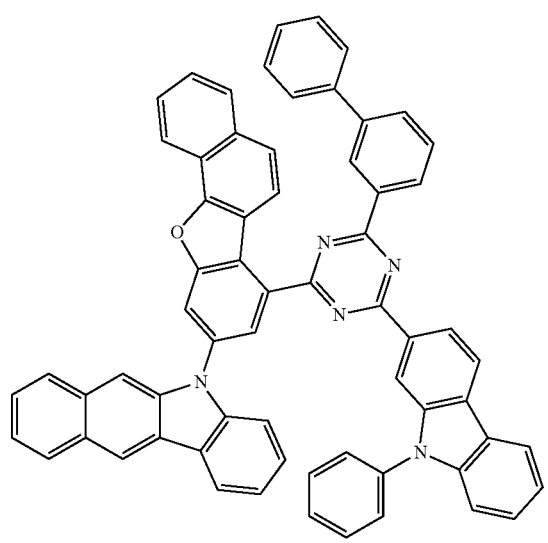
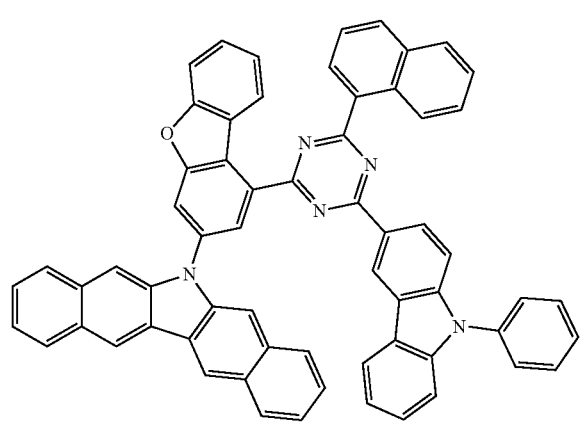
228
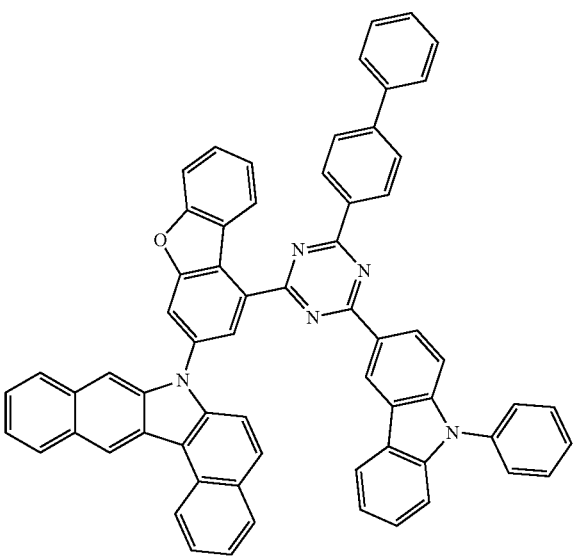
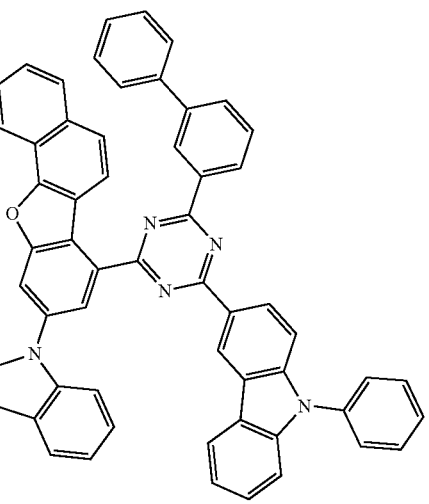
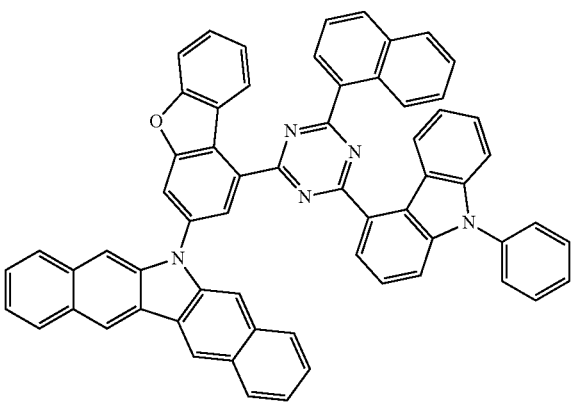

229
-continued
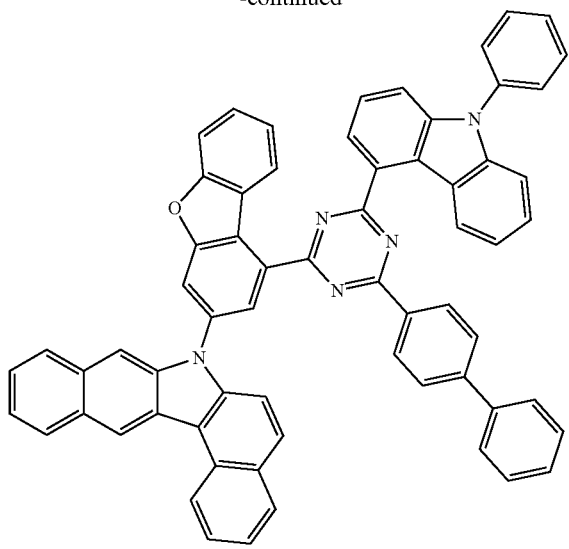
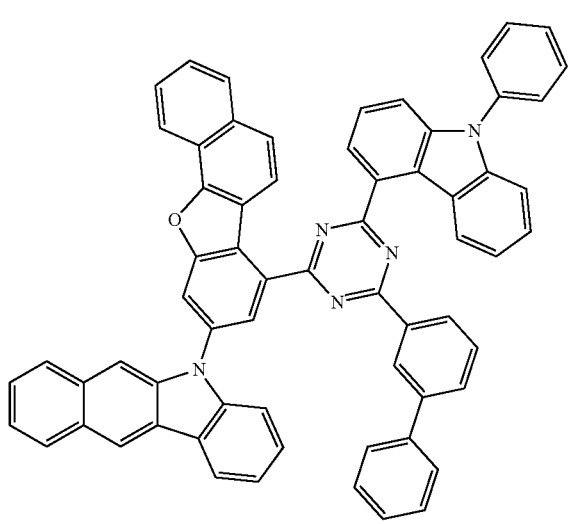
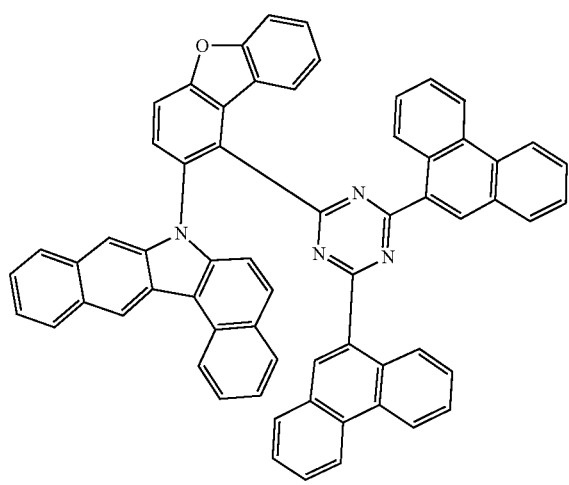
230
-continued
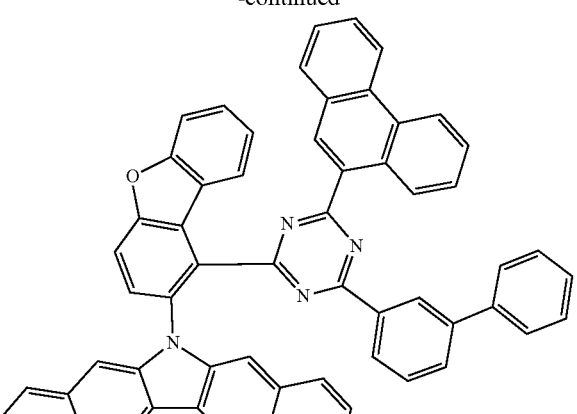
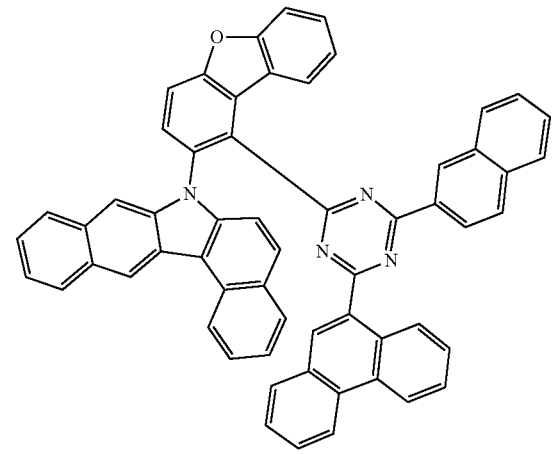
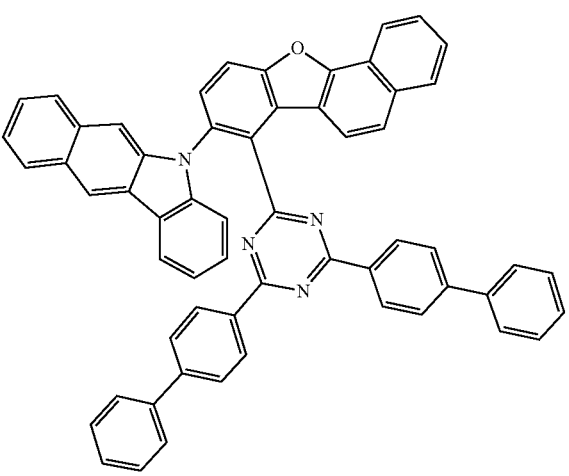

231
-continued
232
-continued
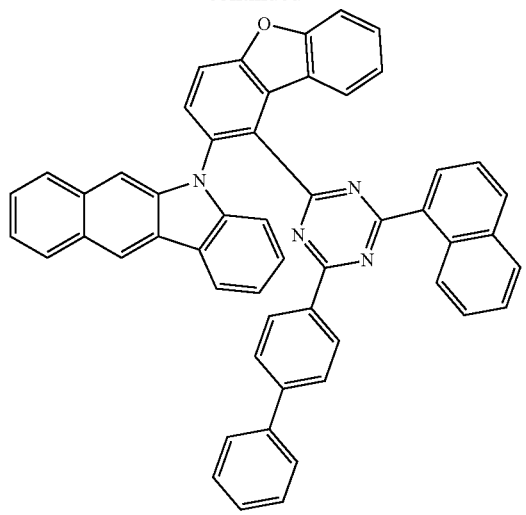
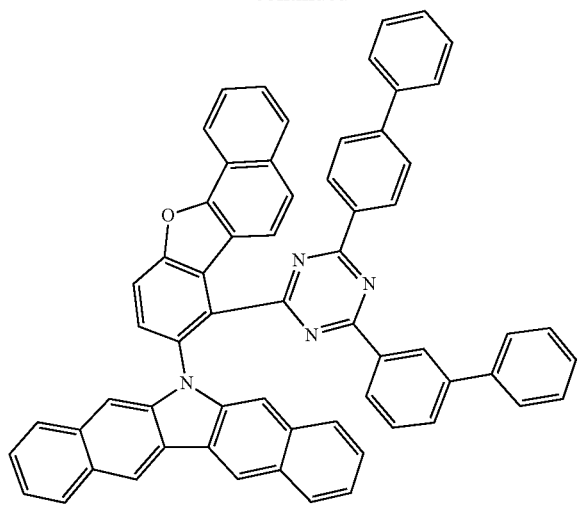
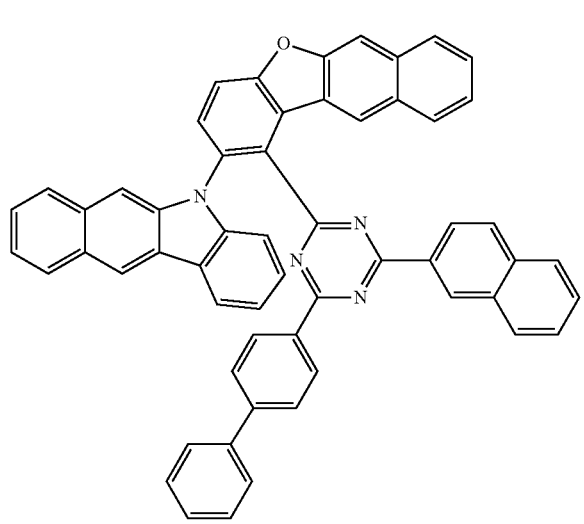
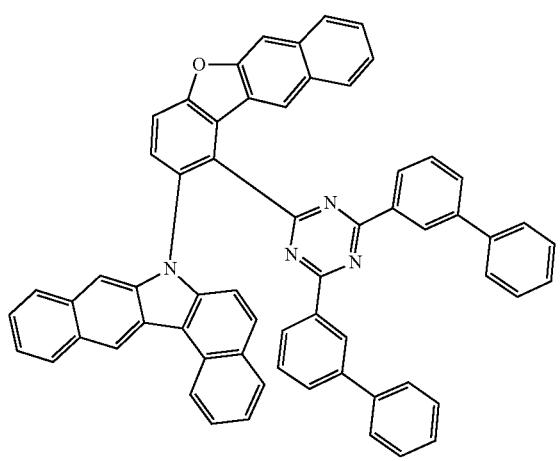
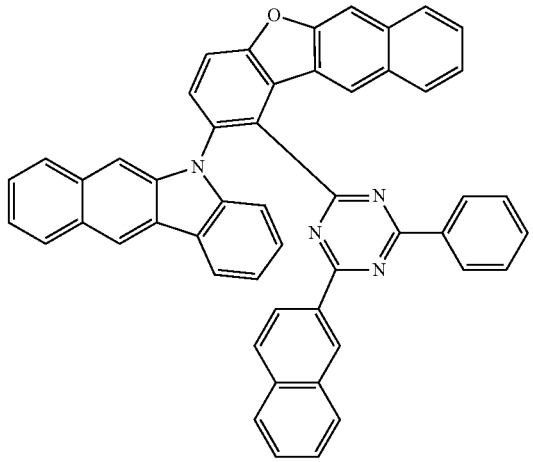

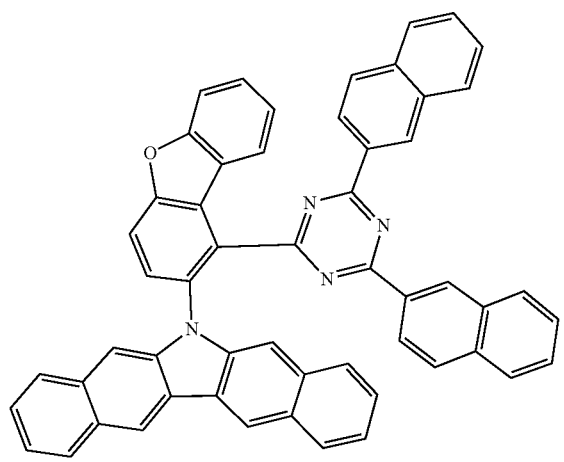
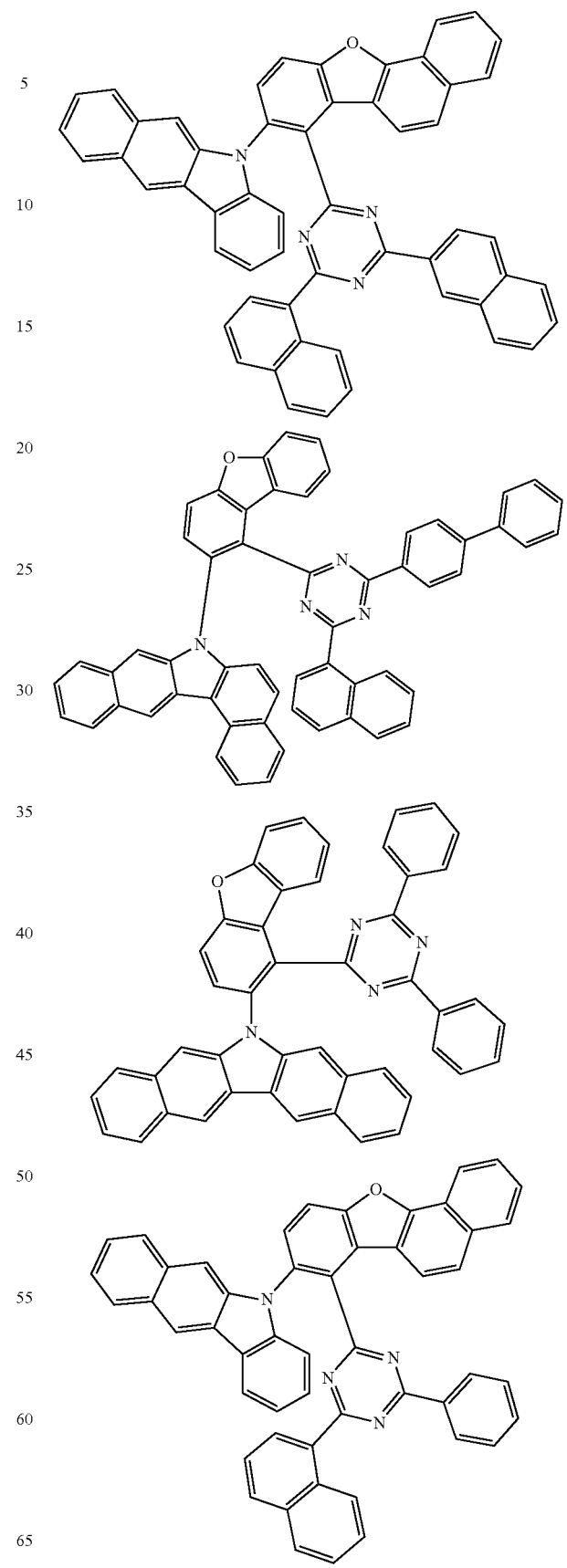

235
-continued
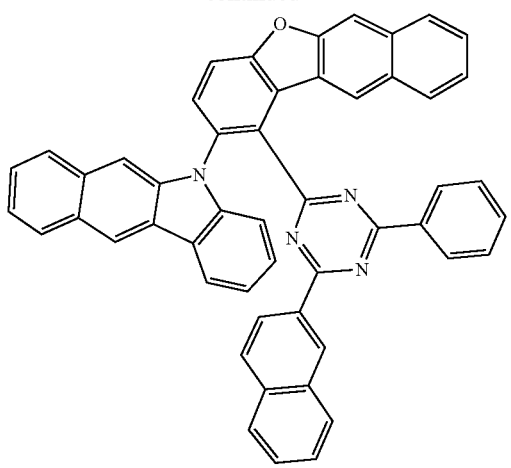
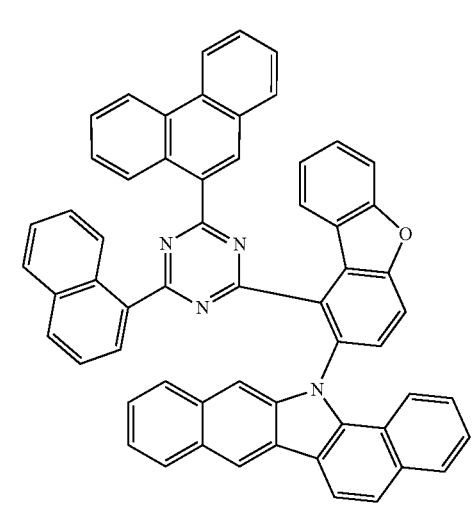
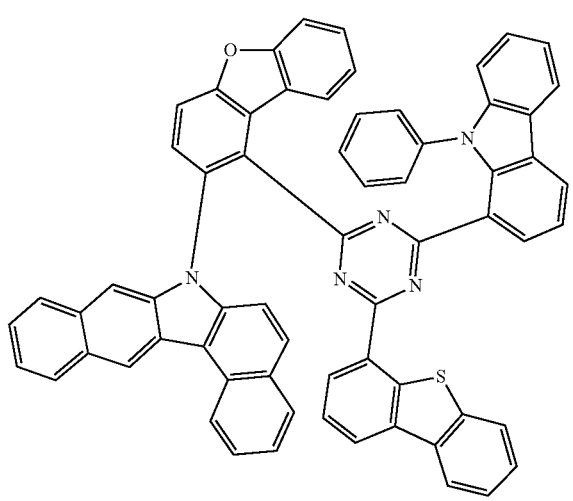
236
-continued
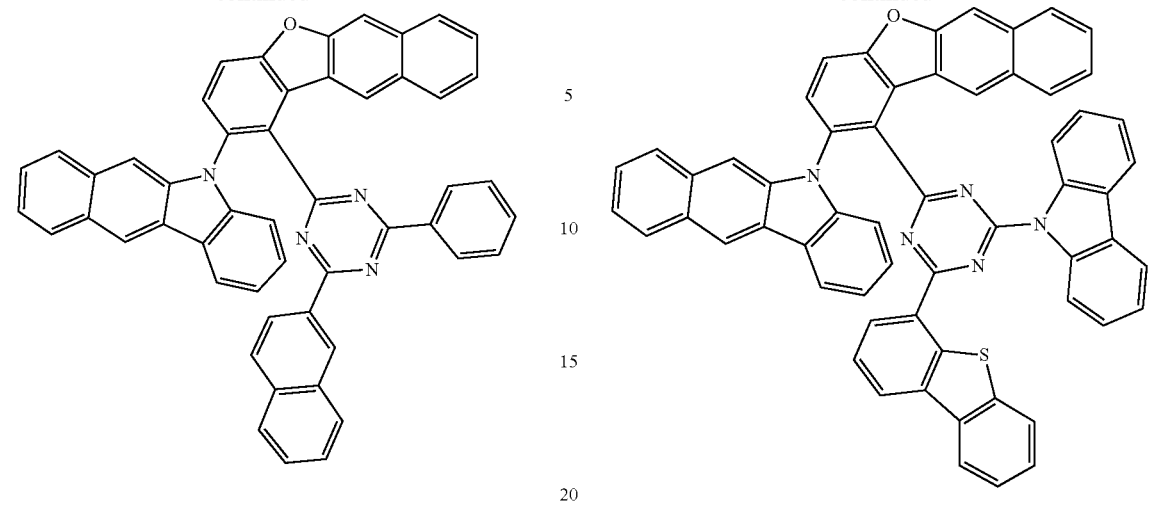
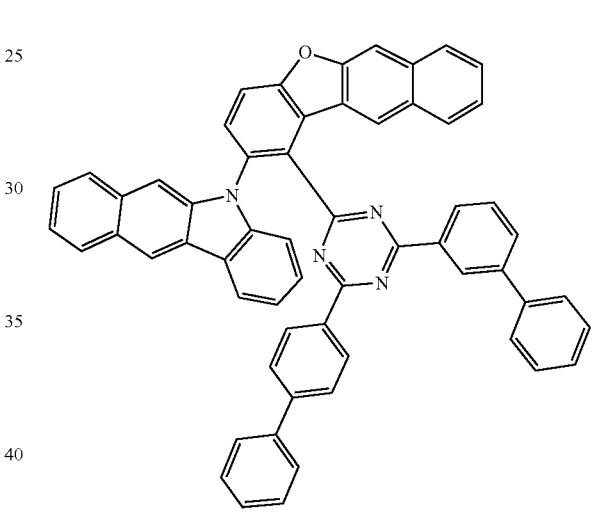
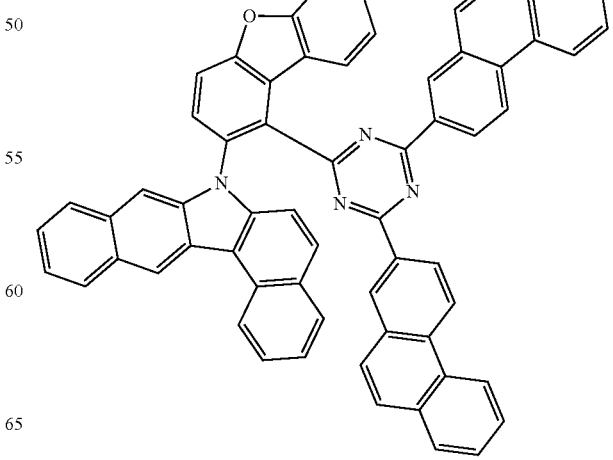

237
-continued
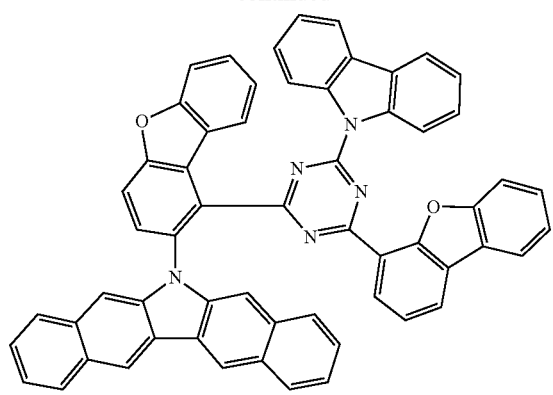
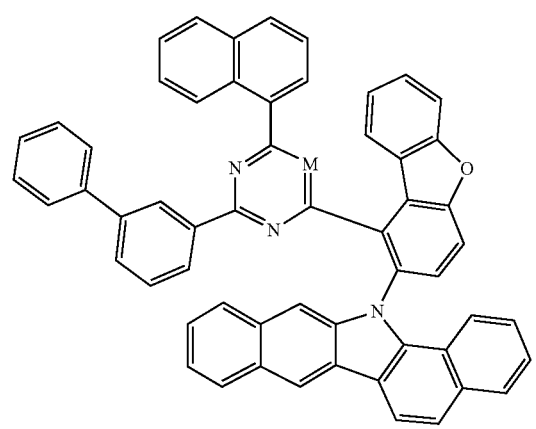
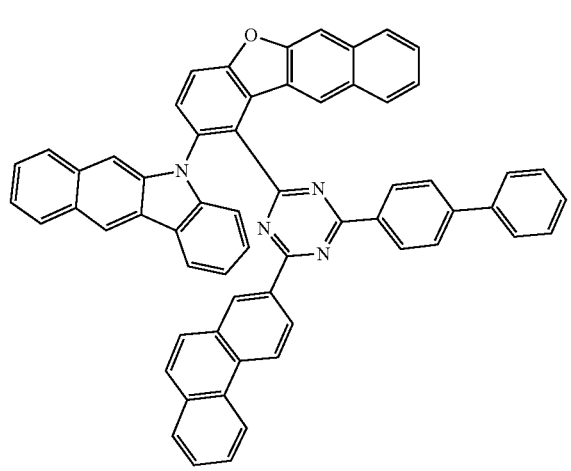
238
-continued
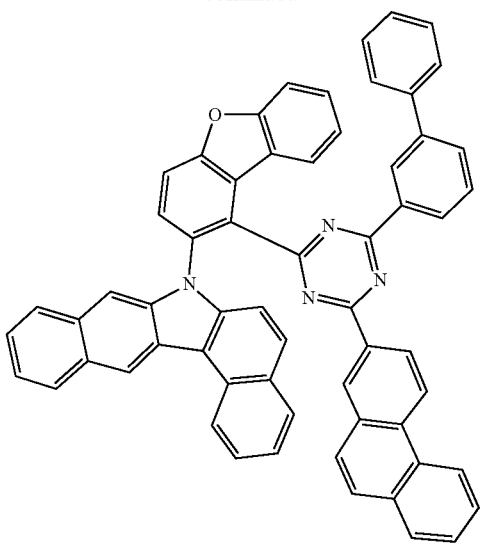
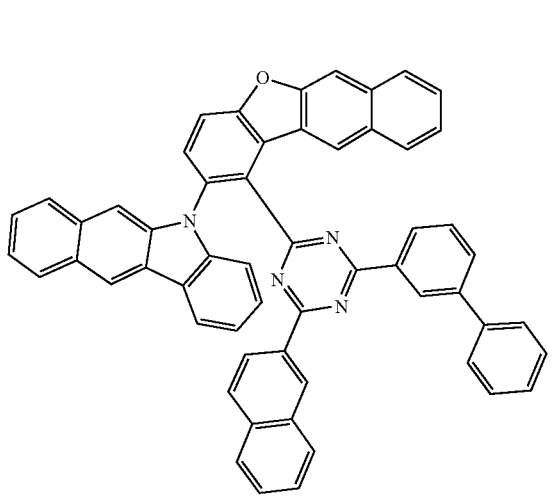
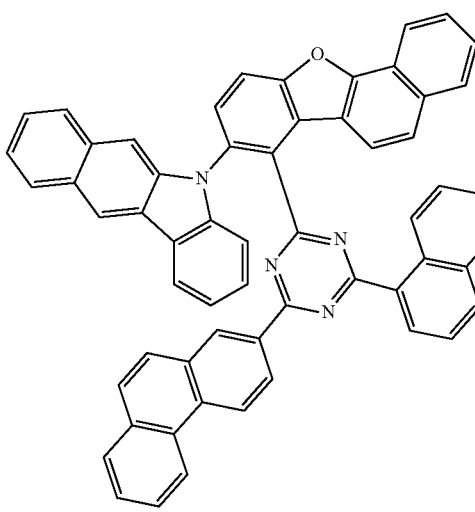

239
-continued
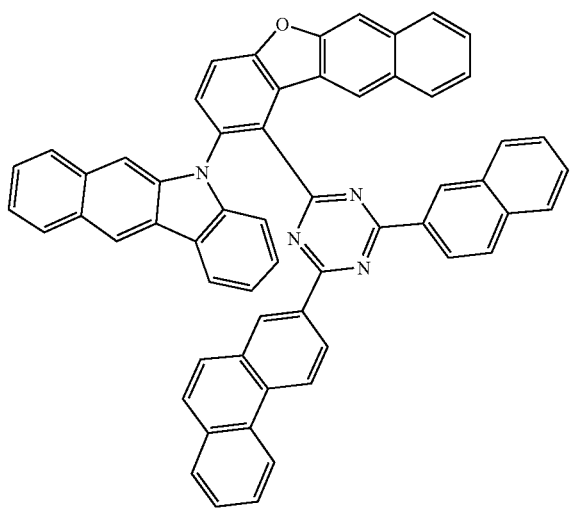
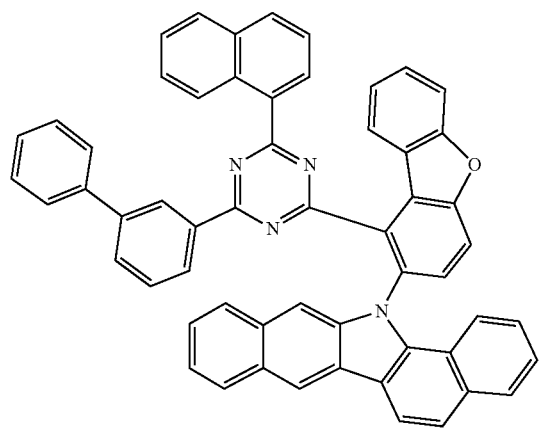
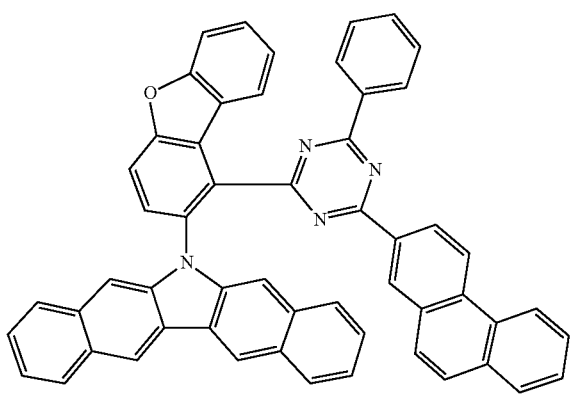
240
-continued
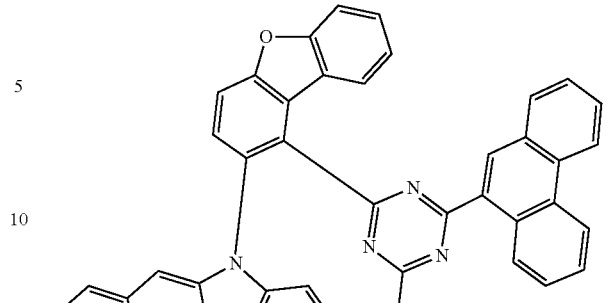
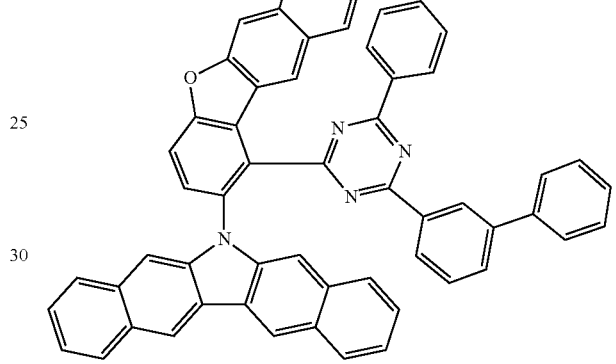
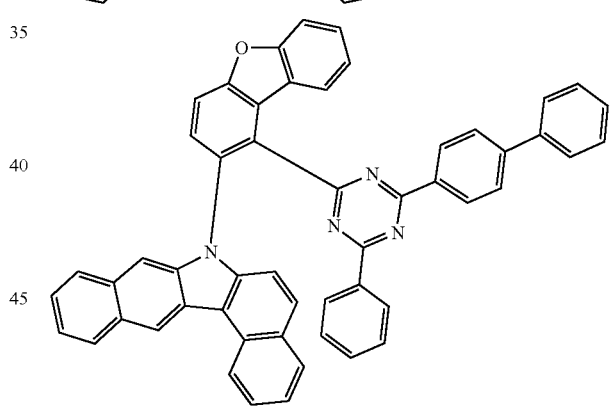
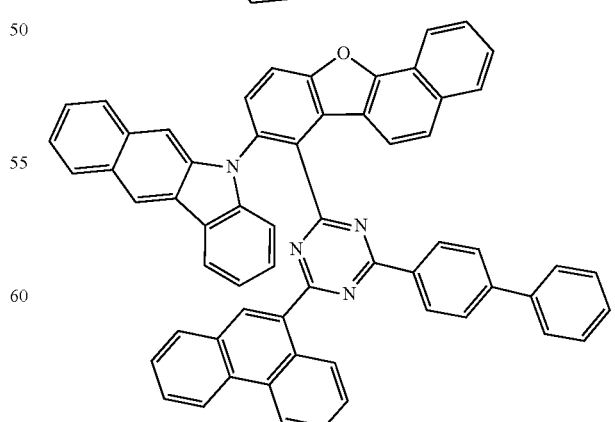

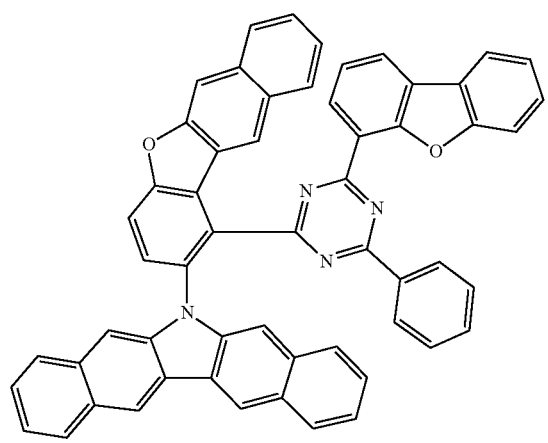
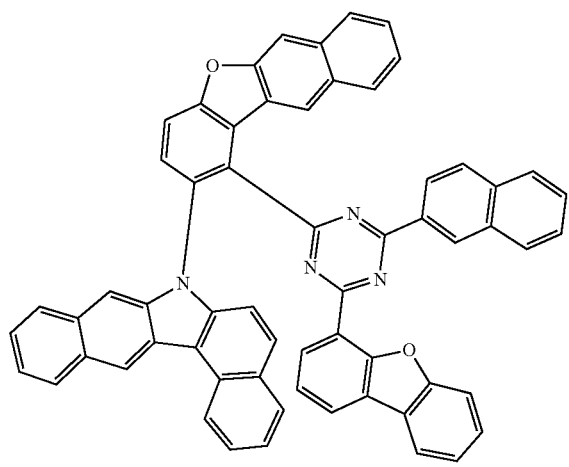
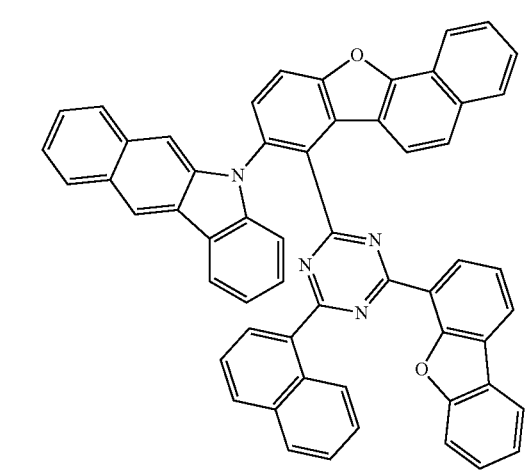
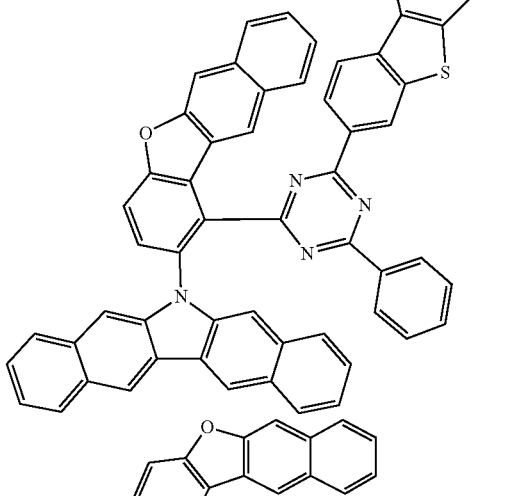
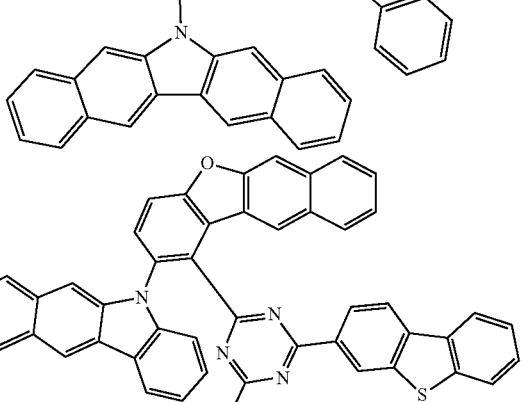
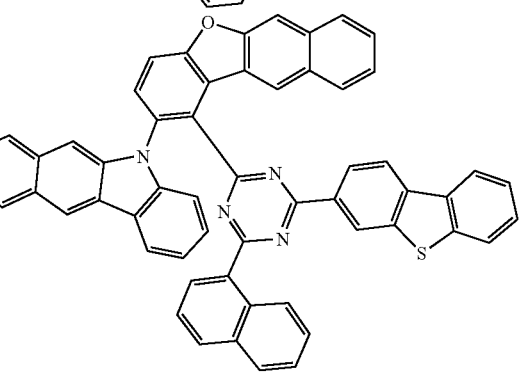
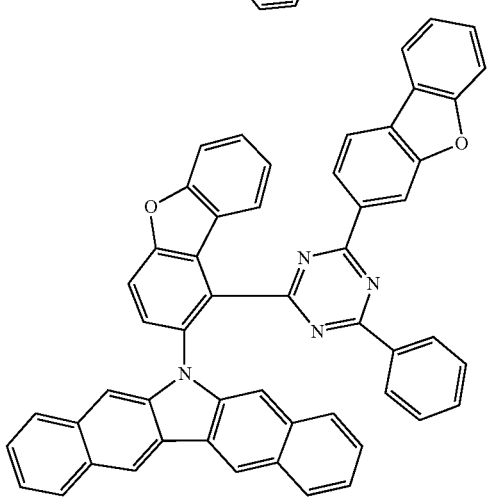

243
-continued
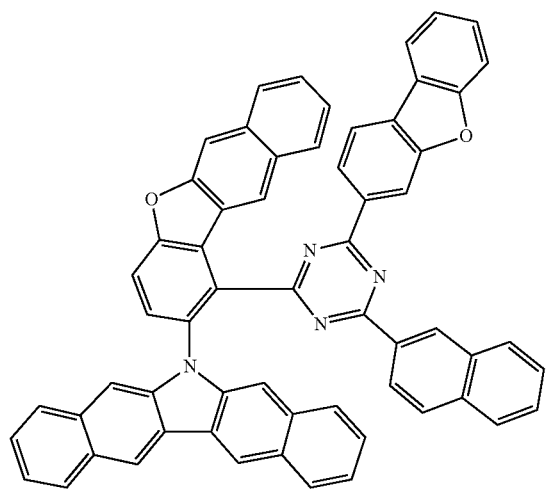
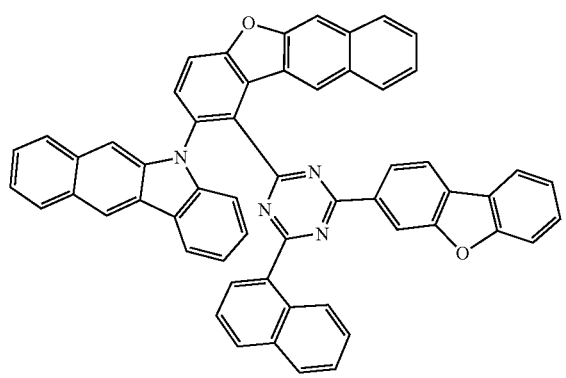
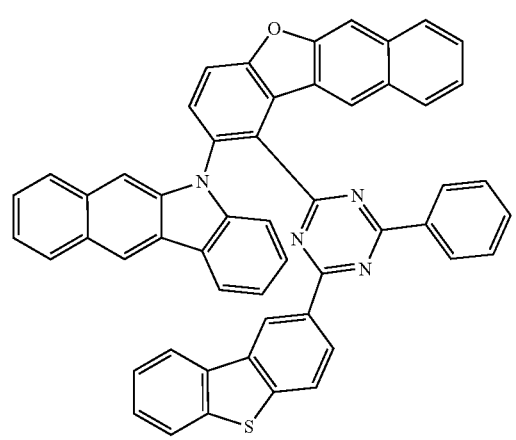
244
-continued
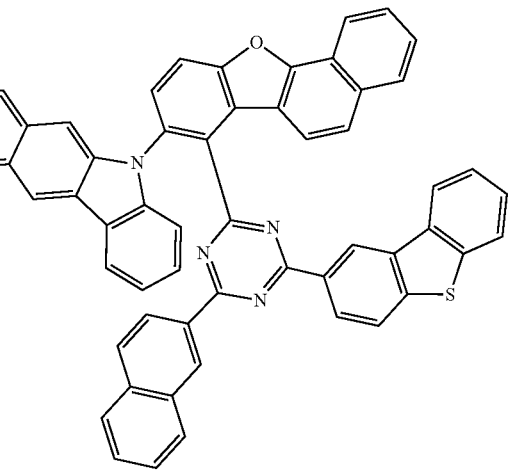
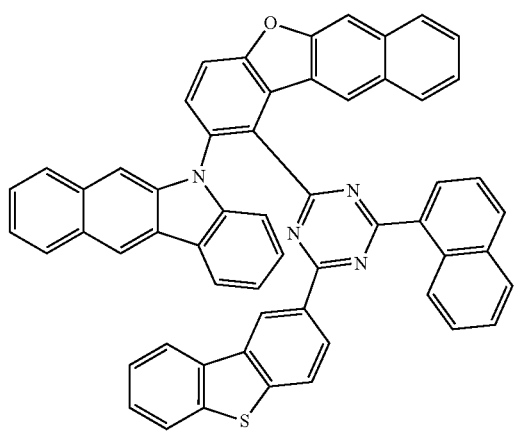
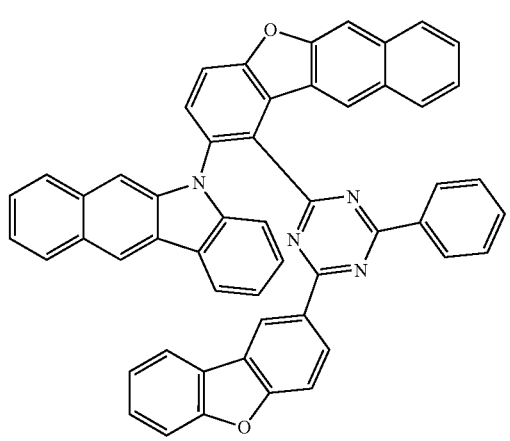

245
-continued
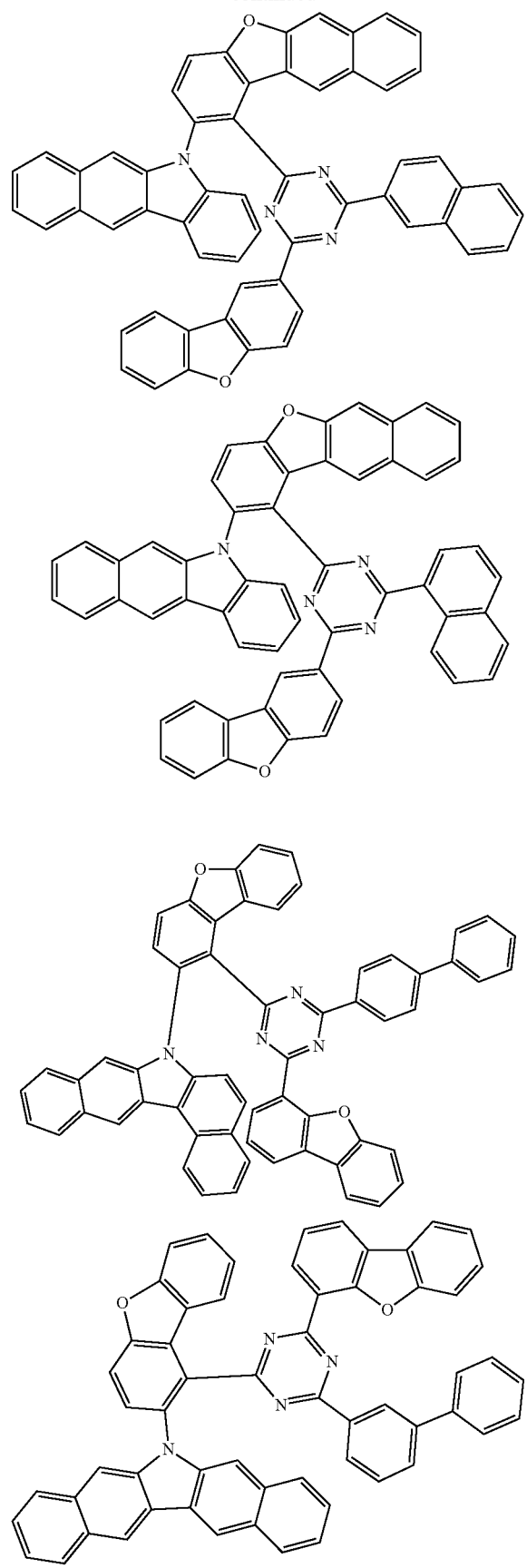
246
-continued
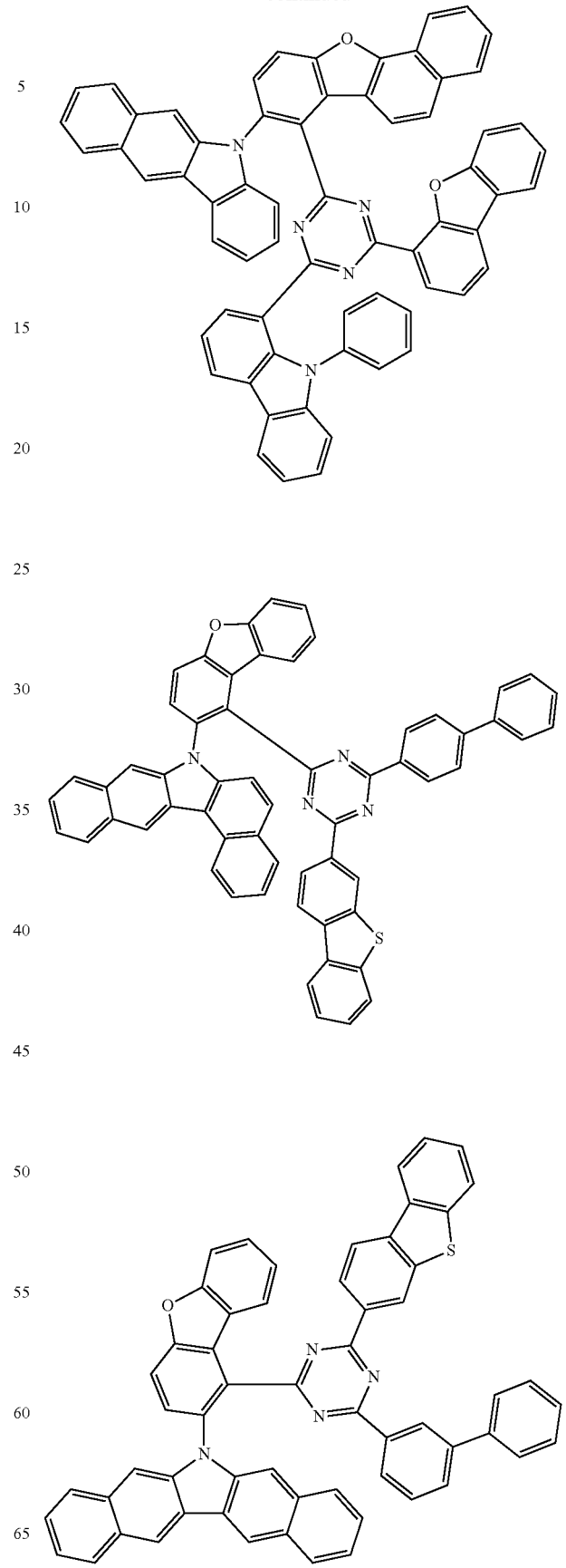

247
-continued
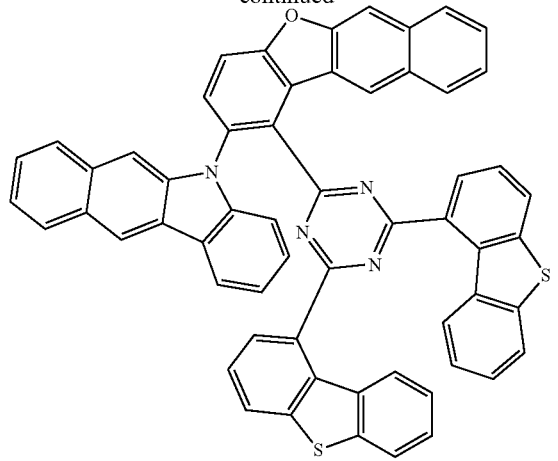
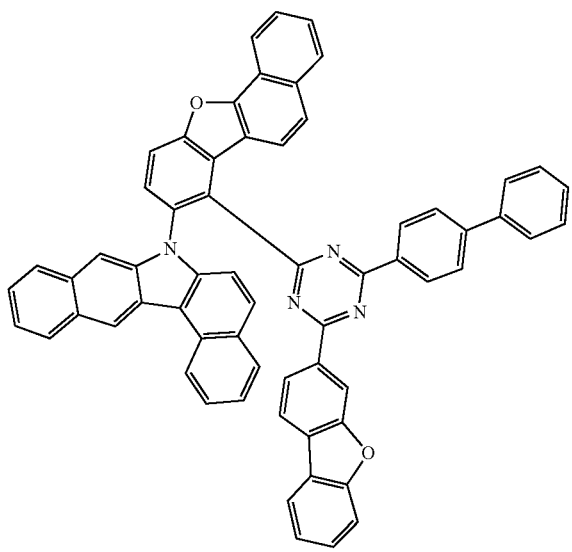
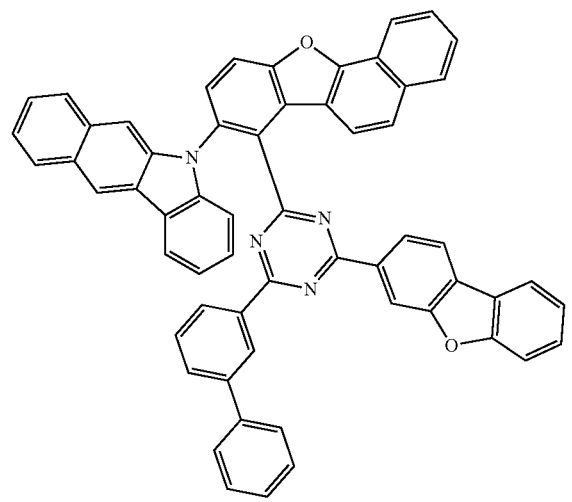
248
-continued
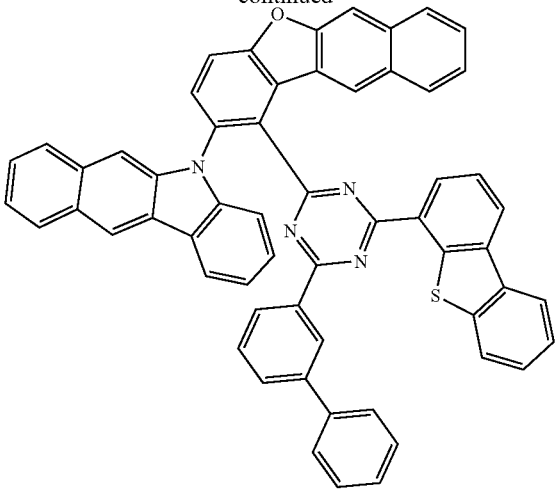
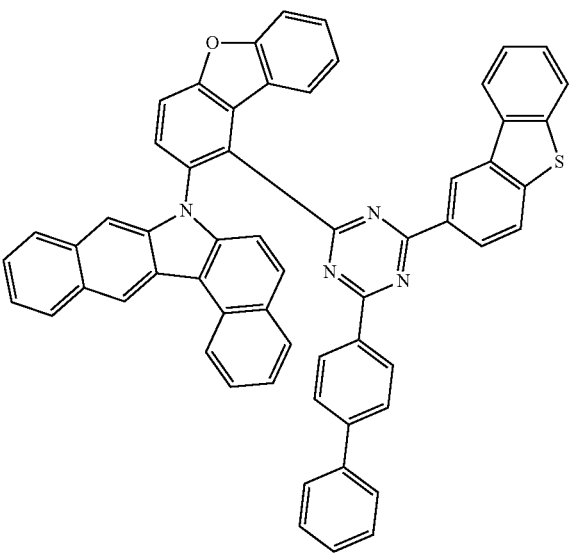
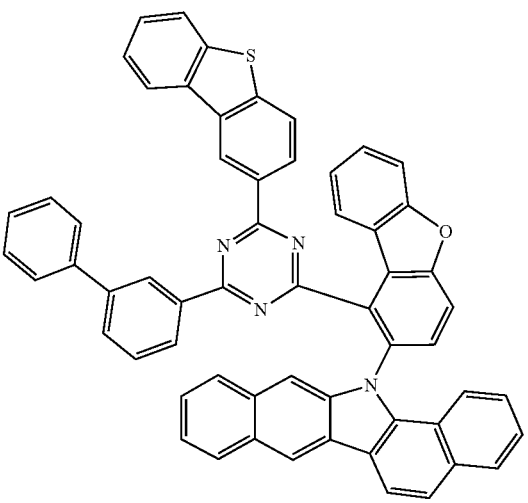

249
-continued
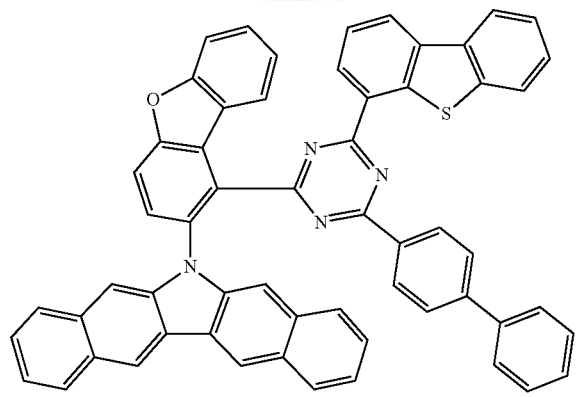
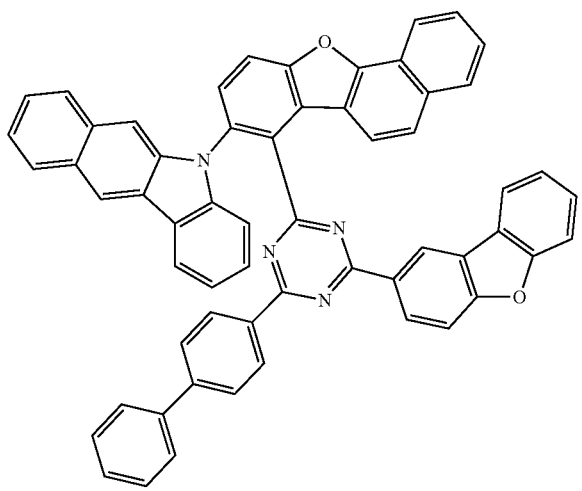
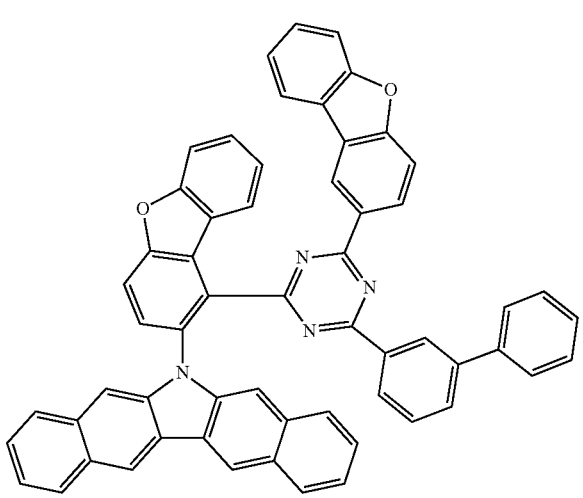
250
-continued
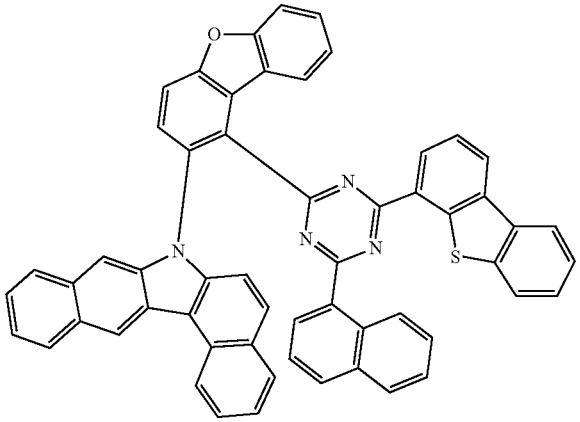
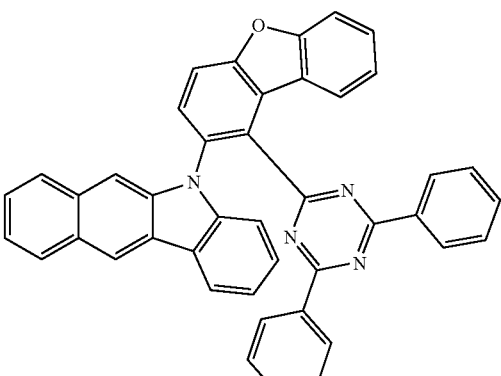
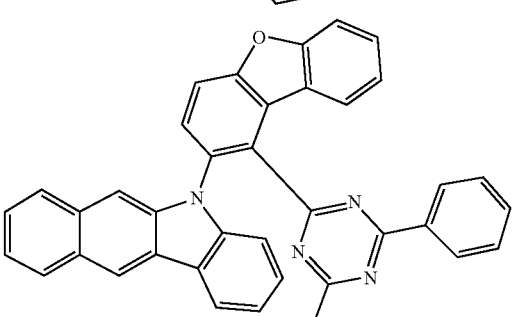
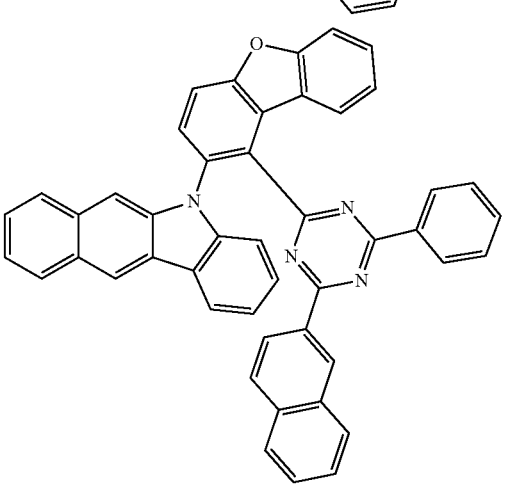

-continued
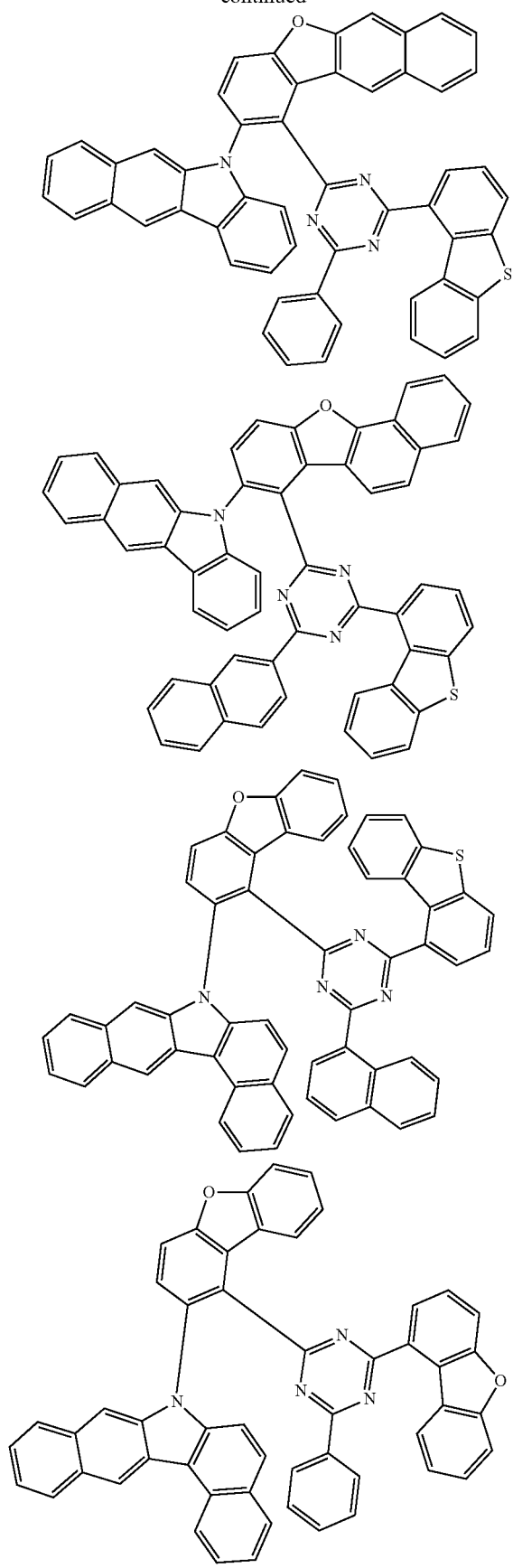
-continued
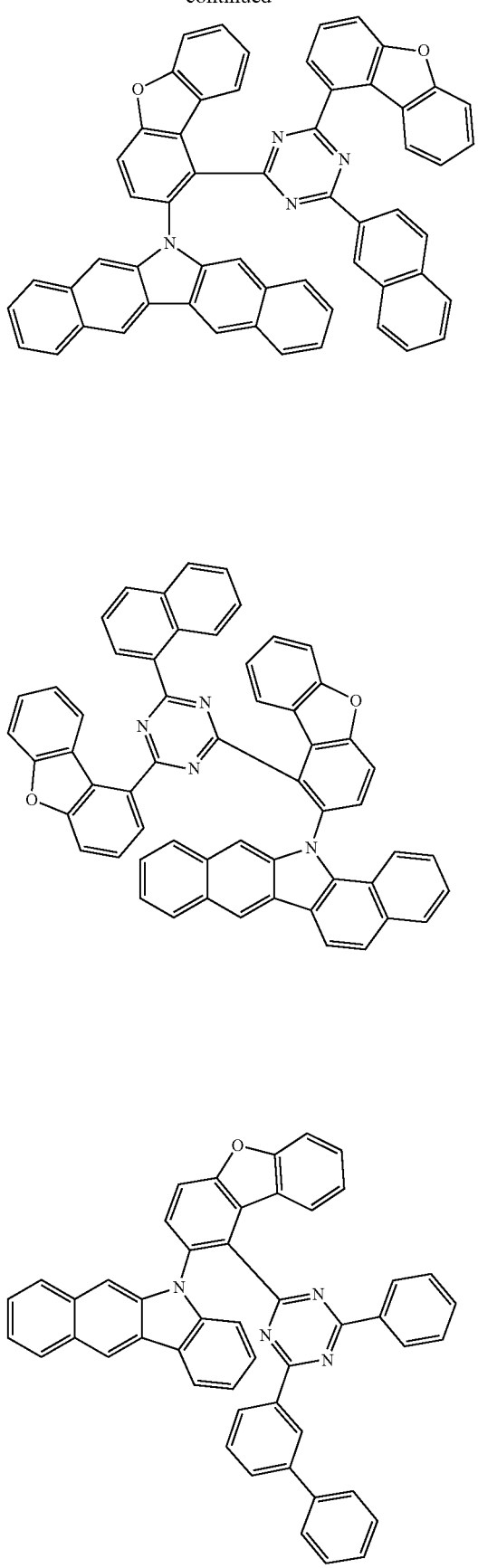

-continued
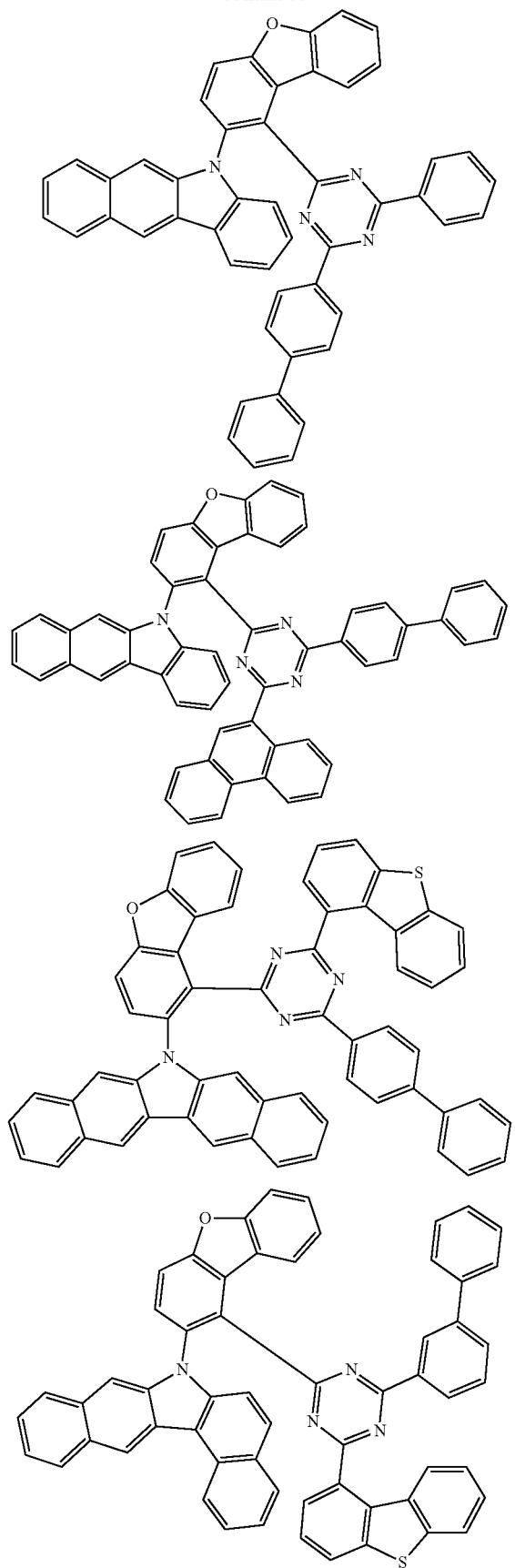
-continued
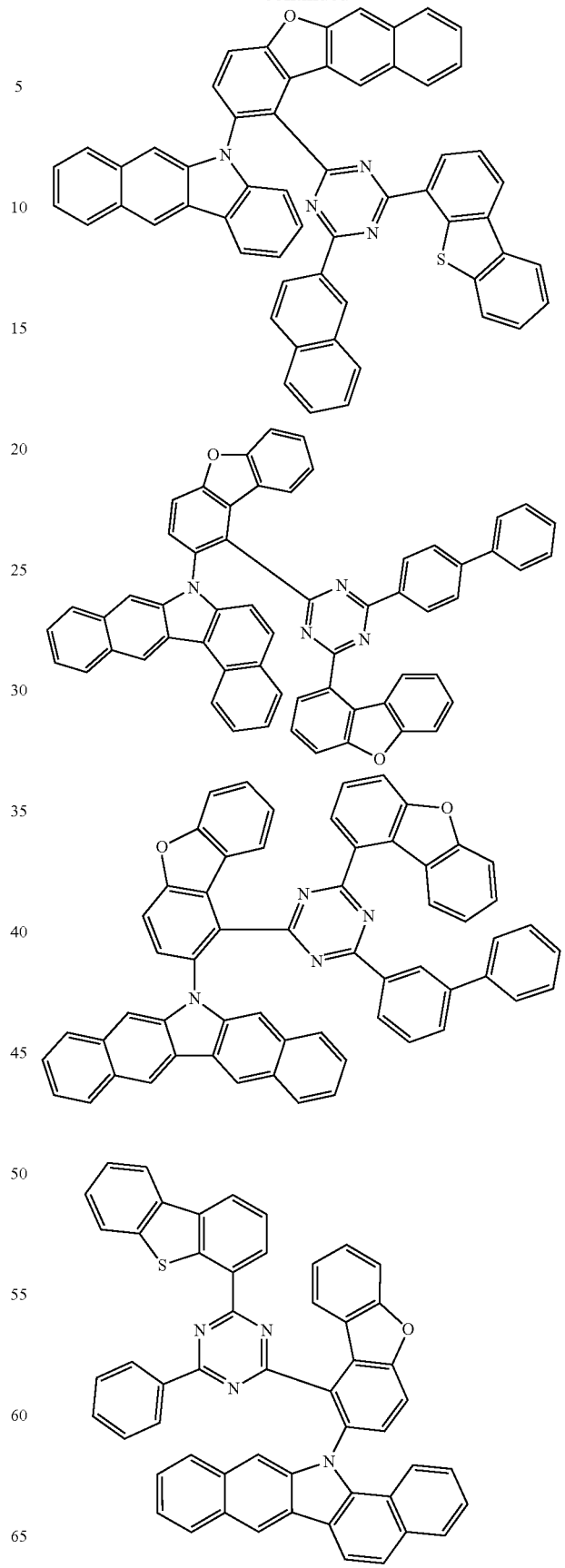

255
-continued
256
-continued
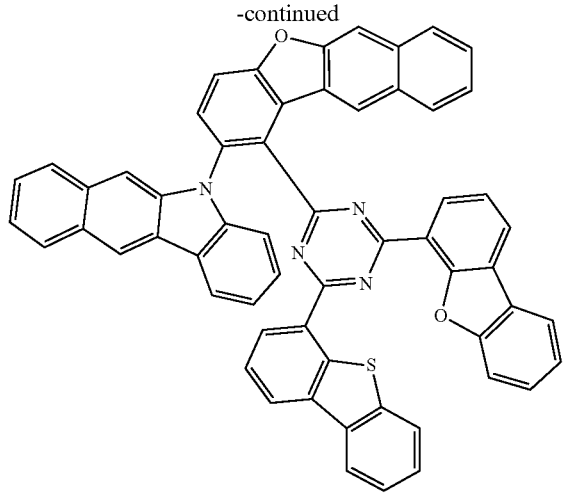
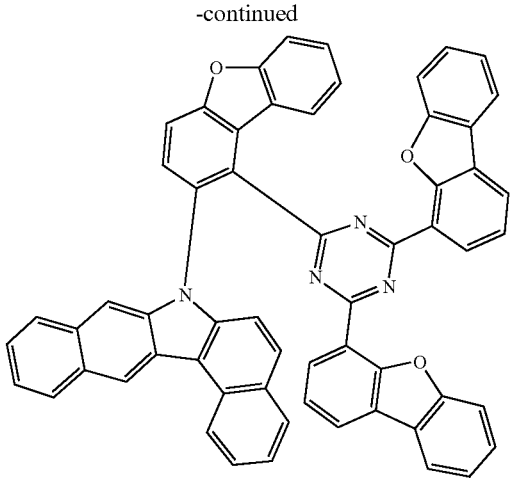
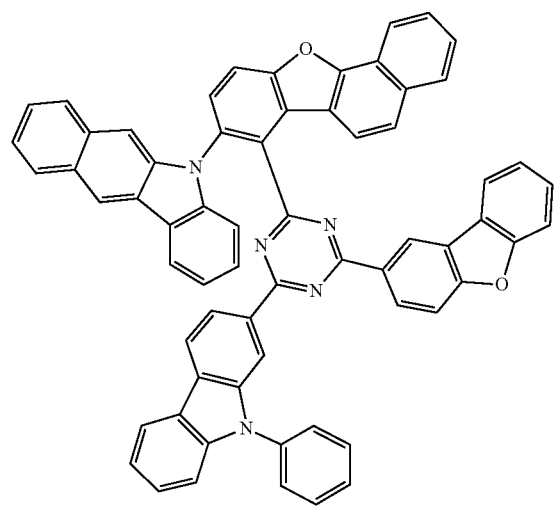
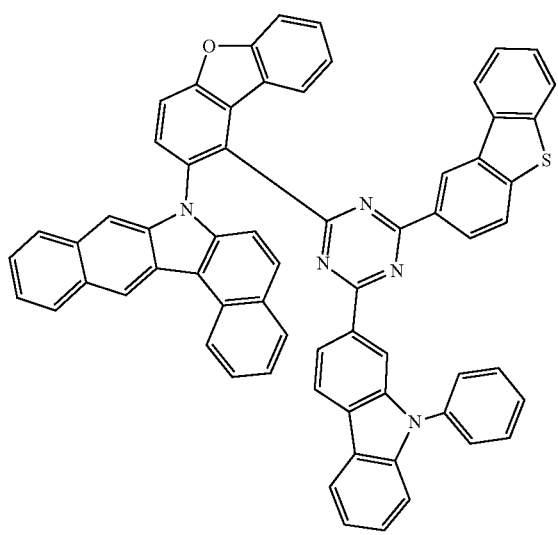

257
-continued
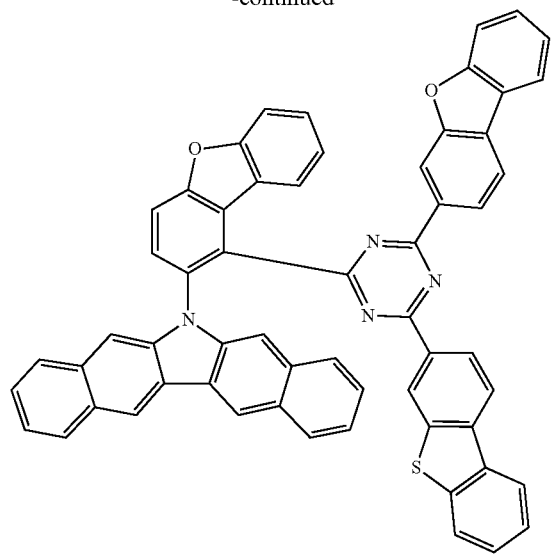
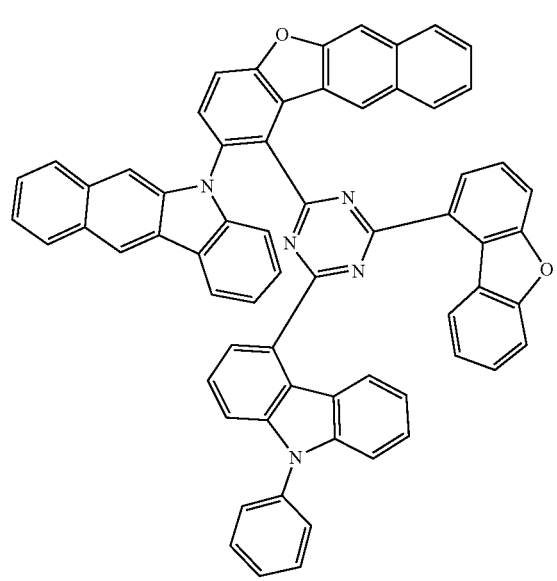
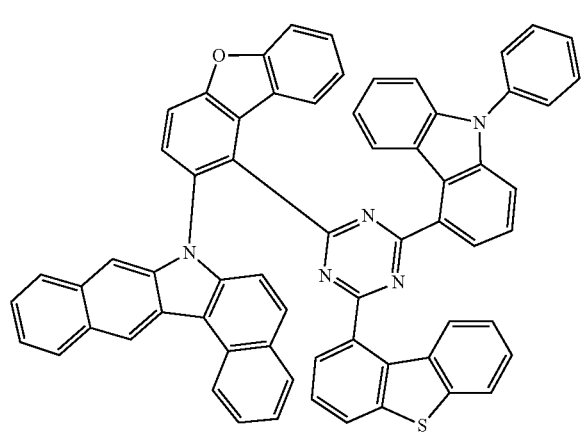
258
-continued
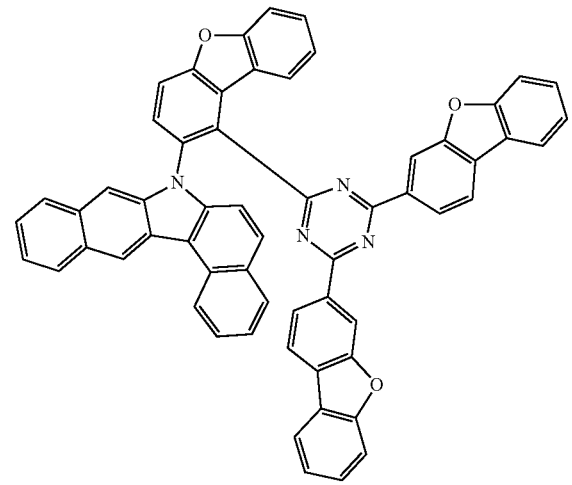
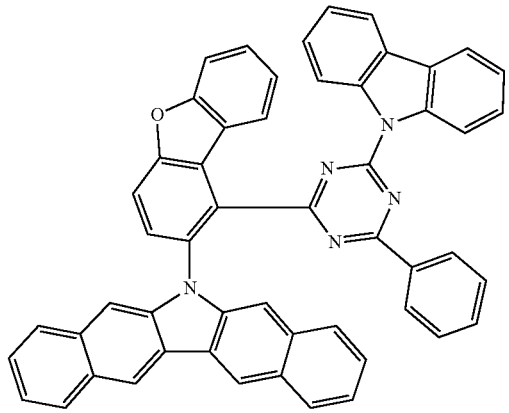
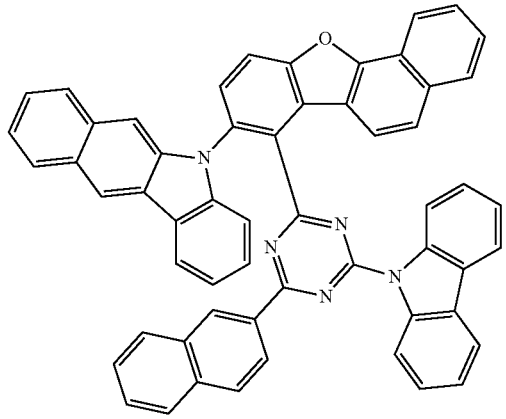

259
-continued
260
-continued
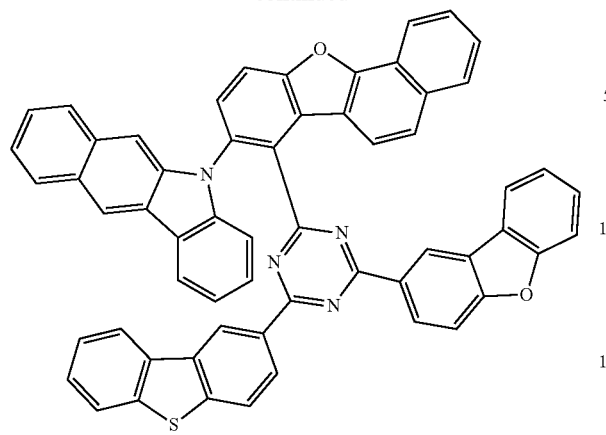
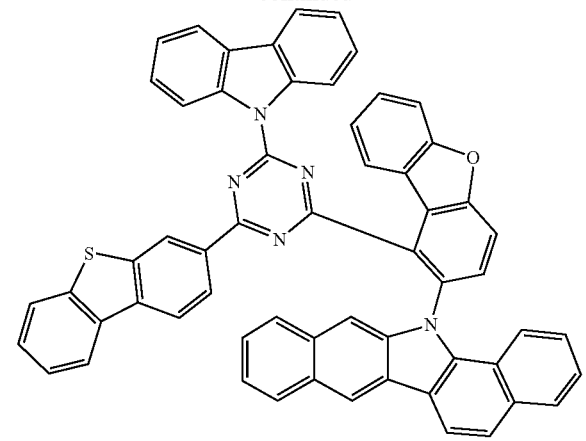
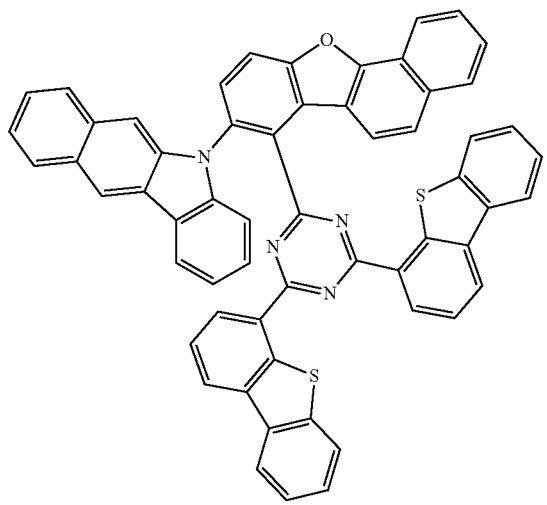
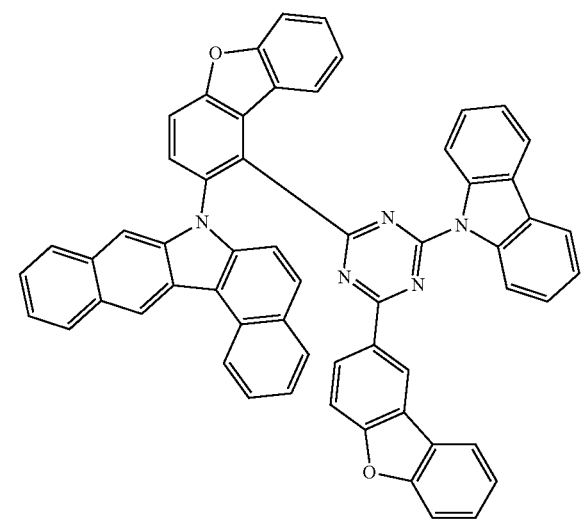

261
-continued
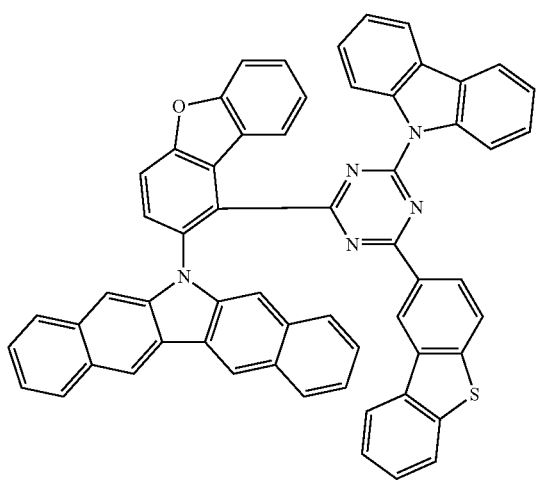
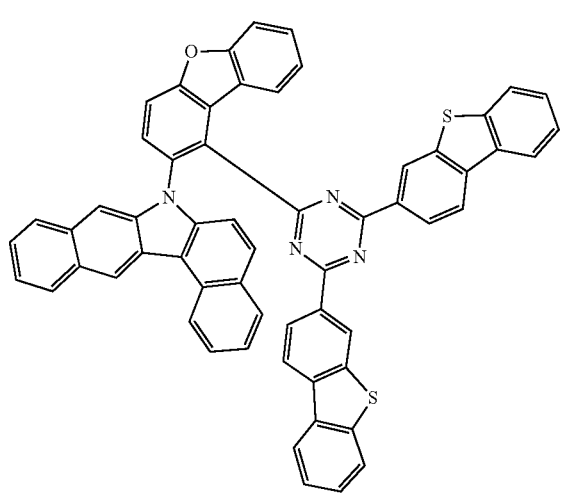
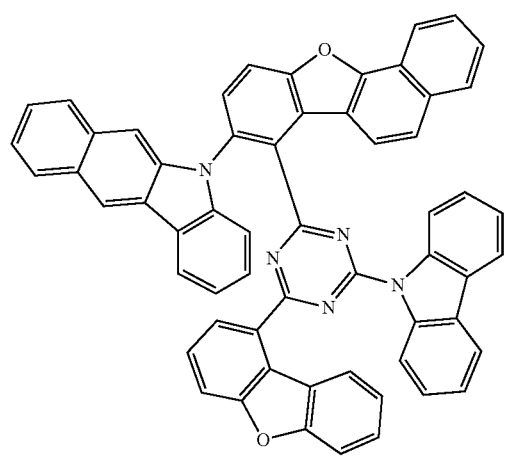
262
-continued
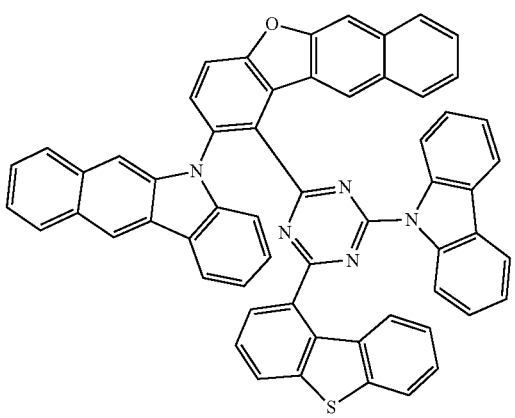
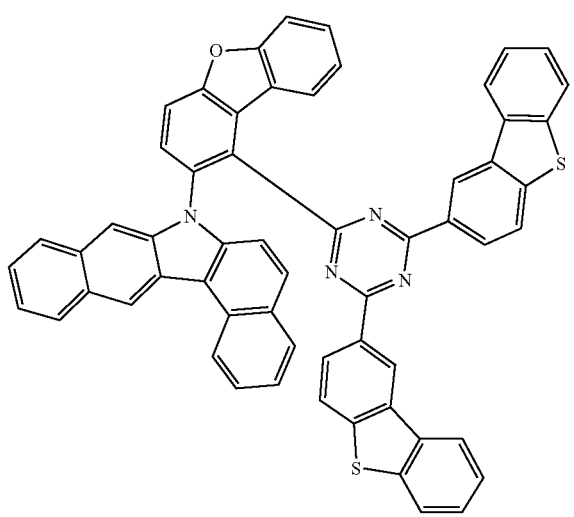
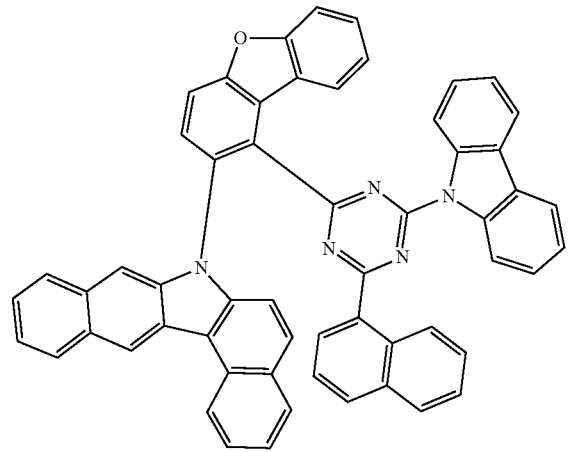

263
-continued
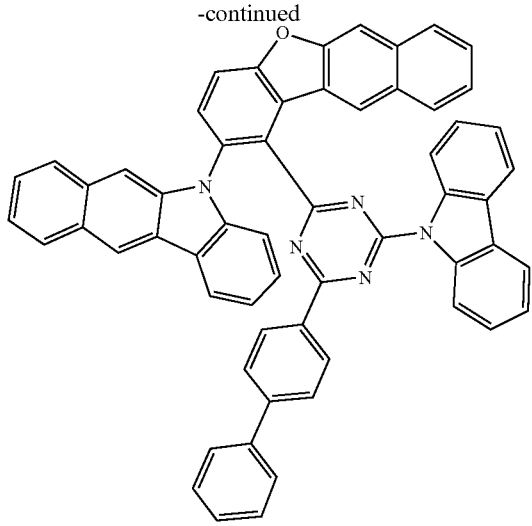
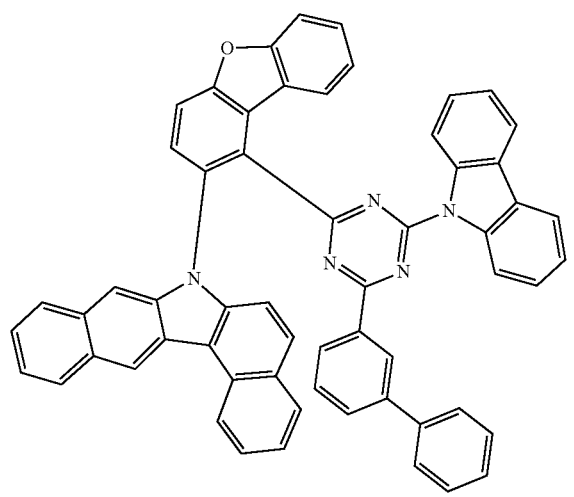
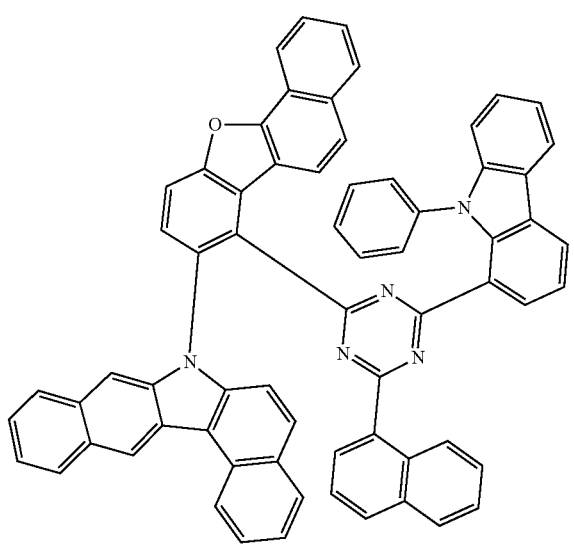
264
-continued
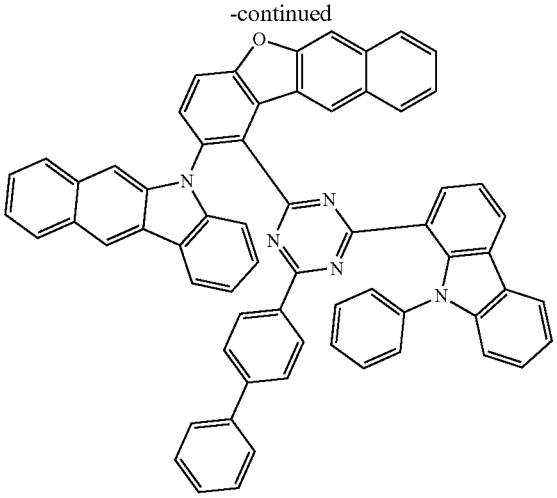
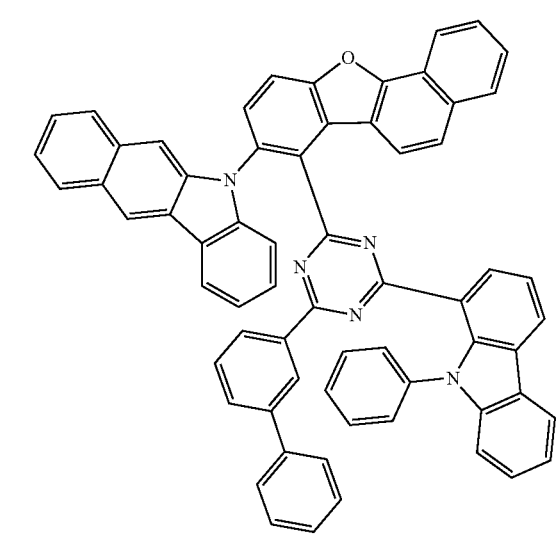
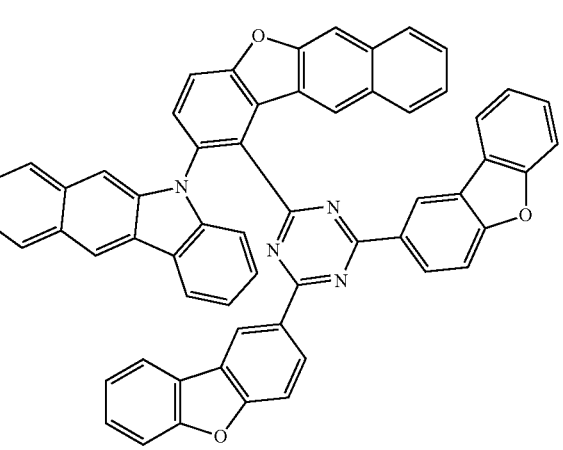

265
-continued
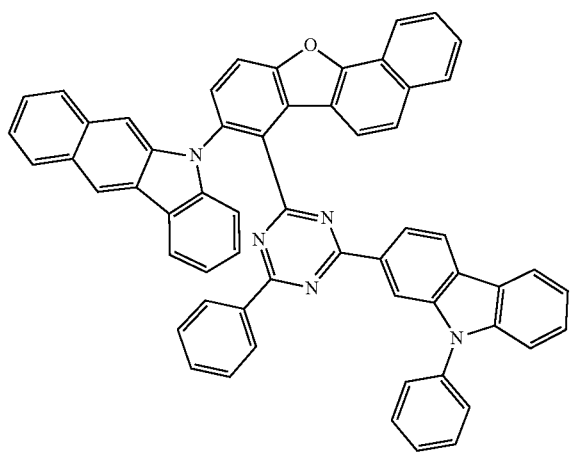
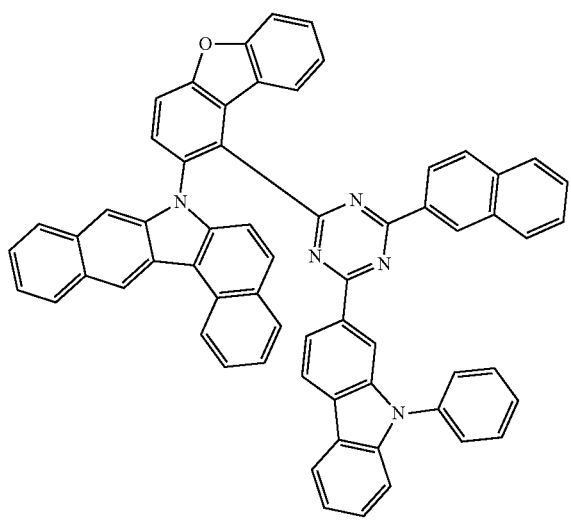
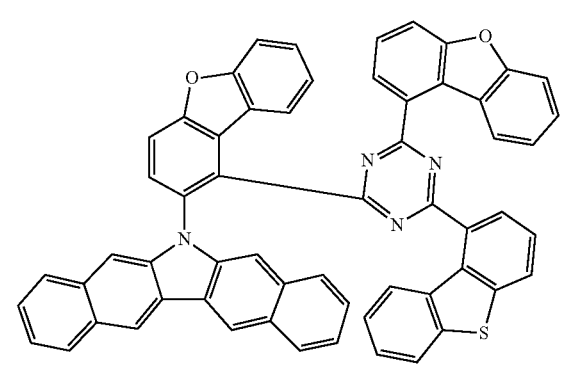
266
-continued
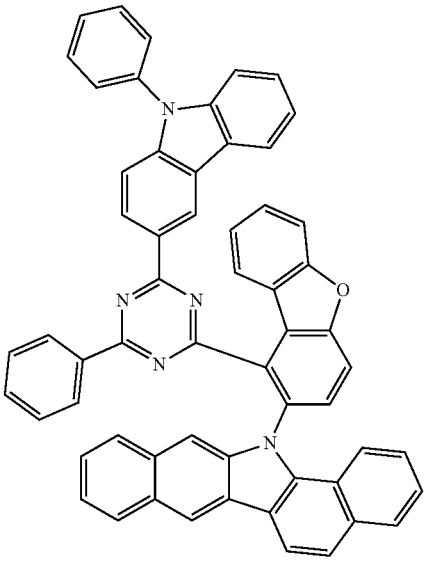
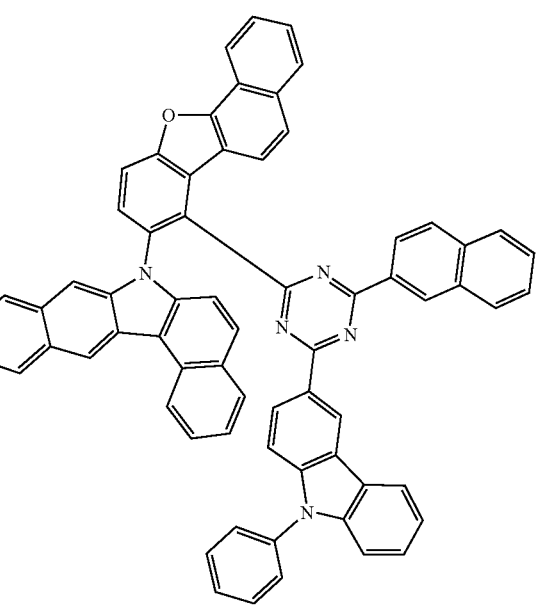
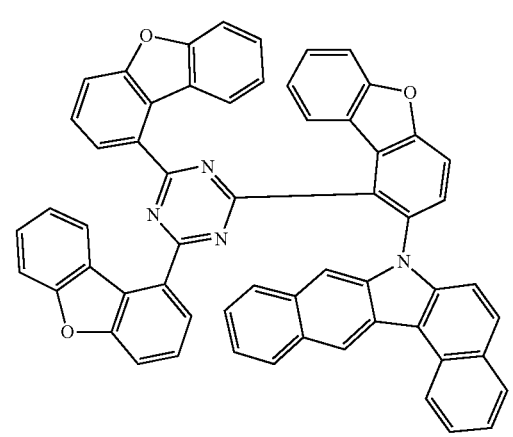

267
-continued
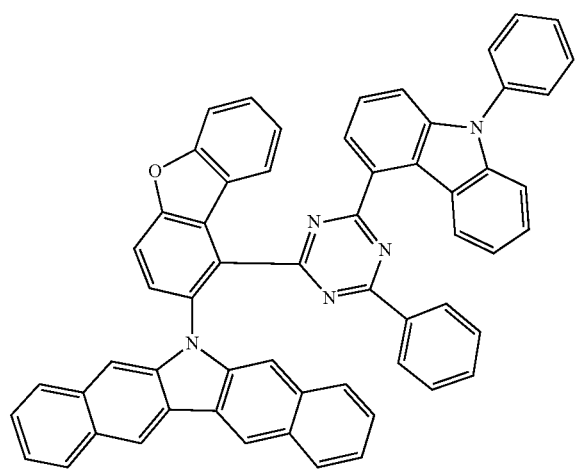
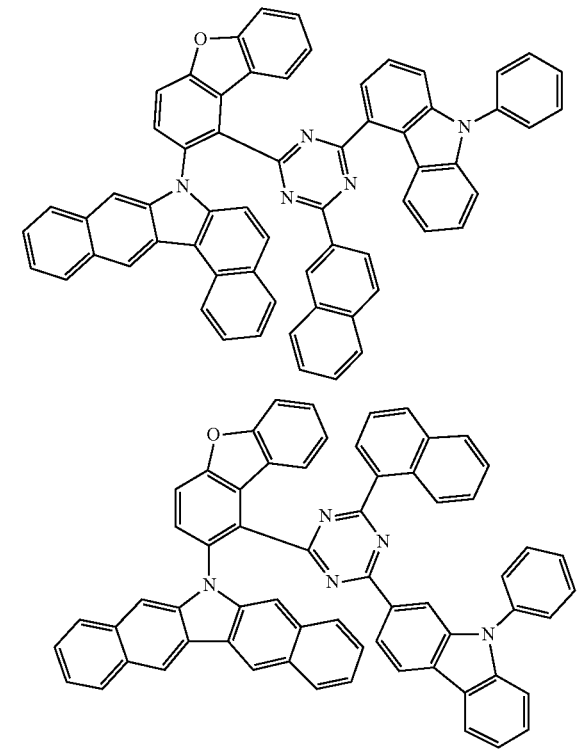
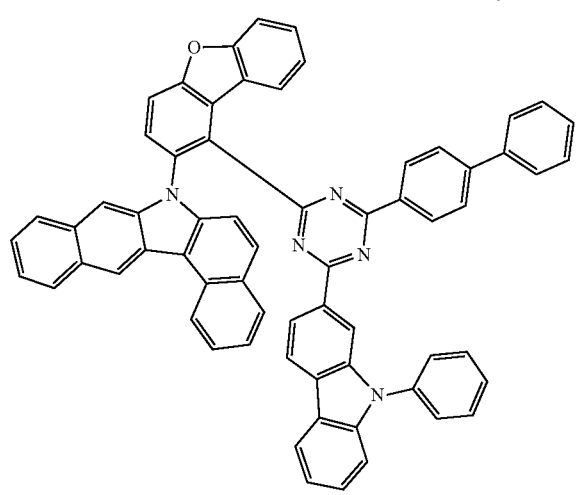
268
-continued
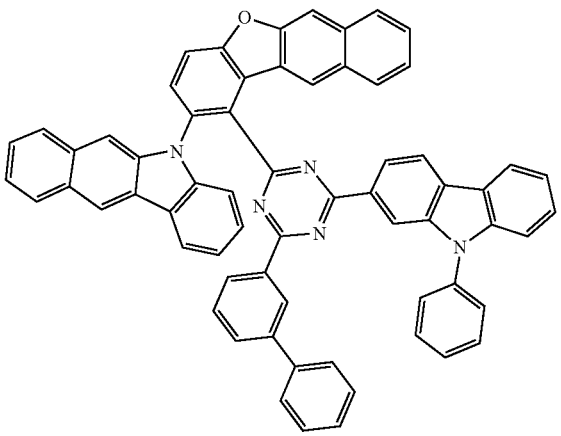
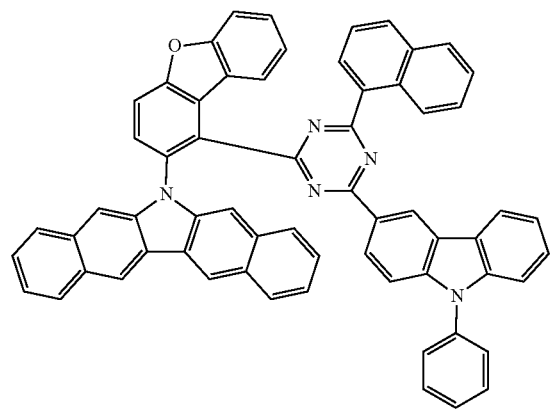
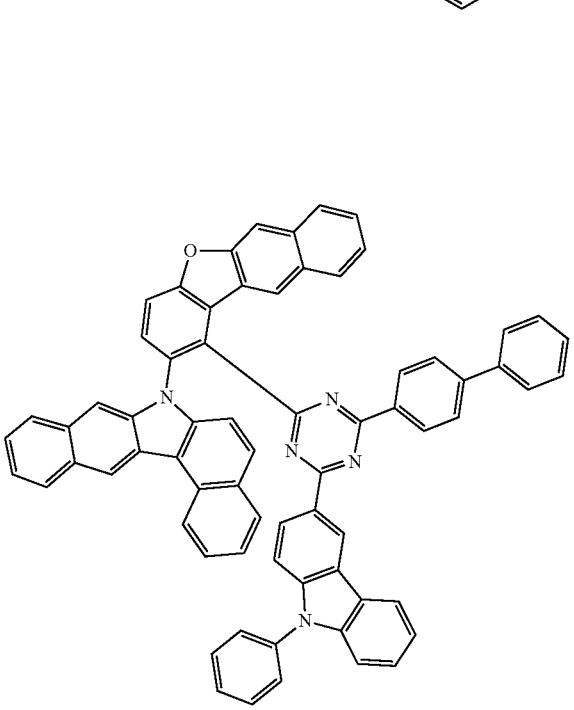

269
-continued

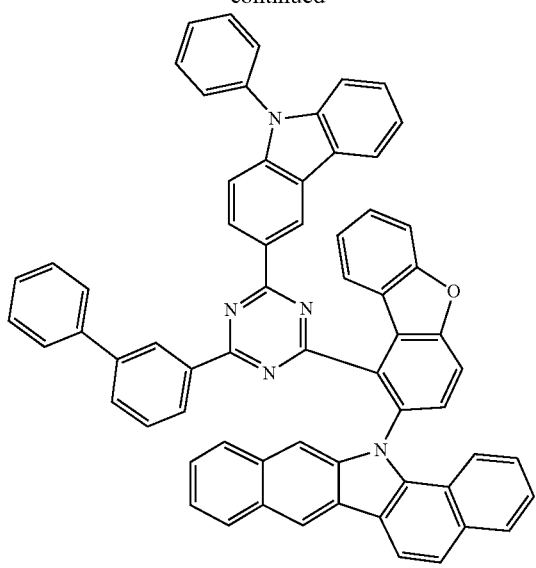

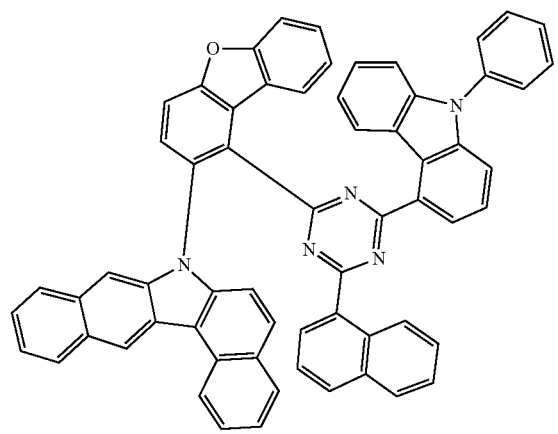

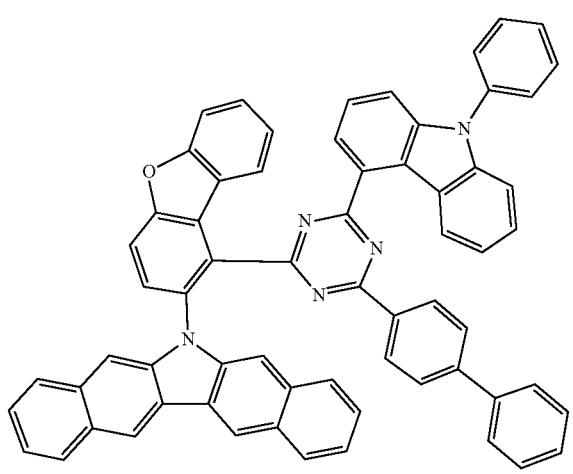

270
-continued

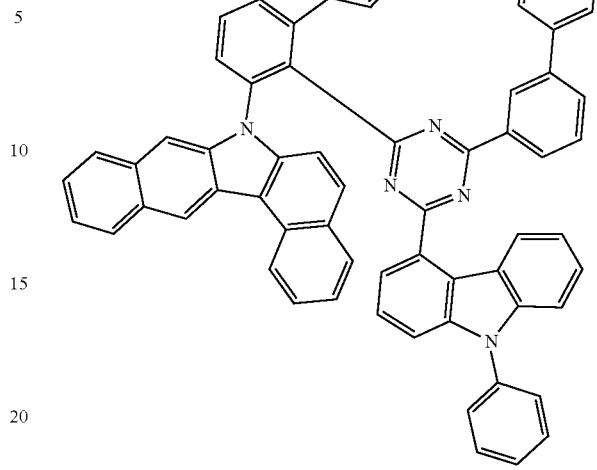

Further, the present specification provides an organic light emitting device including the above-described compound.

An exemplary embodiment of the present specification provides an organic light emitting device including: a first electrode; a second electrode provided to face the first electrode; and an organic material layer having one or more layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element can be further included.

The organic material layer of the organic light emitting device of the present specification can also be composed of a single-layered structure, but can be composed of a multi-layered structure in which an organic material layer having two or more layers is stacked. For example, the organic light emitting device of the present invention can have a structure including a hole injection layer, a hole transport layer, a light emitting layer, an electron transport layer, an electron injection layer, and the like as organic material layers. However, the structure of the organic light emitting device is not limited thereto, and can include a fewer number of organic material layers.

In an exemplary embodiment of the present specification, the organic material layer includes a hole injection layer or a hole transport layer, and the hole injection layer or the hole transport layer includes the compound.

In an exemplary embodiment of the present specification, the organic material layer includes a light emitting layer, and the light emitting layer includes the compound.

In an exemplary embodiment of the present specification, the organic material layer includes a light emitting layer, and the light emitting layer includes the compound as a host.

In an exemplary embodiment of the present specification, the organic material layer includes a light emitting layer, and the light emitting layer includes the compound of Formula 1 as a first host, and further includes a second host of the following Formula H.

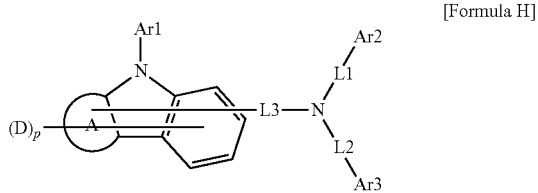

[Formula H]

In Formula H,
A is a substituted or unsubstituted naphthalene ring, Ar1 is a substituted or unsubstituted aryl group having 6 to 60 carbon atoms,
L1 to L3 are each independently a single bond; or a substituted or unsubstituted arylene group having 6 to 60 carbon atoms,
Ar2 and Ar3 are each independently a substituted or unsubstituted aryl group having 6 to 60 carbon atoms; or a substituted or unsubstituted heteroaryl group having 2 to 60 carbon atoms, including one or more heteroatoms selected from N, O, and S, and
p is an integer from 0 to 9.

In an exemplary embodiment of the present specification, A is a substituted or unsubstituted naphthalene ring.

In an exemplary embodiment of the present specification, A is a naphthalene ring which is unsubstituted or substituted with deuterium.

In an exemplary embodiment of the present specification, A is a naphthalene ring.

In an exemplary embodiment of the present specification, p means the number of deuterium substitutions, and the case where p is 0 means a state of all being substituted with hydrogen.

In an exemplary embodiment of the present specification, L1 to L3 are each independently a single bond; or a substituted or unsubstituted arylene group having 6 to 30 carbon atoms.

In an exemplary embodiment of the present specification, L1 to L3 are each independently a single bond; a substituted or unsubstituted phenylene group; or a substituted or unsubstituted divalent naphthalene group.

In an exemplary embodiment of the present specification, L1 to L3 are each independently a single bond; a phenylene group which is unsubstituted or substituted with deuterium; or a divalent naphthalene group which is unsubstituted or substituted with deuterium.

In an exemplary embodiment of the present specification, L1 to L3 are each independently a single bond; a phenylene group; or a divalent naphthalene group.

In an exemplary embodiment of the present specification, Ar1 is a substituted or unsubstituted aryl group having 6 to 30 carbon atoms.

In an exemplary embodiment of the present specification, Ar1 is a substituted or unsubstituted phenyl group; a substituted or unsubstituted biphenyl group; a substituted or unsubstituted terphenyl group; or a substituted or unsubstituted naphthyl group.

In an exemplary embodiment of the present specification, Ar1 is a phenyl group which is unsubstituted or substituted with a group selected from the group consisting of deuterium, an alkyl group, a cycloalkyl group, and an aryl group; a biphenyl group which is unsubstituted or substituted with a group selected from the group consisting of deuterium, an alkyl group, a cycloalkyl group, and an aryl group; a terphenyl group which is unsubstituted or substituted with a group selected from the group consisting of deuterium, an alkyl group, a cycloalkyl group, and an aryl group; or a naphthyl group which is unsubstituted or substituted with a group selected from the group consisting of deuterium, an alkyl group, a cycloalkyl group, and an aryl group.

In an exemplary embodiment of the present specification, Ar1 is a phenyl group which is unsubstituted or substituted with a group selected from the group consisting of deuterium, an alkyl group, a cycloalkyl group, and an aryl group; a biphenyl group; a terphenyl group; or a naphthyl group.

In an exemplary embodiment of the present specification, Ar1 is a phenyl group which is unsubstituted or substituted with a group selected from the group consisting of deuterium, a tert-butyl group, an adamantyl group, a phenyl group, and a naphthyl group; a biphenyl group; a terphenyl group; or a naphthyl group.

In an exemplary embodiment of the present specification, Ar2 and Ar3 are each independently a substituted or unsubstituted aryl group having 6 to 30 carbon atoms; or a substituted or unsubstituted heteroaryl group having 2 to 30 carbon atoms, including one or more heteroatoms selected from N, O, and S.

In an exemplary embodiment of the present specification, Ar2 and Ar3 are each independently a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted dibenzofuranyl group; or a substituted or unsubstituted dibenzothiophenyl group.

In an exemplary embodiment of the present specification, Ar2 and Ar3 are each independently a phenyl group which is unsubstituted or substituted with a group selected from the group consisting of deuterium, an alkyl group, a cycloalkyl group, and an aryl group; a biphenyl group which is unsubstituted or substituted with deuterium; a terphenyl group which is unsubstituted or substituted with deuterium; a naphthyl group which is unsubstituted or substituted with deuterium; a fluorenyl group which is unsubstituted or substituted with an alkyl group; a dibenzofuranyl group which is unsubstituted or substituted with deuterium; or a dibenzothiophenyl group which is unsubstituted or substituted with deuterium.

In an exemplary embodiment of the present specification, Ar2 and Ar3 are each independently a phenyl group which is unsubstituted or substituted with a group selected from the group consisting of deuterium, a tert-butyl group, an adamantyl group, and a phenyl group; a biphenyl group; a terphenyl group; a naphthyl group; a dimethylfluorenyl group; a dibenzofuranyl group; or a dibenzothiophenyl group.

In an exemplary embodiment of the present specification, the second host of Formula H can be of any one of the following compounds, and is not limited thereto.

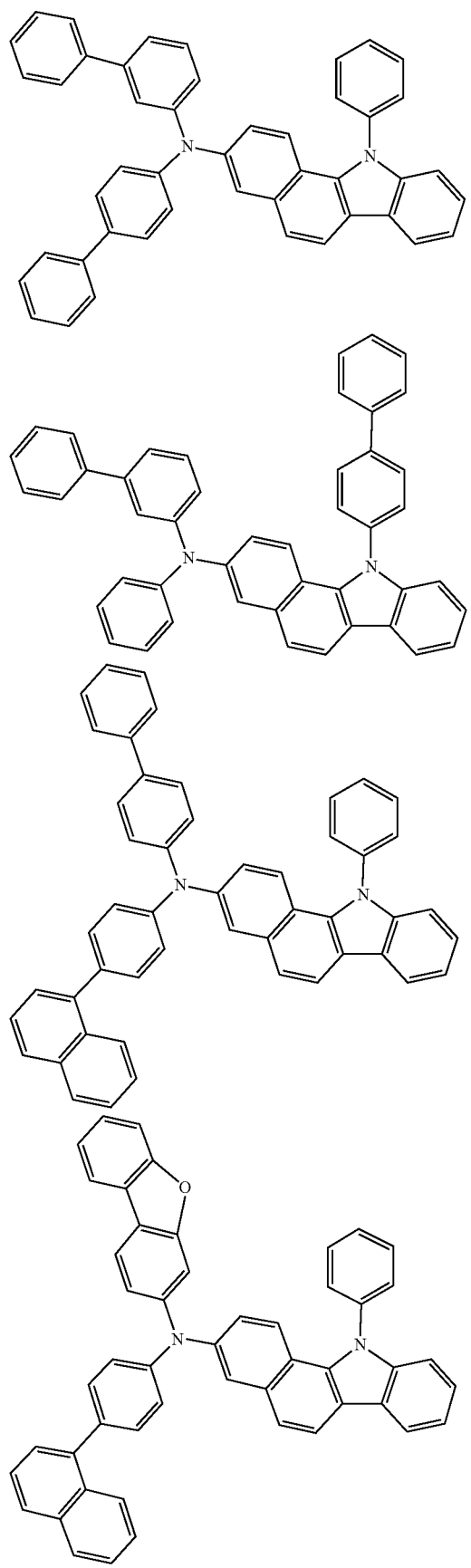
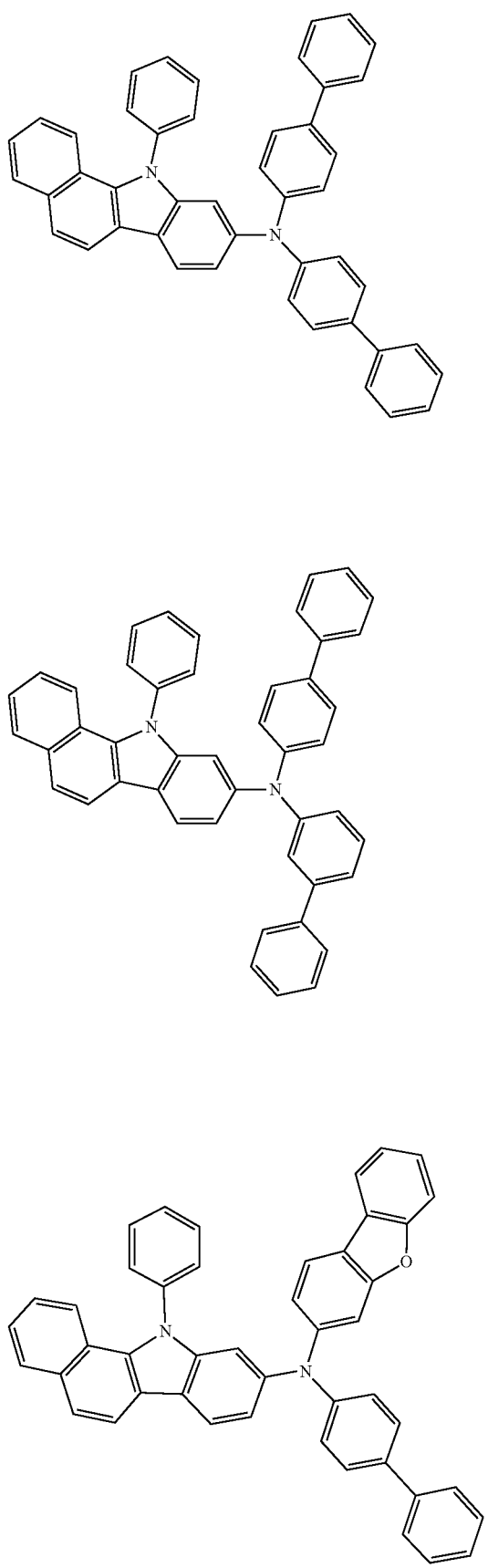

275
-continued
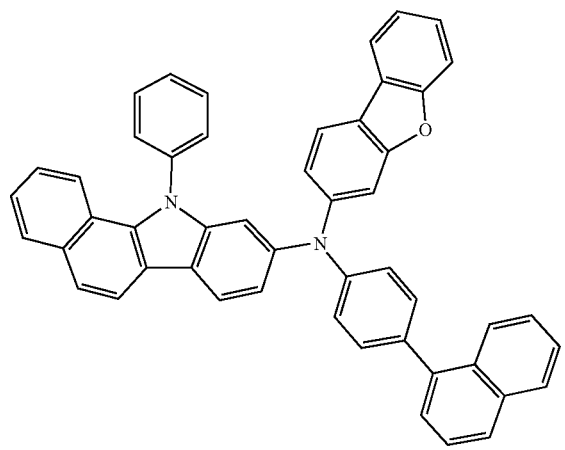
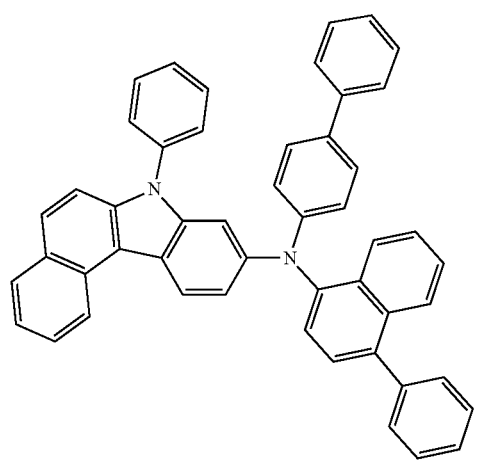
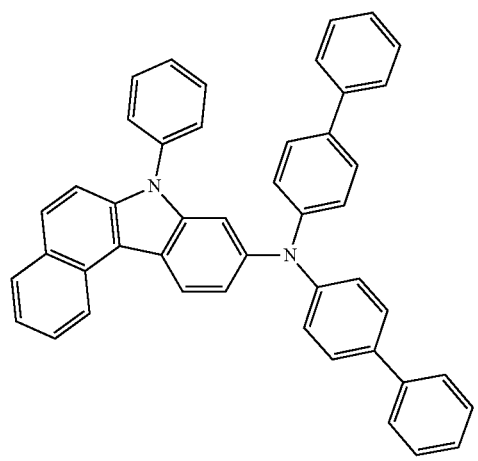
276
-continued
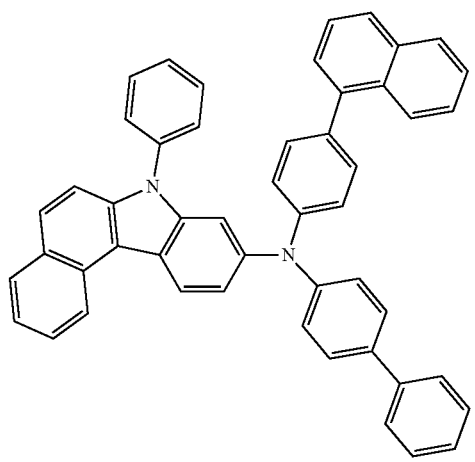
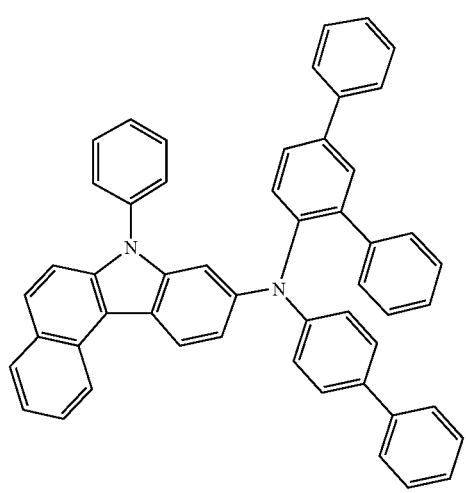
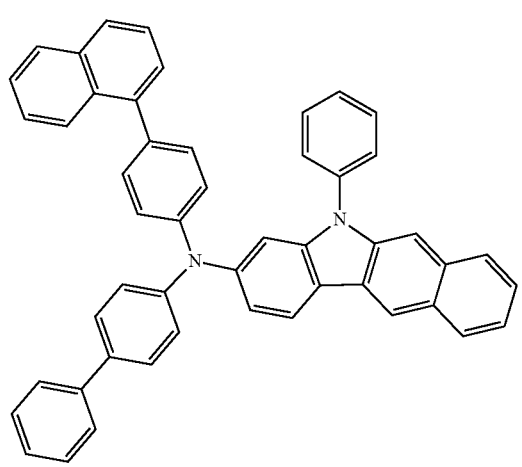

277
-continued
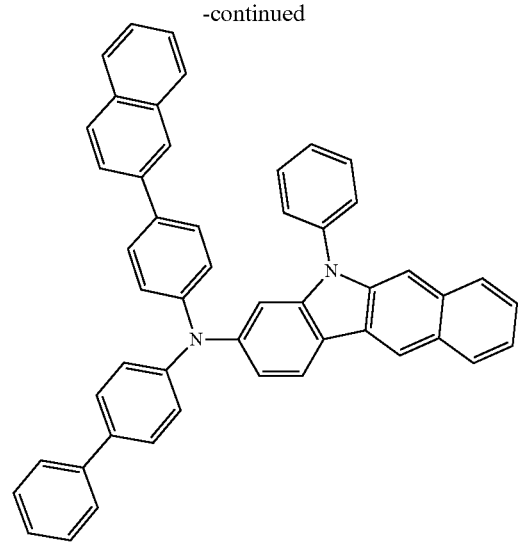
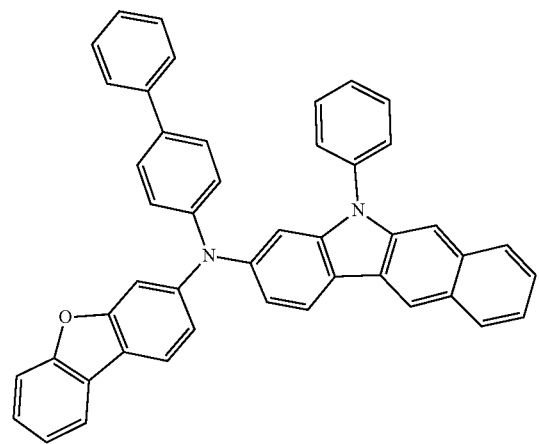
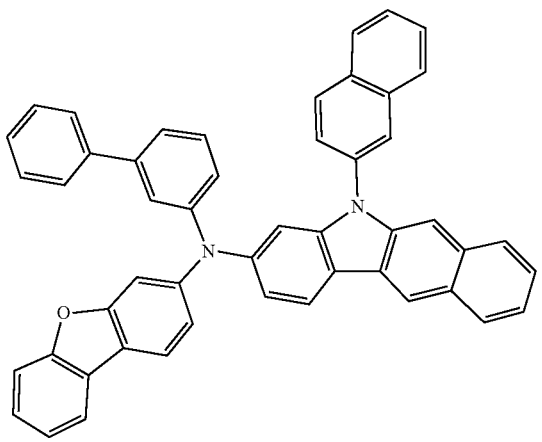
278
-continued
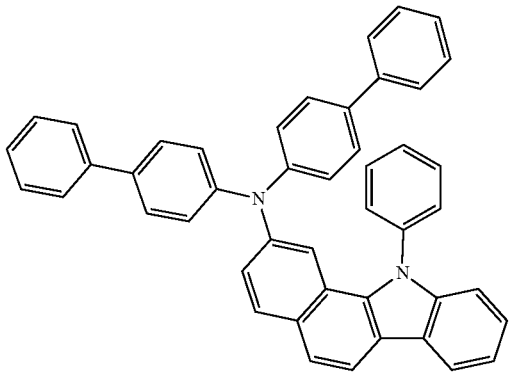
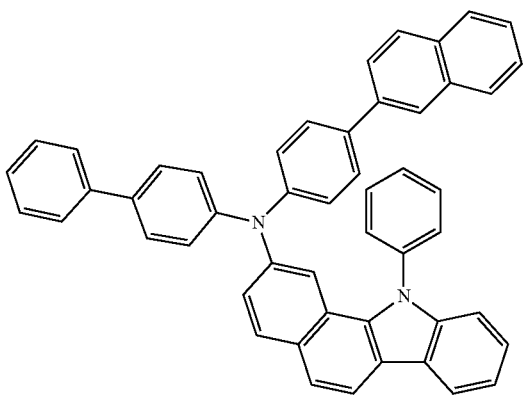
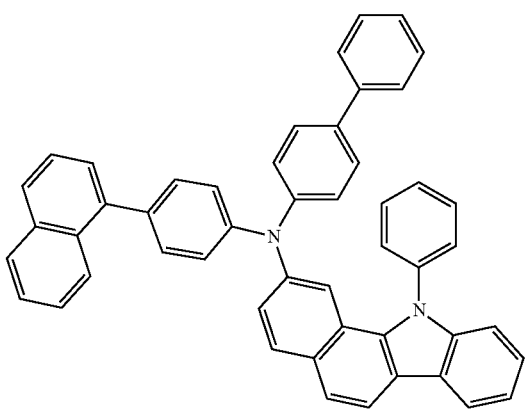
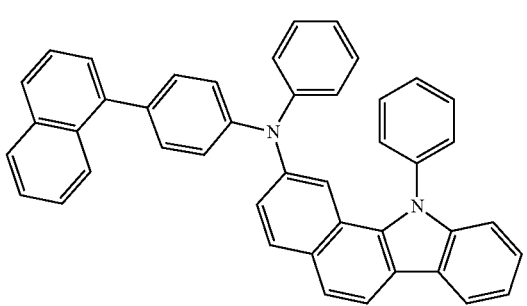

-continued
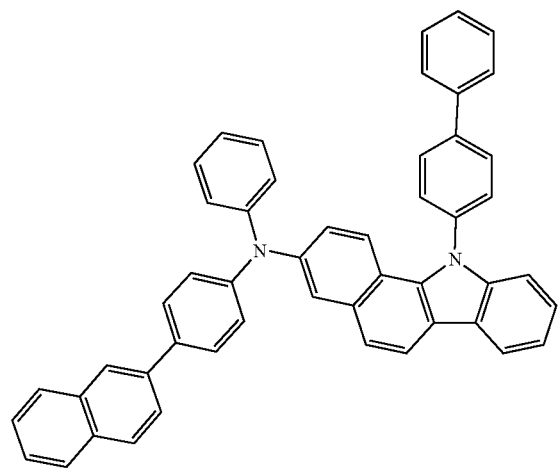
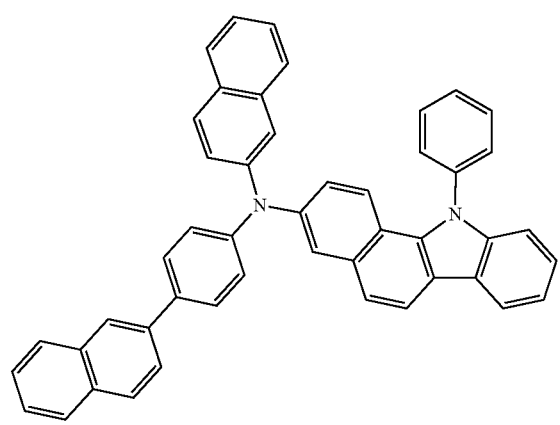
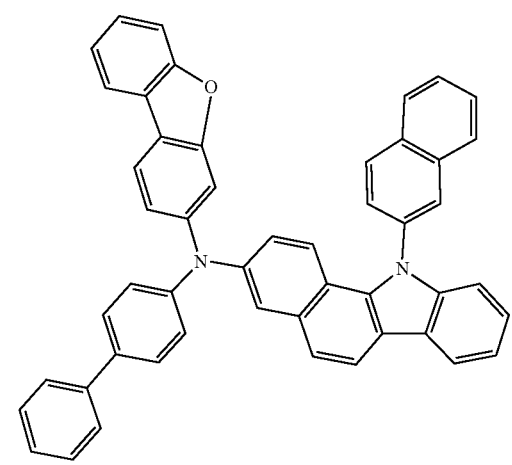
-continued
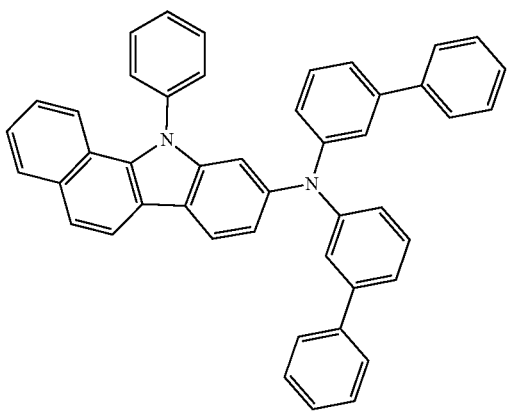
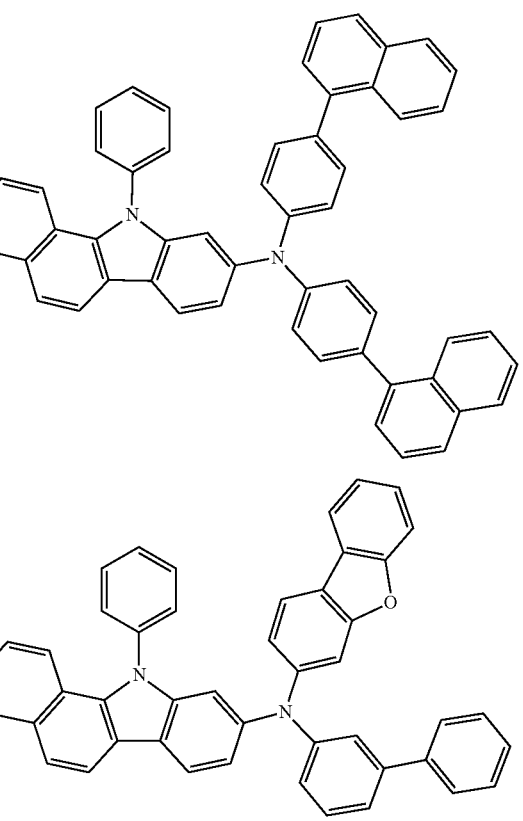
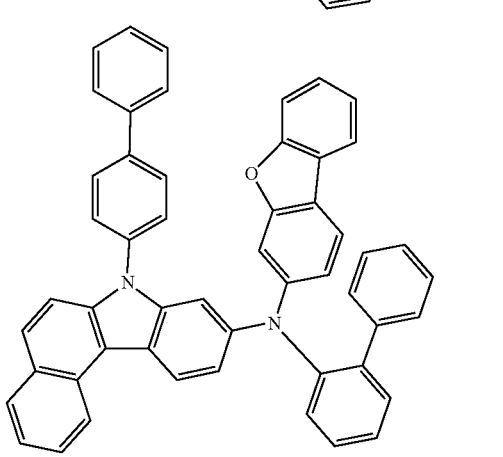

281
-continued
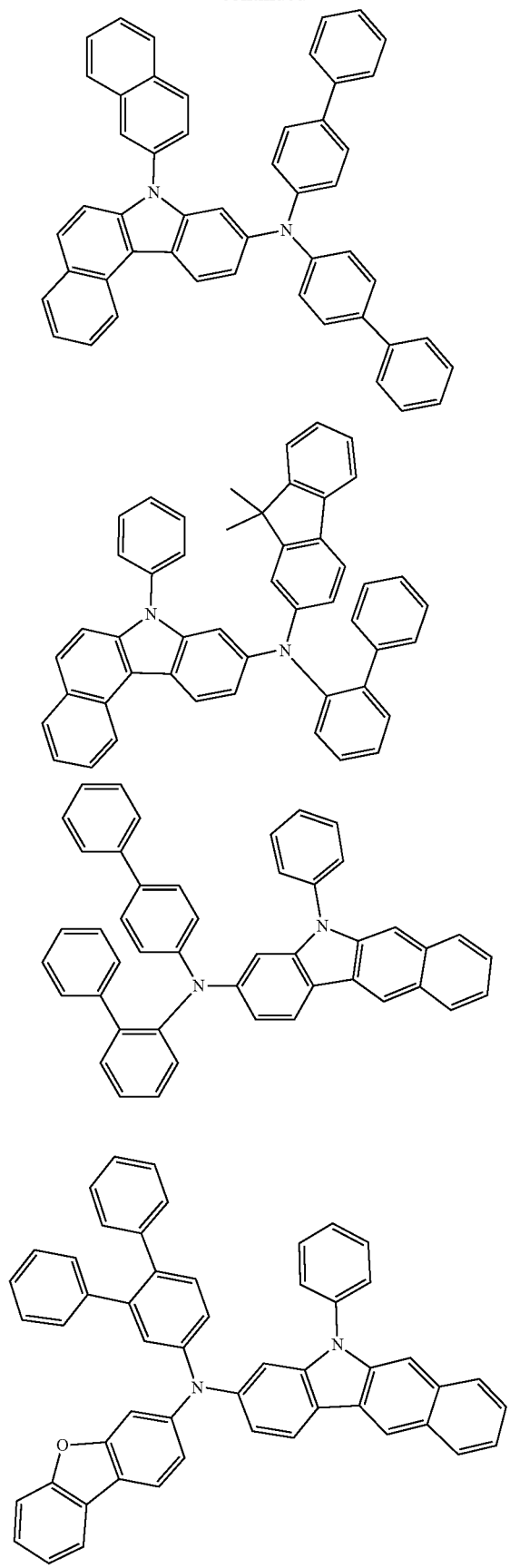
282
-continued
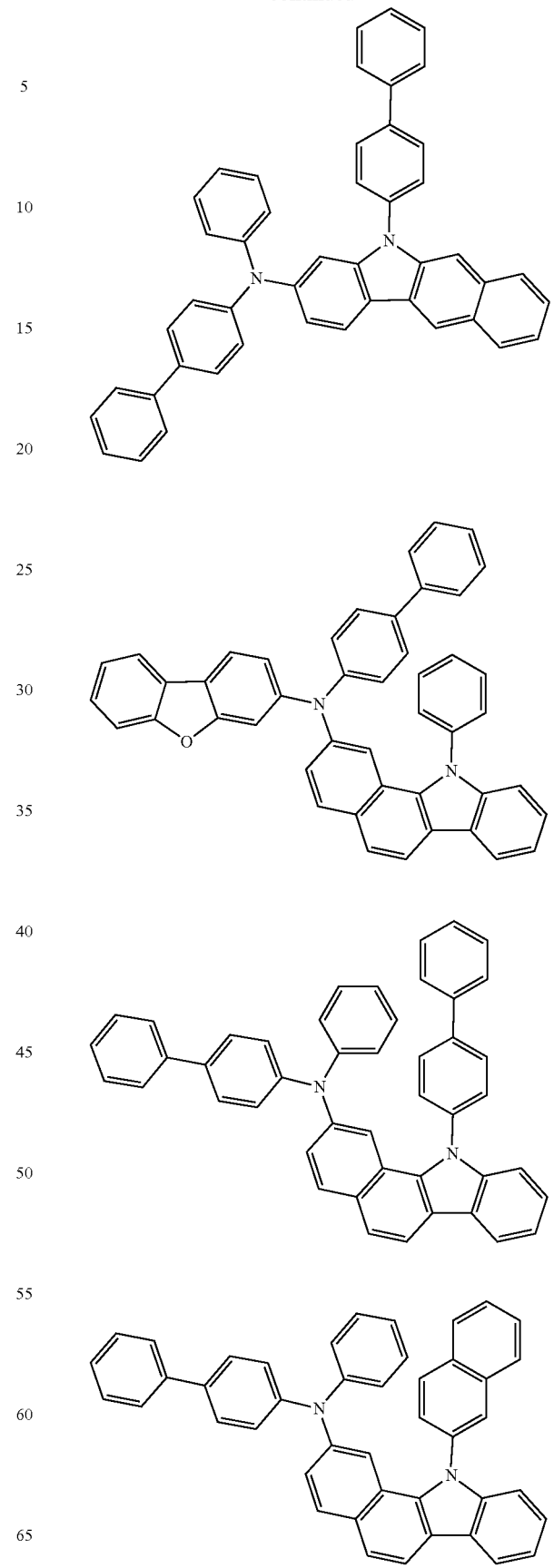

283
-continued
284
-continued
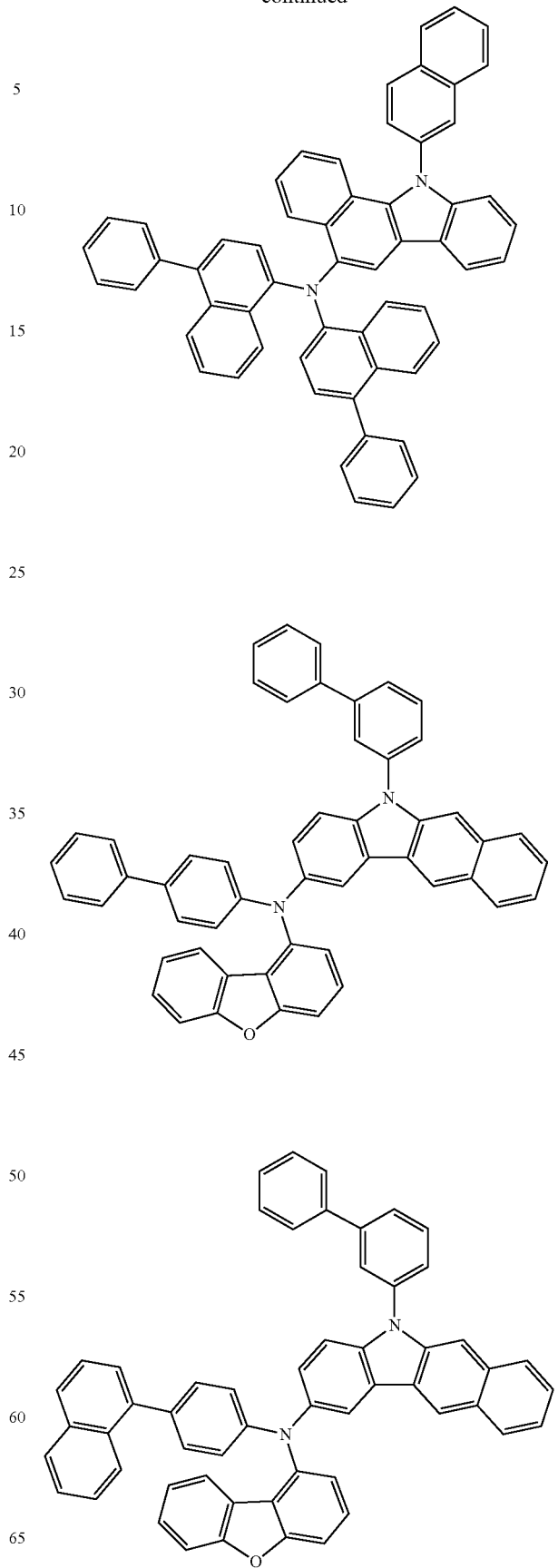

-continued
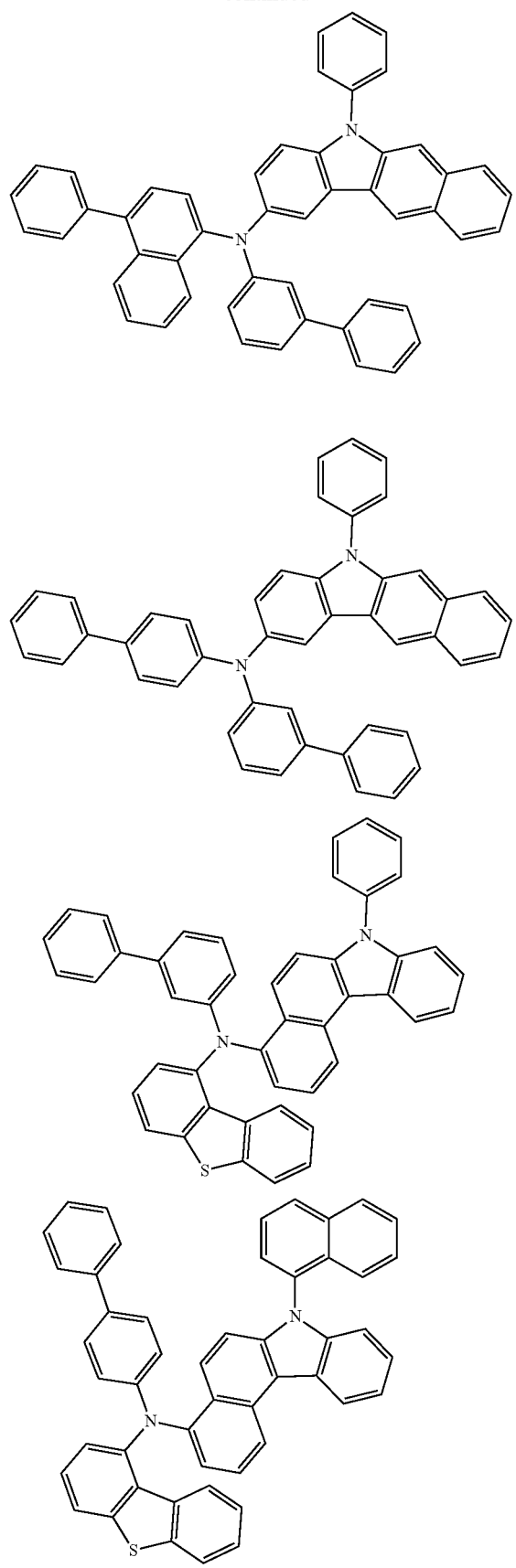
-continued
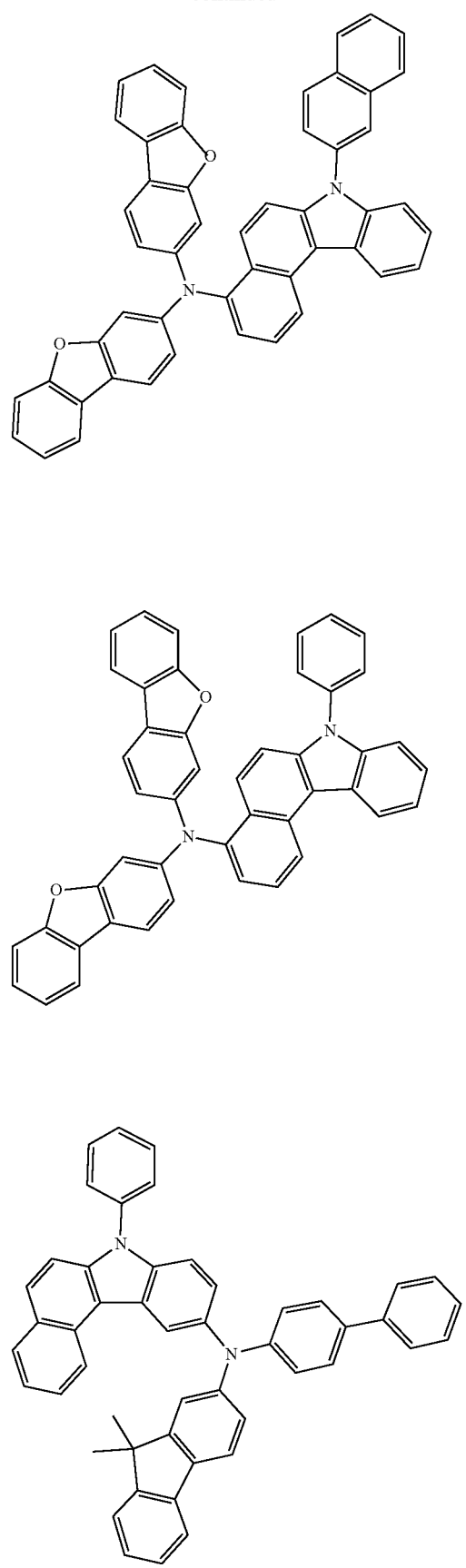

287
-continued
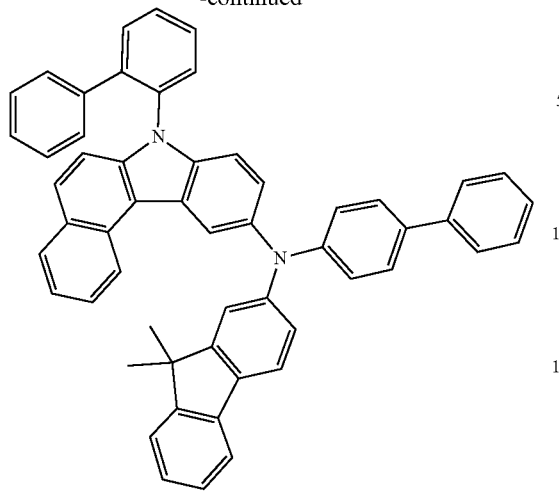
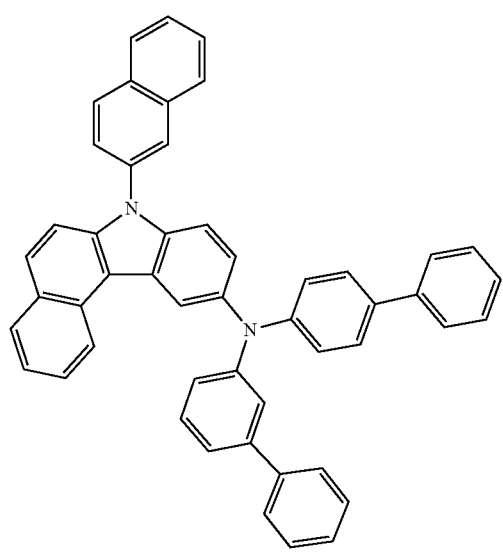
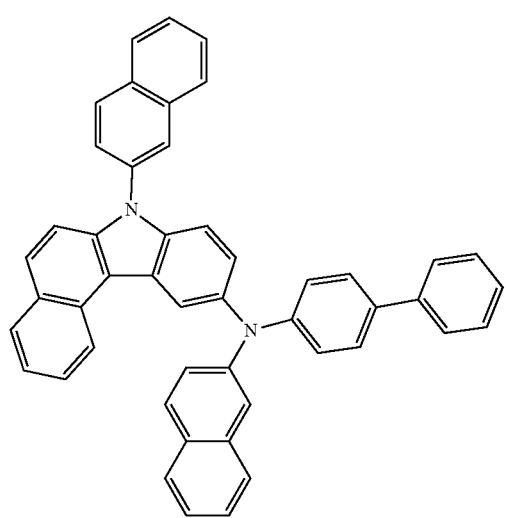
288
-continued
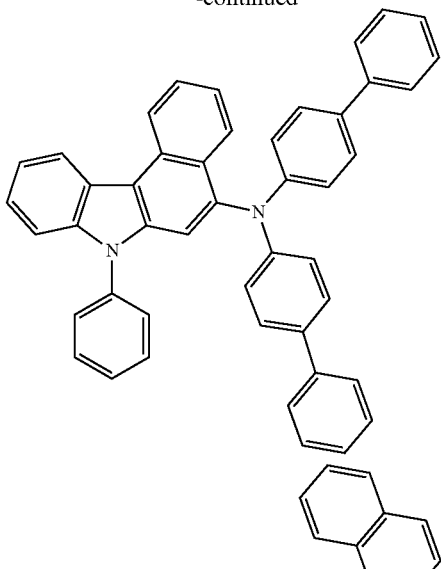
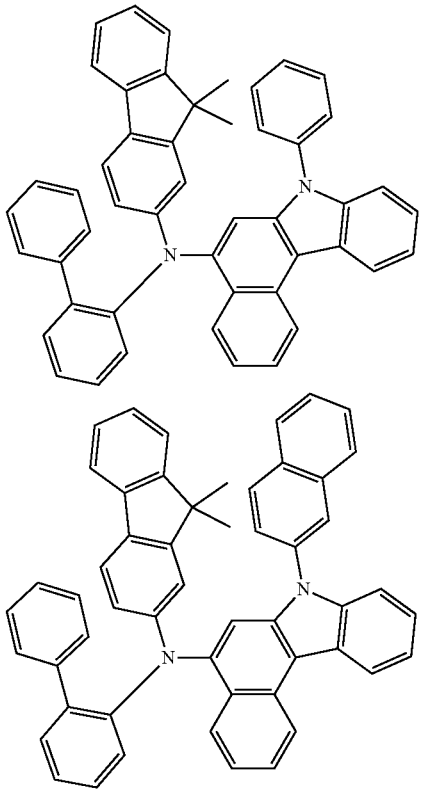

289
-continued
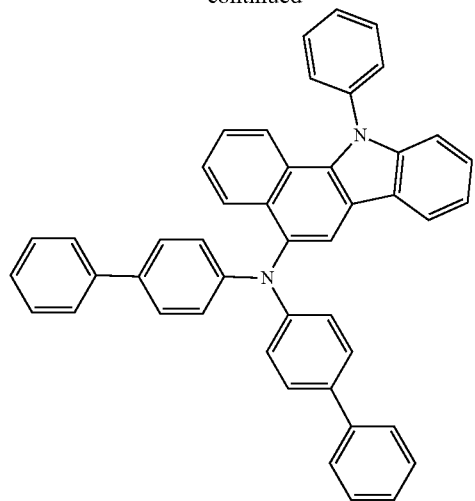
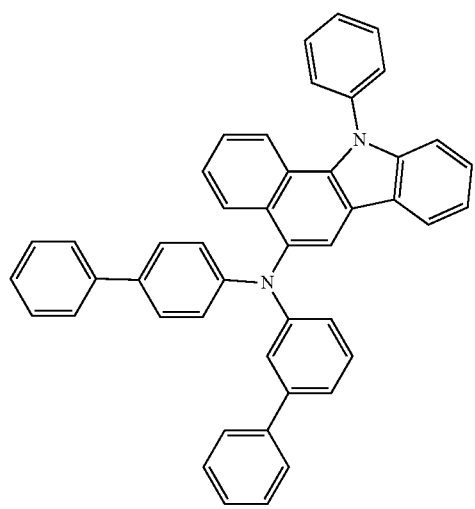
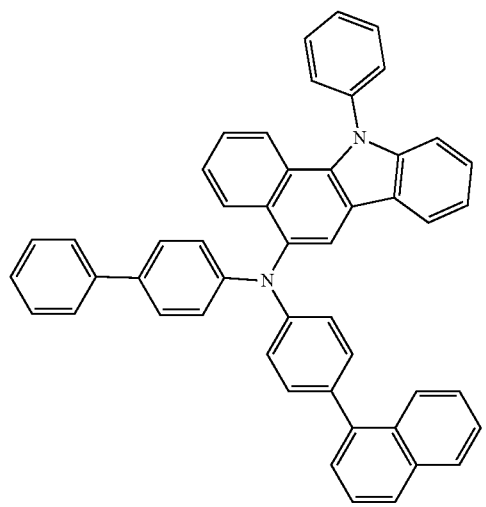
290
-continued
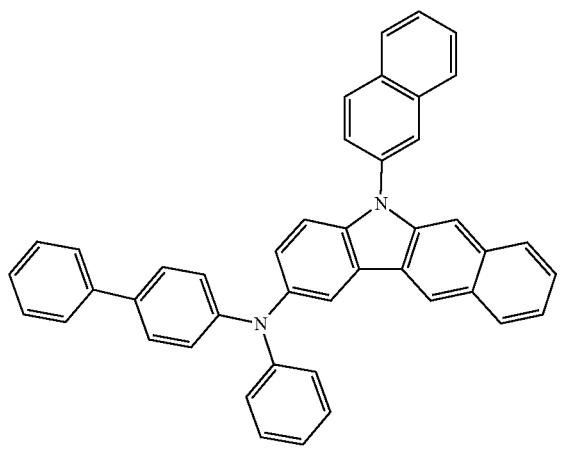
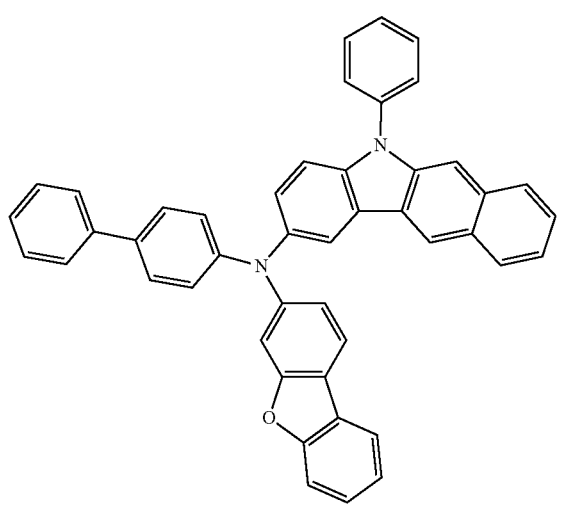
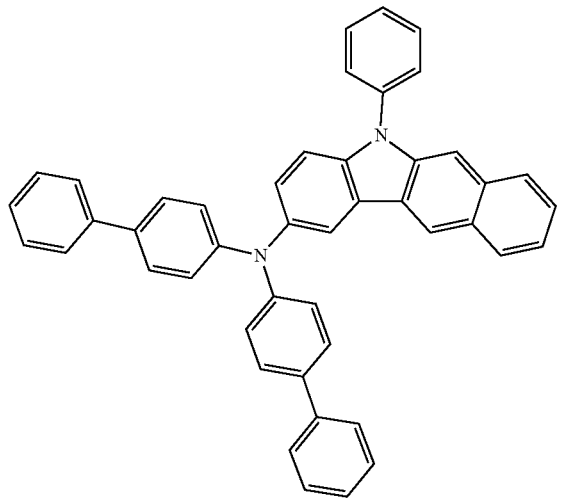

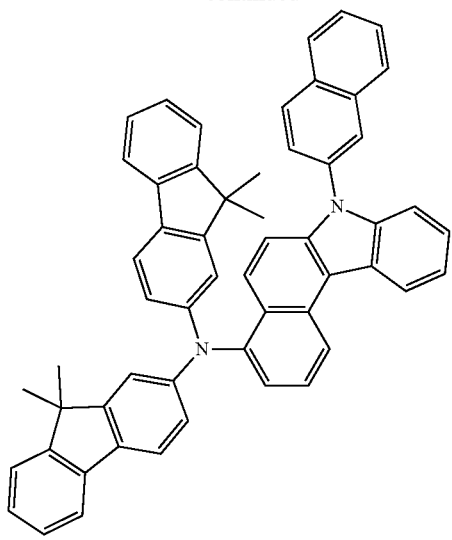
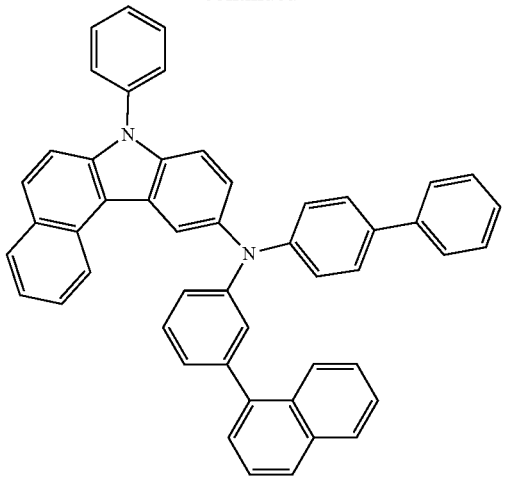
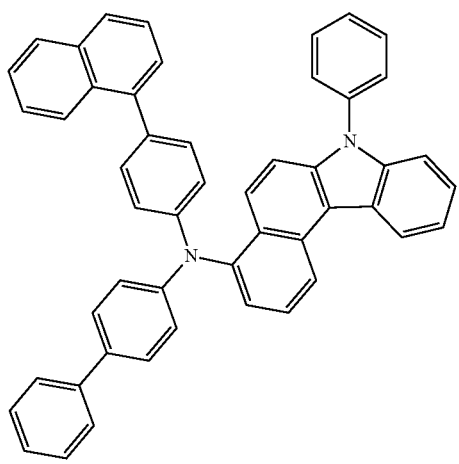
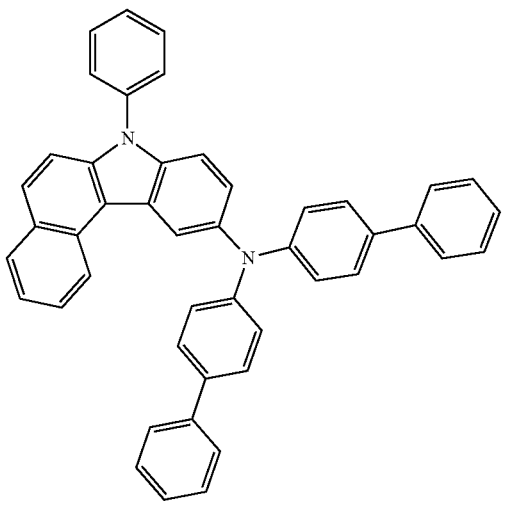
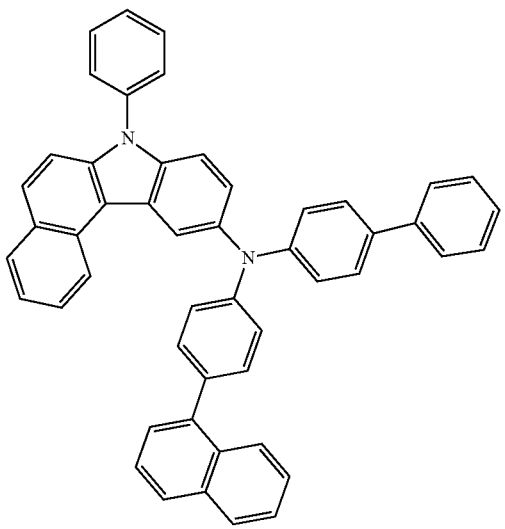

293
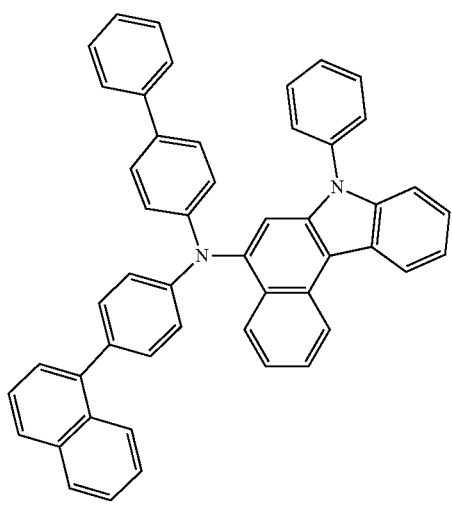
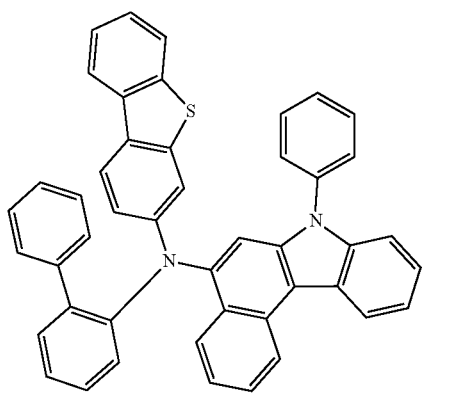
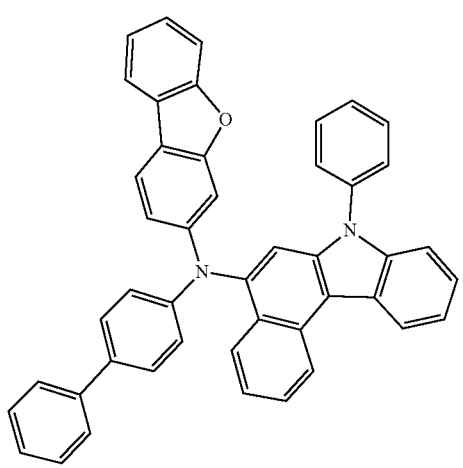
294
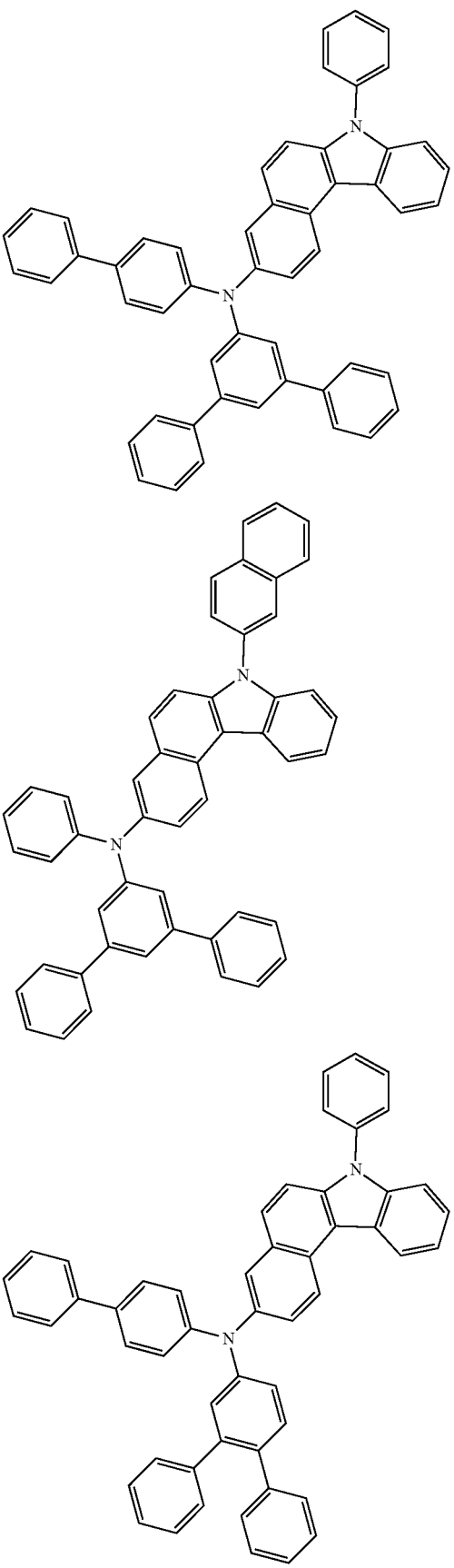

295
-continued
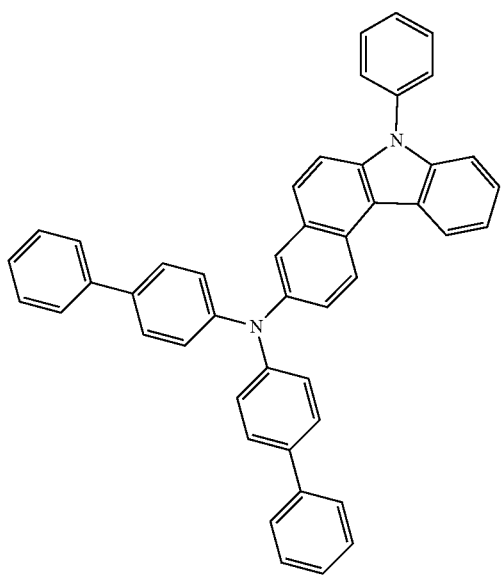
296
-continued
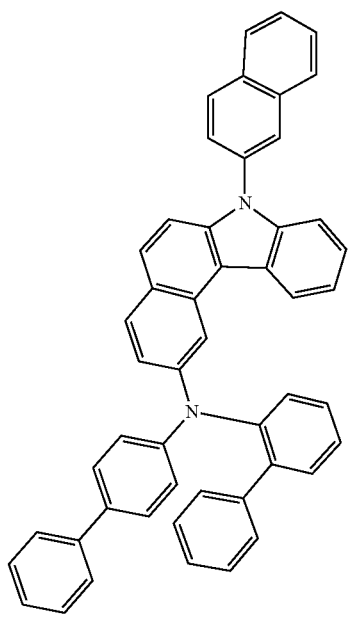
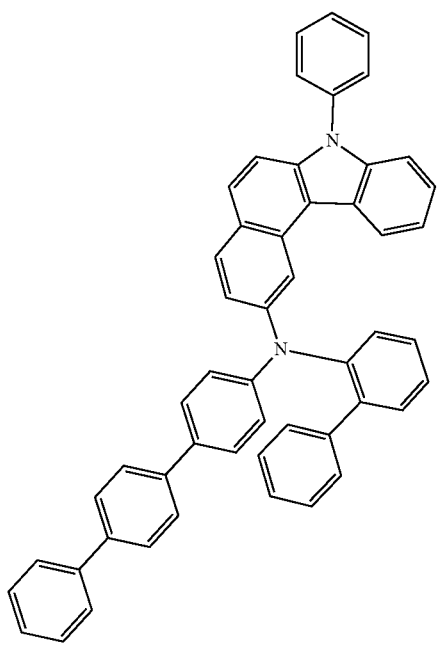
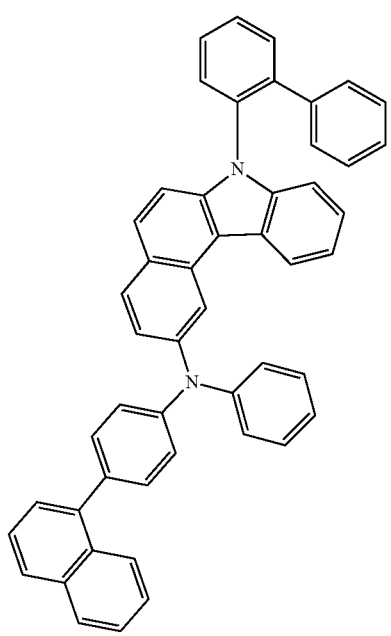

297
-continued
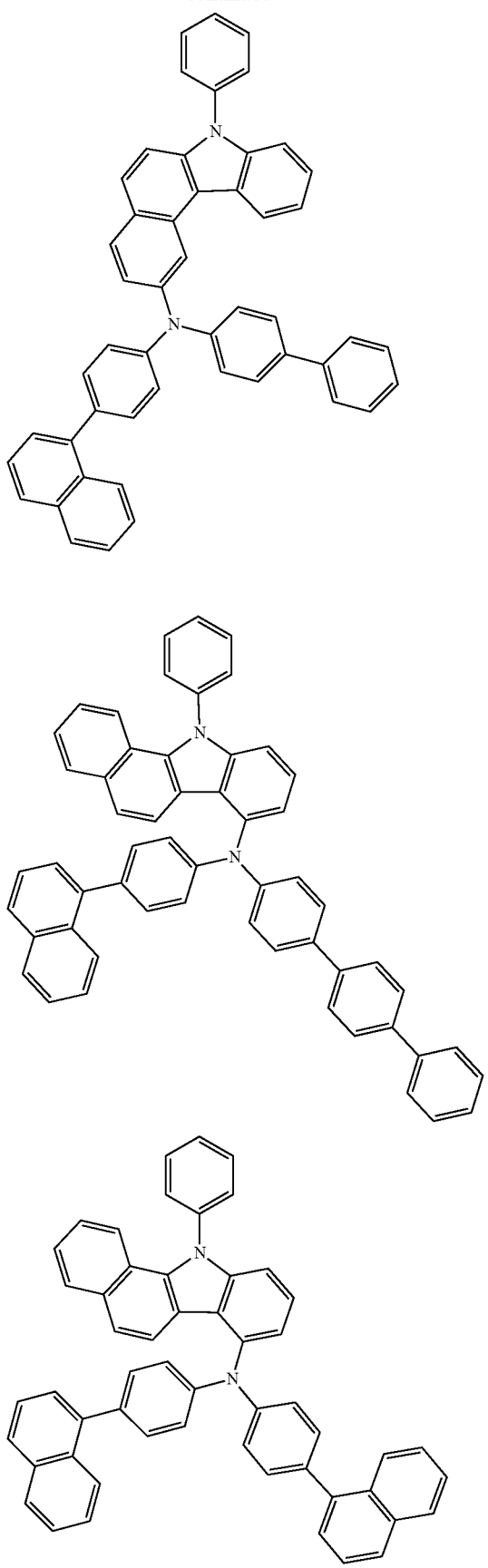
298
-continued
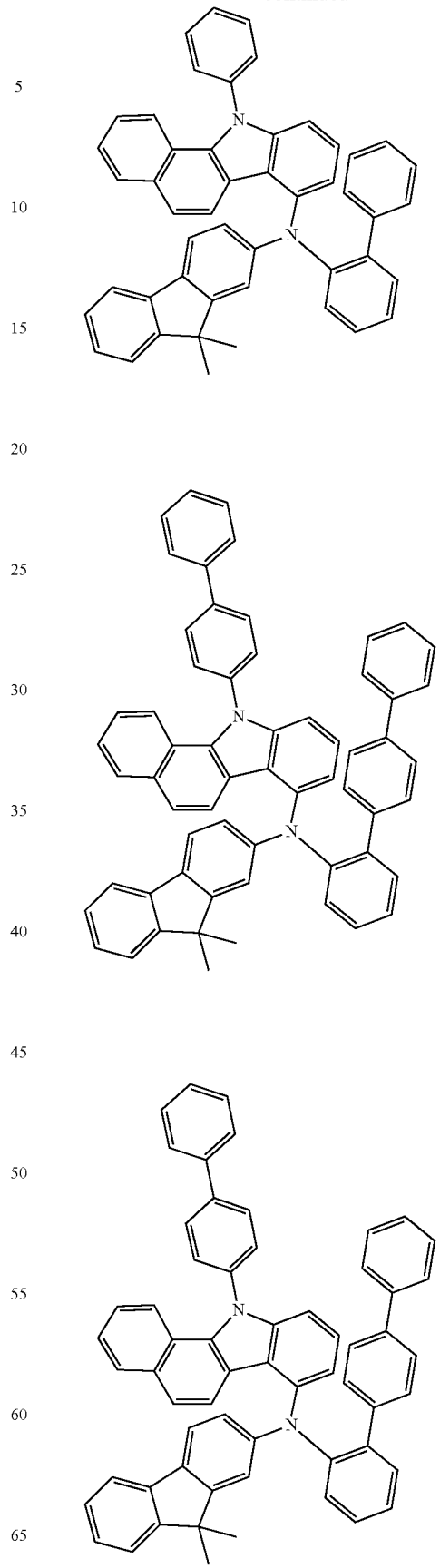

299
-continued
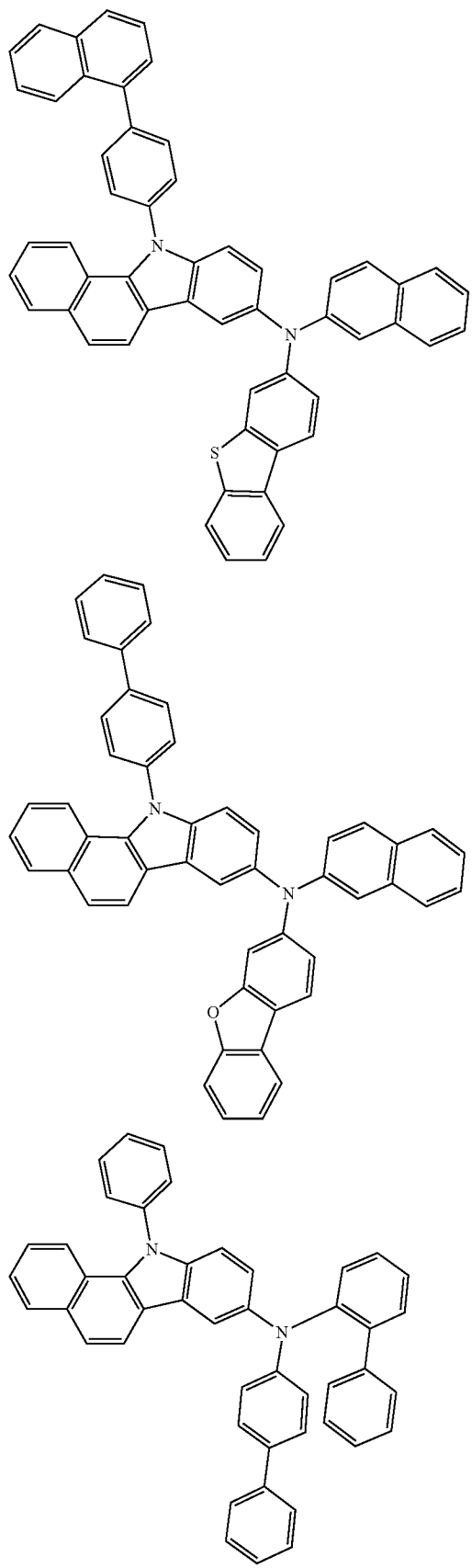
300
-continued
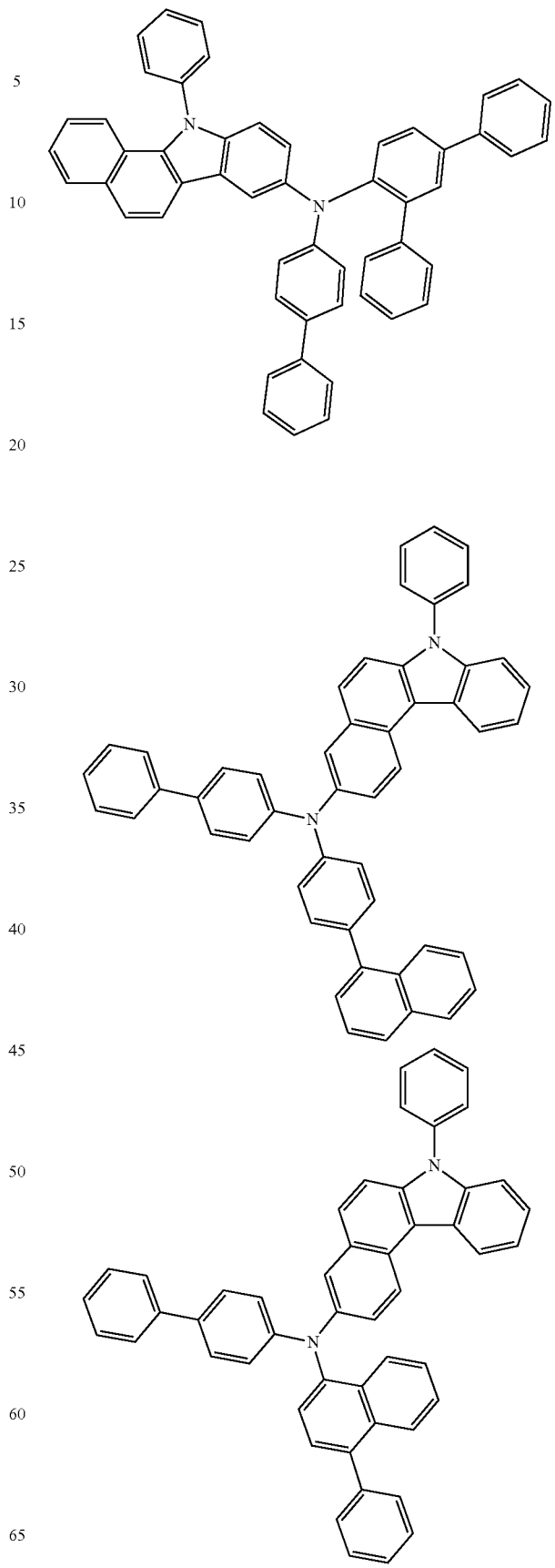

301
-continued
302
-continued
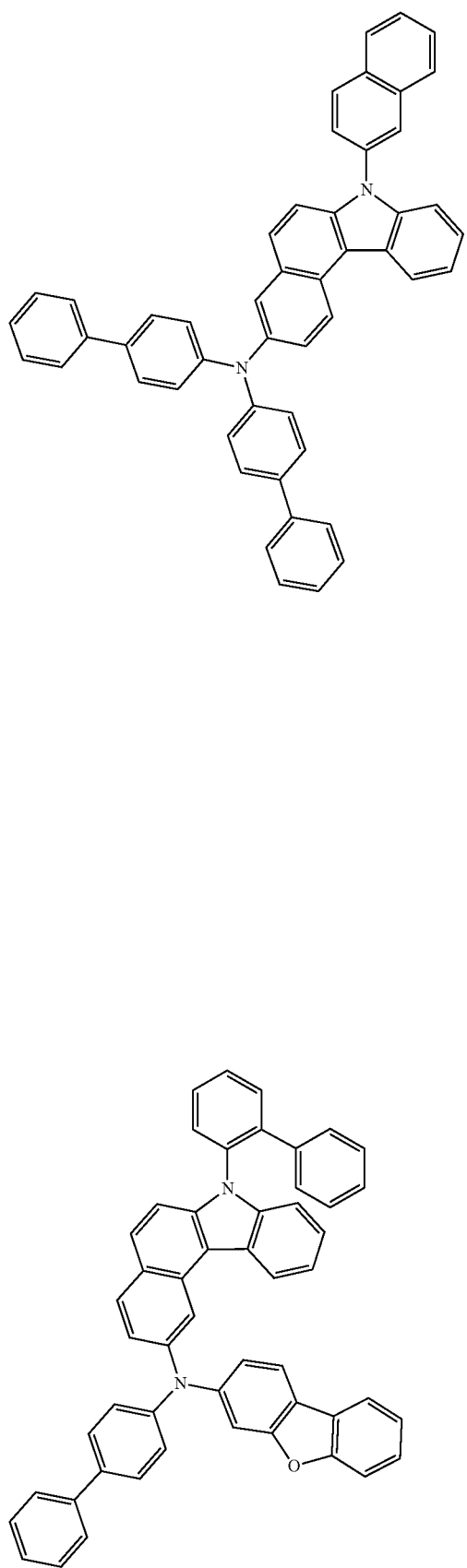
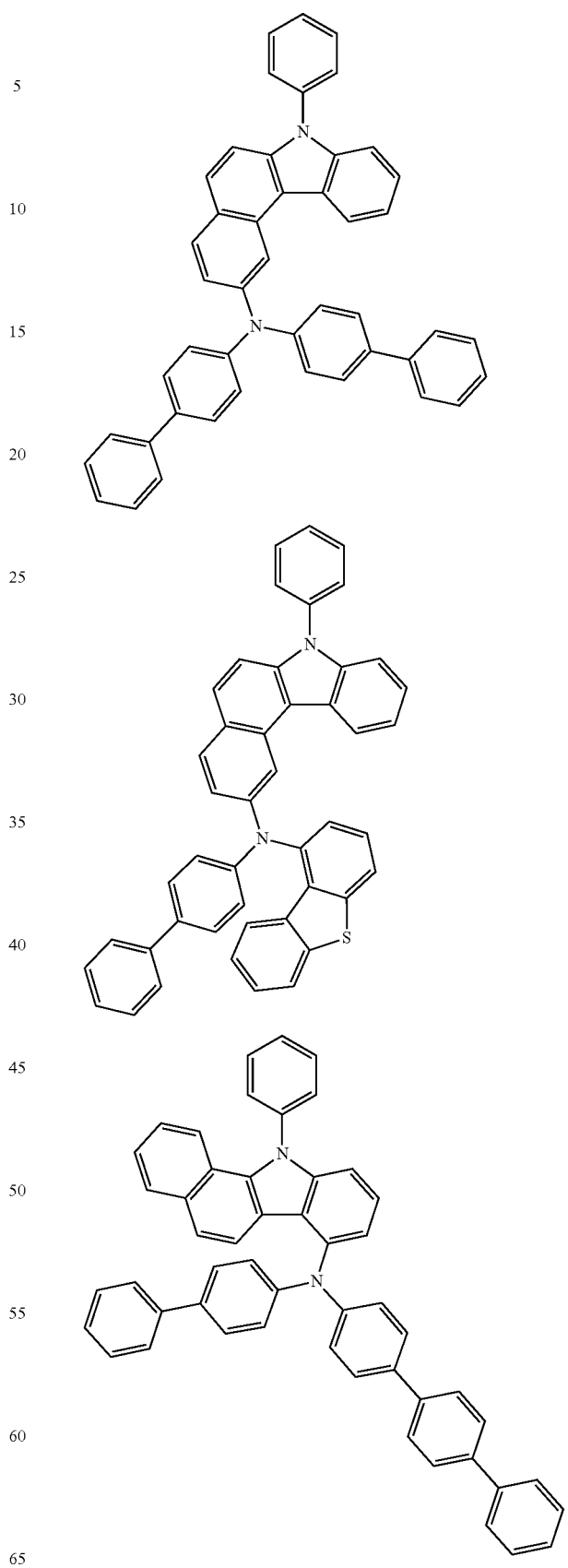

303
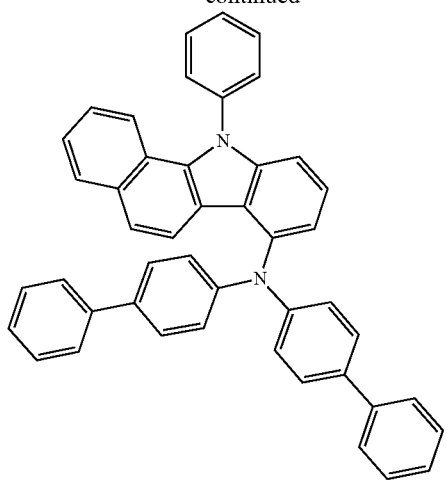
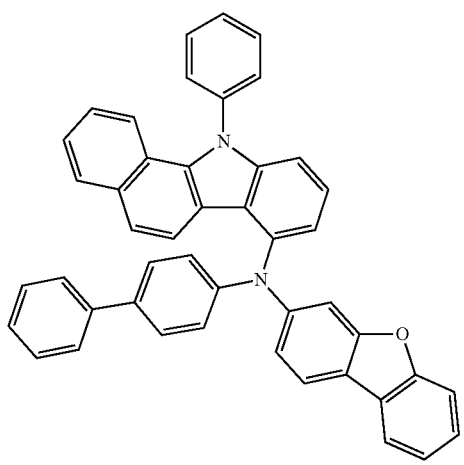
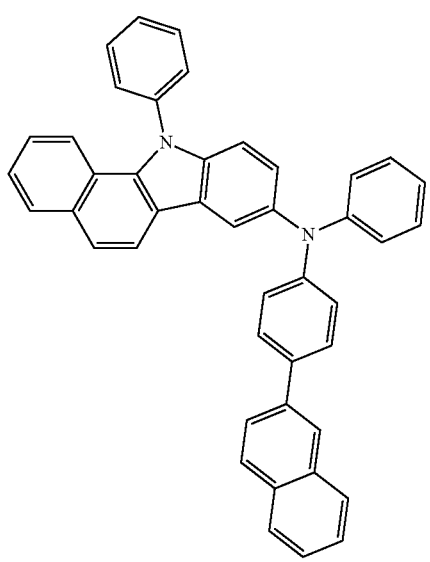
304
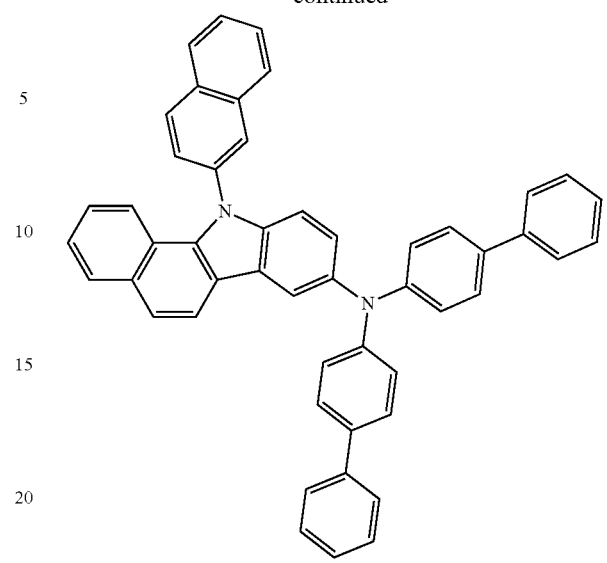

305
-continued
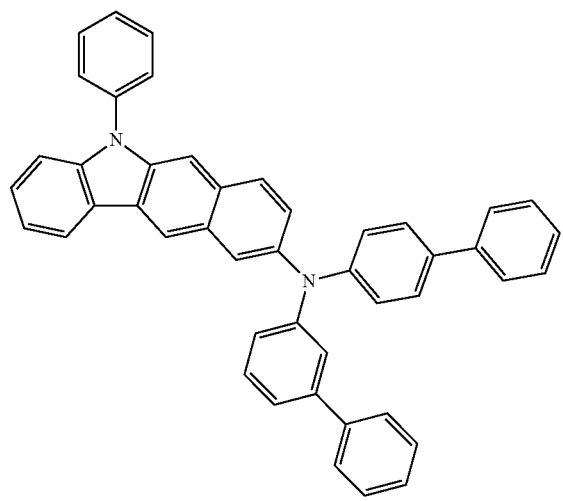
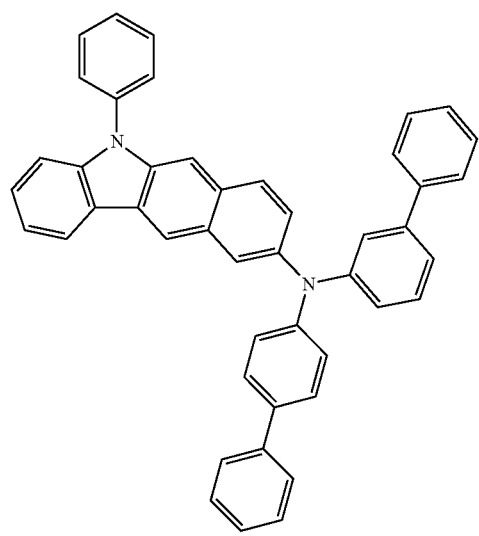
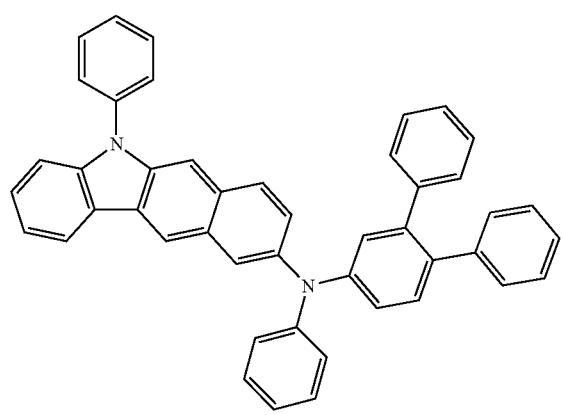
306
-continued
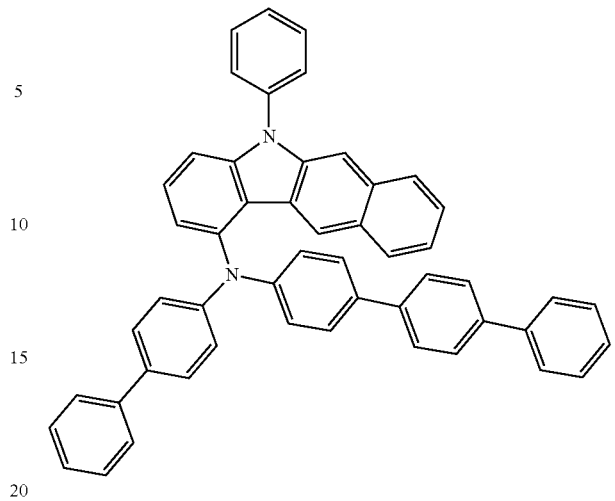
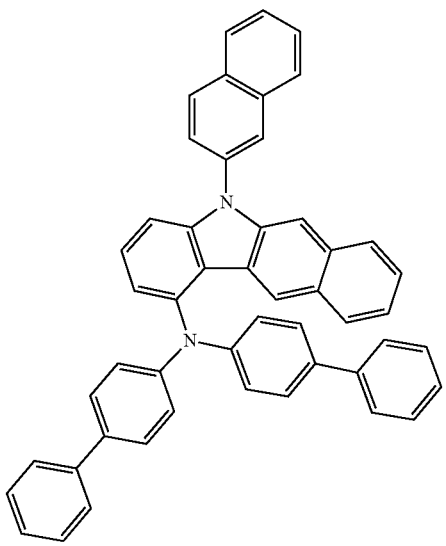
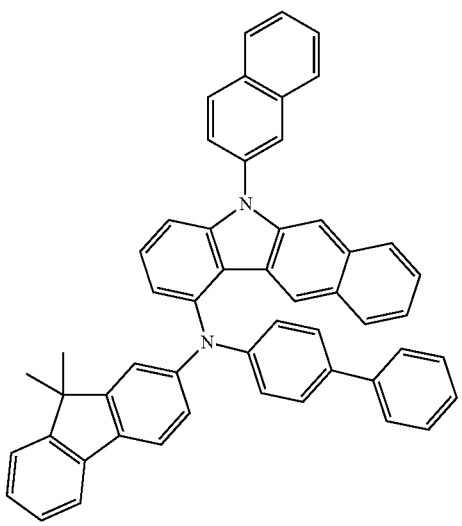

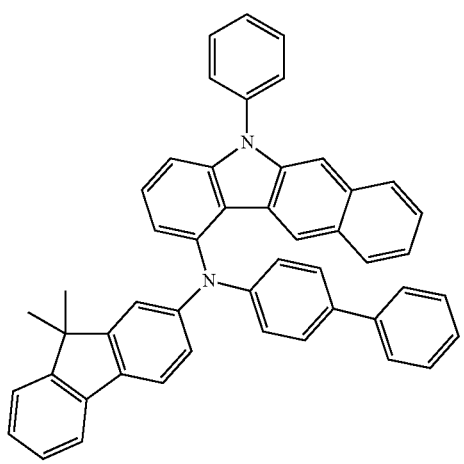
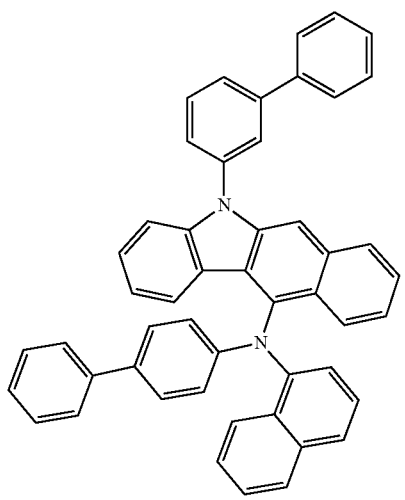
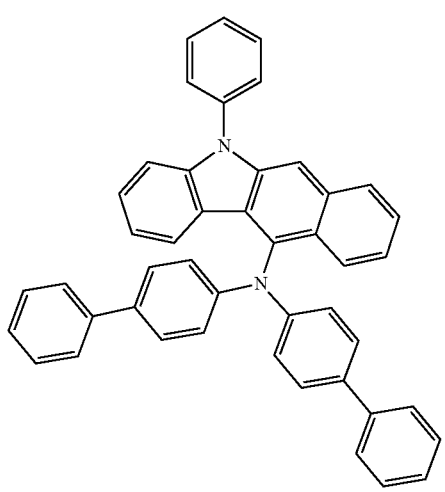
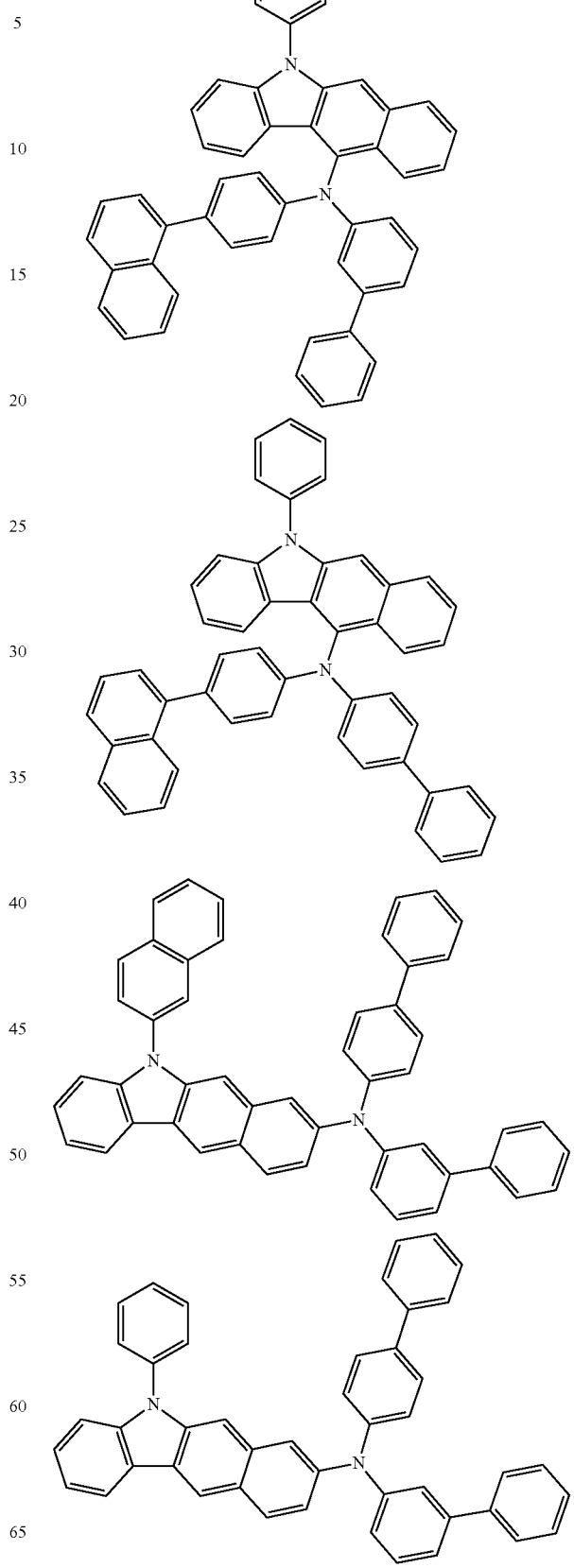

309
-continued
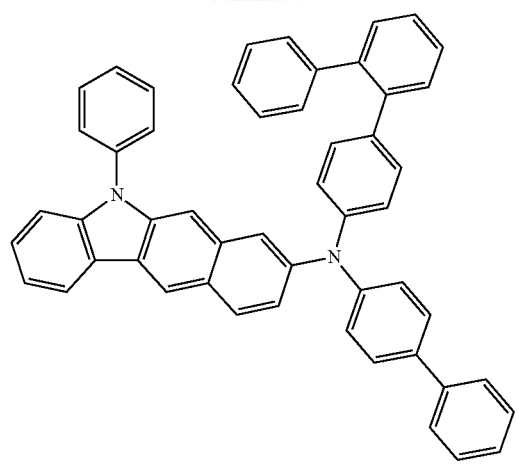
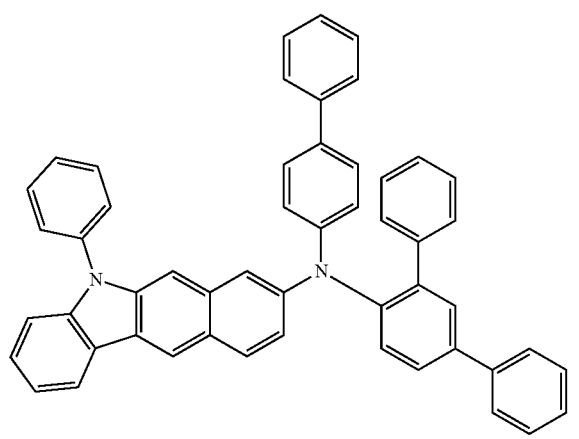
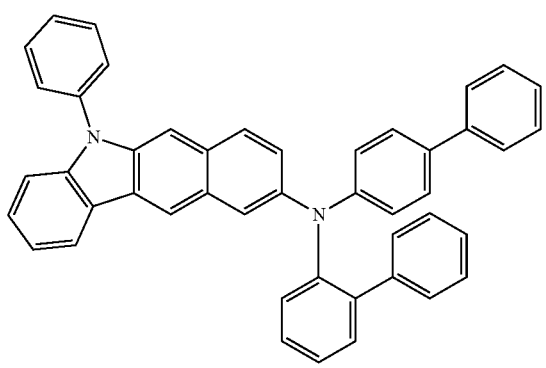
310
-continued
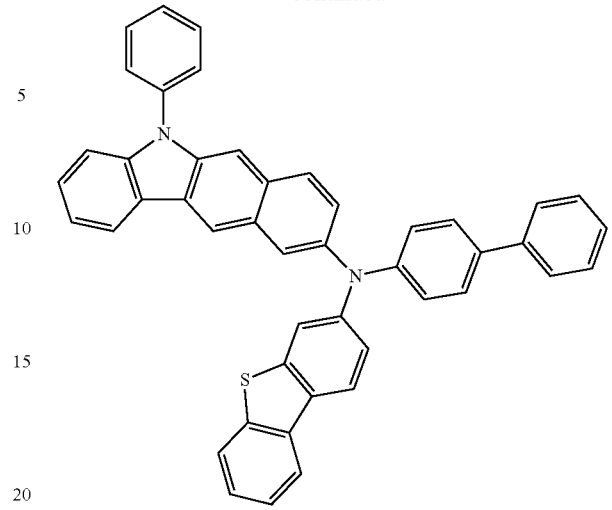
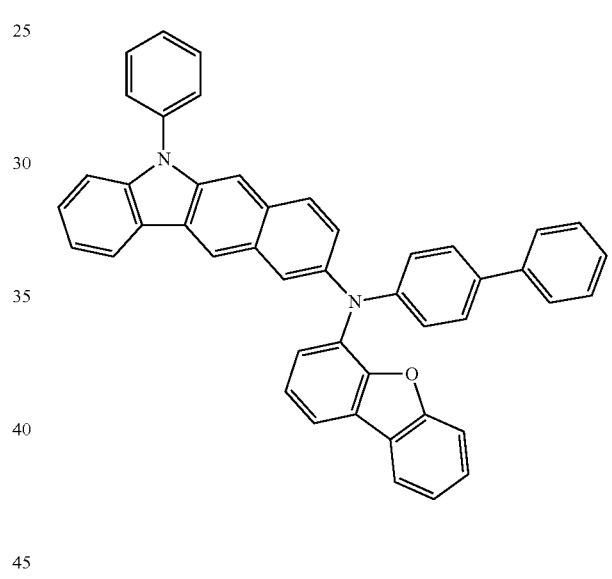
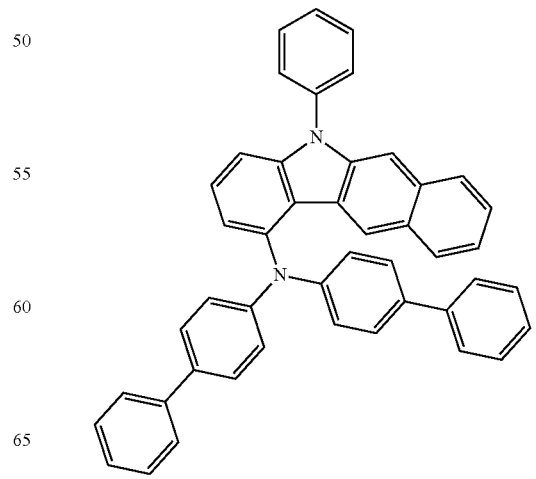

311
-continued
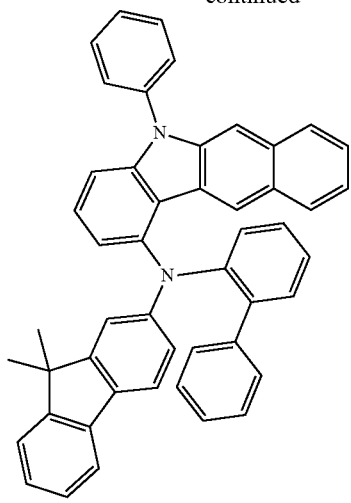
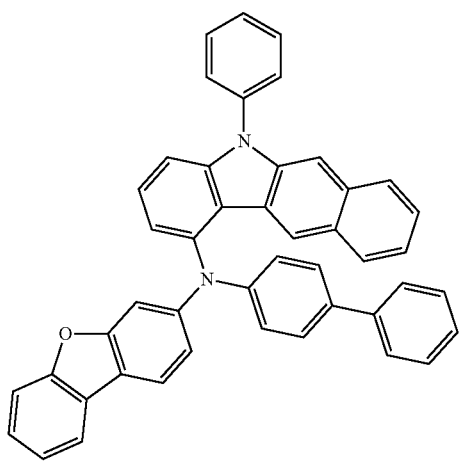
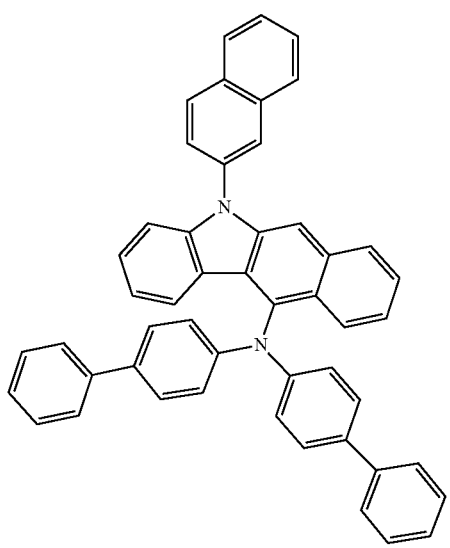
312
-continued
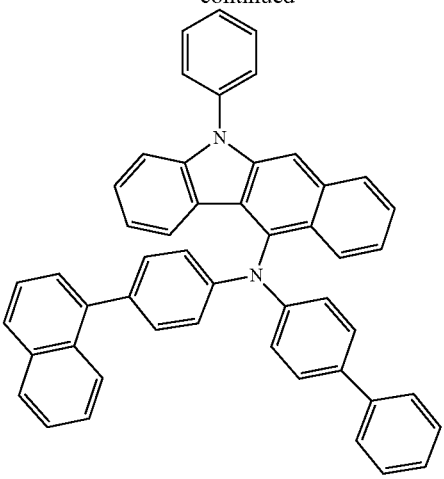
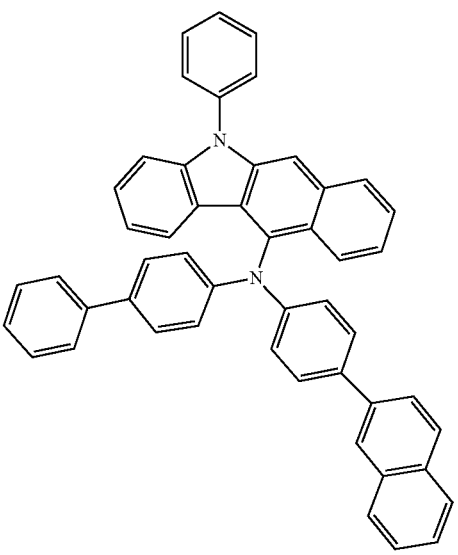
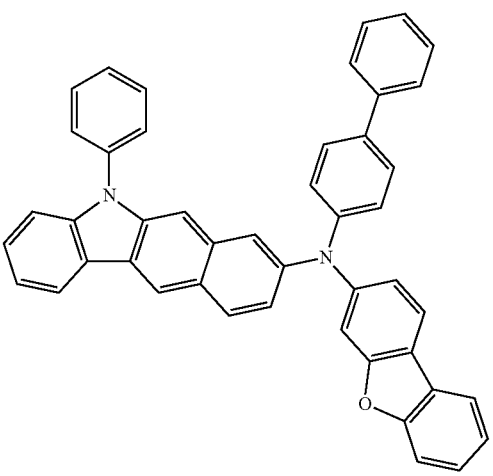

313
-continued
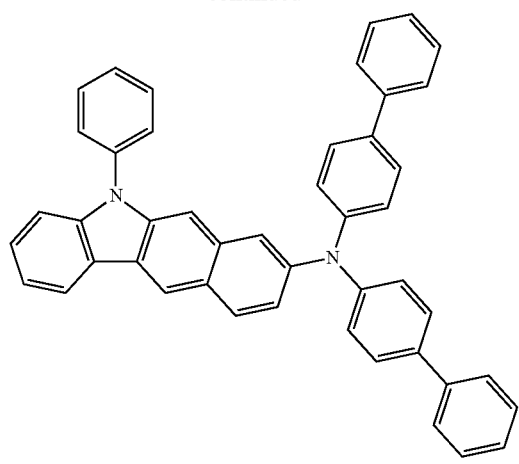
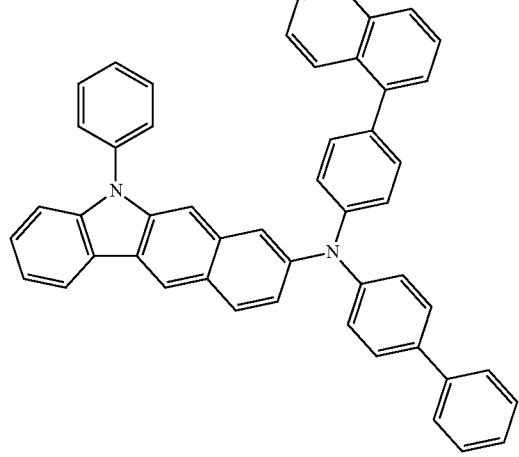
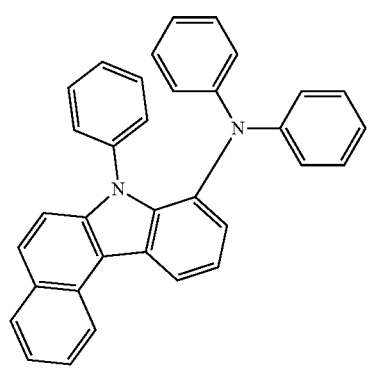
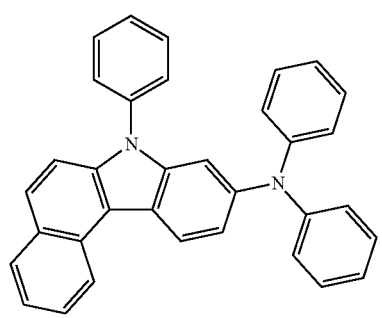
314
-continued
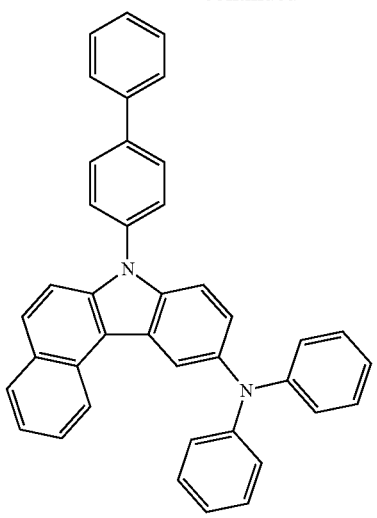
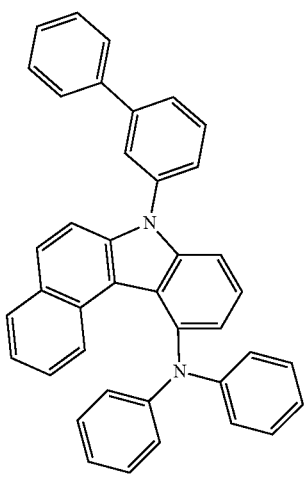
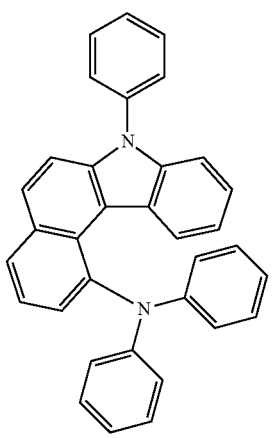

315
-continued
316
-continued
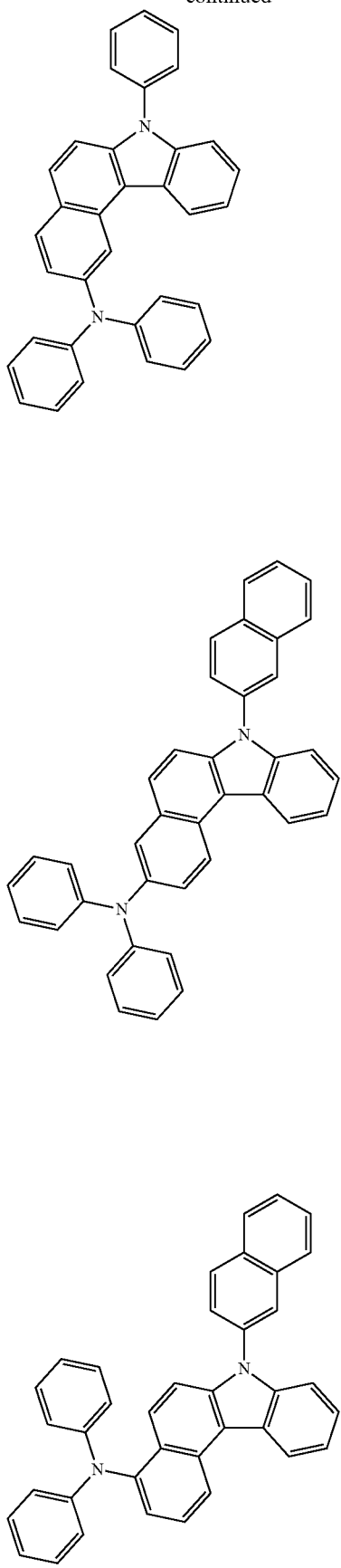

317
-continued
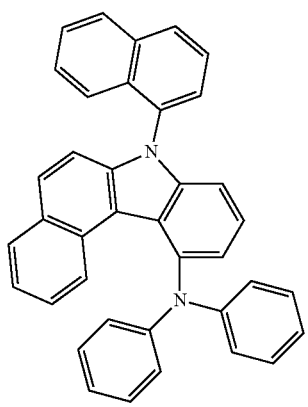
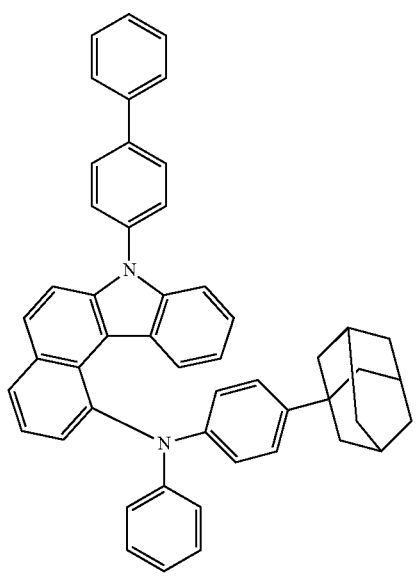
318
-continued
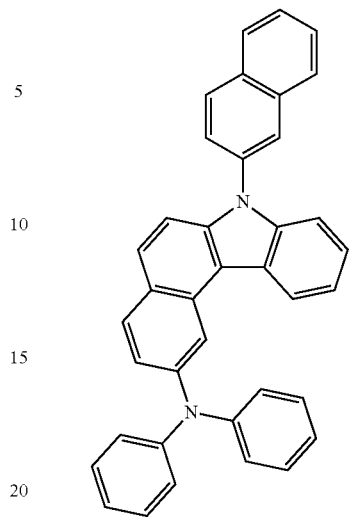
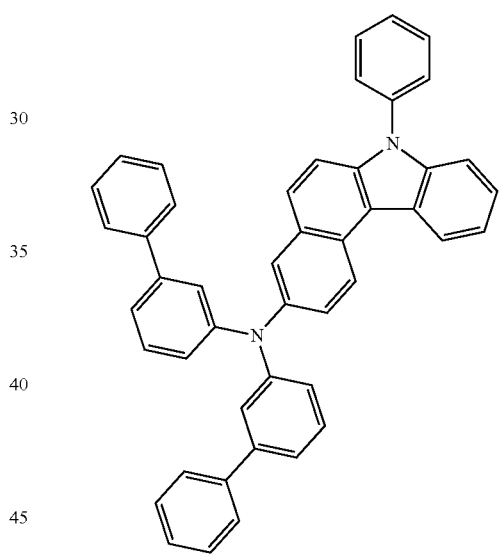
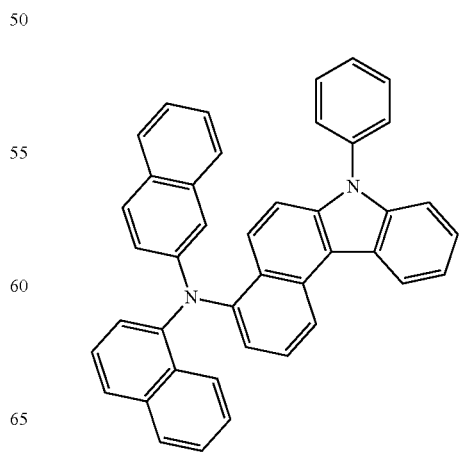

319
-continued
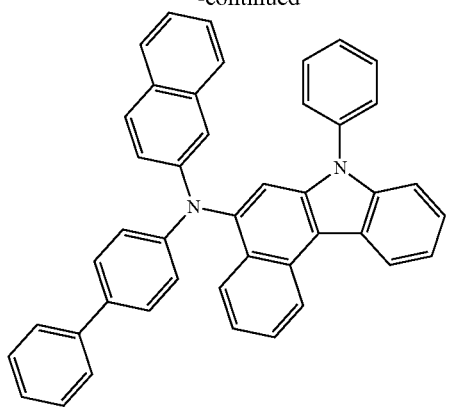
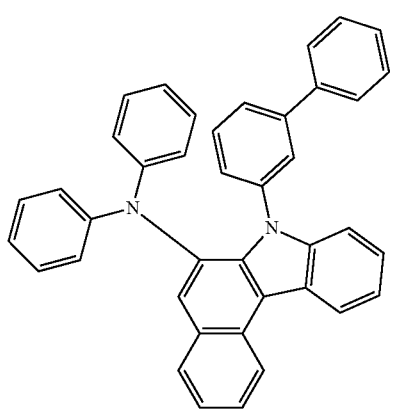
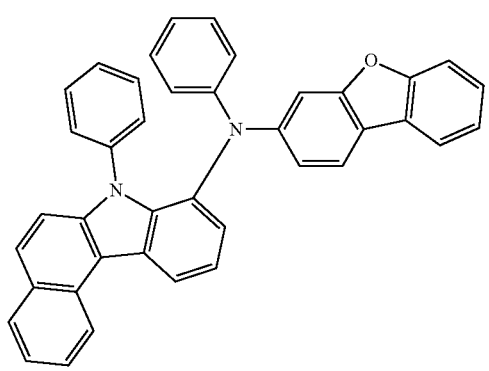
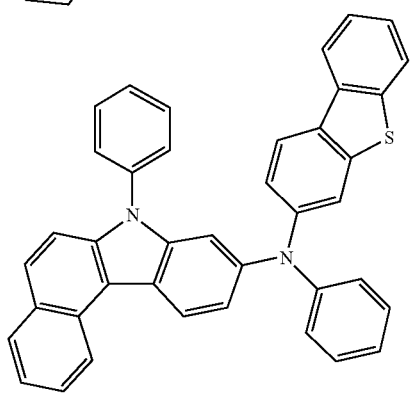
320
-continued
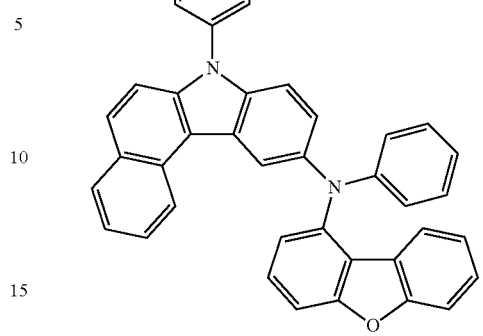

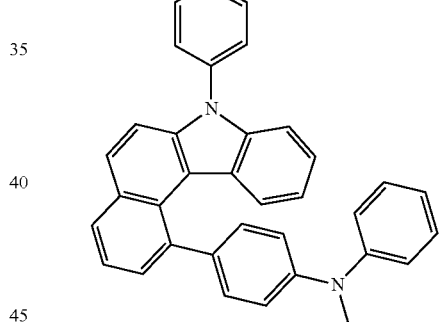
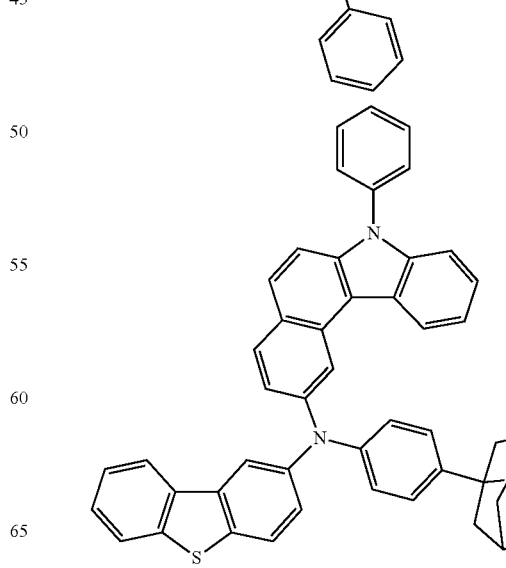

321
-continued
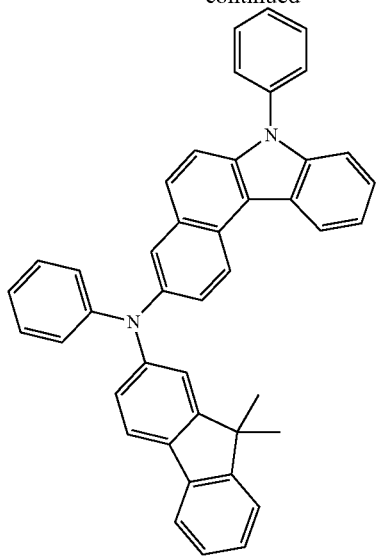
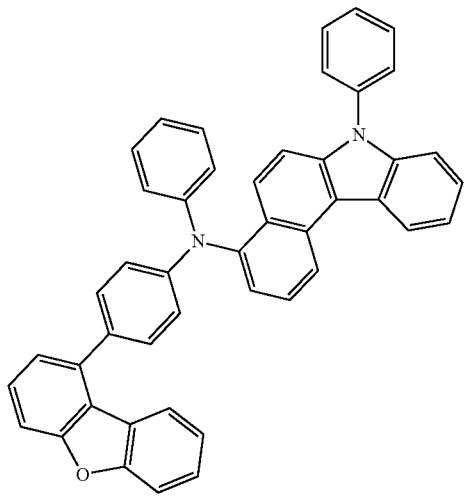
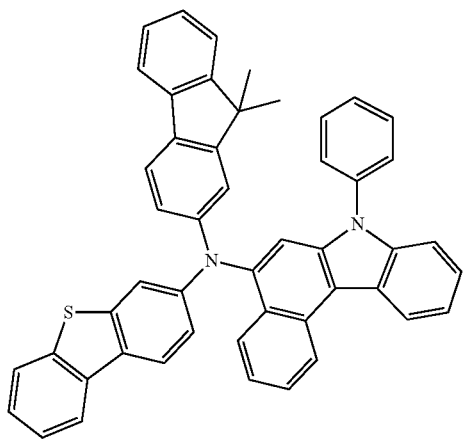
322
-continued
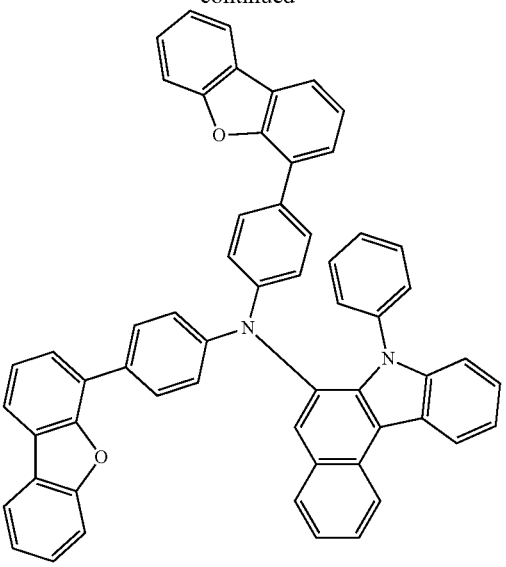
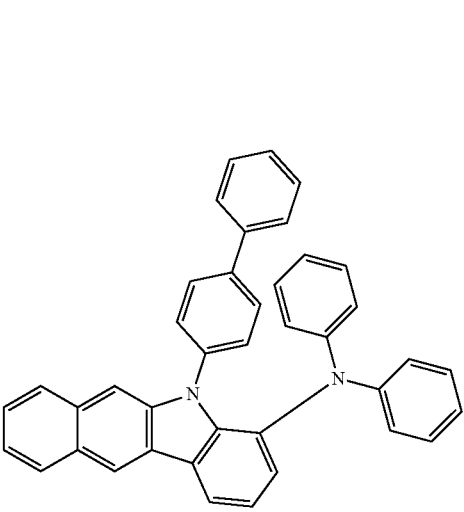
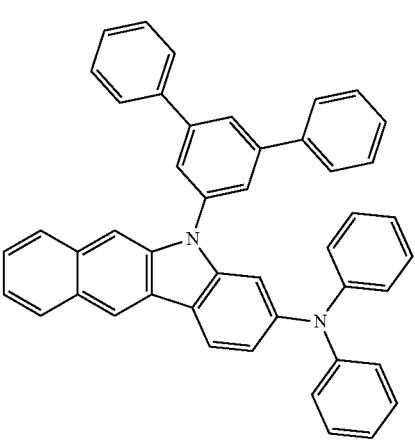

323
-continued
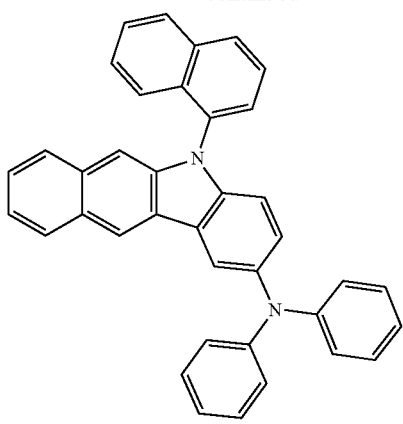
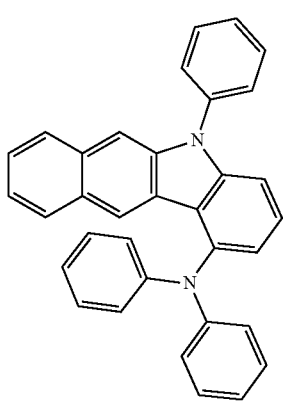
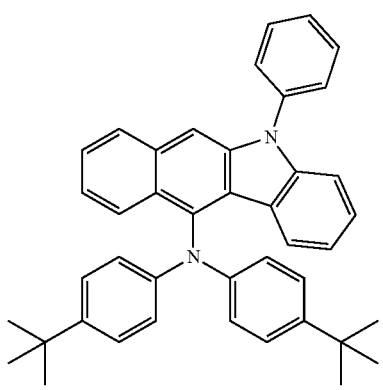
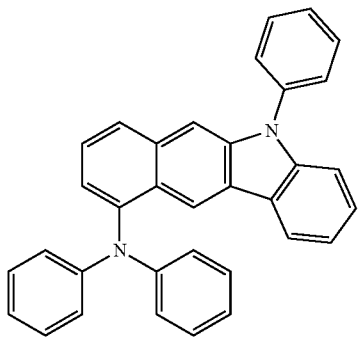
324
-continued
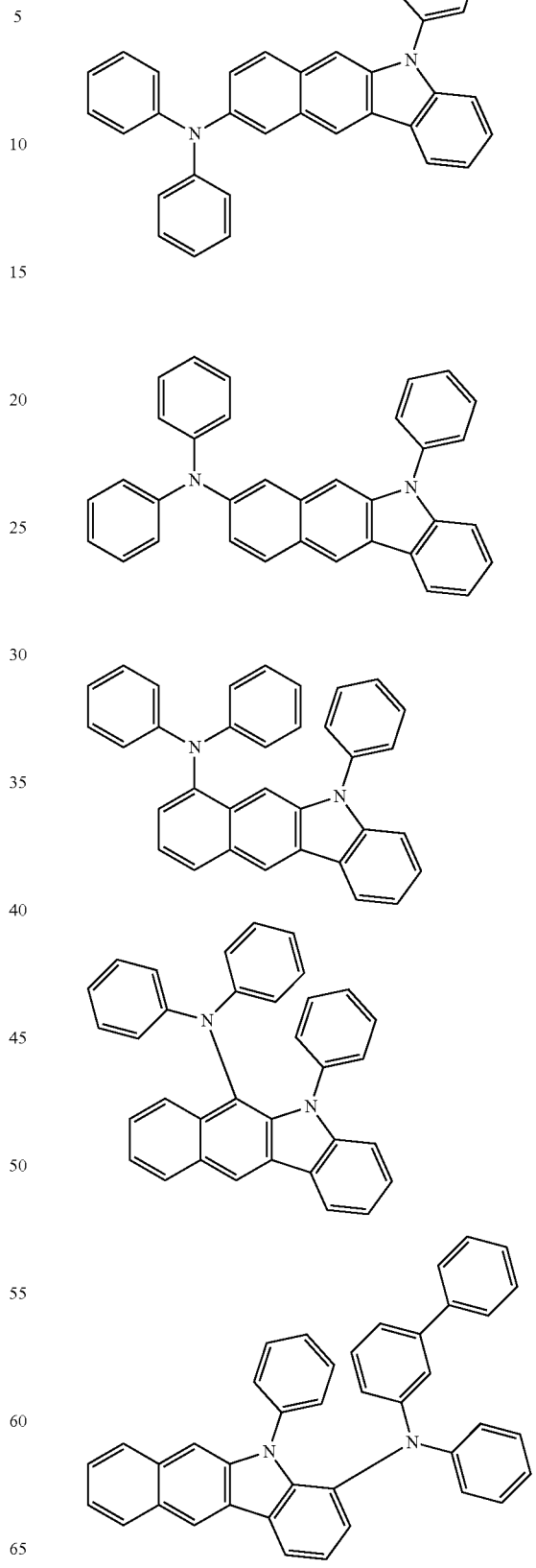

325
-continued
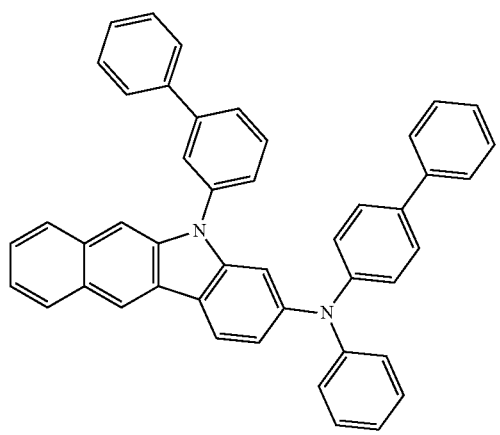
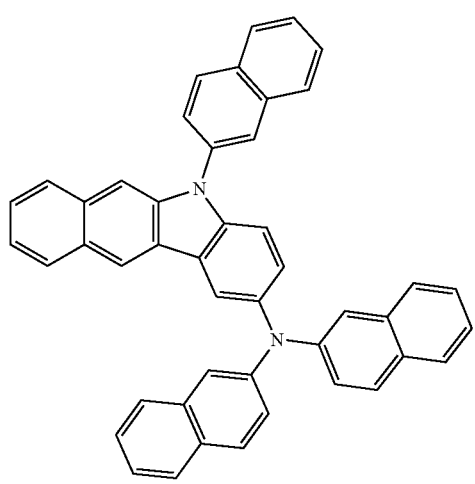
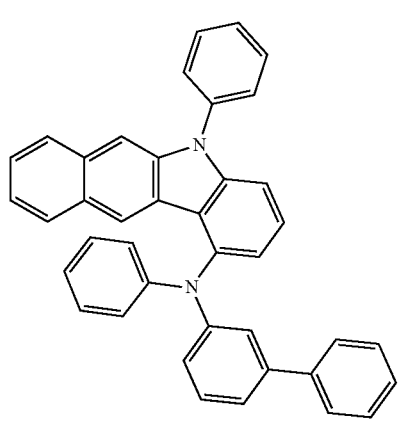
326
-continued
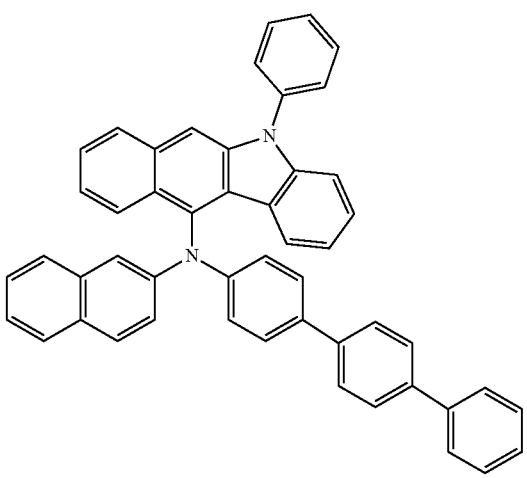
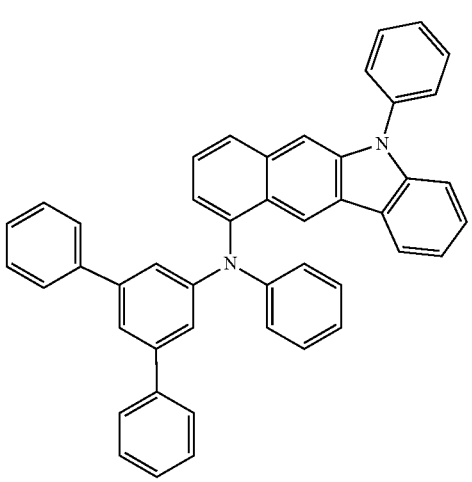
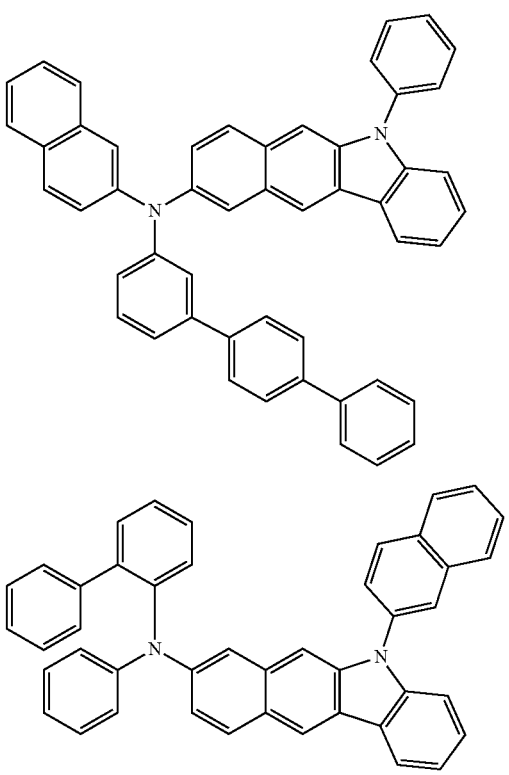

327
-continued
328
-continued
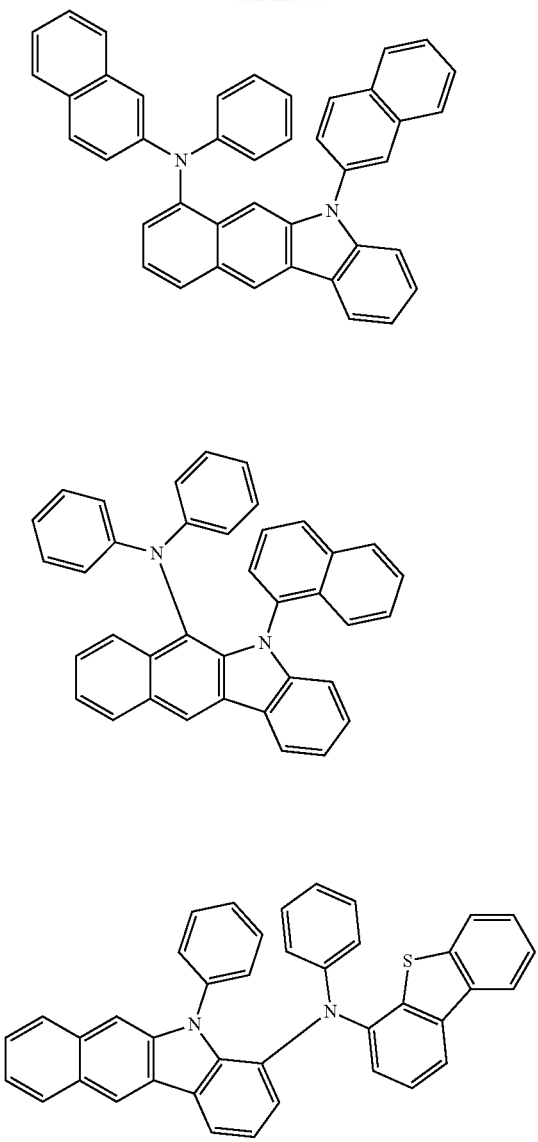
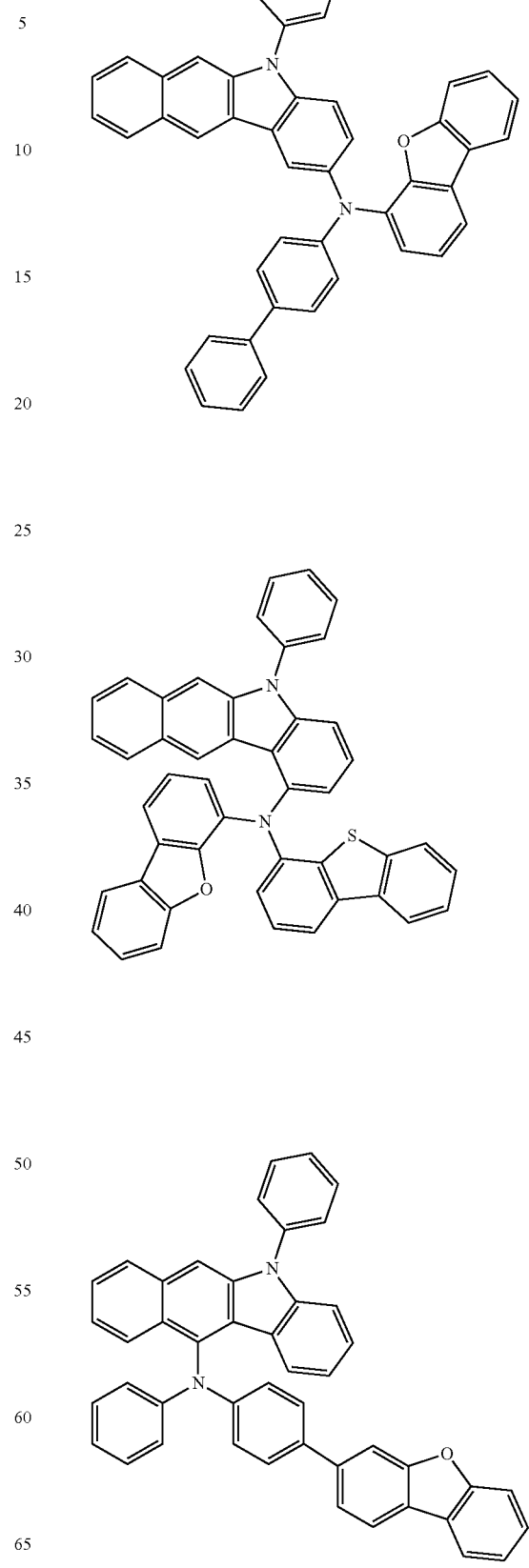

329
-continued
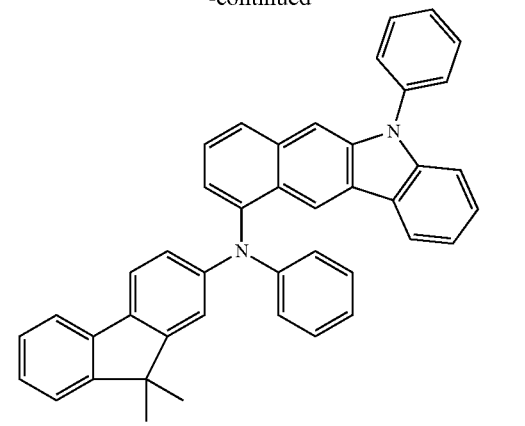
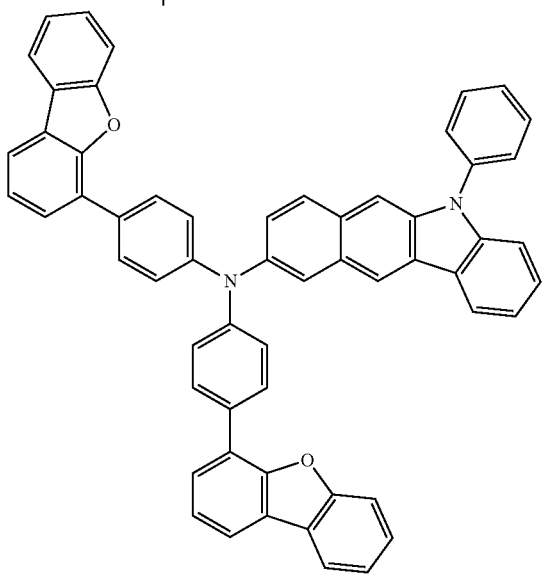
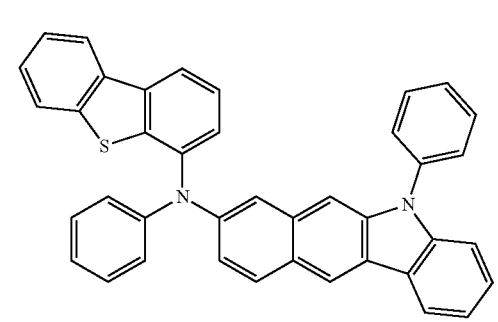
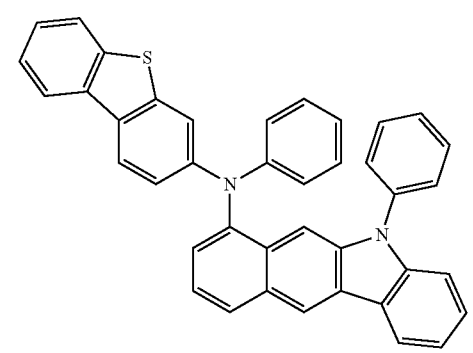
330
-continued
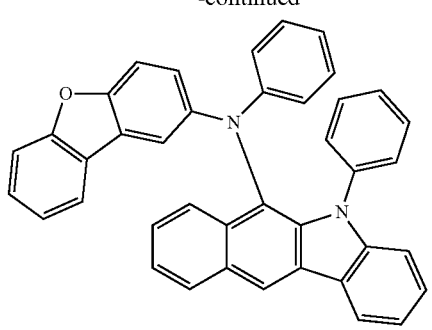
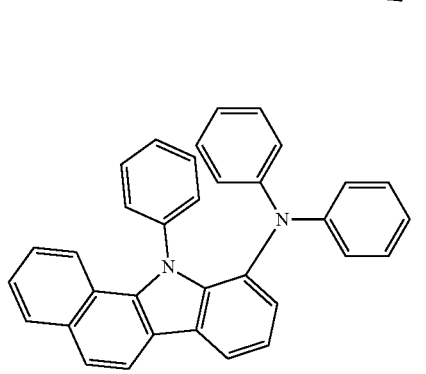
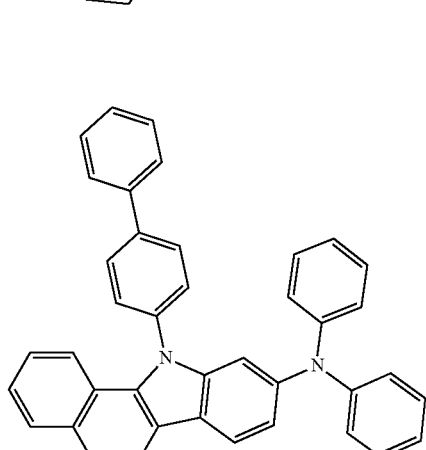
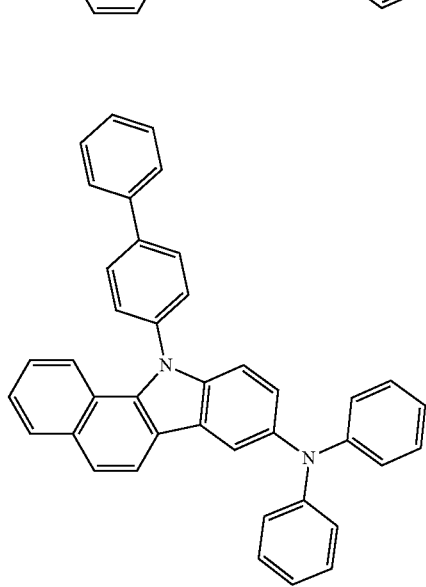

331
-continued
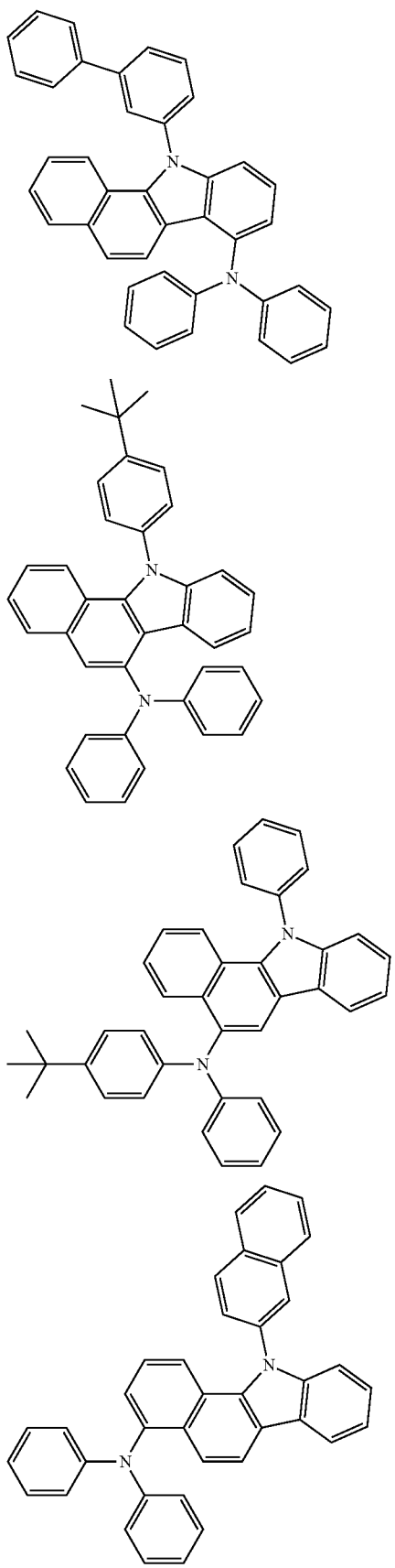
332
-continued
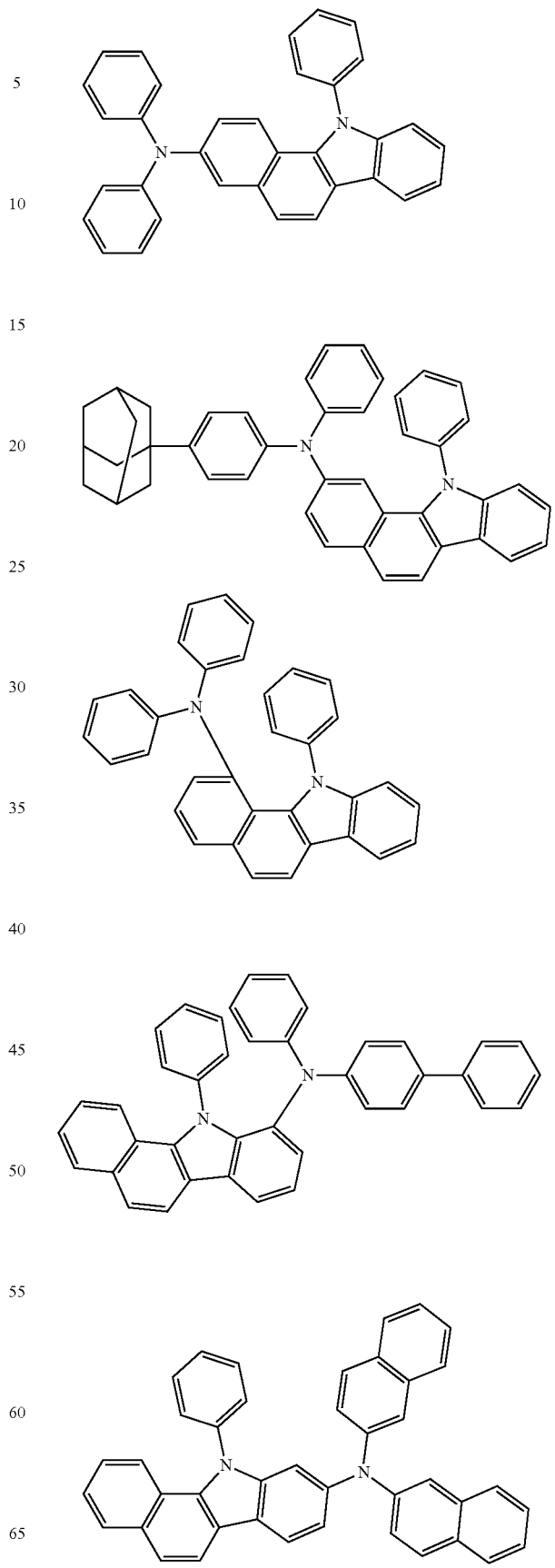

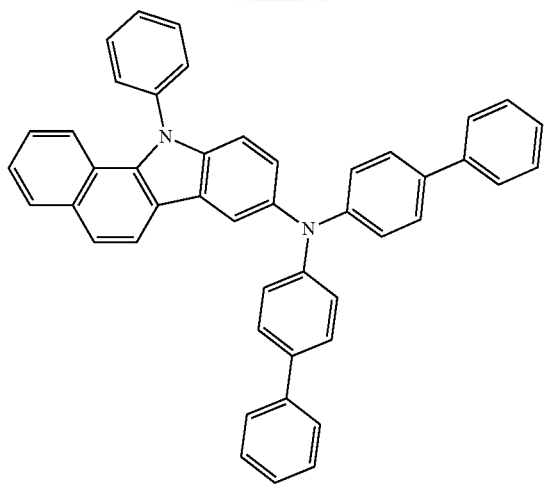
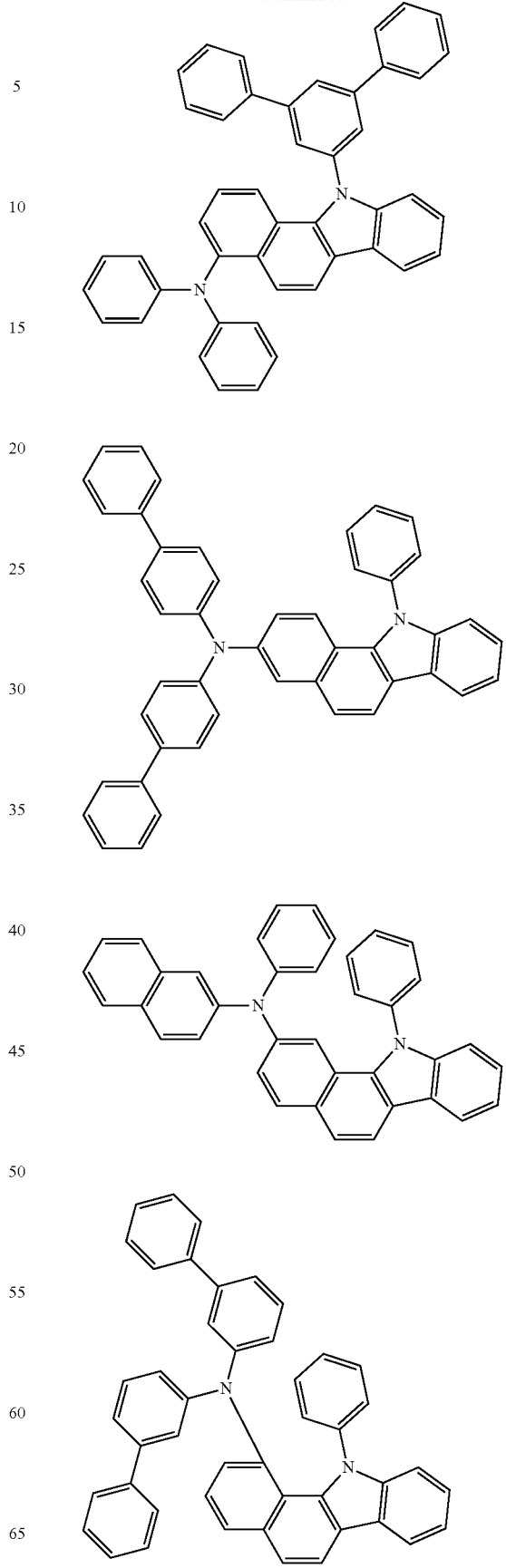

335
-continued
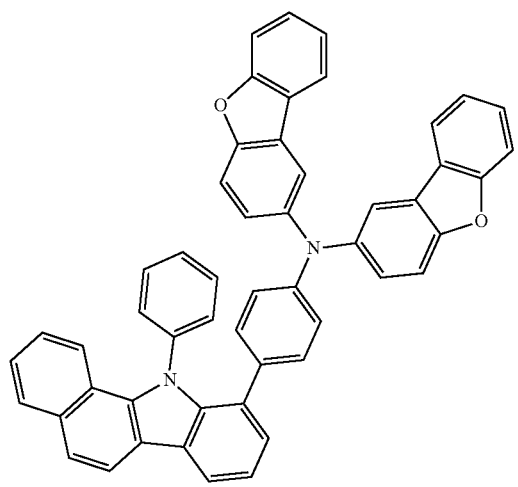
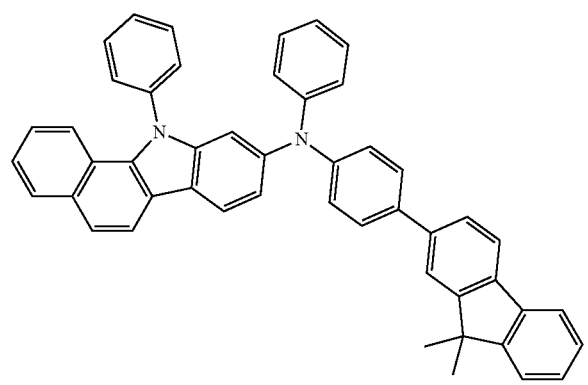
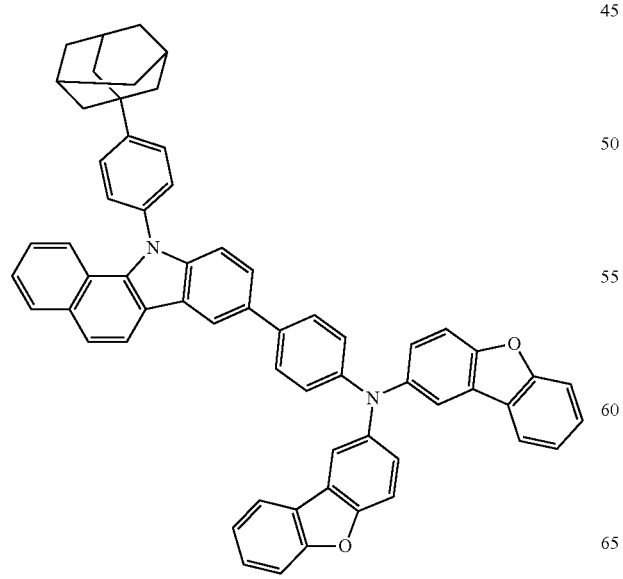
336
-continued
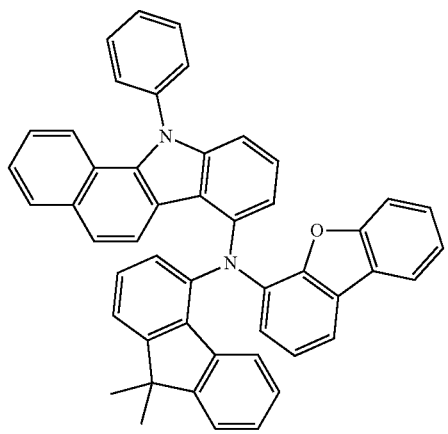
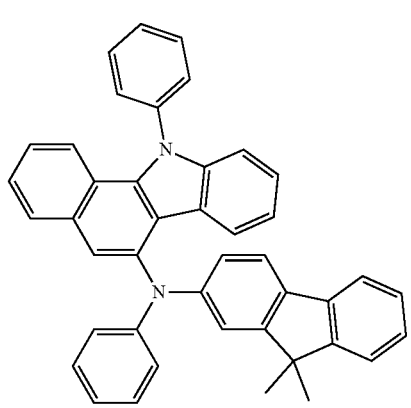
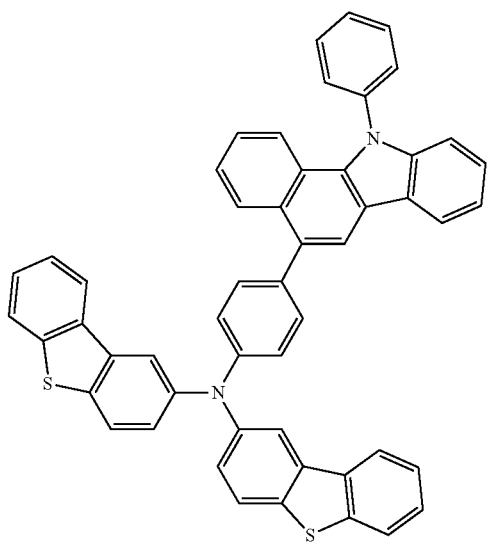

-continued

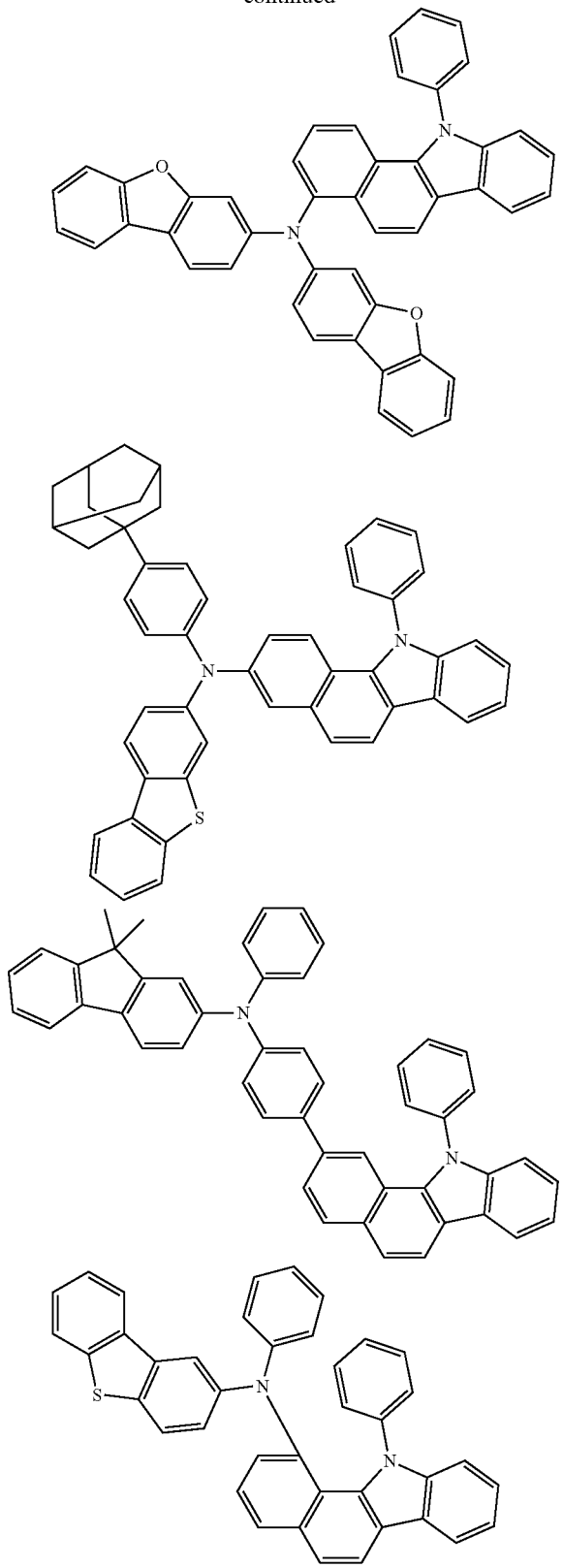

In an exemplary embodiment of the present specification, the organic material layer includes an electron transport layer or an electron injection layer, and the electron transport layer or the electron injection layer includes the compound.

In an exemplary embodiment of the present specification, the organic light emitting device further includes one or two or more layers selected from the group consisting of a hole injection layer, a hole transport layer, an electron transport layer, an electron injection layer, an electron blocking layer, and a hole blocking layer.

In an exemplary embodiment of the present application, the organic light emitting device includes: a first electrode; a second electrode provided to face the first electrode; a light emitting layer provided between the first electrode and the second electrode; and an organic material layer having two or more layers provided between the light emitting layer and the first electrode, or between the light emitting layer and the second electrode, in which at least one of the two or more layers of the organic material layer includes the compound. In an exemplary embodiment of the present application, the two or more layers of the organic material layer can be selected from the group consisting of an electron transport layer, an electron injection layer, a layer which transports and injects electrons simultaneously, and a hole blocking layer.

In another exemplary embodiment, the organic light emitting device can be a normal type organic light emitting device in which a first electrode, an organic material layer having one or more layers, and a second electrode are sequentially stacked on a substrate.

In still another exemplary embodiment, the organic light emitting device can be an inverted type organic light emitting device in which a second electrode, an organic material layer having one or more layers, and a first electrode are sequentially stacked on a substrate.

The organic light emitting device can have, for example, a stacking structure described below, but the stacking structure is not limited thereto.
(1) Anode/Hole transport layer/Light emitting layer/Cathode
(2) Anode/Hole injection layer/Hole transport layer/Light emitting layer/Cathode
(3) Anode/Hole transport layer/Light emitting layer/Electron transport layer/Cathode
(4) Anode/Hole transport layer/Light emitting layer/Electron transport layer/Electron injection layer/Cathode
(5) Anode/Hole injection layer/Hole transport layer/Light emitting layer/Electron transport layer/Cathode
(6) Anode/Hole injection layer/Hole transport layer/Light emitting layer/Electron transport layer/Electron injection layer/Cathode
(7) Anode/Hole transport layer/Electron blocking layer/Light emitting layer/Electron transport layer/Cathode
(8) Anode/Hole transport layer/Electron blocking layer/Light emitting layer/Electron transport layer/Electron injection layer/Cathode
(9) Anode/Hole injection layer/Hole transport layer/Electron blocking layer/Light emitting layer/Electron transport layer/Cathode
(10) Anode/Hole injection layer/Hole transport layer/Electron blocking layer/Light emitting layer/Electron transport layer/Electron injection layer/Cathode
(11) Anode/Hole transport layer/Light emitting layer/Hole blocking layer/Electron transport layer/Cathode
(12) Anode/Hole transport layer/Light emitting layer/Hole blocking layer/Electron transport layer/Electron injection layer/Cathode
(13) Anode/Hole injection layer/Hole transport layer/Light emitting layer/Hole blocking layer/Electron transport layer/Cathode

(14) Anode/Hole injection layer/Hole transport layer/ Light emitting layer/Hole blocking layer/Electron transport layer/Electron injection layer/Cathode

(15) Anode/Hole injection layer/Hole transport layer/ Electron blocking layer/Light emitting layer/Hole blocking layer/Electron transport layer/Electron injection layer/Cathode

Figure 2:
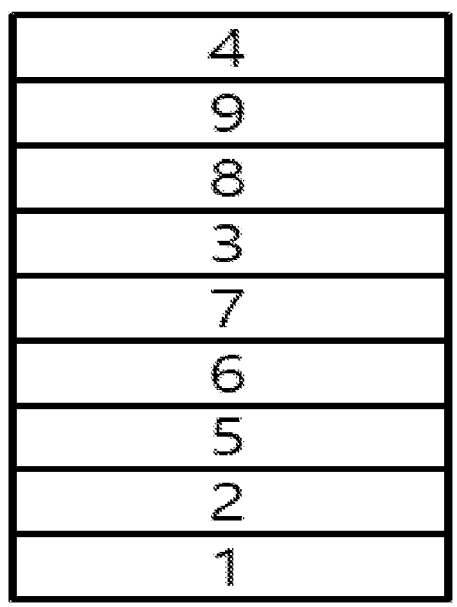
FIG. 2 illustrates an example of an organic light emitting device in which a substrate 1, a first electrode 2, a hole injection layer 5, a hole transport layer 6, an electron blocking layer 7, a light emitting layer 3, a hole blocking layer 8, an electron injection and transport layer 9, and a second electrode 4 are sequentially stacked.

(16) Anode/Hole injection layer/Hole transport layer/ Electron blocking layer/Light emitting layer/Hole blocking layer/Electron transport and injection layer/ Cathode For example, the structure of the organic light emitting device according to an exemplary embodiment of the present specification is exemplified in FIGS. 1 and 2.

FIG. 1 exemplifies a structure of an organic light emitting device in which a substrate 1, a first electrode 2, a light emitting layer 3, and a second electrode 4 are sequentially stacked. In the structure described above, the compound can be included in the light emitting layer 3.

FIG. 2 exemplifies a structure of an organic light emitting device in which a substrate 1, a first electrode 2, a hole injection layer 5, a hole transport layer 6, an electron blocking layer 7, a light emitting layer 3, a hole blocking layer 8, an electron injection and transport layer 9, and a second electrode 4 are sequentially stacked. In the structure described above, the compound can be included in one or more layers of the hole injection layer 5, the hole transport layer 6, the electron blocking layer 7, the light emitting layer 3, the hole blocking layer 8, and the electron injection and transport layer 9. In the structure described above, the compound can be included in the light emitting layer 3.

The organic light emitting device of the present specification can be manufactured by the materials and methods known in the art, except that one or more layers of the organic material layer include the compound of the present specification, that is, the compound.

When the organic light emitting device includes a plurality of organic material layers, the organic material layers can be formed of the same material or different materials.

The organic light emitting device of the present specification can be manufactured by the materials and methods known in the art, except that one or more layers of the organic material layer include the compound, that is, the compound of Formula 1.

For example, the organic light emitting device of the present specification can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which can be used as a second electrode, thereon, by using a physical vapor deposition (PVD) method such as sputtering or e-beam evaporation. In addition to the method described above, an organic light emitting device can be made by sequentially depositing a second electrode material, an organic material layer, and a first electrode material on a substrate.

Further, the compound of Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method described above, an organic light emitting device can also be made by sequentially depositing a second electrode material, an organic material layer, and a first electrode material on a substrate (International Publication No. 2003/012890). However, the manufacturing method is not limited thereto.

In an exemplary embodiment of the present specification, the first electrode is an anode, and the second electrode is a cathode.

In another exemplary embodiment, the first electrode is a cathode, and the second electrode is an anode.

As the first electrode material, materials having a high work function are usually preferred so as to facilitate the injection of holes into an organic material layer. Specific examples of the first electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as $ZnO:Al$ or $SnO_2:Sb$; a conductive polymer such as poly(3-methylthiophene), poly [3,4-(ethylene-1,2-dioxy)thiophene](PEDOT), polypyrrole, and polyaniline; and the like, but are not limited thereto.

As the second electrode material, materials having a low work function are usually preferred so as to facilitate the injection of electrons into an organic material layer. Specific examples of the second electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a first electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the first electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a first electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

An electron blocking layer can be provided between the hole transport layer and the light emitting layer. For the electron blocking layer, materials known in the art can be used.

The light emitting layer can include a host material and a dopant material. The host material includes the compound of Formula 1 of the present application, and can further include other fused aromatic ring derivatives or hetero ring-containing compounds. Specifically, examples of the fused aromatic ring derivative include anthracene derivatives, pyrene derivatives, naphthalene derivatives, pentacene derivatives, phenanthrene compounds, fluoranthene compounds, and the like, and examples of the hetero ring-containing compound include carbazole derivatives, dibenzofuran, dibenzofuran derivatives, dibenzothiophene, dibenzothiophene derivatives, ladder-type furan compounds, pyrimidine derivatives, and the like, but the examples thereof are not limited thereto.

Examples of the dopant material include compounds as described below, but are not limited thereto.

Dp-1

Dp-2

Dp-3

-continued

Dp-4

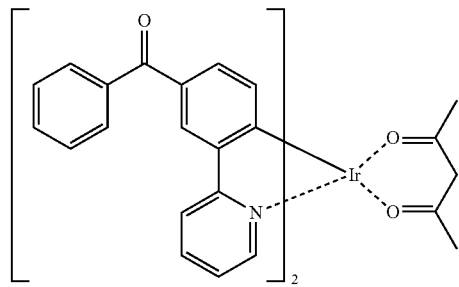

Dp-5

Dp-6

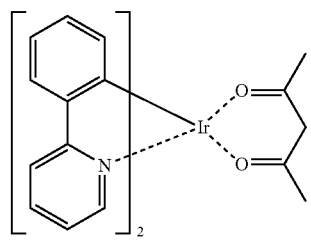

Dp-7

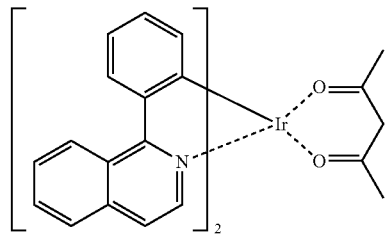

Dp-8

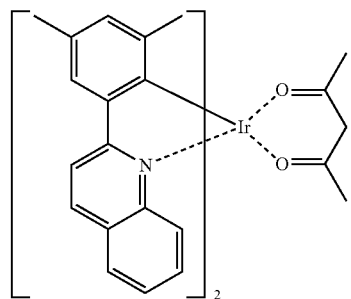

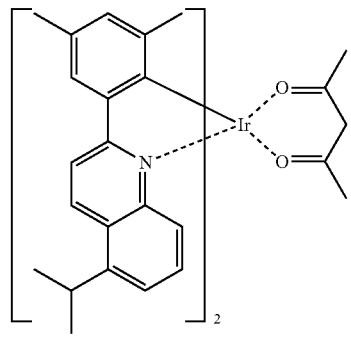

Dp-9
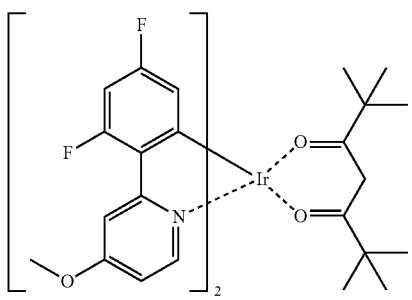
Dp-10
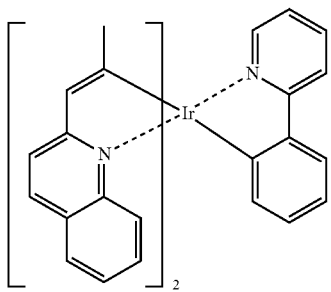
Dp-11
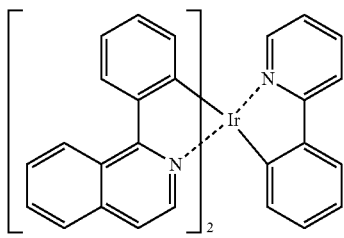
Dp-12
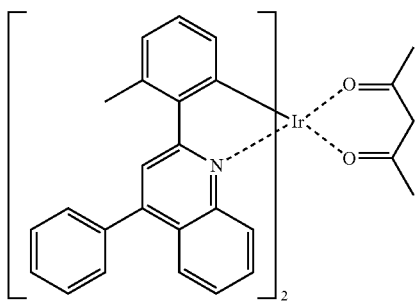
Dp-13
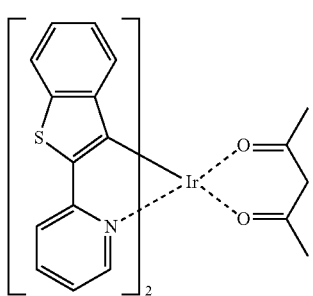
Dp-14
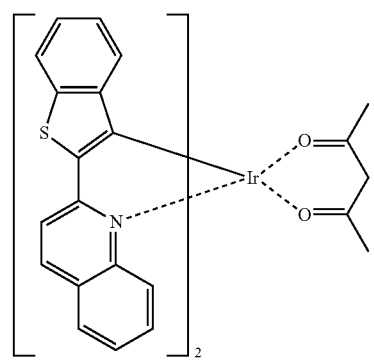
Dp-15
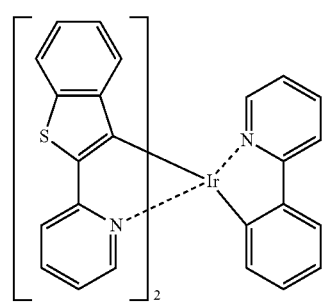
Dp-16
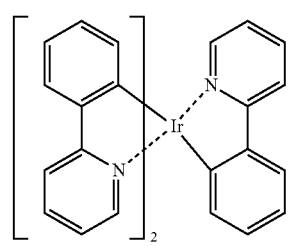
Dp-17
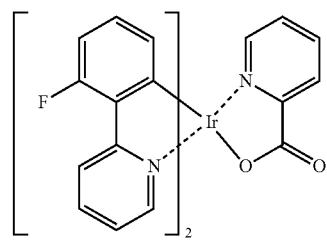
Dp-18
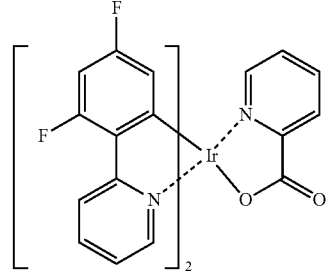

-continued
Dp-19
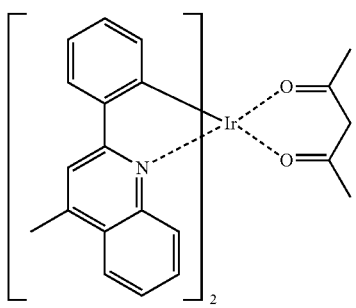
Dp-24
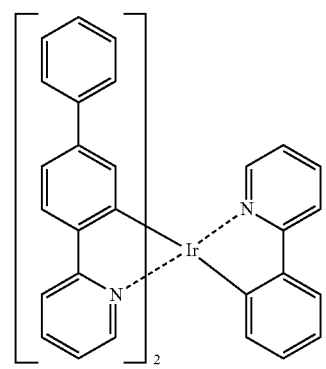
Dp-20
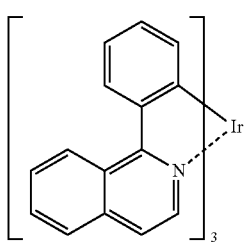
Dp-25
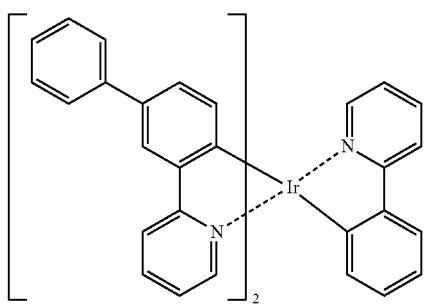
Dp-21
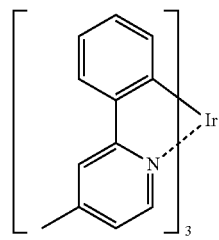
Dp-26
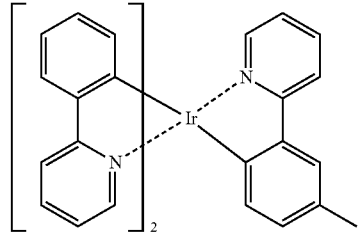
Dp-22
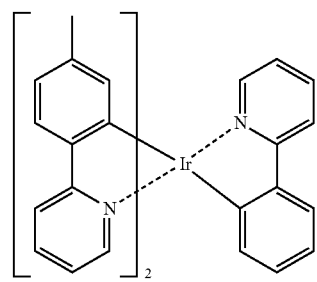
Dp-27
Dp-23
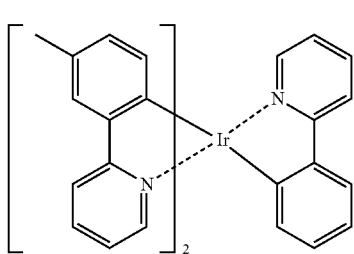
Dp-28
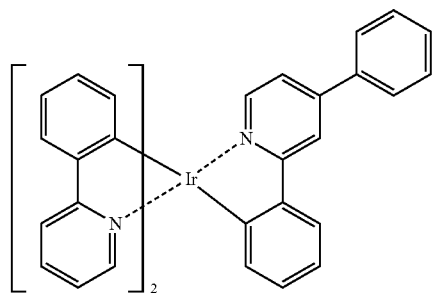

Dp-29
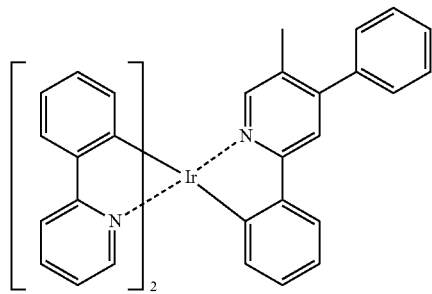
Dp-30
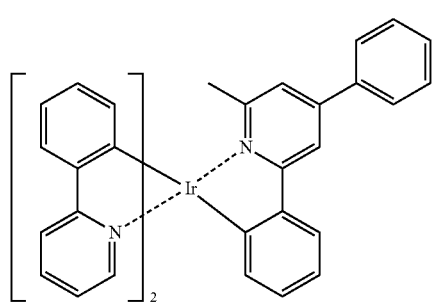
Dp-31
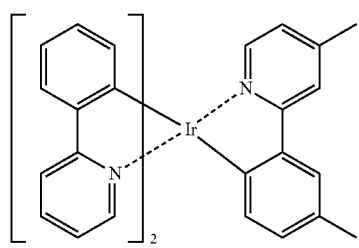
Dp-32
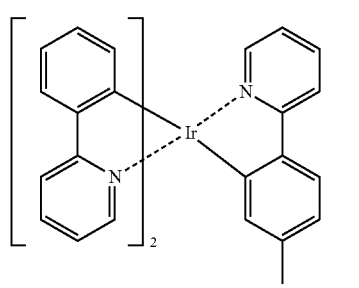
Dp-33
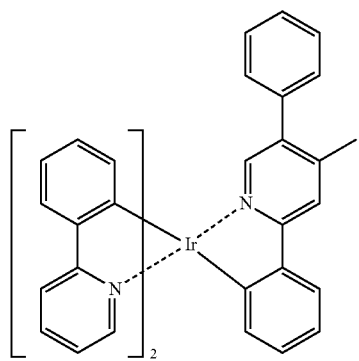
Dp-34
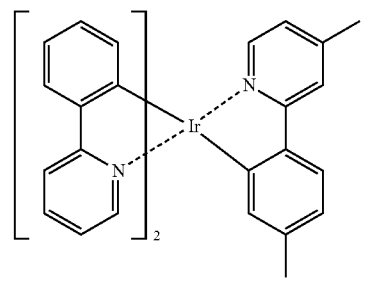
Dp-35
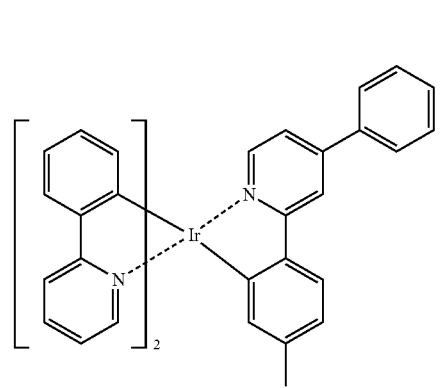
Dp-36
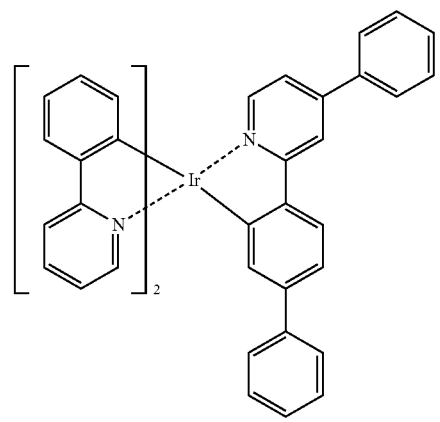
Dp-37
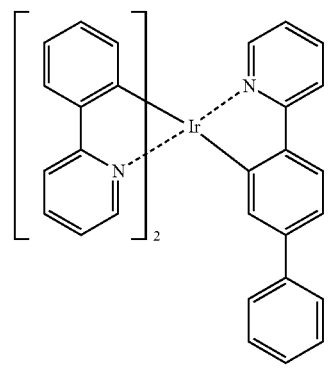

-continued

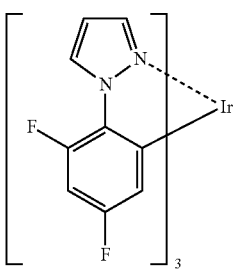
Dp-38

The electron transport layer is a layer which accepts electrons from an electron injection layer and transports the electrons to a light emitting layer, and an electron transport material is suitably a material having high electron mobility which can proficiently accept electrons from a second electrode and transfer the electrons to a light emitting layer. Specific examples thereof include:

Al complexes of 8-hydroxyquinoline; complexes including Alq3; organic radical compounds; hydroxyflavone-metal complexes, and the like, but are not limited thereto. The electron transport layer can be used with any desired cathode material, as used according to the related art. In particular, examples of an appropriate cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a second electrode, and an excellent effect of injecting electrons into a light emitting layer or a light emitting material, prevents excitons produced from a light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a second electrode, and can be generally formed under the same conditions as those of the hole injection layer. Specific examples thereof include oxadiazole derivatives or triazole derivatives, phenanthroline derivatives, BCP, aluminum complexes, and the like, but are not limited thereto.

The organic light emitting device according to the present specification can be a top emission type, a bottom emission type, or a dual emission type according to the materials to be used.

PREPARATION AND SYNTHESIS EXAMPLES

Hereinafter, the present specification will be described in more detail through Examples. However, the following Examples are provided only for exemplifying the present specification, but are not intended to limit the present specification.

The compound according to the present specification was prepared using a Buchwald-Hartwig coupling reaction, a Heck coupling reaction, a Suzuki coupling reaction, and the like as representative reactions.

[Preparation Example 1] Preparation of Formula a (5H-benzo[b]carbazole)

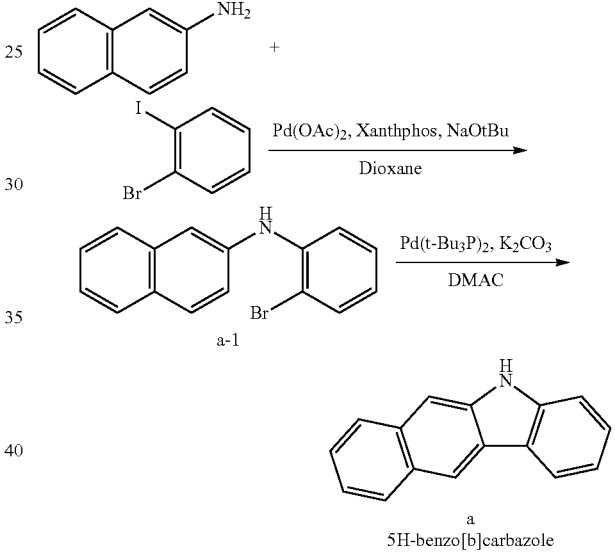

a
5H-benzo[b]carbazole

1) Preparation of Formula a-1

300.0 g (1.0 eq) of naphthalen-2-amine, 592.7 g (1.0 eq) of 1-bromo-2-iodobenzene, 302.0 g (1.5 eq) of NaOtBu, 4.70 g (0.01 eq) of palladium acetate (Pd(OAc)$_2$), and 12.12 g (0.01 eq) of 4,5-bis(diphenylphosphino)-9,9-dimethylxanthene (Xantphos) were dissolved in 5 L of 1,4-dioxane, and the resulting solution was stirred under reflux. When the reaction was terminated after 3 hours, the solvent was removed by reducing pressure. Thereafter, the resulting product was completely dissolved in ethyl acetate, the resulting solution was washed with water, and approximately 70% of the solvent was removed again by reducing pressure. Again, crystals were precipitated while adding hexane thereto in a reflux state, cooled, and then filtered. The resulting product was subjected to column chromatography to obtain 443.5 g (yield 71%) of Formula a-1. [M+H]+=299

2) Preparation of Formula a (5H-benzo[b]carbazole)

443.5 g (1.0 eq) of Formula a-1, 8.56 g (0.01 eq) of Pd(t-Bu$_3$P)$_2$, and 463.2 g (2.00 eq) of K$_2$CO$_3$ were put into 4 L of dimethylacetamide (DMAC), and the resulting mixture was stirred under reflux. After 3 hours, crystals were precipitated by pouring the reactant into water, and filtered.

After the filtered solid was completely dissolved in 1,2-dichlorobenzene, the resulting solution was washed with water, crystals were precipitated by concentrating the solution in which the product was dissolved under reduced pressure, cooled, and then filtered. The resulting product was purified by column chromatography to obtain 174.8 g (yield 48%) of Formula a (5H-benzo[b]carbazole). [M+H]+=218

Here, tBu means tert-butyl.

[Preparation Example 2] Preparation of Formula b (7H-dibenzo[b,g]carbazole)

Formula b (7H-dibenzo[b,g]carbazole) was synthesized in the same manner as in the method of preparing Formula a by using 1-bromo-2-iodonaphthalene instead of 1-bromo-2-iodobenzene.

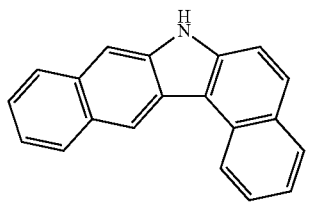

7H-dibenzo[b,g]carbazole

[Preparation Example 3] Preparation of Formula c (6H-dibenzo[b,h]carbazole)

Formula c (6H-dibenzo[b,h]carbazole) was synthesized in the same manner as in the method of preparing Formula a by using 2,3-dibromonaphthalene instead of 1-bromo-2-iodobenzene.

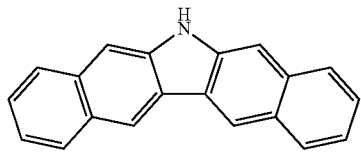

6H-dibenzo[b,h]carbazole

[Preparation Example 4] Preparation of Formula d (13H-dibenzo[a,h]carbazole)

Formula d (13H-dibenzo[a,h]carbazole) was synthesized in the same manner as in the method of preparing Formula a by using 2-bromo-1-iodonaphthalene instead of 1-bromo-2-iodobenzene.

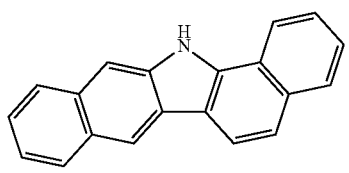

13H-dibenzo[a,h]carbazole

[Preparation Example 5] Preparation of Formula e

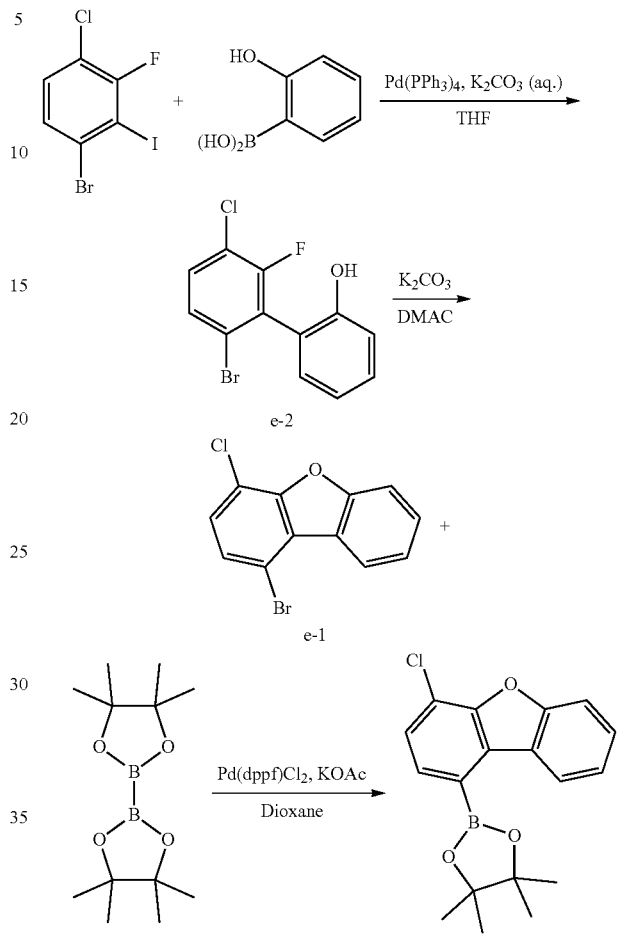

1) Preparation of Formula e-2

200.0 g (1.0 eq) of 1-bromo-4-chloro-3-fluoro-2-iodobenzene, 82.3 g (1.0 eq) of (2-hydroxyphenyl)boronic acid, 164.6 g (2.0 eq) of $K_2CO_3$, and 13.77 g (0.02 eq) of Pd(PPh$_3$)$_4$ (tetrakis(triphenylphosphine)palladium(0)) were dissolved in 3 L of tetrahydrofuran (THF), and the resulting solution was stirred under reflux. When the reaction was terminated after 2 hours, the solvent was removed by reducing pressure. Thereafter, the resulting product was completely dissolved in ethyl acetate and washed with water, and approximately 80% of the solvent was removed again by reducing pressure. Again, crystals were precipitated while adding hexane thereto in a reflux state, cooled, and then filtered. The resulting product was subjected to column chromatography to obtain 129.5 g (yield 72%) of Formula e-2. [M+H]+=300

2) Preparation of Formula e-1

129.5 g (1.0 eq) of Formula e-2 and 118.5 g (2.00 eq) of $K_2CO_3$ were put into 2 L of dimethylacetamide, and the resulting mixture was stirred under reflux. After 1 hours, crystals were precipitated by pouring the reactant into water, and filtered. The filtered solid was completely dissolved in ethyl acetate and washed with water, and approximately 70% of the solvent was removed again by reducing pressure. Again, hexane was put thereinto in a reflux state, and crystals were precipitated, cooled, and then filtered. The resulting product was subjected to column chromatography to obtain 101.6 g (yield 84%) of Formula e-1. [M+H]+=280

3) Preparation of Formula e 101.6 g (1.0 eq) of Formula e-1, 119.1 g (1.3 eq) of bis(pinacolato)diboron, 5.28 g (0.02 eq) of (1,1'-bis(diphenylphosphino)ferrocene)palladium dichloride (Pd(dppf)Cl$_2$) and 40.4 g (2.00 eq) of potassium acetate (KOAc) were put into 2 L of dioxane, and the resulting mixture was stirred under reflux. When the reaction was terminated after 3 hours, the solvent was removed by reducing pressure. The filtered solid was completely dissolved in CHCl$_3$ and then washed with water, and approximately 90% of the solvent was removed by concentrating the solution in which the product was dissolved under reduced pressure. Crystals were precipitated while adding ethanol thereto in a reflux state, cooled, and then filtered to obtain 103.1 g (yield 87%) of Formula e. [M+H]+=329

[Preparation Example 6] Preparation of Formula f

The following Formula f was synthesized in the same manner as in the method of preparing Formula e by using 1-bromo-5-chloro-3-fluoro-2-iodobenzene instead of 1-bromo-4-chloro-3-fluoro-2-iodobenzene. [M+H]+=329

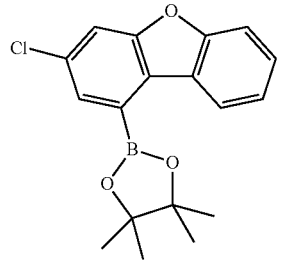

f

[Preparation Example 7] Preparation of Formula g

The following Formula g was synthesized in the same manner as in the method of preparing Formula e by using 2-bromo-1-chloro-4-fluoro-3-iodobenzene instead of 1-bromo-4-chloro-3-fluoro-2-iodobenzene. [M+H]+=329

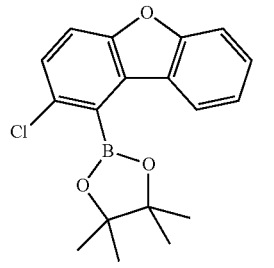

g

[Preparation Example 8] Preparation of Formula h

The following Formula h was synthesized in the same manner as in the method of preparing Formula e by using (3-hydroxynaphthalen-2-yl)boronic acid instead of (2-hydroxyphenyl)boronic acid. [M+H]+=379

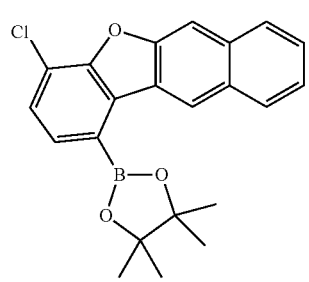

h

[Preparation Example 9] Preparation of Formula i

The following Formula i was synthesized in the same manner as in the method of preparing Formula f by using (3-hydroxynaphthalen-2-yl)boronic acid instead of (2-hydroxyphenyl)boronic acid. [M+H]+=379

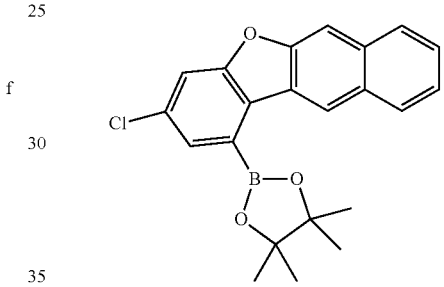

i

[Preparation Example 10] Preparation of Formula j

The following Formula j was synthesized in the same manner as in the method of preparing Formula g by using (3-hydroxynaphthalen-2-yl)boronic acid instead of (2-hydroxyphenyl)boronic acid. [M+H]+=379

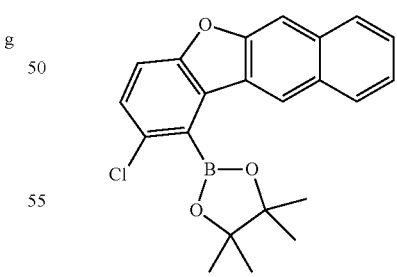

j

[Preparation Example 11] Preparation of Formula k

The following Formula k was synthesized in the same manner as in the method of preparing Formula e by using (1-hydroxynaphthalen-2-yl)boronic acid instead of (2-hydroxyphenyl)boronic acid. [M+H]+=379

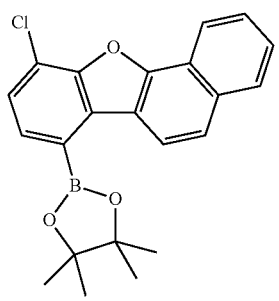

k

[Preparation Example 12] Preparation of Formula 1

The following Formula 1 was synthesized in the same manner as in the method of preparing Formula f by using (1-hydroxynaphthalen-2-yl)boronic acid instead of (2-hydroxyphenyl)boronic acid. [M+H]+=379

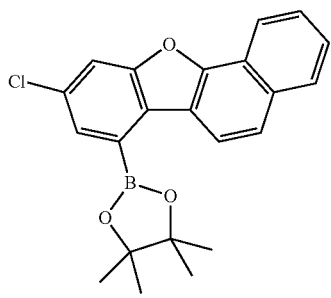

l

[Preparation Example 13] Preparation of Formula m

The following Formula m was synthesized in the same manner as in the method of preparing Formula g by using (1-hydroxynaphthalen-2-yl)boronic acid instead of (2-hydroxyphenyl)boronic acid. [M+H]+=379

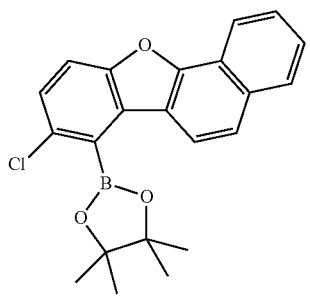

m

[Preparation Example 14] Preparation of Formula n

The following Formula n was synthesized in the same manner as in the method of preparing Formula e by using 2-bromo-1-chloro-4-fluoro-3-iodonaphthalene instead of 1-bromo-4-chloro-3-fluoro-2-iodobenzene. [M+H]+=379

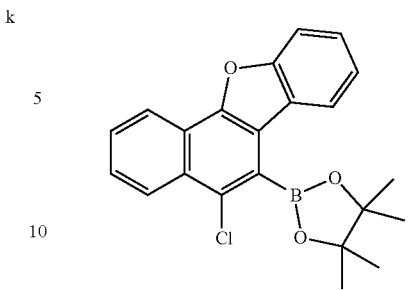

n

[Preparation Example 15] Preparation of Formula o

The following Formula o was synthesized in the same manner as in the method of preparing Formula e by using 1-bromo-4-chloro-3-fluoro-2-iodonaphthalene instead of 1-bromo-4-chloro-3-fluoro-2-iodobenzene. [M+H]+=379

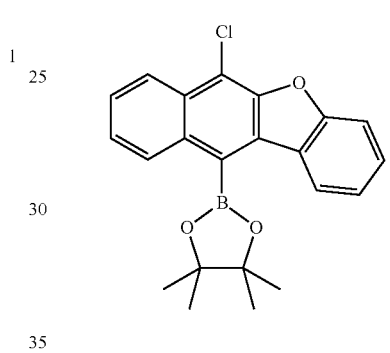

o

Intermediates including triazine were subjected to Suzuki coupling reaction by utilizing the intermediates synthesized in Preparation Examples 1 to 15, and the compounds in the following Synthesis Examples were synthesized.

Synthesis Example 1

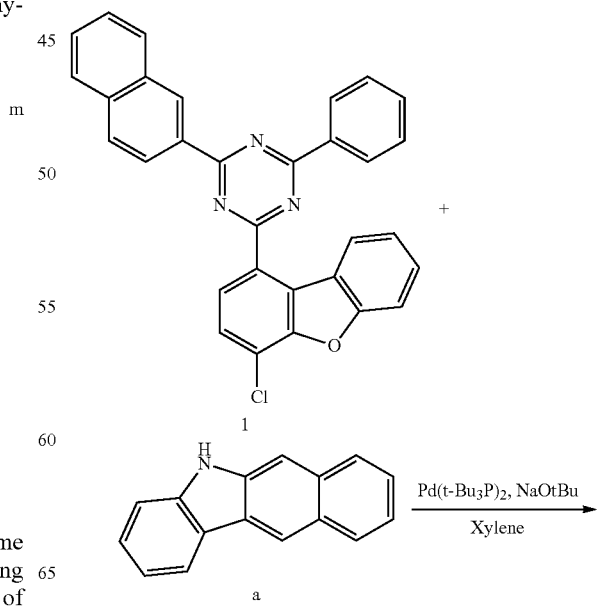

-continued

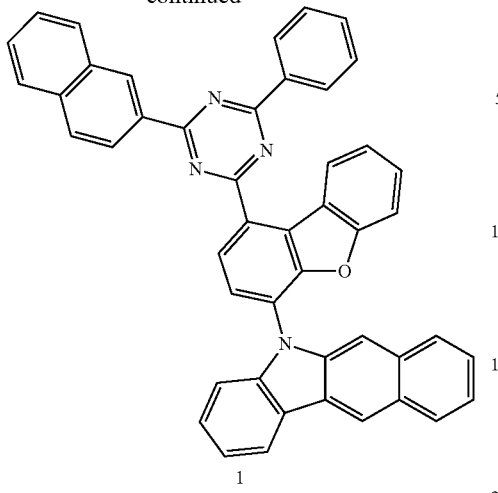

1

-continued

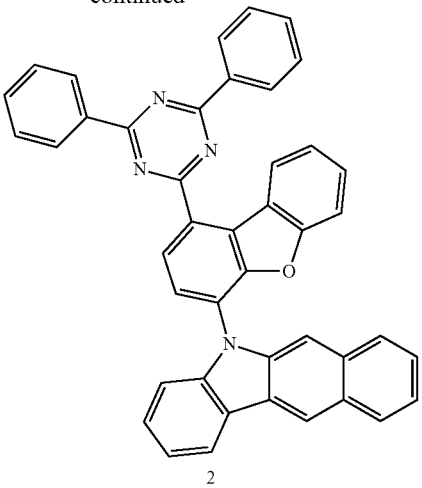

2

Intermediate 1 (10 g, 20.7 mmol) and Formula a (4.5 g, 20.7 mmol) were put into 200 ml of xylene under a nitrogen atmosphere, and the resulting mixture was stirred and refluxed. Thereafter, sodium tertiary-butoxide (NaOtBu) (6 g, 62 mmol) was introduced thereinto, the resulting mixture was sufficiently stirred, and then bis(tri tertiary-butylphosphine)palladium (Pd(t-Bu$_3$P)$_2$) (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 1 (8.2 g, 60%, MS: [M+H]+=665.8) which was a yellow solid compound.

Intermediate 2 (10 g, 23 mmol) and Formula a (5 g, 23 mmol) were put into 200 ml of xylene under a nitrogen atmosphere, and the resulting mixture was stirred and refluxed. Thereafter, sodium tertiary-butoxide (6.6 g, 69.1 mmol) was introduced thereinto, the resulting mixture was sufficiently stirred, and then bis(tri tertiary-butylphosphine) palladium (0.2 g, 0.5 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by a silica column using chloroform and ethyl acetate to prepare Compound 2 (9.9 g, 70%, MS: [M+H]+=615.2) which was a yellow solid compound.

Synthesis Example 2

Synthesis Example 3

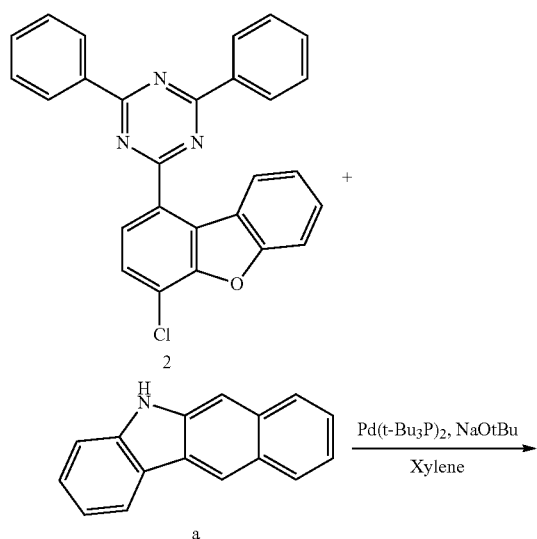

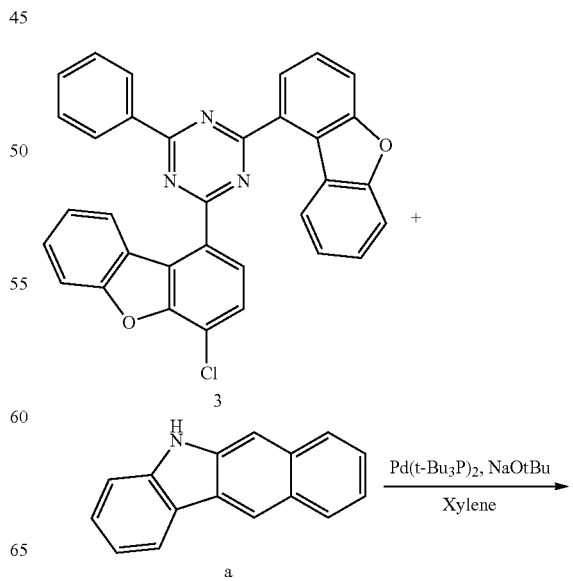

-continued

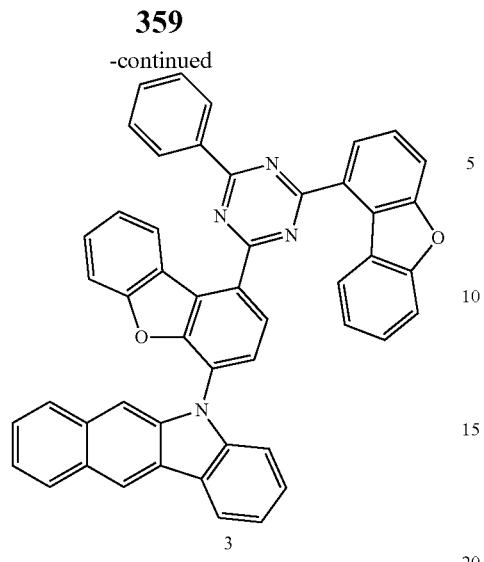

3

Intermediate 3 (10 g, 19.1 mmol) and Formula a (4.1 g, 19.1 mmol) were put into 200 ml of xylene under a nitrogen atmosphere, and the resulting mixture was stirred and refluxed. Thereafter, sodium tertiary-butoxide (5.5 g, 57.3 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 3 (9.3 g, 69%, MS: [M+H]+=705.2) which was a yellow solid compound.

Synthesis Example 4

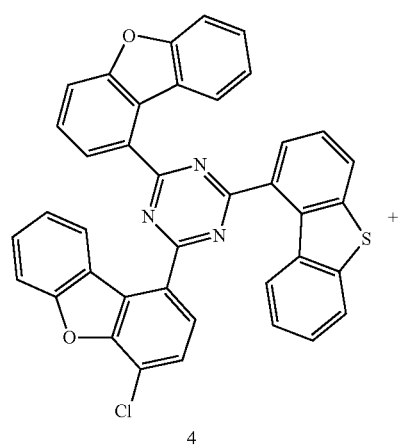

4

-continued

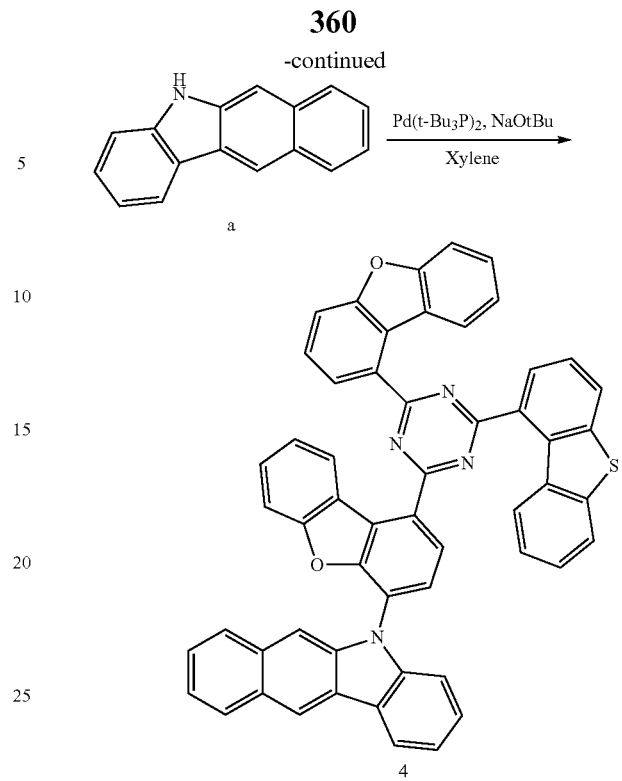

4

Intermediate 4 (10 g, 15.9 mmol) and Formula a (3.4 g, 15.9 mmol) were put into 200 ml of xylene under a nitrogen atmosphere, and the resulting mixture was stirred and refluxed. Thereafter, sodium tertiary-butoxide (4.6 g, 47.6 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 4 (8.7 g, 68%, MS: [M+H]+=811.2) which was a yellow solid compound.

Synthesis Example 5

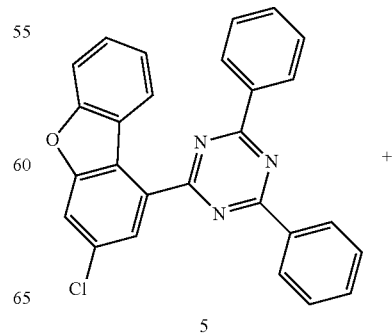

5

-continued

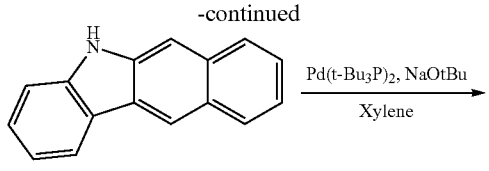

a

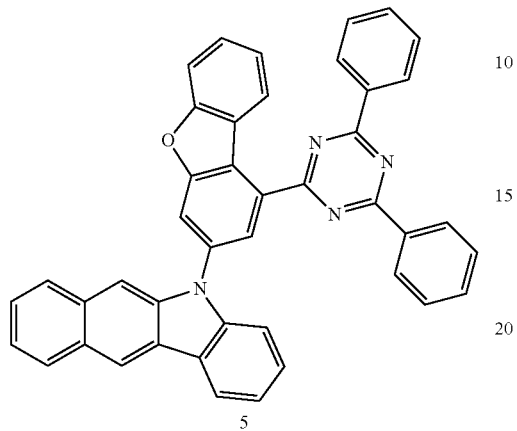

5

Intermediate 5 (10 g, 23 mmol) and Formula a (5 g, 23 mmol) were put into 200 ml of xylene under a nitrogen atmosphere, and the resulting mixture was stirred and refluxed. Thereafter, sodium tertiary-butoxide (6.6 g, 69.1 mmol) was introduced thereinto, the resulting mixture was sufficiently stirred, and then bis(tri tertiary-butylphosphine) palladium (0.2 g, 0.5 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 5 (8.5 g, 60%, MS: [M+H]+=615.2) which was a yellow solid compound.

Synthesis Example 6

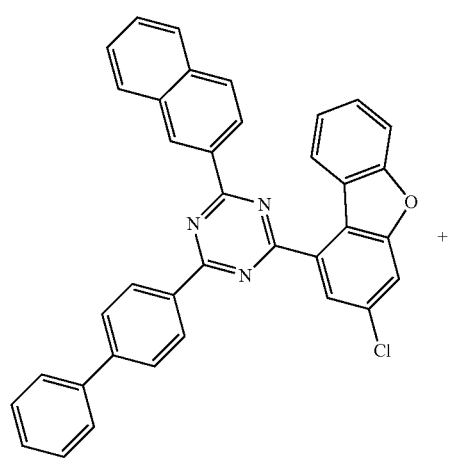

6

-continued

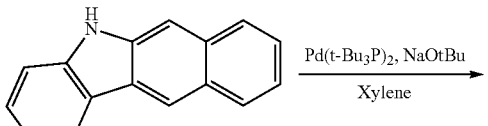

a

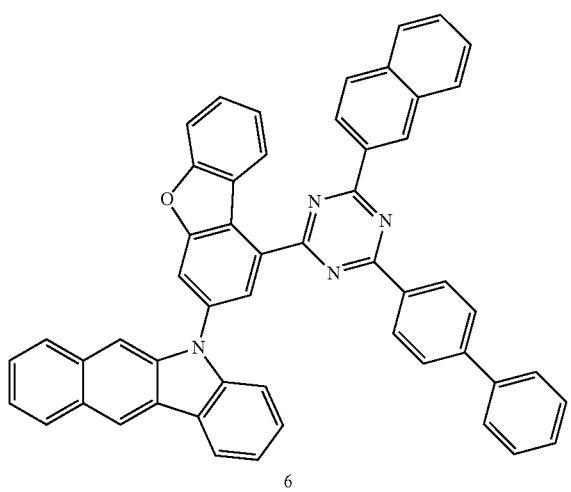

6

Intermediate 6 (10 g, 17.9 mmol) and Formula a (3.9 g, 17.9 mmol) were put into 200 ml of xylene under a nitrogen atmosphere, and the resulting mixture was stirred and refluxed. Thereafter, sodium tertiary-butoxide (5.1 g, 53.6 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by silica column using chloroform and ethyl acetate to prepare Compound 6 (8.3 g, 63%, MS: [M+H]+=741.3) which was a yellow solid compound.

Synthesis Example 7

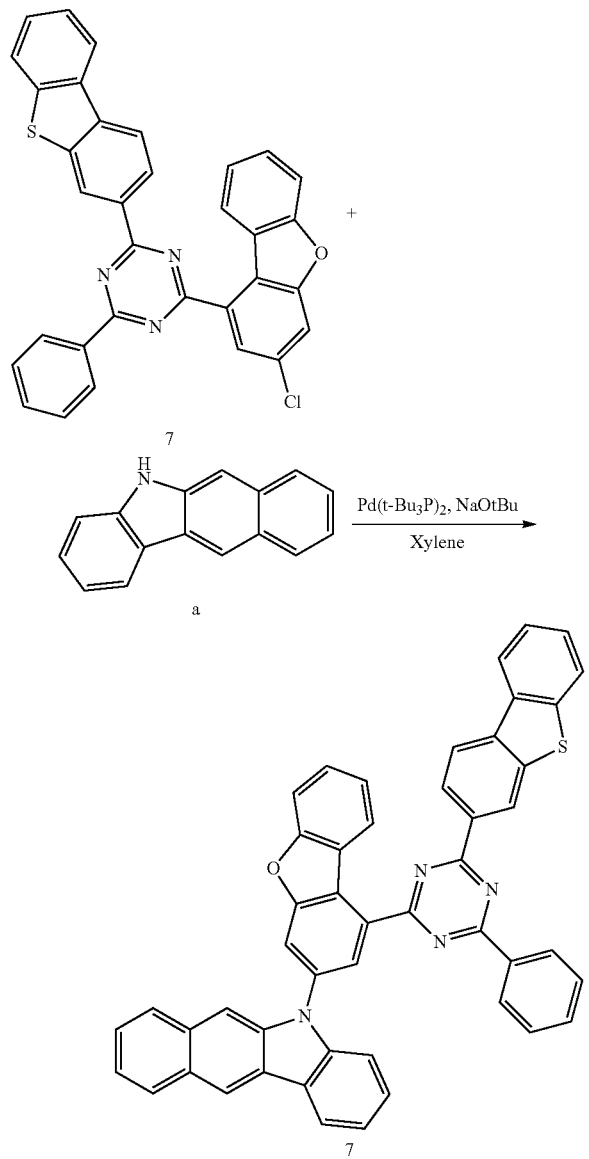

Intermediate 7 (10 g, 18.5 mmol) and Formula a (4 g, 18.5 mmol) were put into 200 ml of xylene under a nitrogen atmosphere, and the resulting mixture was stirred and refluxed. Thereafter, sodium tertiary-butoxide (5.3 g, 55.6 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 7 (8.7 g, 65%, MS: [M+H]+=721.2) which was a yellow solid compound.

Synthesis Example 8

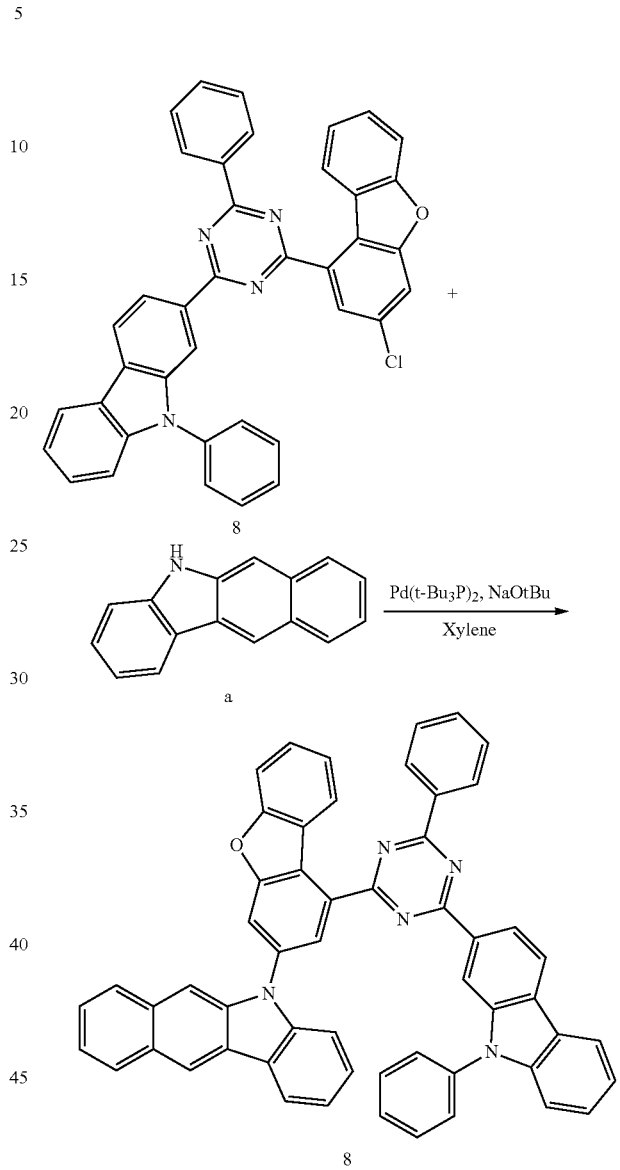

Intermediate 8 (10 g, 16.7 mmol) and Formula a (3.6 g, 16.7 mmol) were put into 200 ml of xylene under a nitrogen atmosphere, and the resulting mixture was stirred and refluxed. Thereafter, sodium tertiary-butoxide (4.8 g, 50.1 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by silica column using chloroform and ethyl acetate to prepare Compound 8 (8.2 g, 63%, MS: [M+H]+=780.3) which was a yellow solid compound.

Synthesis Example 9

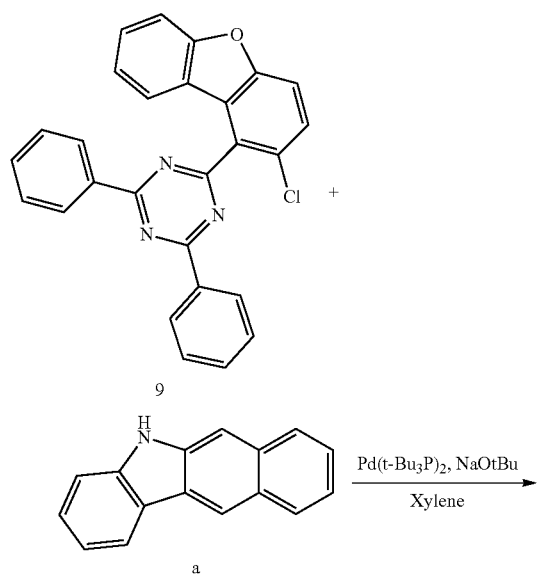

Synthesis Example 10

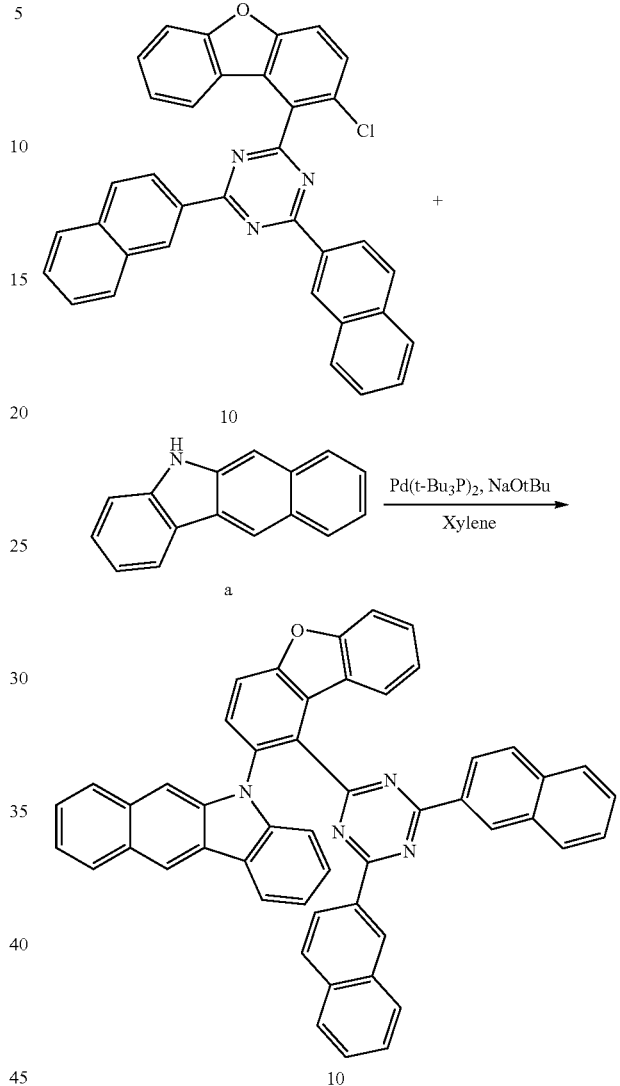

Intermediate 9 (10 g, 23 mmol) and Formula a (5 g, 23 mmol) were put into 200 ml of xylene under a nitrogen atmosphere, and the resulting mixture was stirred and refluxed. Thereafter, sodium tertiary-butoxide (6.6 g, 69.1 mmol) was introduced thereinto, the resulting mixture was sufficiently stirred, and then bis(tri tertiary-butylphosphine) palladium (0.2 g, 0.5 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 9 (9.1 g, 64%, MS: [M+H]+=615.2) which was a yellow solid compound.

Intermediate 10 (10 g, 18.7 mmol) and Formula a (4.1 g, 18.7 mmol) were put into 200 ml of xylene under a nitrogen atmosphere, and the resulting mixture was stirred and refluxed. Thereafter, sodium tertiary-butoxide (5.4 g, 56.2 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 10 (7.9 g, 59%, MS: [M+H]+=715.2) which was a yellow solid compound.

Synthesis Example 11

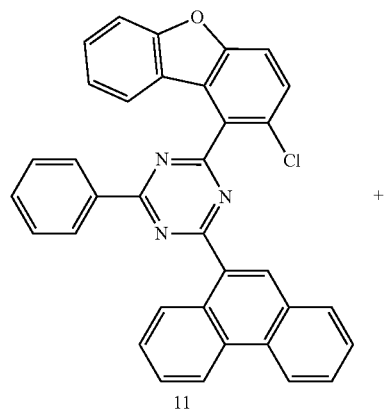

11

+

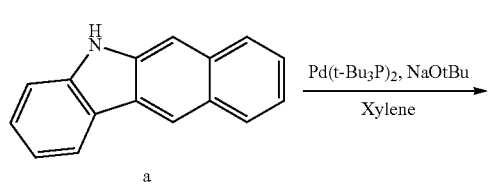

a

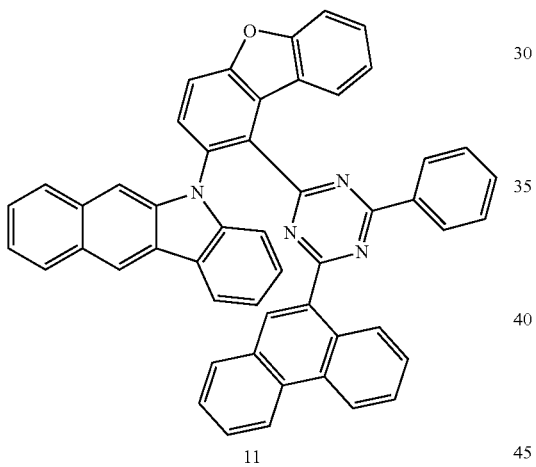

11

Intermediate 11 (10 g, 18.7 mmol) and Formula a (4.1 g, 18.7 mmol) were put into 200 ml of xylene under a nitrogen atmosphere, and the resulting mixture was stirred and refluxed. Thereafter, sodium tertiary-butoxide (5.4 g, 56.2 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by silica column using chloroform and ethyl acetate to prepare Compound 11 (8.6 g, 64%, MS: [M+H]+=715.2) which was a yellow solid compound.

Synthesis Example 12

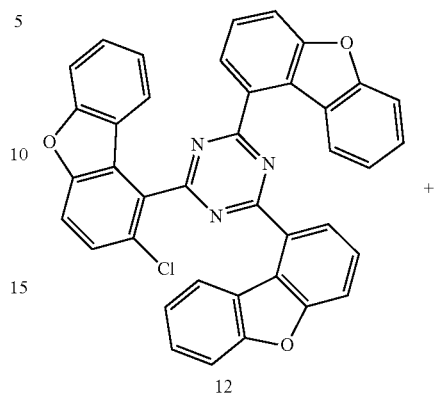

12

+

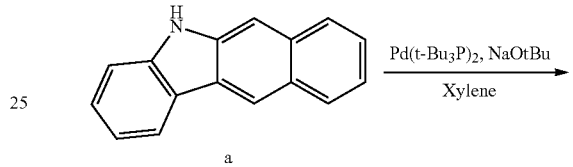

a

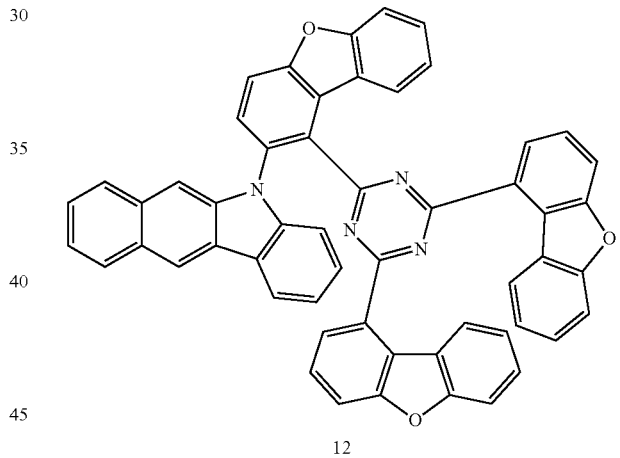

12

Intermediate 12 (10 g, 16.3 mmol) and Formula a (3.5 g, 16.3 mmol) were put into 200 ml of xylene under a nitrogen atmosphere, and the resulting mixture was stirred and refluxed. Thereafter, sodium tertiary-butoxide (4.7 g, 48.9 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was put thereinto, the resulting mixture was stirred, and then filtered, and the filtrate was distilled under reduced pressure. The concentrated compound was purified by a silica column using chloroform and ethyl acetate to prepare Compound 12 (8.9 g, 69%, MS: [M+H]+=795.2) which was a yellow solid compound.

Synthesis Example 13

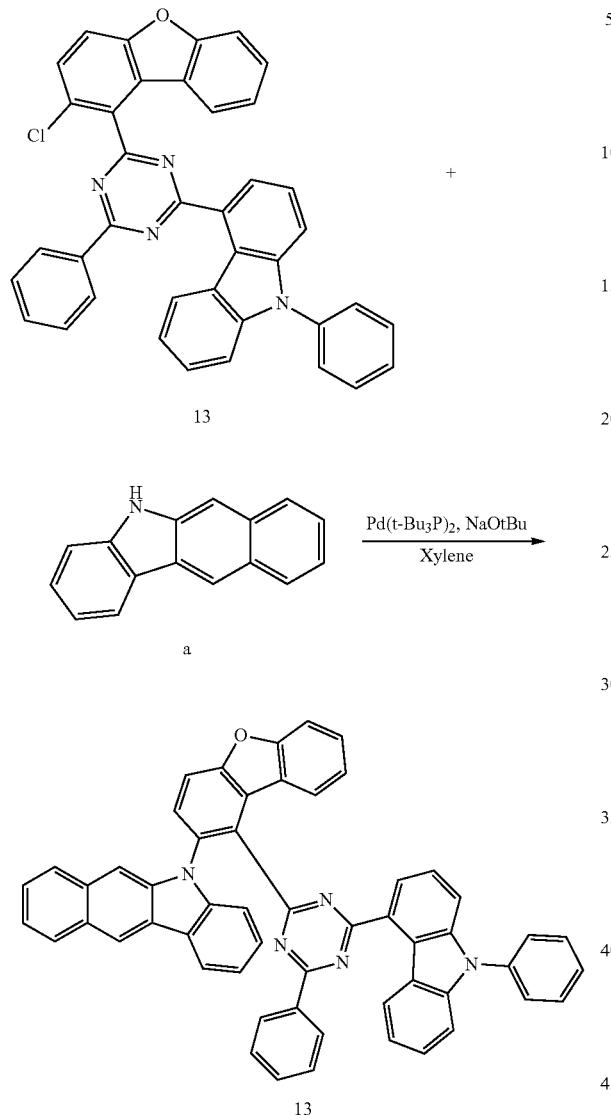

Intermediate 13 (10 g, 16.7 mmol) and Formula a (3.6 g, 16.7 mmol) were put into 200 ml of xylene under a nitrogen atmosphere, and the resulting mixture was stirred and refluxed. Thereafter, sodium tertiary-butoxide (4.8 g, 50.1 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 13 (8.6 g, 66%, MS: [M+H]+=780.3) which was a yellow solid compound.

Synthesis Example 14

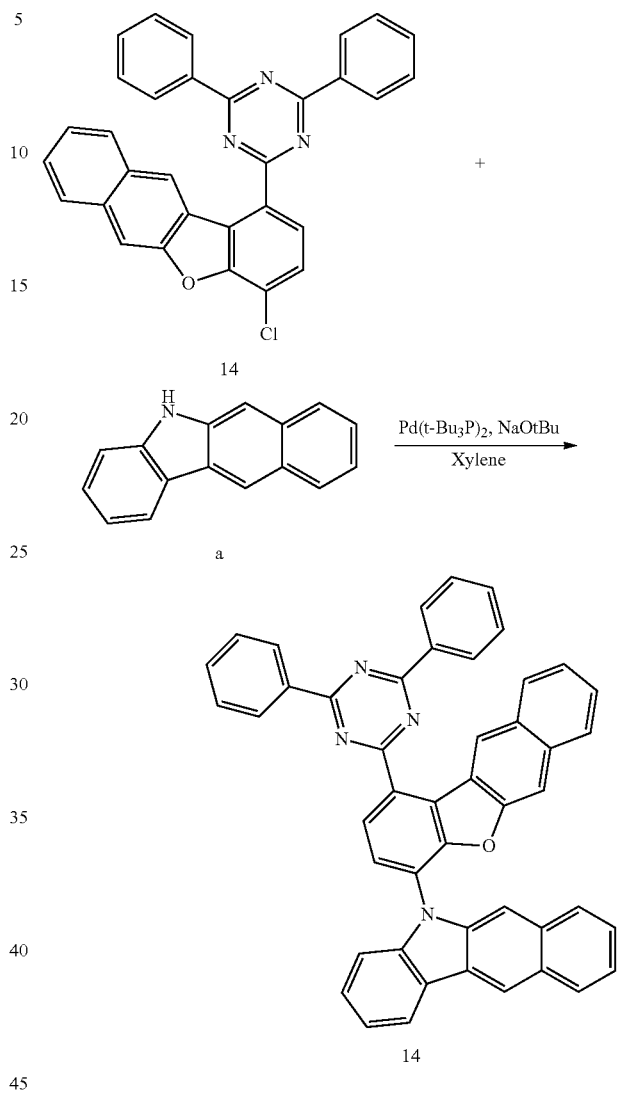

Intermediate 14 (10 g, 20.7 mmol) and Formula a (4.5 g, 20.7 mmol) were put into 200 ml of xylene under a nitrogen atmosphere, and the resulting mixture was stirred and refluxed. Thereafter, sodium tertiary-butoxide (6 g, 62 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 14 (9.1 g, 66%, MS: [M+H]+=665.2) which was a yellow solid compound.

Synthesis Example 15

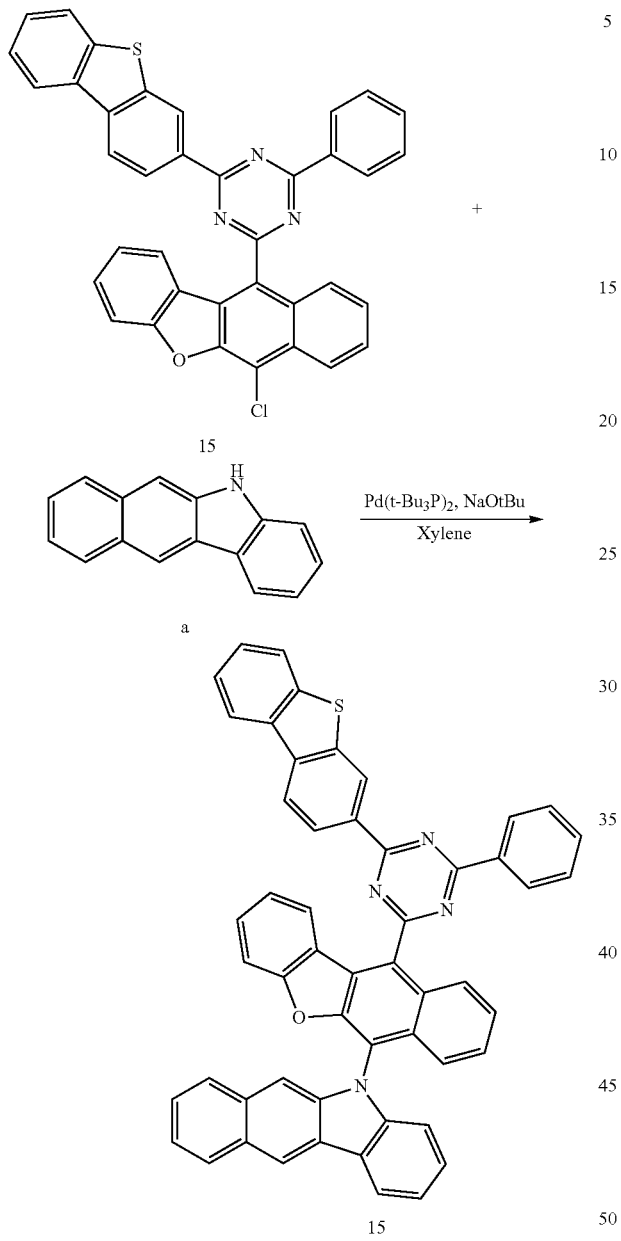

Synthesis Example 16

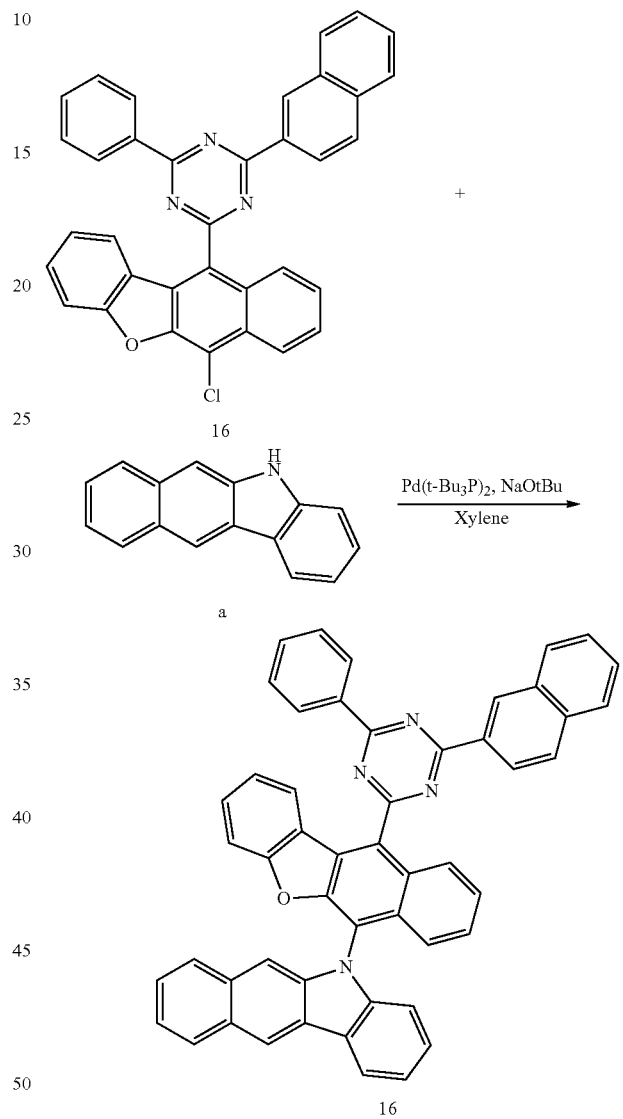

distilled under reduced pressure. The concentrated compound was purified by a silica column using chloroform and ethyl acetate to prepare Compound 15 (8.4 g, 64%, MS: [M+H]+=771.2) which was a yellow solid compound.

Intermediate 15 (10 g, 16.9 mmol) and Formula a (3.7 g, 16.9 mmol) were put into 200 ml of xylene under a nitrogen atmosphere, and the resulting mixture was stirred and refluxed. Thereafter, sodium tertiary-butoxide (4.9 g, 50.8 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was Intermediate 16 (10 g, 18.7 mmol) and Formula a (4.1 g, 18.7 mmol) were put into 200 ml of xylene under a nitrogen atmosphere, and the resulting mixture was stirred and refluxed. Thereafter, sodium tertiary-butoxide (5.4 g, 56.2 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 16 (7.8 g, 58%, MS: [M+H]+=715.2) which was a yellow solid compound.

Synthesis Example 17

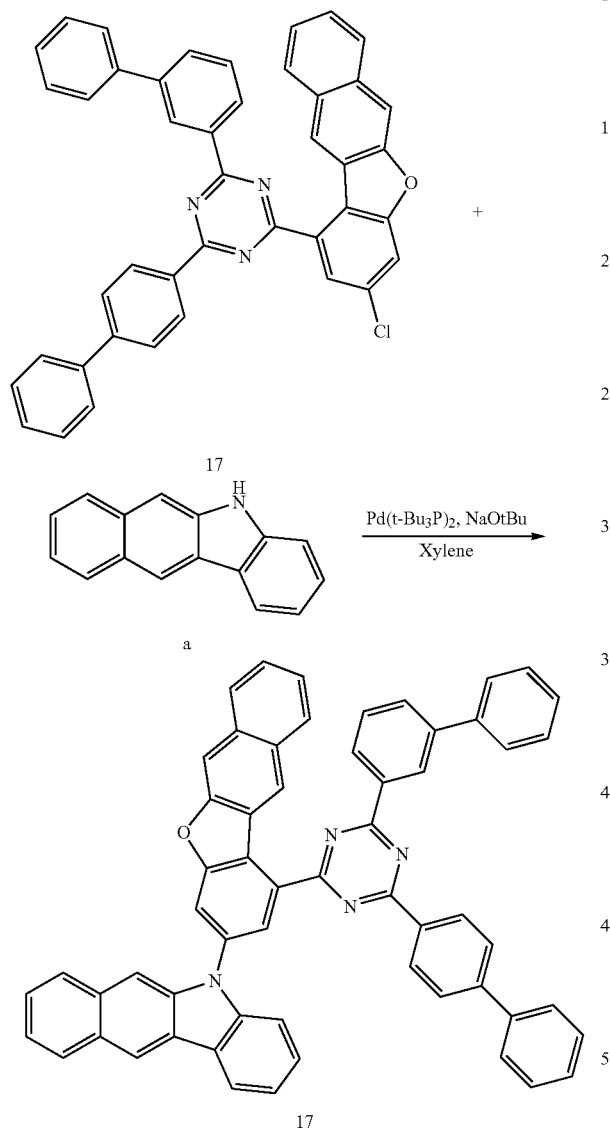

Intermediate 17 (10 g, 15.7 mmol) and Formula a (3.4 g, 15.7 mmol) were put into 200 ml of xylene under a nitrogen atmosphere, and the resulting mixture was stirred and refluxed. Thereafter, sodium tertiary-butoxide (4.5 g, 47.2 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 17 (7.6 g, 59%, MS: [M+H]+=817.3) which was a yellow solid compound.

Synthesis Example 18

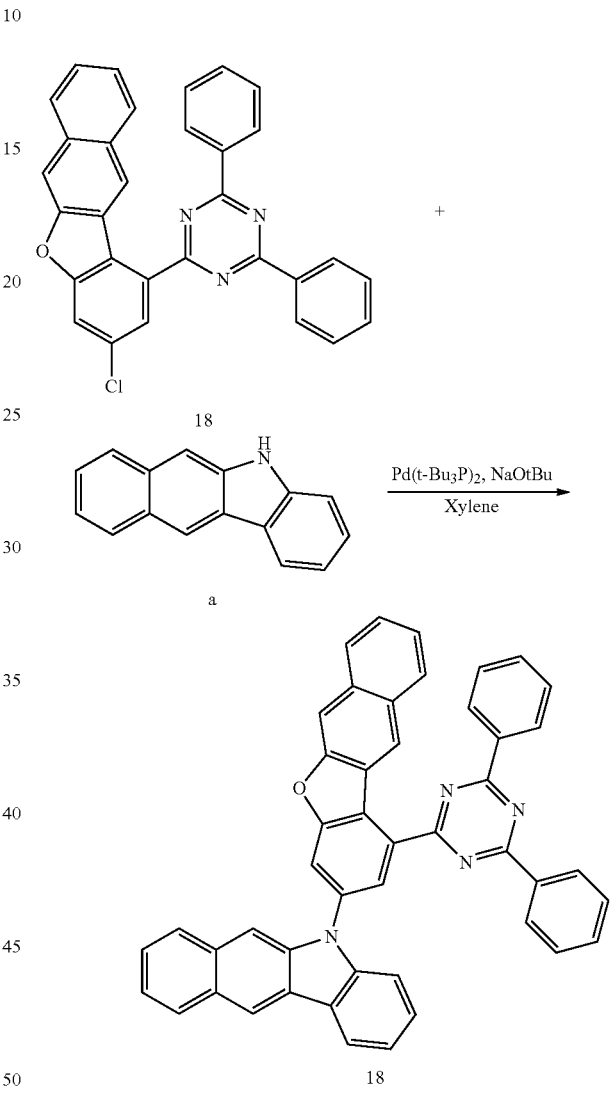

Intermediate 18 (10 g, 20.7 mmol) and Formula a (4.5 g, 20.7 mmol) were put into 200 ml of xylene under a nitrogen atmosphere, and the resulting mixture was stirred and refluxed. Thereafter, sodium tertiary-butoxide (6 g, 62 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 18 (7.8 g, 57%, MS: [M+H]+=665.2) which was a yellow solid compound.

Synthesis Example 19

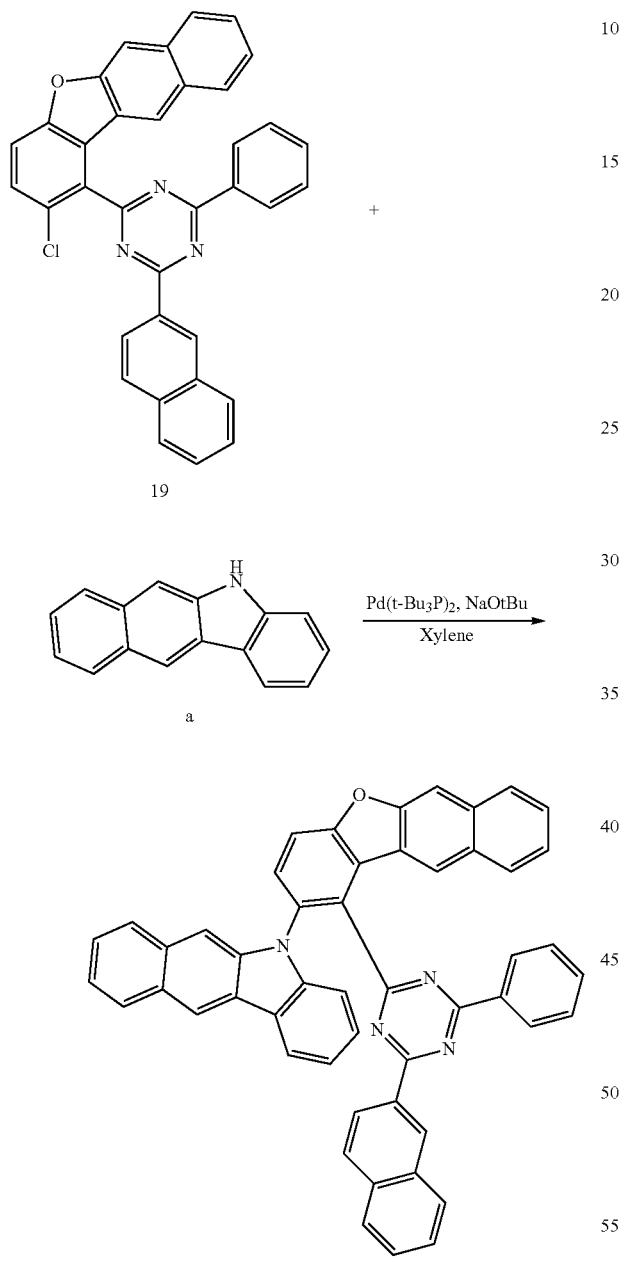

Intermediate 19 (10 g, 18.7 mmol) and Formula a (4.1 g, 18.7 mmol) were put into 200 ml of xylene under a nitrogen atmosphere, and the resulting mixture was stirred and refluxed. Thereafter, sodium tertiary-butoxide (5.4 g, 56.2 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 19 (8.7 g, 65%, MS: [M+H]+=715.2) which was a yellow solid compound.

Synthesis Example 20

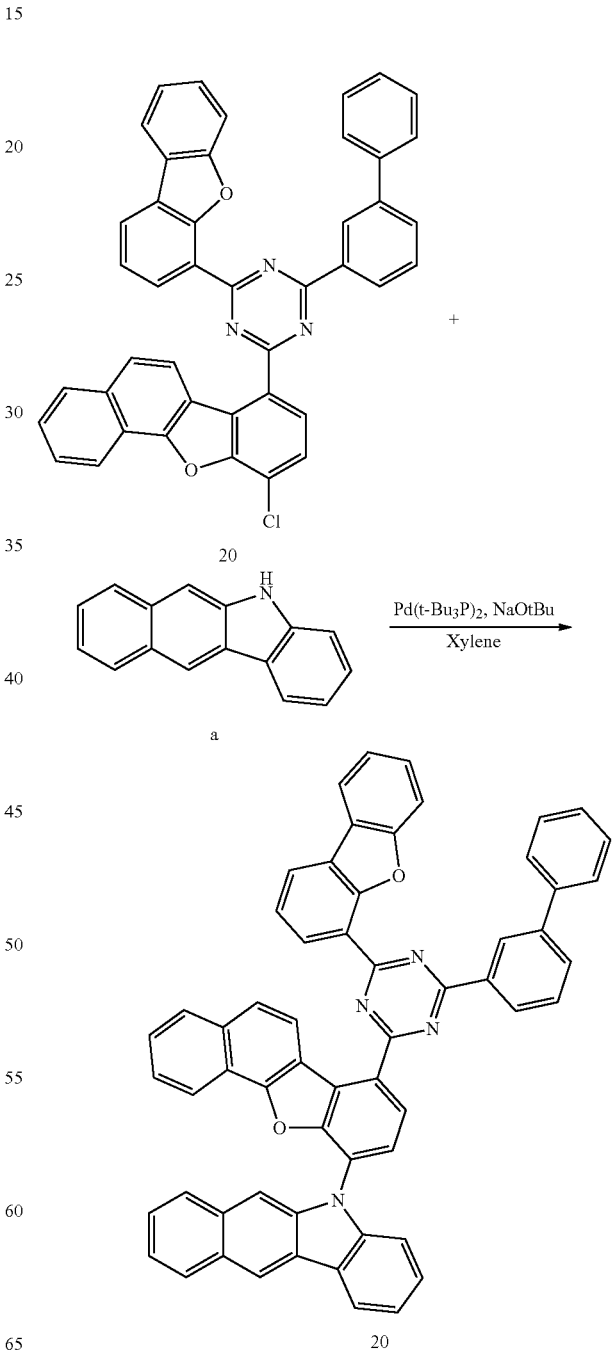

Intermediate 20 (10 g, 15.4 mmol) and Formula a (3.3 g, 15.4 mmol) were put into 200 ml of xylene under a nitrogen atmosphere, and the resulting mixture was stirred and refluxed. Thereafter, sodium tertiary-butoxide (4.4 g, 46.1 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 20 (7.7 g, 60%, MS: [M+H]+=831.3) which was a yellow solid compound.

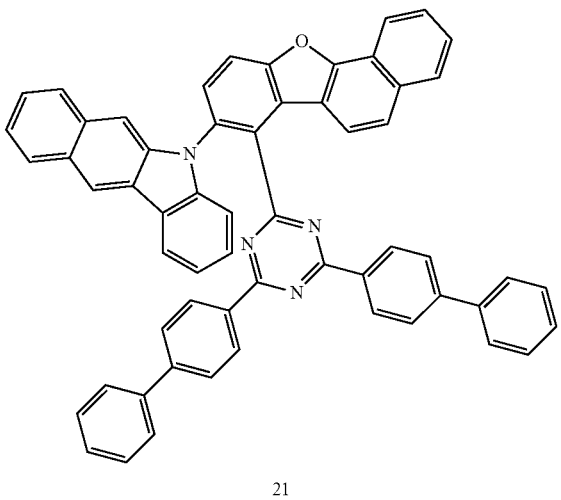

21

Intermediate 21 (10 g, 15.7 mmol) and Formula a (3.4 g, 15.7 mmol) were put into 200 ml of xylene under a nitrogen atmosphere, and the resulting mixture was stirred and refluxed. Thereafter, sodium tertiary-butoxide (4.5 g, 47.2 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 21 (7.3 g, 57%, MS: [M+H]+=817.3) which was a yellow solid compound.

Synthesis Example 21

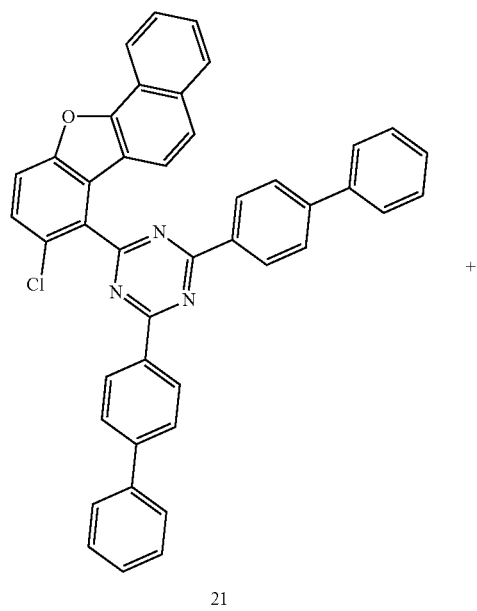

21

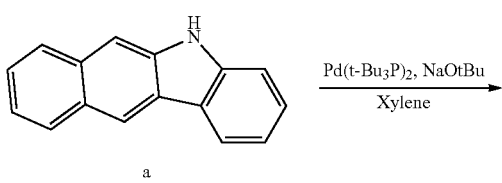

a

Synthesis Example 22

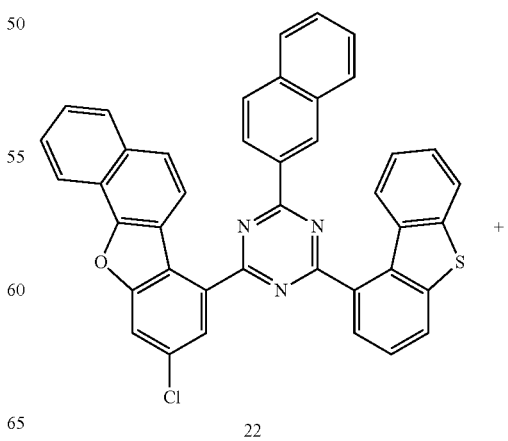

22

Synthesis Example 23

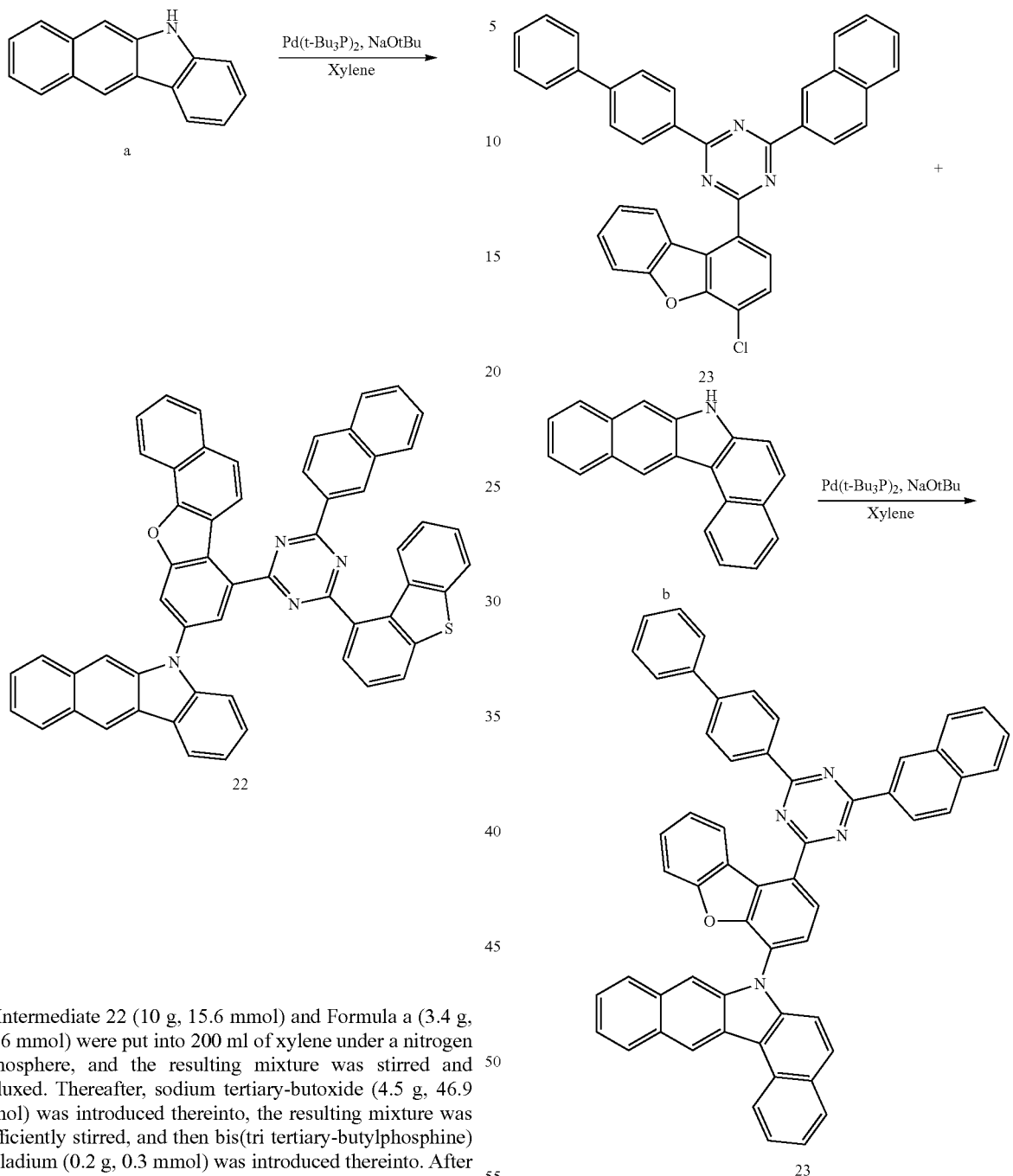

Intermediate 22 (10 g, 15.6 mmol) and Formula a (3.4 g, 15.6 mmol) were put into 200 ml of xylene under a nitrogen atmosphere, and the resulting mixture was stirred and refluxed. Thereafter, sodium tertiary-butoxide (4.5 g, 46.9 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 22 (8.2 g, 64%, MS: [M+H]+=821.2) which was a yellow solid compound.

Intermediate 23 (10 g, 17.9 mmol) and Formula b (4.8 g, 17.9 mmol) were put into 200 ml of xylene under a nitrogen atmosphere, and the resulting mixture was stirred and refluxed. Thereafter, sodium tertiary-butoxide (5.1 g, 53.6 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 23 (7.8 g, 55%, MS: [M+H]+=791.3) which was a yellow solid compound.

Synthesis Example 24

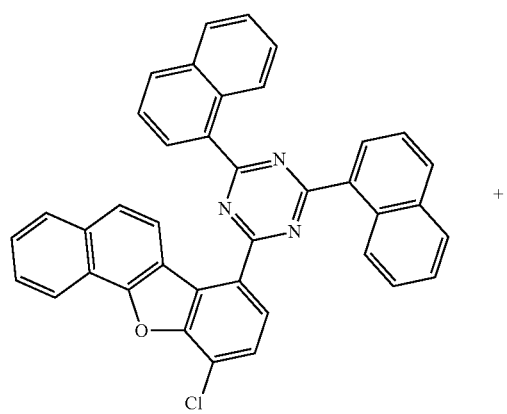

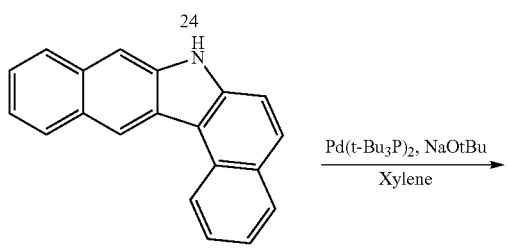

Intermediate 24 (10 g, 17.1 mmol) and Formula b (4.6 g, 17.1 mmol) were put into 200 ml of xylene under a nitrogen atmosphere, and the resulting mixture was stirred and refluxed. Thereafter, sodium tertiary-butoxide (4.9 g, 51.4 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 24 (8.8 g, 63%, MS: [M+H]+=815.3) which was a yellow solid compound.

Synthesis Example 25

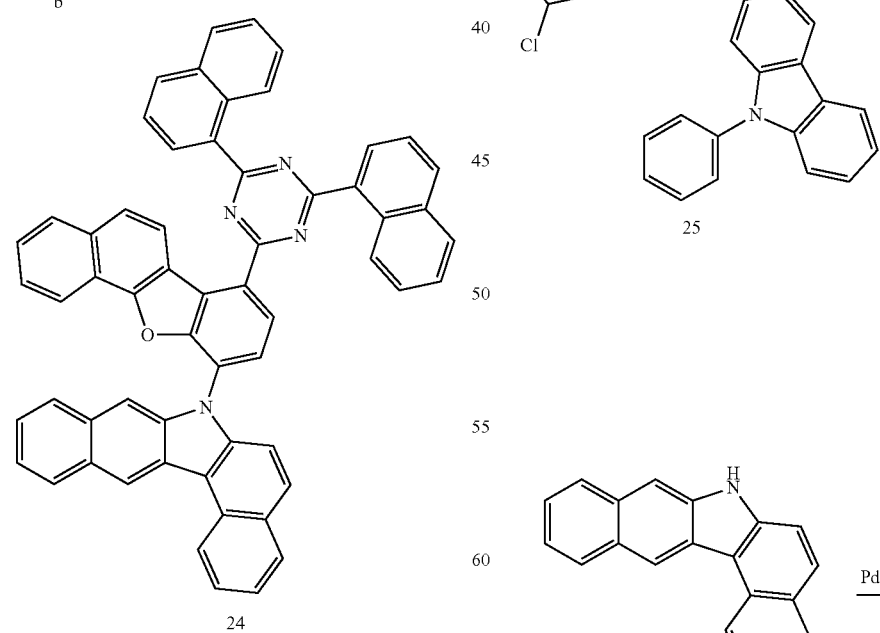

-continued

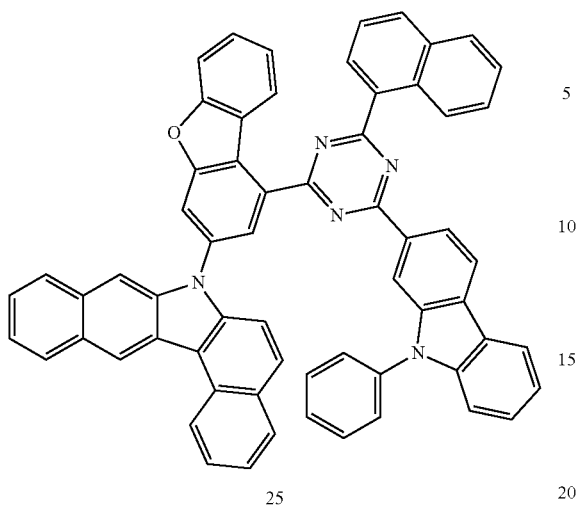

25

Intermediate 25 (10 g, 15.4 mmol) and Formula b (4.1 g, 15.4 mmol) were put into 200 ml of xylene under a nitrogen atmosphere, and the resulting mixture was stirred and refluxed. Thereafter, sodium tertiary-butoxide (4.4 g, 46.2 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 25 (7.6 g, 56%, MS: [M+H]+=880.3) which was a yellow solid compound.

Synthesis Example 26

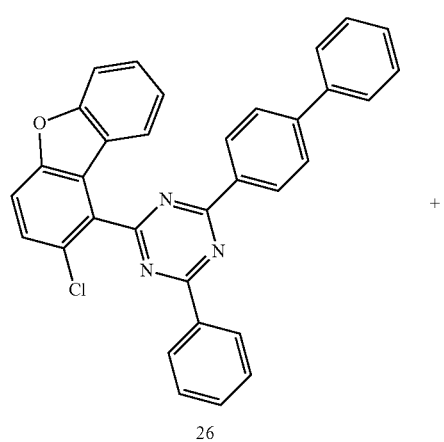

26

+

-continued

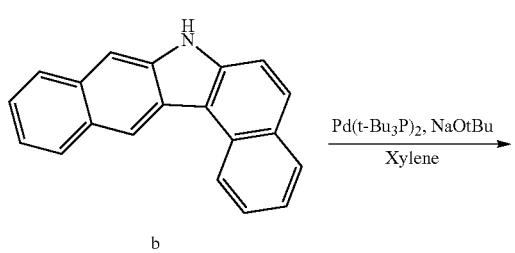

b

26

Intermediate 26 (10 g, 19.6 mmol) and Formula b (5.2 g, 19.6 mmol) were put into 200 ml of xylene under a nitrogen atmosphere, and the resulting mixture was stirred and refluxed. Thereafter, sodium tertiary-butoxide (5.7 g, 58.8 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 26 (9.4 g, 65%, MS: [M+H]+=741.3) which was a yellow solid compound.

Synthesis Example 27

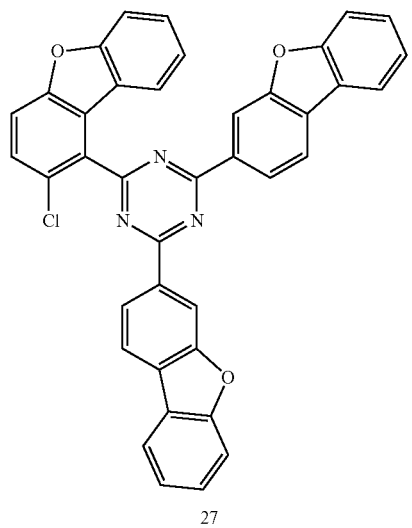

Intermediate 27 (10 g, 16.3 mmol) and Formula b (4.4 g, 16.3 mmol) were put into 200 ml of xylene under a nitrogen atmosphere, and the resulting mixture was stirred and refluxed. Thereafter, sodium tertiary-butoxide (4.7 g, 48.9 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 27 (8.5 g, 62%, MS: [M+H]+=845.3) which was a yellow solid compound.

Synthesis Example 28

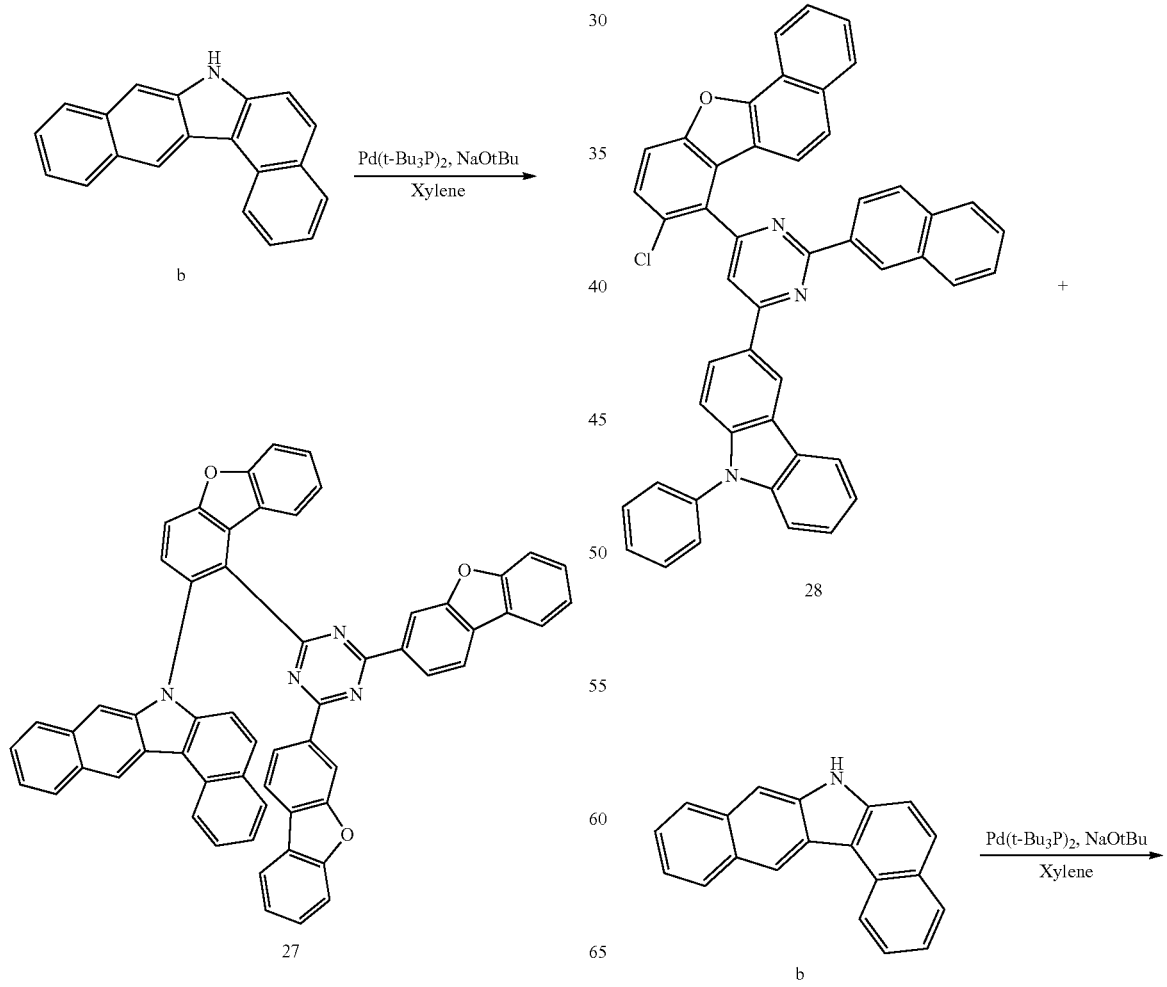

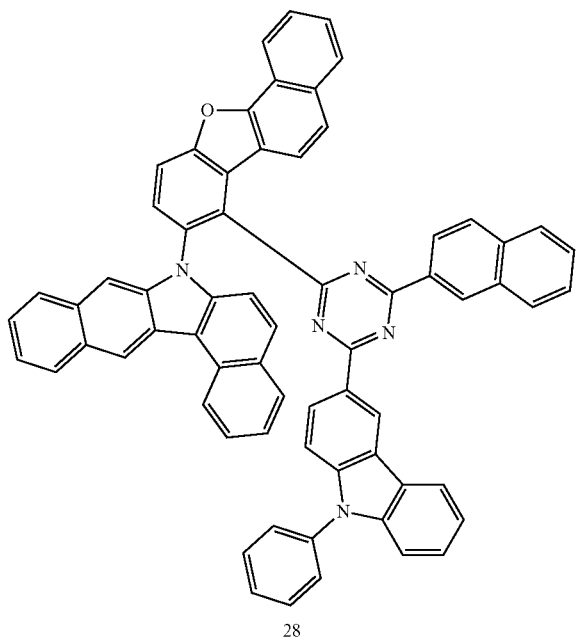

28

Intermediate 28 (10 g, 14.3 mmol) and Formula b (3.8 g, 14.3 mmol) were put into 200 ml of xylene under a nitrogen atmosphere, and the resulting mixture was stirred and refluxed. Thereafter, sodium tertiary-butoxide (4.1 g, 42.9 mmol) was introduced thereinto, the resulting mixture was sufficiently stirred, and then bis(tri tertiary-butylphosphine) palladium (0.1 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 28 (7.3 g, 55%, MS: [M+H]+=930.3) which was a yellow solid compound.

Synthesis Example 29

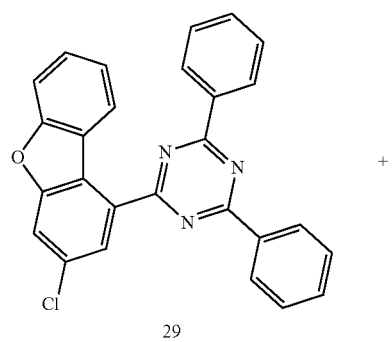

29

+

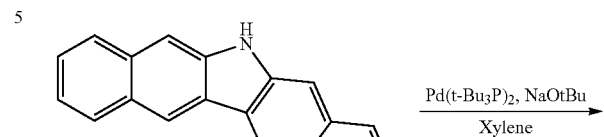

c

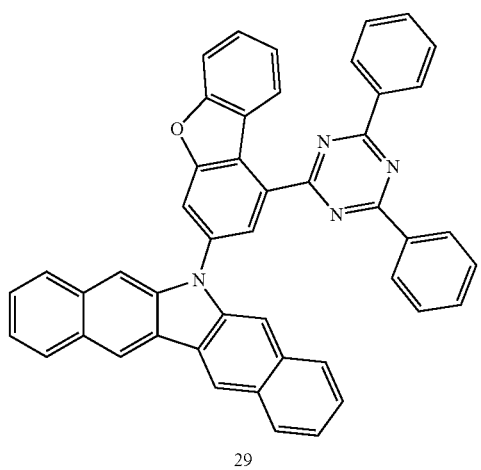

29

Intermediate 29 (10 g, 23 mmol) and Formula c (6.2 g, 23 mmol) were put into 200 ml of xylene under a nitrogen atmosphere, and the resulting mixture was stirred and refluxed. Thereafter, sodium tertiary-butoxide (6.6 g, 69.1 mmol) was introduced thereinto, the resulting mixture was sufficiently stirred, and then bis(tri tertiary-butylphosphine) palladium (0.2 g, 0.5 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 29 (9 g, 59%, MS: [M+H]+=665.2) which was a yellow solid compound.

Synthesis Example 30

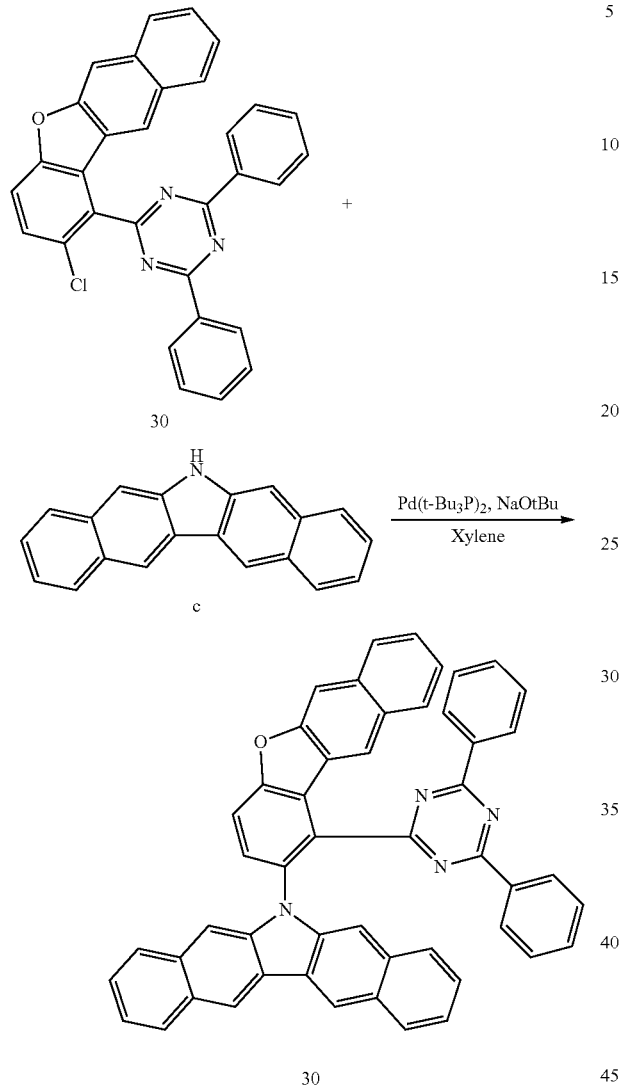

Intermediate 30 (10 g, 20.7 mmol) and Formula c (5.5 g, 20.7 mmol) were put into 200 ml of xylene under a nitrogen atmosphere, and the resulting mixture was stirred and refluxed. Thereafter, sodium tertiary-butoxide (6 g, 62 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 30 (10.2 g, 69%, MS: [M+H]+=715.2) which was a yellow solid compound.

Synthesis Example 31

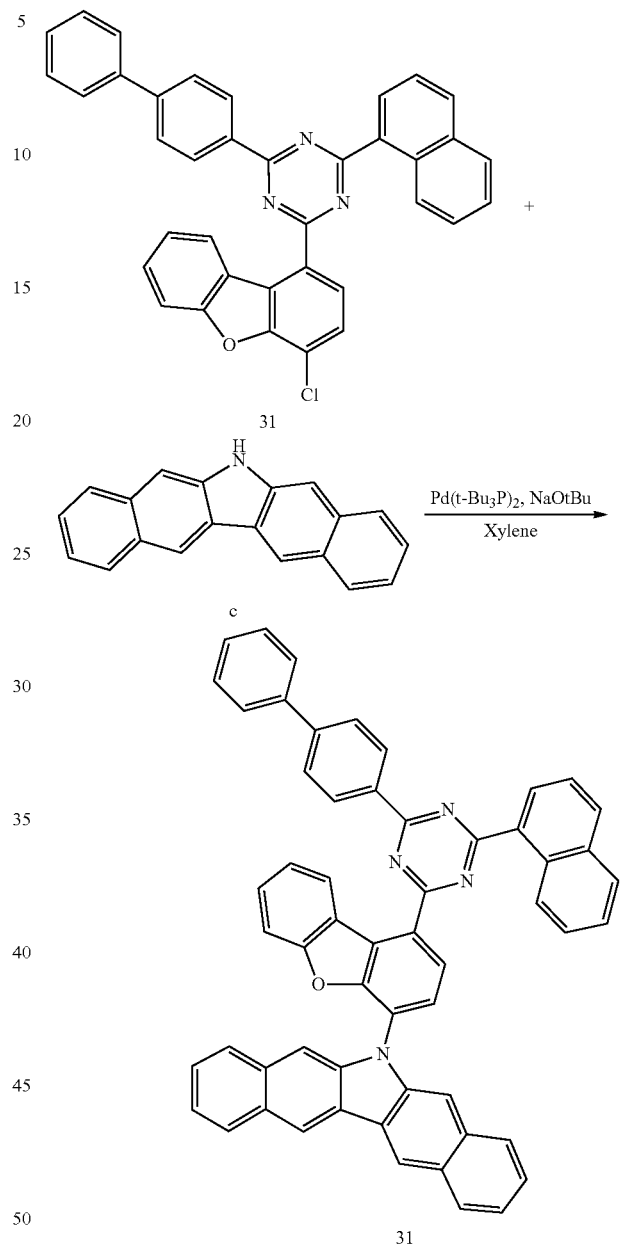

Intermediate 31 (10 g, 17.9 mmol) and Formula c (4.8 g, 17.9 mmol) were put into 200 ml of xylene under a nitrogen atmosphere, and the resulting mixture was stirred and refluxed. Thereafter, sodium tertiary-butoxide (5.1 g, 53.6 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 31 (8 g, 57%, MS: [M+H]+=791.3) which was a yellow solid compound.

Synthesis Example 32

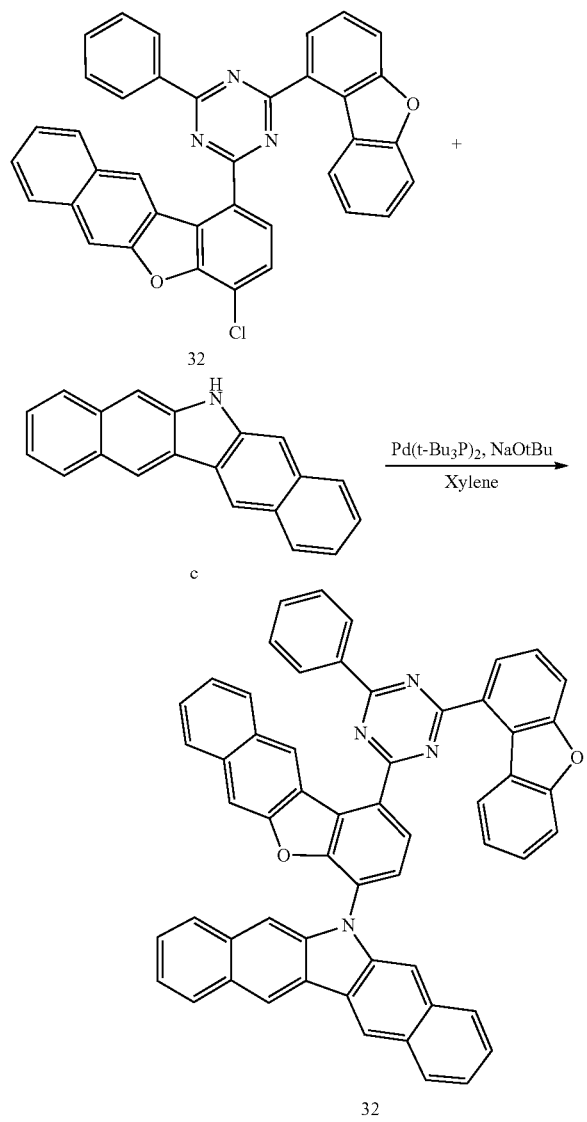

Intermediate 32 (10 g, 17.4 mmol) and Formula c (4.7 g, 17.4 mmol) were put into 200 ml of xylene under a nitrogen atmosphere, and the resulting mixture was stirred and refluxed. Thereafter, sodium tertiary-butoxide (5 g, 52.3 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 32 (8 g, 57%, MS: [M+H]+=805.2) which was a yellow solid compound.

Synthesis Example 33

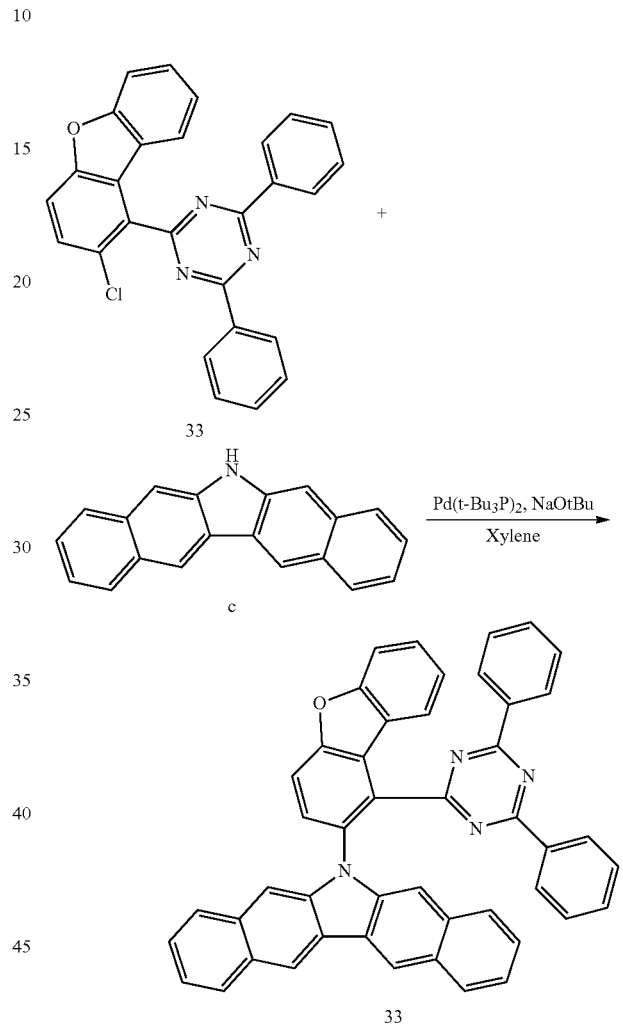

Intermediate 33 (10 g, 23 mmol) and Formula c (6.2 g, 23 mmol) were put into 200 ml of xylene under a nitrogen atmosphere, and the resulting mixture was stirred and refluxed. Thereafter, sodium tertiary-butoxide (6.6 g, 69.1 mmol) was introduced thereinto, the resulting mixture was sufficiently stirred, and then bis(tri tertiary-butylphosphine) palladium (0.2 g, 0.5 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 33 (10.4 g, 68%, MS: [M+H]+=665.2) which was a yellow solid compound.

Synthesis Example 34

Synthesis Example 35

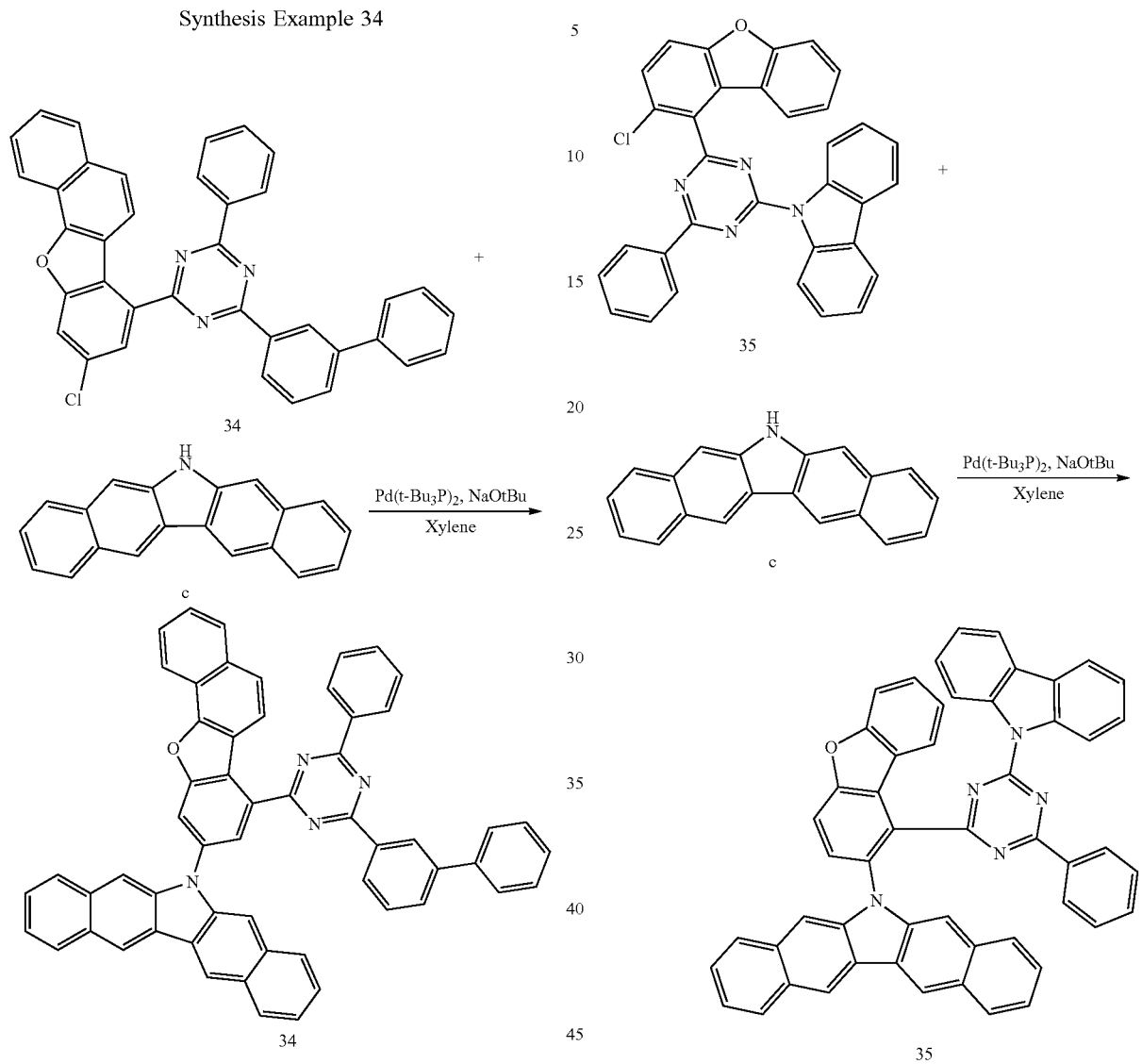

34

35

Intermediate 34 (10 g, 17.9 mmol) and Formula c (4.8 g, 17.9 mmol) were put into 200 ml of xylene under a nitrogen atmosphere, and the resulting mixture was stirred and refluxed. Thereafter, sodium tertiary-butoxide (5.1 g, 53.6 mmol) was introduced thereinto, the resulting mixture was sufficiently stirred, and then bis(tri tertiary-butylphosphine) palladium (0.2 g, 0.4 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 34 (9 g, 64%, MS: [M+H]+=791.9) which was a yellow solid compound.

Intermediate 35 (10 g, 19.1 mmol) and Formula c (5.1 g, 19.1 mmol) were put into 200 ml of xylene under a nitrogen atmosphere, and the resulting mixture was stirred and refluxed. Thereafter, sodium tertiary-butoxide (5.5 g, 57.4 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 35 (9.9 g, 69%, MS: [M+H]+=754.3) which was a yellow solid compound.

Synthesis Example 36

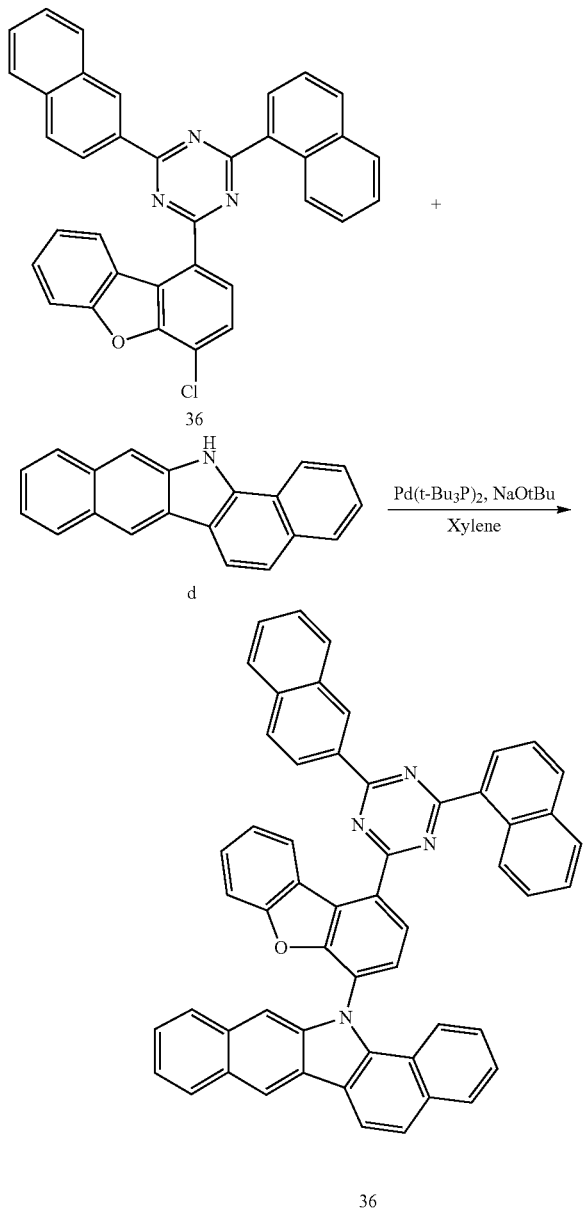

Intermediate 36 (10 g, 19.1 mmol) and Formula d (5.1 g, 19.1 mmol) were put into 200 ml of xylene under a nitrogen atmosphere, and the resulting mixture was stirred and refluxed. Thereafter, sodium tertiary-butoxide (5.5 g, 57.4 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 36 (9.9 g, 69%, MS: [M+H]+=754.3) which was a yellow solid compound.

Synthesis Example 37

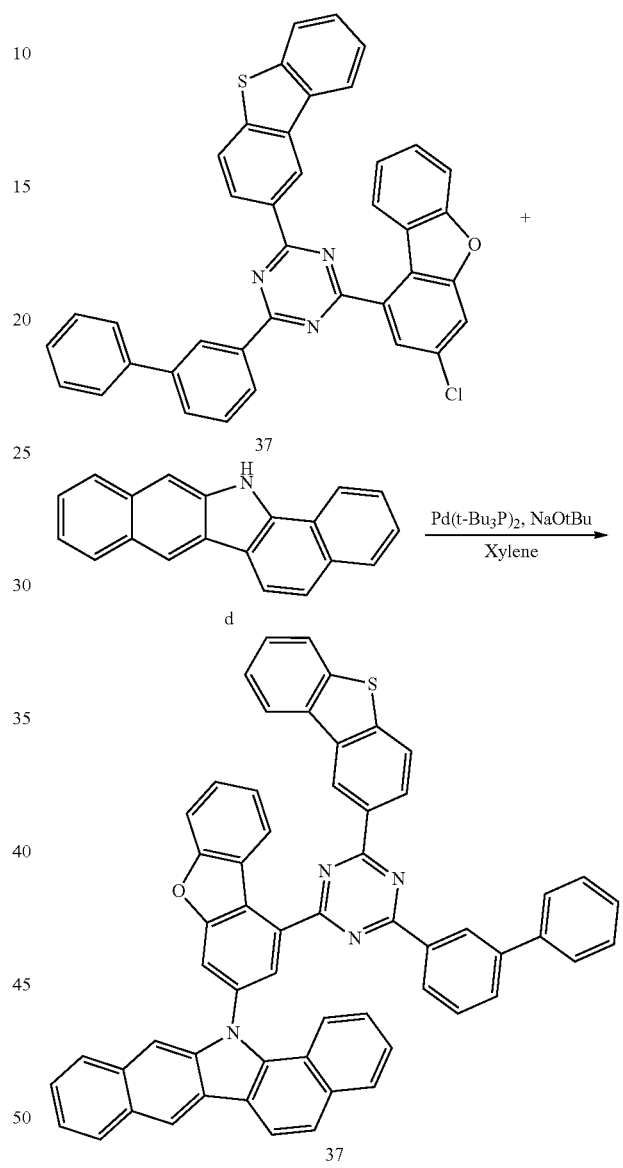

Intermediate 37 (10 g, 16.2 mmol) and Formula d (4.3 g, 16.2 mmol) were put into 200 ml of xylene under a nitrogen atmosphere, and the resulting mixture was stirred and refluxed. Thereafter, sodium tertiary-butoxide (4.7 g, 48.7 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 37 (8.1 g, 59%, MS: [M+H]+=847.3) which was a yellow solid compound.

Synthesis Example 38

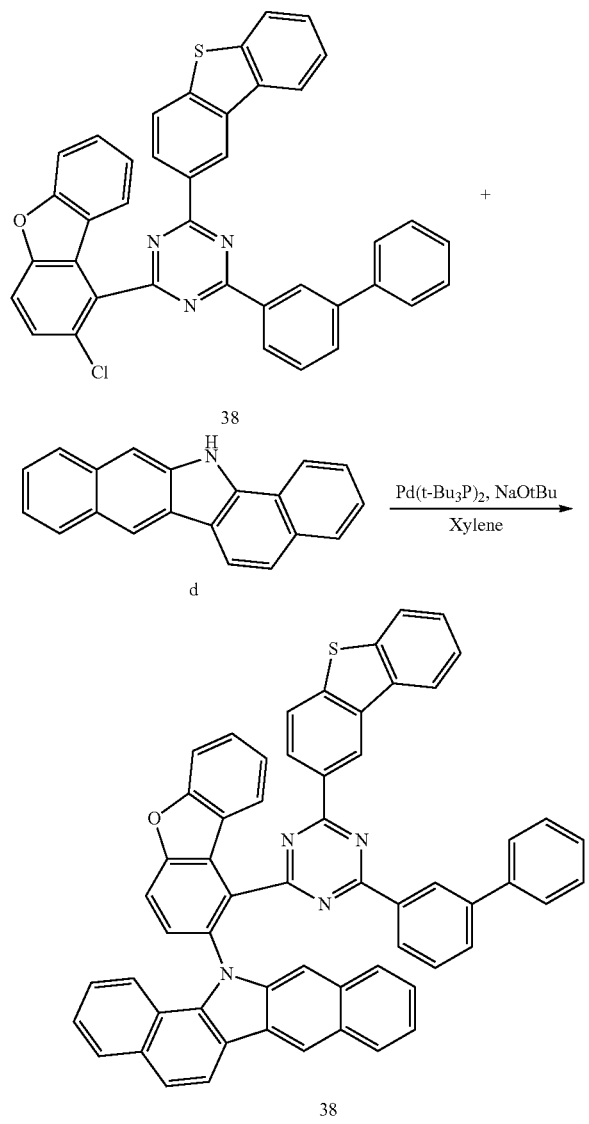

Intermediate 38 (10 g, 16.2 mmol) and Formula d (4.3 g, 16.2 mmol) were put into 200 ml of xylene under a nitrogen atmosphere, and the resulting mixture was stirred and refluxed. Thereafter, sodium tertiary-butoxide (4.7 g, 48.7 mmol) was introduced thereinto, the resulting mixture was sufficiently stirred, and then bis(tri tertiary-butylphosphine) palladium (0.2 g, 0.3 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 38 (7.7 g, 56%, MS: [M+H]+=847.3) which was a yellow solid compound.

Synthesis Example 39

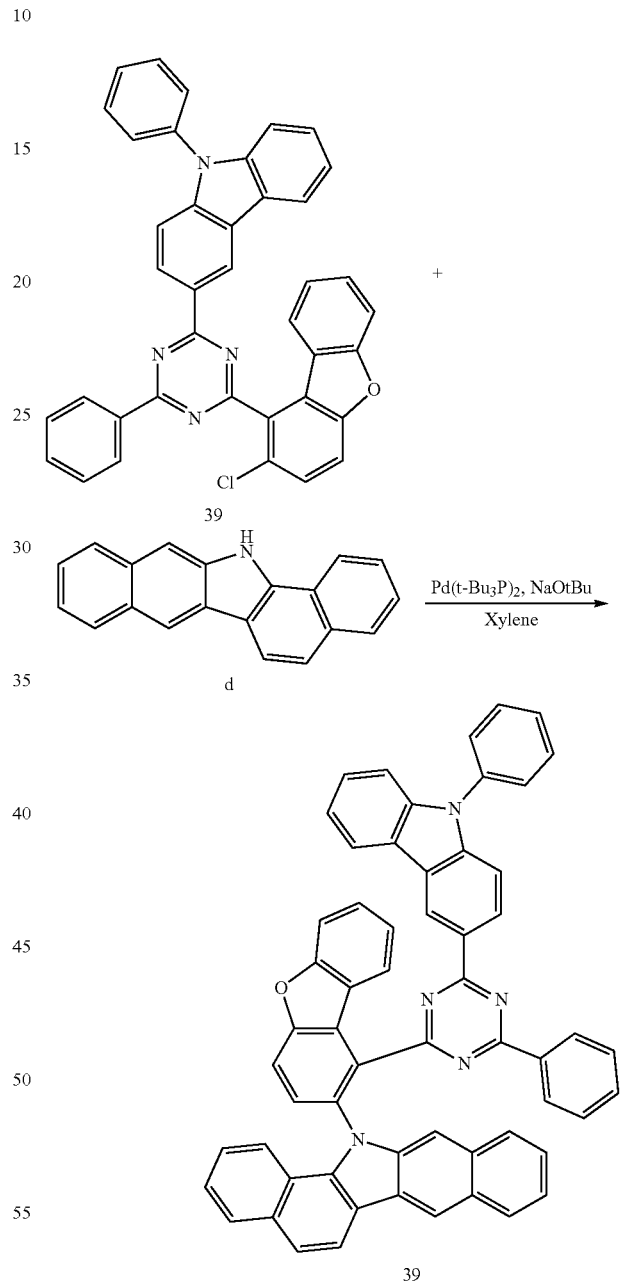

Intermediate 39 (10 g, 16.7 mmol) and Formula d (4.5 g, 16.7 mmol) were put into 200 ml of xylene under a nitrogen atmosphere, and the resulting mixture was stirred and refluxed. Thereafter, sodium tertiary-butoxide (4.8 g, 50.2 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 39 (8 g, 58%, MS: [M+H]+=830.3) which was a yellow solid compound.

Synthesis Example 40

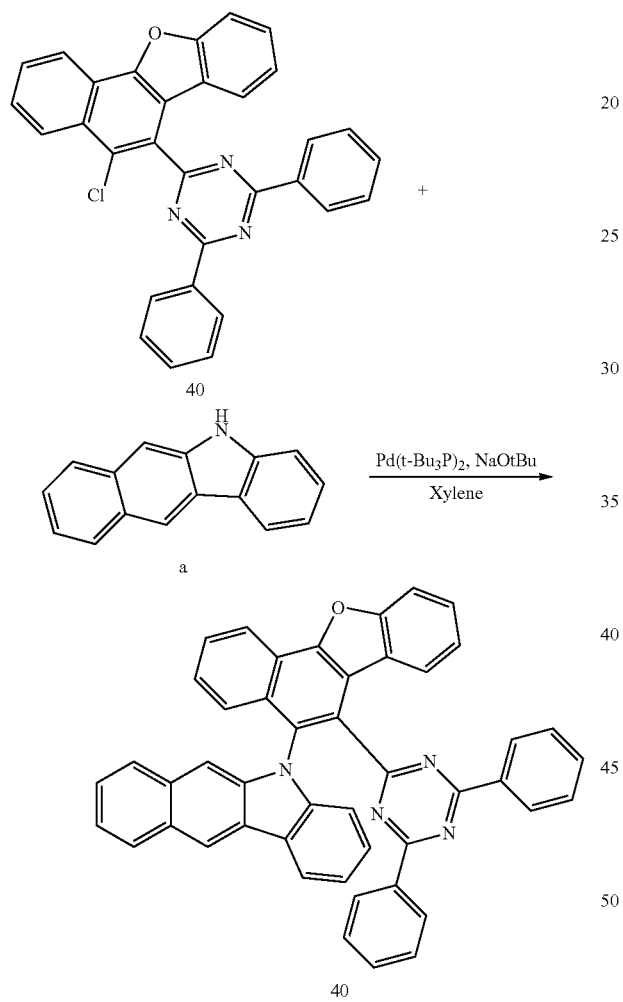

Intermediate 40 (10 g, 20.7 mmol) and Formula a (4.5 g, 20.7 mmol) were put into 200 ml of xylene under a nitrogen atmosphere, and the resulting mixture was stirred and refluxed. Thereafter, sodium tertiary-butoxide (6 g, 62 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 40 (8.5 g, 62%, MS: [M+H]+=665.2) which was a yellow solid compound.

Synthesis Example 41

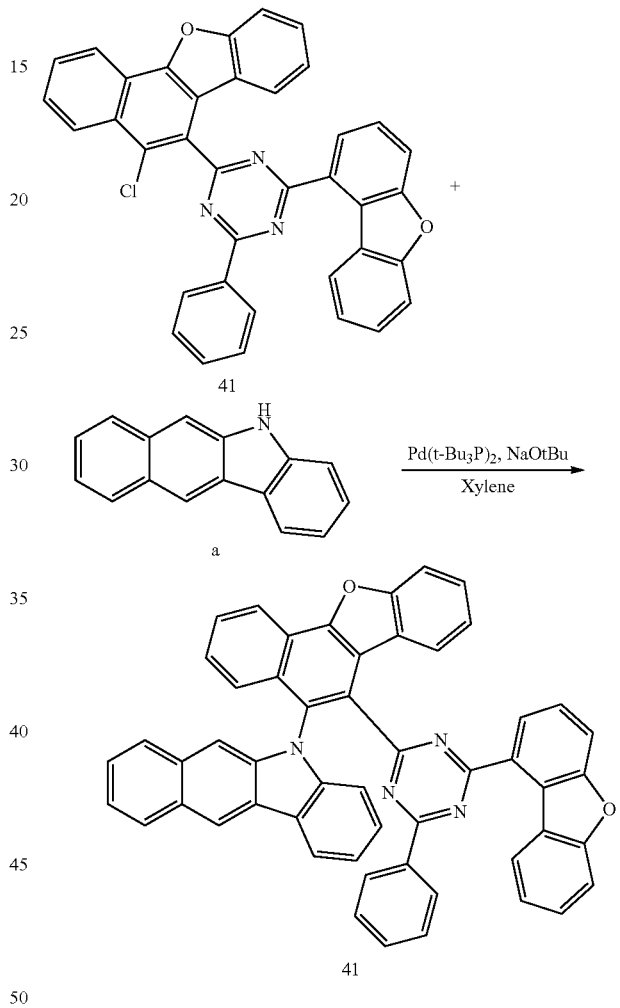

Intermediate 41 (10 g, 17.4 mmol) and Formula a (3.8 g, 17.4 mmol) were put into 200 ml of xylene under a nitrogen atmosphere, and the resulting mixture was stirred and refluxed. Thereafter, sodium tertiary-butoxide (5 g, 52.3 mmol) was introduced thereinto, the resulting mixture was sufficiently stirred, and then bis(tri tertiary-butylphosphine) palladium (0.2 g, 0.3 mmol) was introduced thereinto. After the reaction for 3 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 41 (8.3 g, 63%, MS: [M+H]+=755.2) which was a yellow solid compound.

Synthesis Example 42

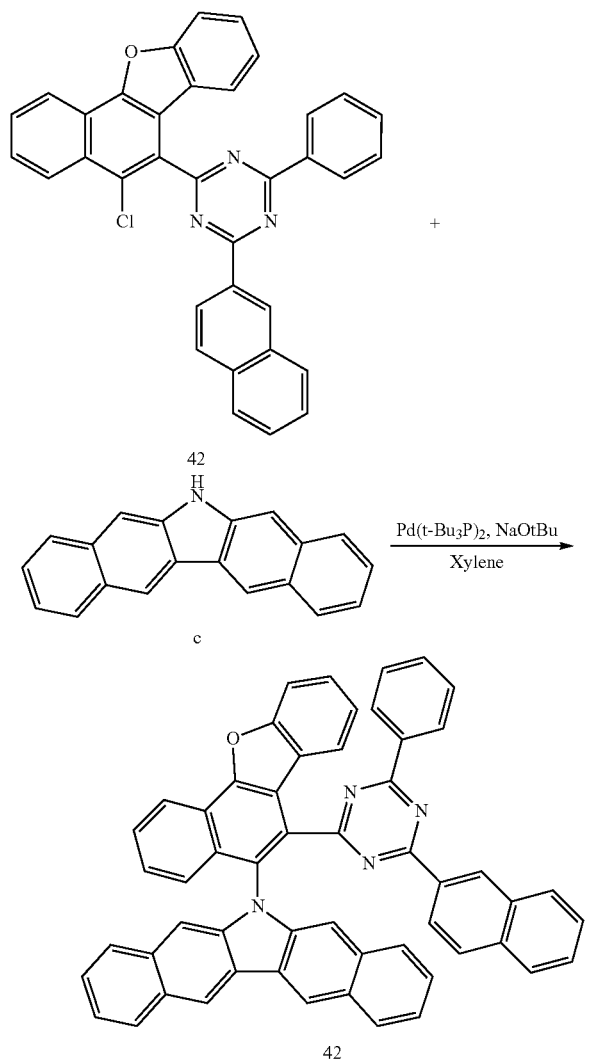

Intermediate 42 (10 g, 18.7 mmol) and Formula c (5 g, 18.7 mmol) were put into 200 ml of xylene under a nitrogen atmosphere, and the resulting mixture was stirred and refluxed. Thereafter, sodium tertiary-butoxide (5.4 g, 56.2 mmol) was introduced thereinto, the resulting mixture was sufficiently stirred, and then bis(tri tertiary-butylphosphine) palladium (0.2 g, 0.4 mmol) was introduced thereinto. After the reaction for 2 hours, the resulting product was cooled to room temperature, and then salts were removed by filtering the organic layer, and then the filtered organic layer was distilled. The distilled organic layer was again introduced into chloroform and dissolved, the solution was washed twice with water, and then the organic layer was separated, anhydrous magnesium sulfate was added thereto, the resulting mixture was stirred, and then filtered, and the filtrate was distilled under reduced pressure. The concentrated compound was purified by a silica column using chloroform and ethyl acetate to prepare Compound 42 (9.3 g, 65%, MS: [M+H]+=765.3) which was a yellow solid compound.

EXAMPLES AND COMPARATIVE EXAMPLES

Comparative Example 1

A glass substrate thinly coated with indium tin oxide (ITO) to have a thickness of 1,000 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. Furthermore, the substrate was cleaned by using oxygen plasma for 5 minutes, and then was transported to a vacuum deposition machine. The following HI-1 compound was formed to have a thickness of 1,150 Å as a hole injection layer on thus prepared ITO transparent electrode, and the hole injection layer was p-doped with the following A-1 compound at a concentration of 1.5%. The following HT-1 compound was vacuum deposited on the hole injection layer, thereby forming a hole transport layer having a film thickness of 800 Å. Subsequently, the following EB-1 compound was vacuum deposited to have a film thickness of 150 Å on the hole transport layer, thereby forming an electron blocking layer. Subsequently, the following RH-1 compound and the following Dp-7 compound were vacuum deposited at a weight ratio of 98:2 on the EB-1 deposition film, thereby forming a red light emitting layer having a thickness of 400 Å. The following HB-1 compound was vacuum deposited to have a film thickness of 30 Å on the light emitting layer, thereby forming a hole blocking layer. Subsequently, the following ET-1 compound and the following LiQ compound were vacuum deposited at a weight ratio of 2:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 1,000 Å, respectively, thereby forming a cathode.

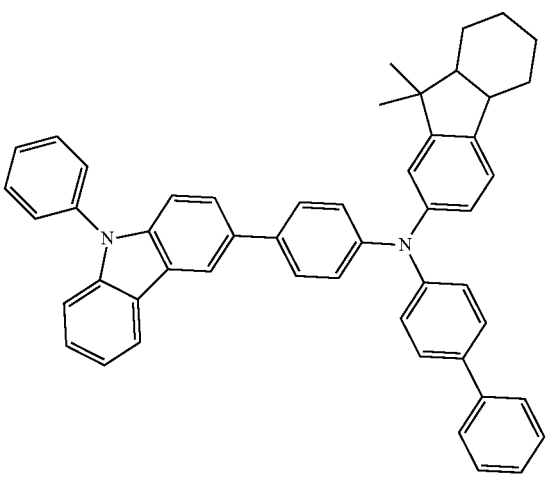

HI-1

A-1
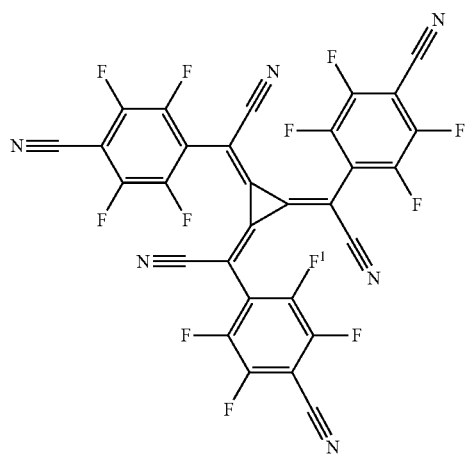
RH-1
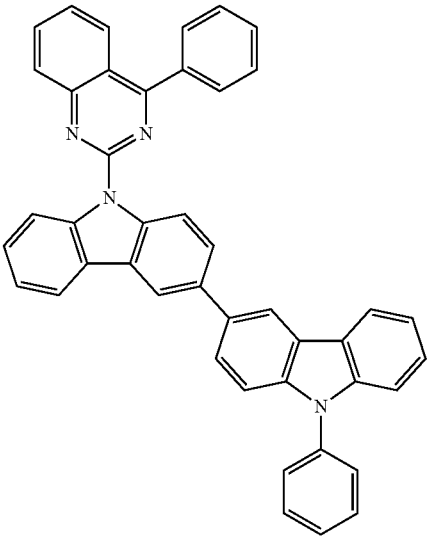
HT-1
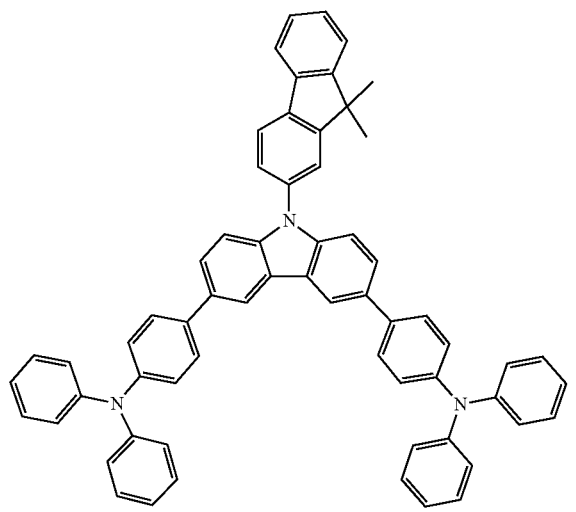
Dp-7
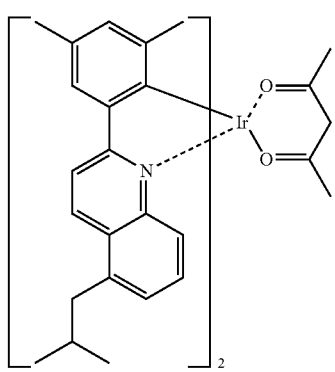
HB-1
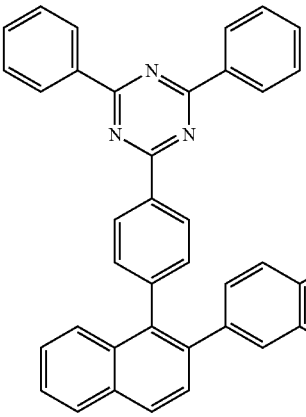
EB-1
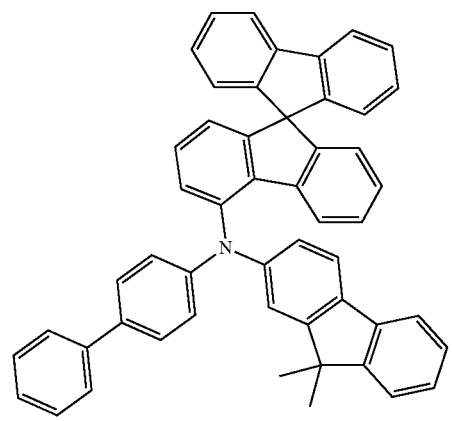
ET-1
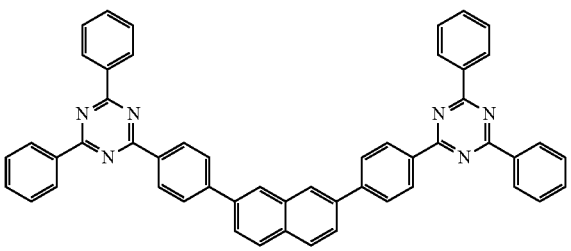

LiQ
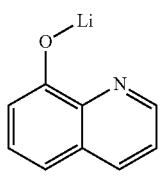
C-1
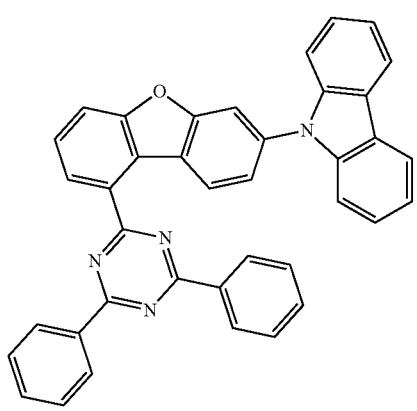
C-2
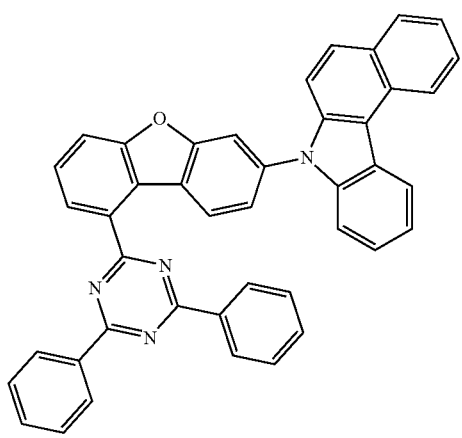
C-3
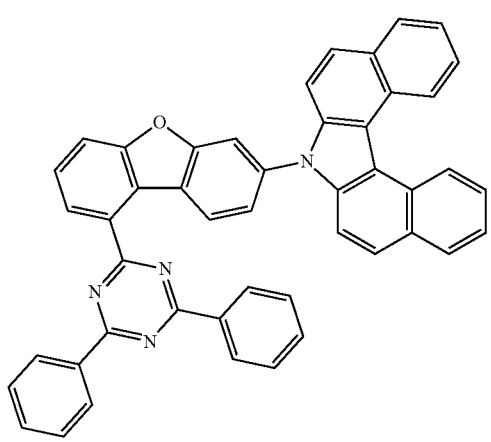
C-4
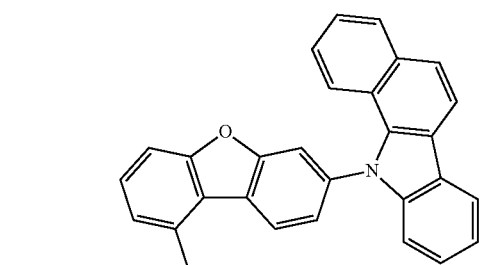
C-5
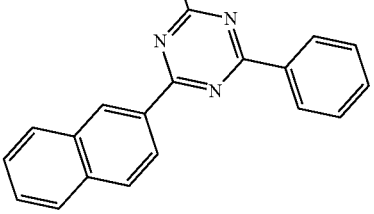
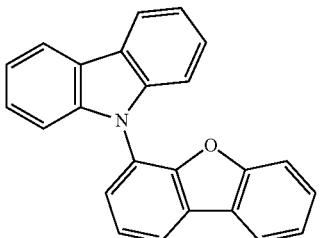
C-6
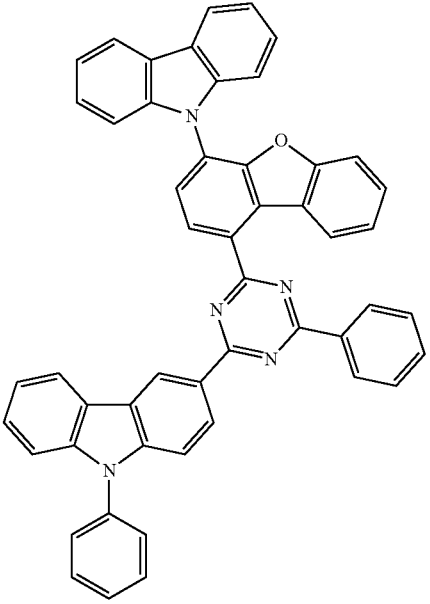

-continued
C-7
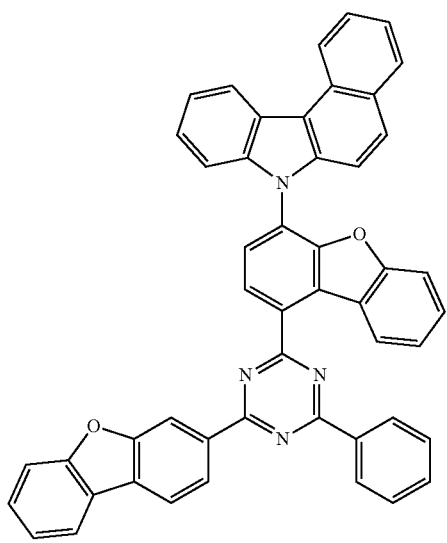
C-8
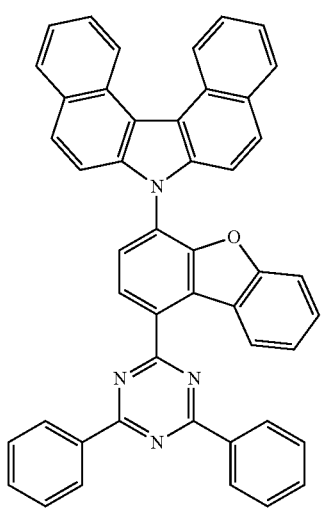
C-9
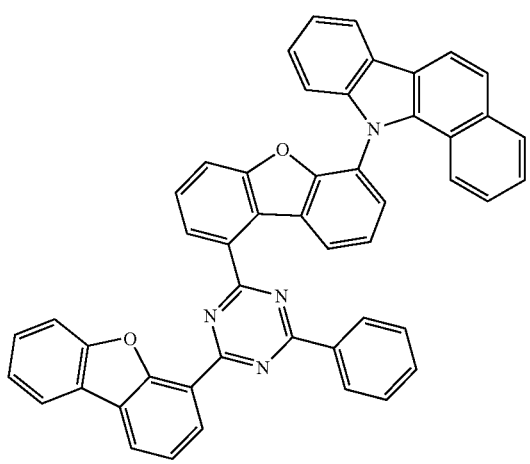
-continued
C-10
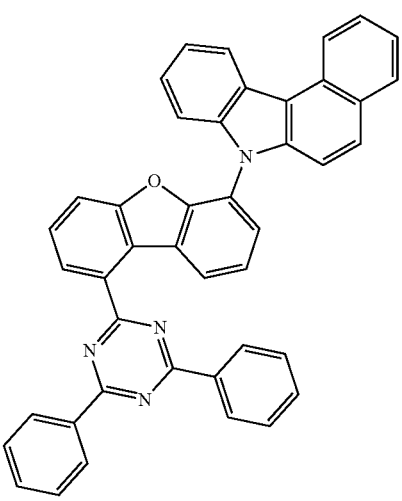
C-11
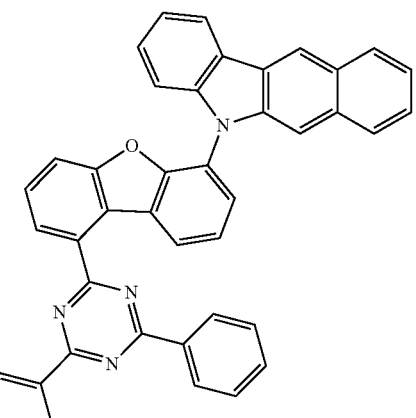
C-12
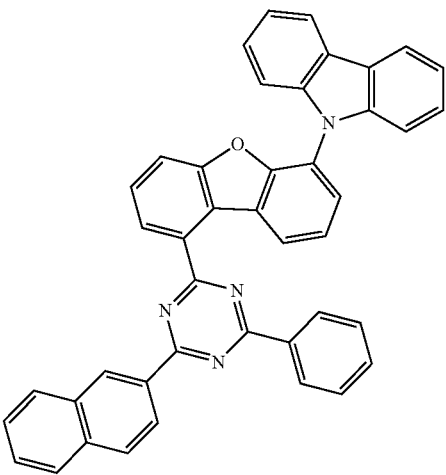

Z-1
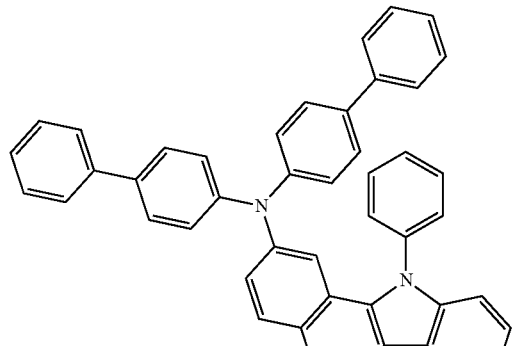
Z-2
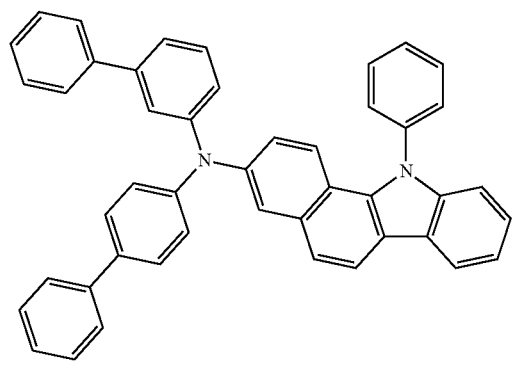
Z-3
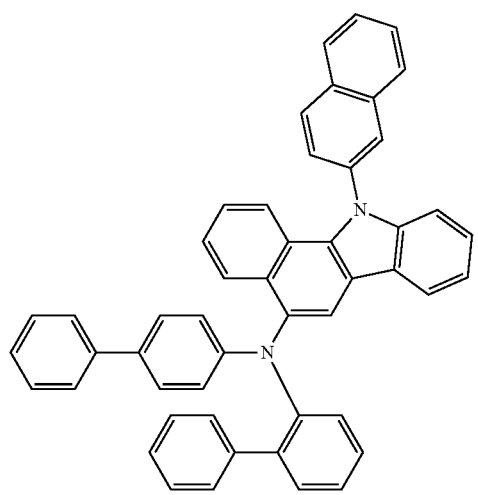
Z-4
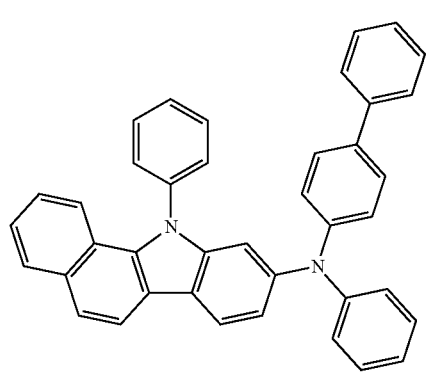
Z-5
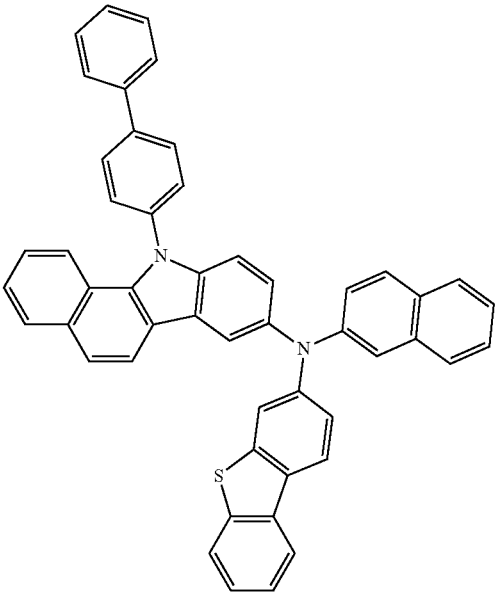
Z-6
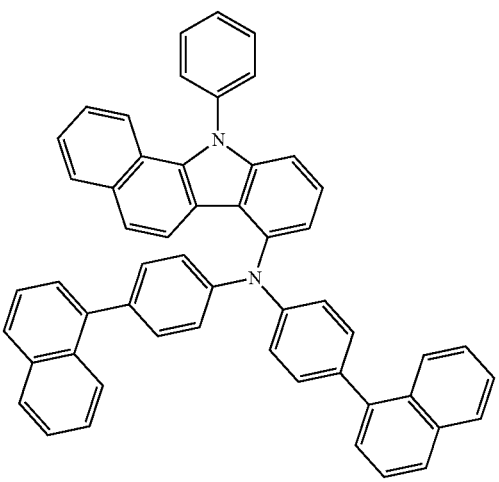
Z-7
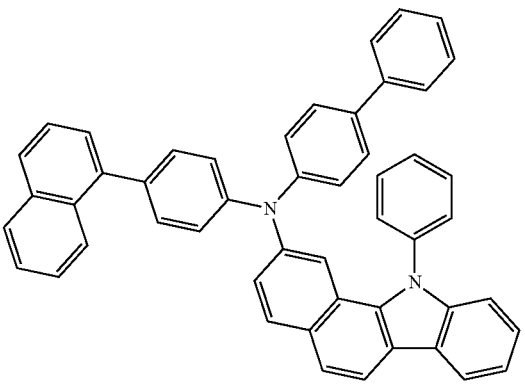

Z-8
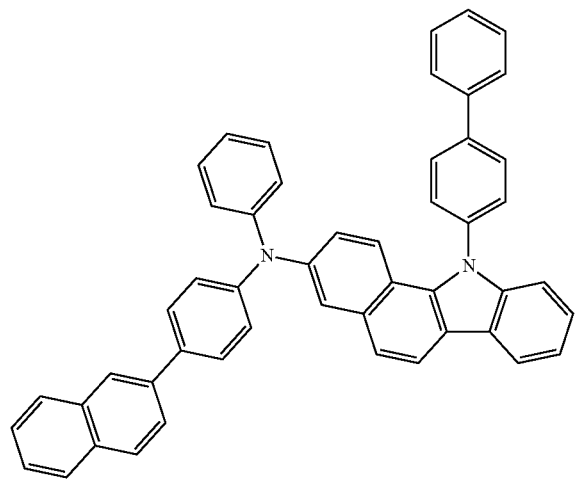
Z-11
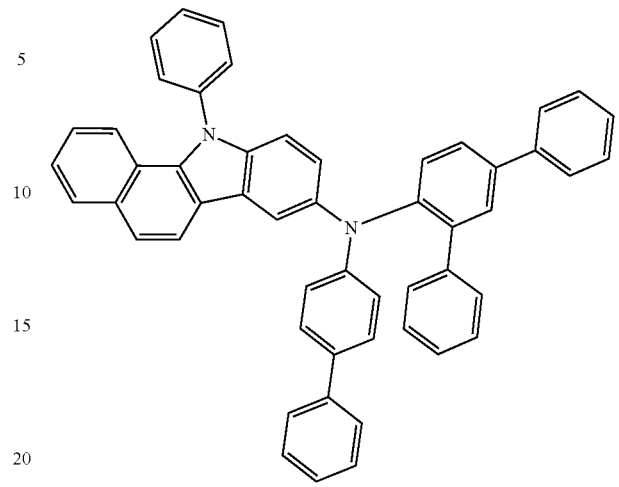
Z-9
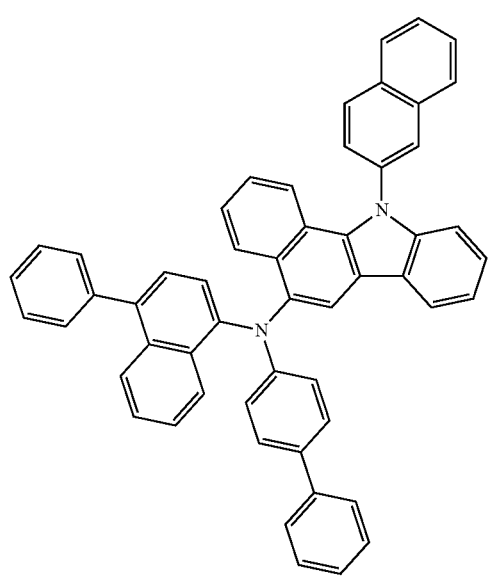
Z-12
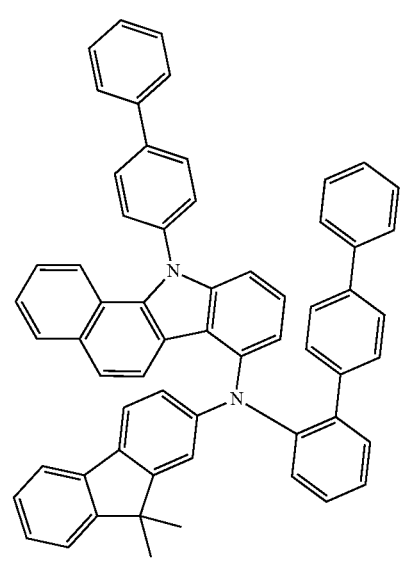
Z-10
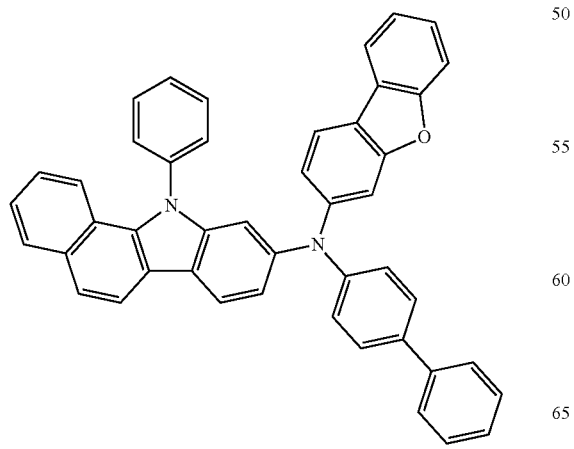
Z-13
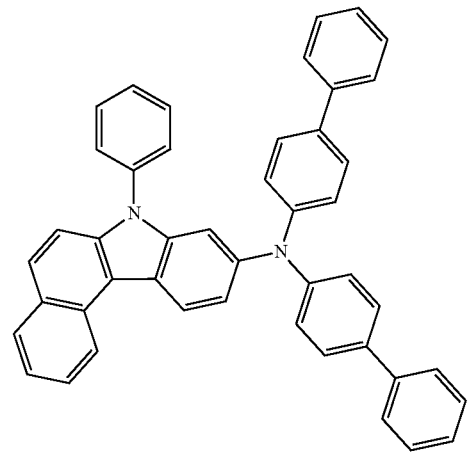

Z-14
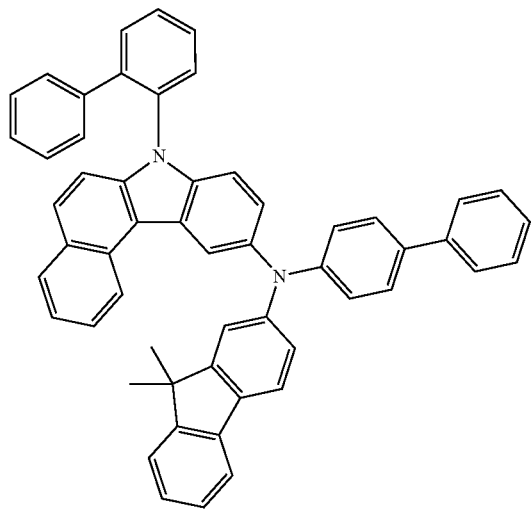
Z-15
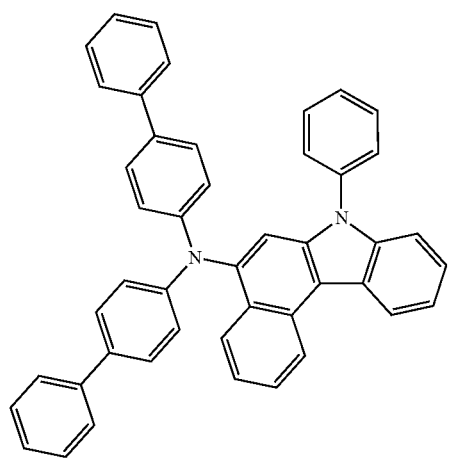
Z-16
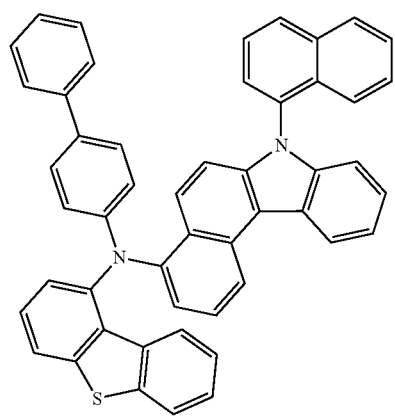
Z-17
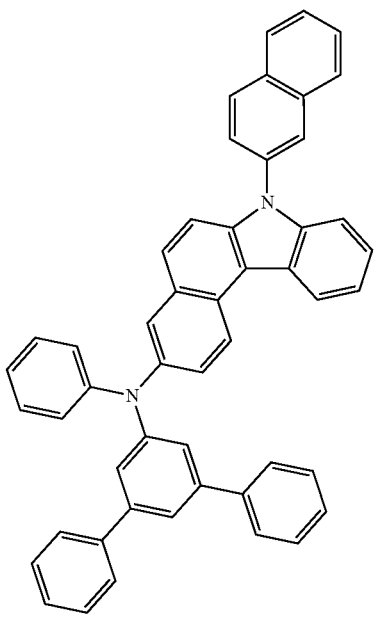
Z-18
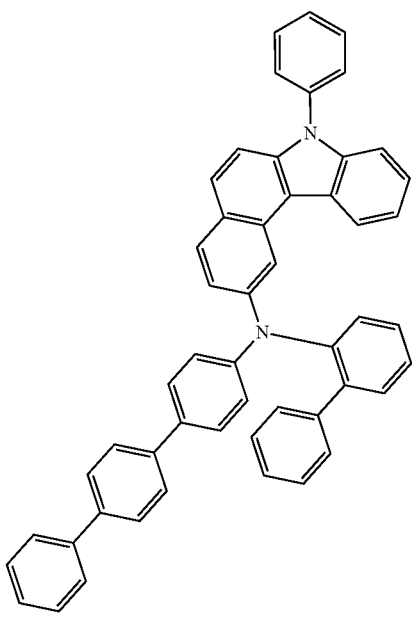

Z-19
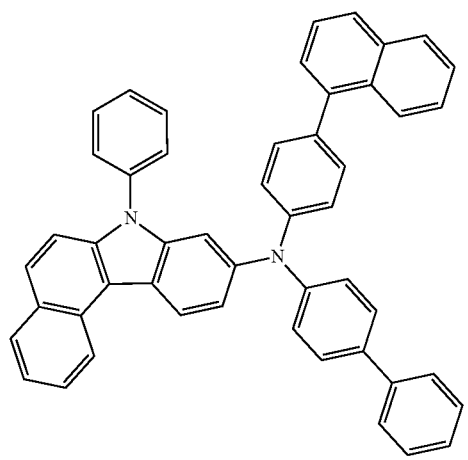
Z-20
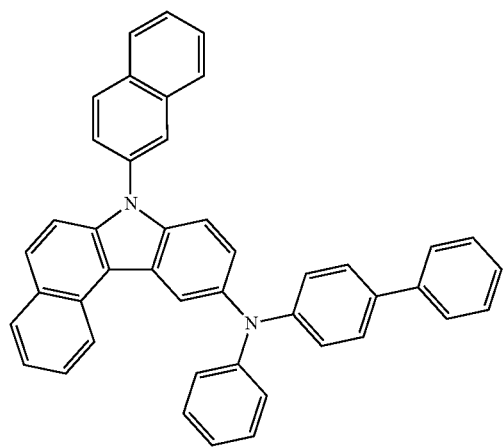
Z-21
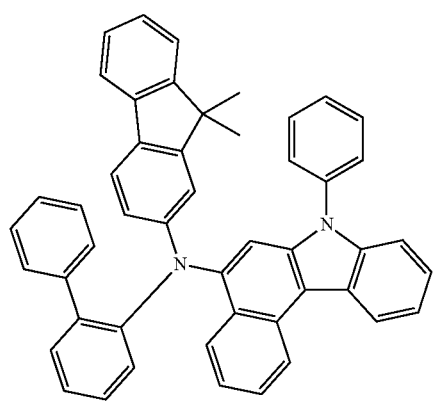
Z-22
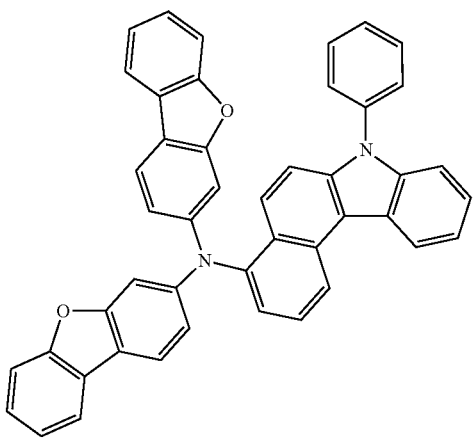
Z-23
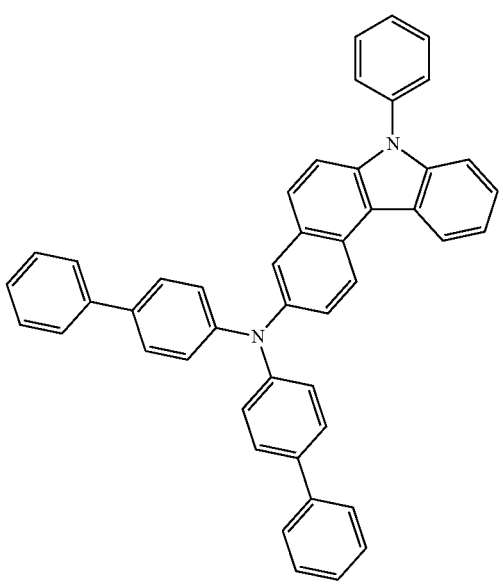
Z-24
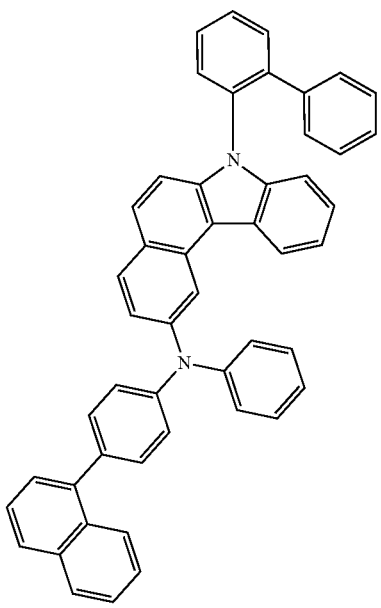

-continued
Z-25
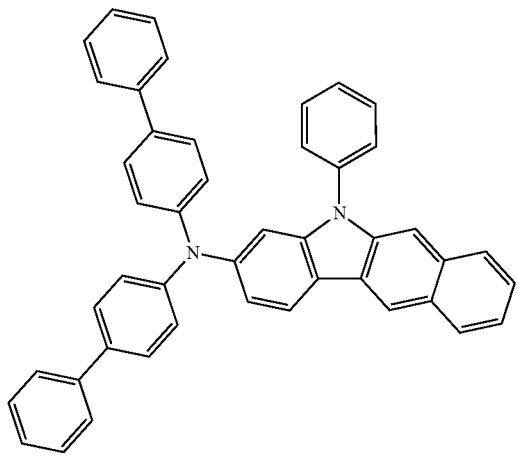
Z-26
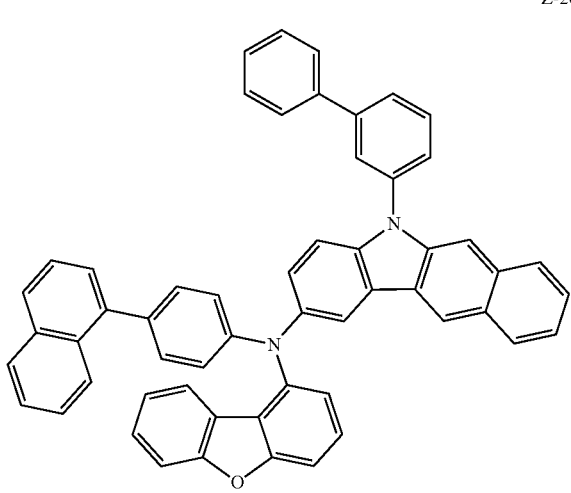
Z-27
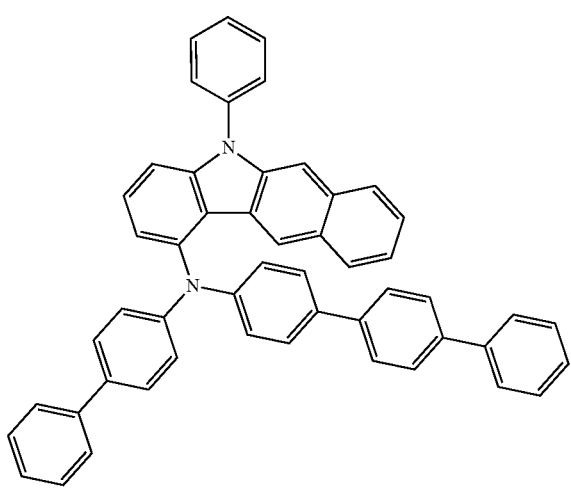
-continued
Z-28
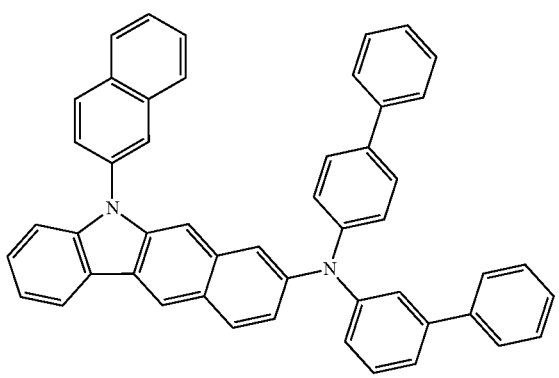
Z-29
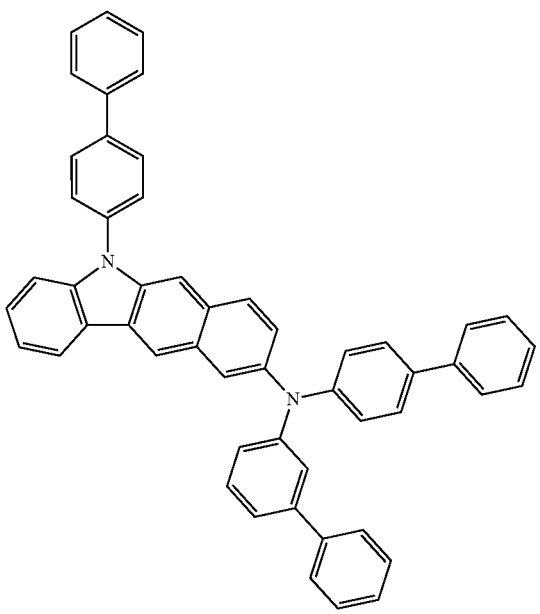
Z-30
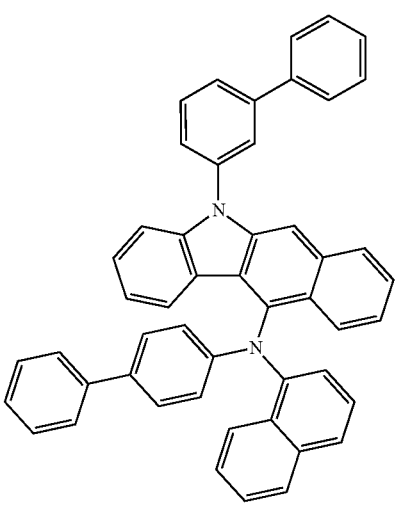

Z-31
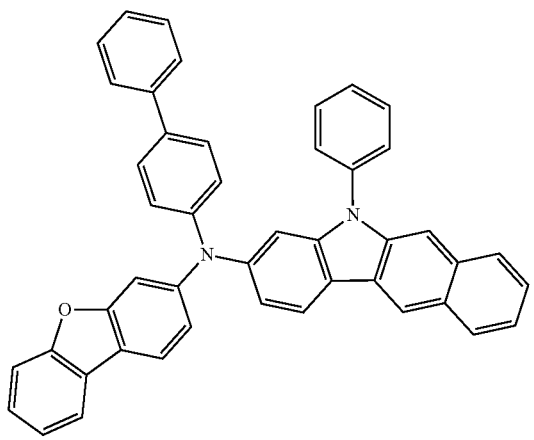

Z-32
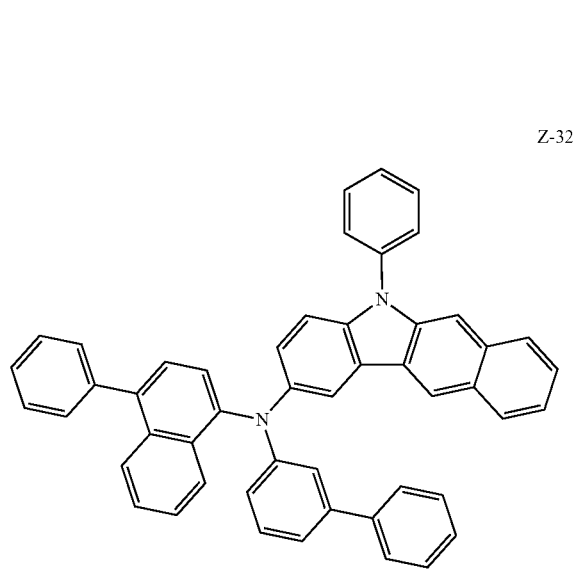

Z-33
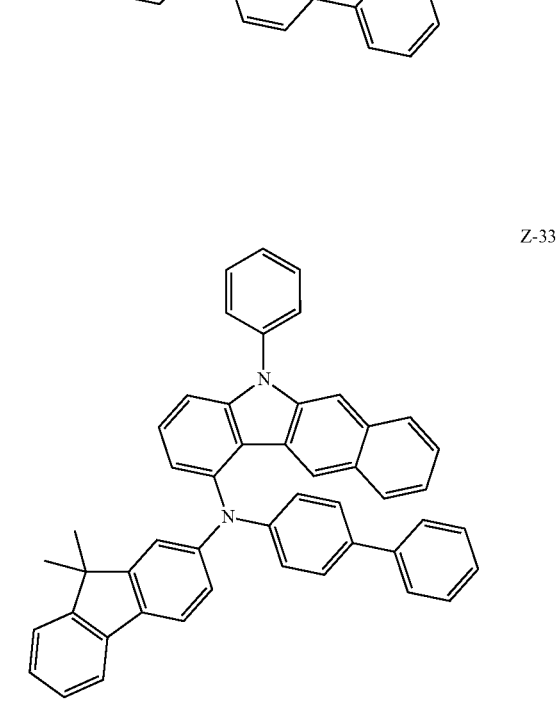

Z-34
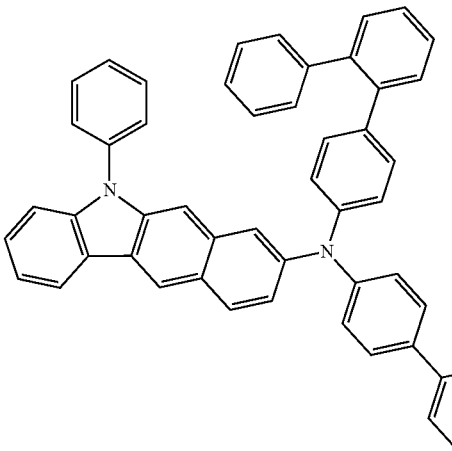

Z-35
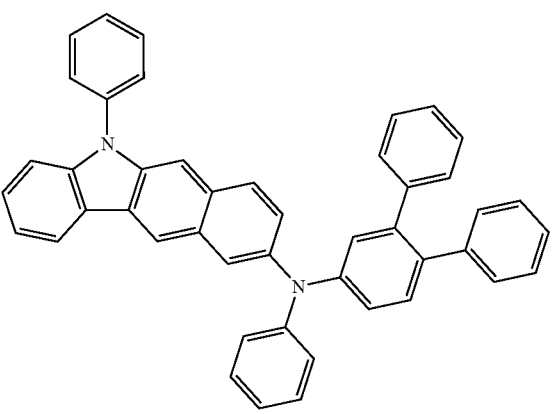

Z-36
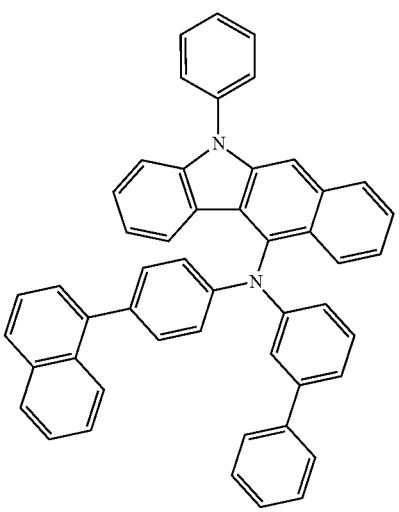

In the aforementioned procedure, the deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Examples 1 to 42

Organic light emitting devices were manufactured in the same manner as in Comparative Example 1, except that the compounds described in the following Table 1 were used instead of RH-1 in the organic light emitting device in Comparative Example 1.

Comparative Examples 2 to 13

Organic light emitting devices were manufactured in the same manner as in Comparative Example 1, except that in the organic light emitting device in Comparative Example 1, the compounds described in the following Table 1 were used instead of RH-1.

When current was applied to the organic light emitting devices manufactured in Examples 1 to 42 and Comparative Examples 1 to 13, the voltage, efficiency, and service life of each organic light emitting device were measured (based on 6,000 nit), and the results thereof are shown in the following Table 1. Service life T95 means the time taken for the luminance to be reduced to 95% of the initial luminance (6,000 nit).

TABLE 1

| Classification | Material | Driving Voltage (V) | Efficiency (cd/A) | Service life T95 (hr) | Light emission color |
|---|---|---|---|---|---|
| Comparative Example 1 | RH-1 | 4.34 | 38.3 | 193 | Red |
| Example 1 | Compound 1 | 3.61 | 44.5 | 241 | Red |
| Example 2 | Compound 2 | 3.63 | 43.7 | 250 | Red |
| Example 3 | Compound 3 | 3.69 | 44.8 | 247 | Red |
| Example 4 | Compound 4 | 3.62 | 44.1 | 258 | Red |
| Example 5 | Compound 5 | 3.74 | 44.5 | 306 | Red |
| Example 6 | Compound 6 | 3.77 | 44.3 | 301 | Red |
| Example 7 | Compound 7 | 3.72 | 42.9 | 298 | Red |
| Example 8 | Compound 8 | 3.71 | 44.5 | 307 | Red |
| Example 9 | Compound 9 | 3.50 | 47.3 | 293 | Red |
| Example 10 | Compound 10 | 3.55 | 47.1 | 292 | Red |
| Example 11 | Compound 11 | 3.53 | 47.8 | 287 | Red |
| Example 12 | Compound 12 | 3.51 | 47.3 | 299 | Red |
| Example 13 | Compound 13 | 3.54 | 47.9 | 285 | Red |
| Example 14 | Compound 14 | 3.49 | 45.1 | 267 | Red |
| Example 15 | Compound 15 | 3.51 | 45.0 | 264 | Red |
| Example 16 | Compound 16 | 3.63 | 45.2 | 257 | Red |
| Example 17 | Compound 17 | 3.58 | 44.6 | 319 | Red |
| Example 18 | Compound 18 | 3.43 | 43.9 | 313 | Red |
| Example 19 | Compound 19 | 3.52 | 49.1 | 303 | Red |
| Example 20 | Compound 20 | 3.38 | 45.5 | 254 | Red |
| Example 21 | Compound 21 | 3.63 | 49.6 | 304 | Red |
| Example 22 | Compound 22 | 3.51 | 44.3 | 315 | Red |
| Example 23 | Compound 23 | 3.57 | 45.7 | 261 | Red |
| Example 24 | Compound 24 | 3.39 | 45.2 | 267 | Red |
| Example 25 | Compound 25 | 3.40 | 46.3 | 314 | Red |
| Example 26 | Compound 26 | 3.42 | 48.8 | 297 | Red |
| Example 27 | Compound 27 | 3.51 | 49.1 | 305 | Red |
| Example 28 | Compound 28 | 3.38 | 49.8 | 303 | Red |
| Example 29 | Compound 29 | 3.54 | 49.1 | 329 | Red |
| Example 30 | Compound 30 | 3.52 | 51.8 | 304 | Red |
| Example 31 | Compound 31 | 3.33 | 49.3 | 291 | Red |
| Example 32 | Compound 32 | 3.57 | 49.4 | 299 | Red |
| Example 33 | Compound 33 | 3.52 | 49.8 | 308 | Red |
| Example 34 | Compound 34 | 3.43 | 47.3 | 306 | Red |
| Example 35 | Compound 35 | 3.51 | 49.7 | 301 | Red |
| Example 36 | Compound 36 | 3.47 | 47.9 | 297 | Red |
| Example 37 | Compound 37 | 3.54 | 47.3 | 318 | Red |
| Example 38 | Compound 38 | 3.43 | 48.0 | 308 | Red |
| Example 39 | Compound 39 | 3.49 | 48.7 | 297 | Red |
| Example 40 | Compound 40 | 3.47 | 49.5 | 285 | Red |
| Example 41 | Compound 41 | 3.46 | 49.3 | 279 | Red |
| Example 42 | Compound 42 | 3.45 | 49.0 | 297 | Red |
| Comparative Example 2 | C-1 | 4.13 | 37.2 | 131 | Red |
| Comparative Example 3 | C-2 | 4.81 | 34.1 | 140 | Red |
| Comparative Example 4 | C-3 | 4.30 | 35.1 | 167 | Red |
| Comparative Example 5 | C-4 | 4.68 | 33.0 | 79 | Red |
| Comparative Example 6 | C-5 | 4.41 | 32.4 | 97 | Red |
| Comparative Example 7 | C-6 | 4.77 | 29.7 | 61 | Red |
| Comparative Example 8 | C-7 | 4.21 | 34.0 | 103 | Red |
| Comparative Example 9 | C-8 | 4.19 | 35.7 | 114 | Red |
| Comparative Example 10 | C-9 | 4.71 | 31.3 | 73 | Red |
| Comparative Example 11 | C-10 | 4.19 | 35.7 | 114 | Red |
| Comparative Example 12 | C-11 | 4.71 | 31.3 | 73 | Red |
| Comparative Example 13 | C-12 | 4.71 | 31.3 | 73 | Red |

When current was applied to the organic light emitting devices manufactured in Examples 1 to 42 and Comparative Examples 1 to 13, the results of Table 1 were obtained.

A material widely used in the related art was used for the red organic light emitting device in Comparative Example 1, and the red organic light emitting device has a structure that Compound [EB-1] and RH-1/Dp-7 are used as an electron blocking layer and a red light emitting layer, respectively. In Comparative Examples 2 to 13, the organic light emitting devices were manufactured by using C-1 to C-12 instead of RH-1.

Referring to the results in Table 1, it was observed that when the compound of the present invention was used as a host of the red light emitting layer, the driving voltage was reduced by up to about 30% and the efficiency was increased by 25% or more as compared to the materials in the Comparative Examples, and it could be seen that energy was transferred well from the host to the red dopant. Further, it could be seen that while maintaining high efficiency, service life characteristics could be significantly improved by two times or more. The reason can be ultimately determined to be due to the fact that the compound of the present invention has higher stability for electrons and holes than the compounds in the Comparative Examples.

Examples 43 to 142

Organic light emitting devices were manufactured in the same manner as in Comparative Example 1, except that the vacuum co-deposition was performed by using a first host and a second host described in the following Table 2 at a weight ratio of 1:1 instead of RH-1 in the organic light emitting device in Comparative Example 1, the performance of each device was evaluated in the same manner as in Table 1, and the results thereof are shown in Table 2.

TABLE 2

| Classification | First host | Second host | Driving voltage (V) | Efficiency (cd/A) | Service life T95 (hr) | Light emission color |
|---|---|---|---|---|---|---|
| Example 43 | Compound 2 | Z-1 | 3.65 | 45.2 | 402 | Red |
| Example 44 | | Z-4 | 3.68 | 44.9 | 411 | Red |
| Example 45 | | Z-10 | 3.69 | 46.0 | 408 | Red |
| Example 46 | | Z-13 | 3.68 | 44.2 | 423 | Red |
| Example 47 | | Z-21 | 3.65 | 43.9 | 417 | Red |
| Example 48 | | Z-25 | 3.67 | 44.1 | 408 | Red |
| Example 49 | | Z-31 | 3.70 | 45.3 | 421 | Red |
| Example 50 | | Z-33 | 3.68 | 44.0 | 417 | Red |
| Example 51 | Compound 5 | Z-1 | 3.79 | 45.5 | 465 | Red |
| Example 52 | | Z-4 | 3.78 | 45.8 | 469 | Red |
| Example 53 | | Z-10 | 3.82 | 46.9 | 458 | Red |
| Example 54 | | Z-13 | 3.78 | 44.5 | 461 | Red |
| Example 55 | | Z-21 | 3.83 | 45.7 | 454 | Red |
| Example 56 | | Z-25 | 3.80 | 45.9 | 451 | Red |
| Example 57 | | Z-31 | 3.82 | 45.2 | 467 | Red |
| Example 58 | | Z-33 | 3.77 | 44.8 | 462 | Red |
| Example 59 | Compound 9 | Z-1 | 3.58 | 47.6 | 453 | Red |
| Example 60 | | Z-4 | 3.57 | 47.9 | 451 | Red |
| Example 61 | | Z-10 | 3.59 | 48.1 | 449 | Red |
| Example 62 | | Z-13 | 3.55 | 47.8 | 467 | Red |
| Example 63 | | Z-21 | 3.61 | 47.5 | 452 | Red |
| Example 64 | | Z-25 | 3.59 | 48.9 | 461 | Red |
| Example 65 | | Z-31 | 3.62 | 47.9 | 468 | Red |
| Example 66 | | Z-33 | 3.58 | 48.0 | 455 | Red |
| Example 67 | Compound 16 | Z-2 | 3.69 | 46.2 | 427 | Red |
| Example 68 | | Z-7 | 3.68 | 45.9 | 3.97 | Red |
| Example 69 | | Z-11 | 3.70 | 45.9 | 419 | Red |
| Example 70 | | Z-15 | 3.68 | 45.7 | 410 | Red |
| Example 71 | | Z-18 | 3.67 | 46.5 | 391 | Red |
| Example 72 | | Z-19 | 3.71 | 45.8 | 415 | Red |
| Example 73 | | Z-22 | 3.69 | 45.7 | 493 | Red |
| Example 74 | | Z-23 | 3.70 | 45.9 | 395 | Red |
| Example 75 | | Z-27 | 3.72 | 46.7 | 411 | Red |
| Example 76 | | Z-34 | 3.68 | 45.8 | 498 | Red |
| Example 77 | Compound 18 | Z-2 | 3.49 | 45.9 | 461 | Red |
| Example 78 | | Z-7 | 3.48 | 44.3 | 472 | Red |
| Example 79 | | Z-11 | 3.49 | 44.8 | 462 | Red |
| Example 80 | | Z-15 | 3.51 | 44.5 | 454 | Red |
| Example 81 | | Z-18 | 3.45 | 45.3 | 458 | Red |
| Example 82 | | Z-19 | 3.48 | 44.7 | 449 | Red |
| Example 83 | | Z-22 | 3.52 | 45.9 | 486 | Red |
| Example 84 | | Z-23 | 3.50 | 46.4 | 467 | Red |
| Example 85 | | Z-27 | 3.47 | 44.5 | 466 | Red |
| Example 86 | | Z-34 | 3.49 | 46.0 | 458 | Red |
| Example 87 | Compound 26 | Z-2 | 3.49 | 50.0 | 462 | Red |
| Example 88 | | Z-7 | 3.47 | 49.3 | 481 | Red |
| Example 89 | | Z-11 | 3.52 | 49.4 | 473 | Red |
| Example 90 | | Z-15 | 3.49 | 49.9 | 462 | Red |
| Example 91 | | Z-18 | 3.47 | 50.5 | 468 | Red |
| Example 92 | | Z-19 | 3.46 | 49.7 | 477 | Red |
| Example 93 | | Z-22 | 3.50 | 49.5 | 486 | Red |
| Example 94 | | Z-23 | 3.48 | 50.3 | 471 | Red |
| Example 95 | | Z-27 | 3.51 | 49.7 | 469 | Red |
| Example 96 | | Z-34 | 3.53 | 50.5 | 473 | Red |
| Example 97 | Compound 28 | Z-2 | 3.48 | 50.5 | 461 | Red |
| Example 98 | | Z-7 | 3.45 | 51.6 | 457 | Red |
| Example 99 | | Z-11 | 3.40 | 51.7 | 449 | Red |
| Example 100 | | Z-15 | 3.49 | 51.1 | 468 | Red |
| Example 101 | | Z-18 | 3.51 | 50.7 | 471 | Red |
| Example 102 | | Z-19 | 3.43 | 51.4 | 466 | Red |
| Example 103 | | Z-22 | 3.47 | 50.6 | 481 | Red |
| Example 104 | | Z-23 | 3.44 | 50.9 | 458 | Red |
| Example 105 | | Z-27 | 3.49 | 52.1 | 467 | Red |
| Example 106 | | Z-34 | 3.50 | 51.4 | 463 | Red |
| Example 107 | Compound 32 | Z-3 | 3.61 | 51.3 | 461 | Red |
| Example 108 | | Z-8 | 3.63 | 50.8 | 475 | Red |
| Example 109 | | Z-12 | 3.61 | 52.7 | 454 | Red |
| Example 110 | | Z-16 | 3.60 | 51.5 | 460 | Red |
| Example 111 | | Z-20 | 3.67 | 51.8 | 447 | Red |
| Example 112 | | Z-29 | 3.64 | 51.6 | 476 | Red |
| Example 113 | | Z-30 | 3.61 | 52.0 | 440 | Red |
| Example 114 | | Z-32 | 3.65 | 50.6 | 479 | Red |
| Example 115 | Compound 33 | Z-3 | 3.62 | 51.0 | 481 | Red |
| Example 116 | | Z-8 | 3.69 | 52.7 | 498 | Red |
| Example 117 | | Z-12 | 3.58 | 51.2 | 470 | Red |
| Example 118 | | Z-16 | 3.54 | 51.4 | 467 | Red |
| Example 119 | | Z-20 | 3.59 | 51.9 | 465 | Red |
| Example 120 | | Z-29 | 3.58 | 52.3 | 443 | Red |
| Example 121 | | Z-30 | 3.60 | 50.9 | 465 | Red |
| Example 122 | | Z-32 | 3.58 | 53.3 | 473 | Red |
| Example 123 | Compound 38 | Z-5 | 3.49 | 49.6 | 431 | Red |
| Example 124 | | Z-6 | 3.48 | 49.7 | 438 | Red |
| Example 125 | | Z-9 | 3.49 | 50.1 | 405 | Red |
| Example 126 | | Z-14 | 3.46 | 49.5 | 418 | Red |
| Example 127 | | Z-17 | 3.51 | 51.6 | 438 | Red |
| Example 128 | | Z-24 | 3.49 | 50.3 | 429 | Red |
| Example 129 | | Z-26 | 3.47 | 49.2 | 437 | Red |
| Example 130 | | Z-28 | 3.52 | 48.8 | 458 | Red |
| Example 131 | | Z-35 | 3.50 | 51.9 | 451 | Red |
| Example 132 | | Z-36 | 3.48 | 48.7 | 455 | Red |
| Example 133 | Compound 41 | Z-5 | 3.49 | 50.5 | 399 | Red |
| Example 134 | | Z-6 | 3.51 | 51.3 | 401 | Red |
| Example 135 | | Z-9 | 3.49 | 50.8 | 388 | Red |
| Example 136 | | Z-14 | 3.53 | 49.7 | 379 | Red |
| Example 137 | | Z-17 | 3.55 | 52.0 | 412 | Red |
| Example 138 | | Z-24 | 3.59 | 51.3 | 388 | Red |
| Example 139 | | Z-26 | 3.49 | 50.8 | 403 | Red |
| Example 140 | | Z-28 | 3.53 | 51.7 | 389 | Red |
| Example 141 | | Z-35 | 3.50 | 52.3 | 393 | Red |
| Example 142 | | Z-36 | 3.56 | 50.3 | 387 | Red |

The results in Table 2 show the results of co-depositing two types of hosts, and the case where the first host and the second host were used at a ratio of 1:1 shows a better result than the result when only the first host was used. It could be confirmed that as the second host was used, electrons and holes in a red light emitting layer maintained a more stable balance while the amount of holes was increased, and the efficiency and service life were significantly increased.

In conclusion, it could be confirmed that when the compound of the present invention was used as a host of a red light emitting layer, the driving voltage, light emitting efficiency, and service life characteristics of the organic light emitting device could be improved.

The invention claimed is:
1. A compound of the following Formula 1:

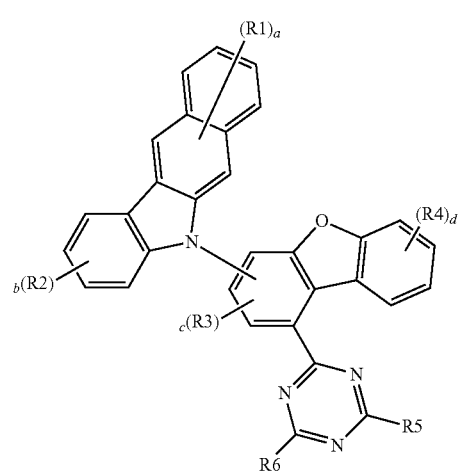

[Formula 1]

wherein, in Formula 1,

R1 is deuterium,

R2 to R4 are deuterium; or two or more adjacent R2's, R3's, and R4's are optionally bonded to each other respectively to form a ring, provided that b to d are each independently 2 or higher, R5 and R6 are each independently a substituted or unsubstituted aryl group; or a substituted or unsubstituted heterocyclic group, a is an integer from 0 to 6, b and d are each independently an integer from 0 to 4, c is an integer from 0 to 2, and substituents in the parentheses are the same as or different from each other provided that a to d are each independently an integer of 2 or higher.

2. The compound of claim 1, wherein the compound of Formula 1 is any one selected from the following Formulae 2 to 4:

[Formula 2]

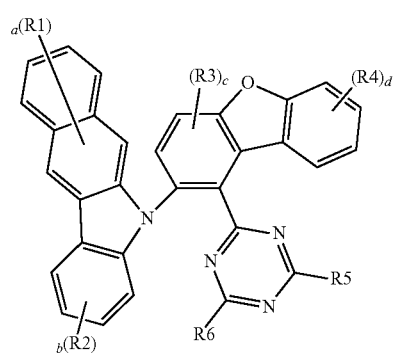

[Formula 3]

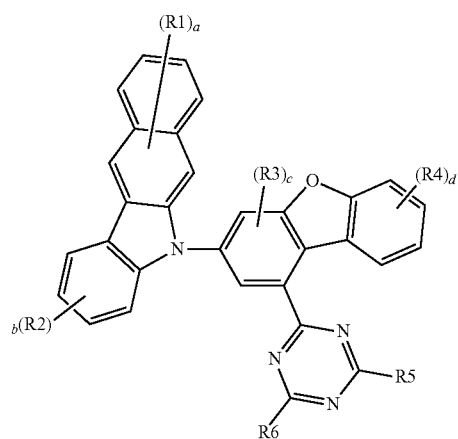

[Formula 4]

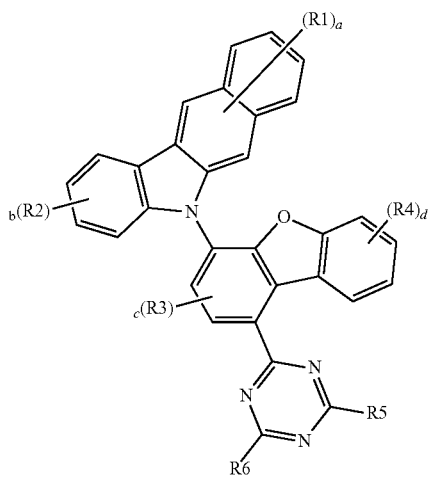

wherein, in Formulae 2 to 4, R1 to R6 and a to d are the same as those defined in Formula 1.

3. The compound of claim 1, wherein the compound of Formula 1 is any one selected from the following Formulae 2-1 to 2-8:

[Formula 2-1]

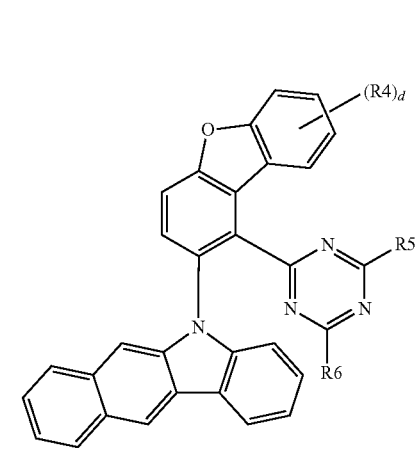

[Formula 2-2]

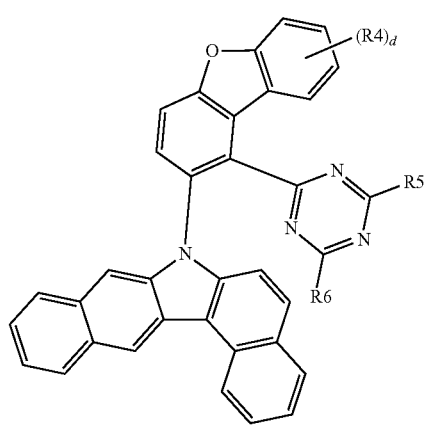

[Formula 2-3], [Formula 2-4], [Formula 2-5], [Formula 2-6], [Formula 2-7], [Formula 2-8]

wherein, in Formulae 2-1 to 2-8, R4 to R6 and d are the same as those defined in Formula 1, R7 is deuterium, e1 and e2 are each 0 or 1, and a sum of e1 and e2 is 1 or 2, e is an integer from 0 to 10, and a plurality of R7's are the same as or different from each other provided that e is 2 or higher.

4. The compound of claim 1, wherein the compound of Formula 1 is any one selected from the following Formulae 3-1 to 3-8:
[Formula 3-1]
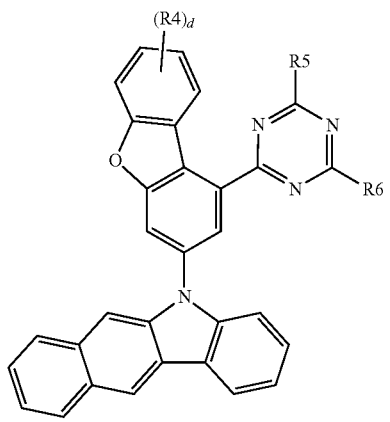
[Formula 3-2]
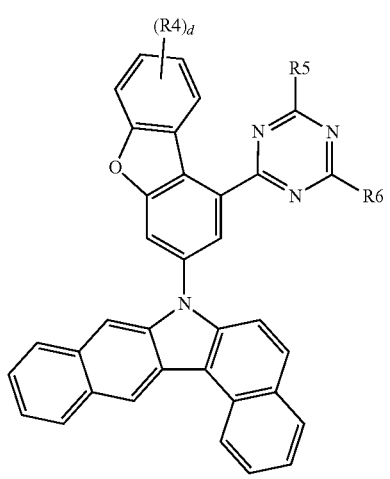
[Formula 3-3]
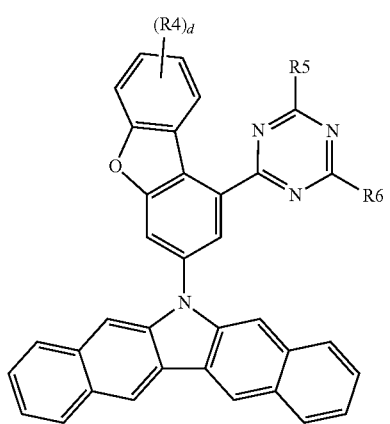
-continued
[Formula 3-4]
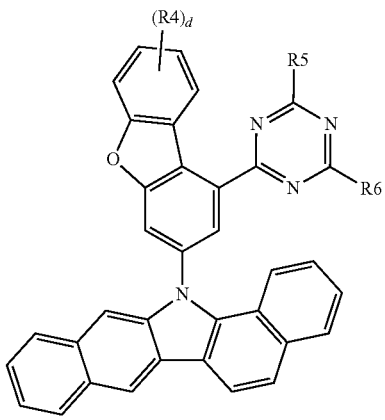
[Formula 3-5]
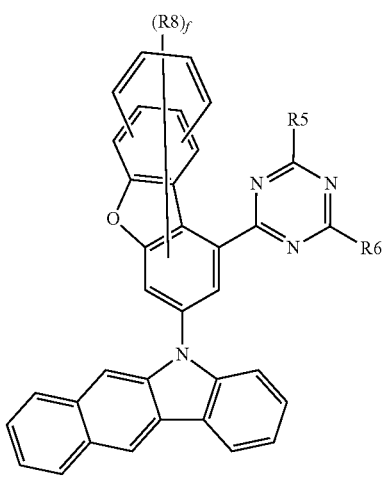
[Formula 3-6]
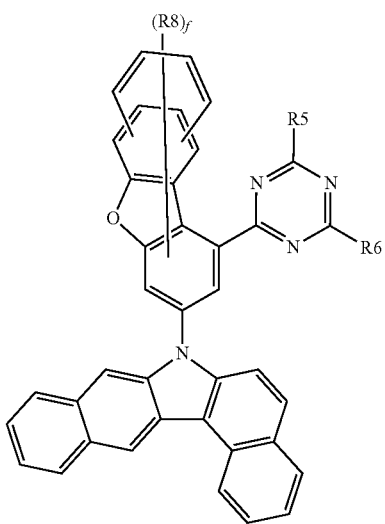

[Formula 3-7]
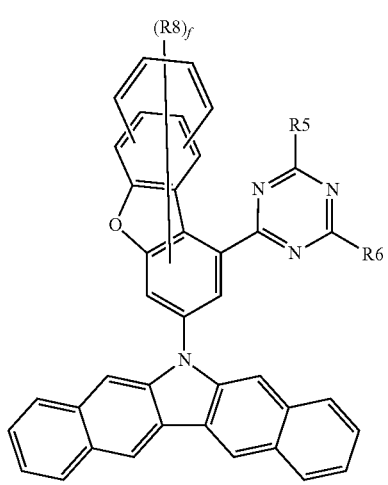
[Formula 4-2]
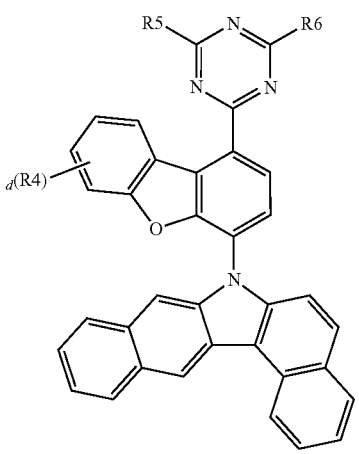
[Formula 3-8]
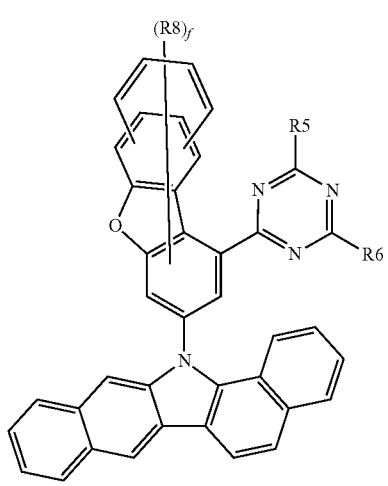
[Formula 4-3]
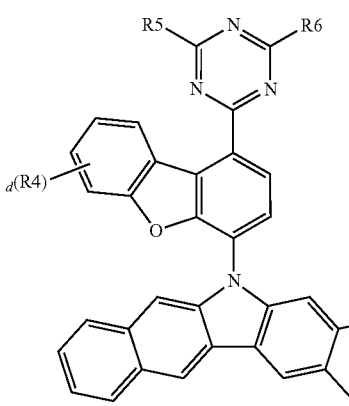
wherein in Formulae 3-1 to 3-8, R4 to R6 and d are the same as those defined in Formula 1,
R8 is deuterium,
f is an integer from 0 to 8, and
a plurality of R8's are the same as or different from each other provided that f is 2 or higher.
5. The compound of claim 1, wherein the compound of Formula 1 is any one selected from the following Formulae 4-1 to 4-8:
[Formula 4-1]
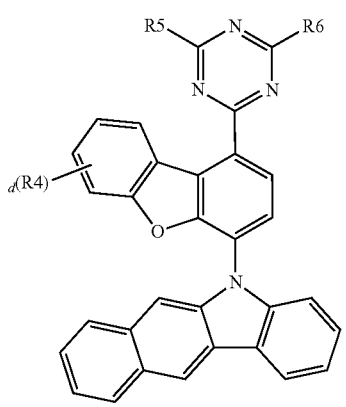
[Formula 4-4]
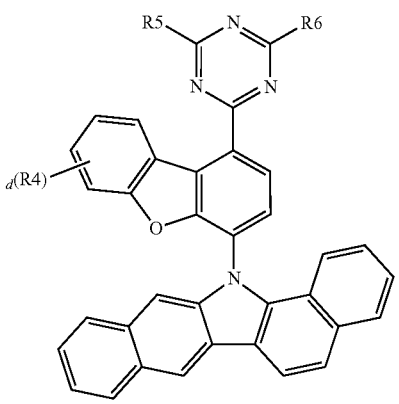

[Formula 4-5]

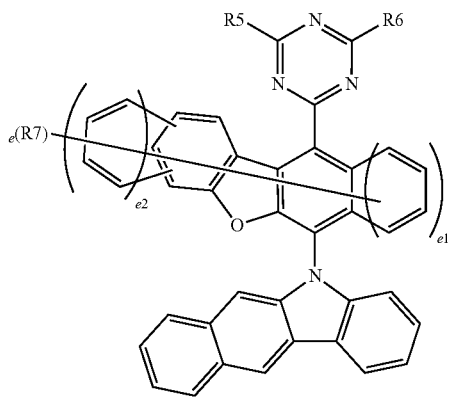

[Formula 4-8]

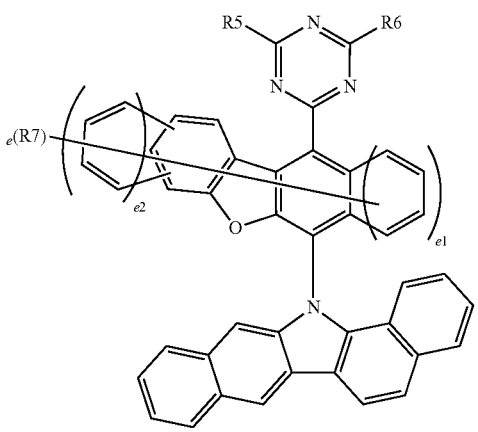

[Formula 4-6]

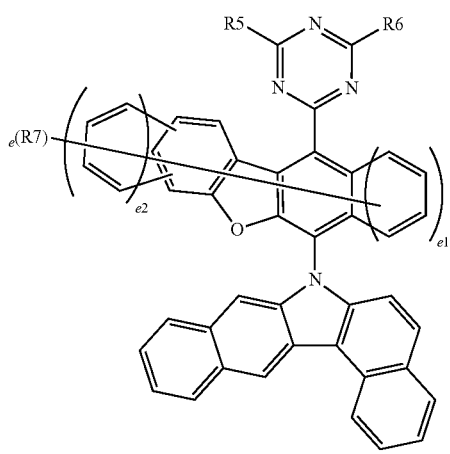

wherein, in Formulae 4-1 to 4-8, R4 to R6 and d are the same as those defined in Formula 1, R7 is deuterium, e1 and e2 are each 0 or 1, and a sum of e1 and e2 is 1 or 2, e is an integer from 0 to 10, a plurality of R7's are the same as or different from each other provided that e is 2 or higher.

6. The compound of claim 1, wherein the compound of Formula 1 is any one selected from the following compounds:

[Formula 4-7]

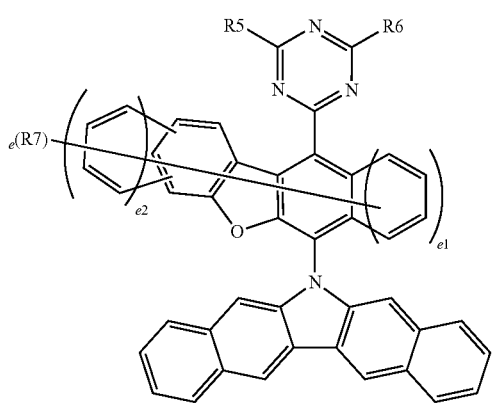

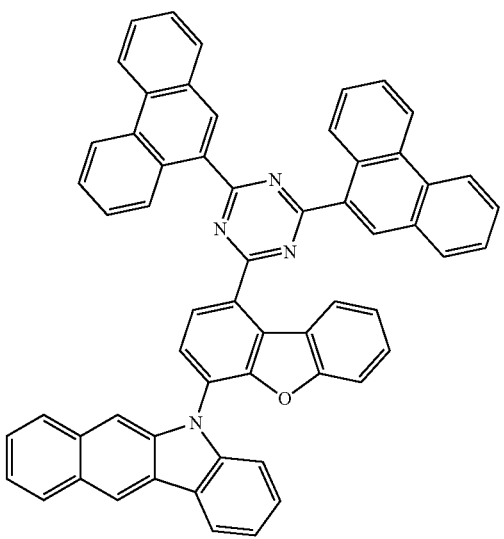

435
-continued
436
-continued
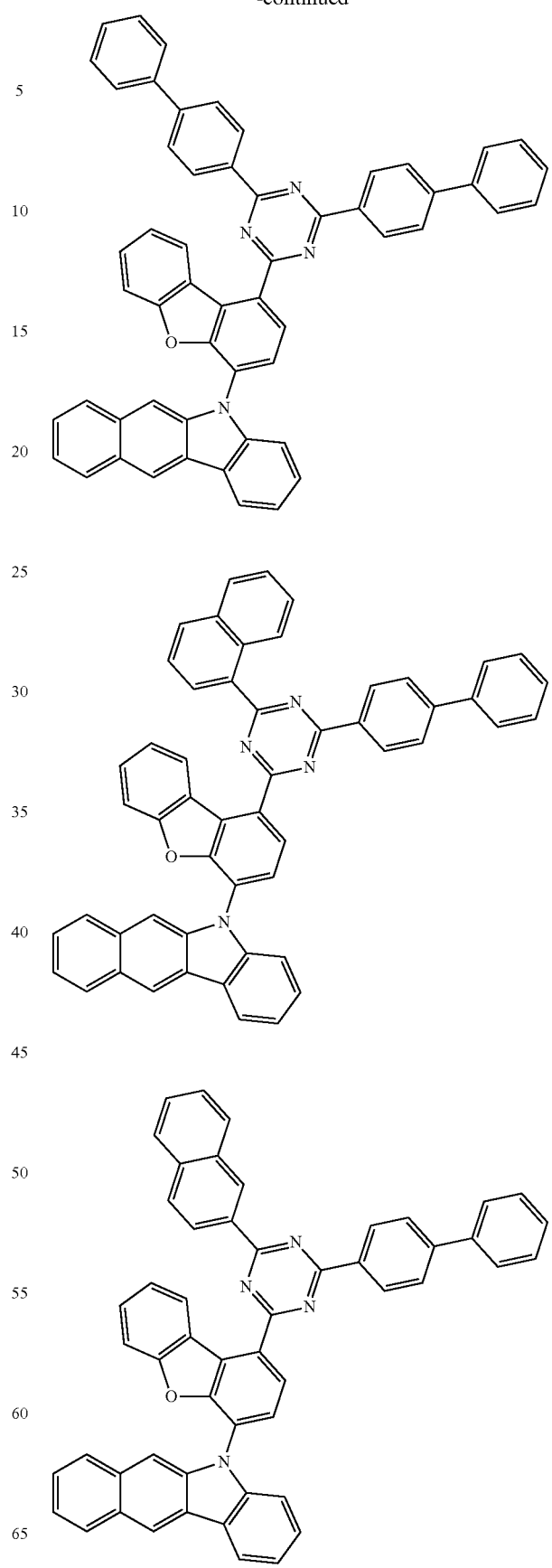

-continued
437
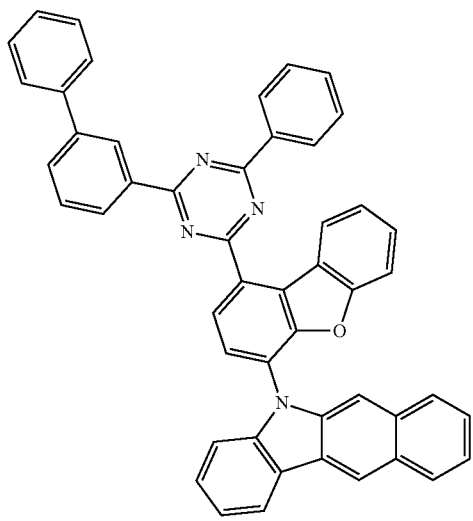
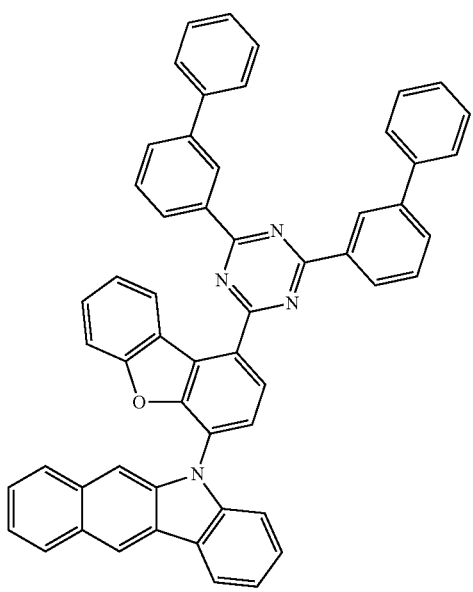
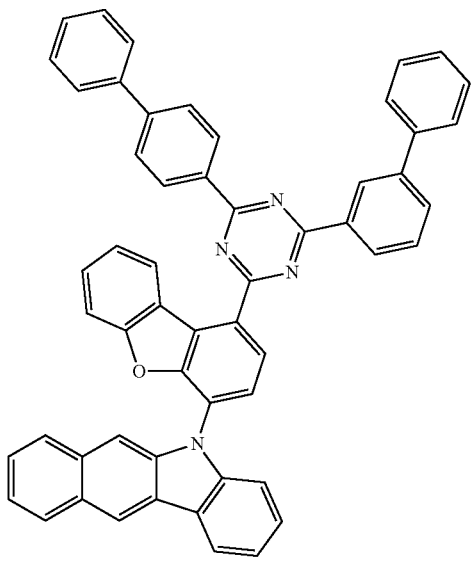
438
-continued
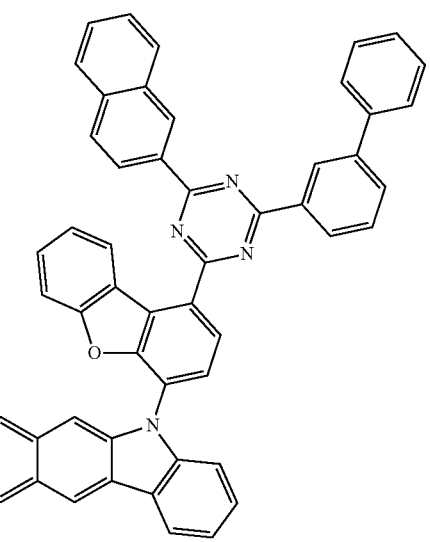
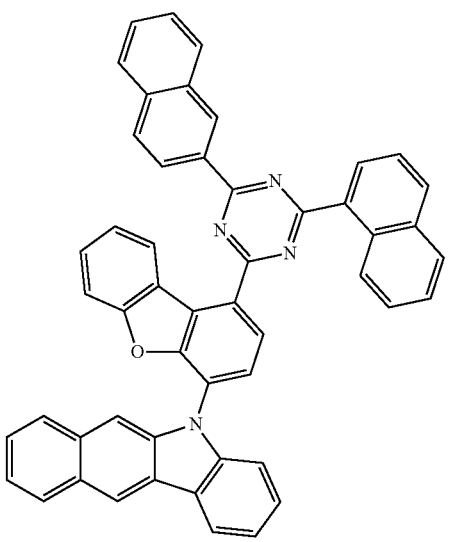
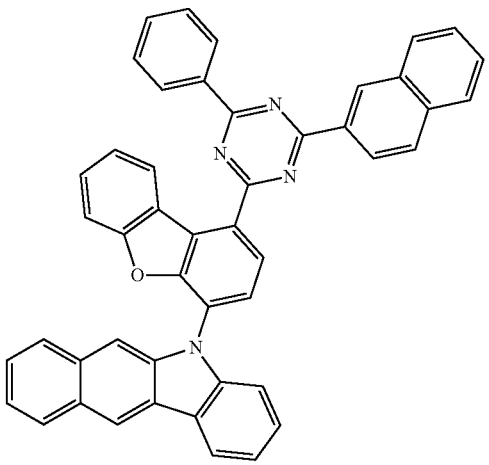

439
-continued
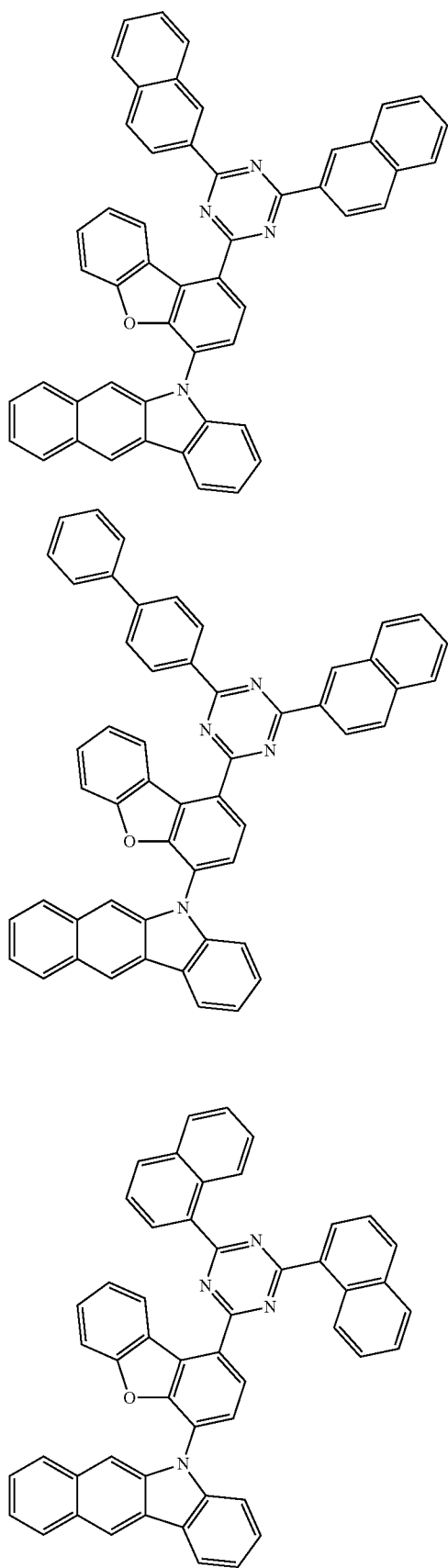
440
-continued
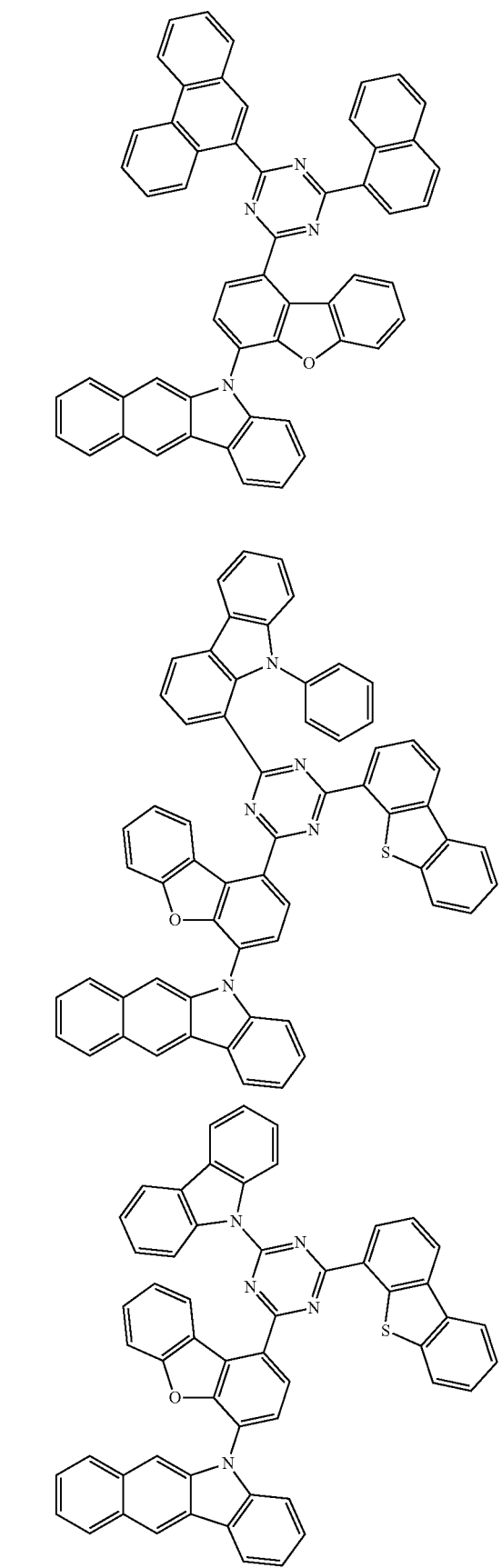

441
-continued
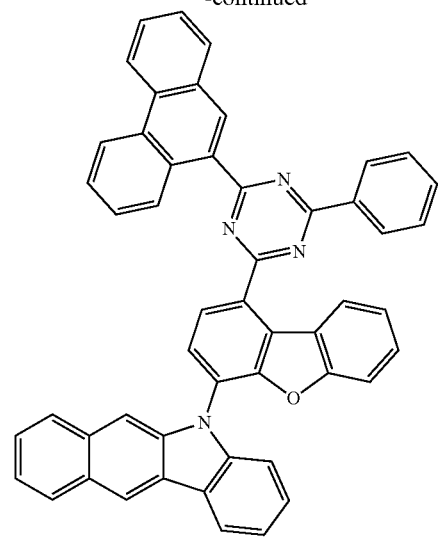
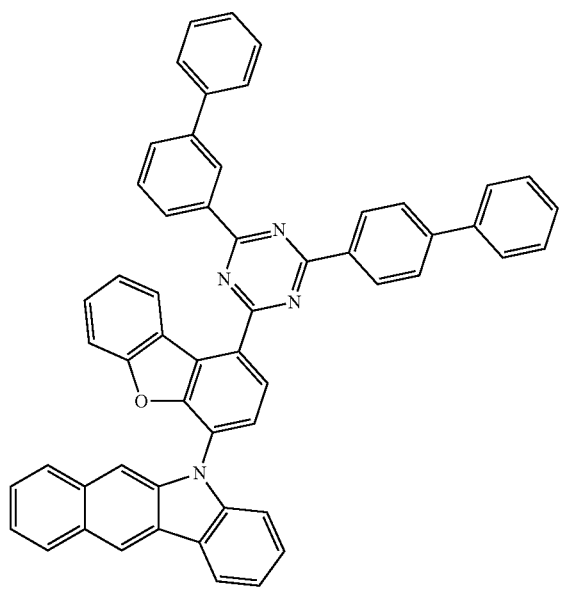
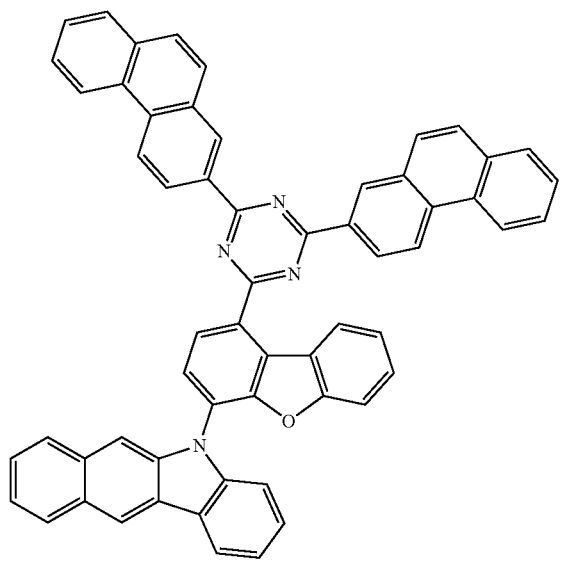
442
-continued
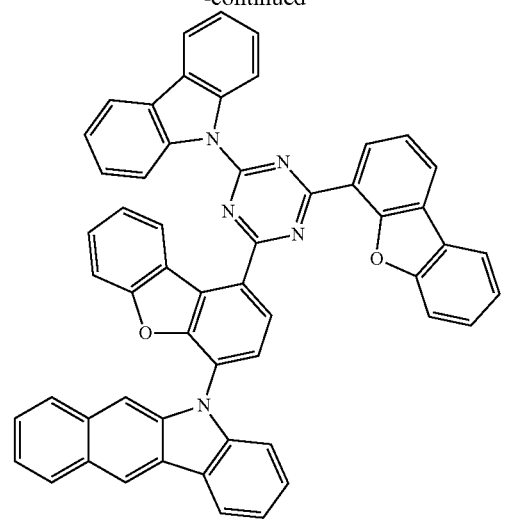
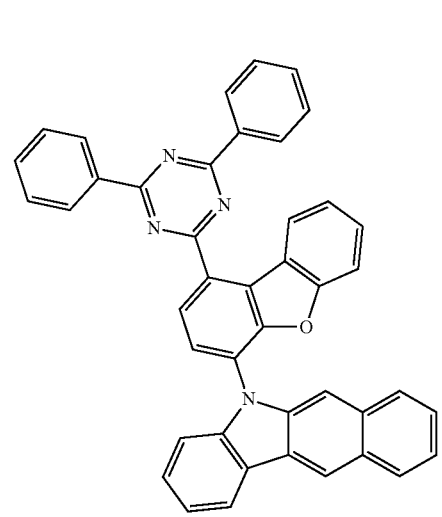
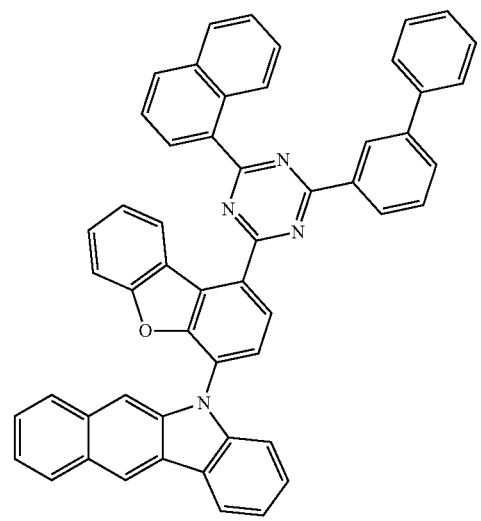

443
-continued
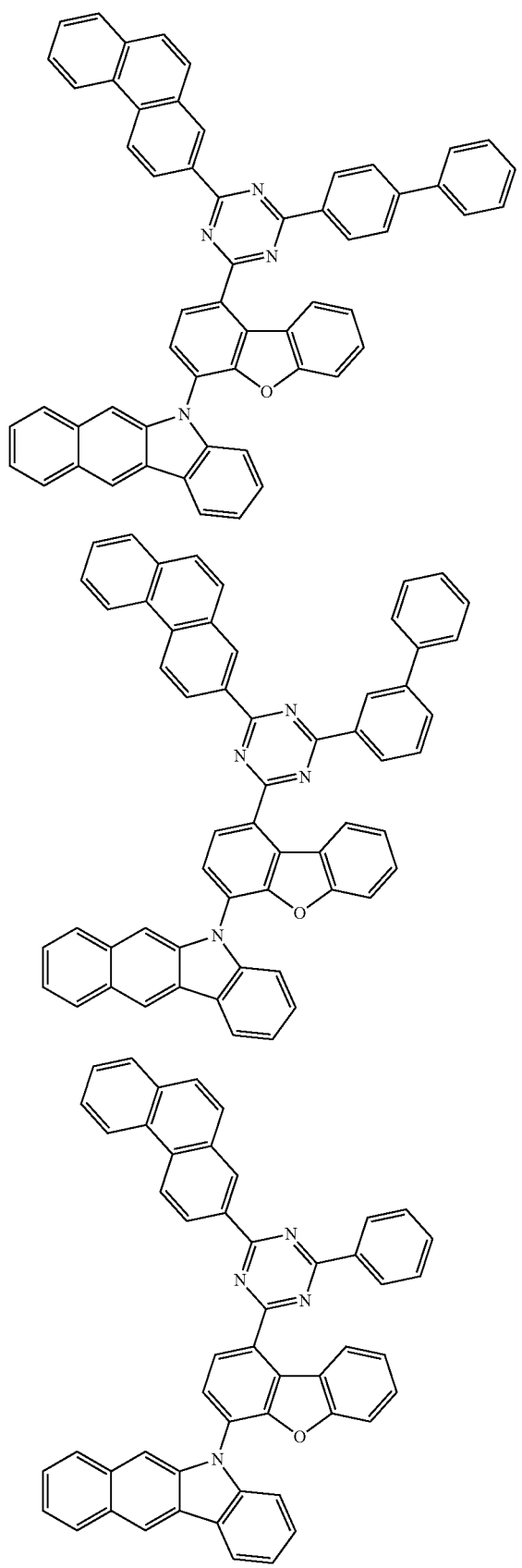
444
-continued
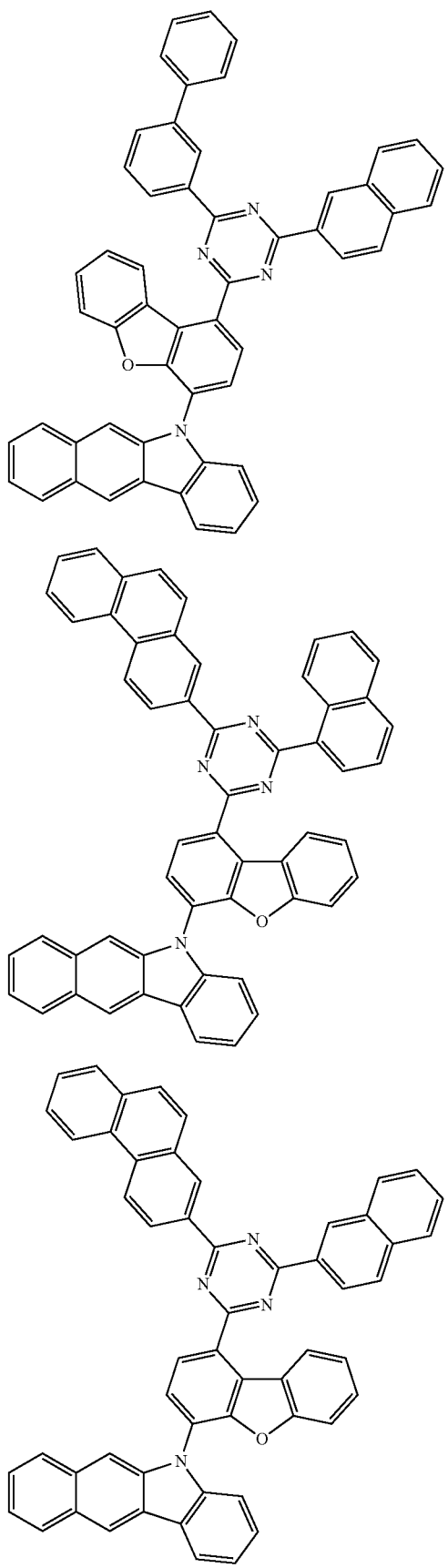

-continued
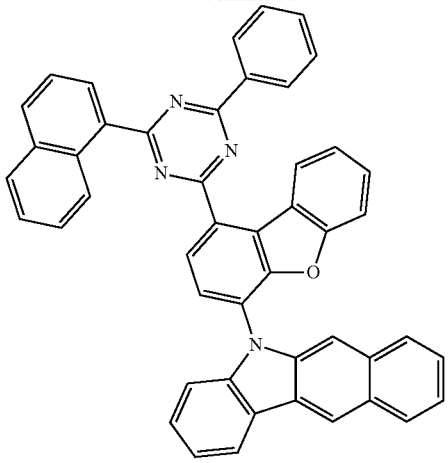
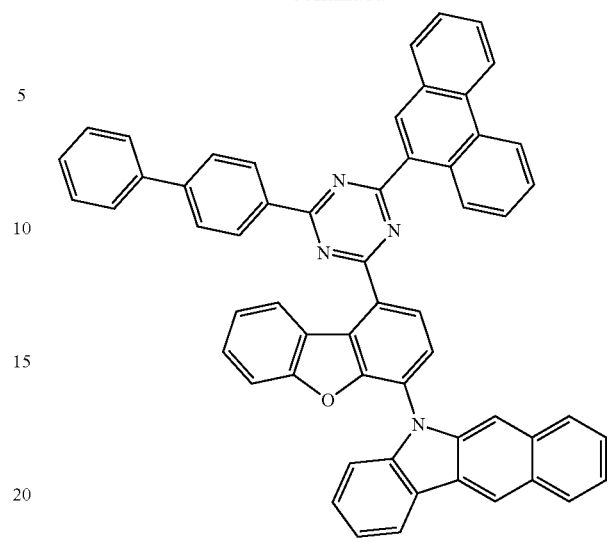
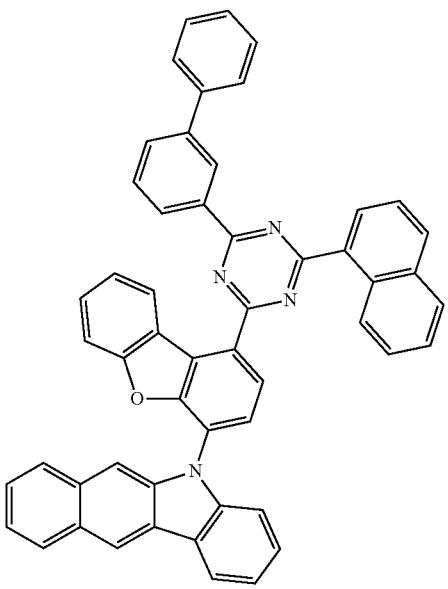
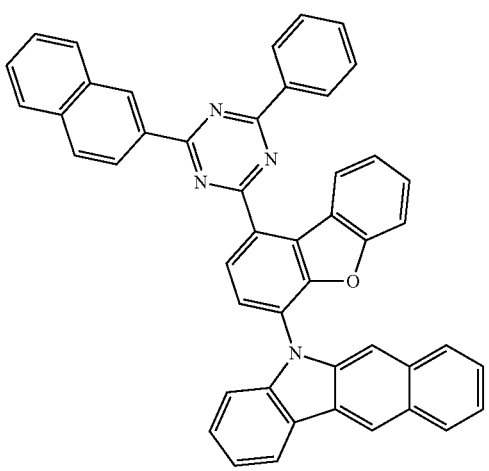
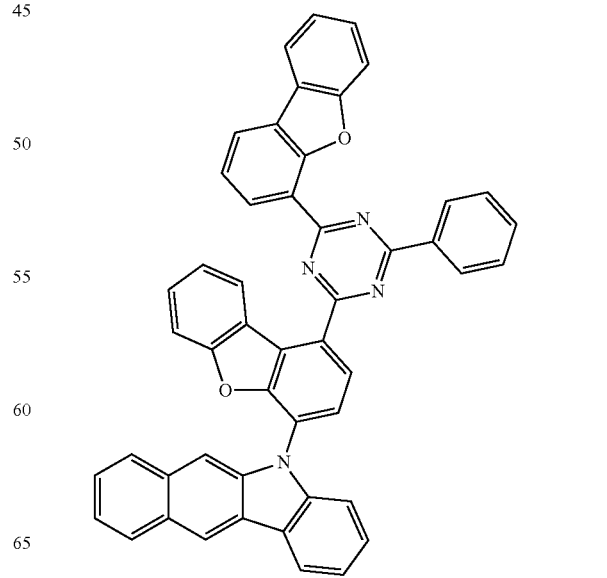

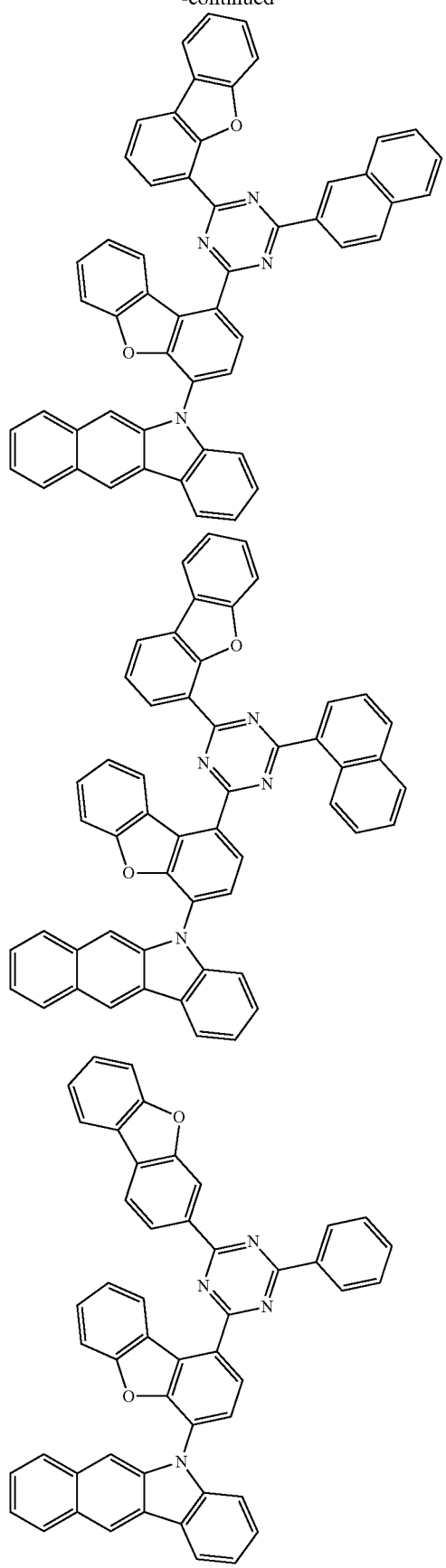
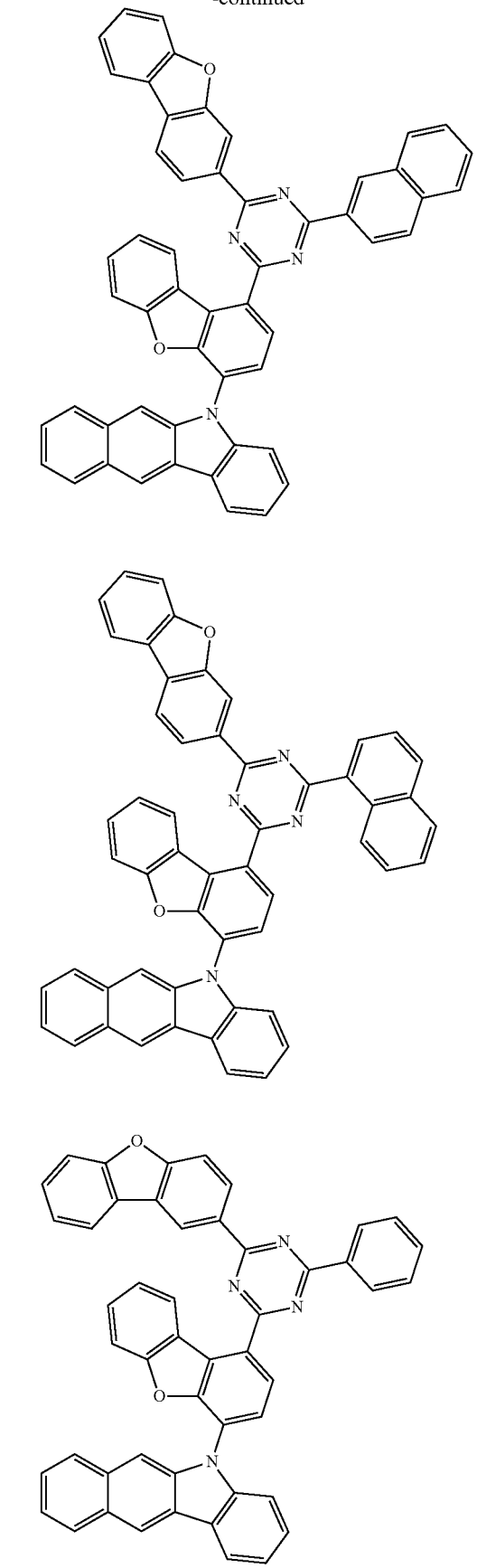

449
-continued
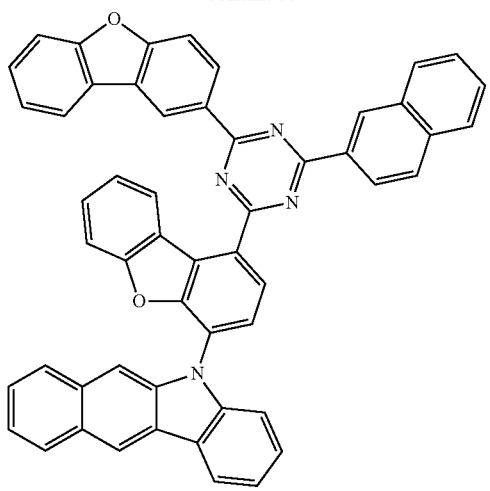
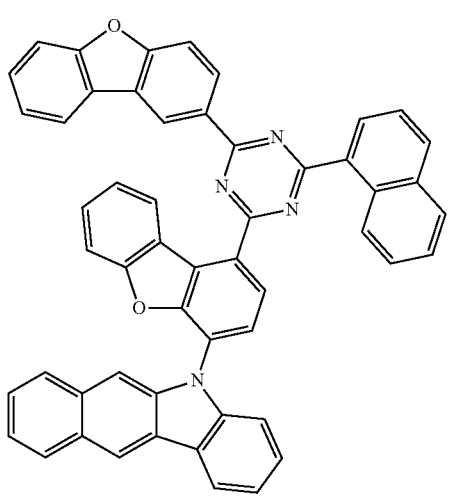
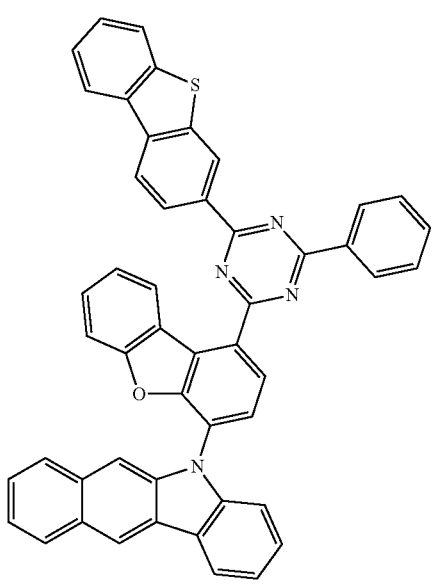
450
-continued
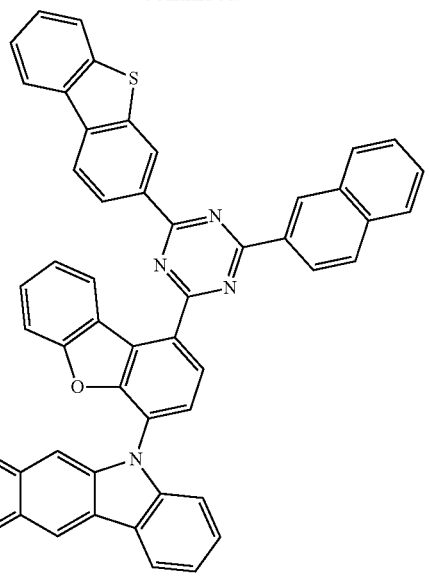
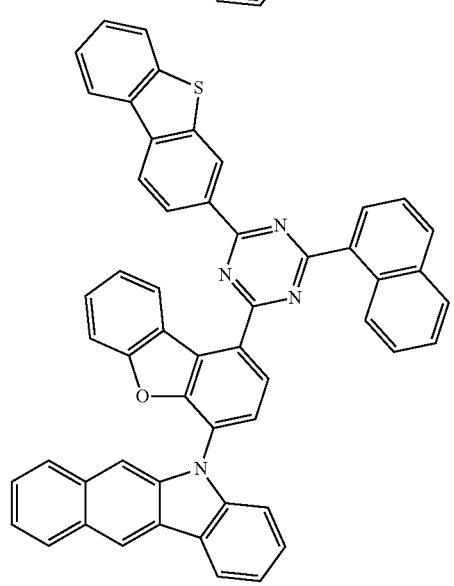
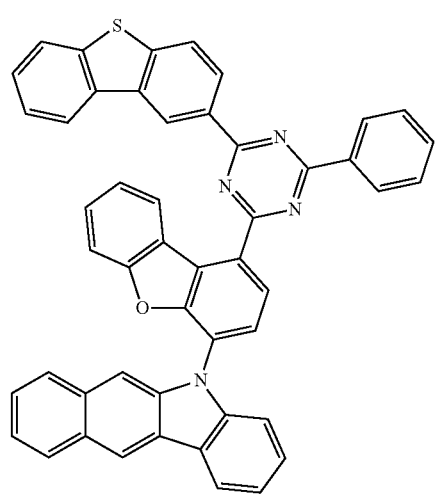

451
-continued
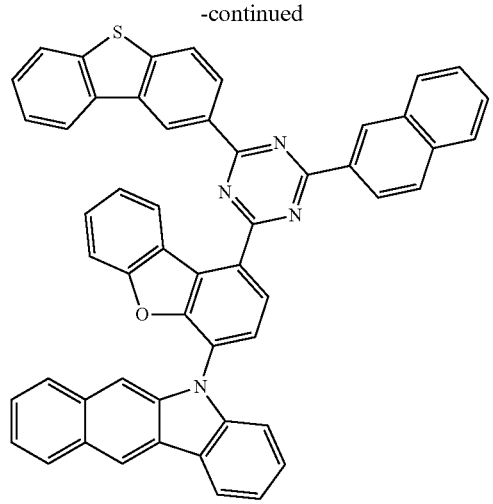
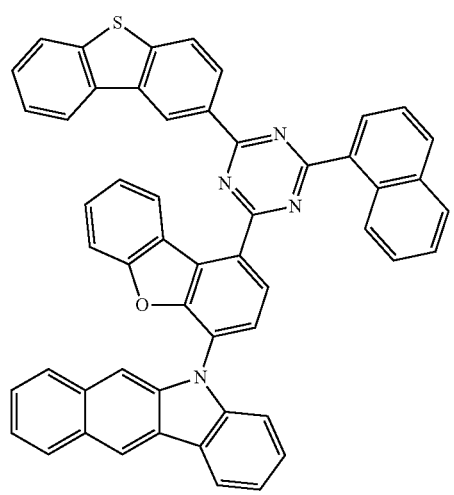
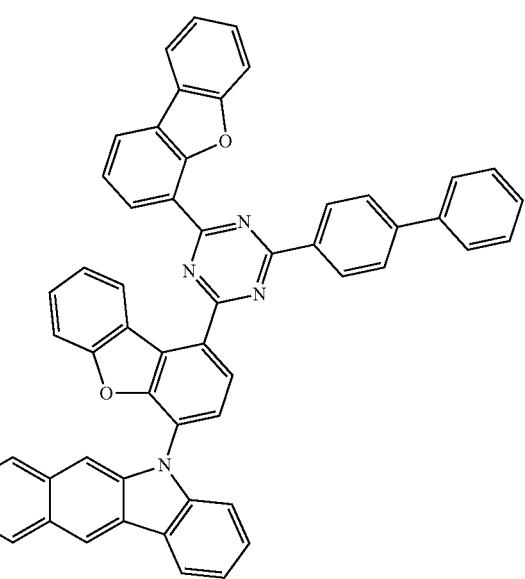
452
-continued
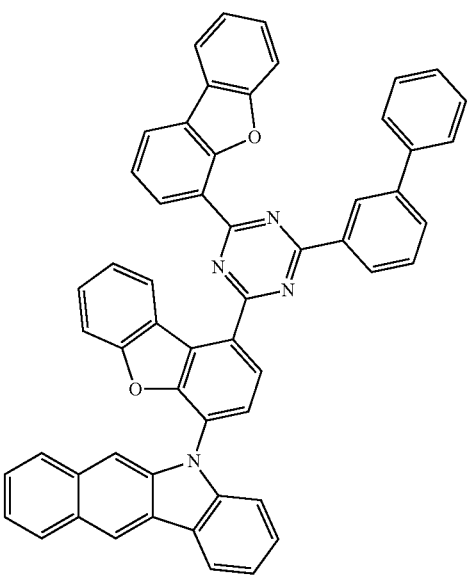
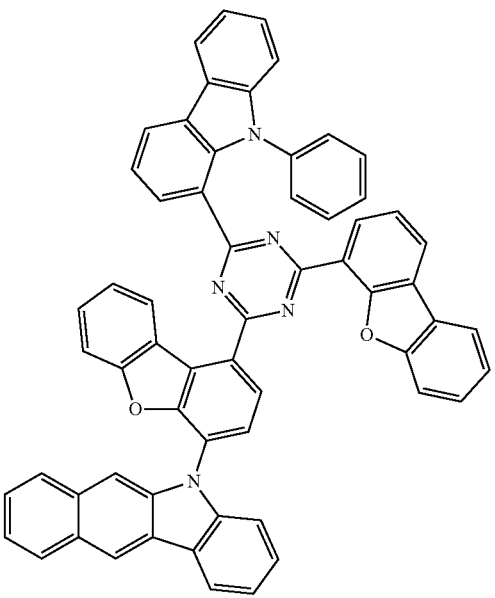

453
-continued
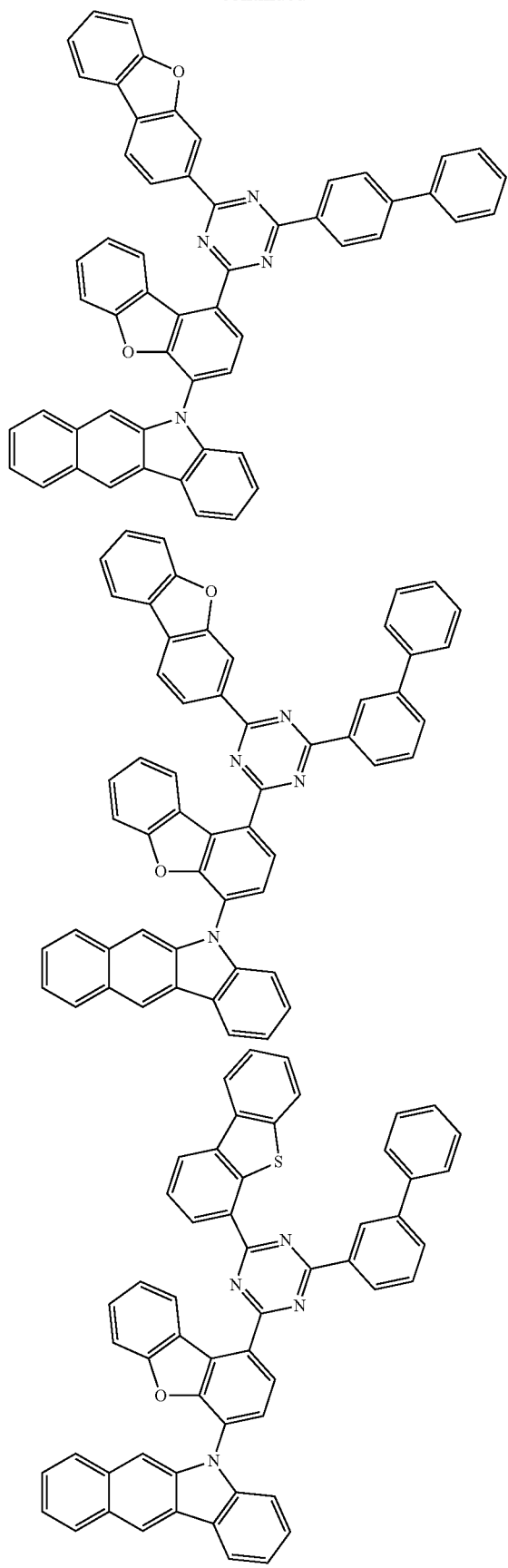
454
-continued
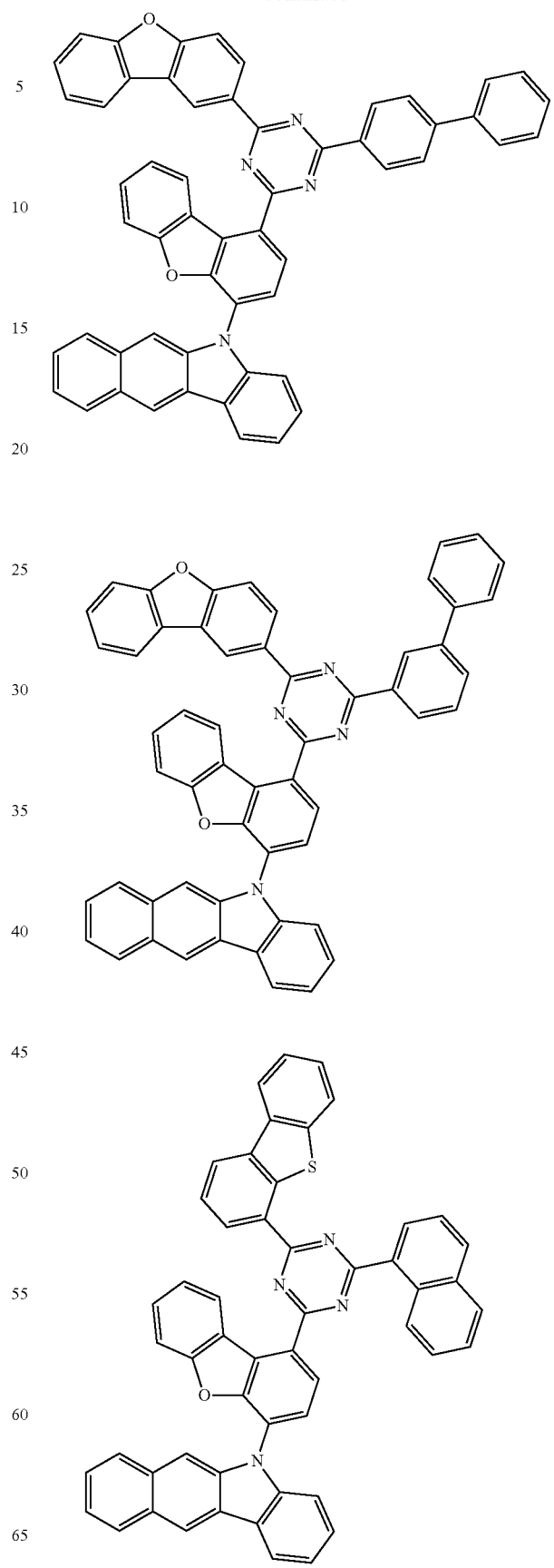

455
-continued
456
-continued
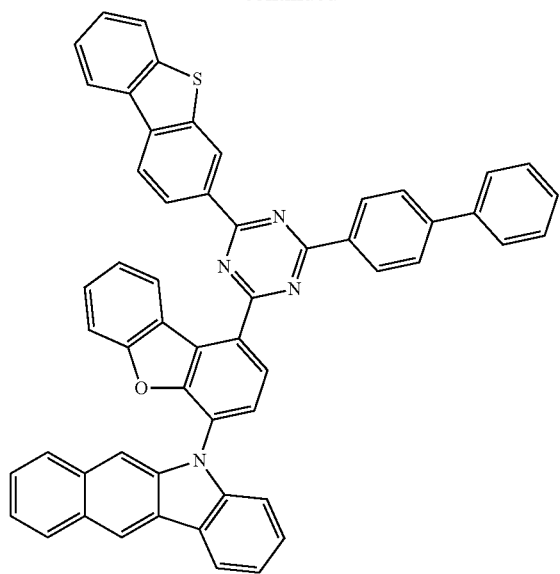
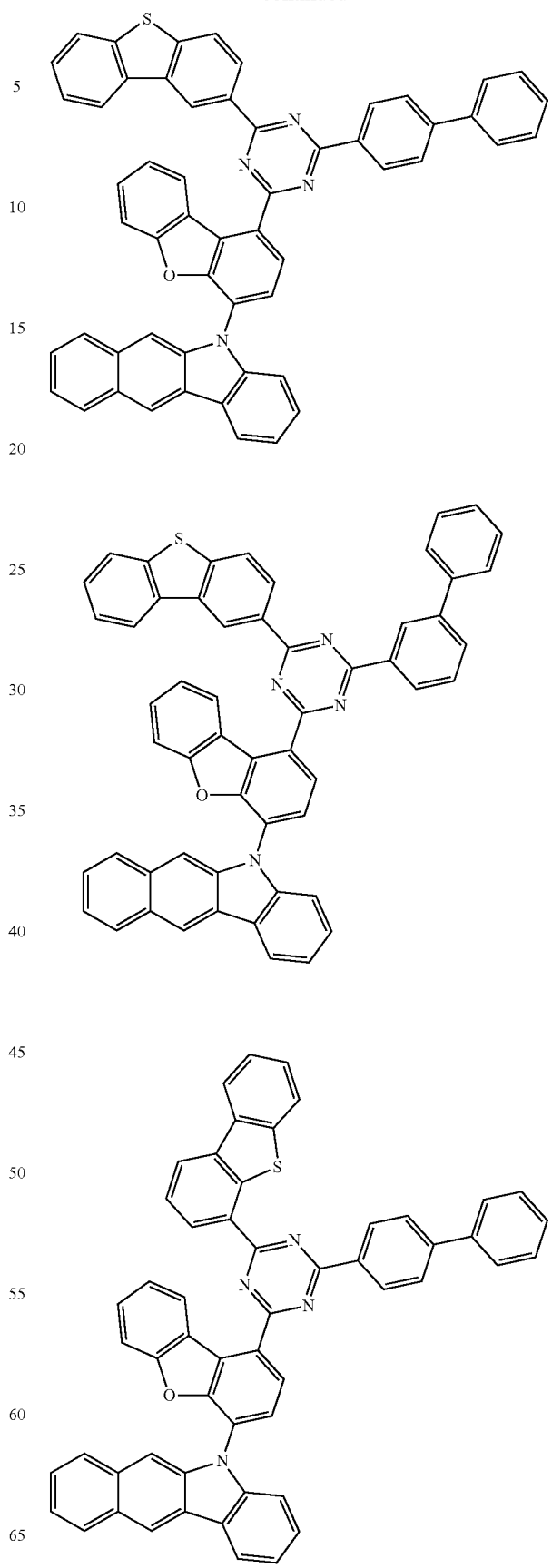

457
-continued
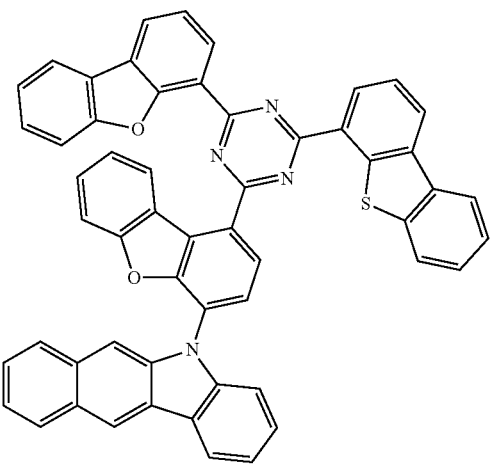
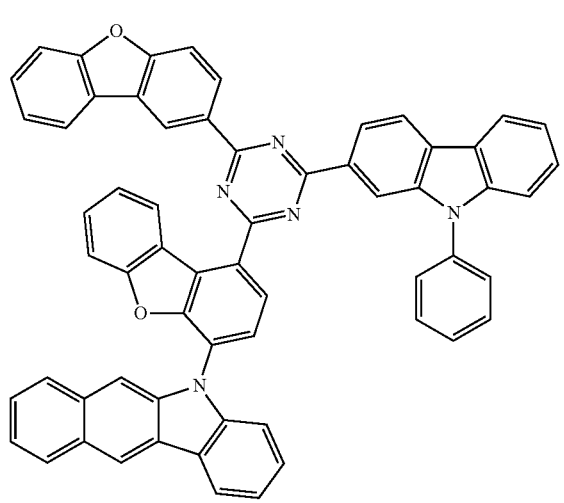
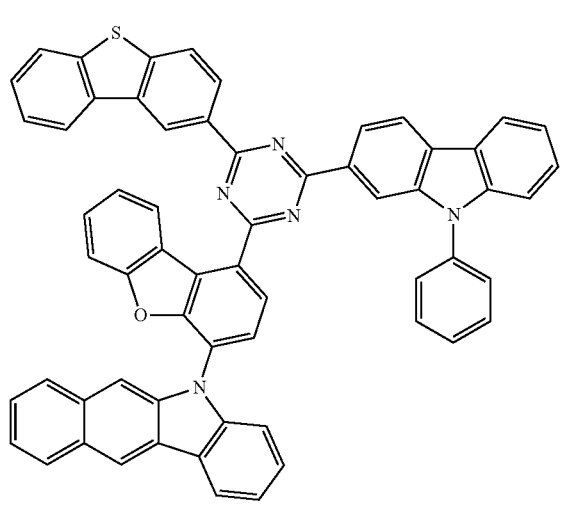
458
-continued
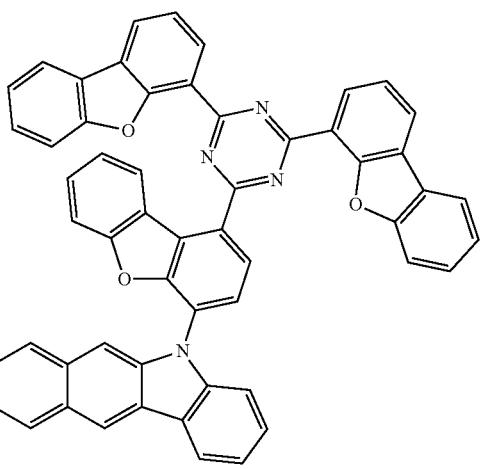
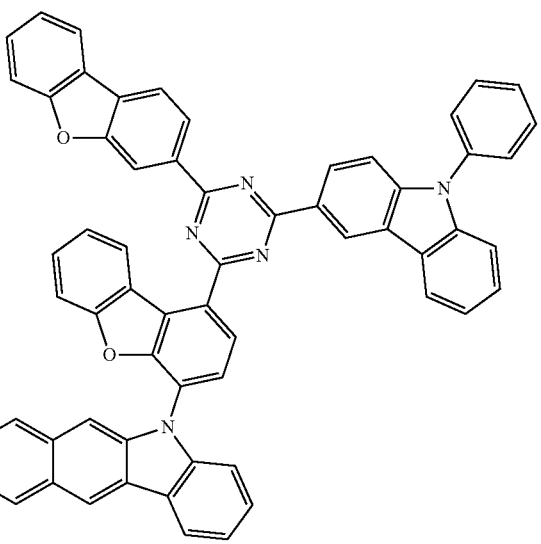
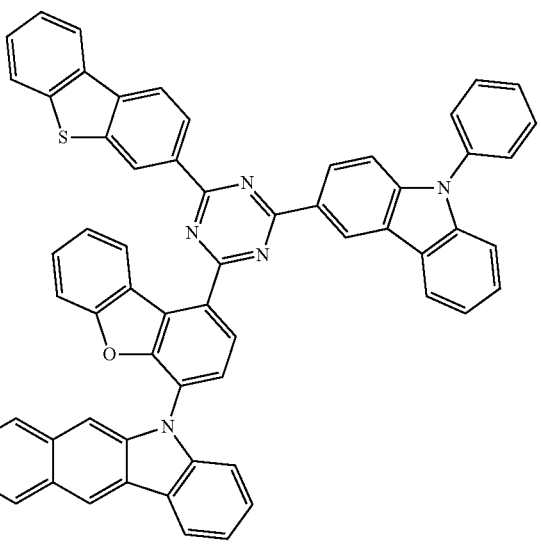

459
-continued
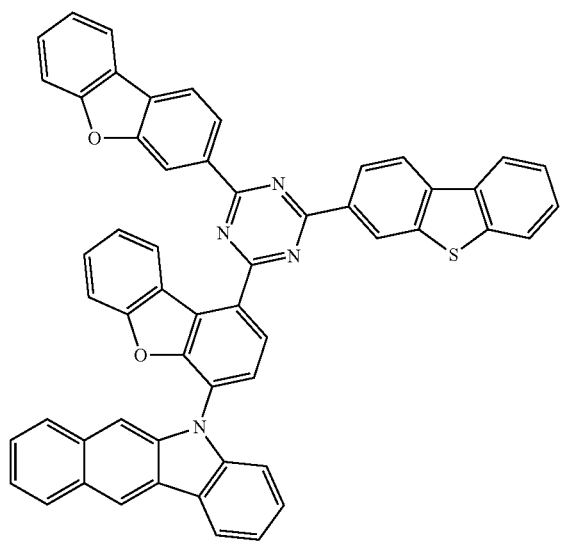
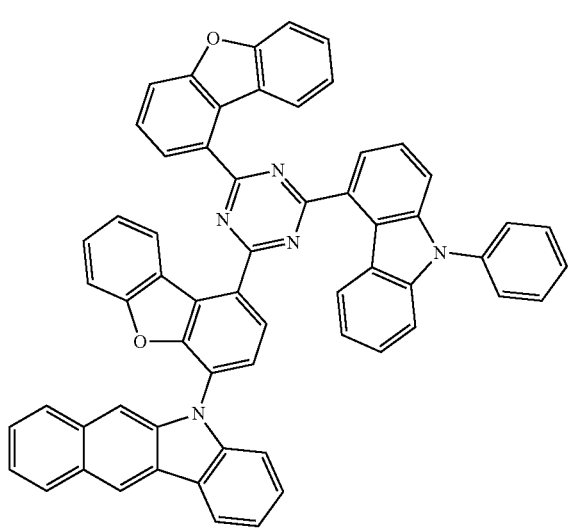
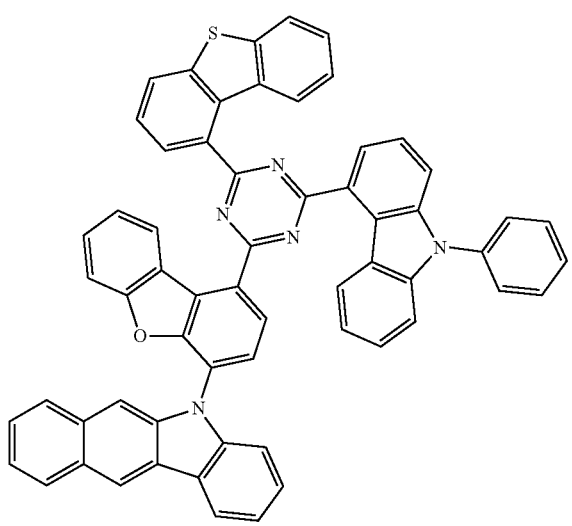
460
-continued
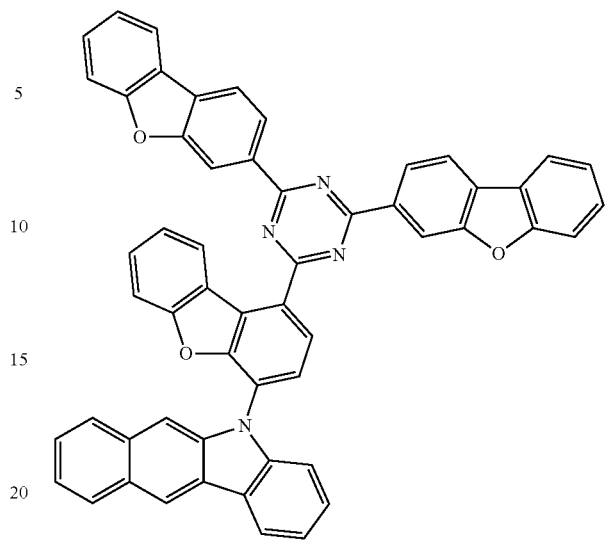
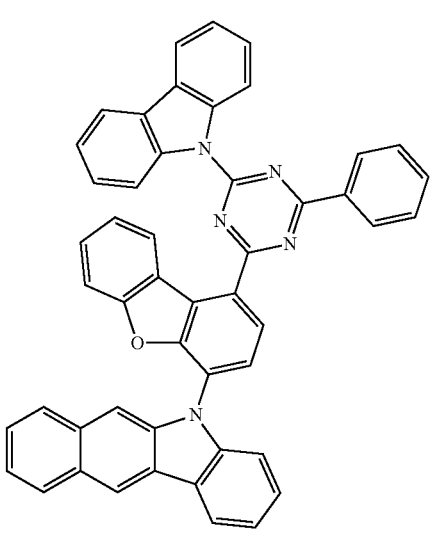
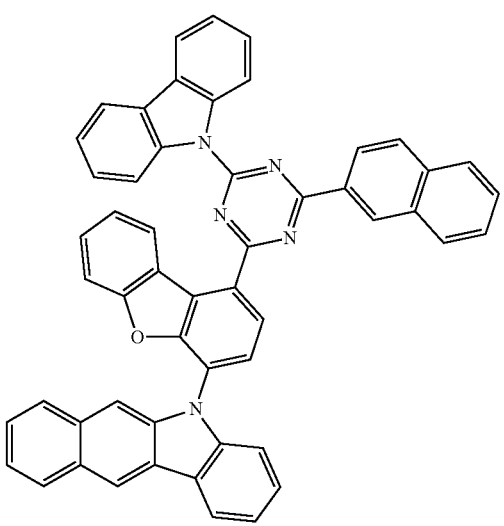

461
-continued
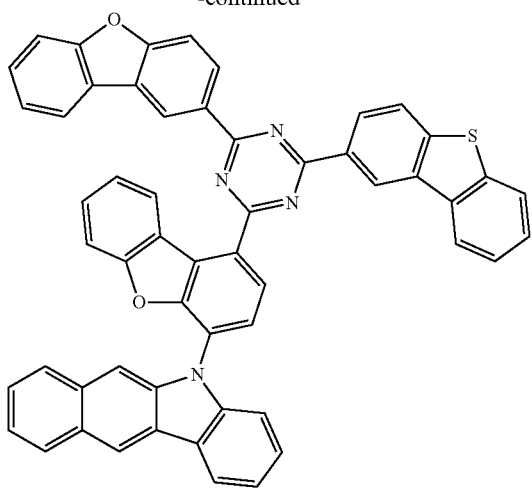
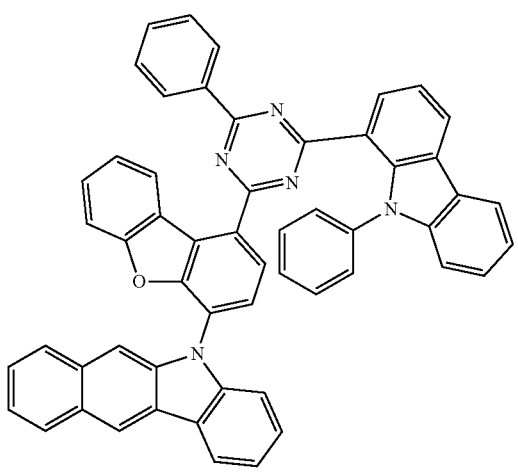
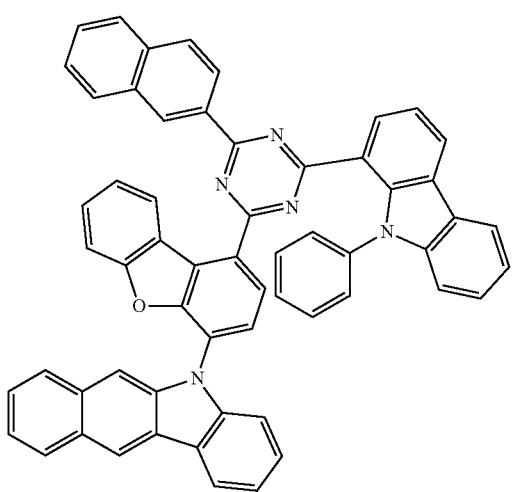
462
-continued
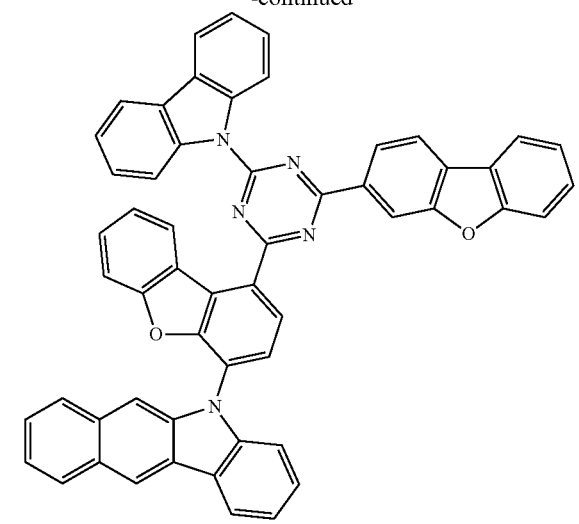
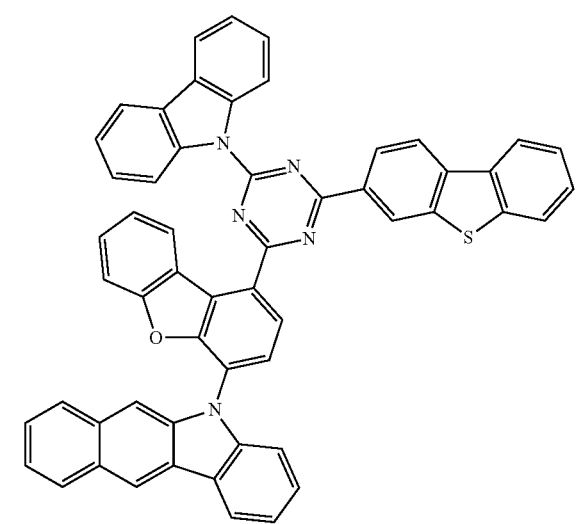
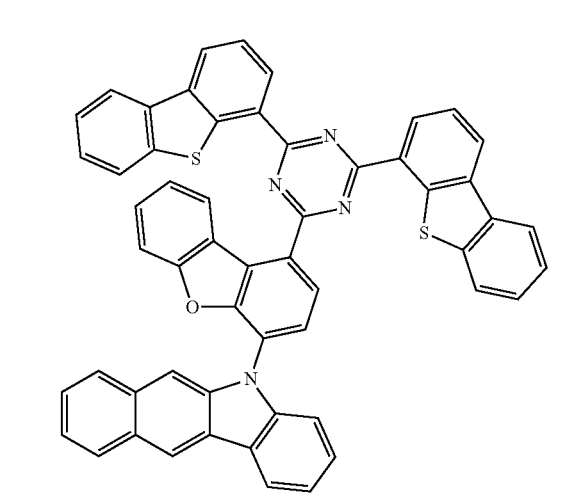

463
-continued
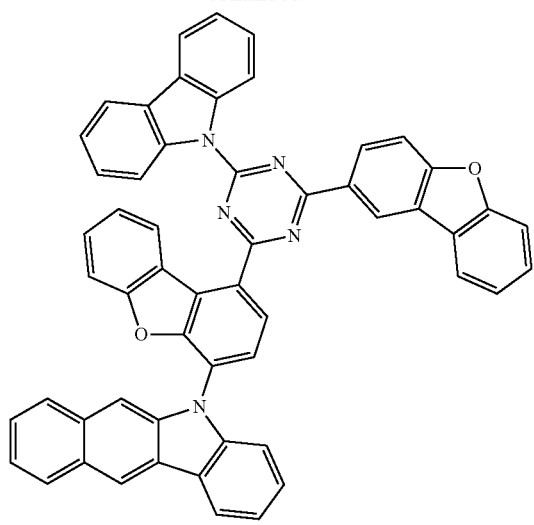
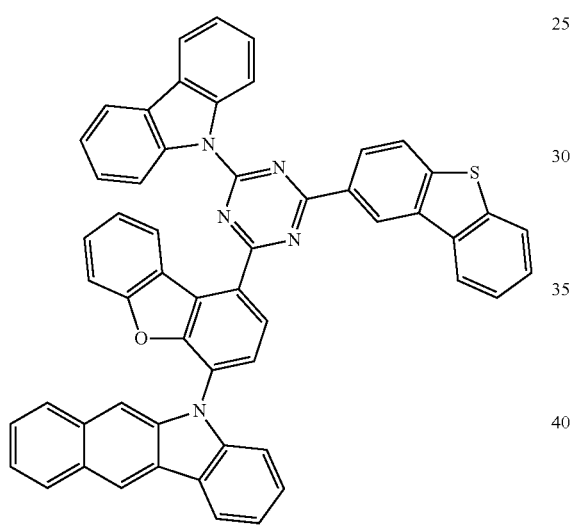
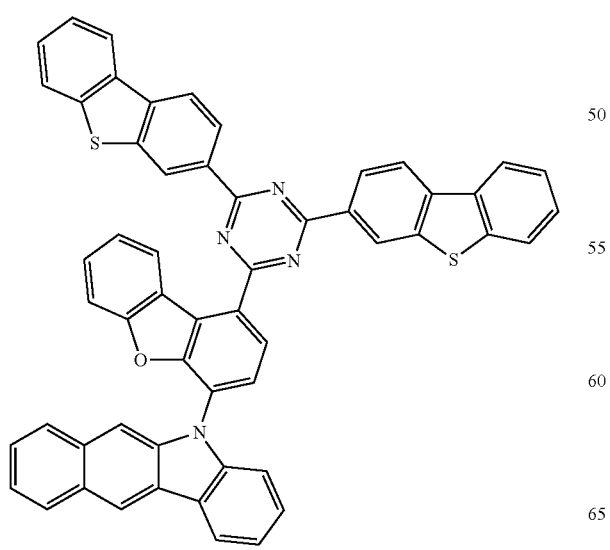
464
-continued
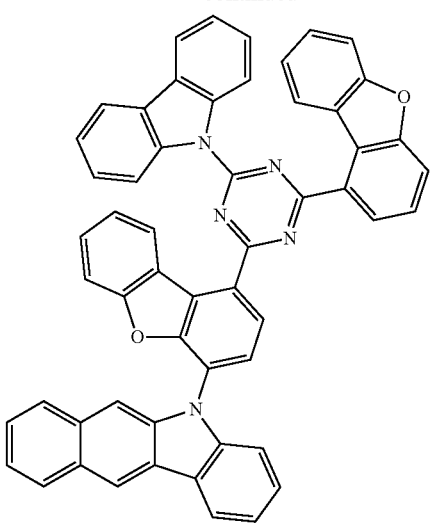
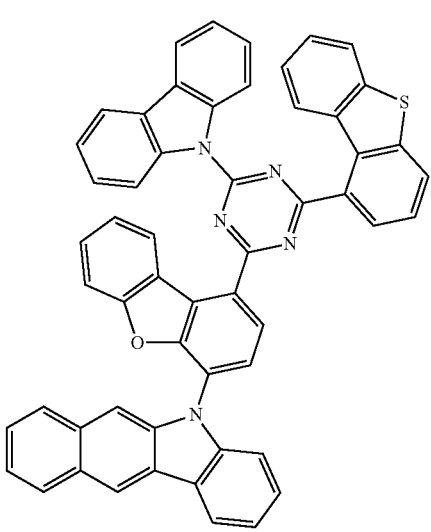
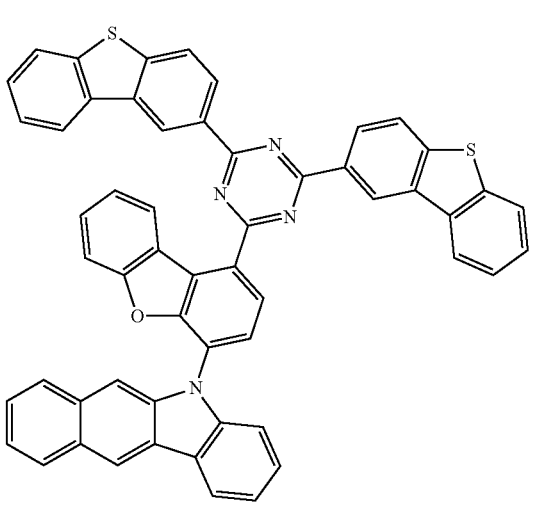

465
-continued
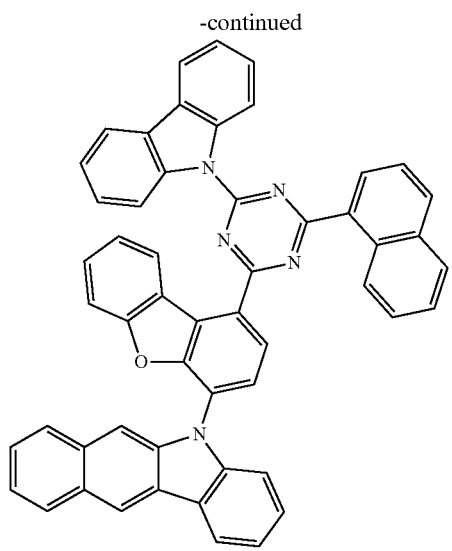
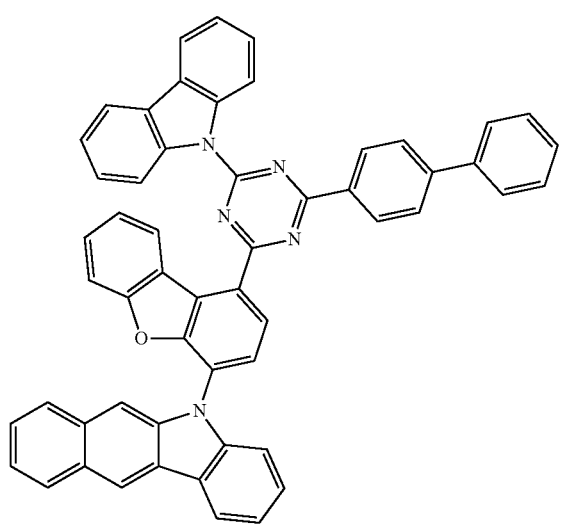
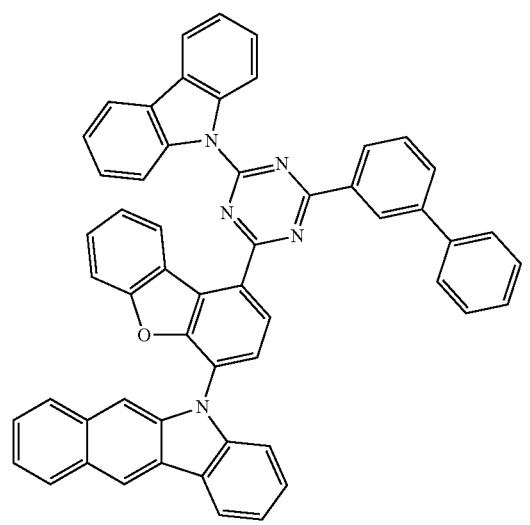
466
-continued
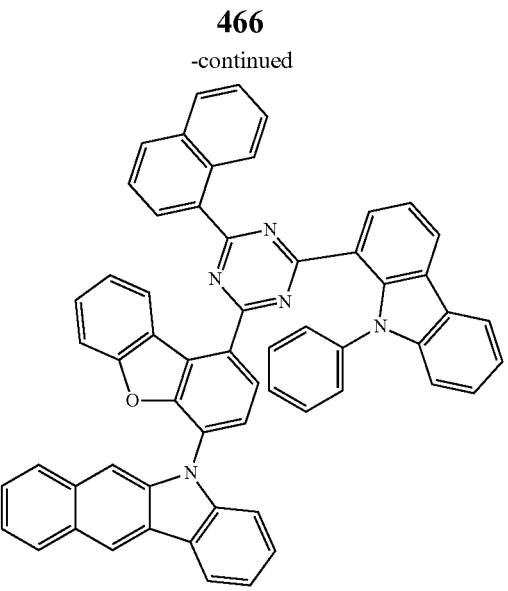
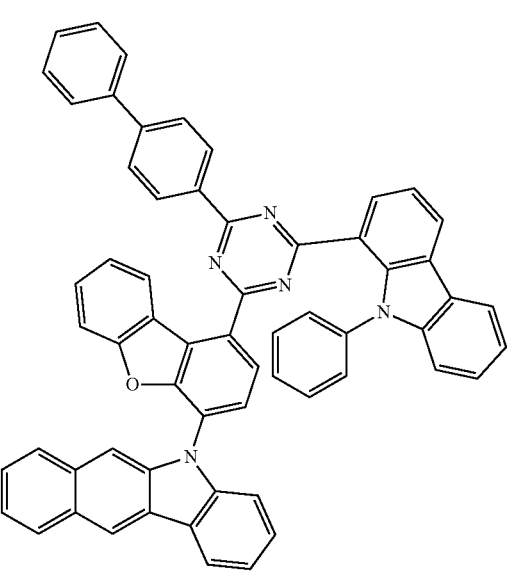
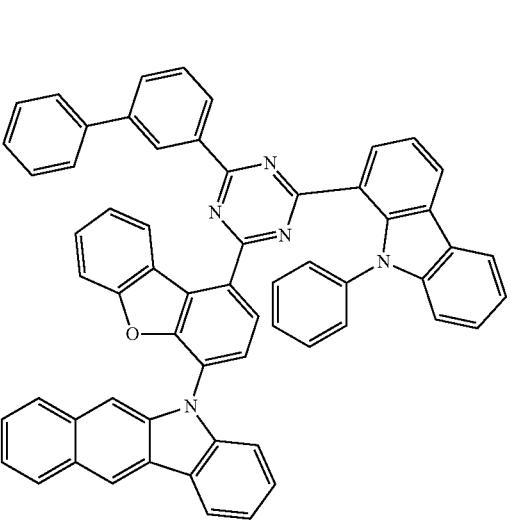

467
-continued
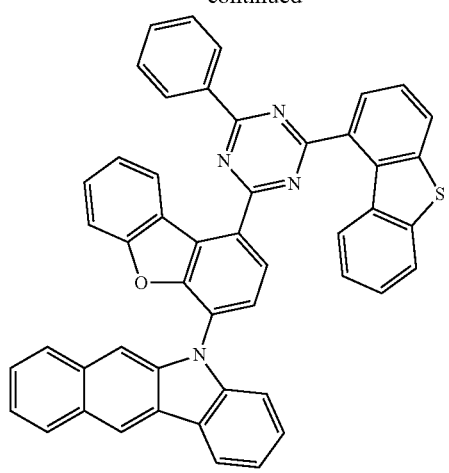
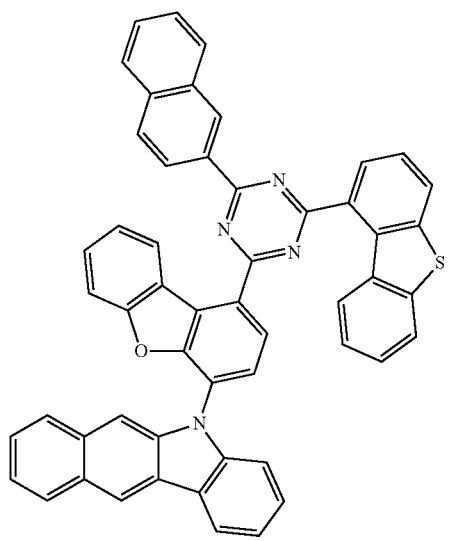
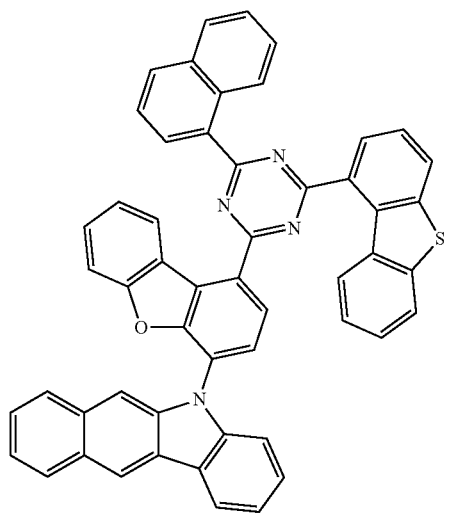
468
-continued
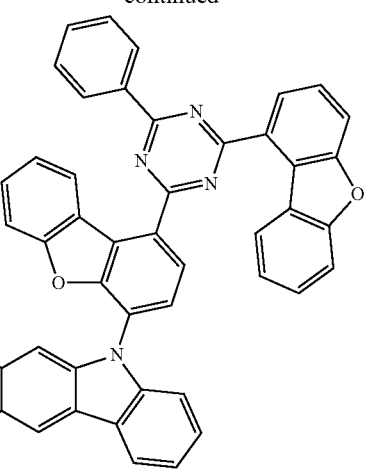
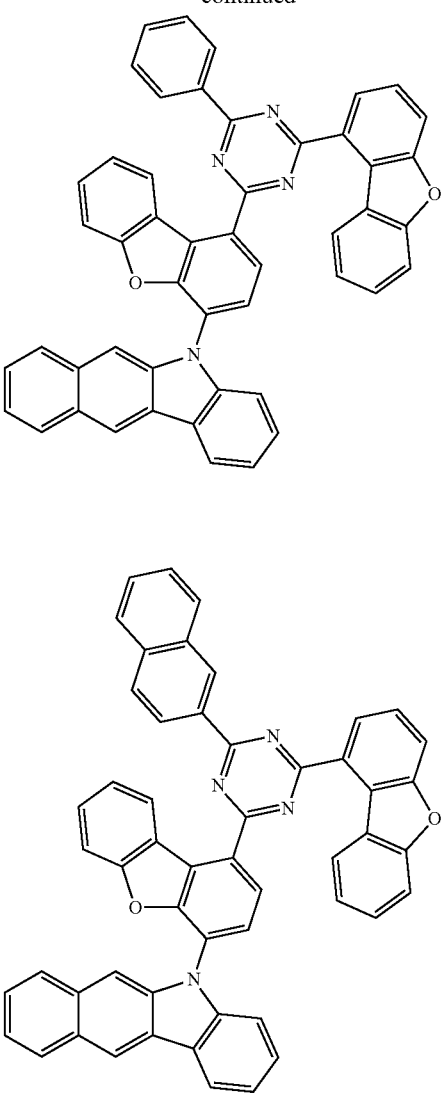
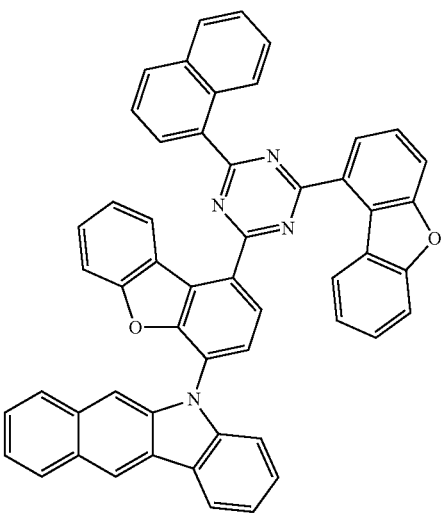

469
-continued
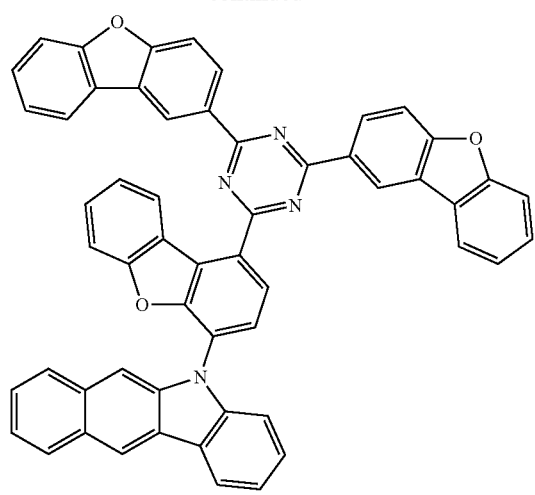
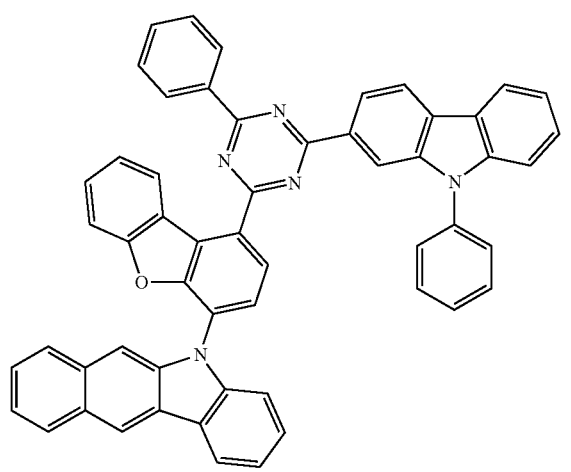
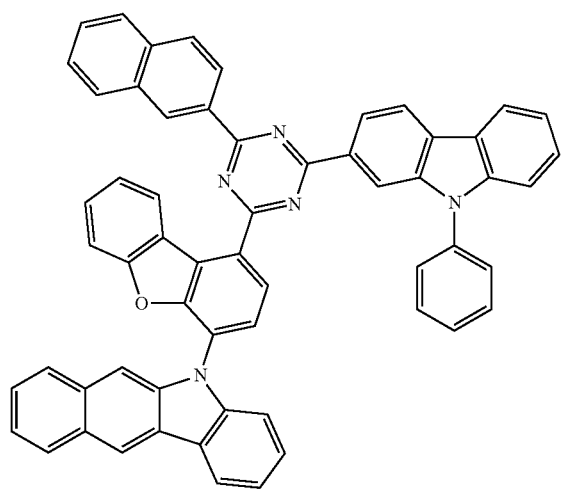
470
-continued
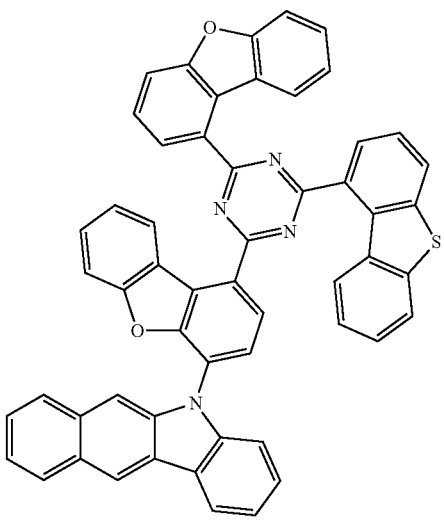
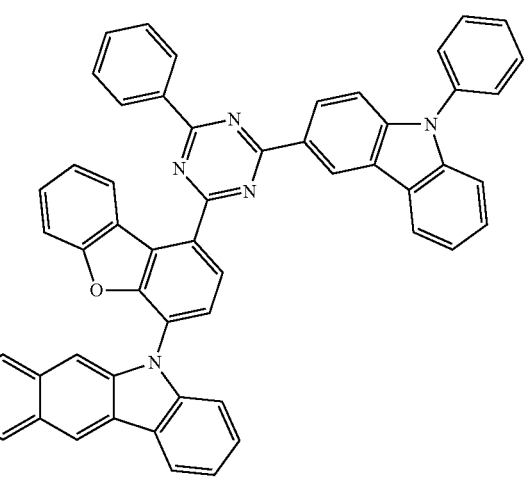
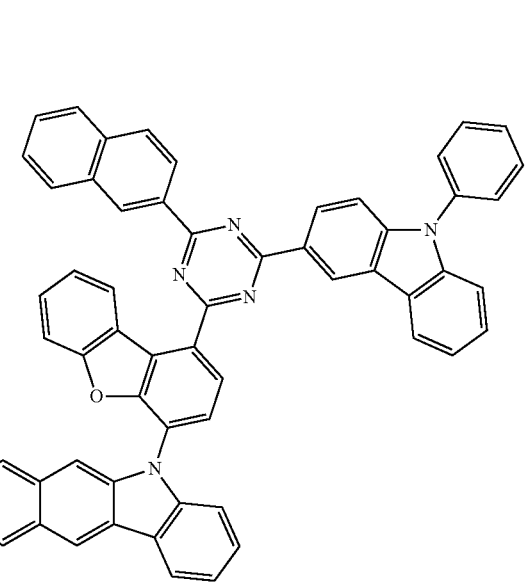

471
-continued
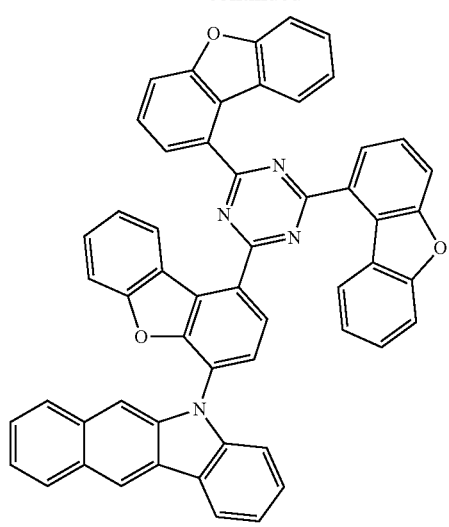
472
-continued
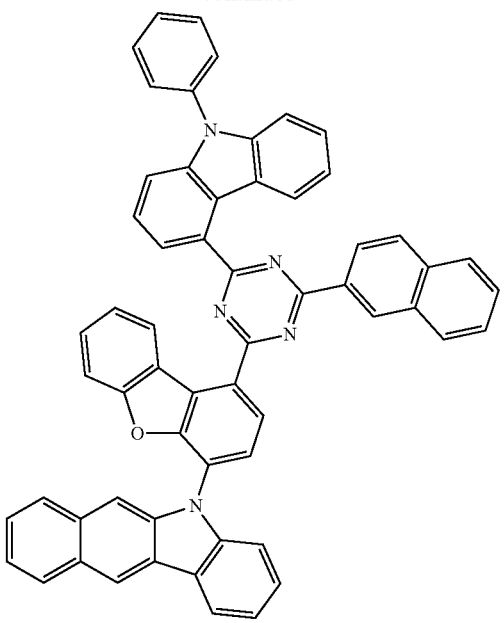
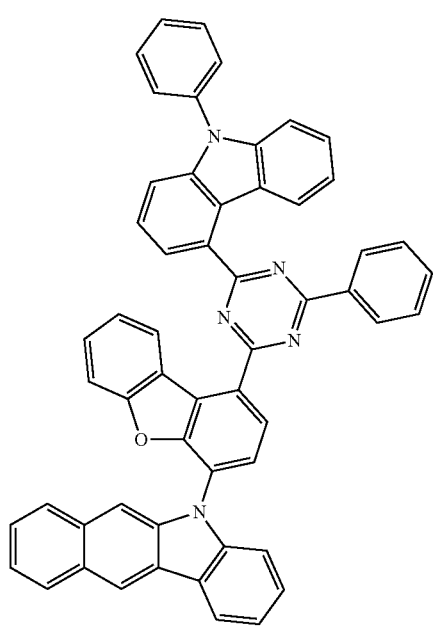
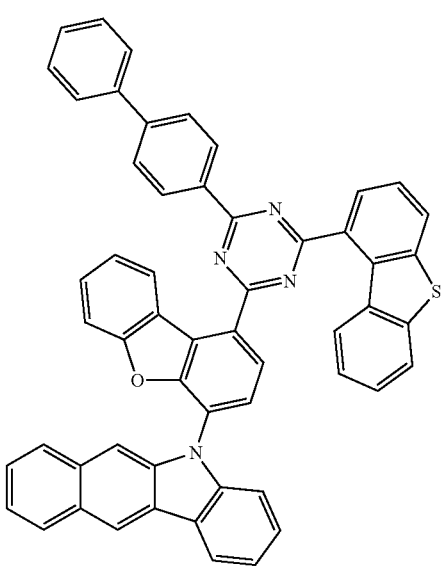

473
-continued
474
-continued
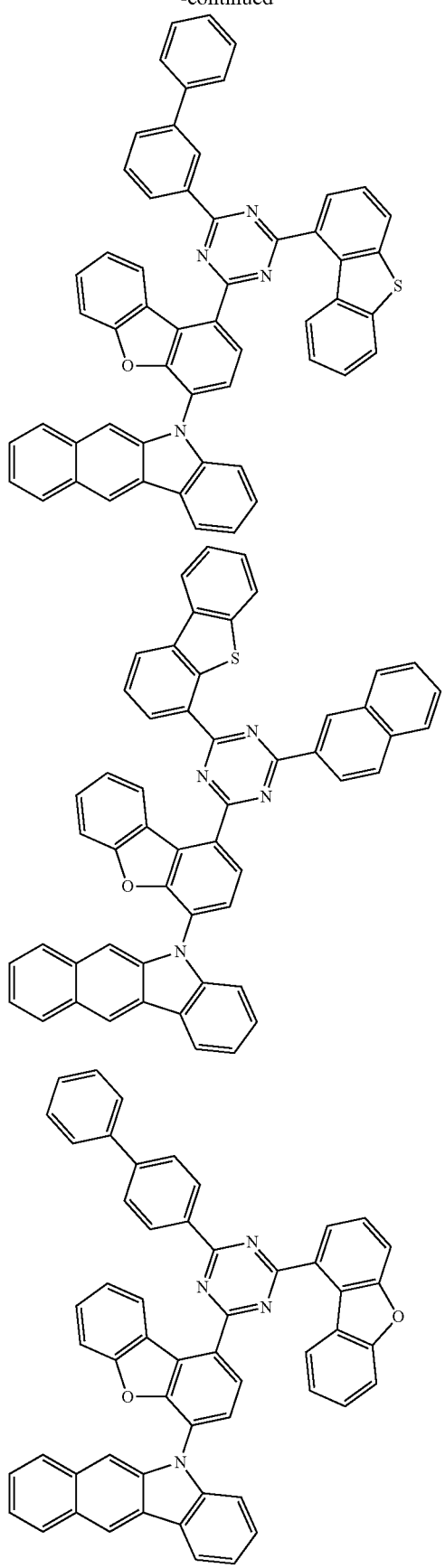
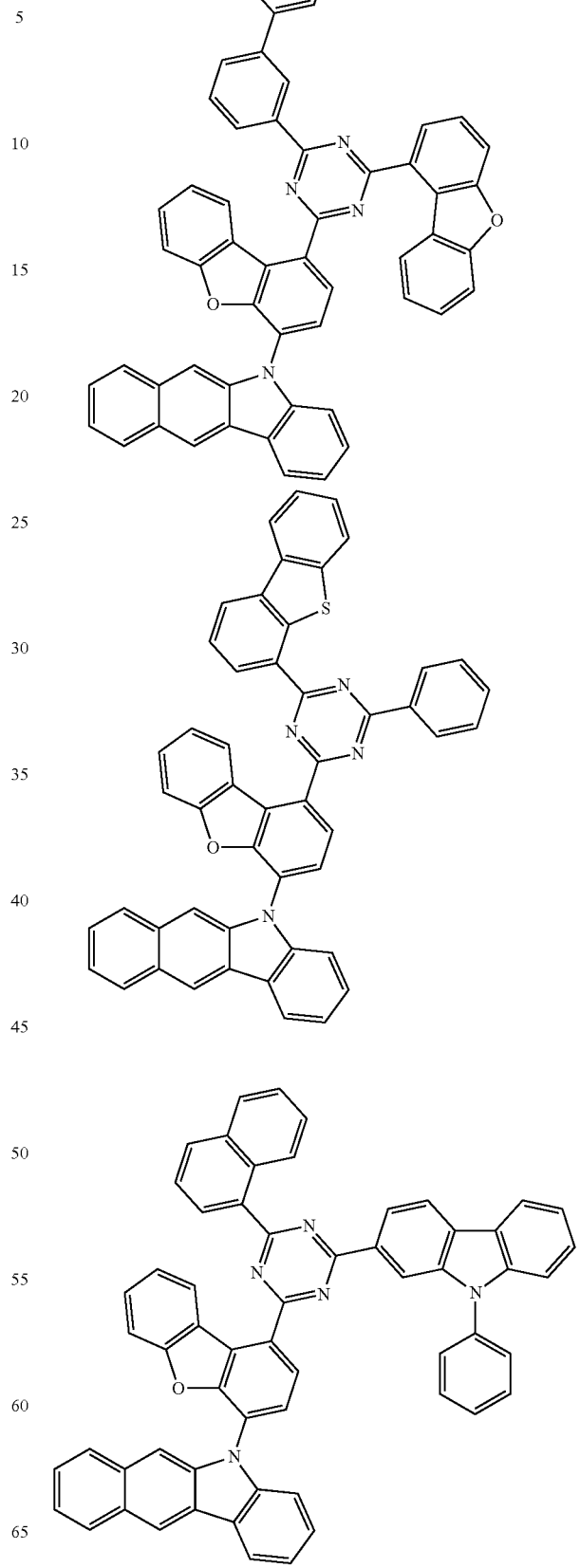

475
-continued
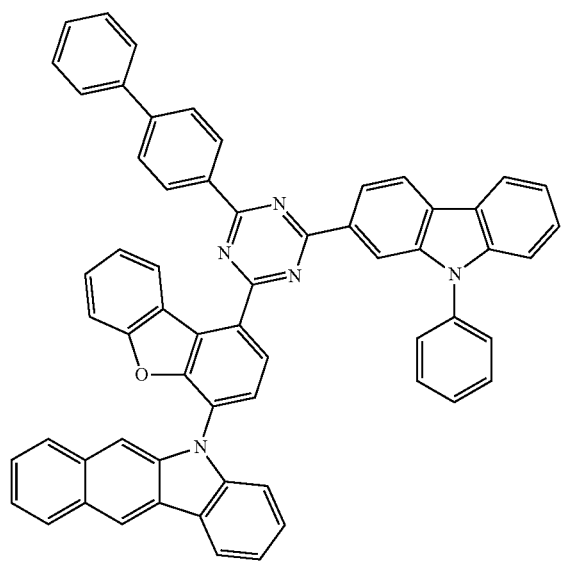
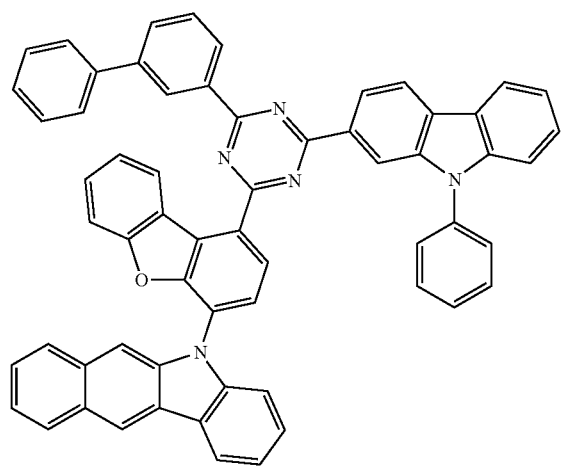
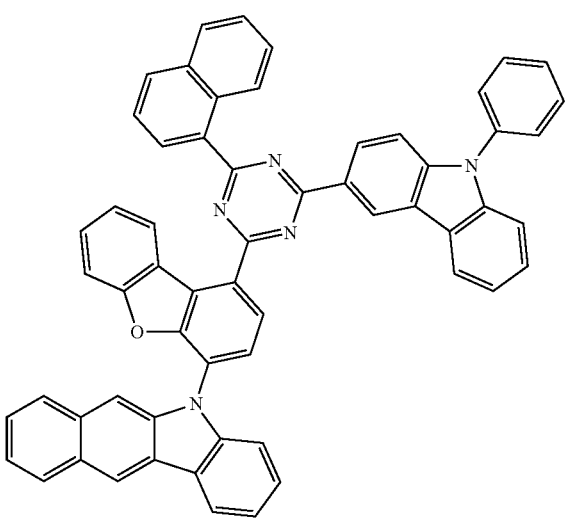
476
-continued
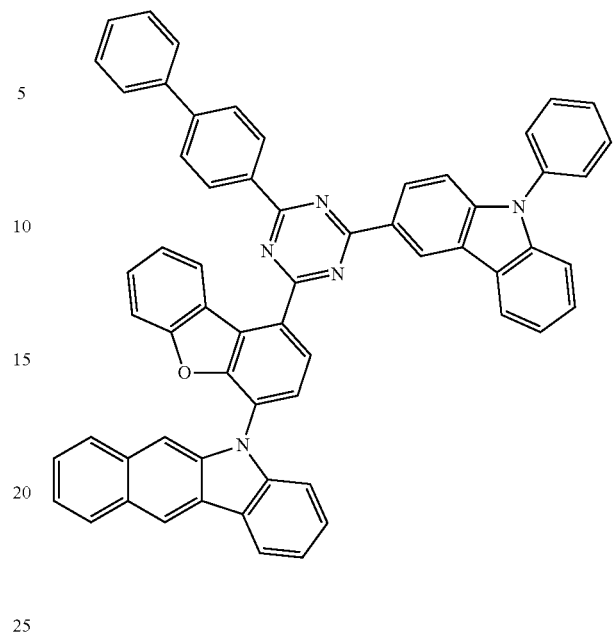
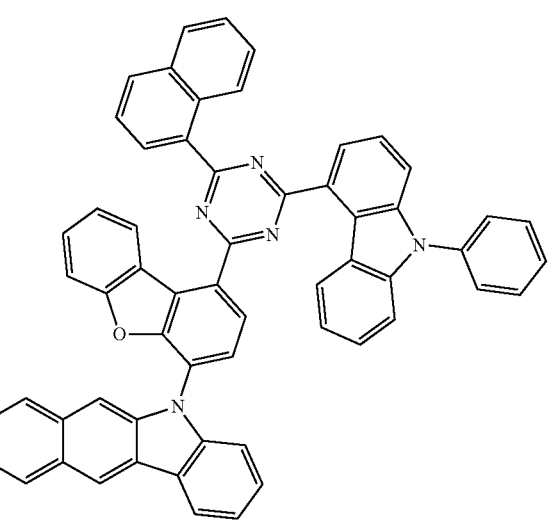

477
-continued
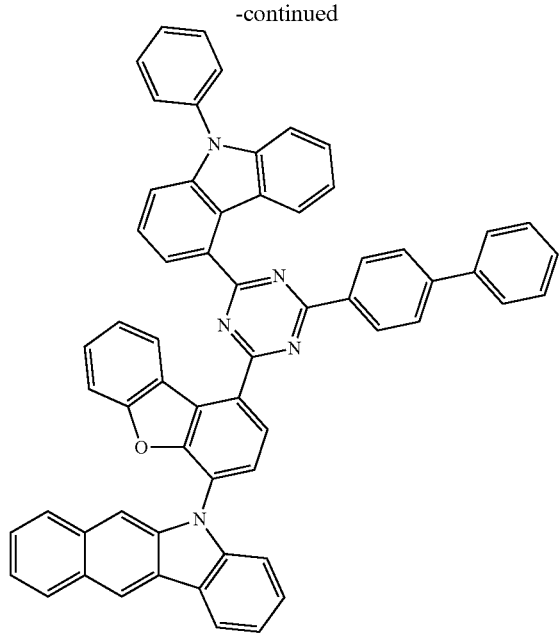
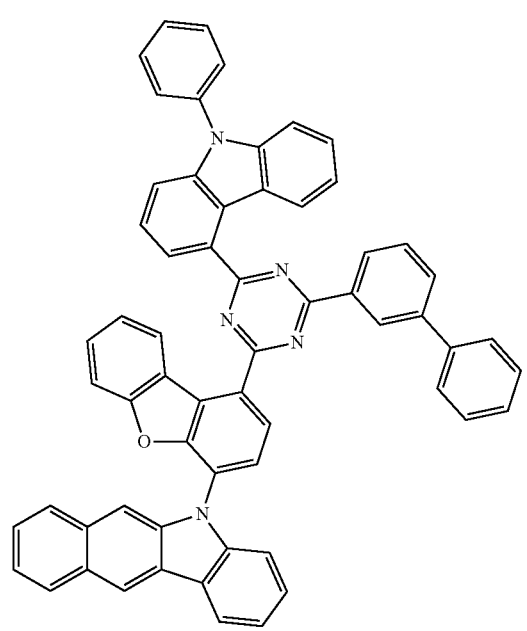
478
-continued
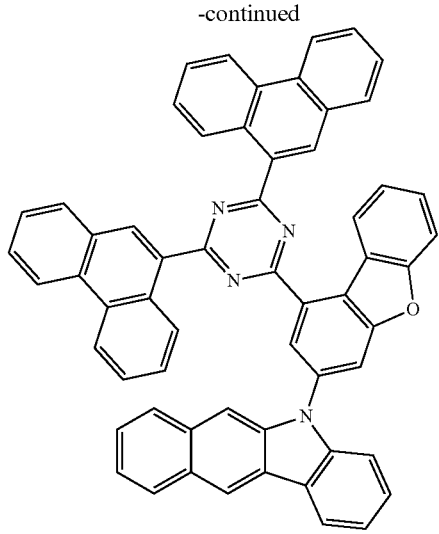
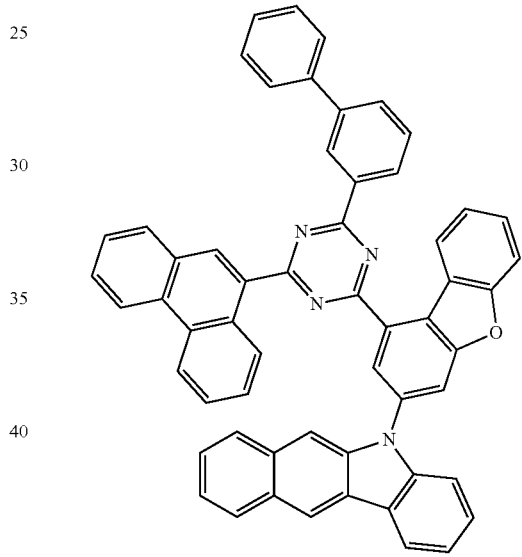
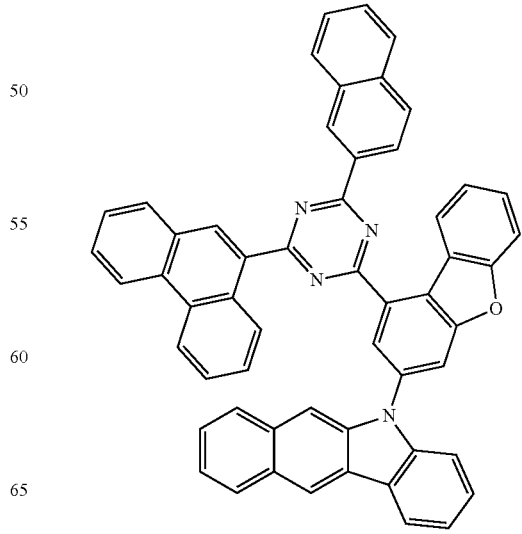

479
-continued
480
-continued
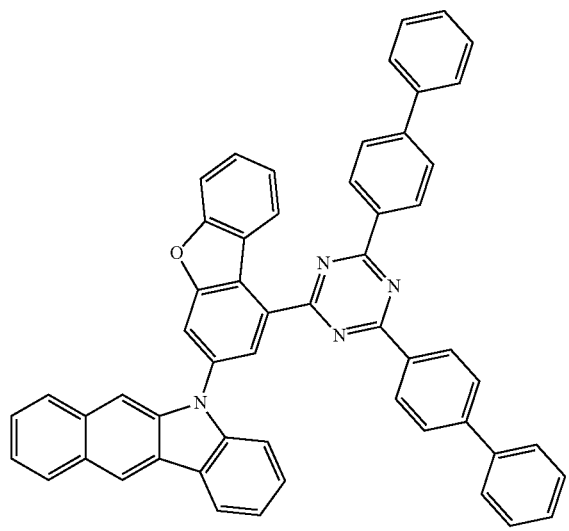
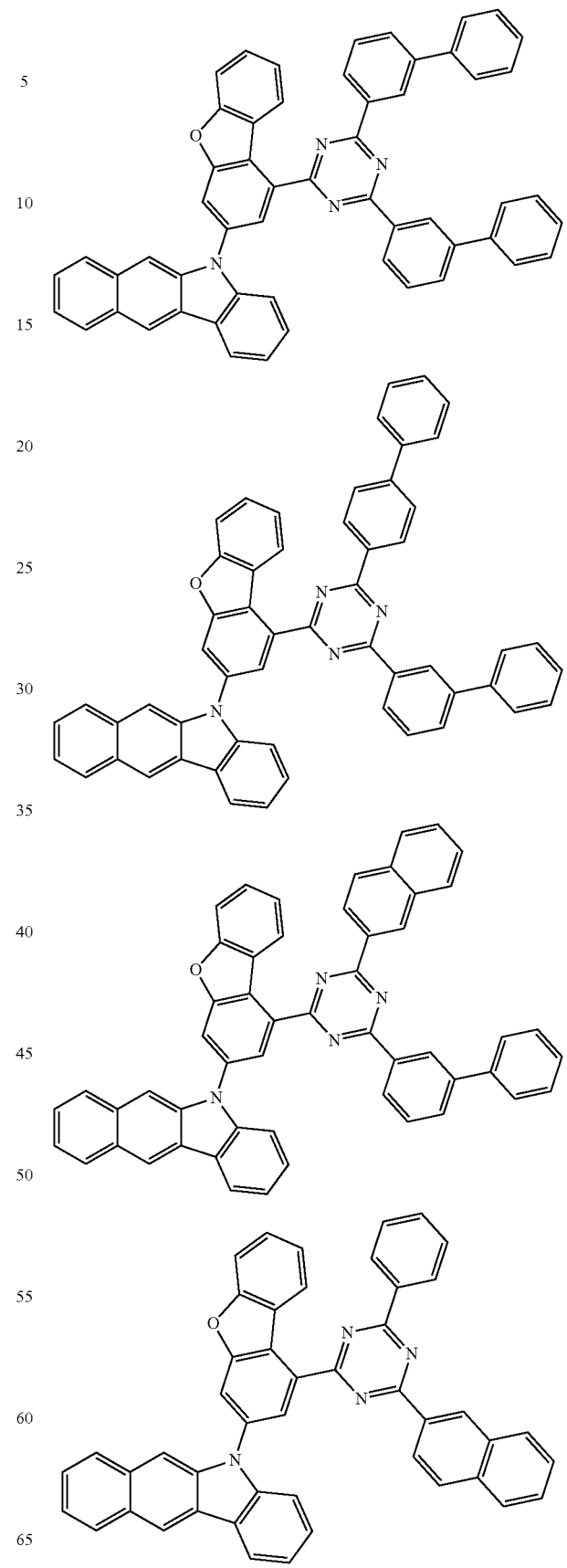

481
-continued
482
-continued
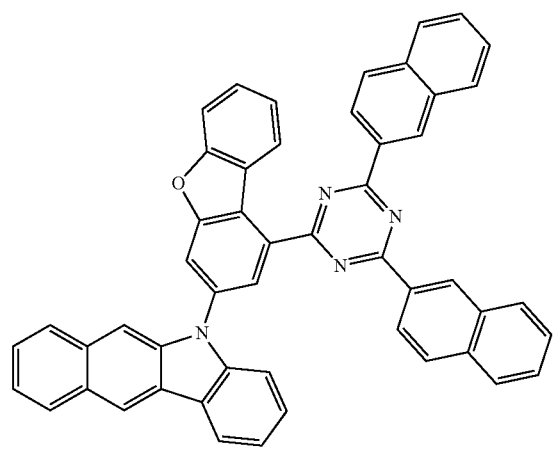
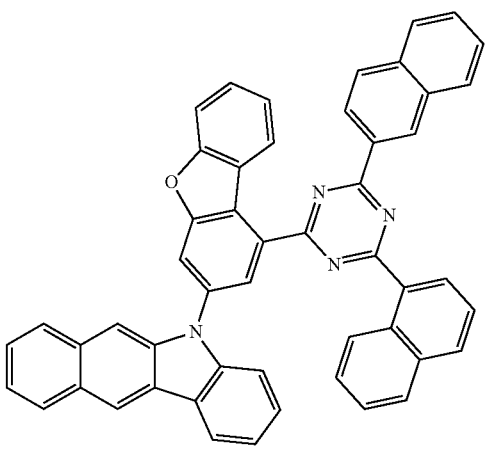

483
-continued
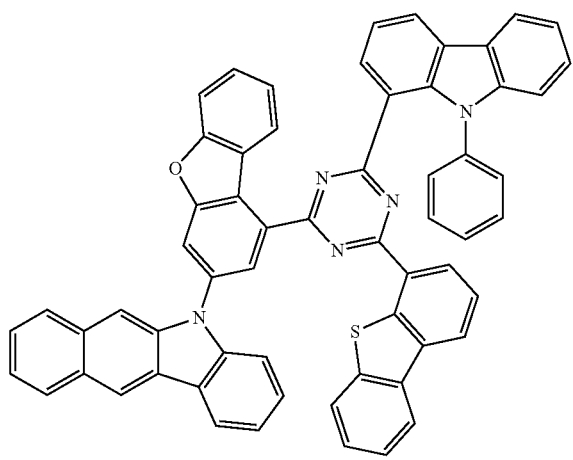
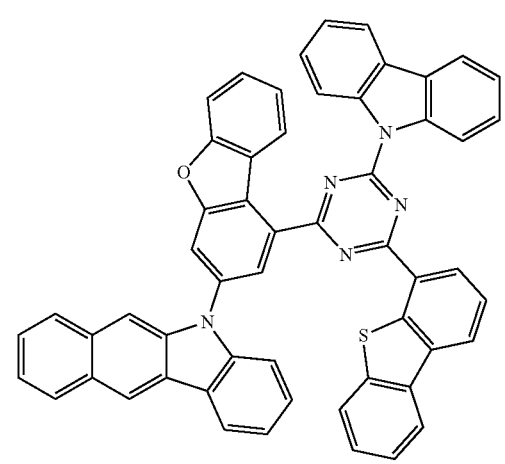
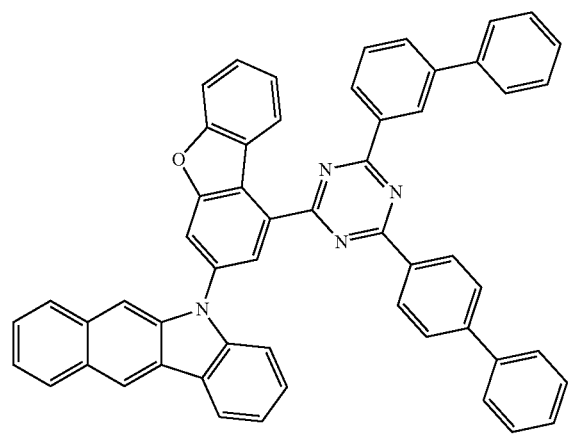
484
-continued
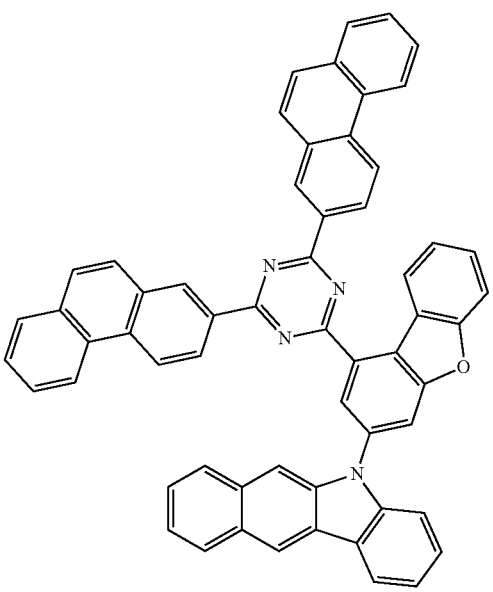
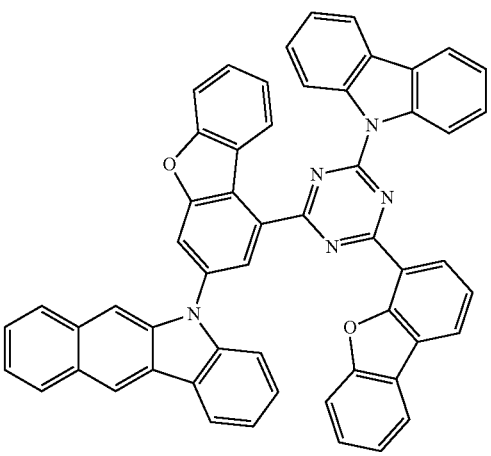
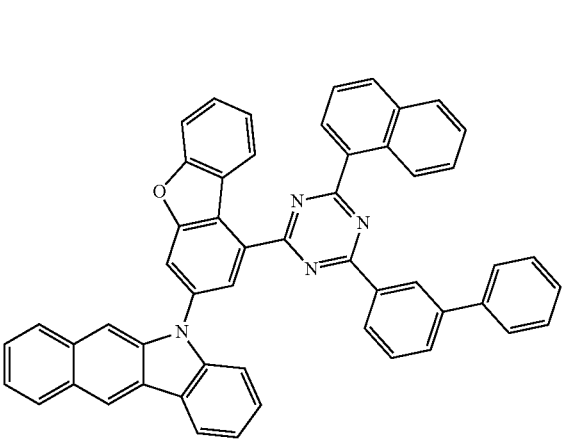

485
-continued
486
-continued
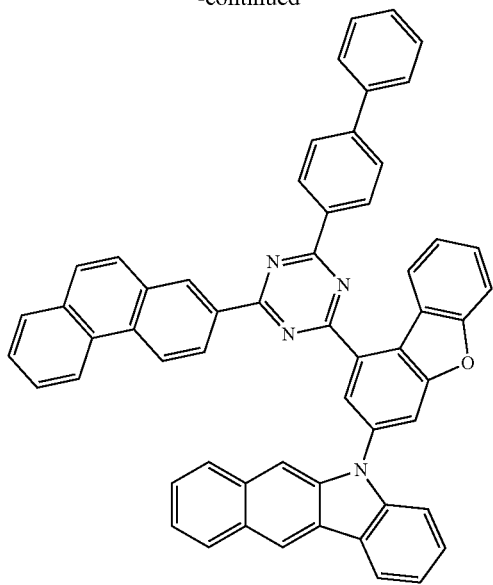
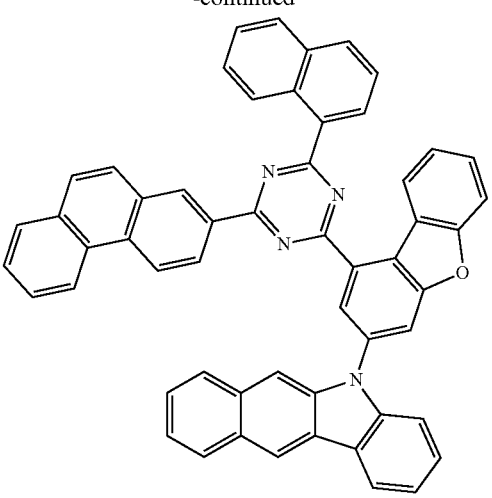
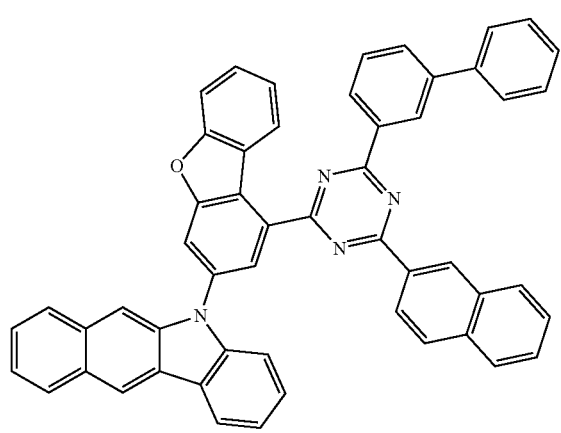
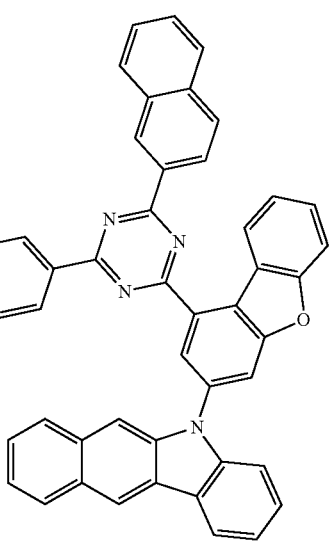
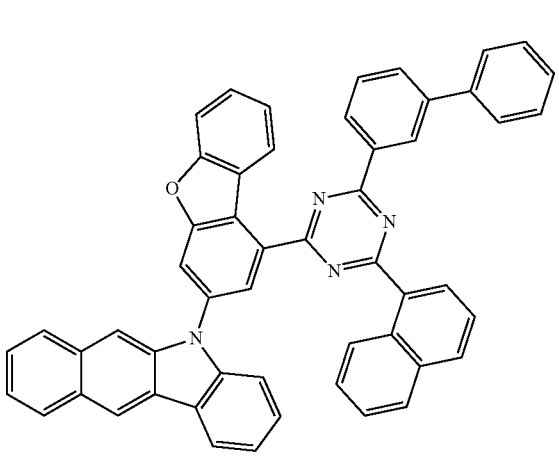

487
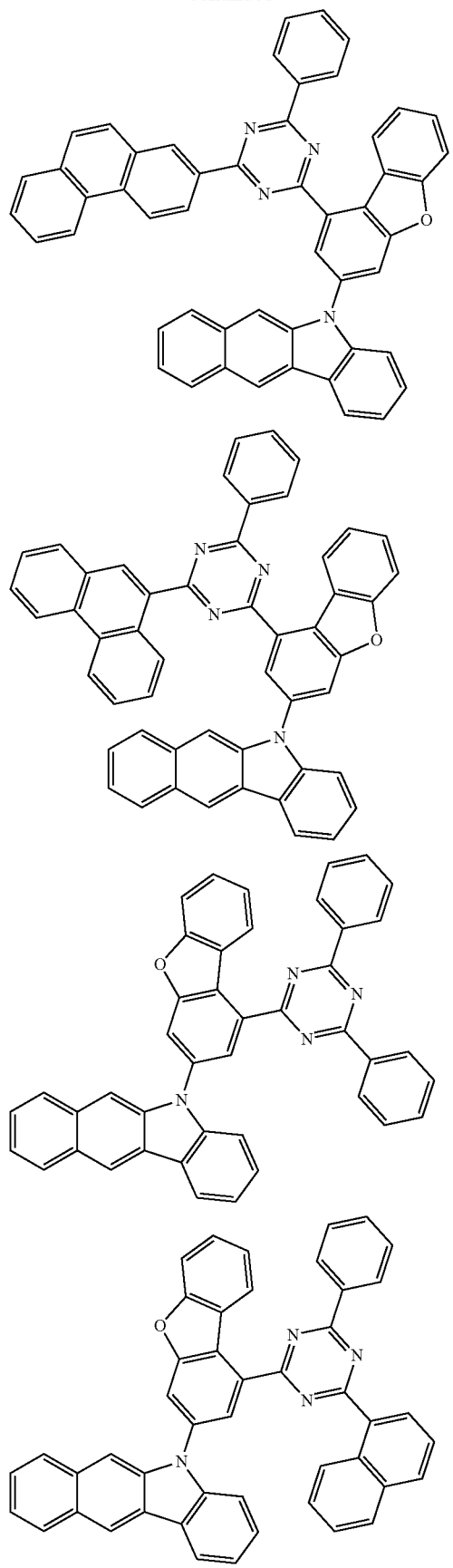
488
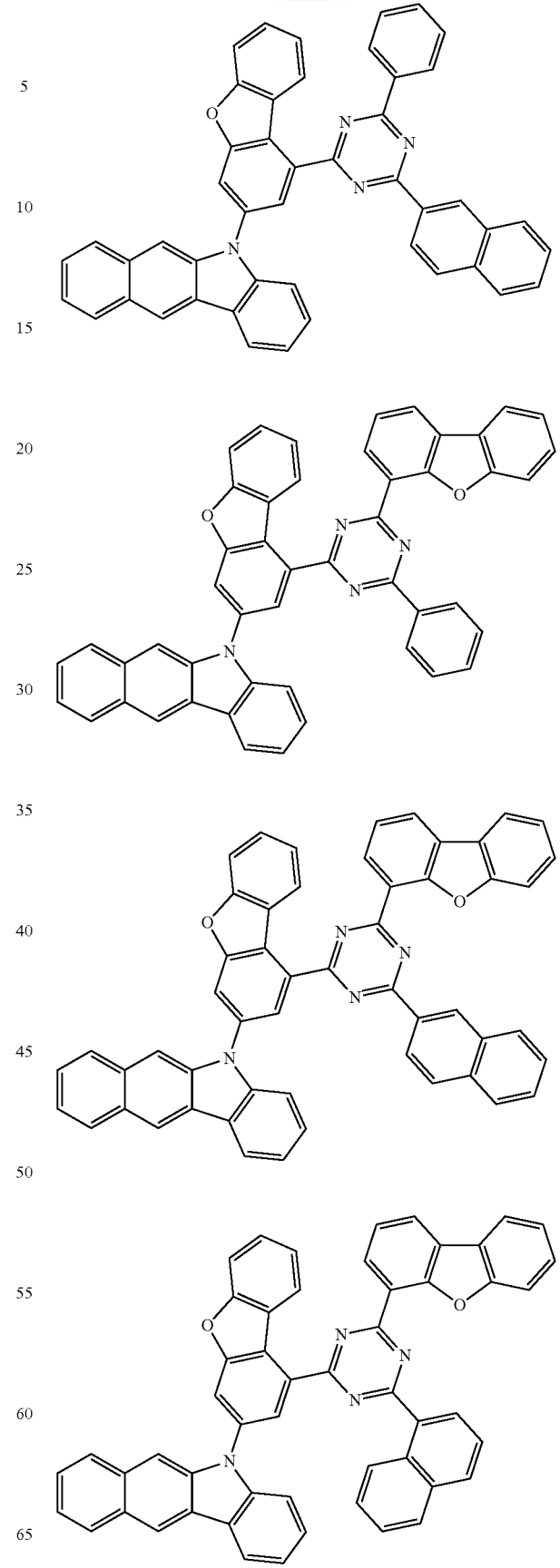

489
-continued
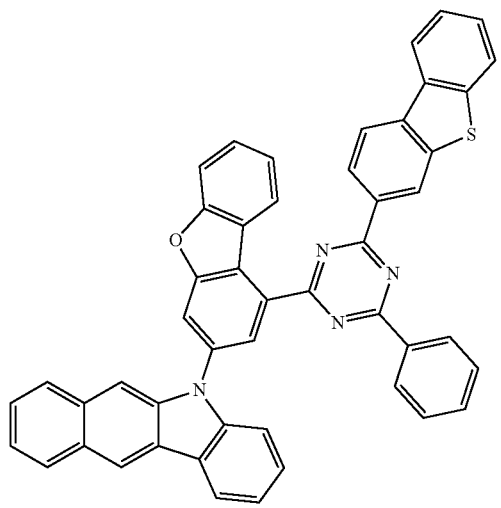
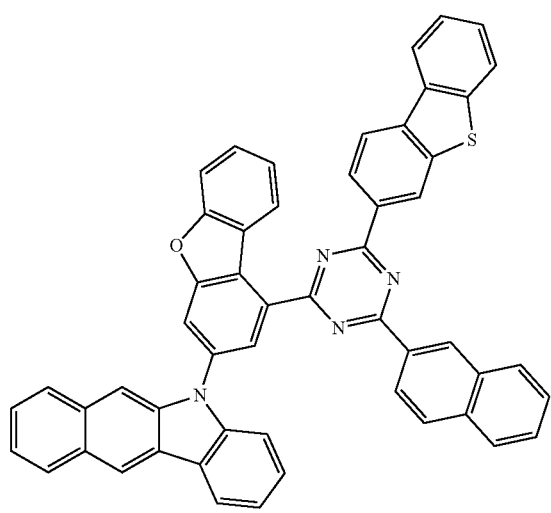
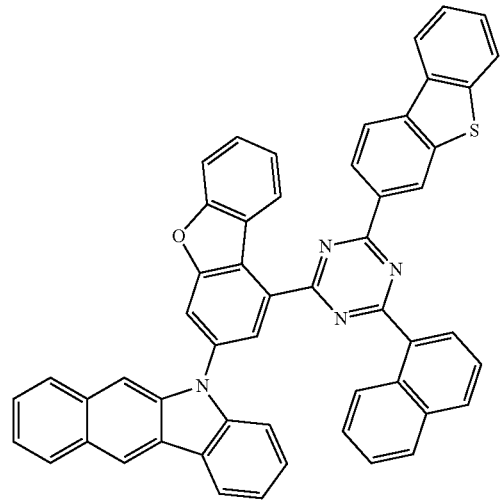
490
-continued
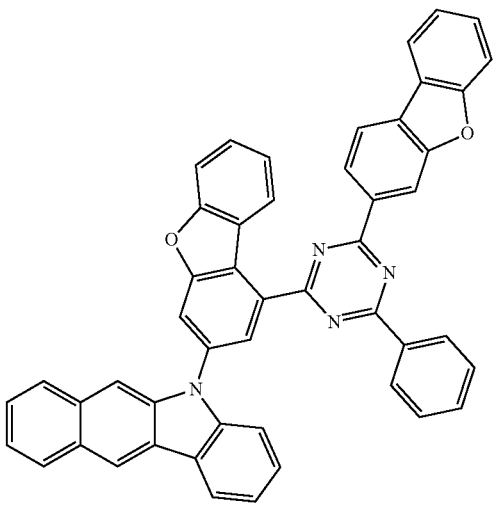
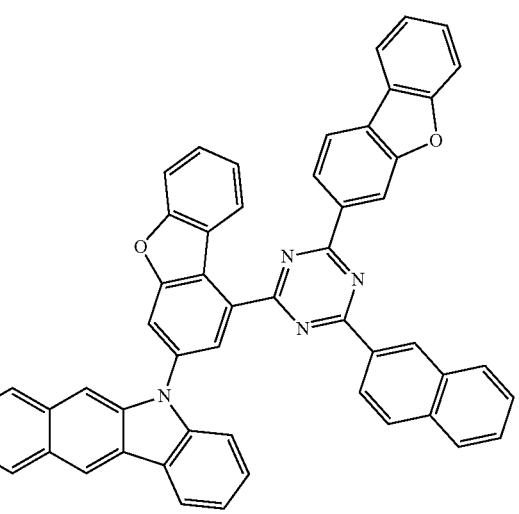
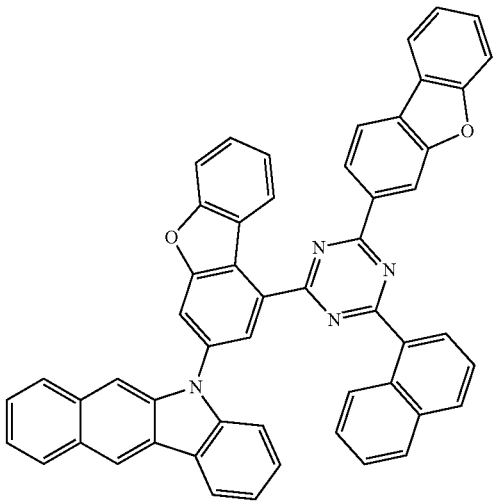

491
-continued
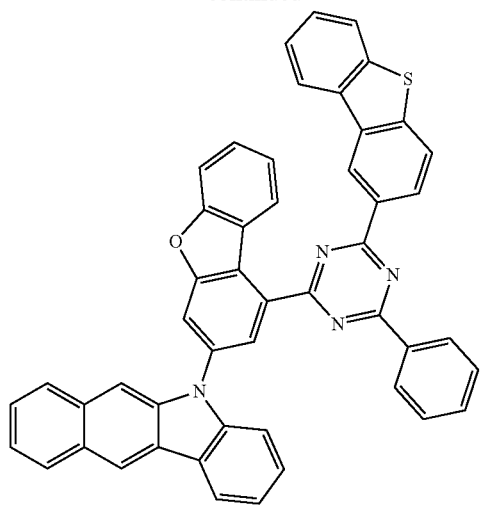
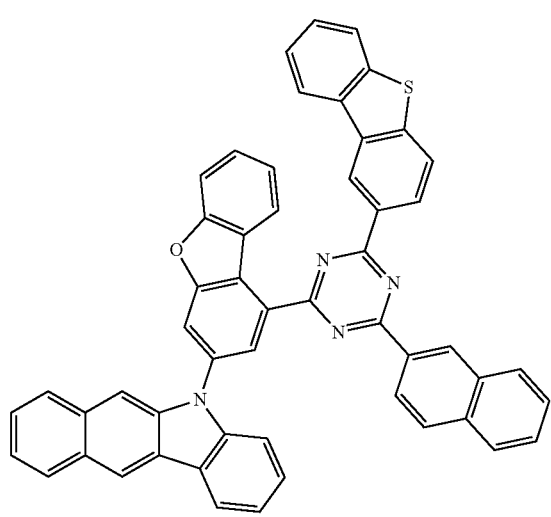
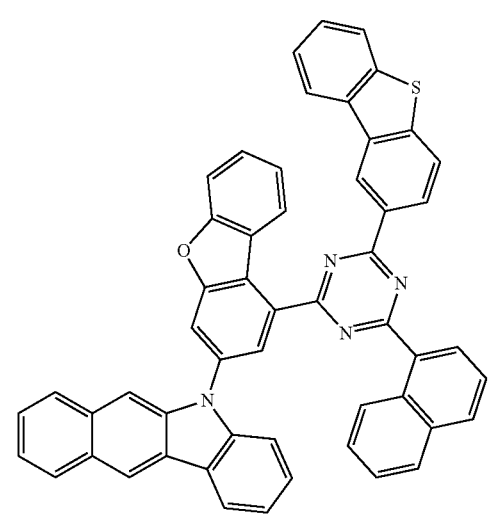
492
-continued
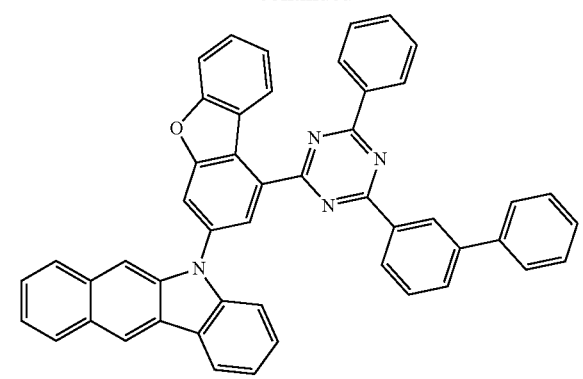
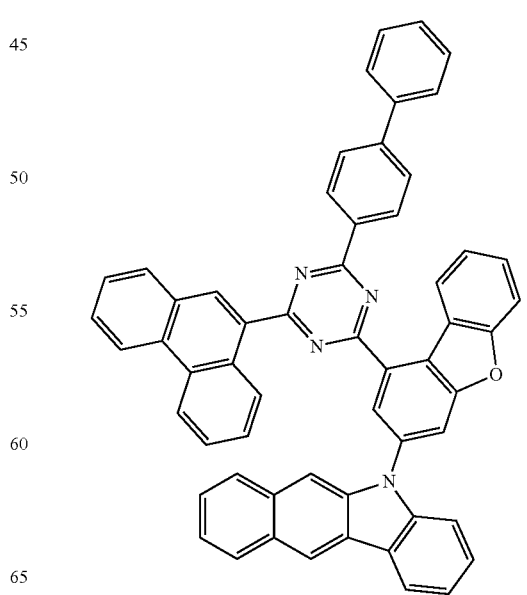

493
-continued
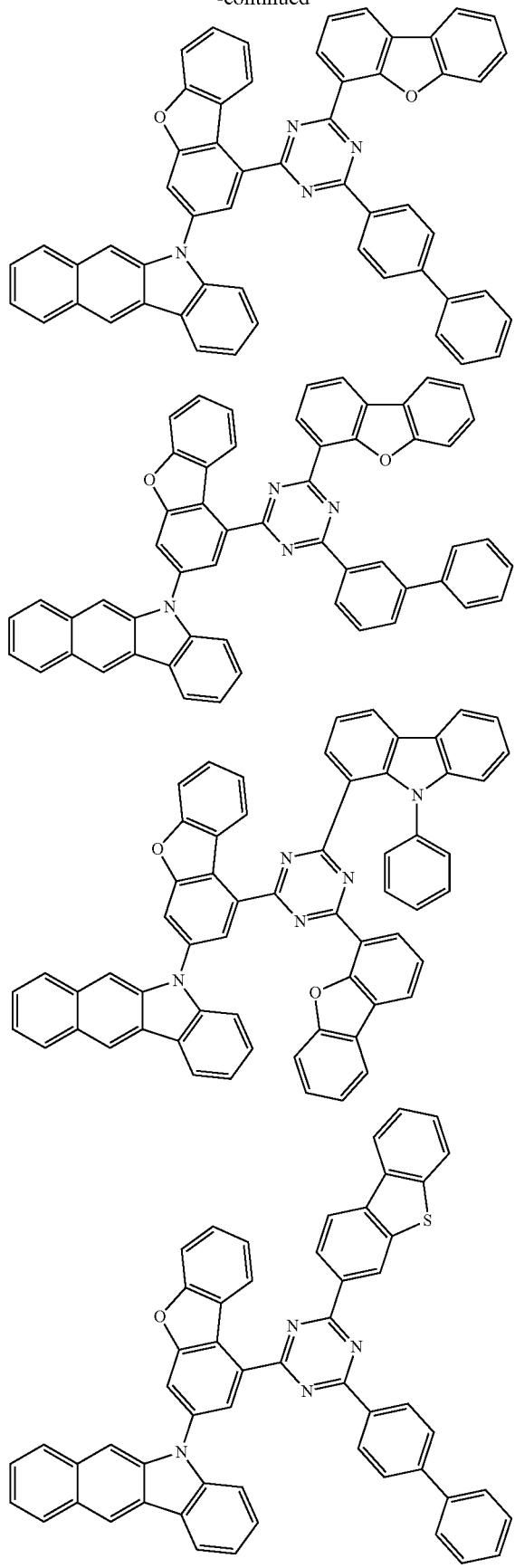
494
-continued
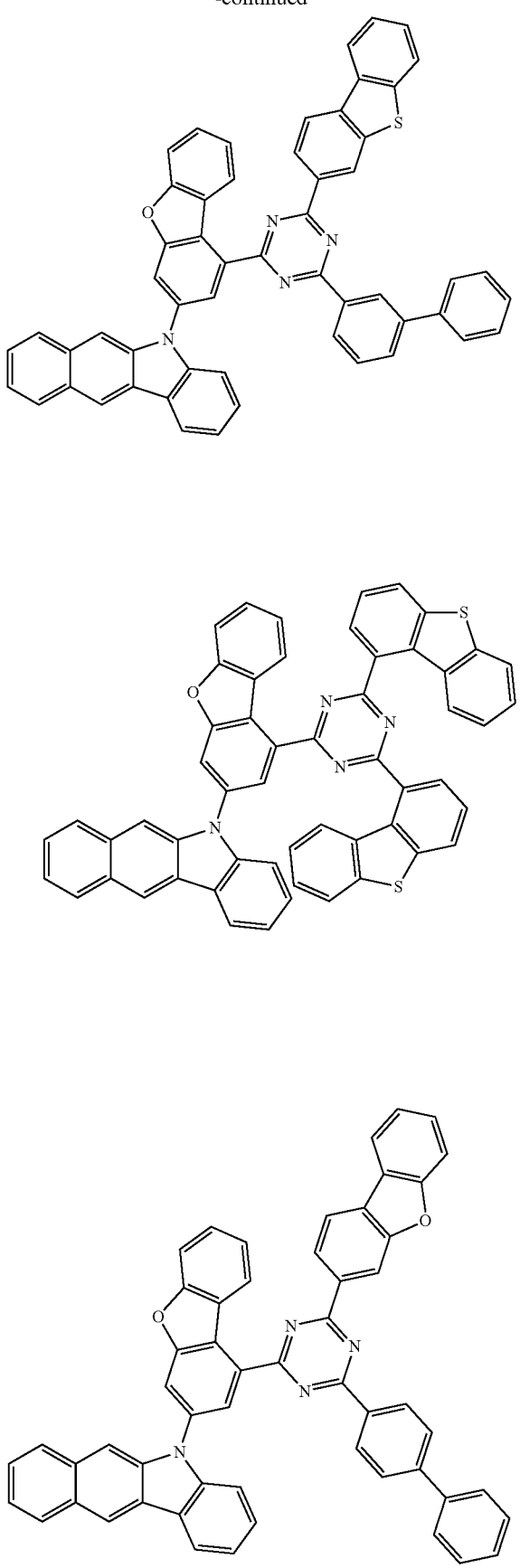

495
-continued
496
-continued
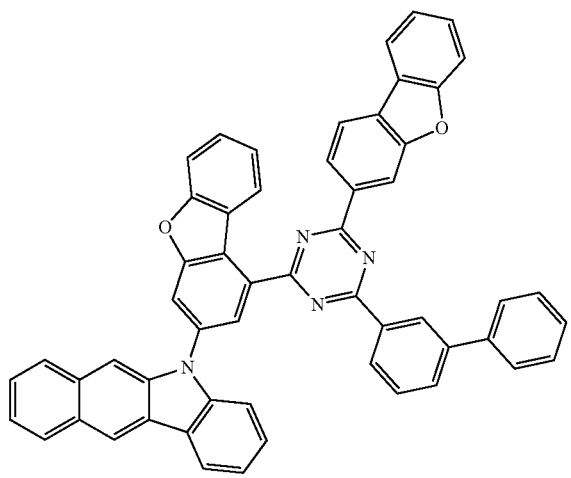
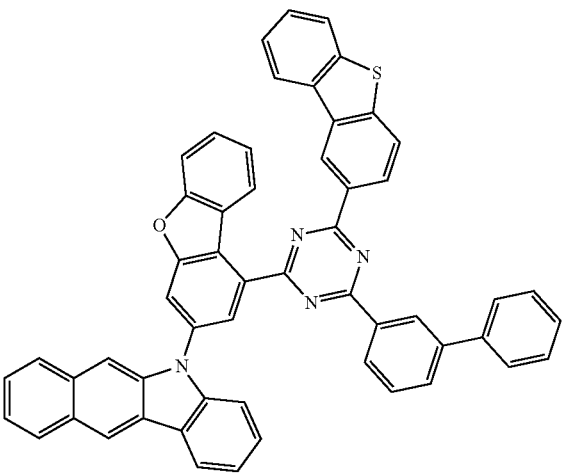
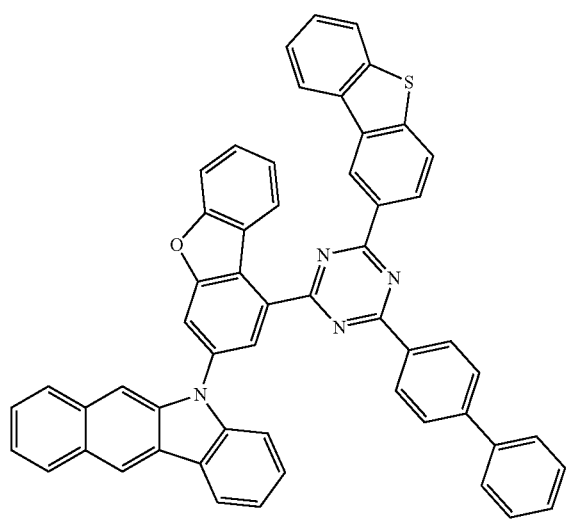
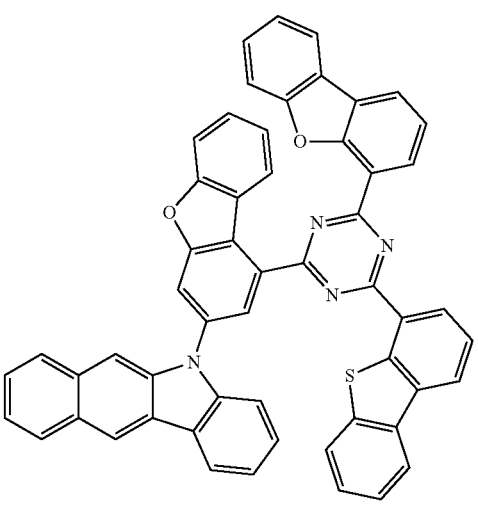

497
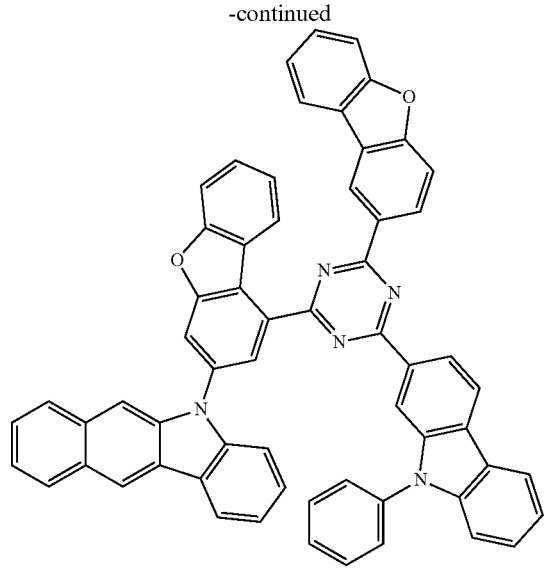
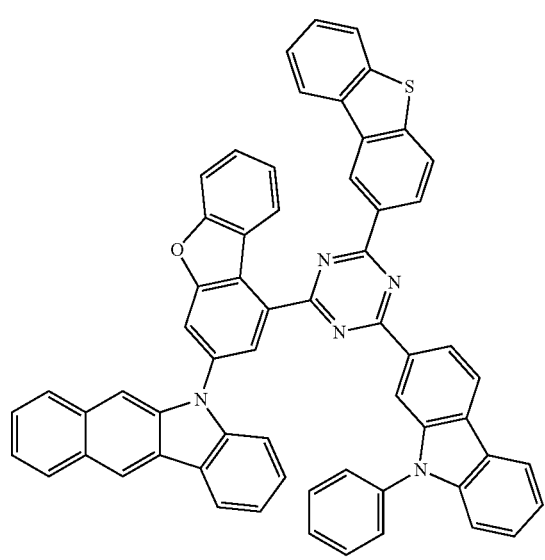
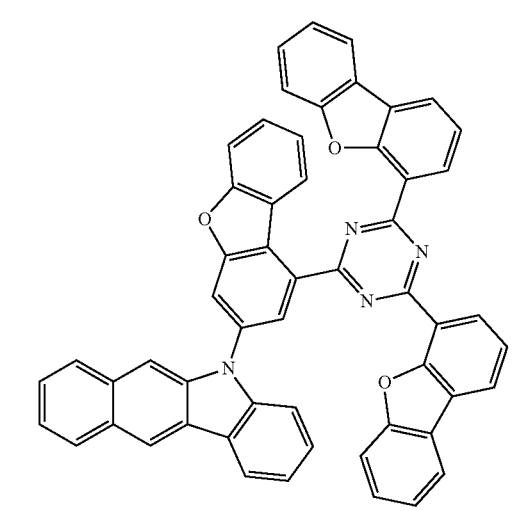
498
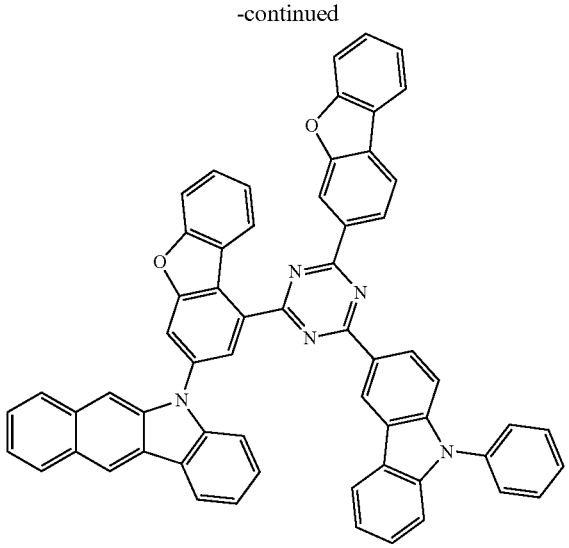
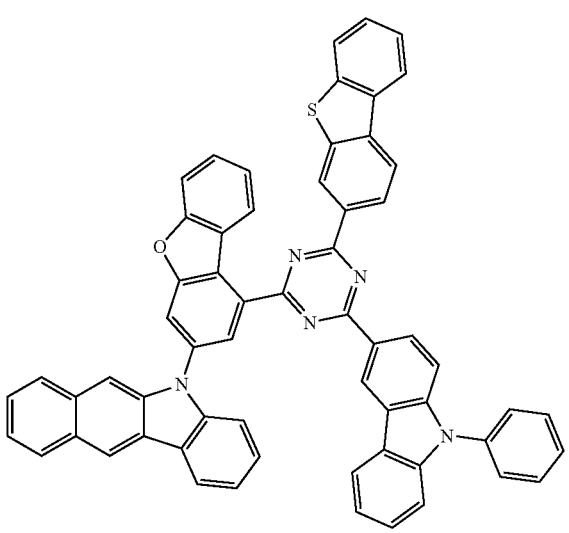
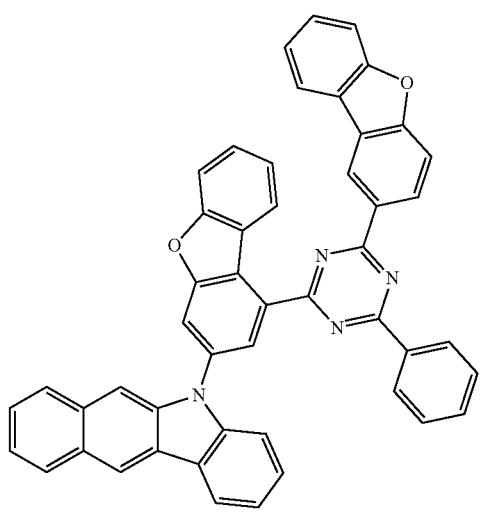

499
-continued
500
-continued
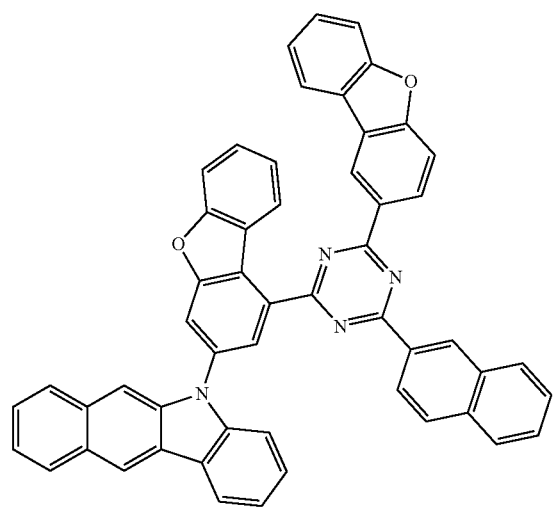
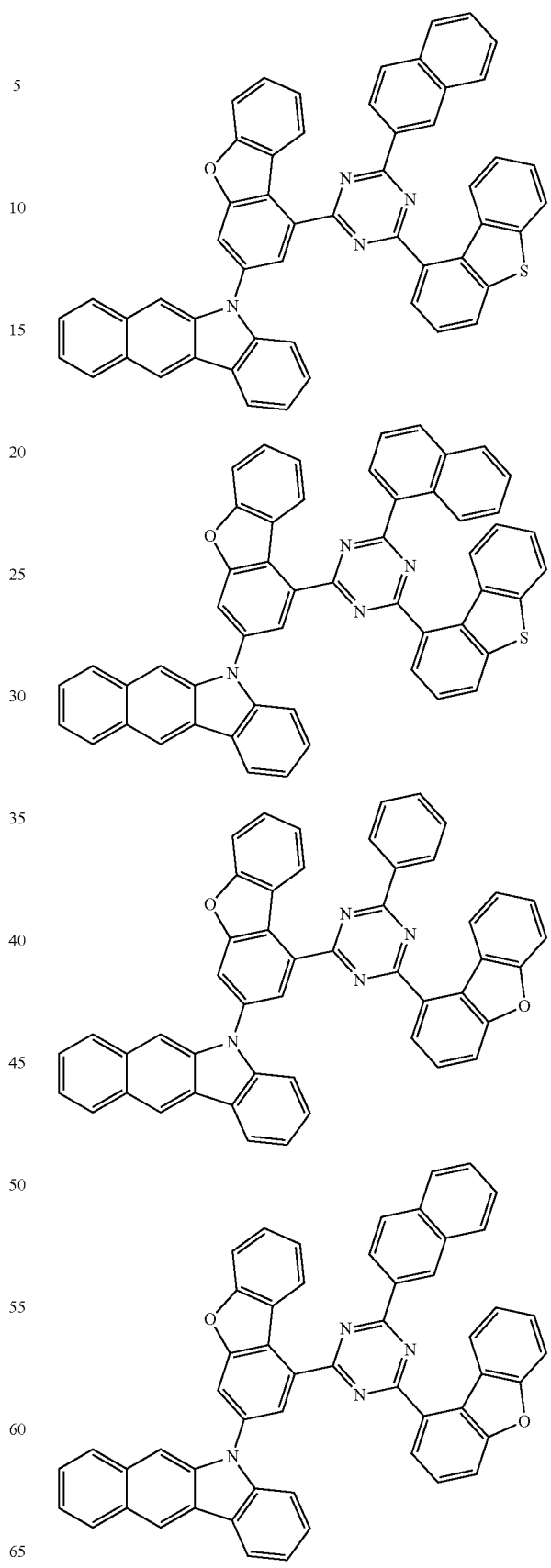

501
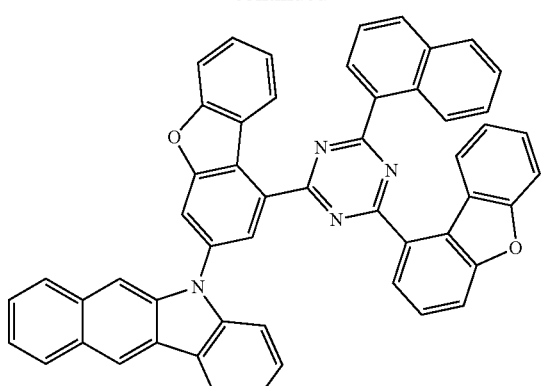
502
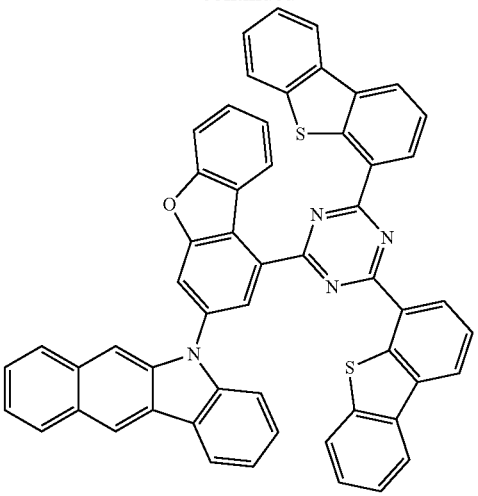
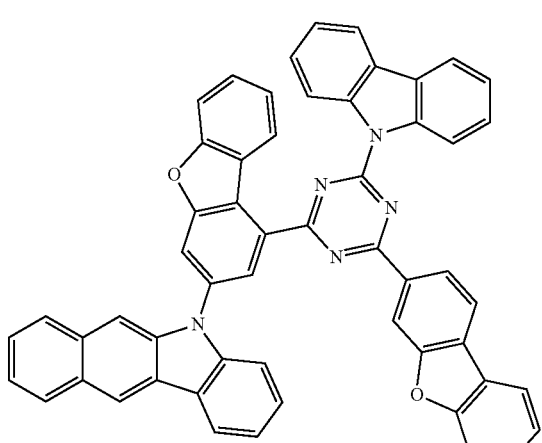
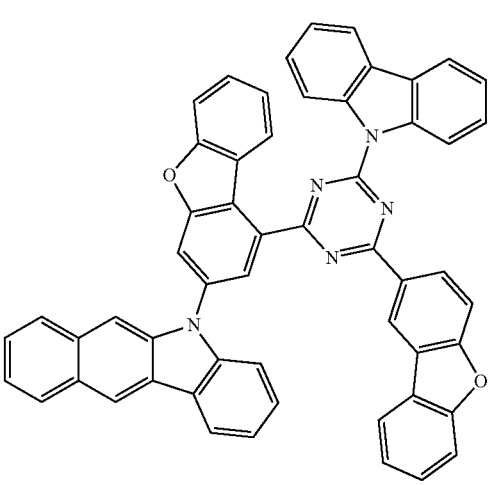
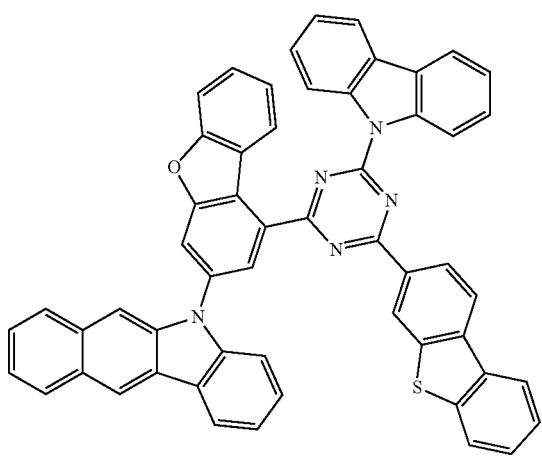
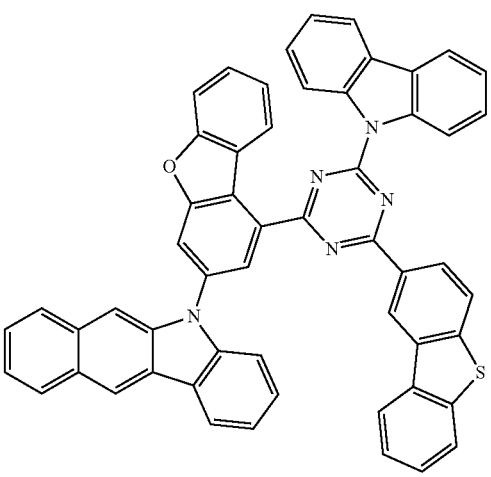

503
-continued
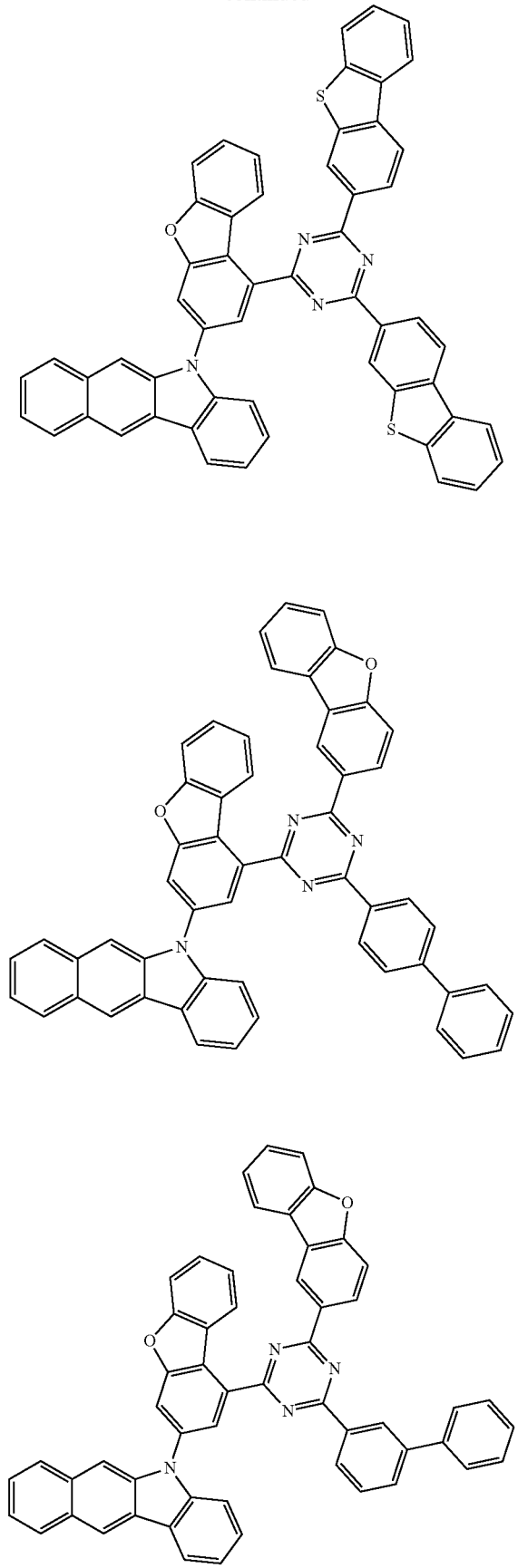
504
-continued
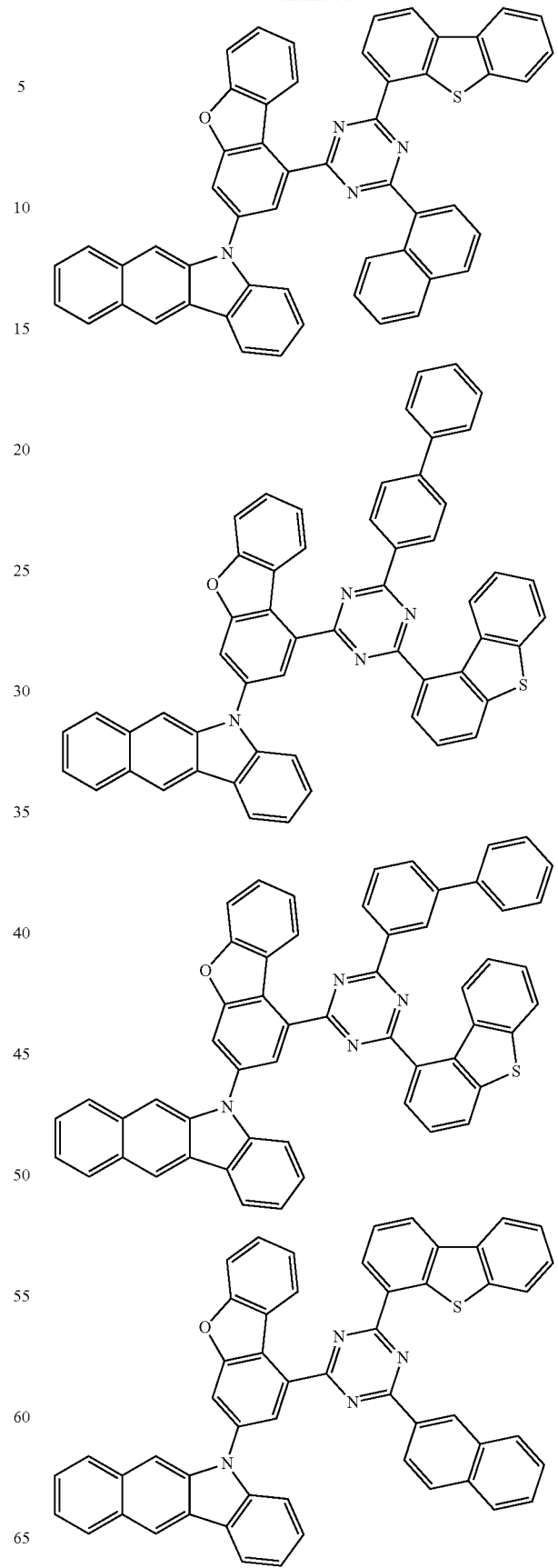

505
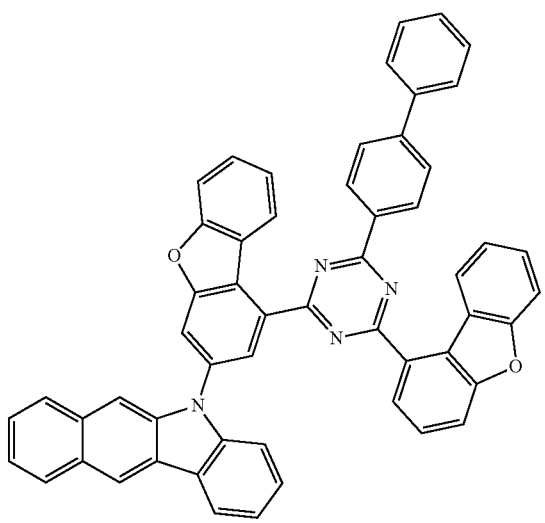
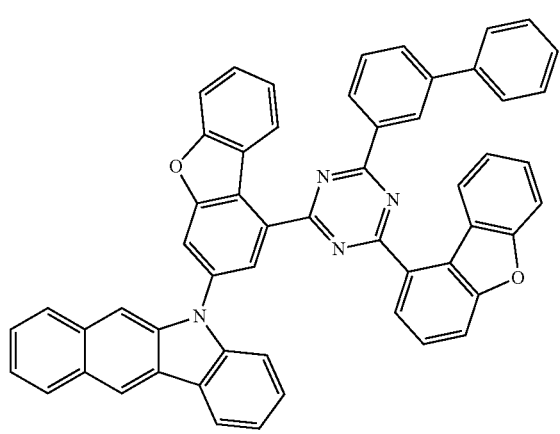
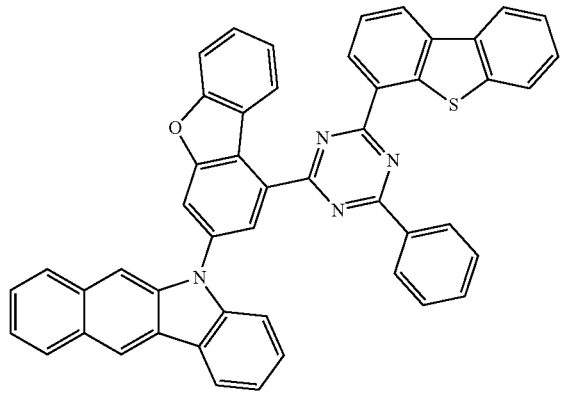
506
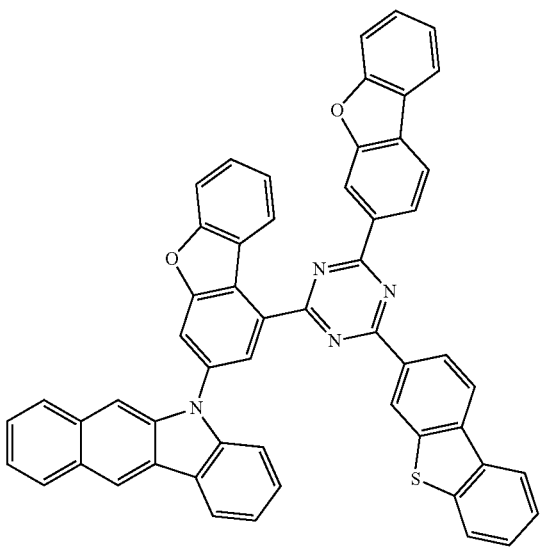
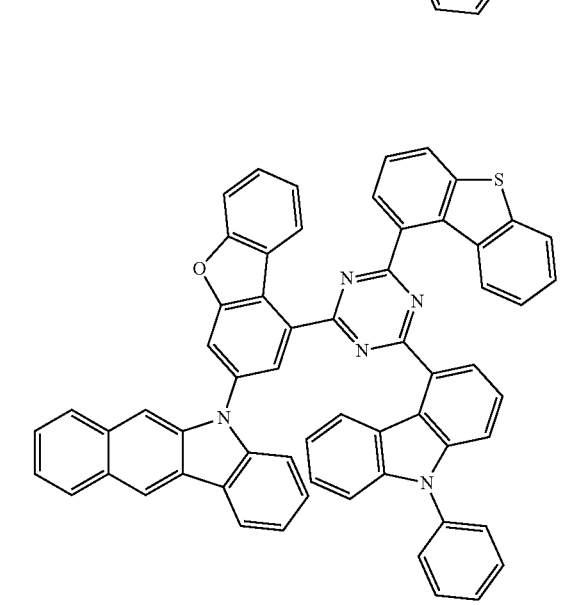

507
-continued
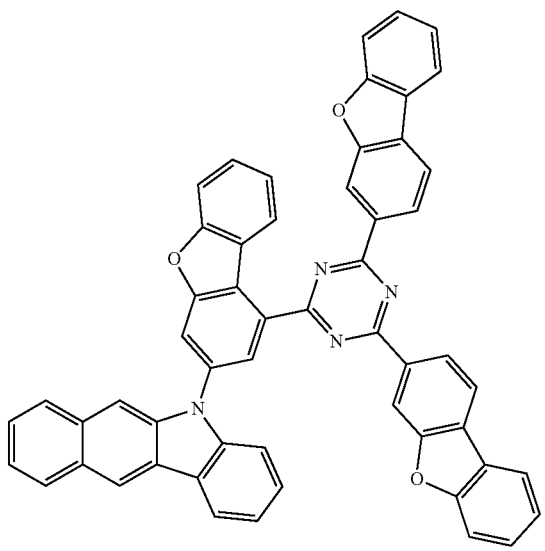
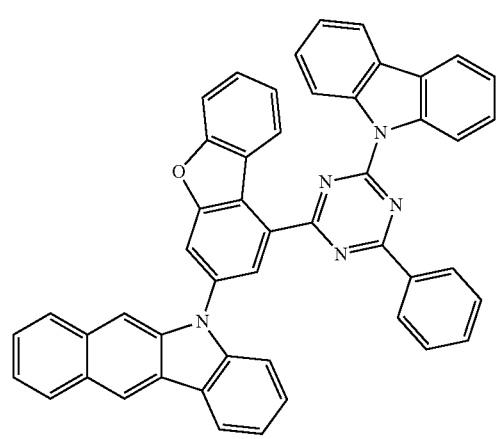
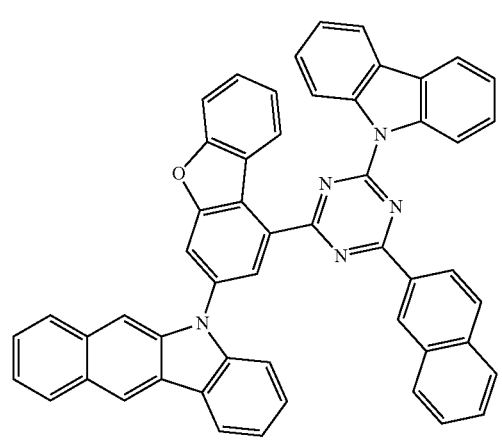
508
-continued
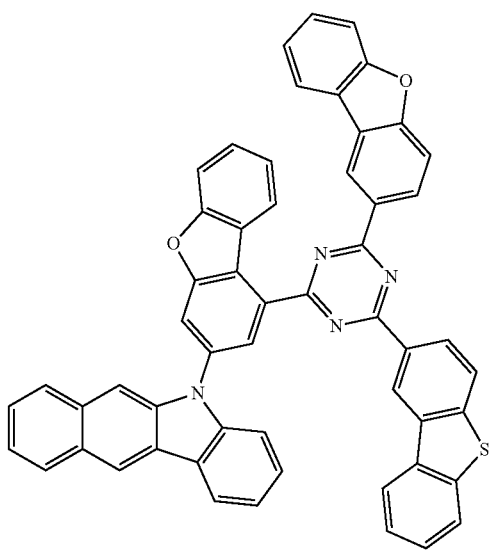
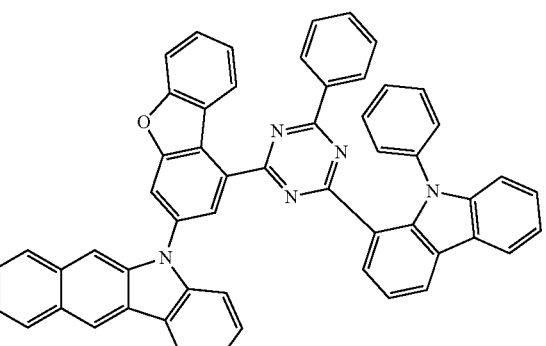
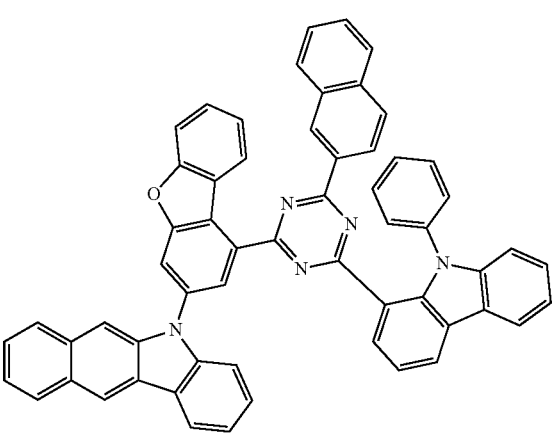

509
-continued
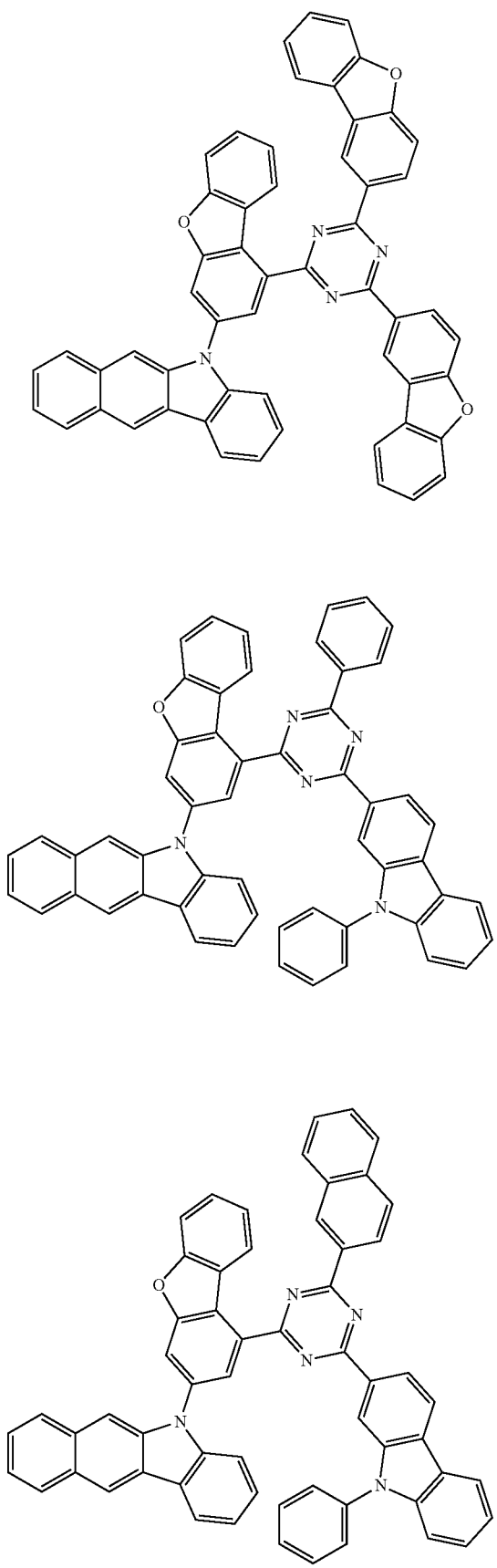
510
-continued
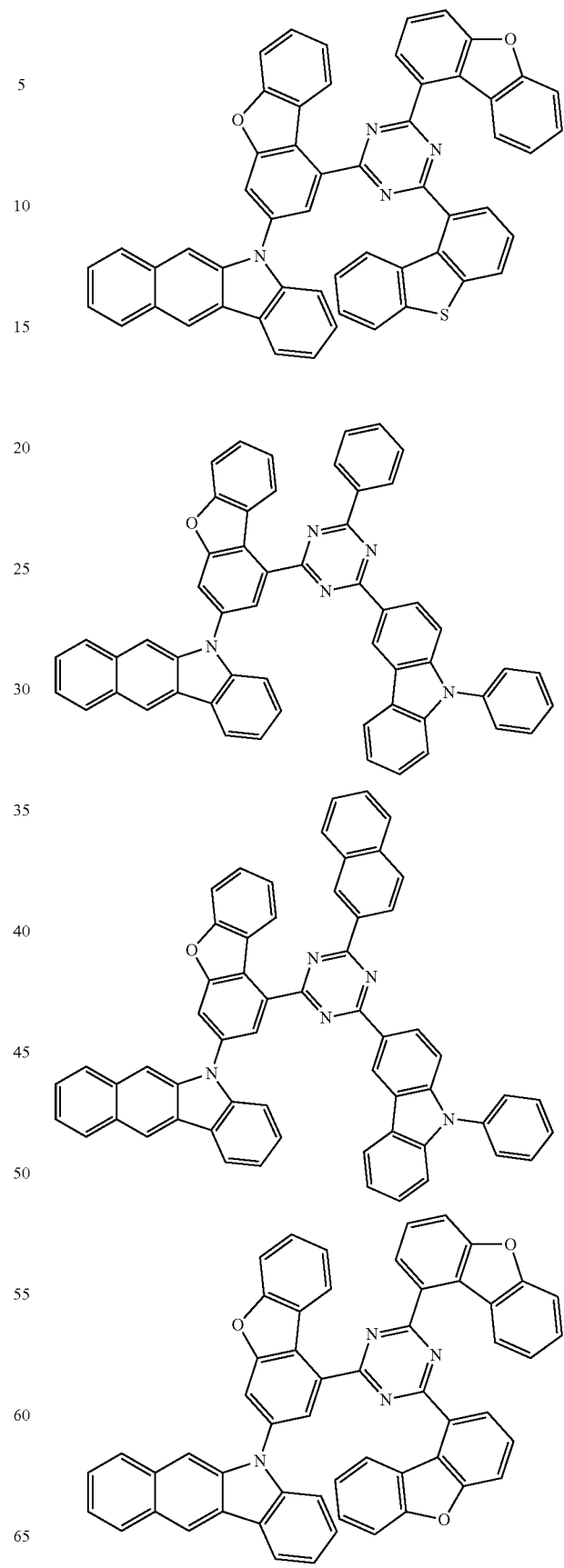

511
-continued
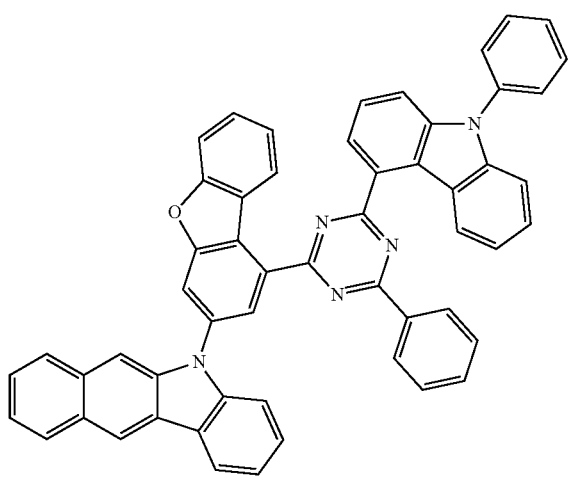
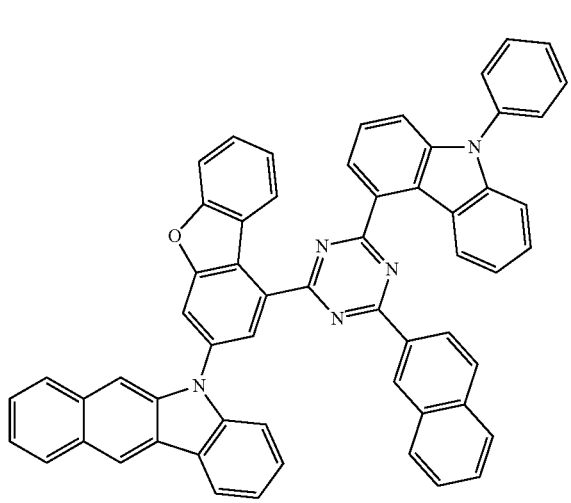
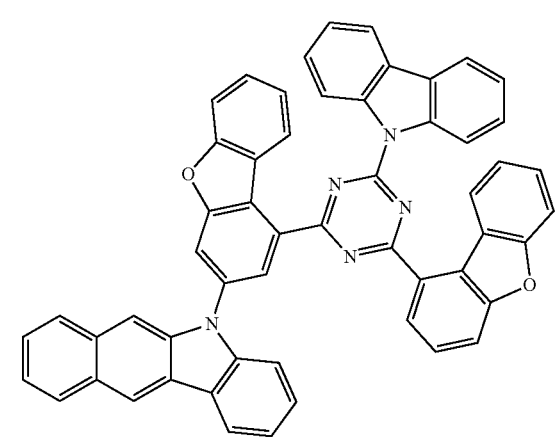
512
-continued
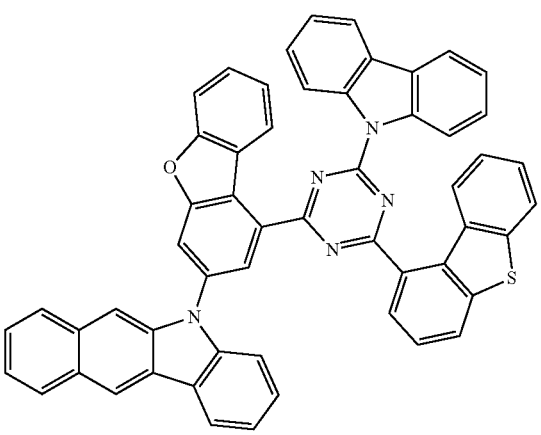
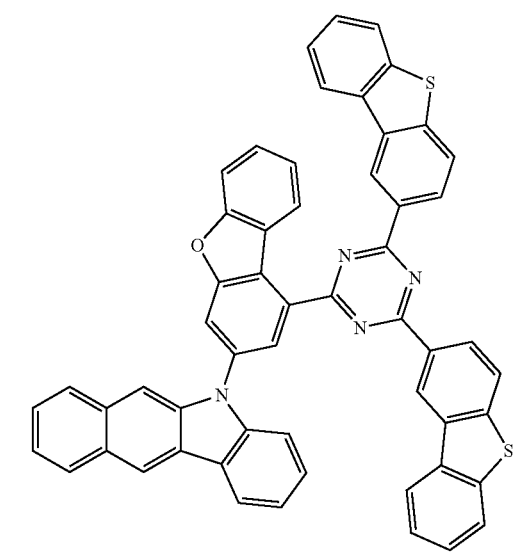
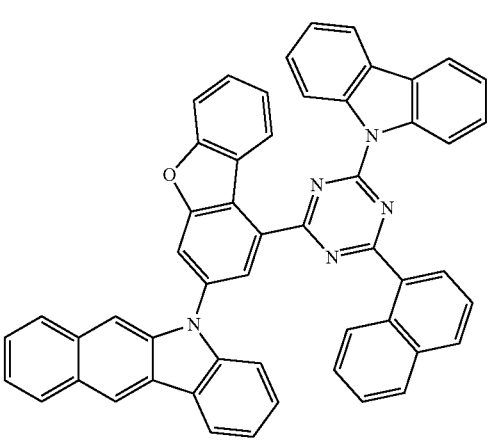

513
-continued
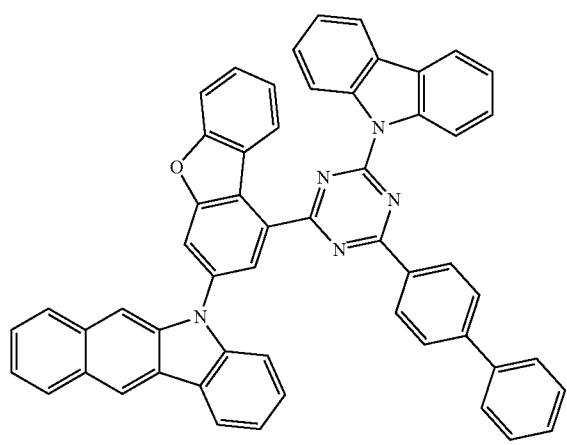
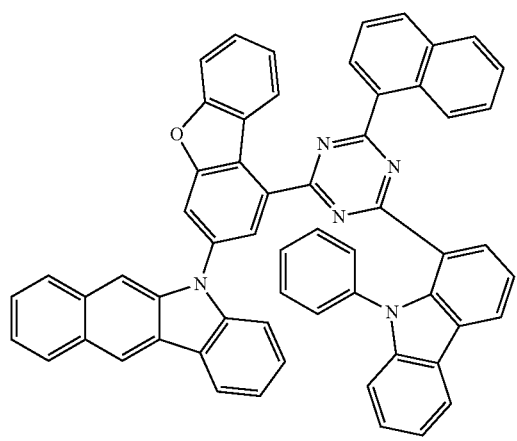
514
-continued
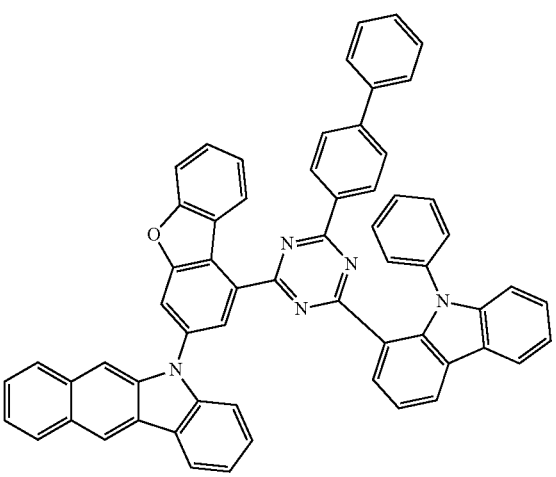
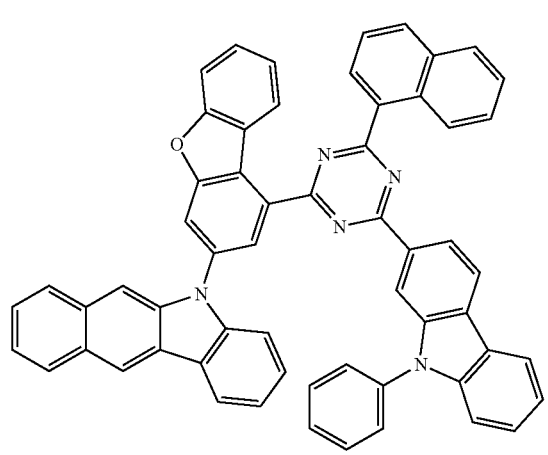

515
-continued
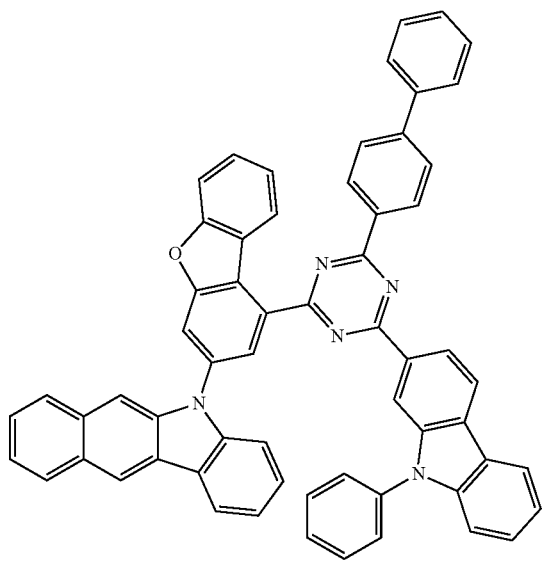
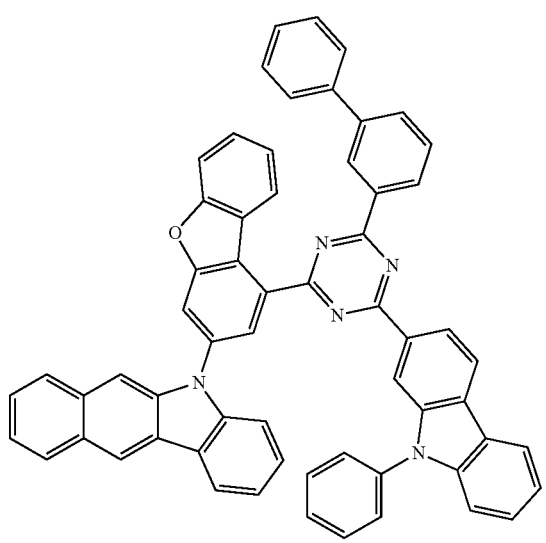
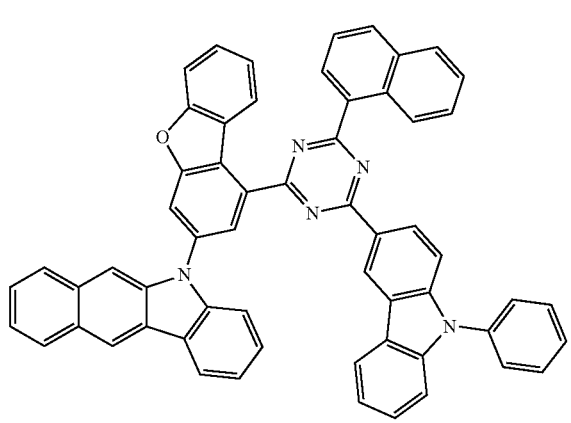
516
-continued
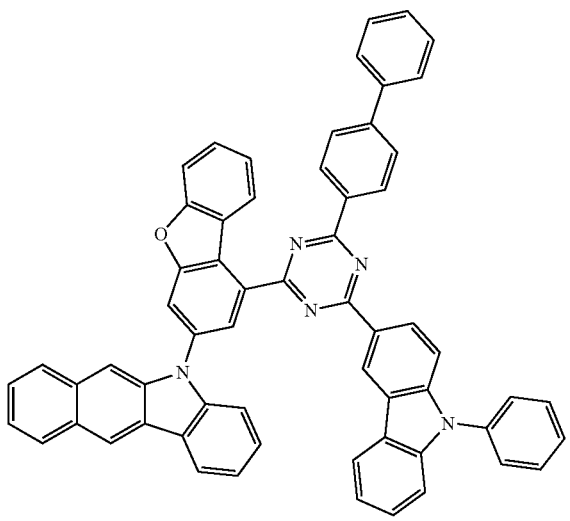
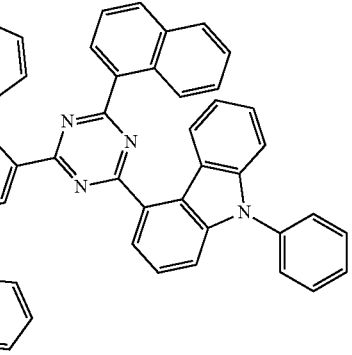

517
-continued
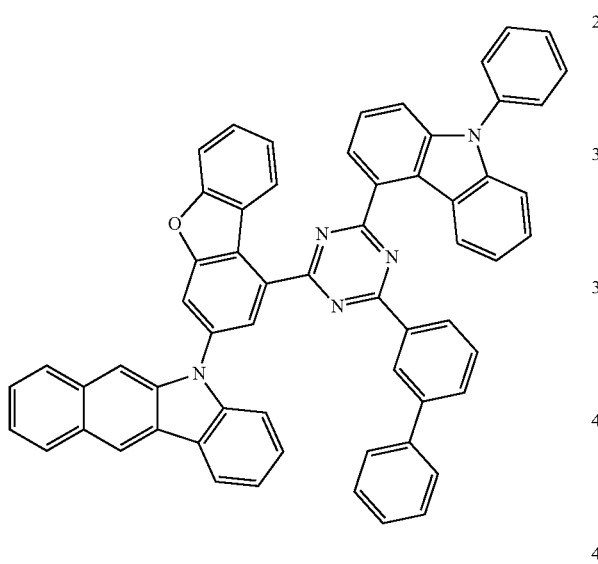
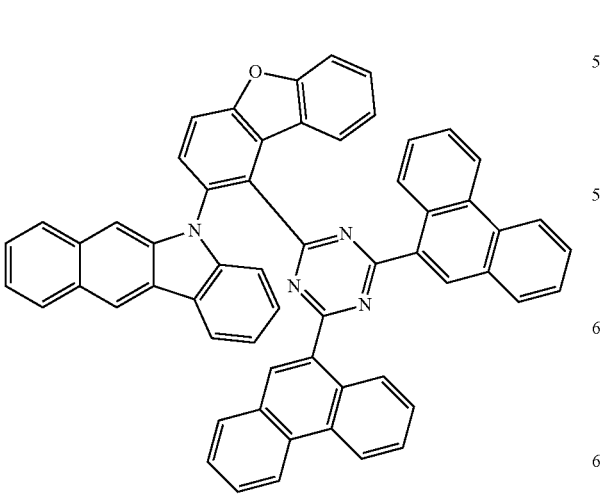
518
-continued
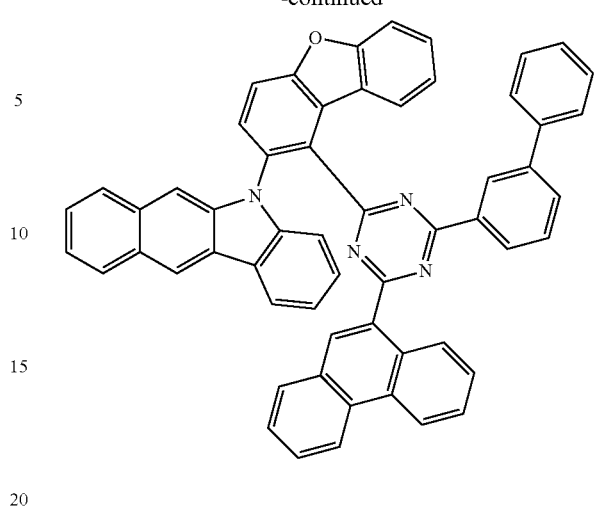
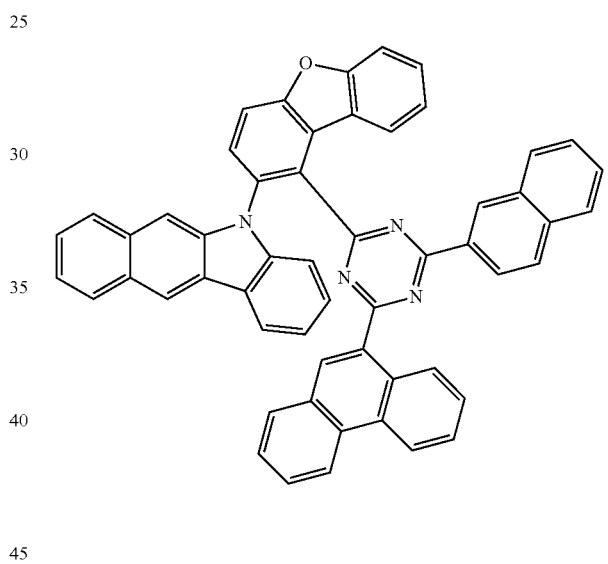
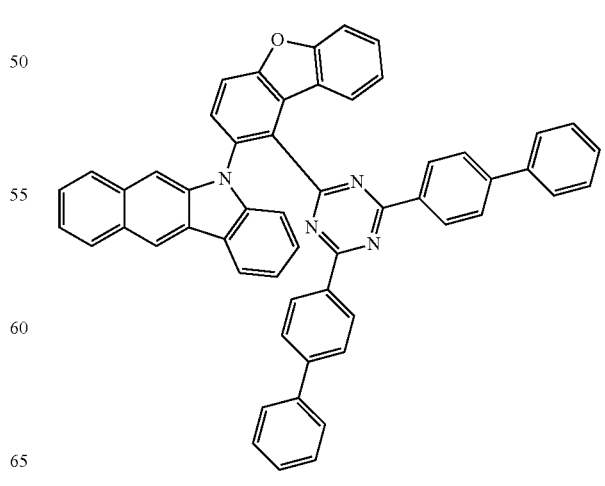

519
-continued
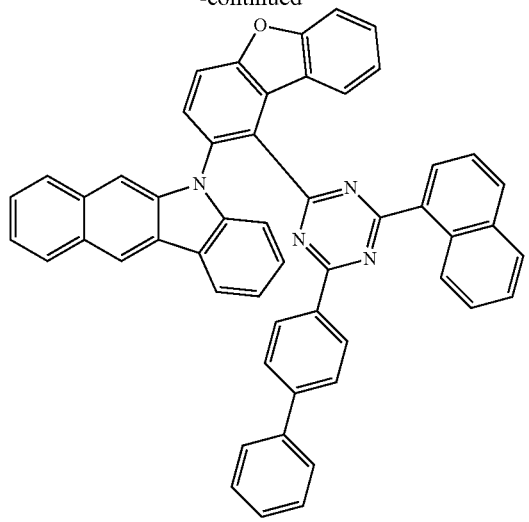
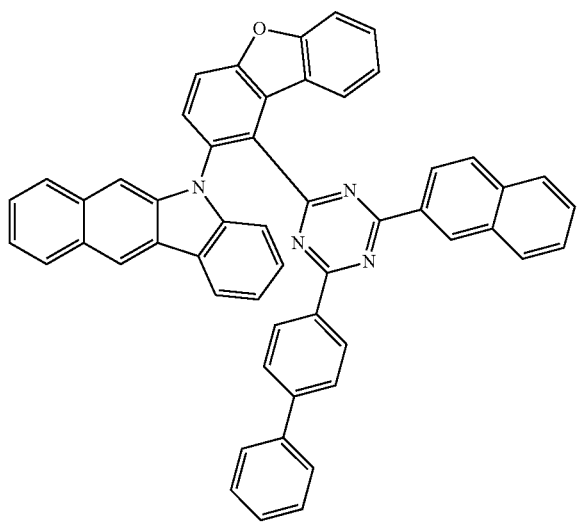
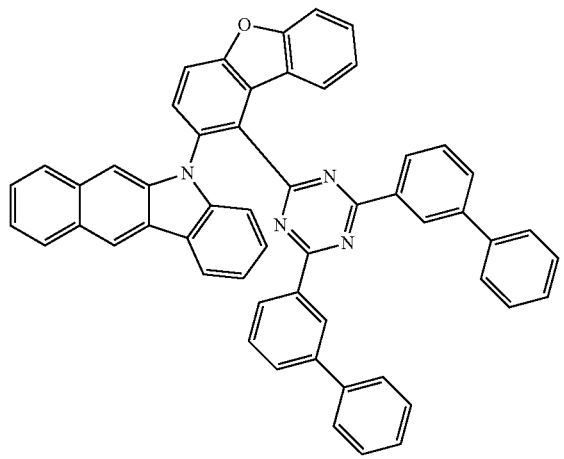
520
-continued
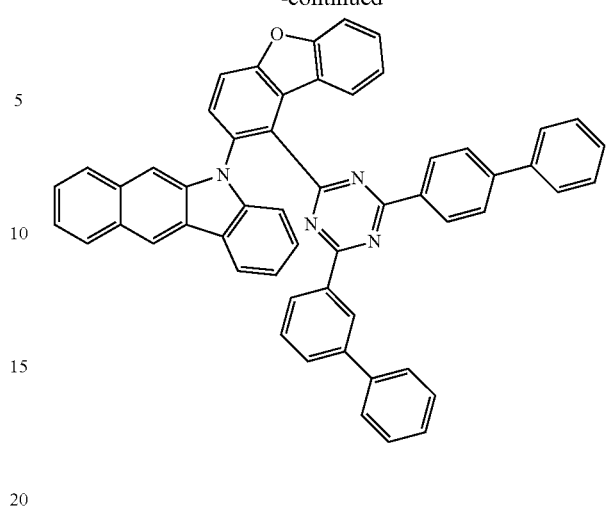
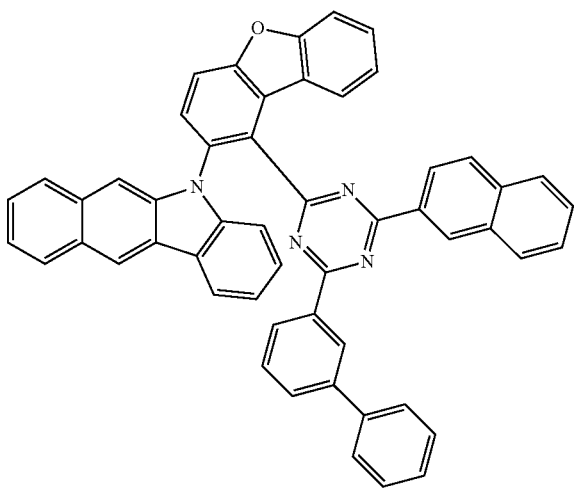
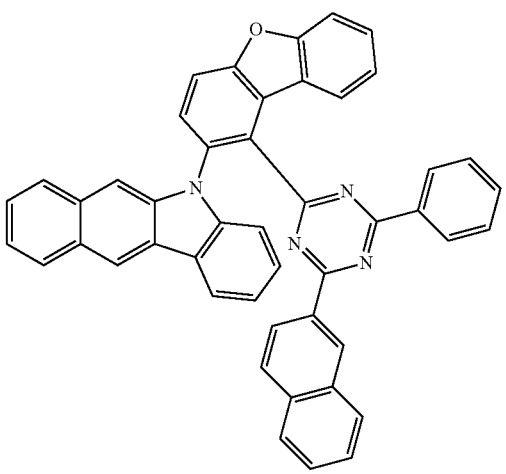

521
-continued
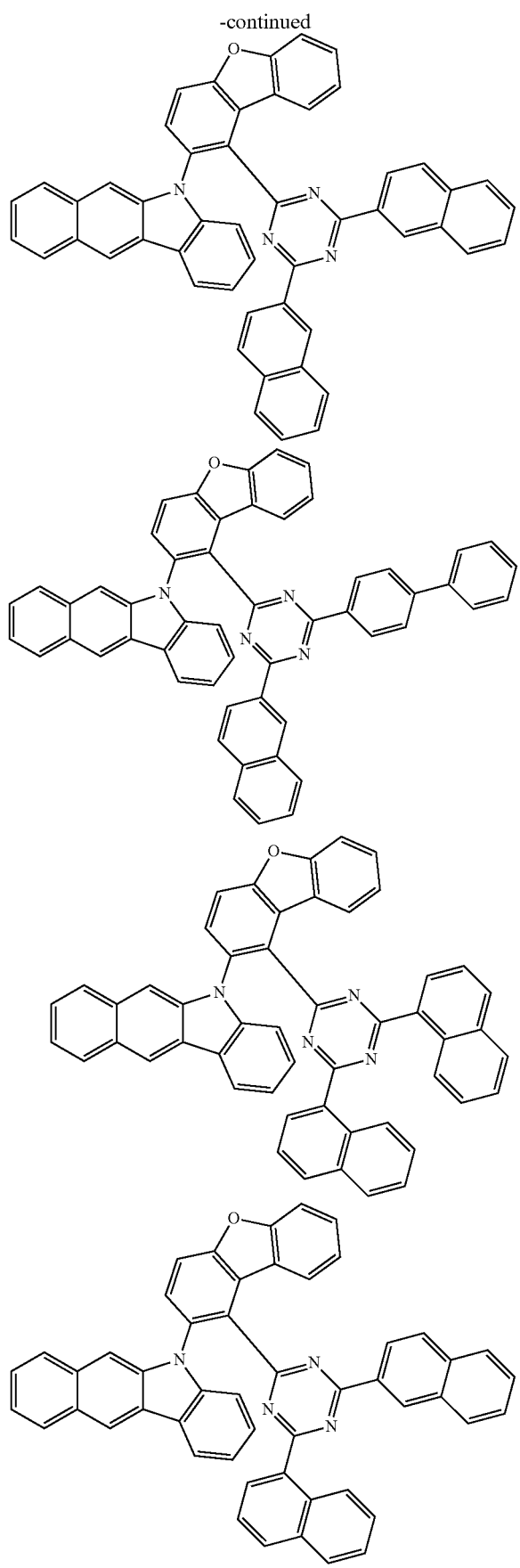
522
-continued
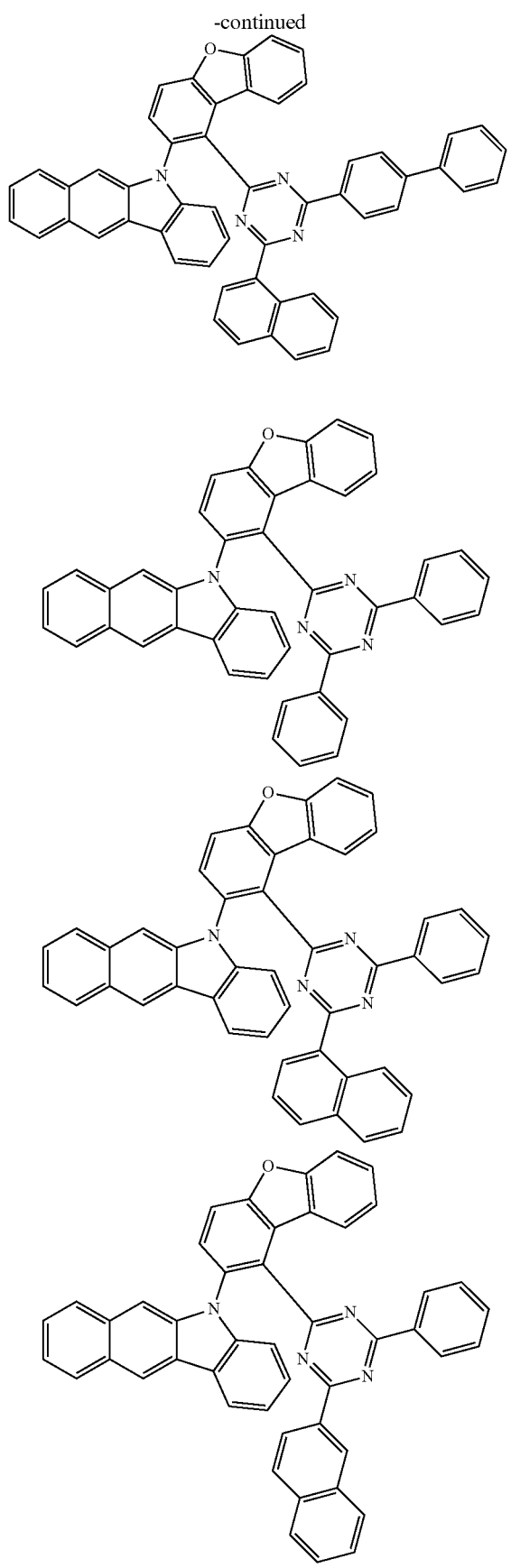

523
524
-continued
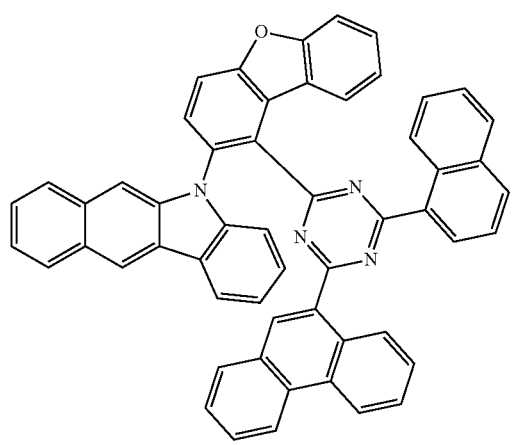
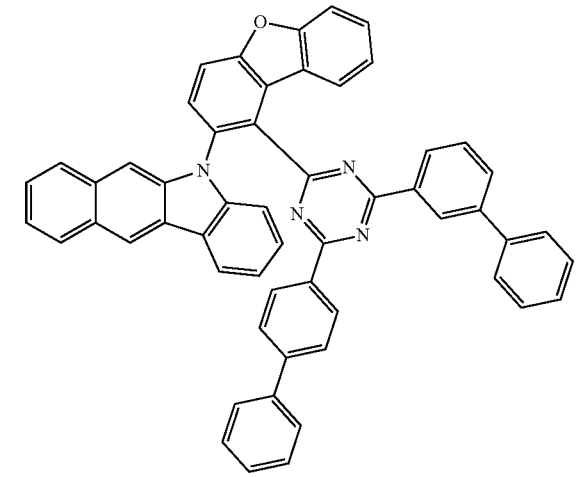
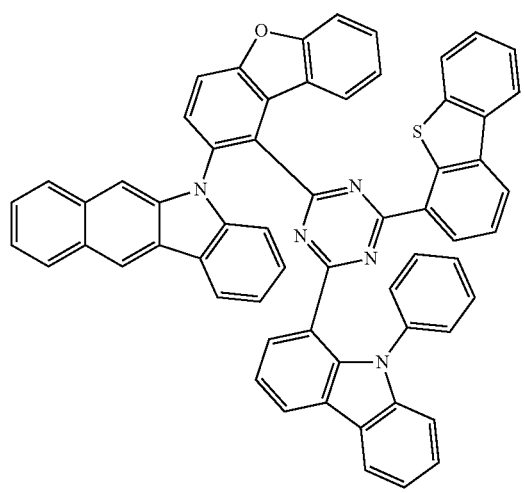
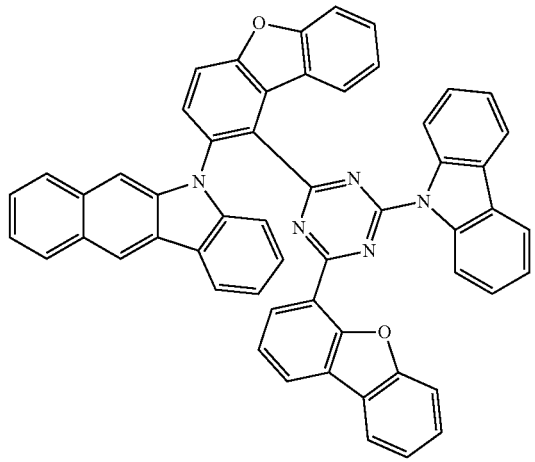

525
-continued
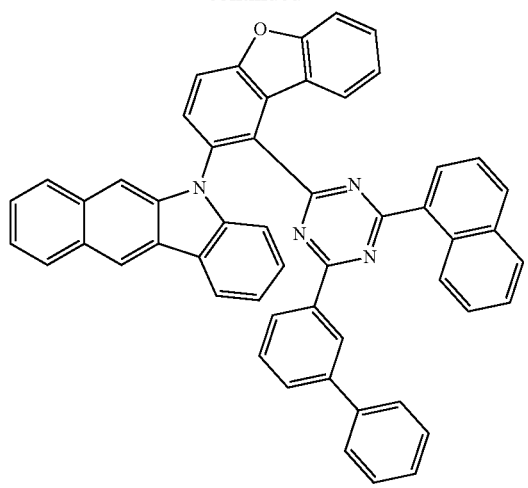
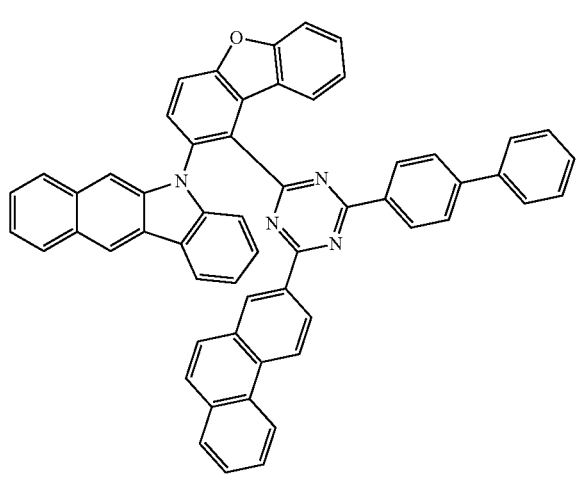
526
-continued
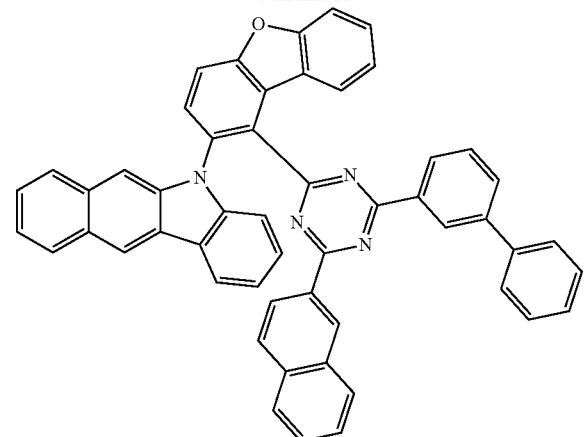
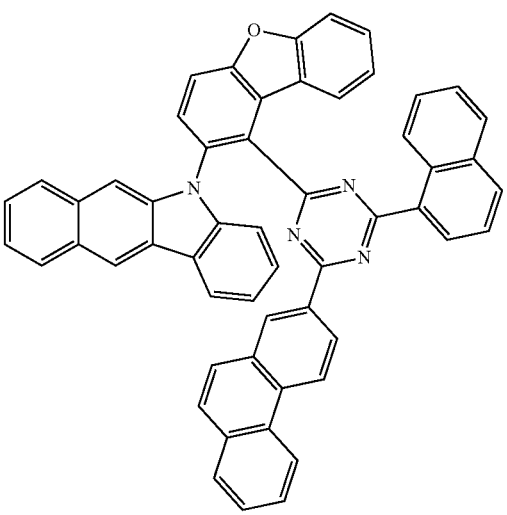
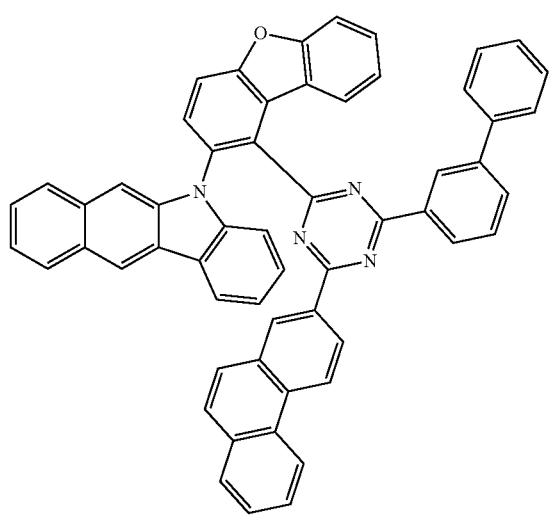
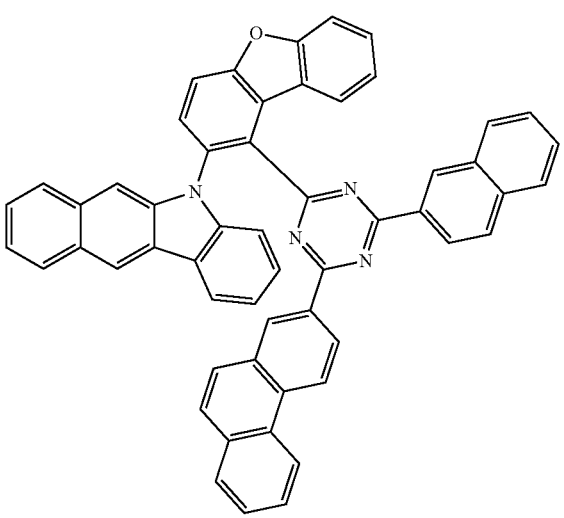

527
-continued
528
-continued
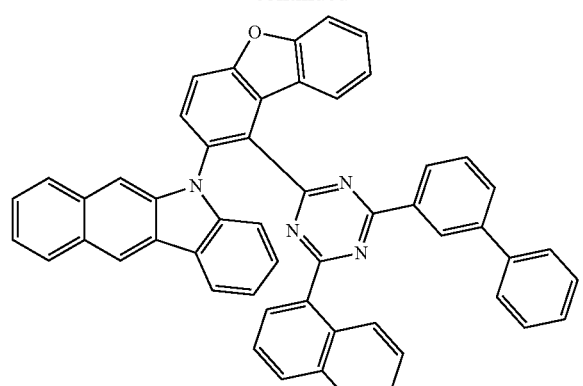
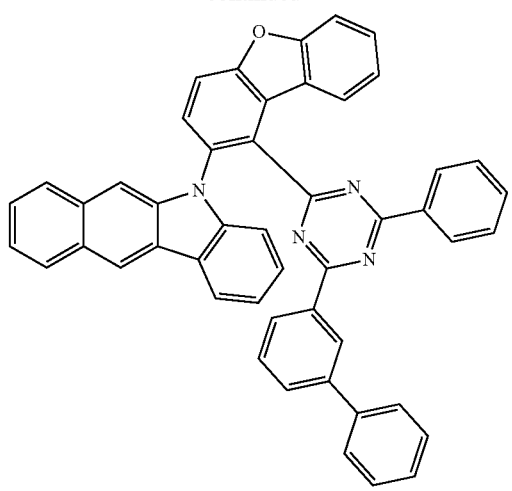
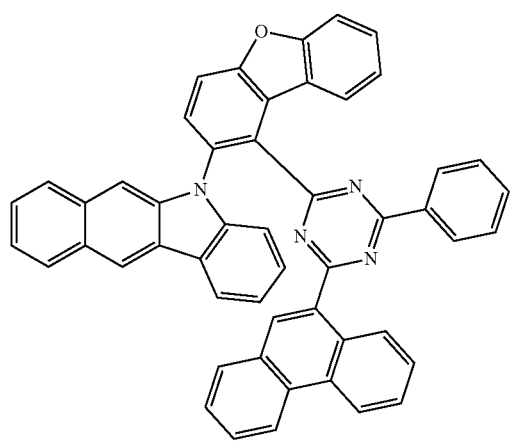
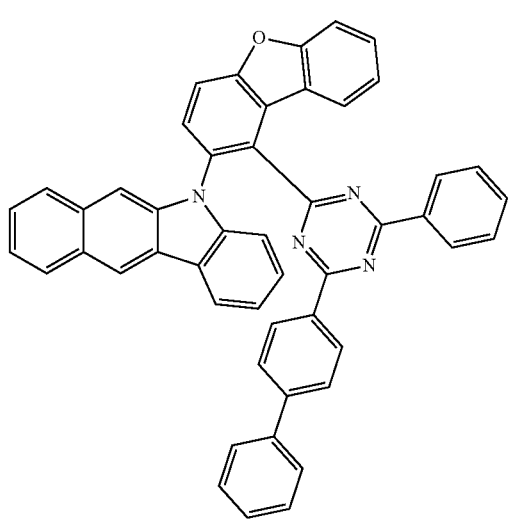
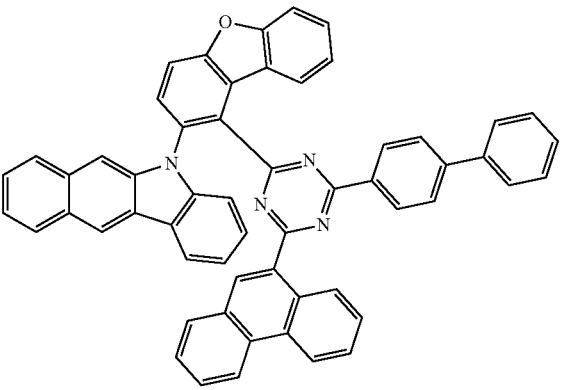

529
-continued
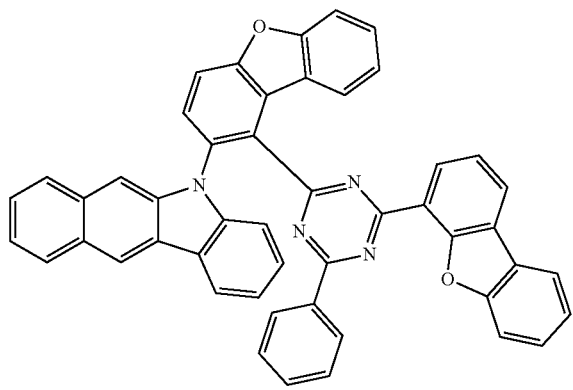
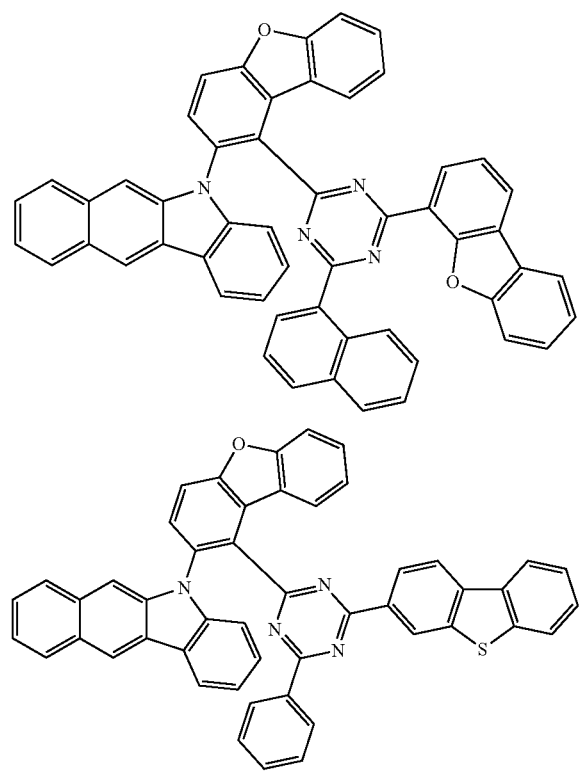
530
-continued
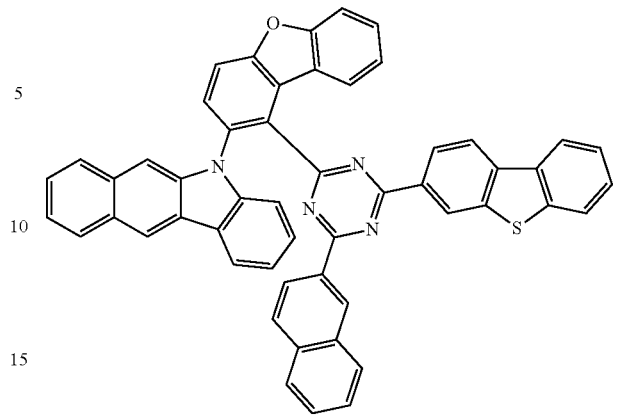
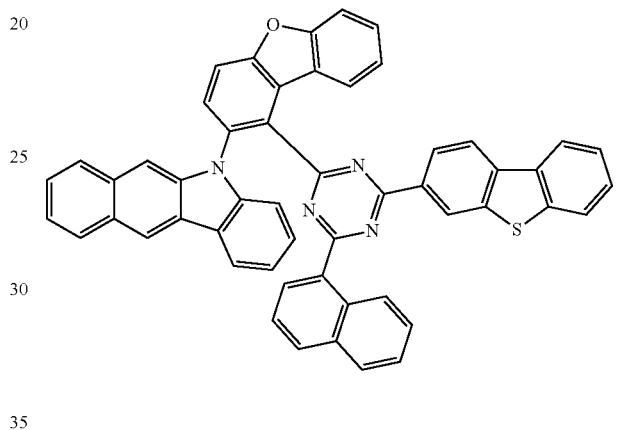
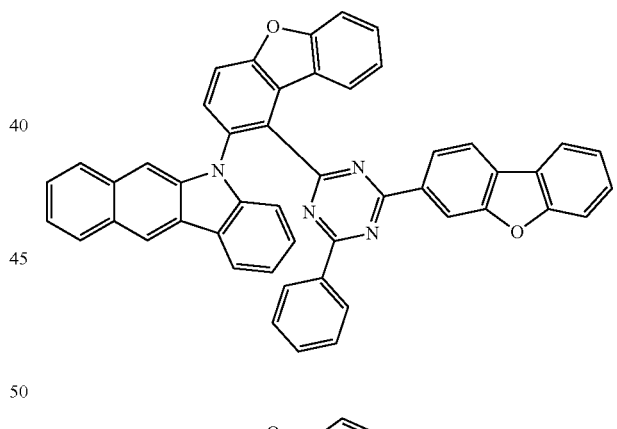
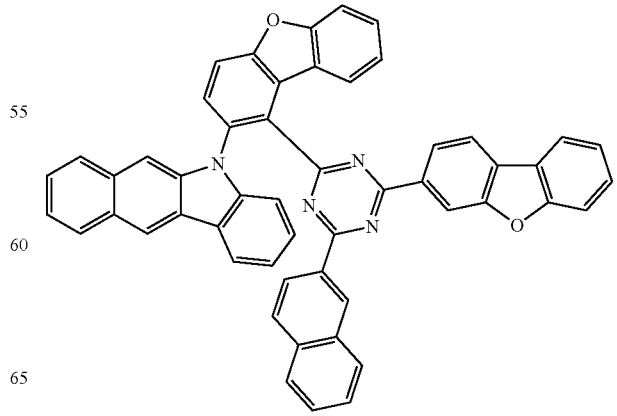

531
-continued

532
-continued

533
-continued
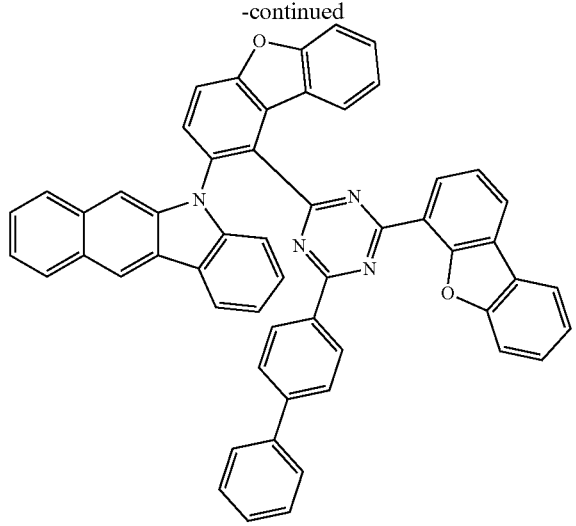
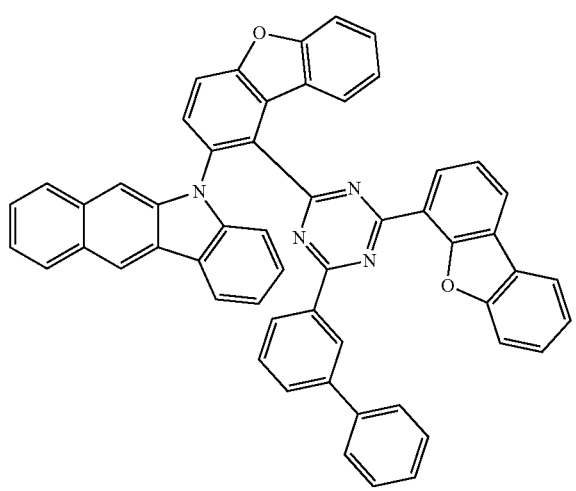
534
-continued
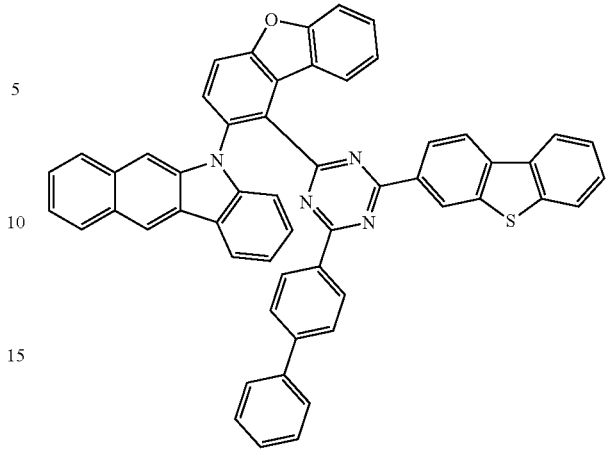
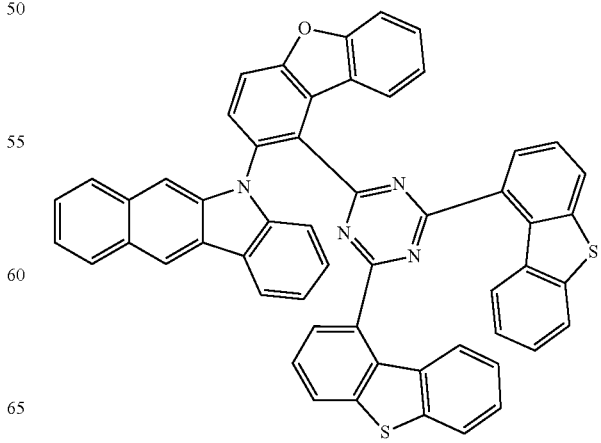

535
-continued
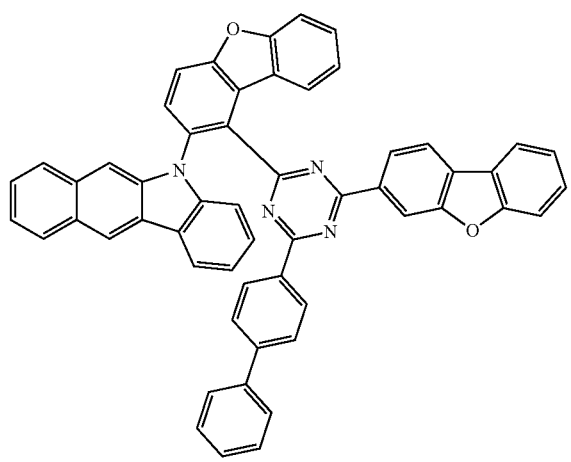
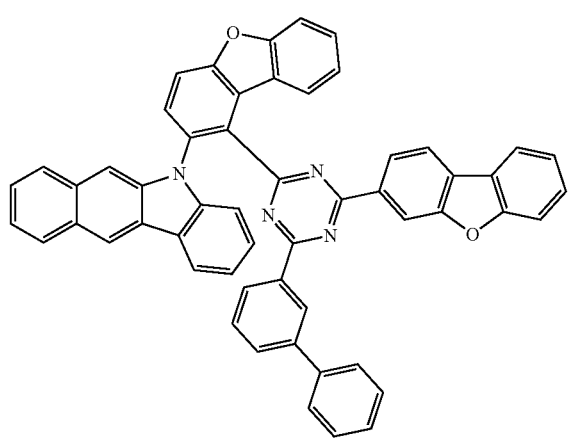
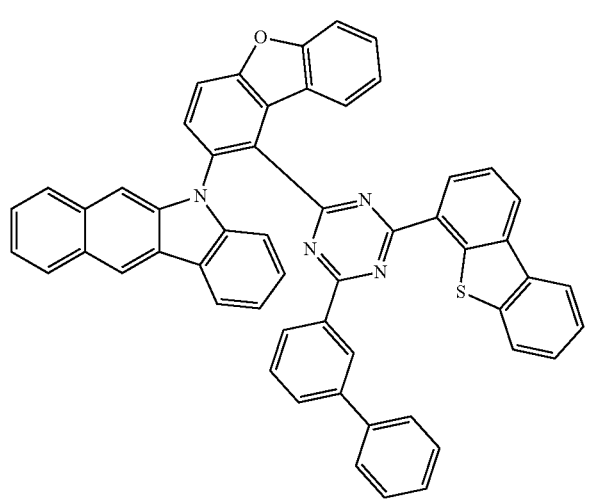
536
-continued
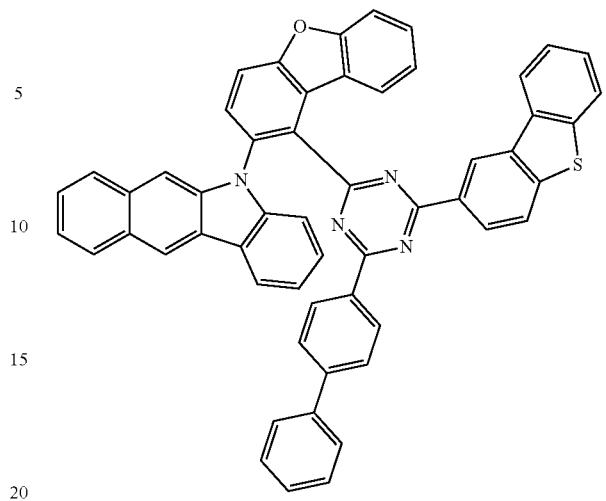
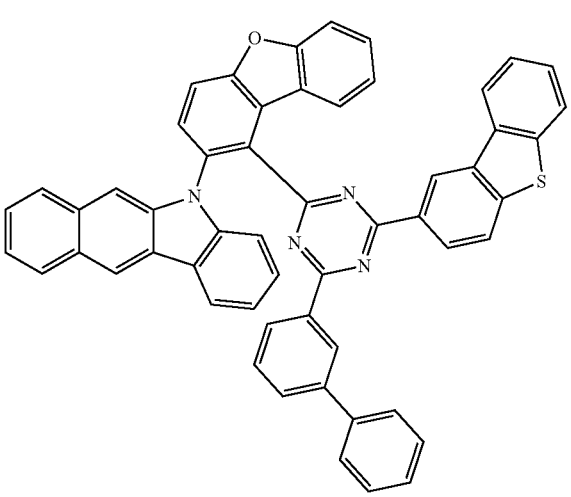
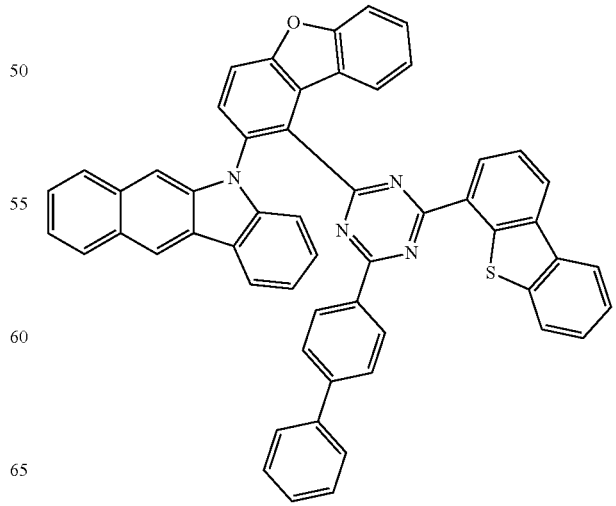

537
-continued
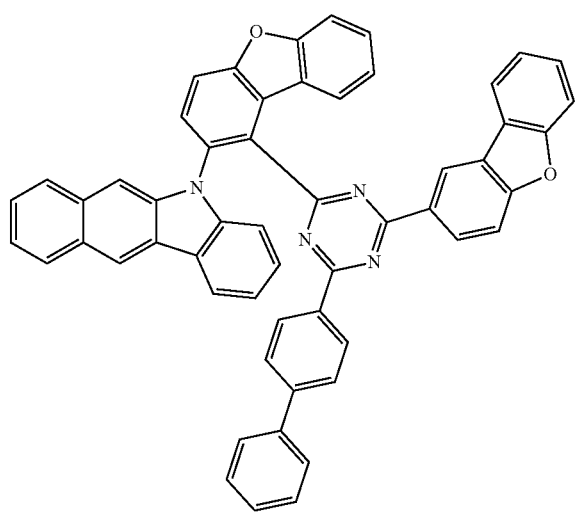
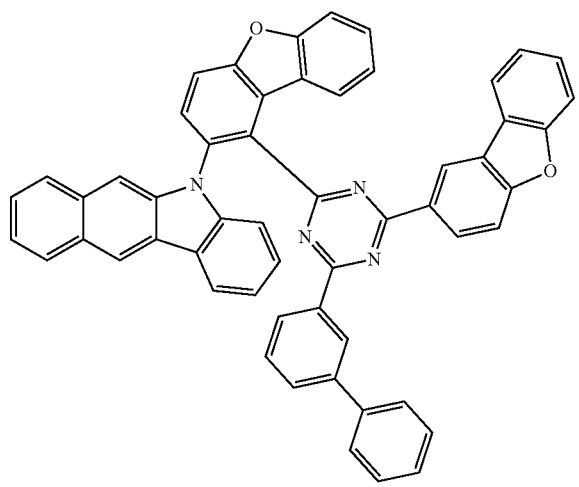
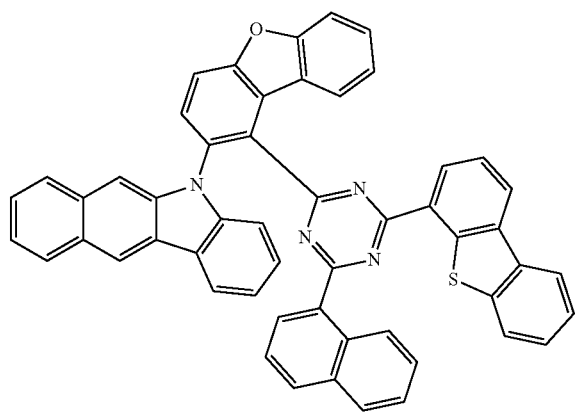
538
-continued
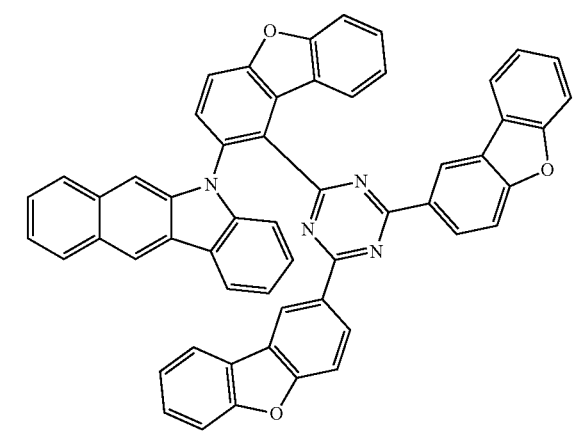
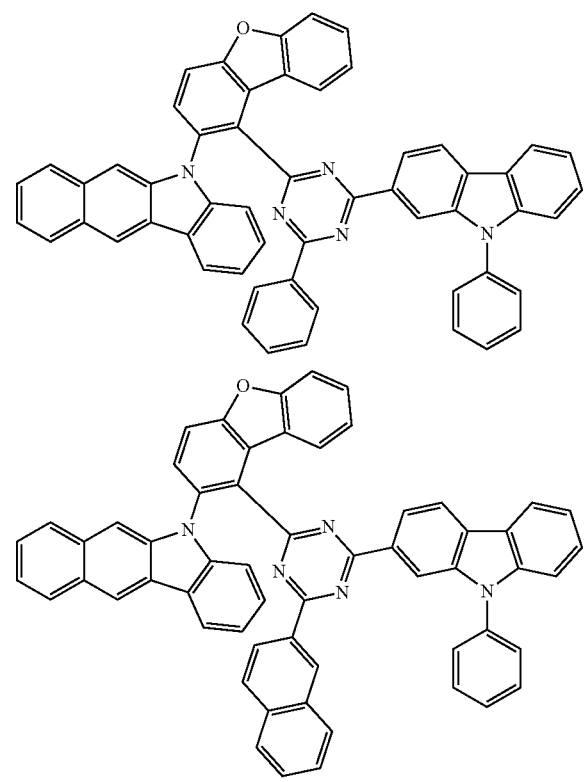
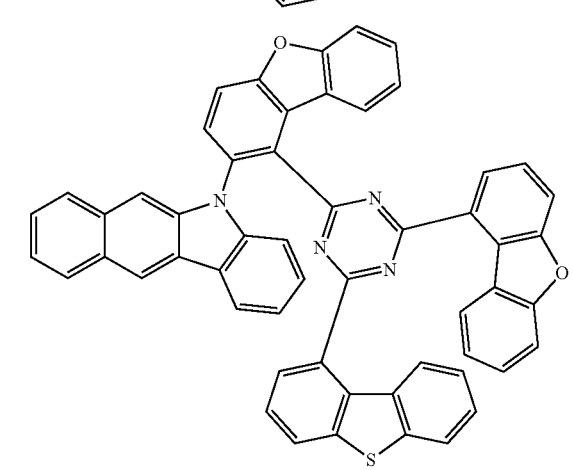

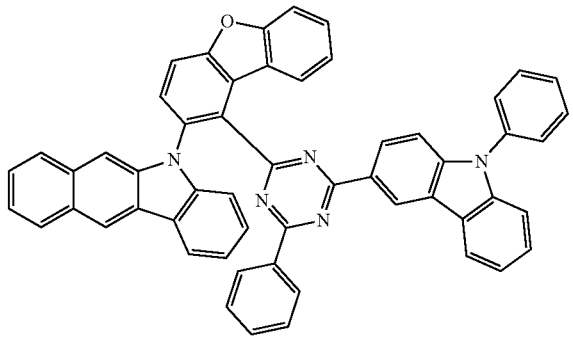
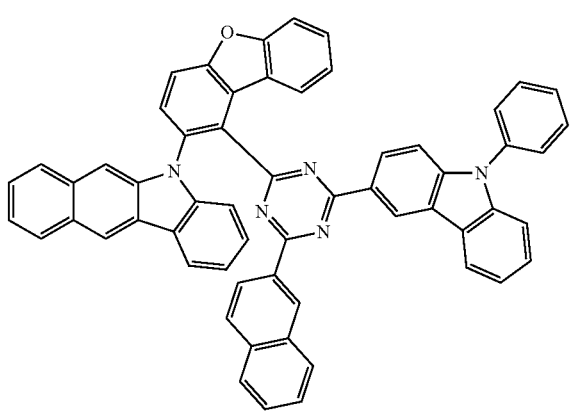
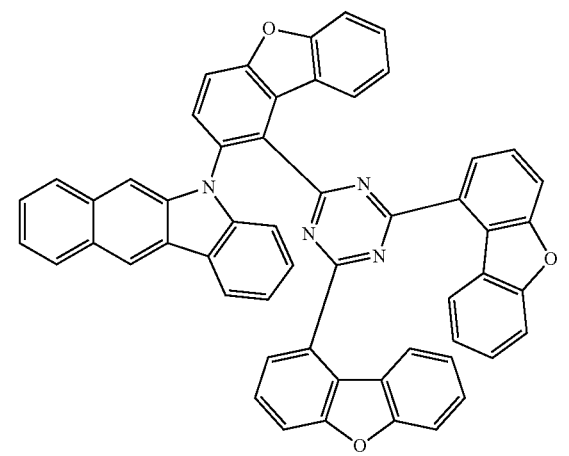
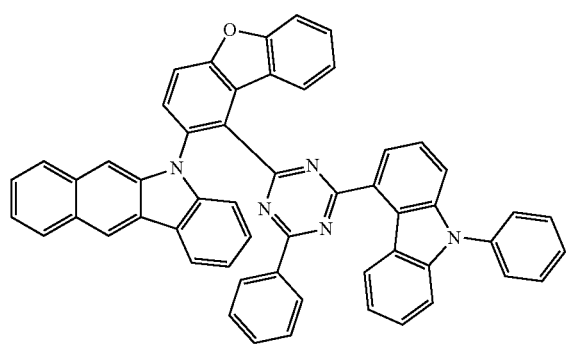
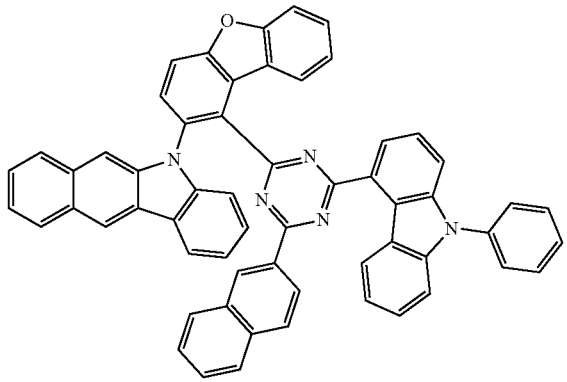
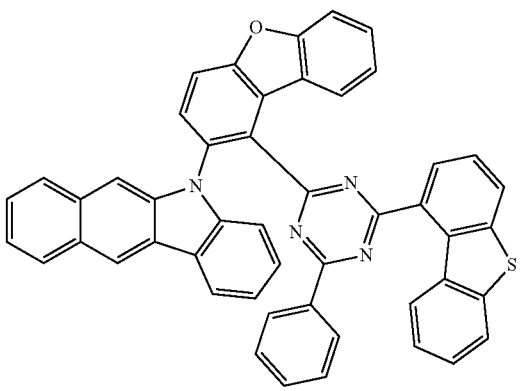
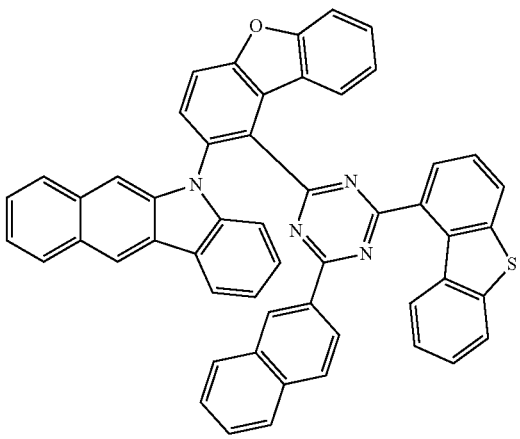
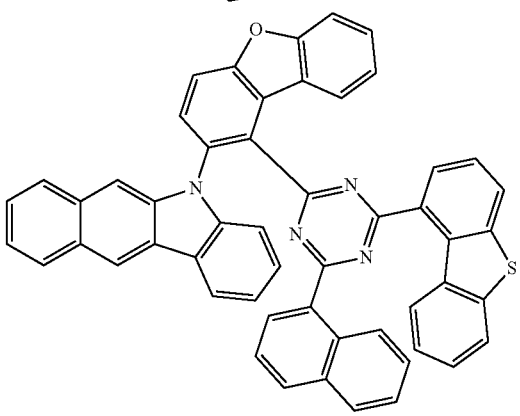

541
-continued
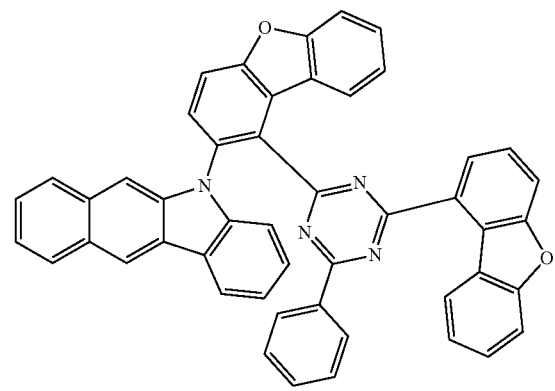
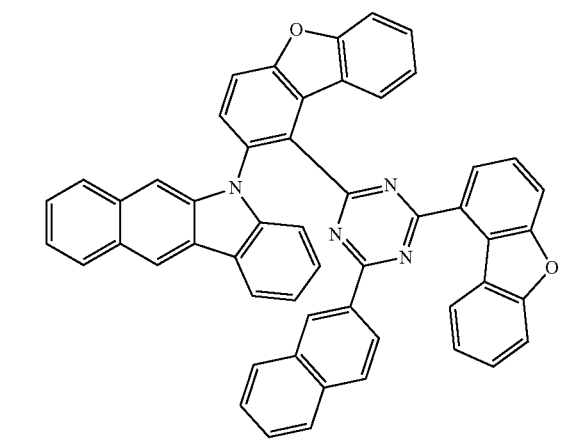
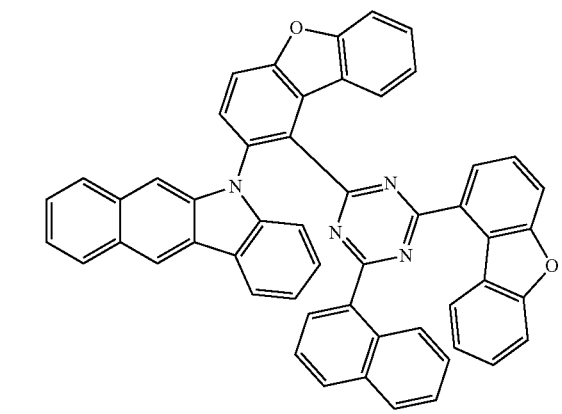
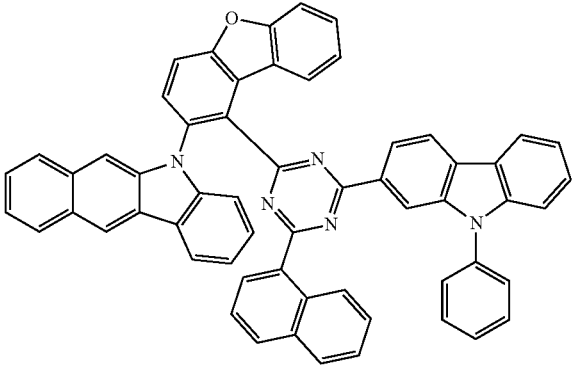
542
-continued
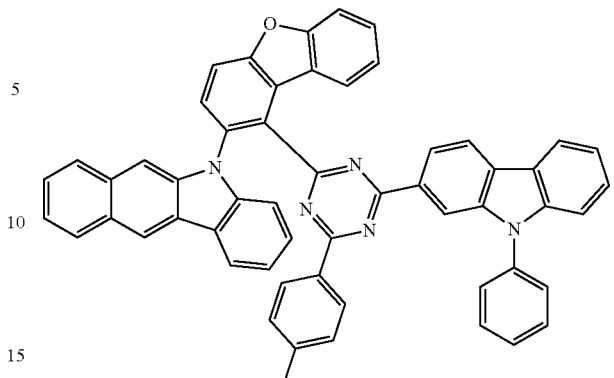

543
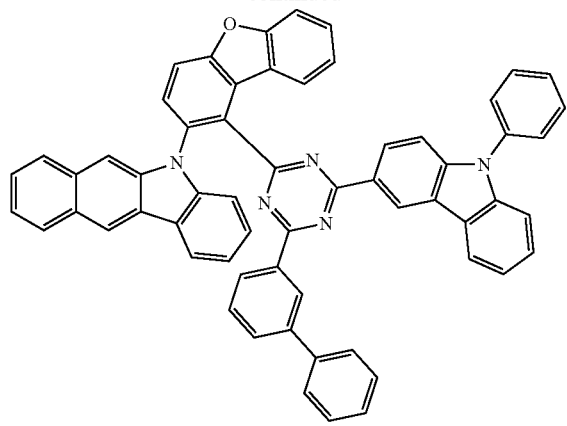
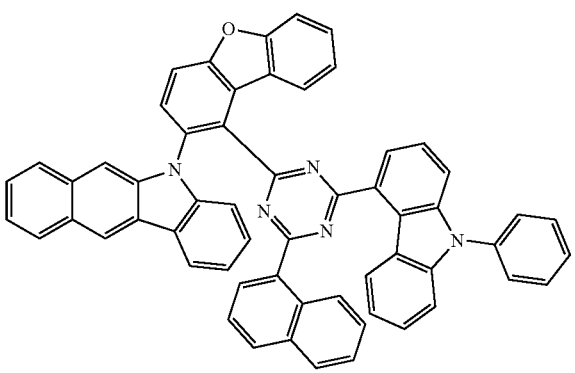
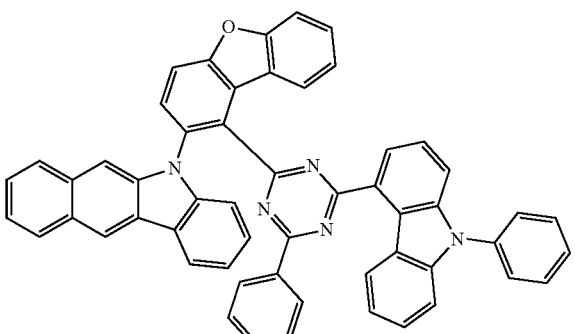
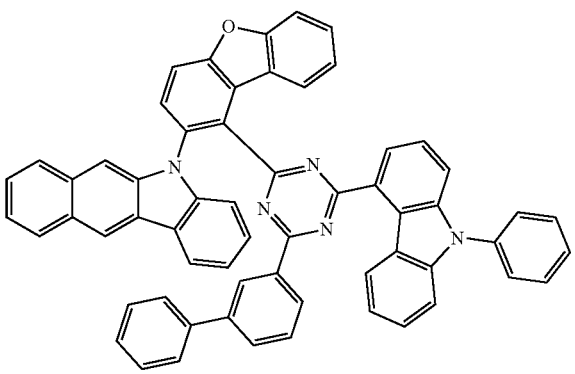
544
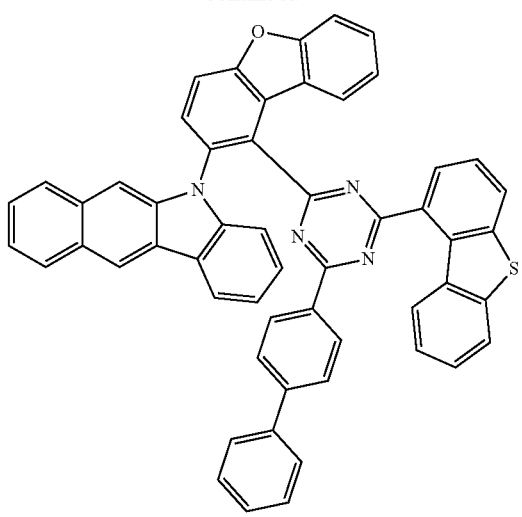
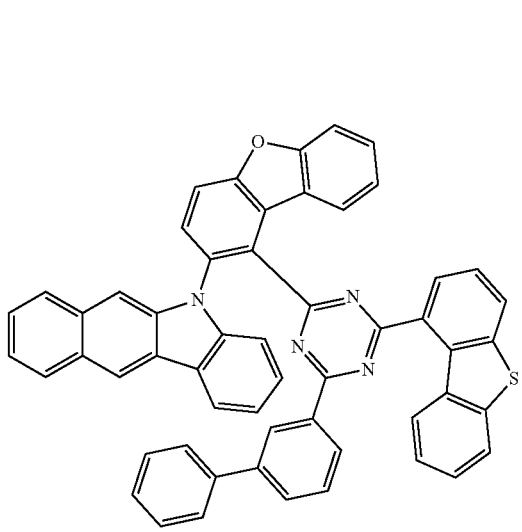
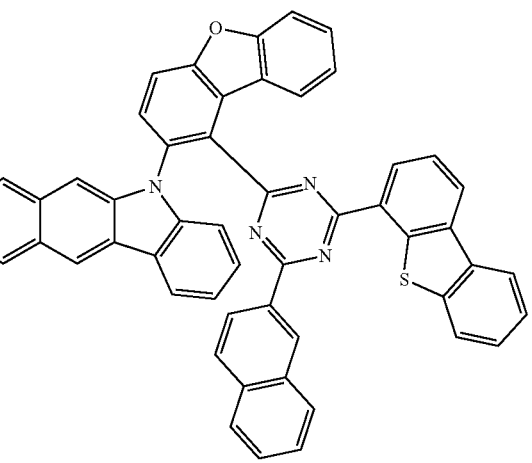

545
-continued
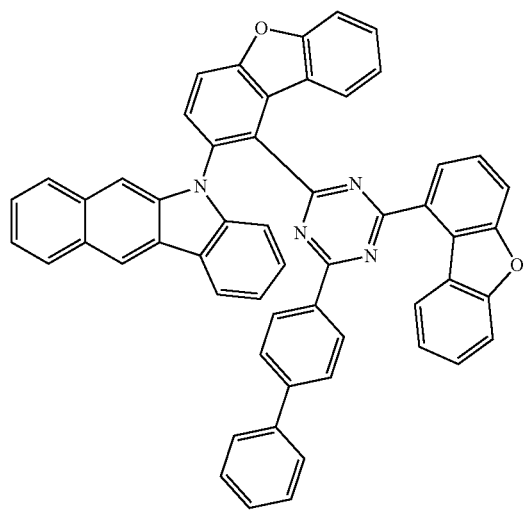
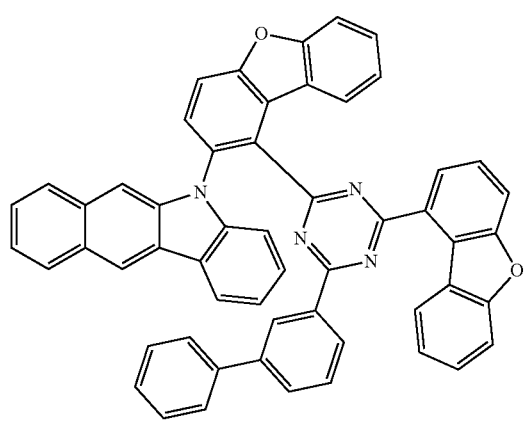
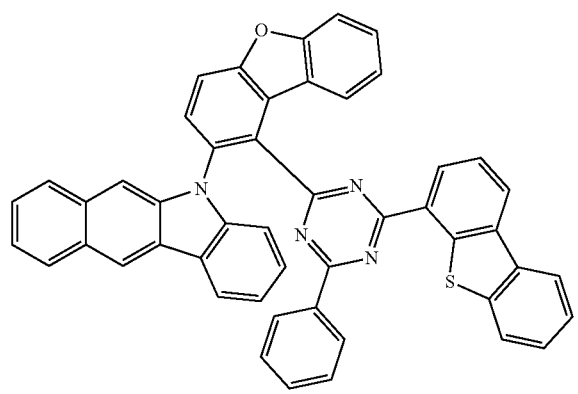
546
-continued
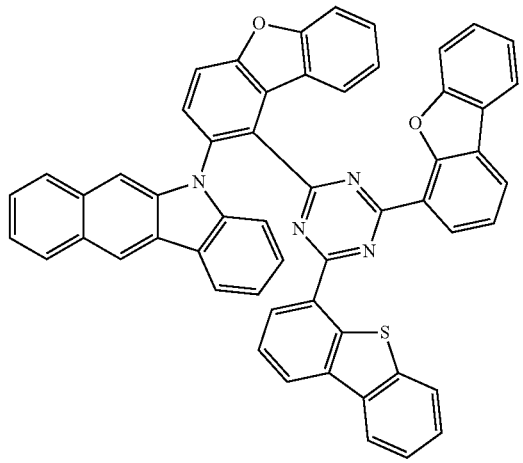
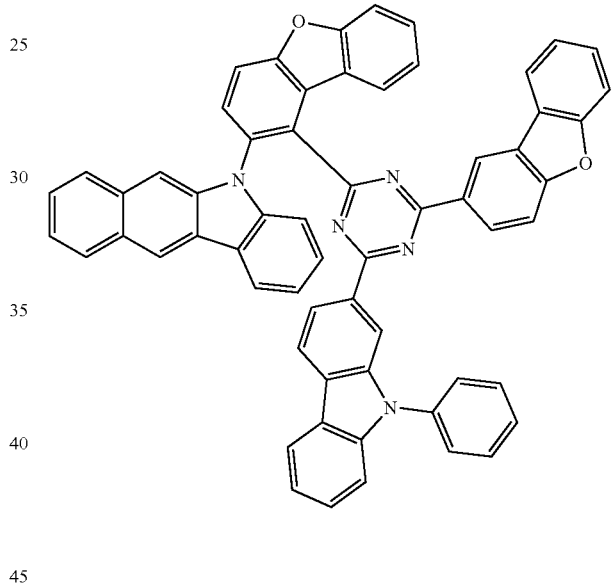
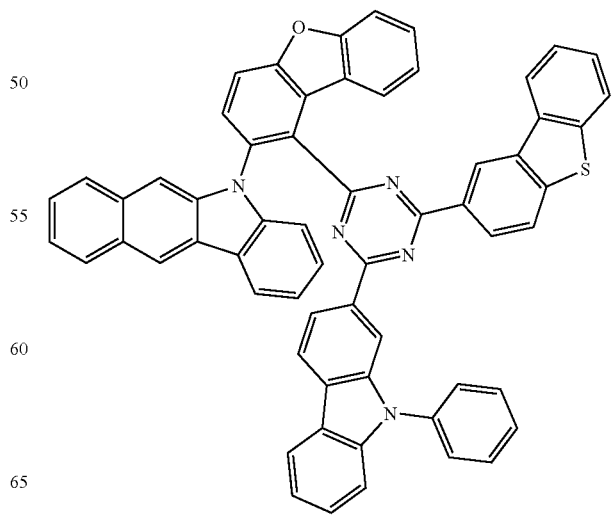

547
-continued
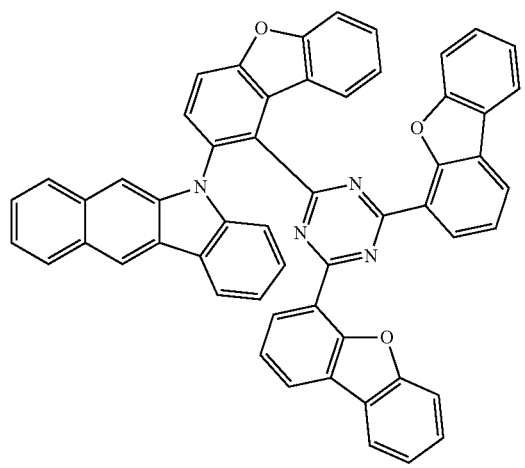
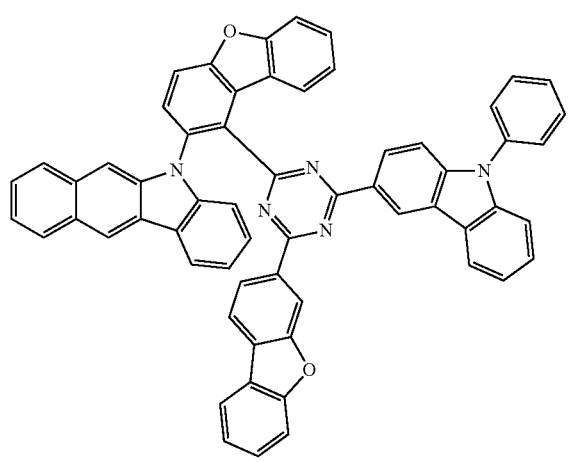
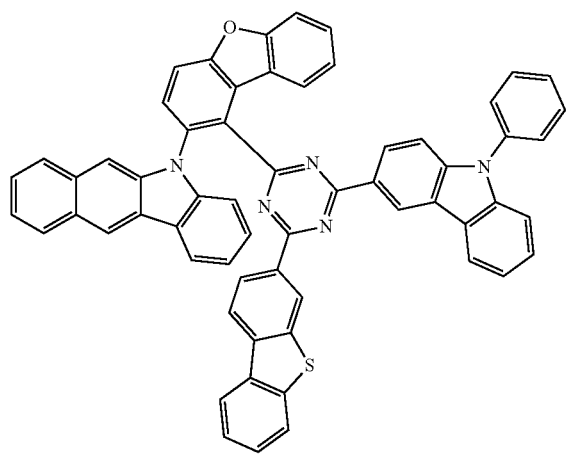
548
-continued
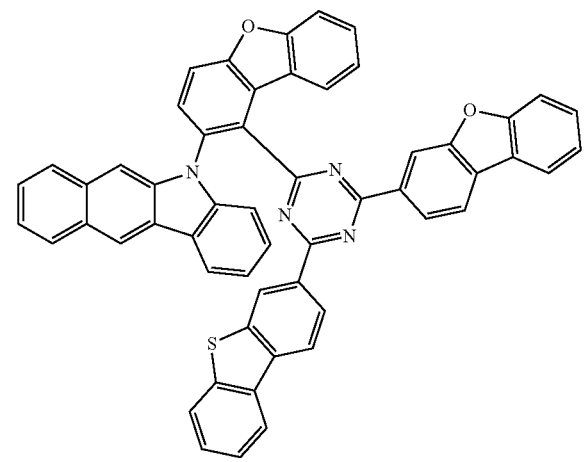
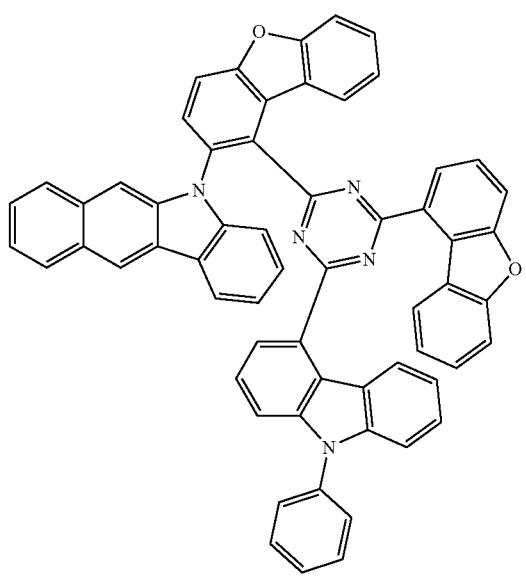
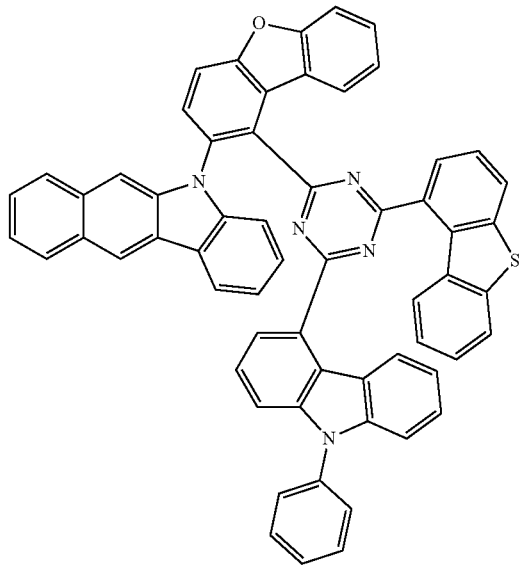

549
-continued
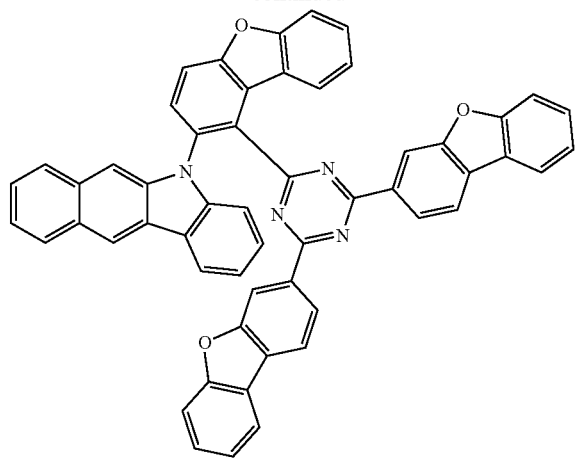
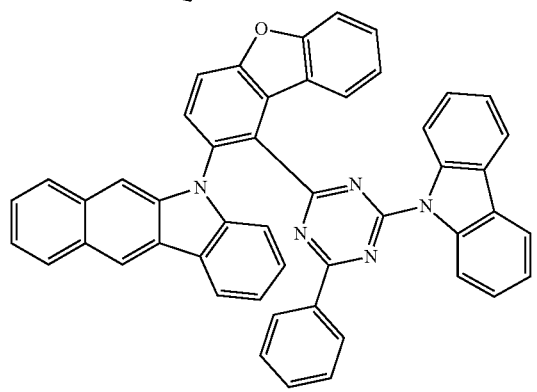
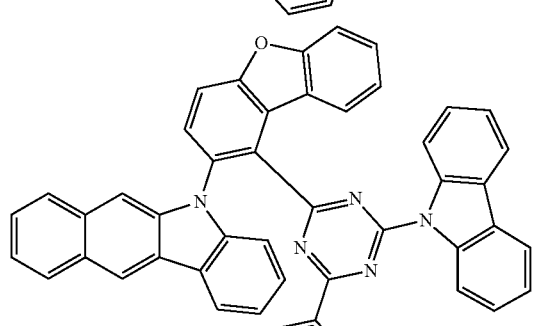
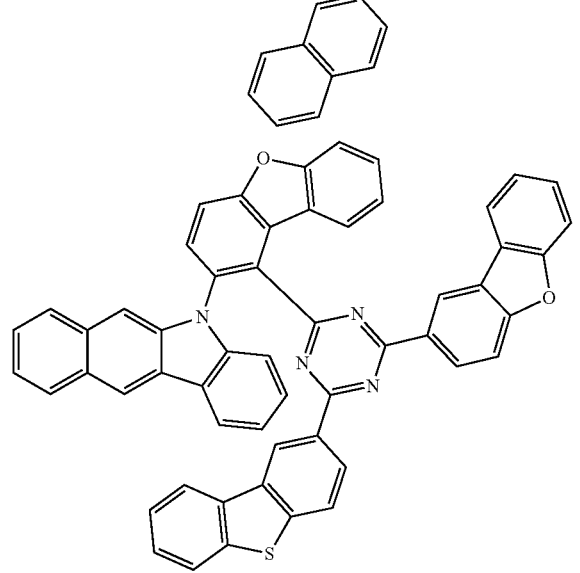
550
-continued
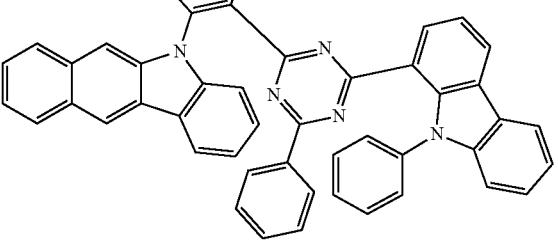
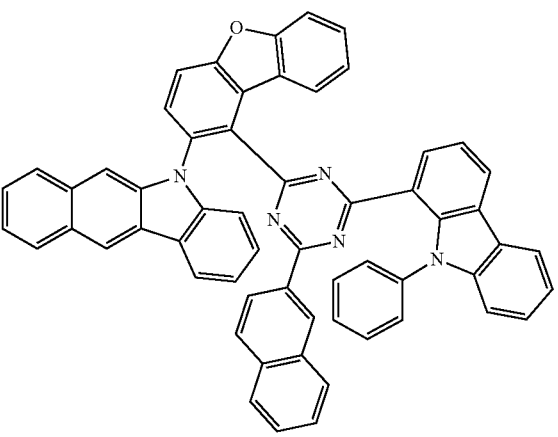
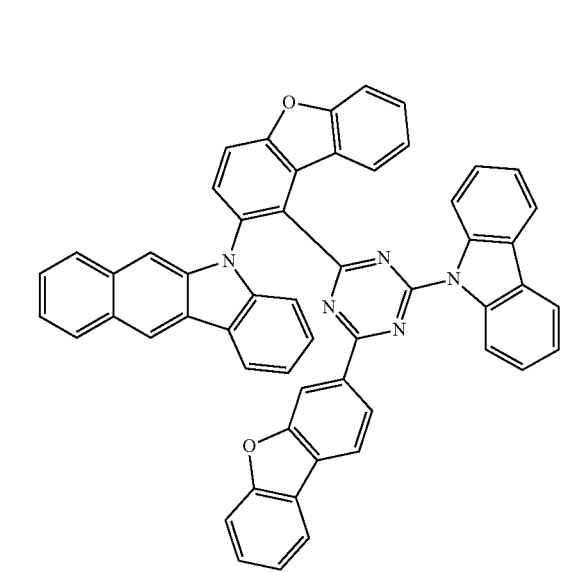

551
-continued
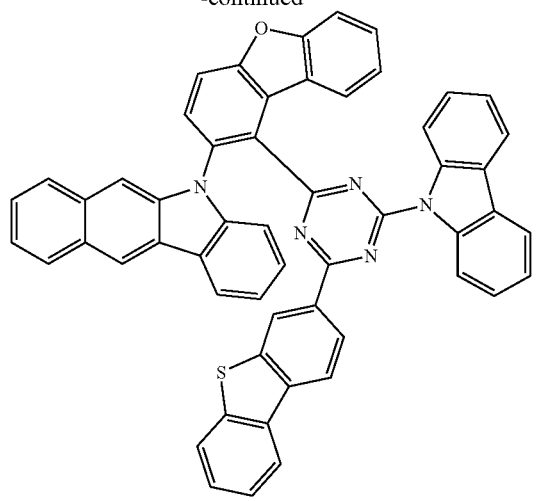
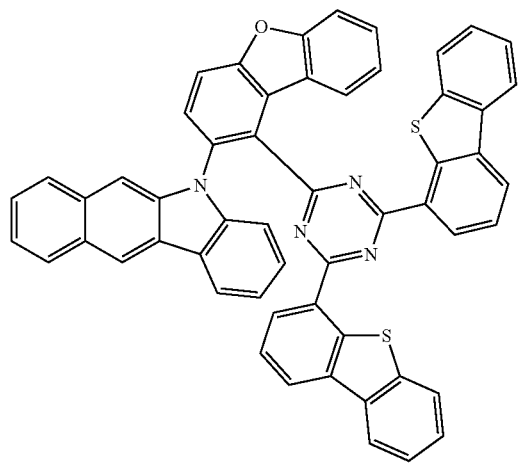
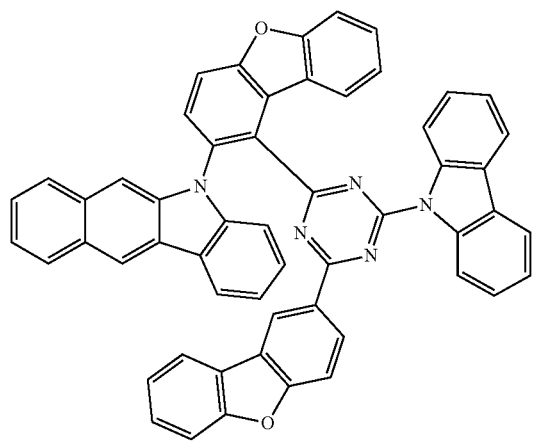
552
-continued
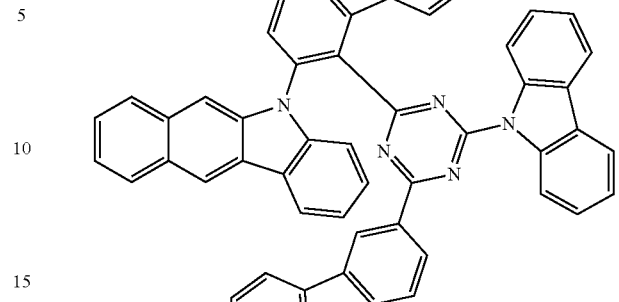
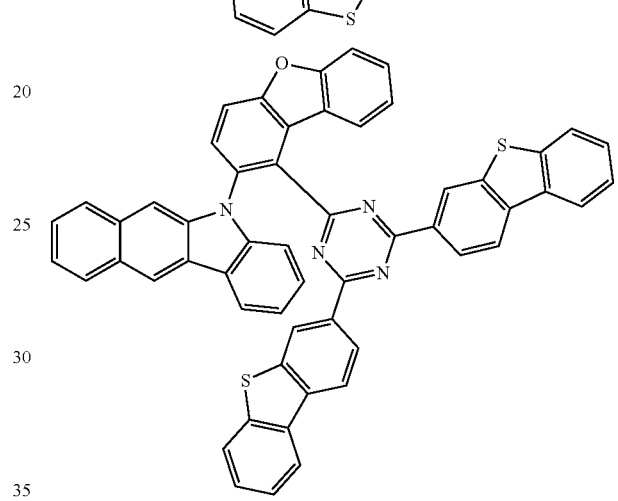
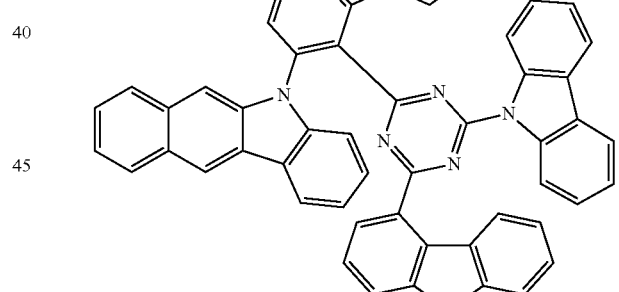
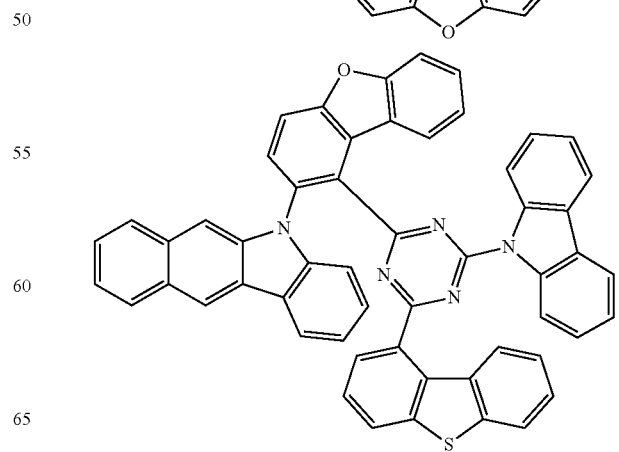

553
-continued
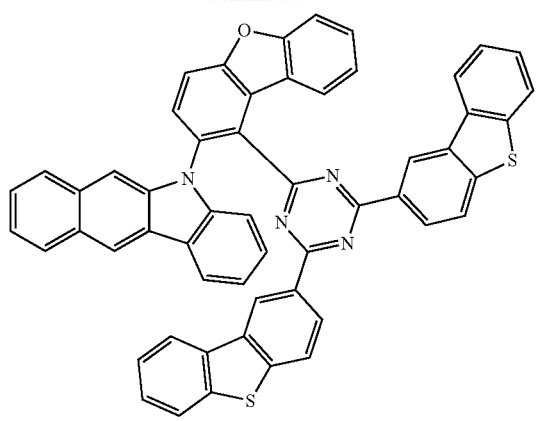
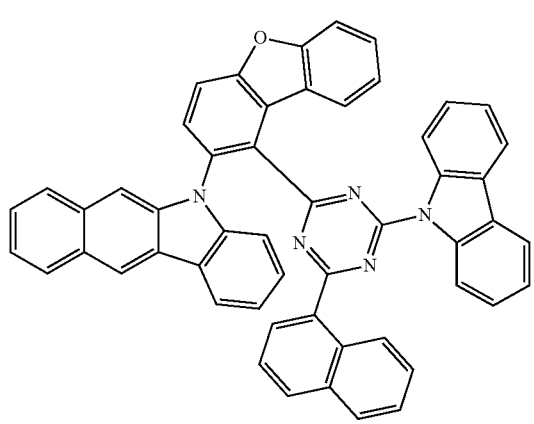
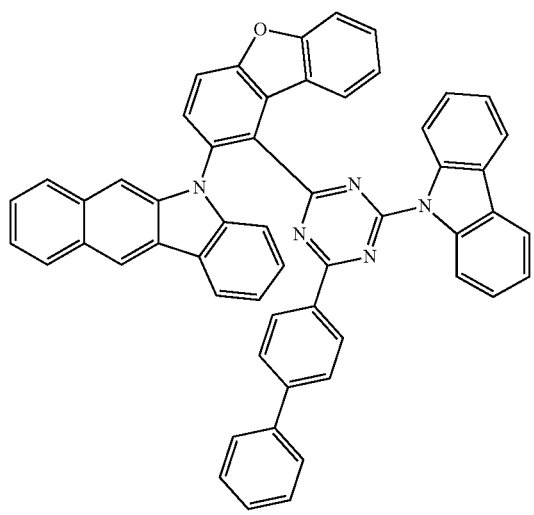
554
-continued
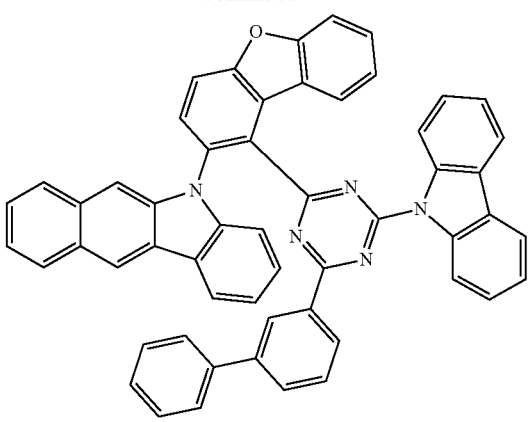
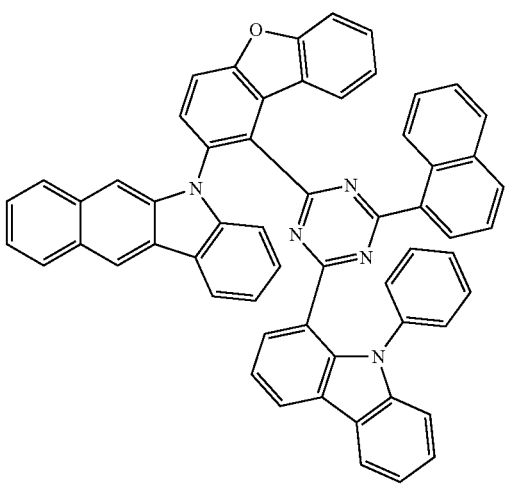
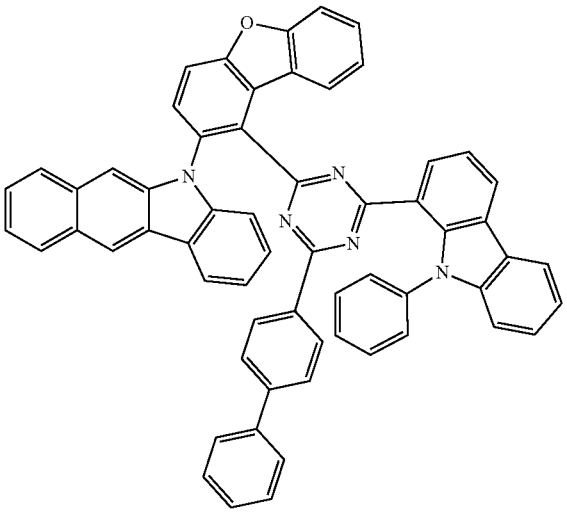

555
-continued
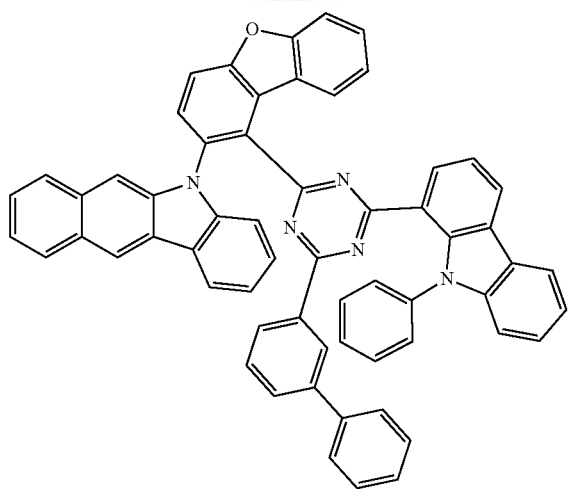
556
-continued
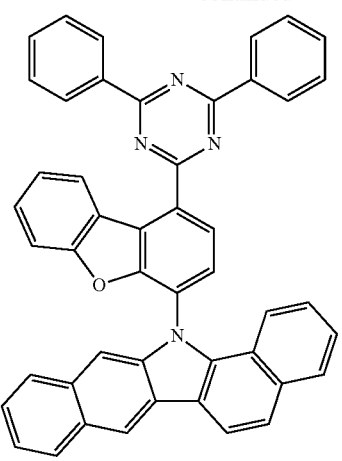
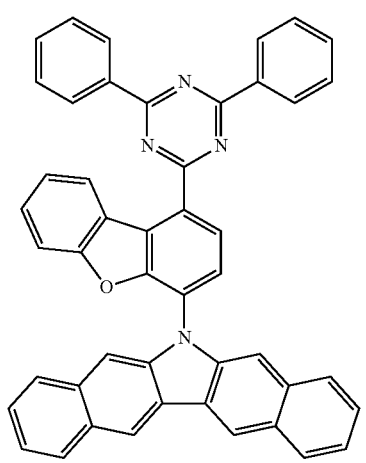
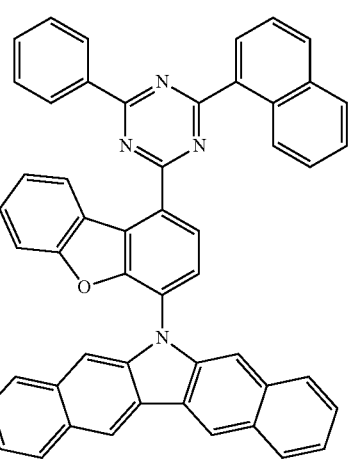
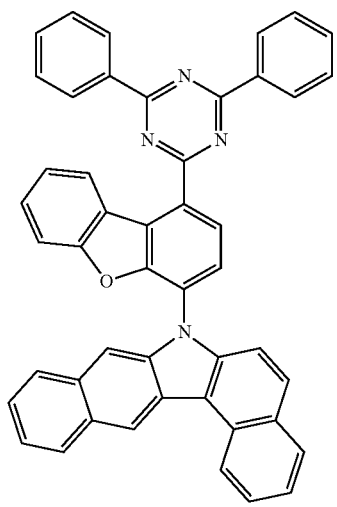
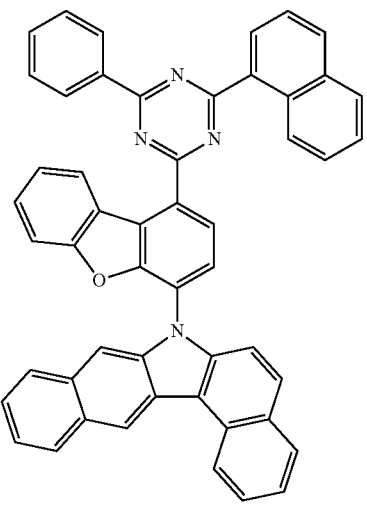

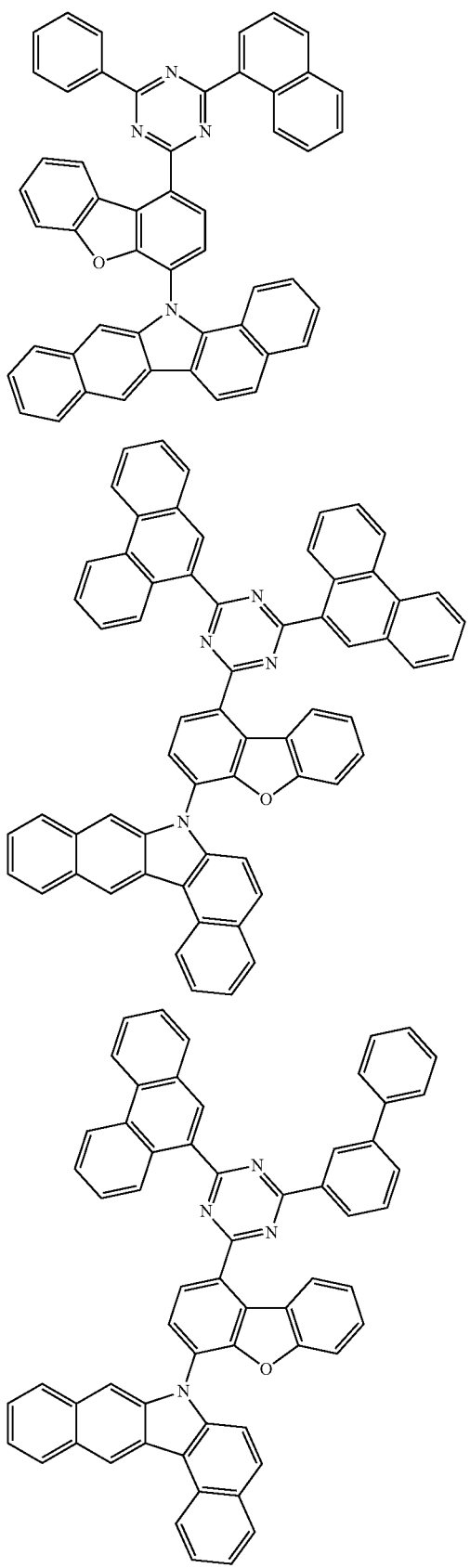
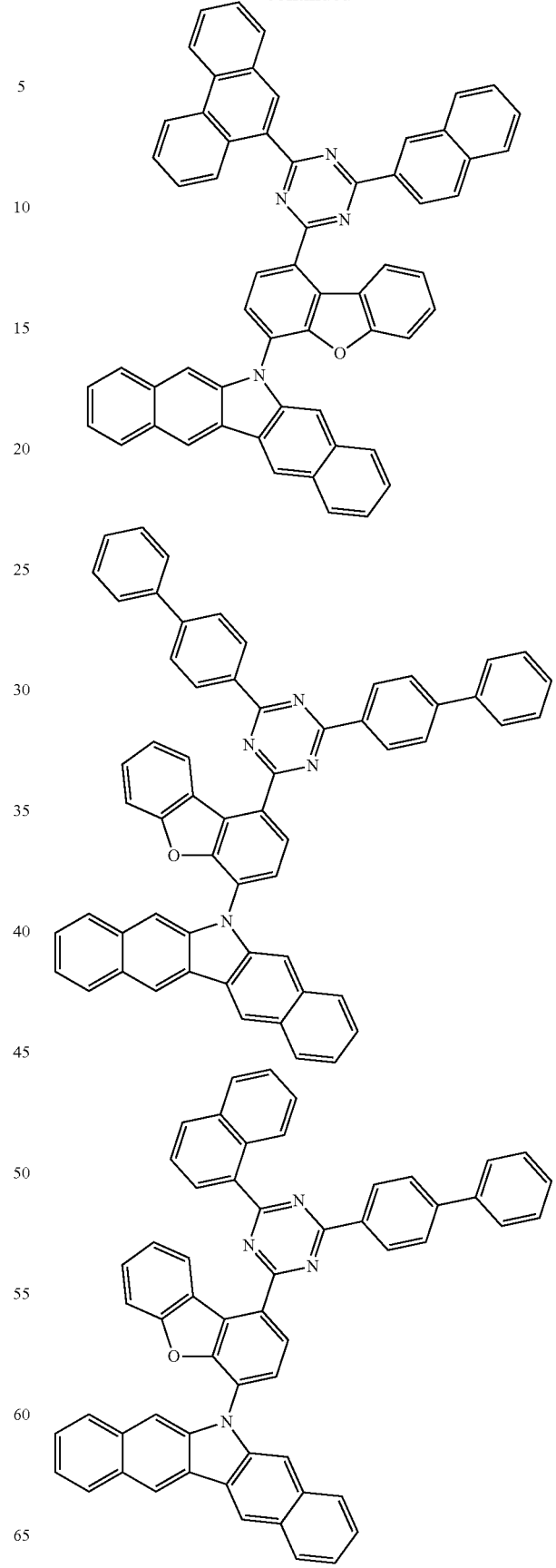

559
-continued
560
-continued
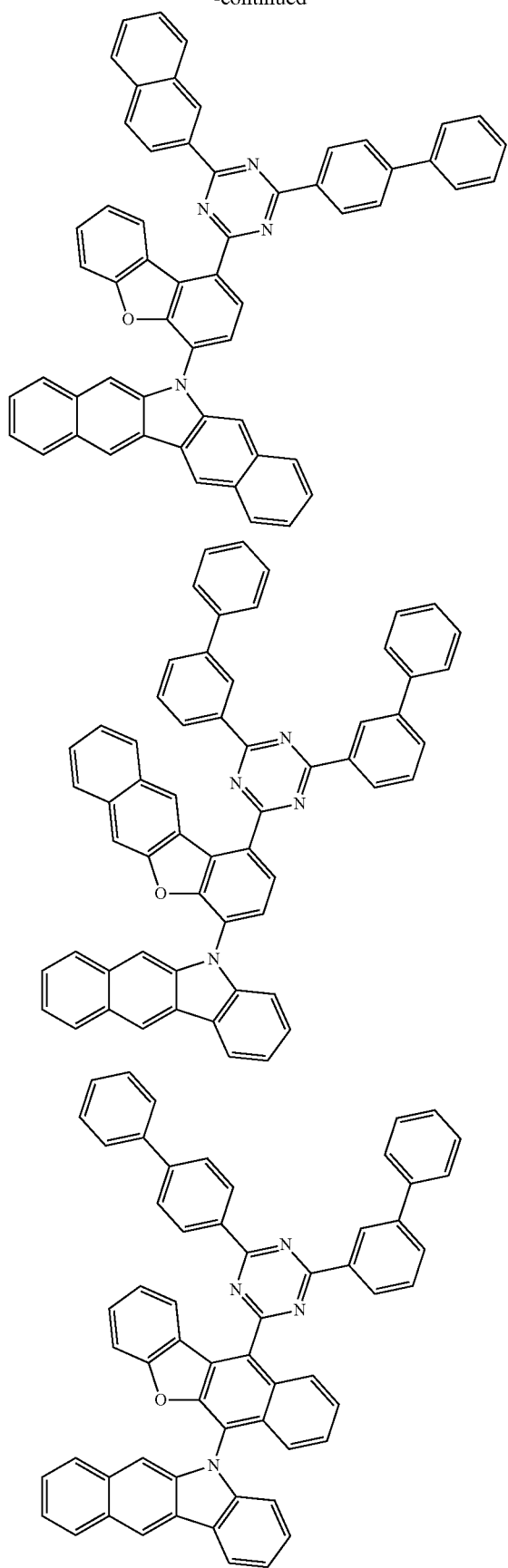
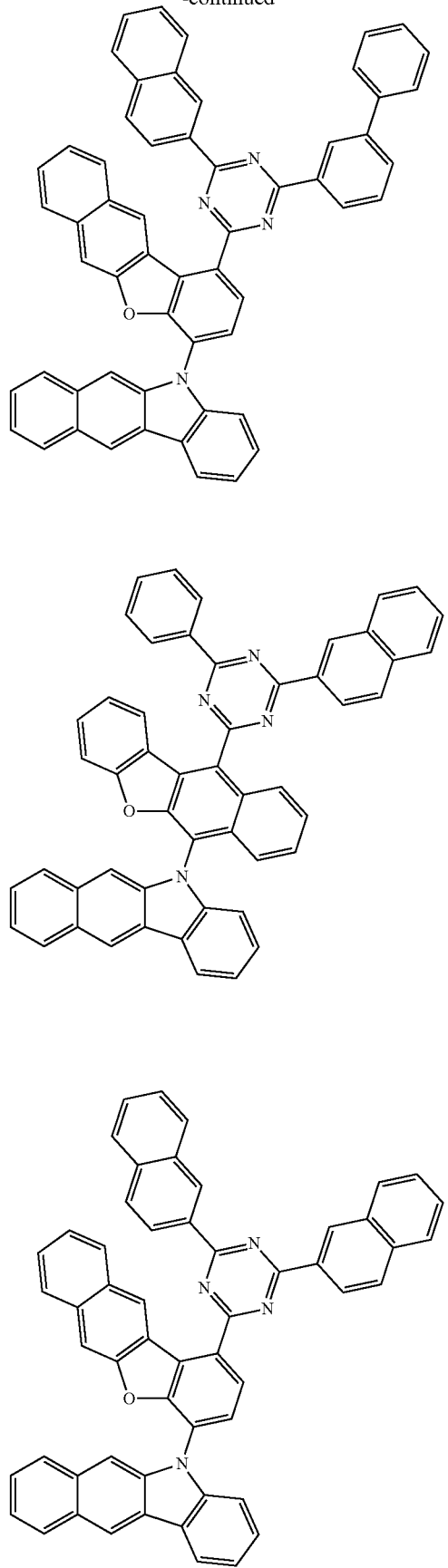

561
-continued
562
-continued
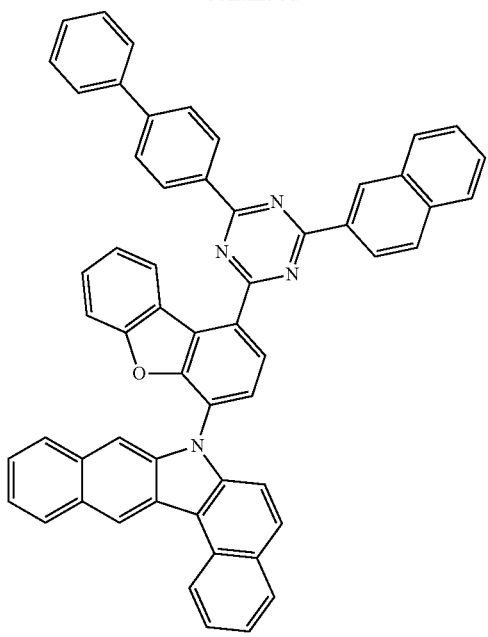
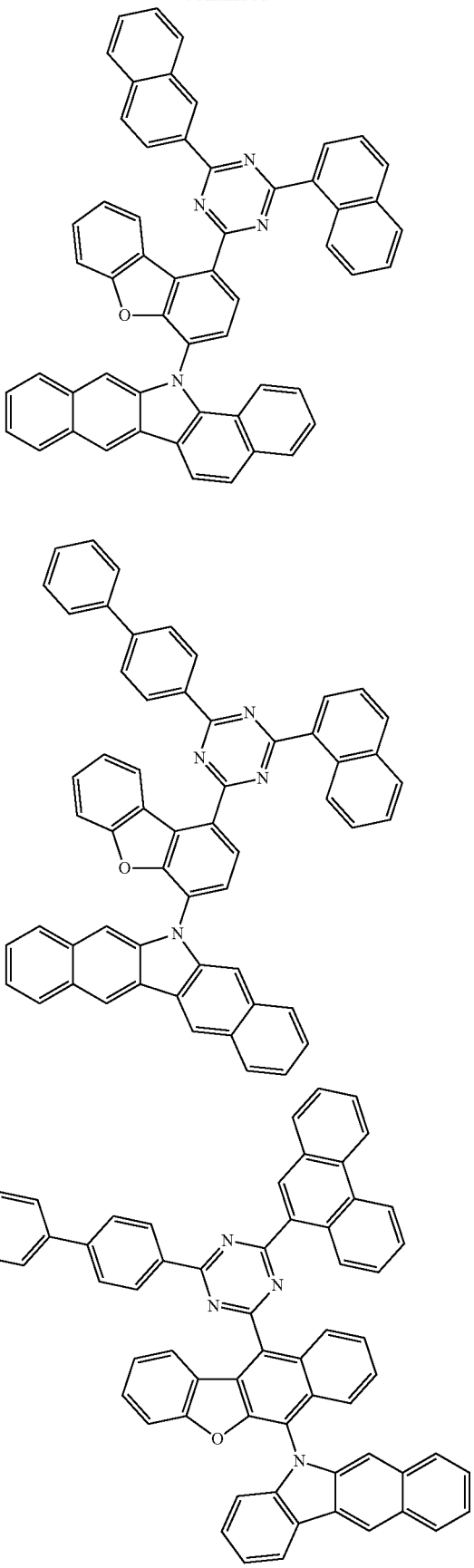

563
-continued
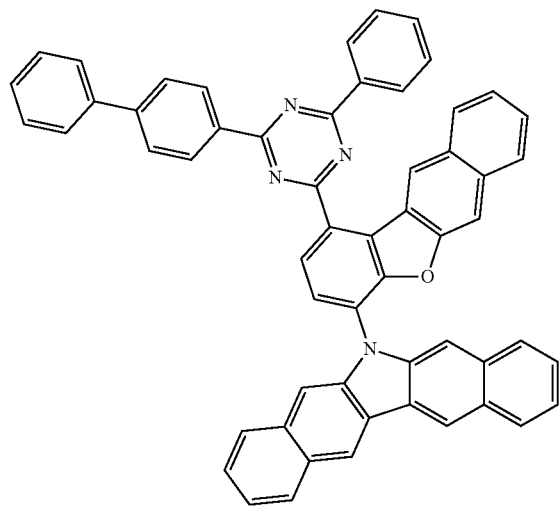
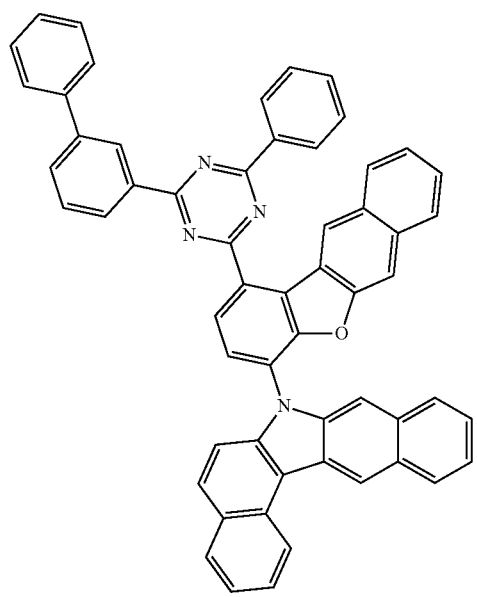
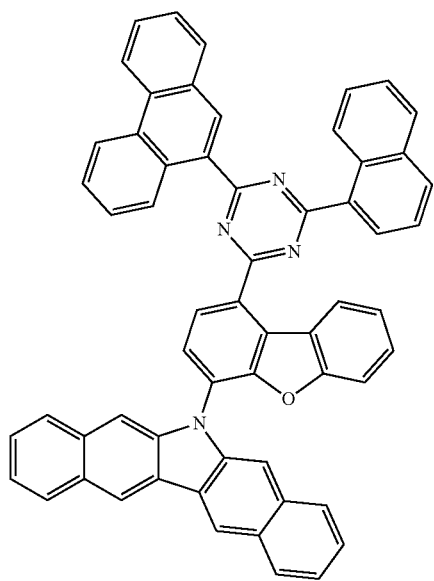
564
-continued
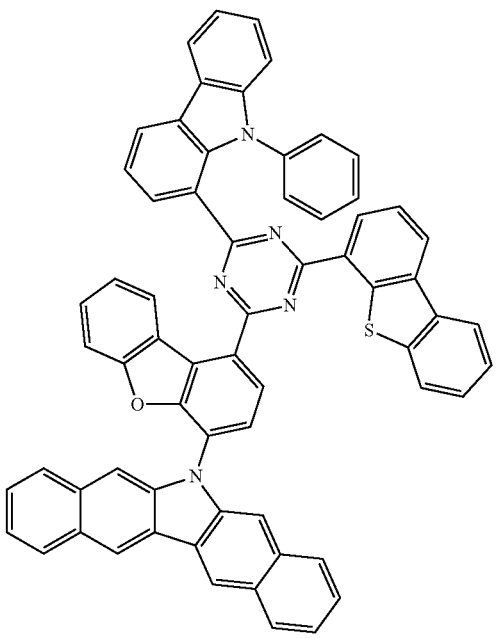
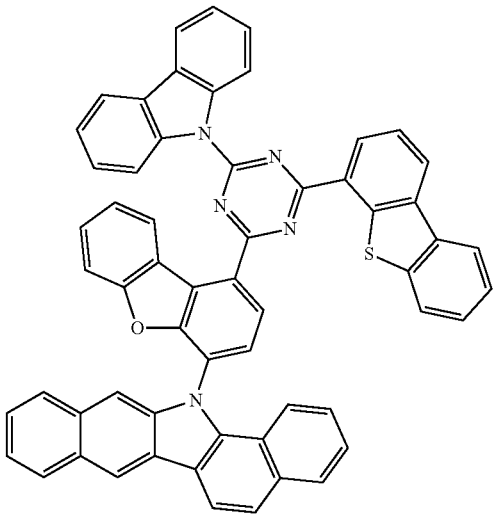

565
-continued
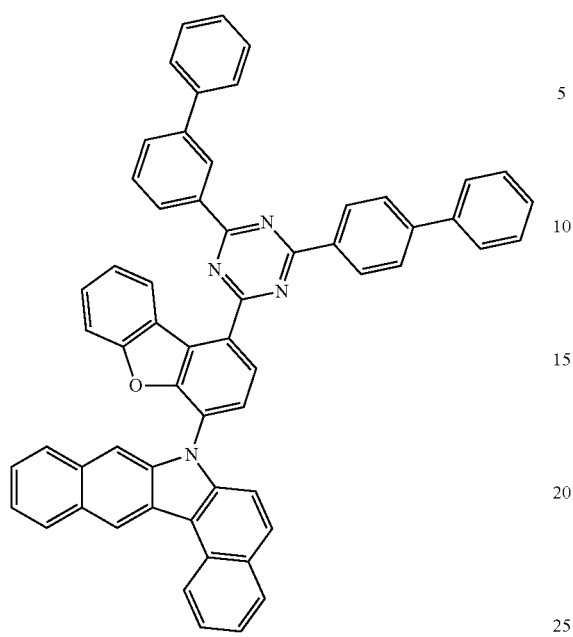
566
-continued
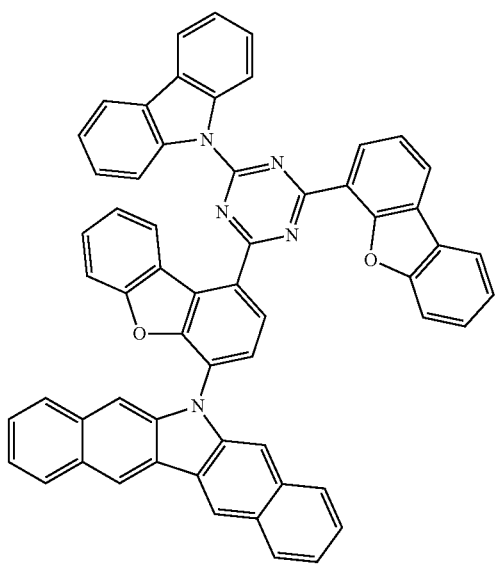
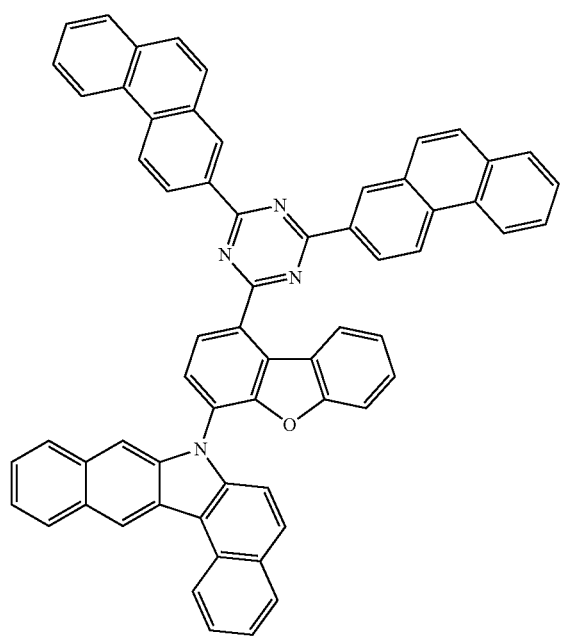
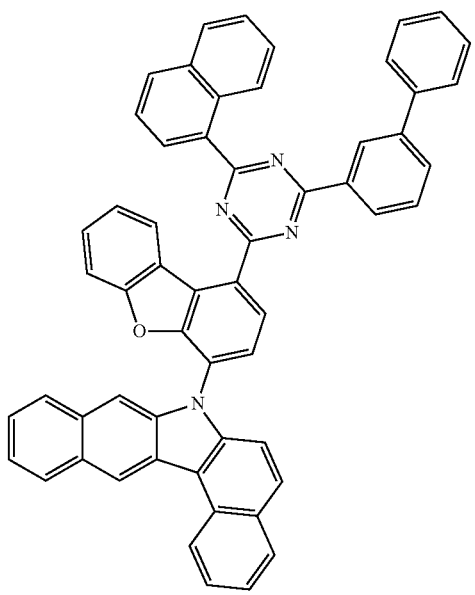

567
-continued
568
-continued
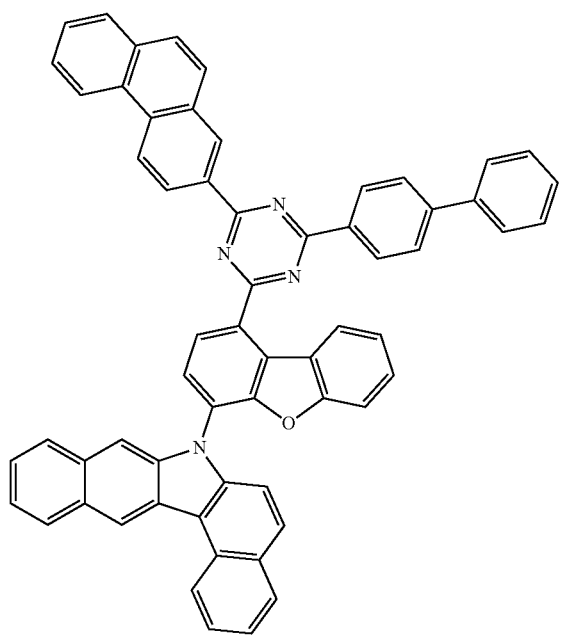
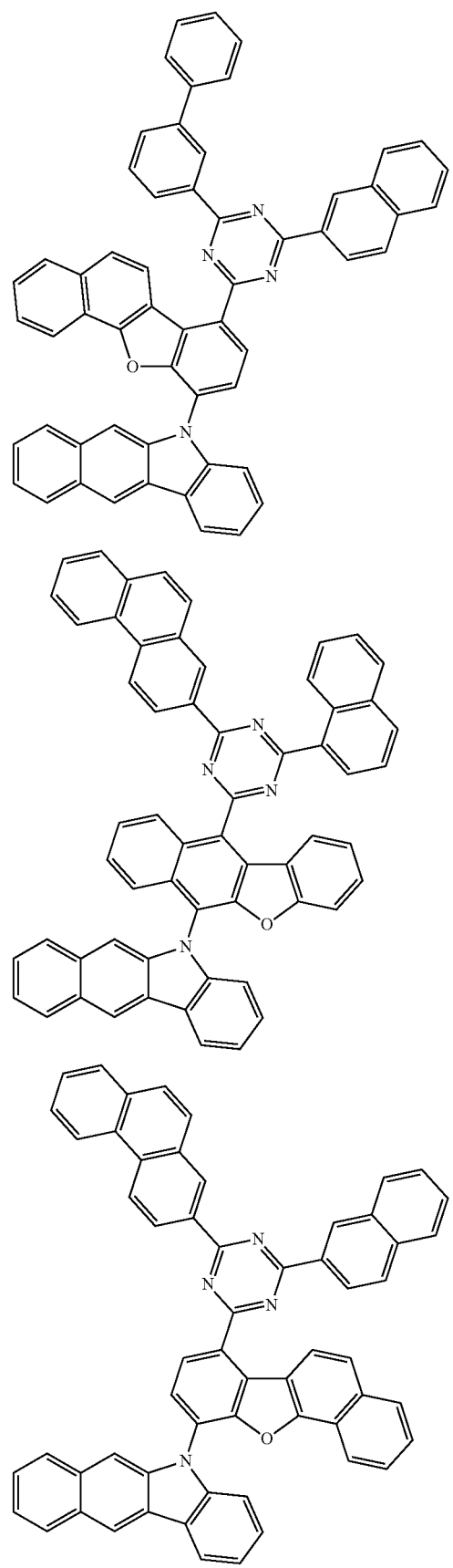

569
-continued
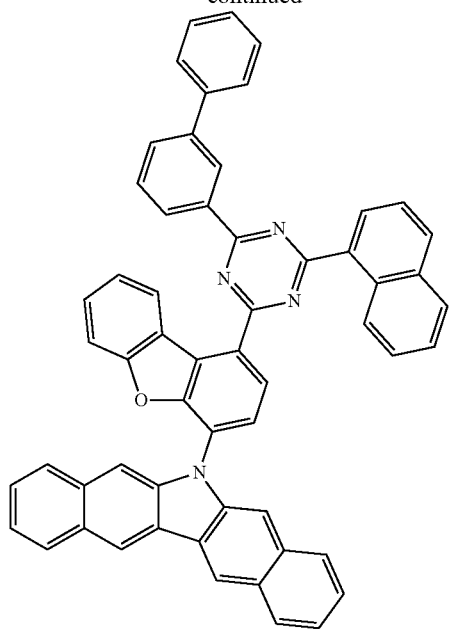
570
-continued
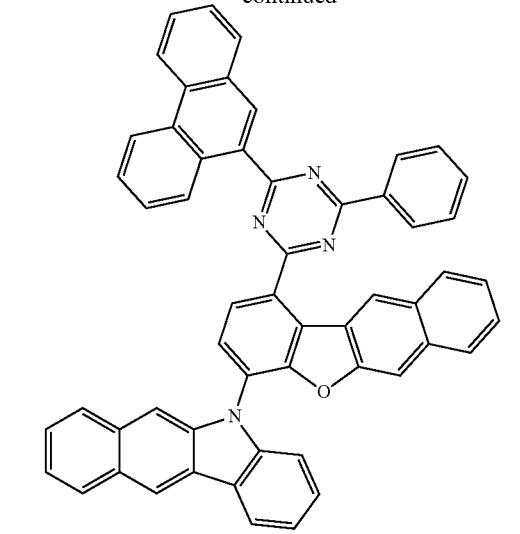
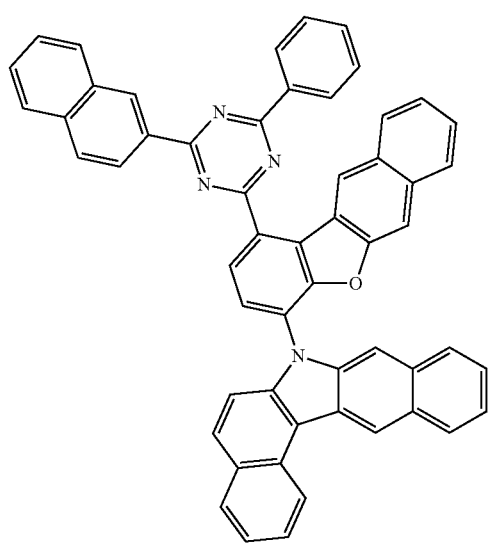
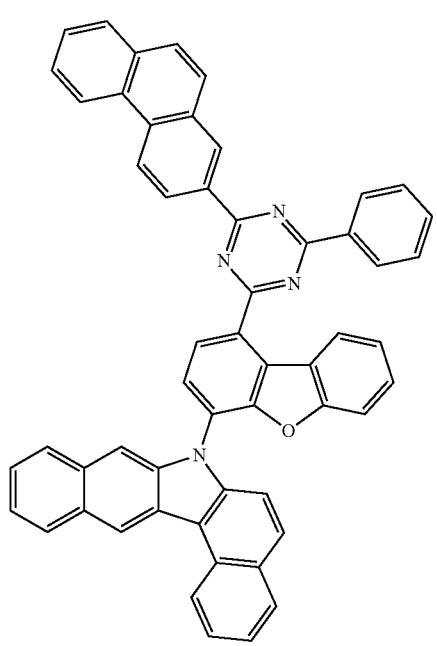
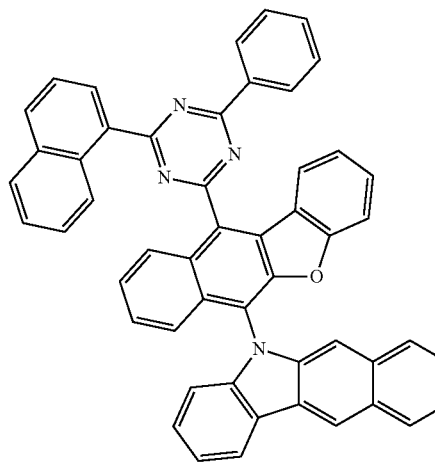

571
-continued
572
-continued
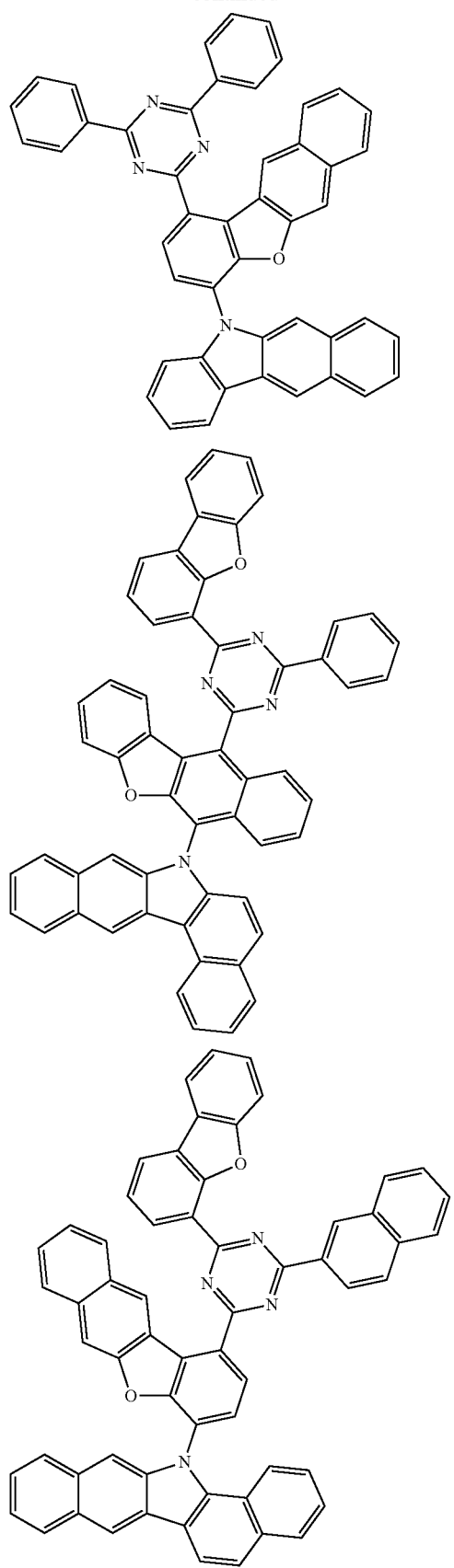

573
-continued
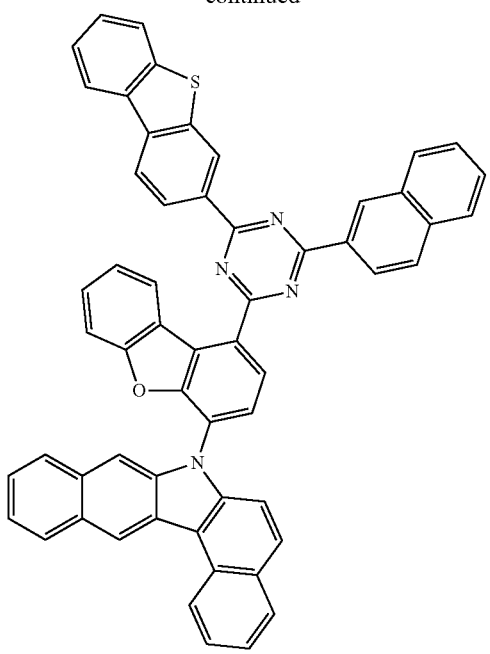
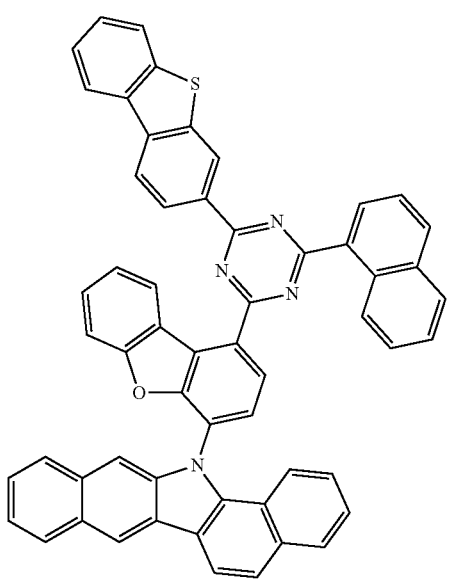
574
-continued
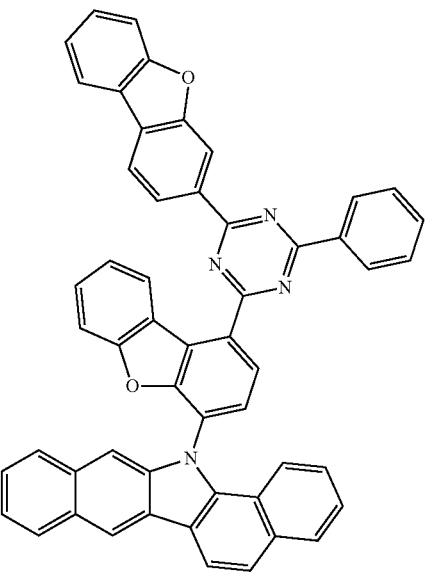
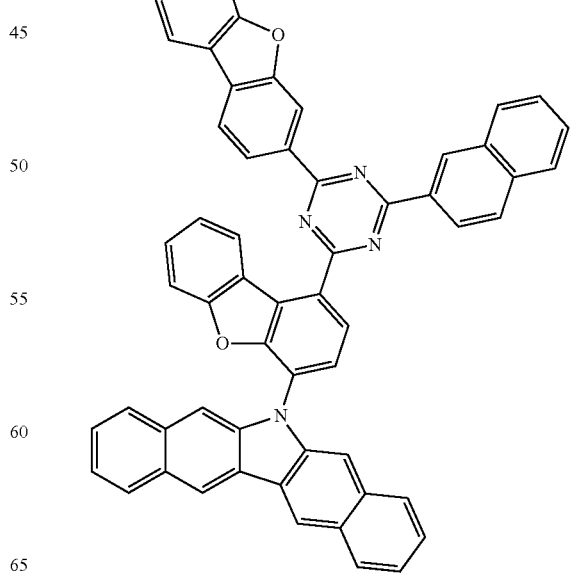

575
-continued
576
-continued
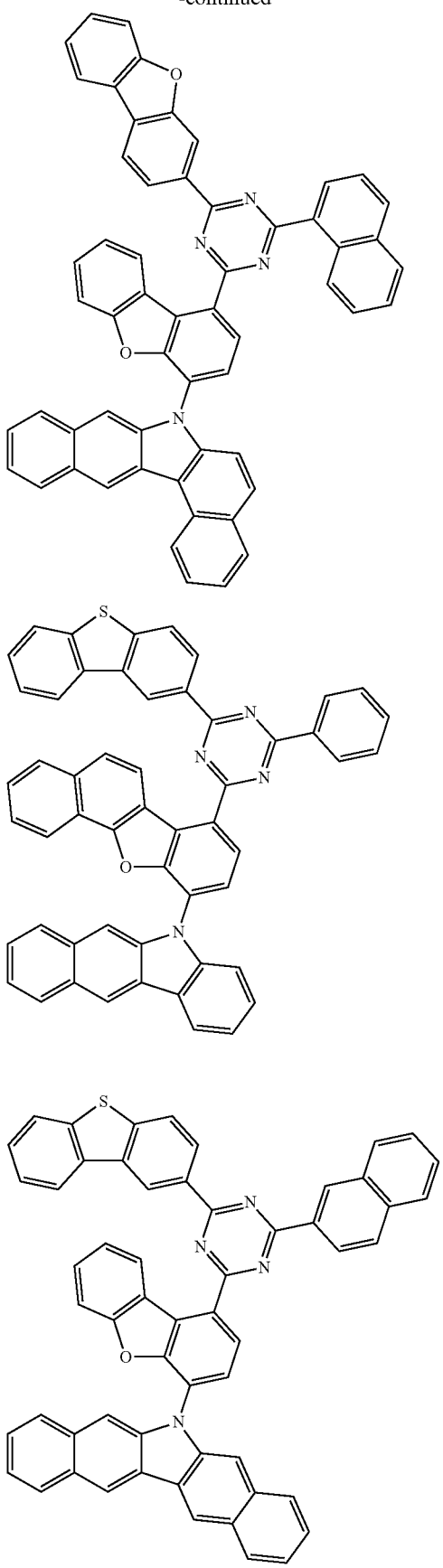
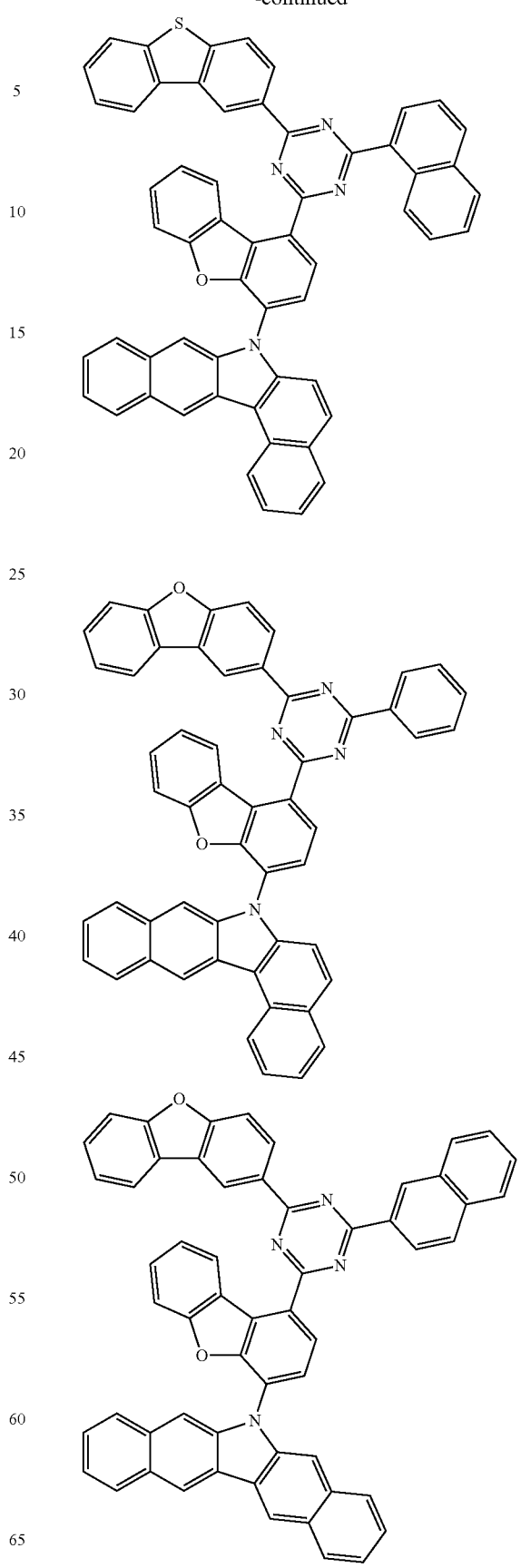

577
-continued
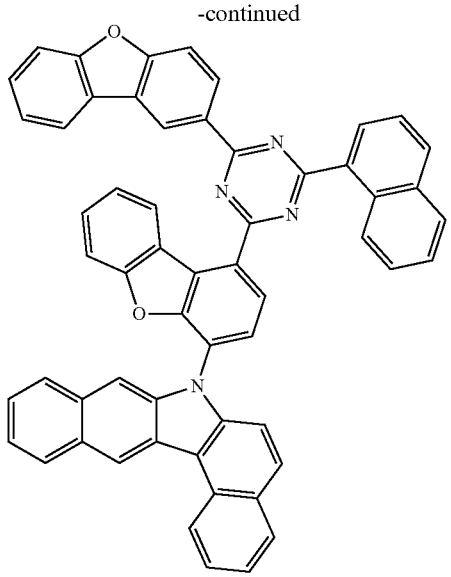
578
-continued
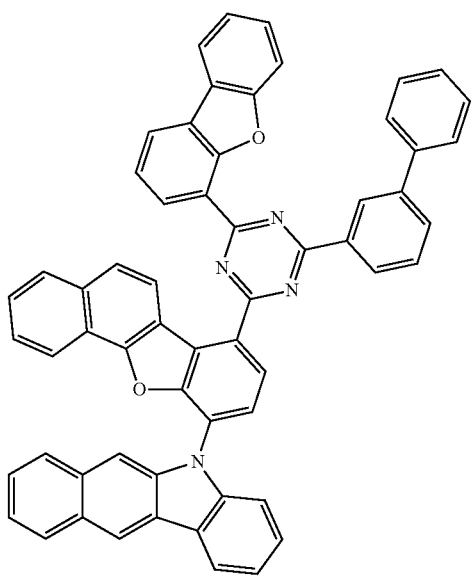
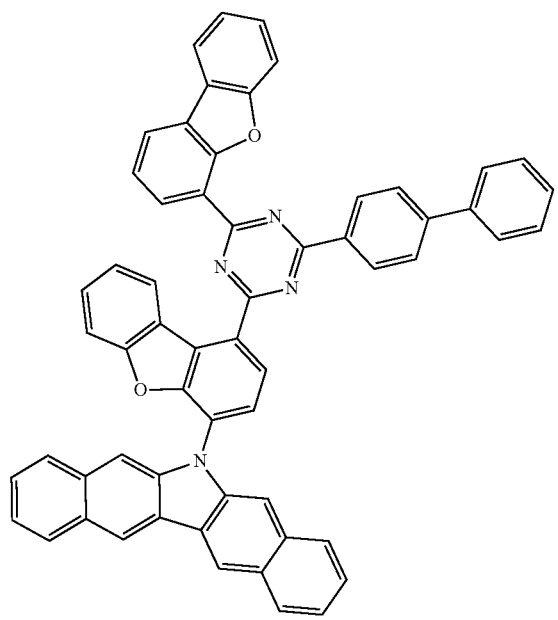
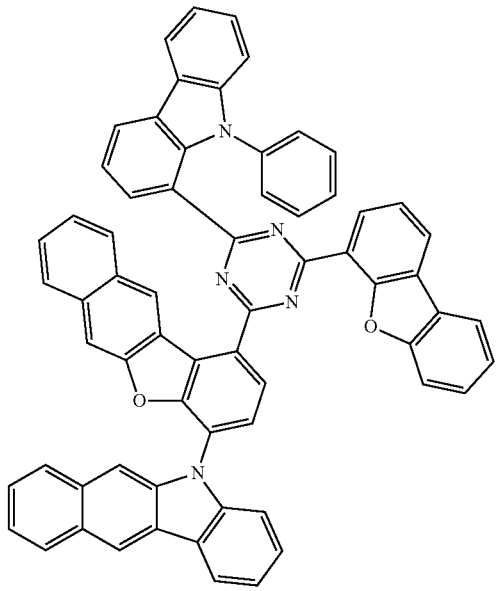

579
-continued
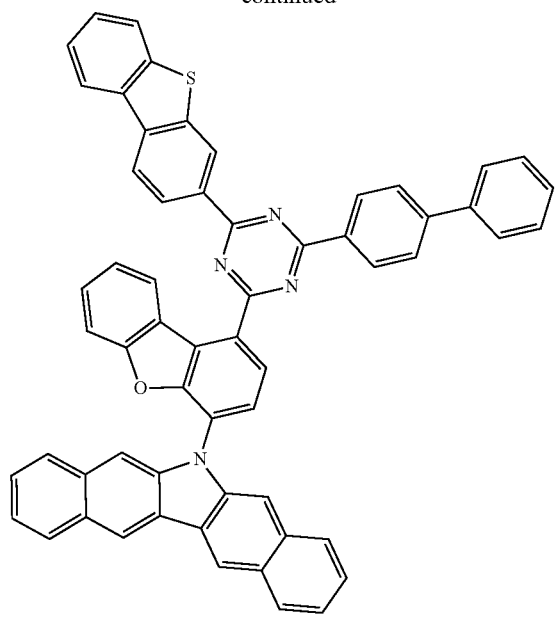
580
-continued
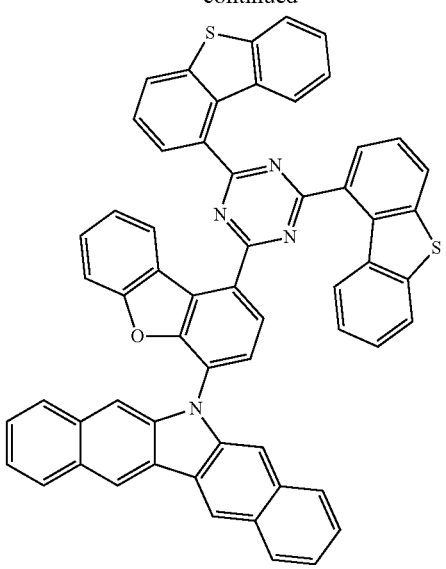
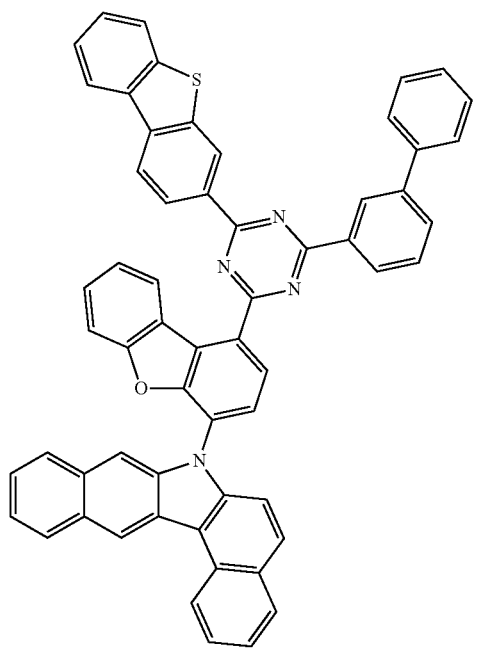
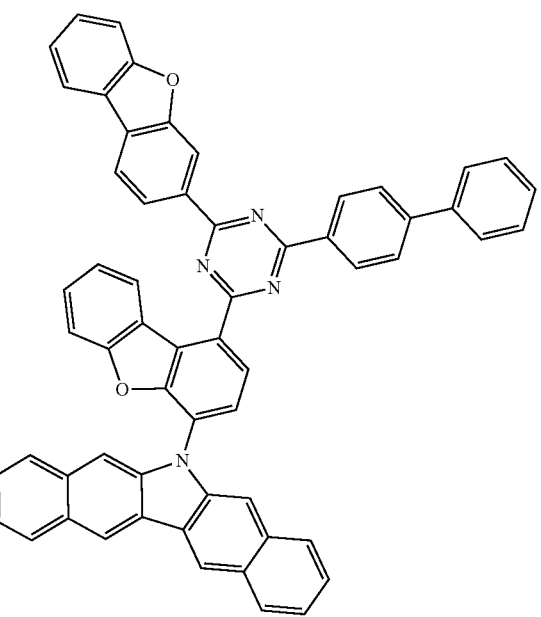

581
-continued
582
-continued
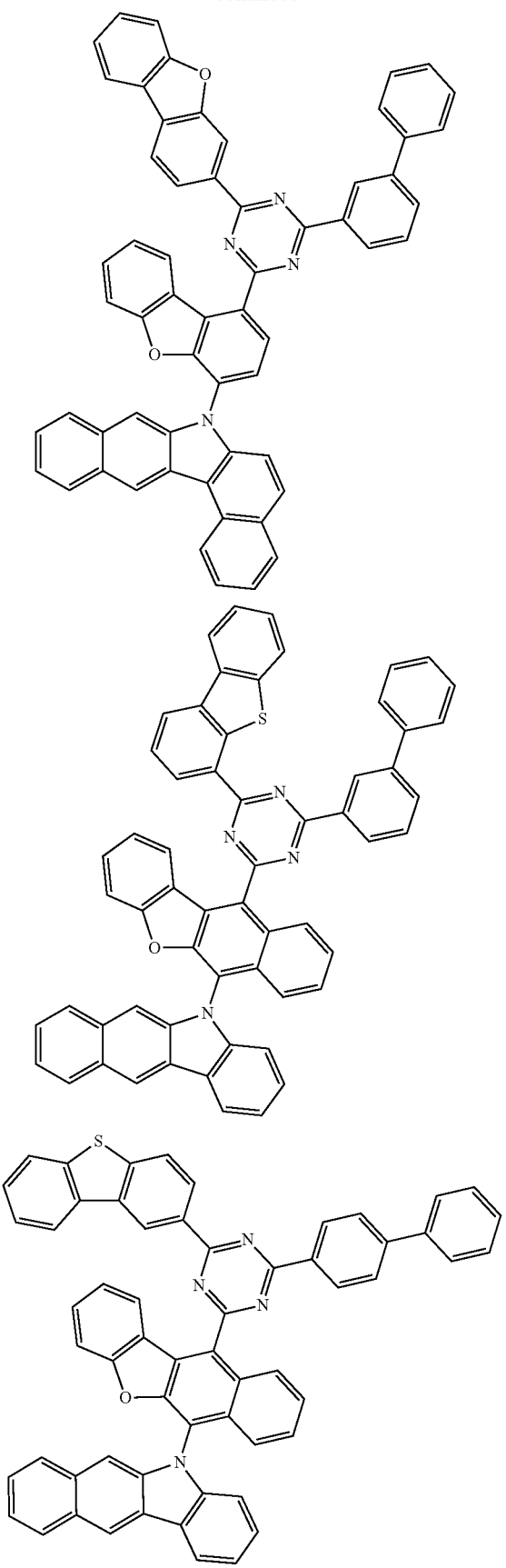
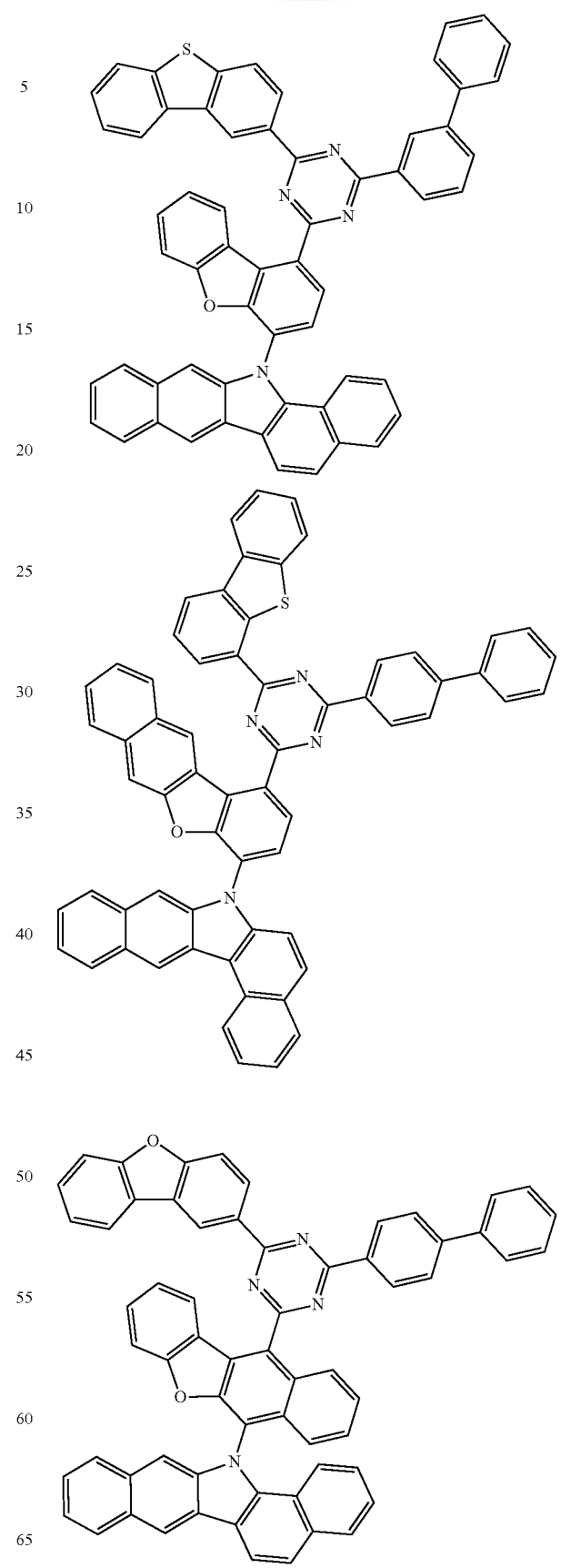

583
-continued
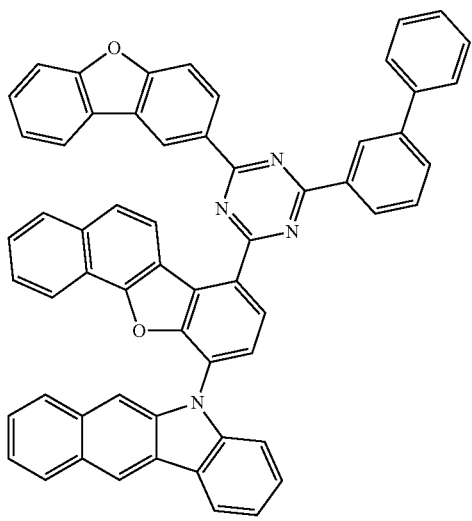
584
-continued
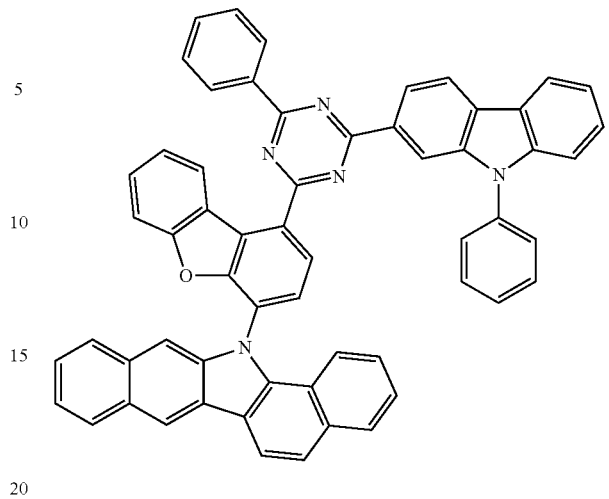
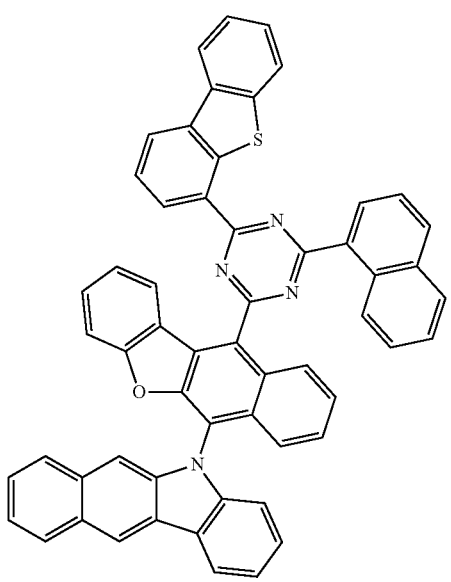
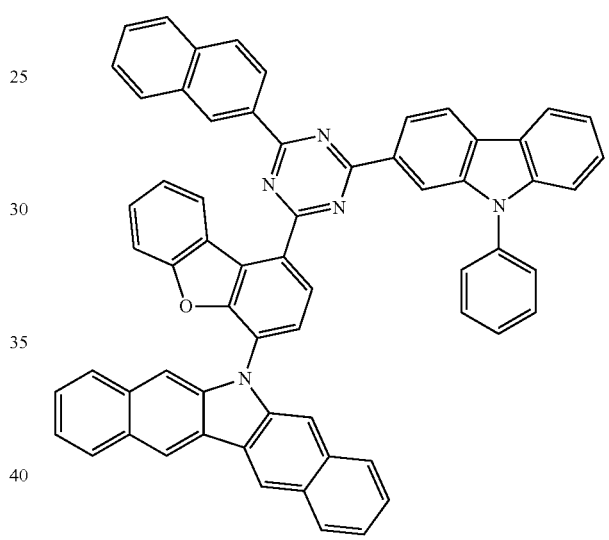
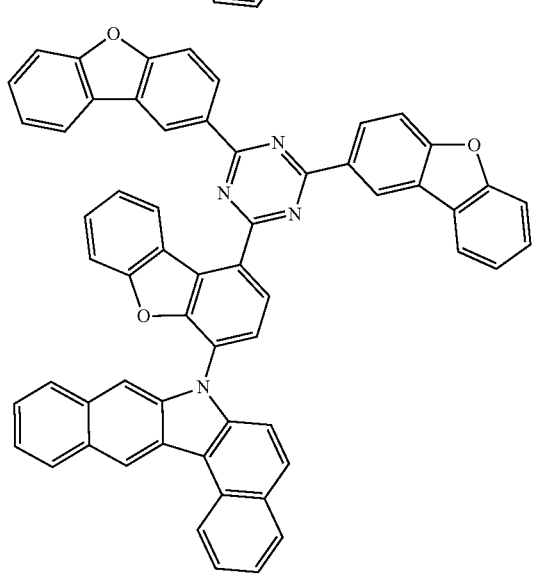
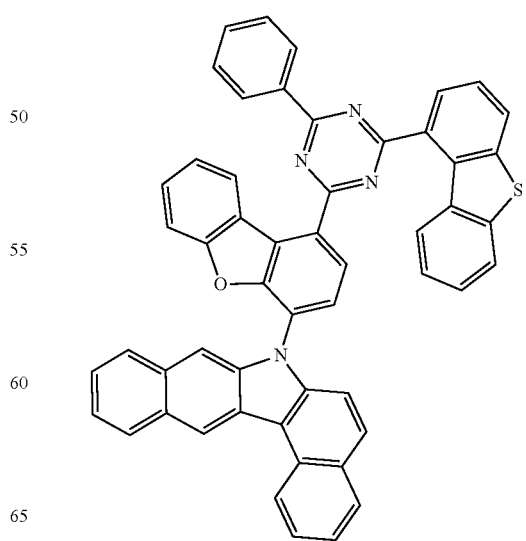

585
-continued
586
-continued
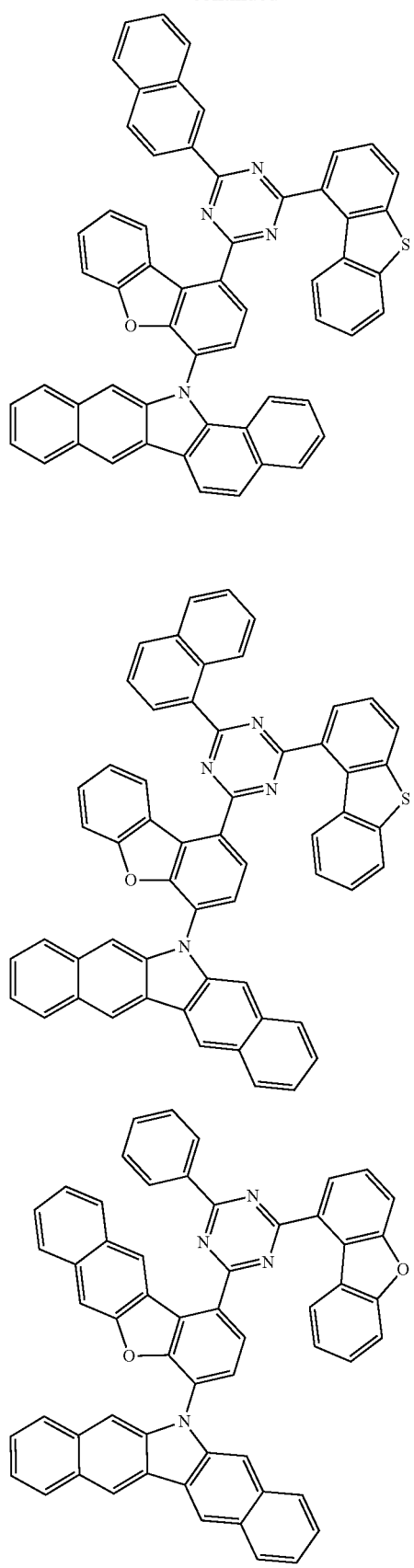
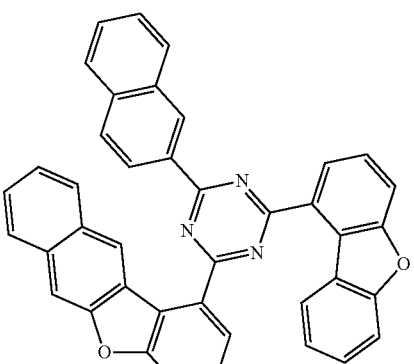
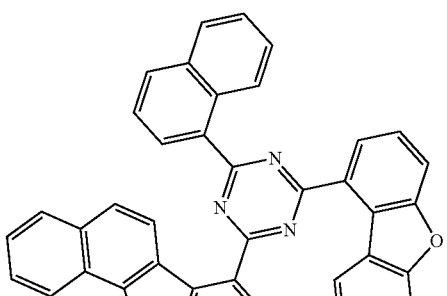

587
-continued
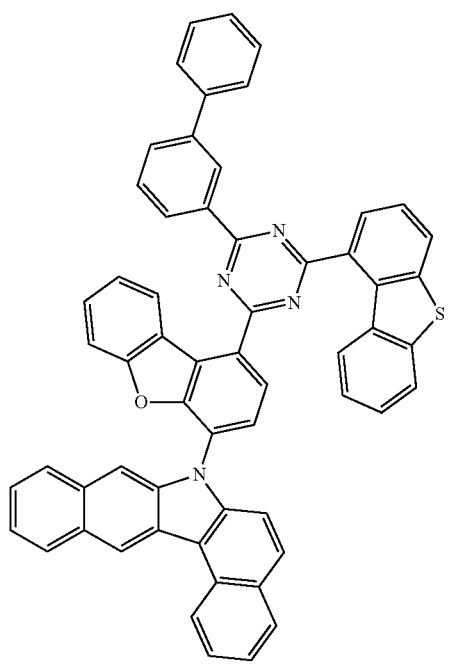
588
-continued
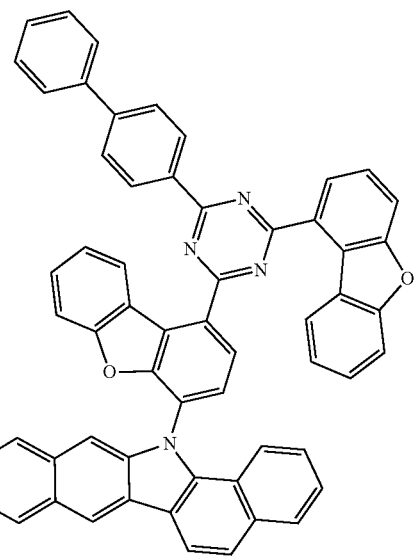
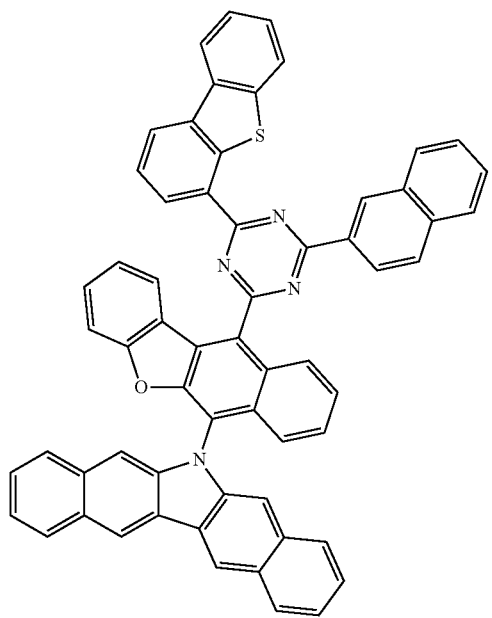
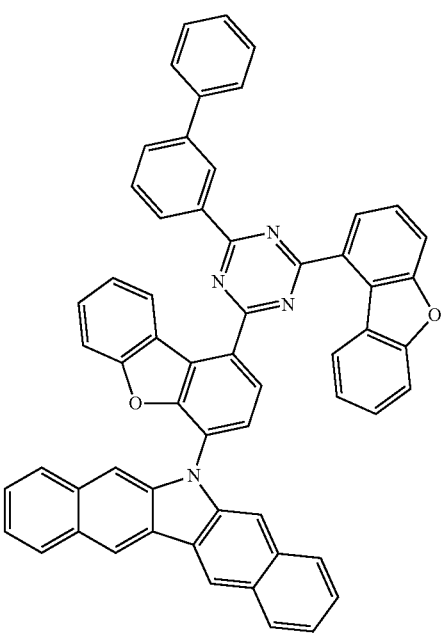

589
-continued
590
-continued
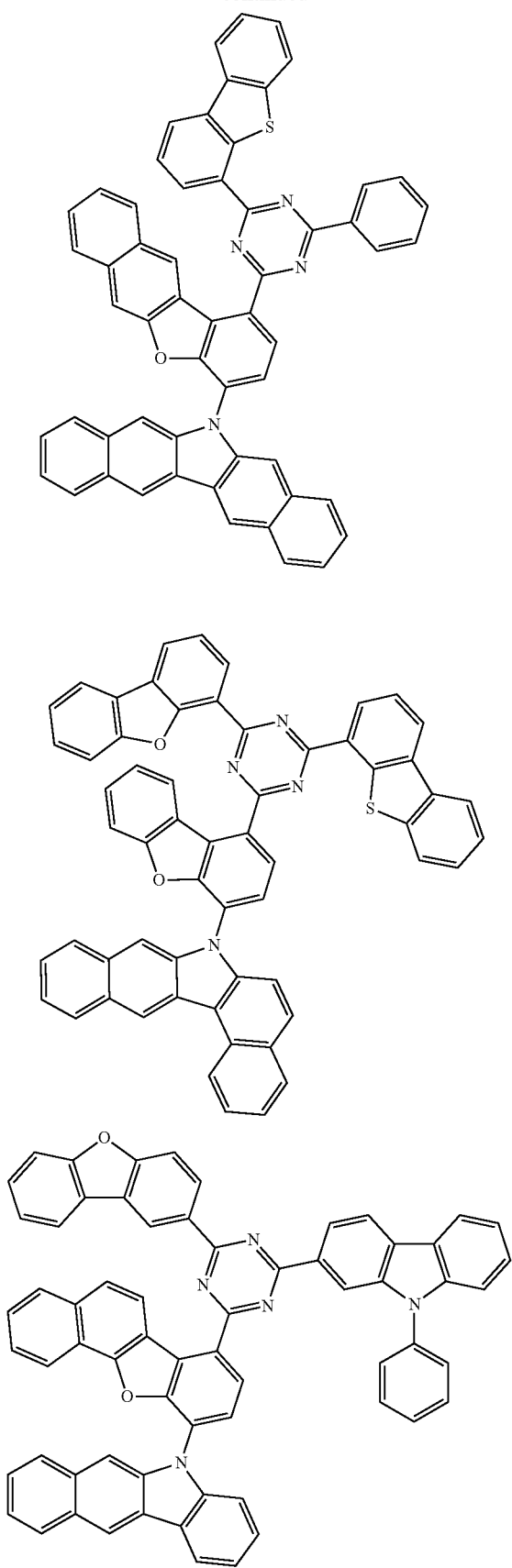
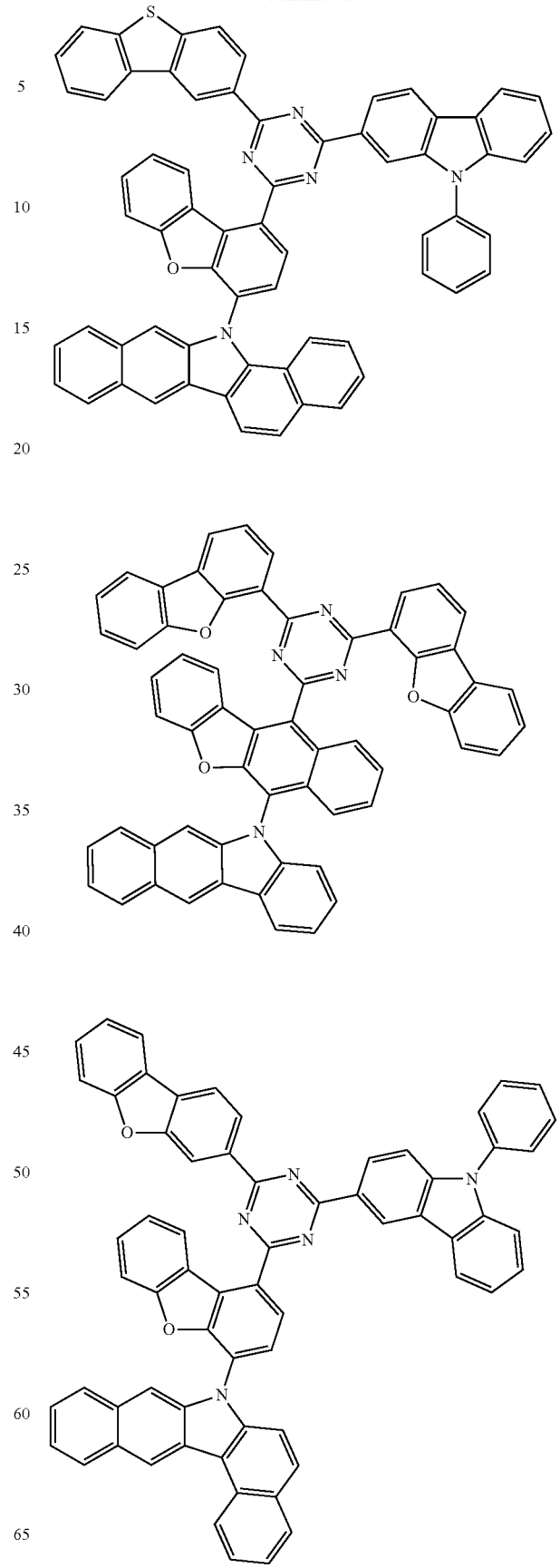

591
-continued
592
-continued
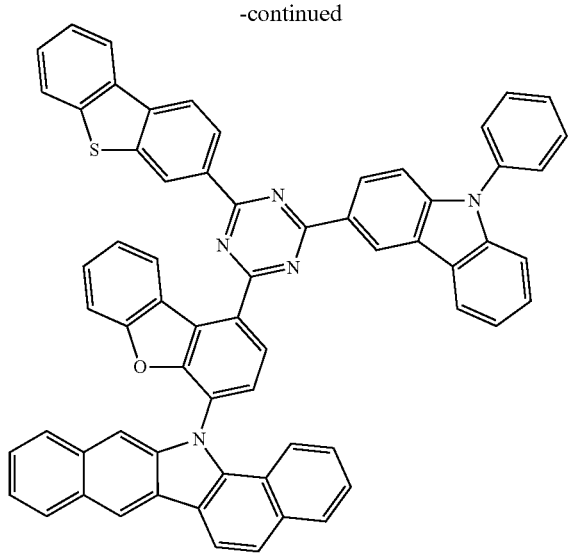
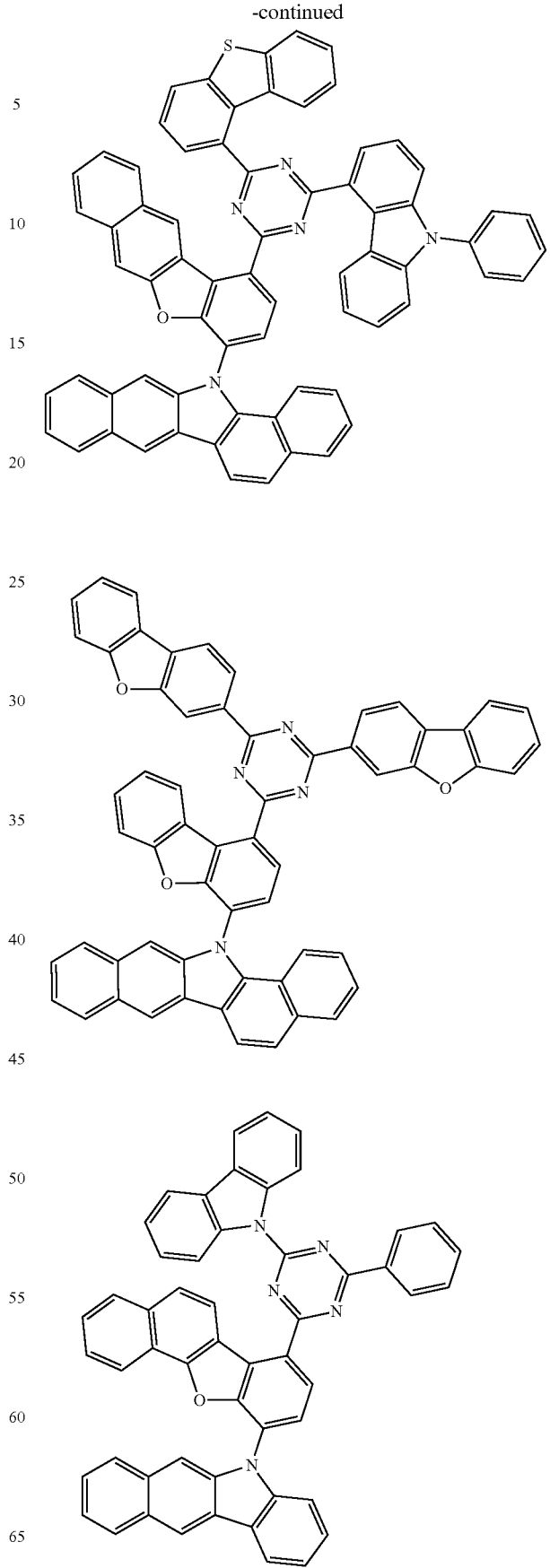

593
-continued
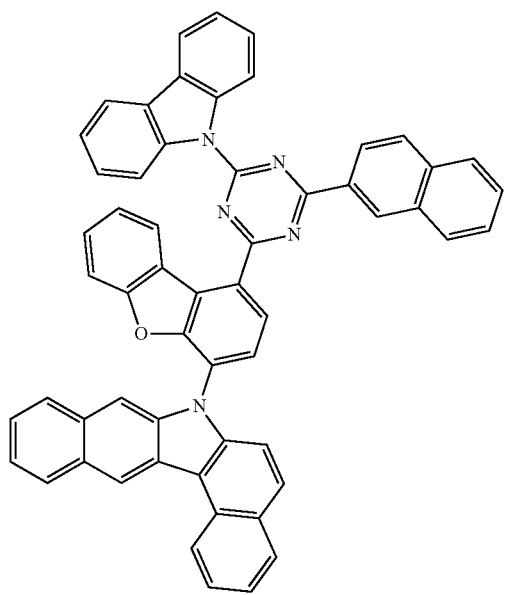
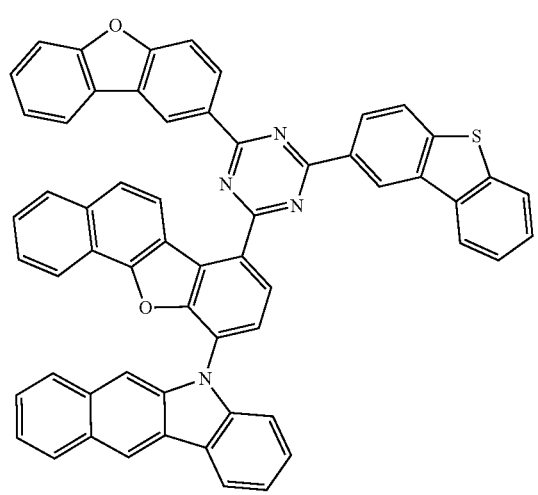
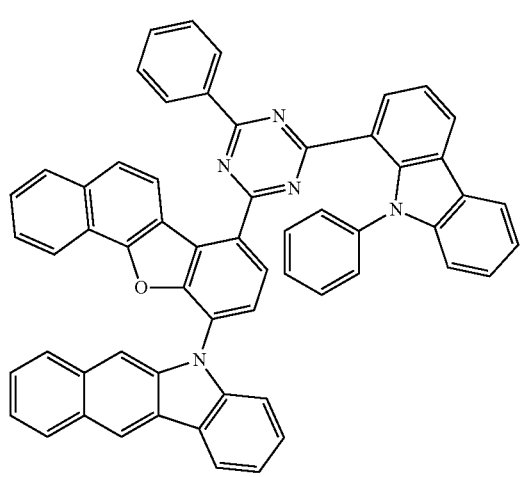
594
-continued
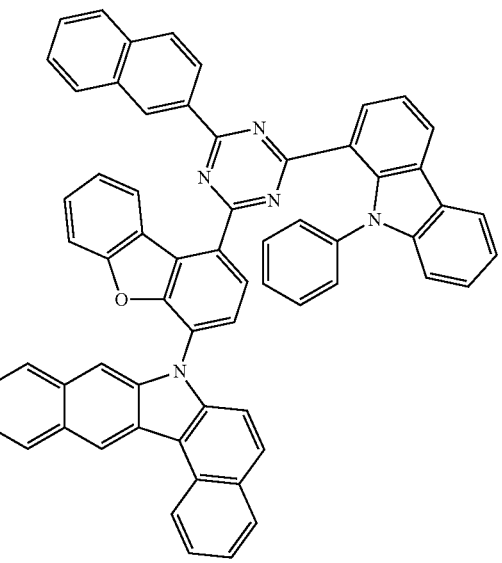
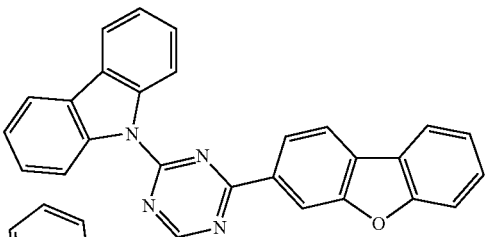
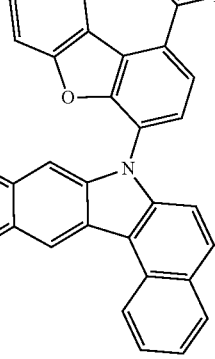

595
-continued
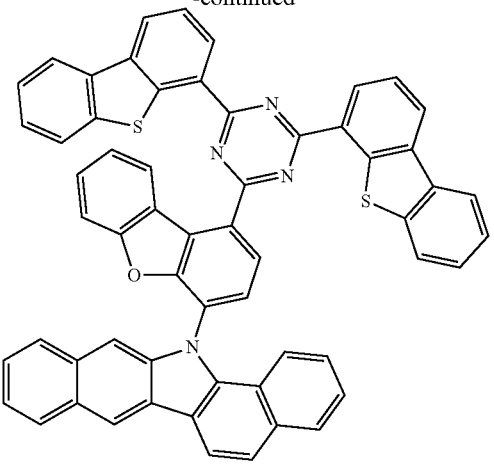
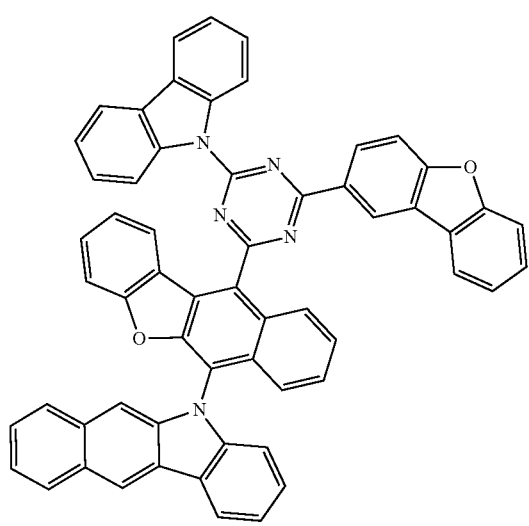
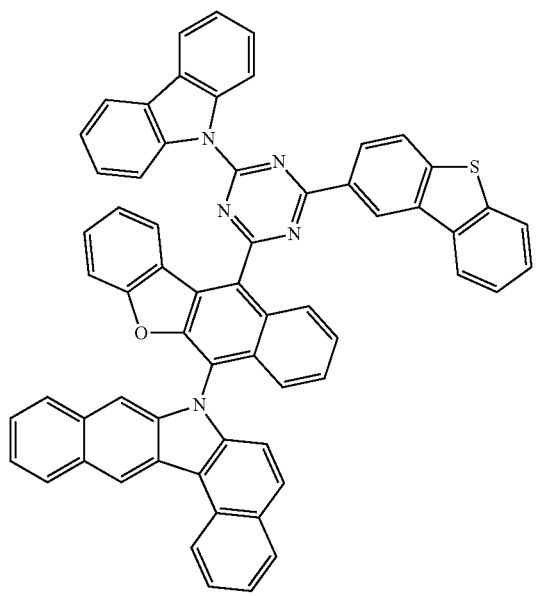
596
-continued
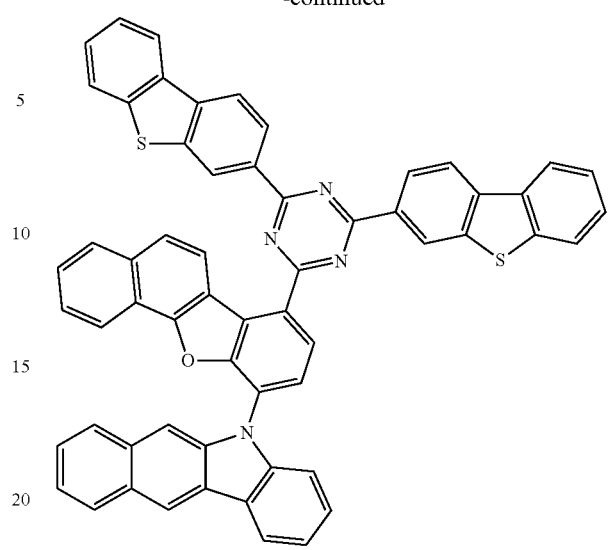
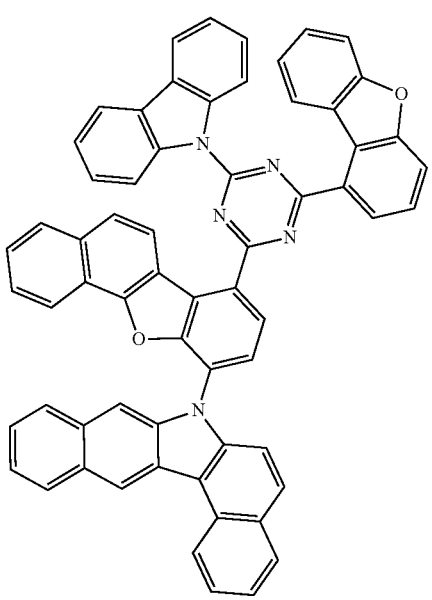
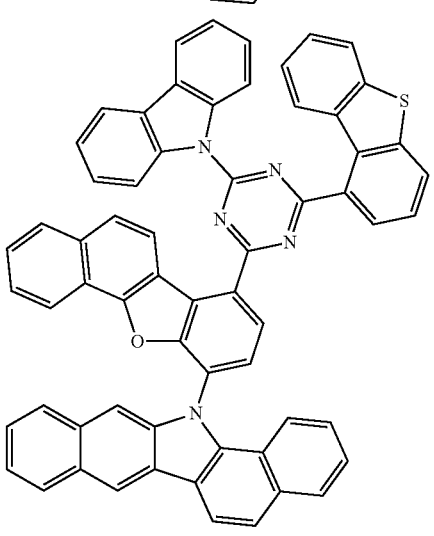

597
-continued
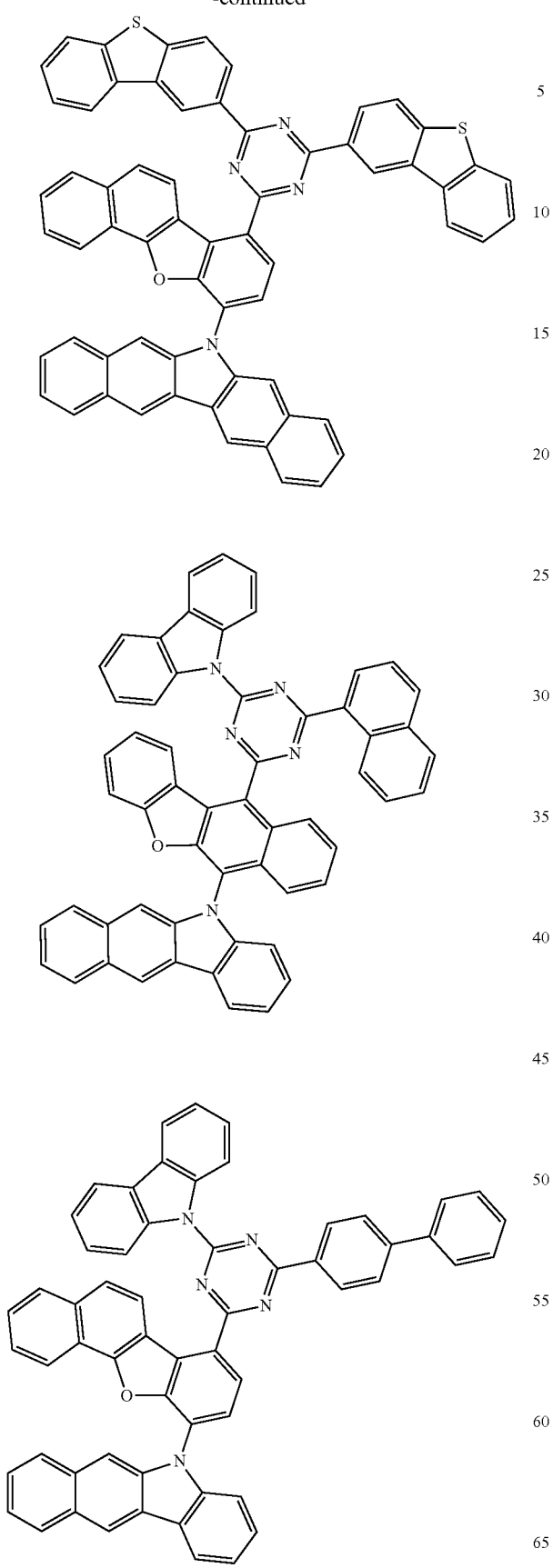
598
-continued
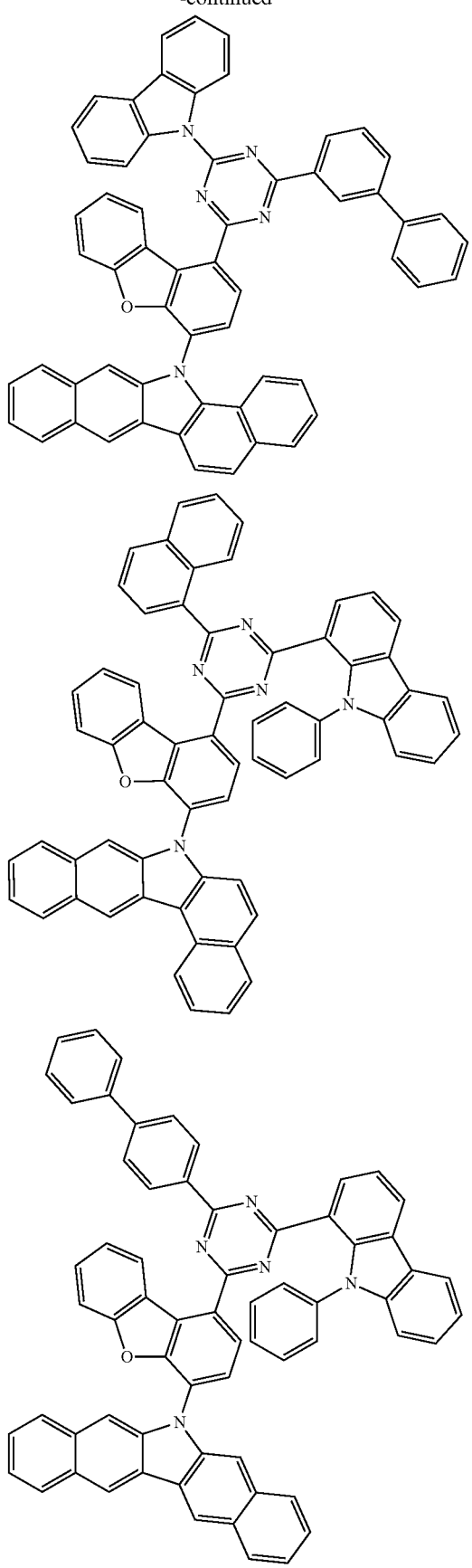

599
-continued
600
-continued
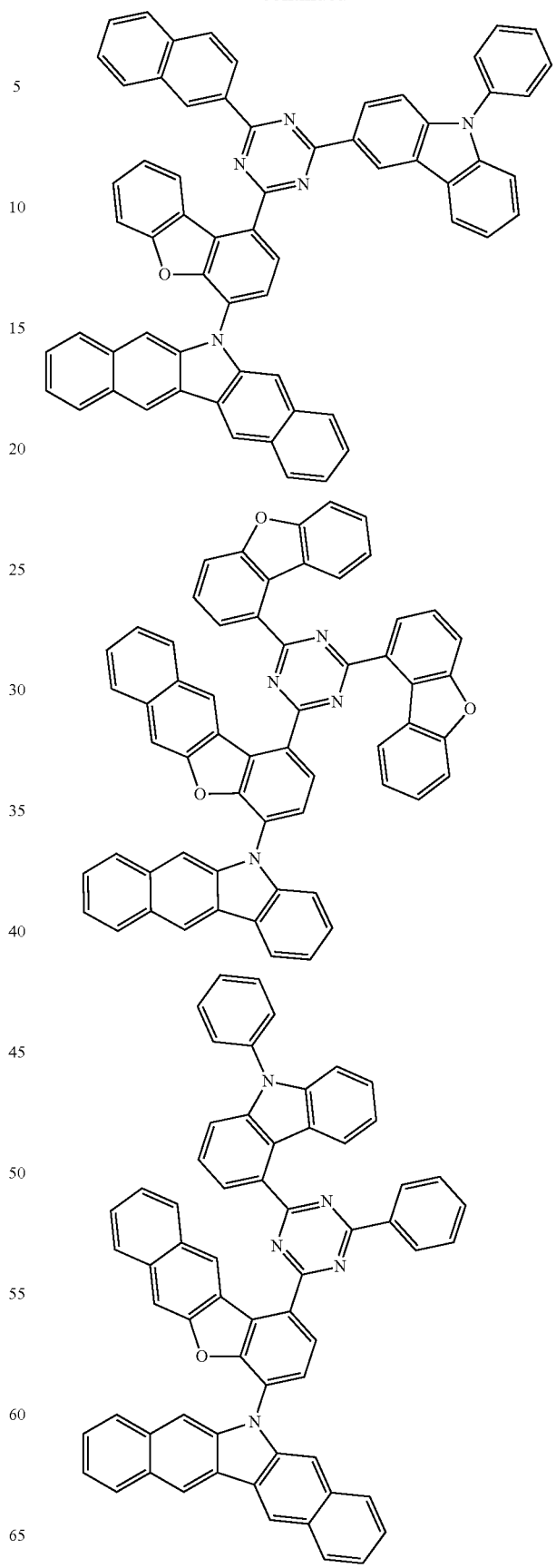

601
-continued
602
-continued
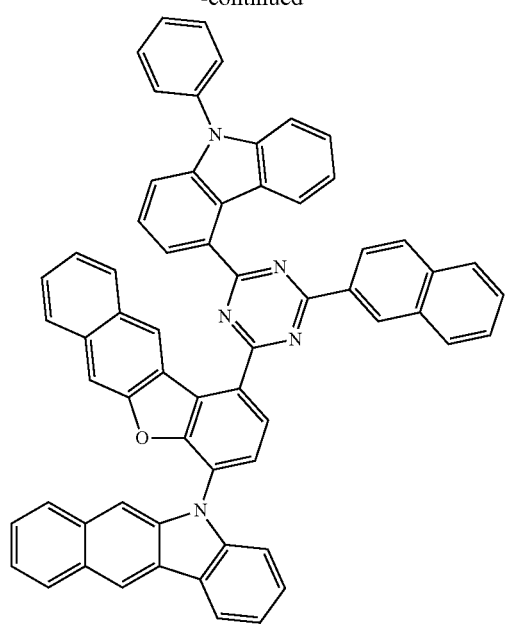
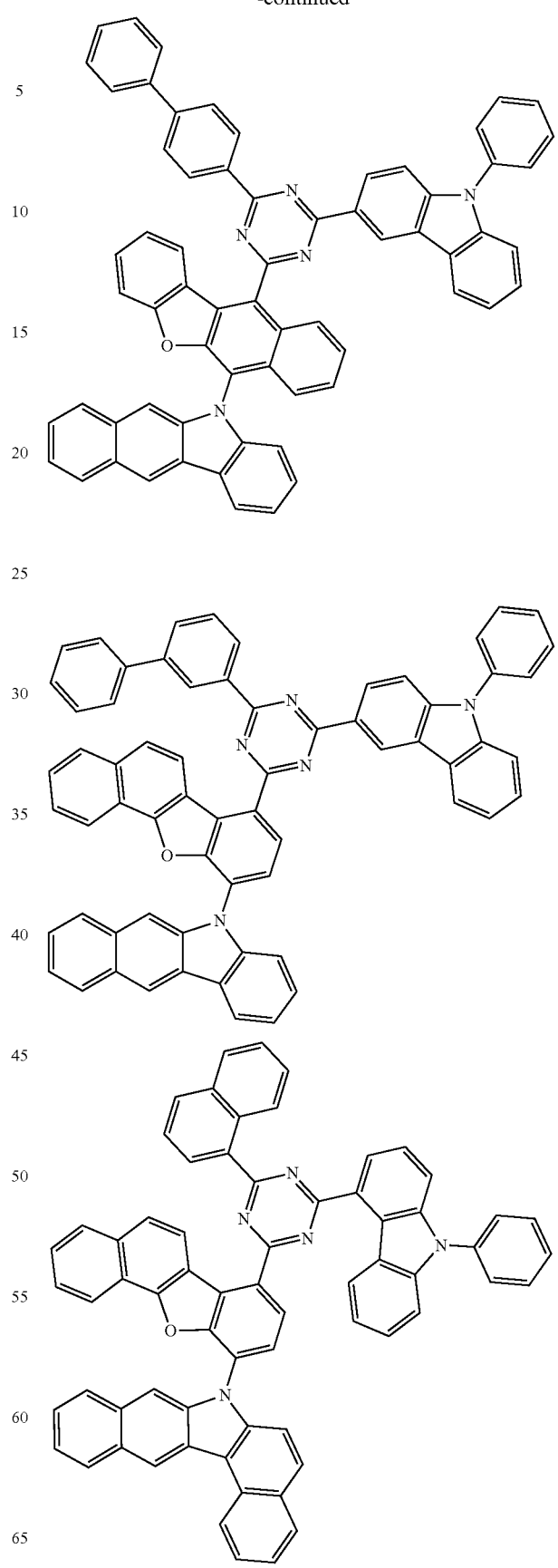

603
-continued
604
-continued
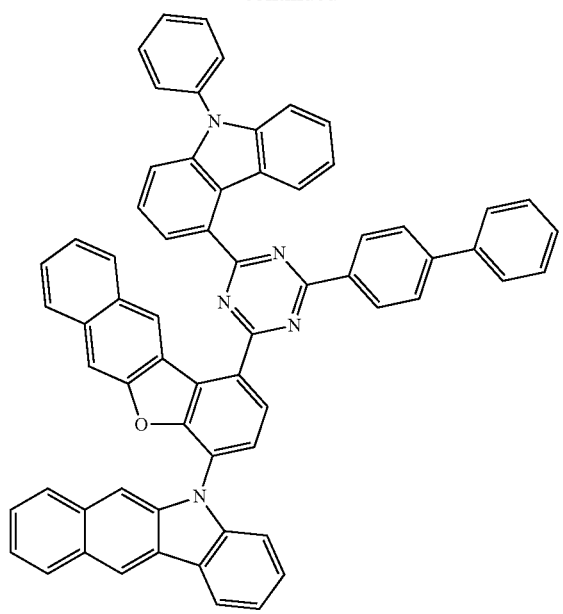
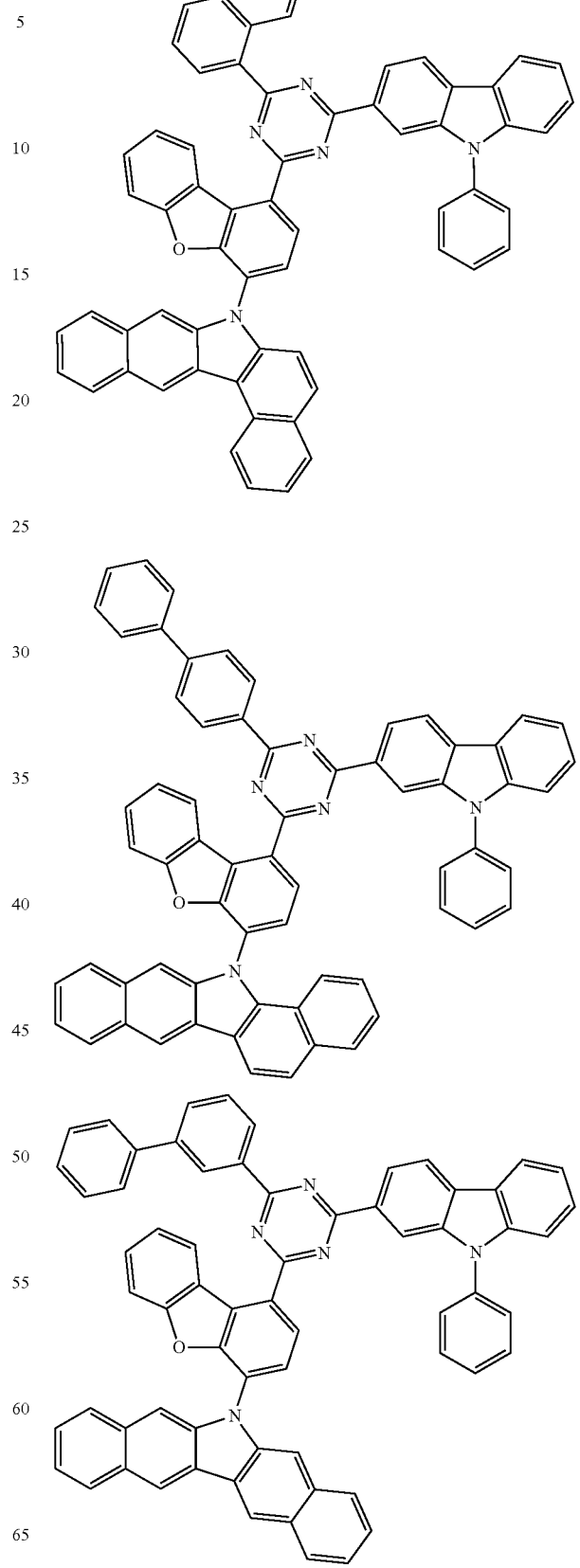

605
-continued
606
-continued
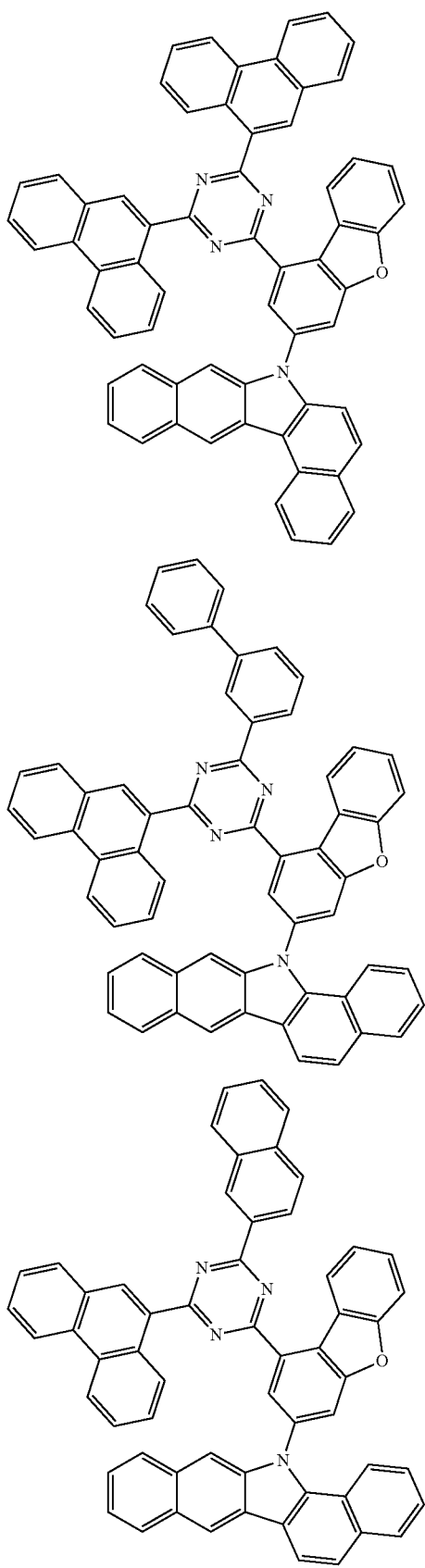
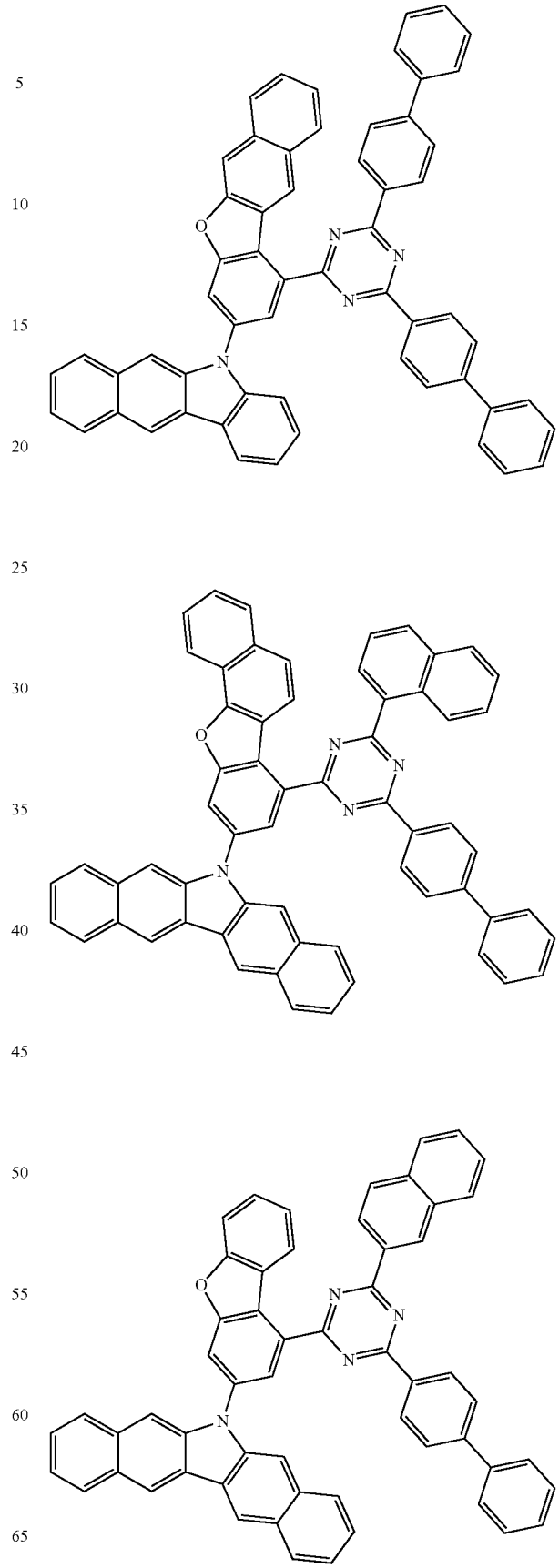

607
-continued
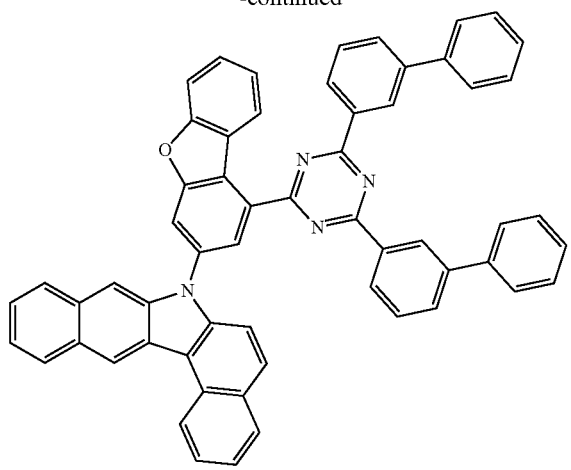
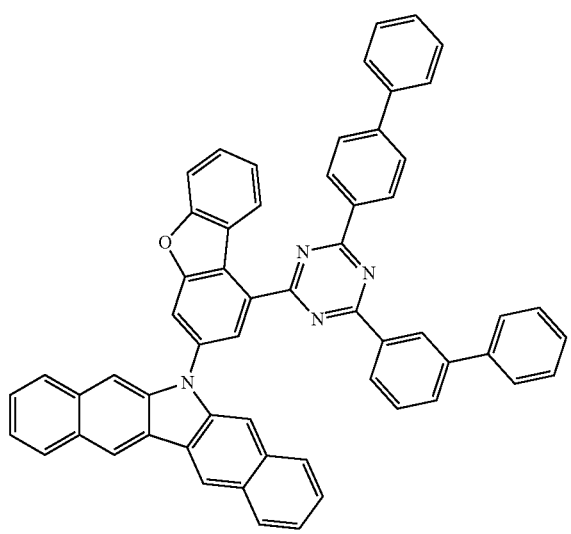
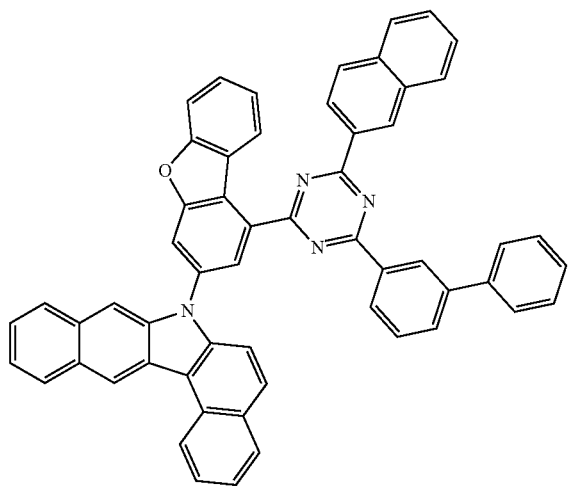
608
-continued
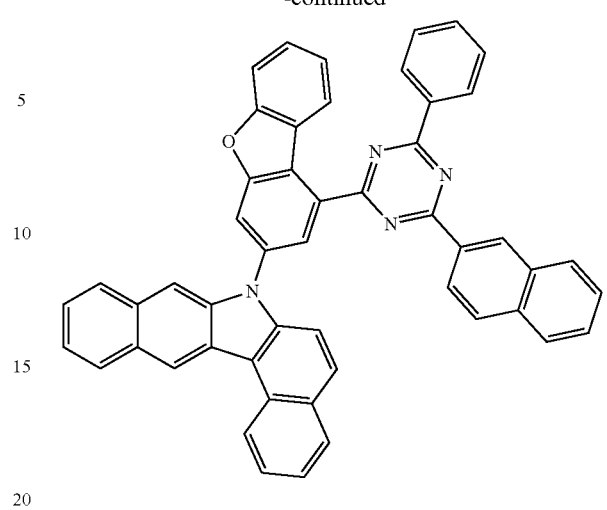
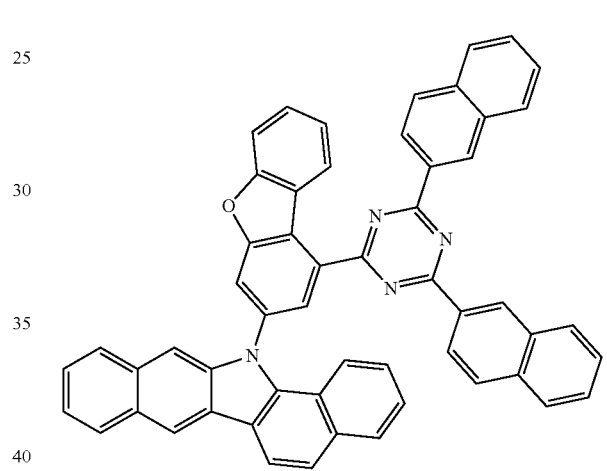
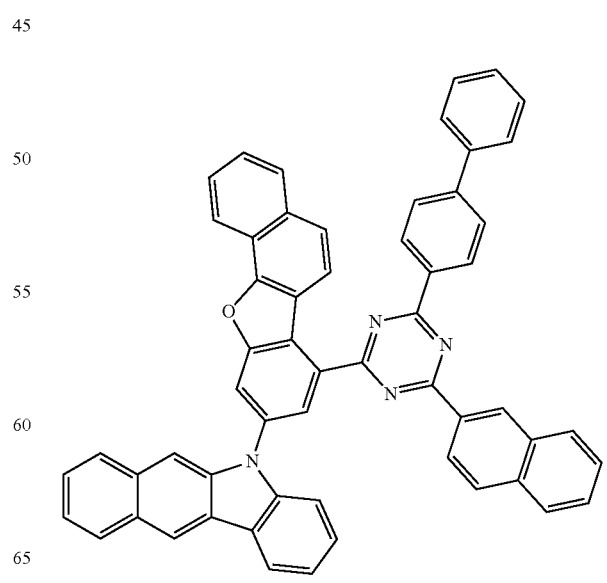

609
-continued
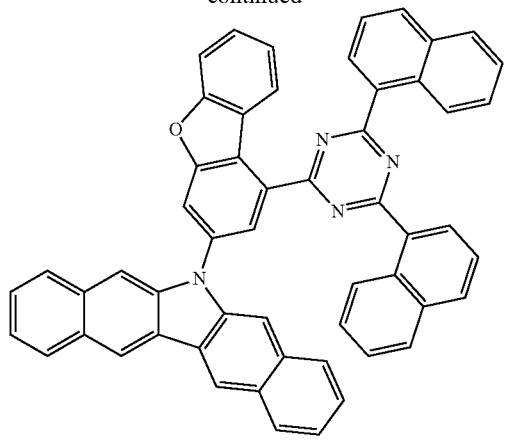
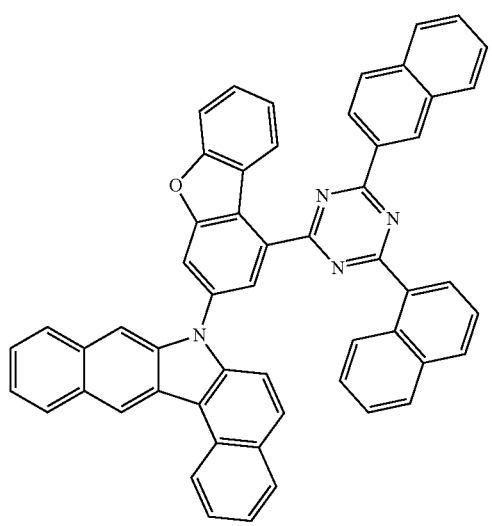
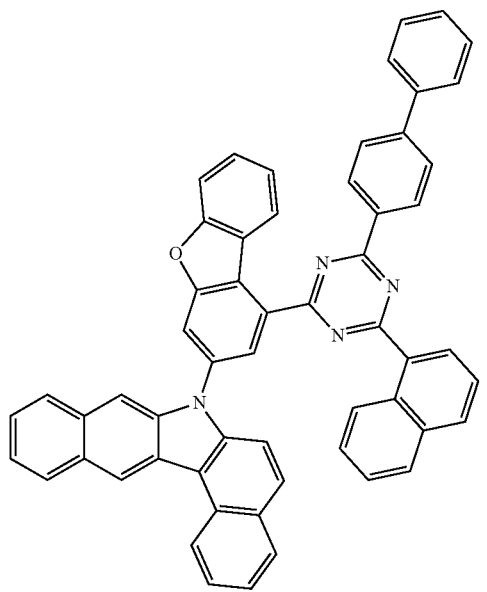
610
-continued
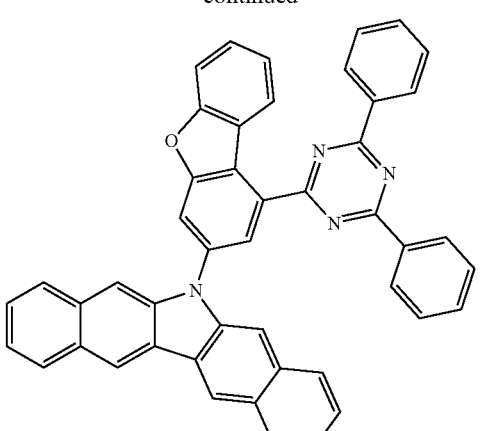
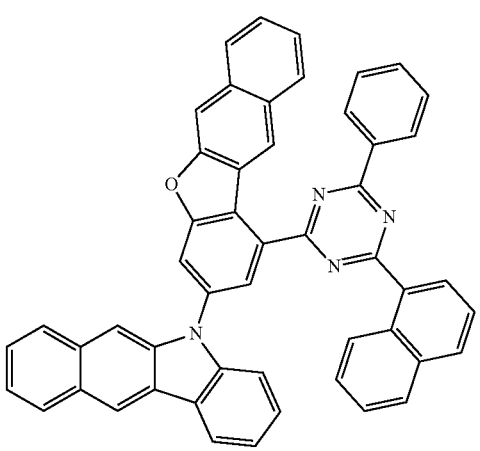
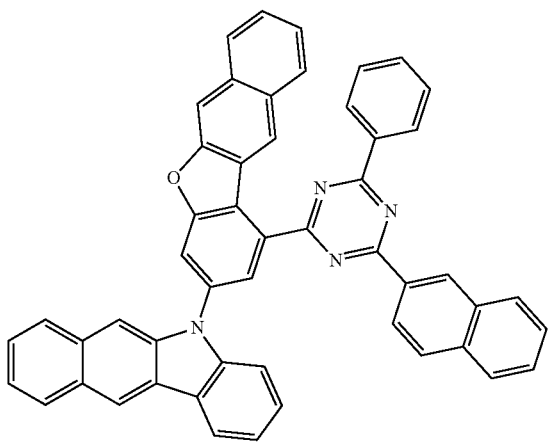

611
-continued
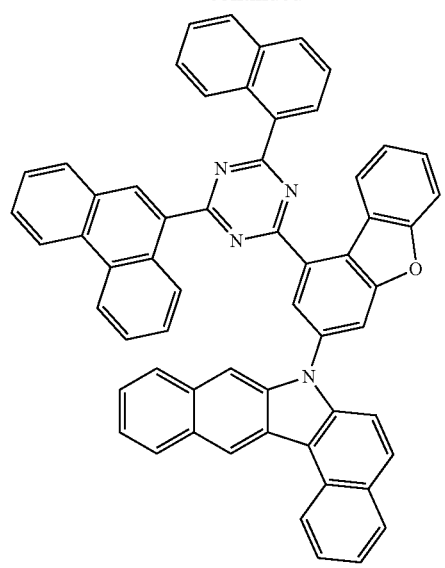
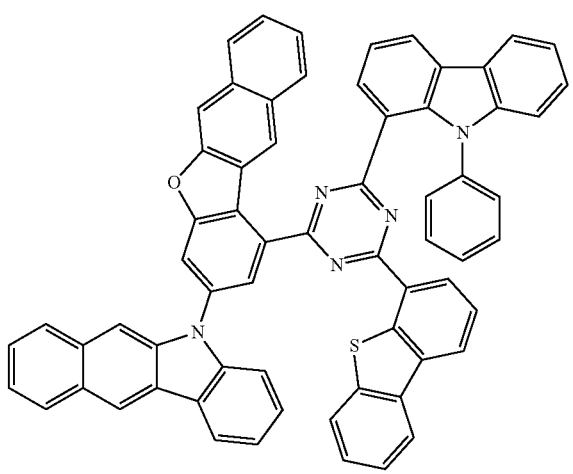
612
-continued
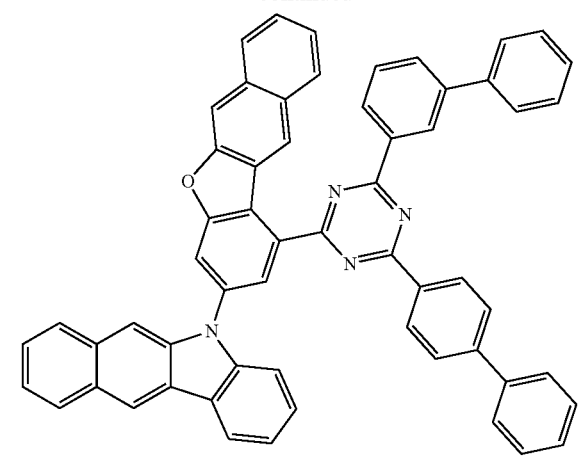
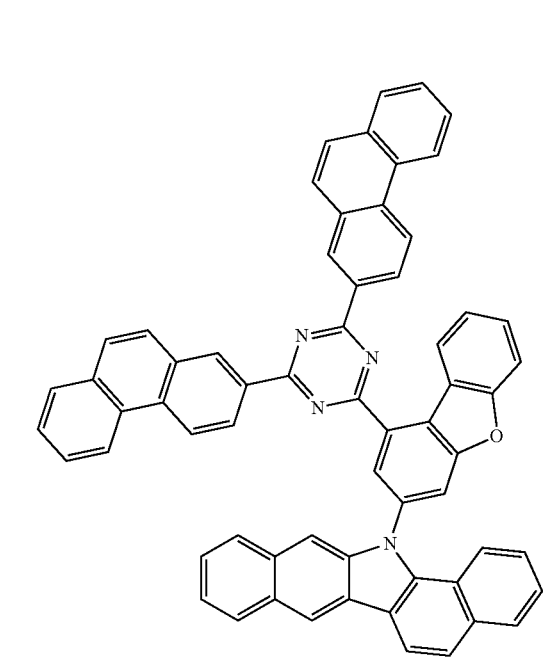
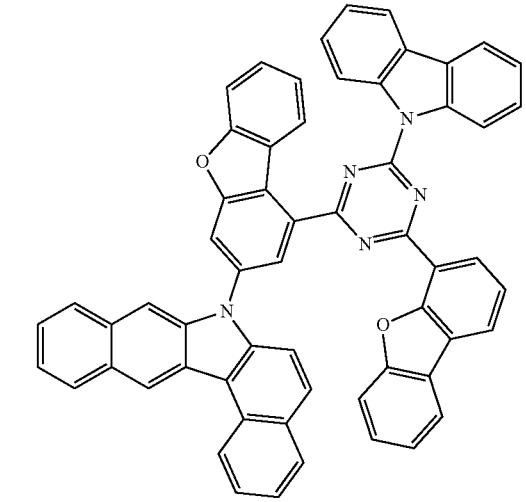

613
-continued
614
-continued
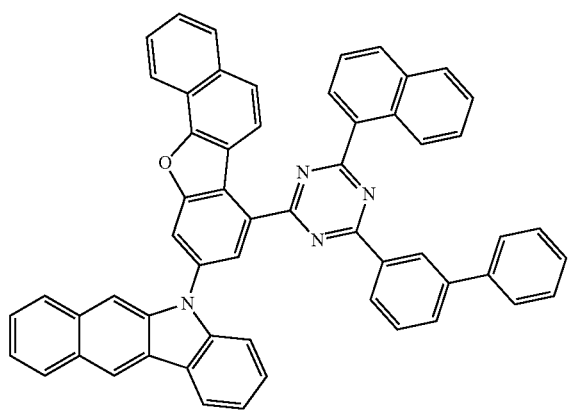
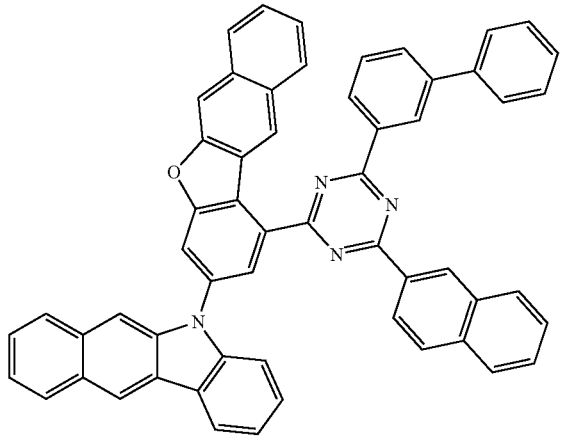
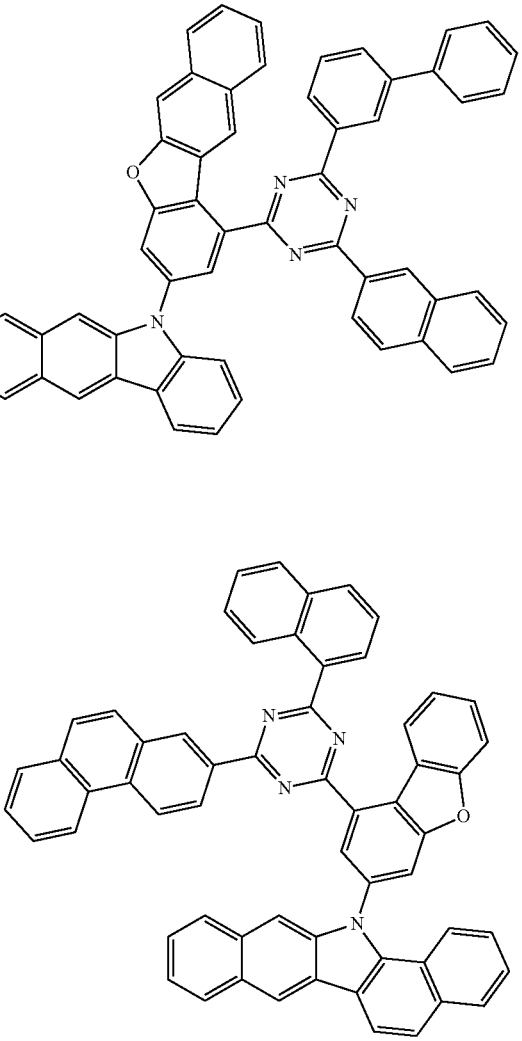
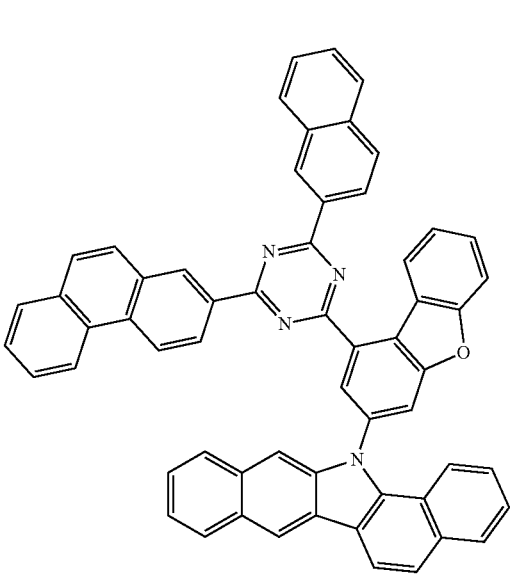

615
-continued
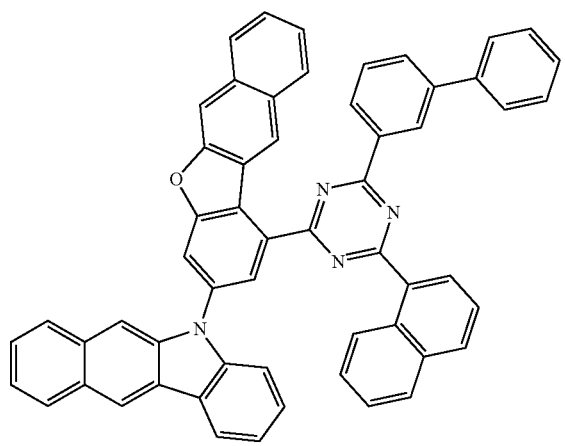
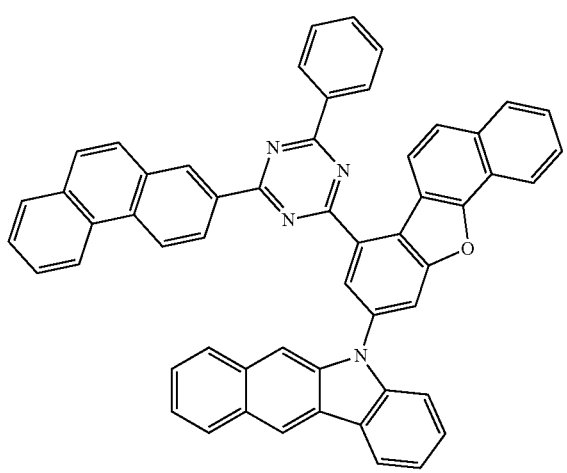
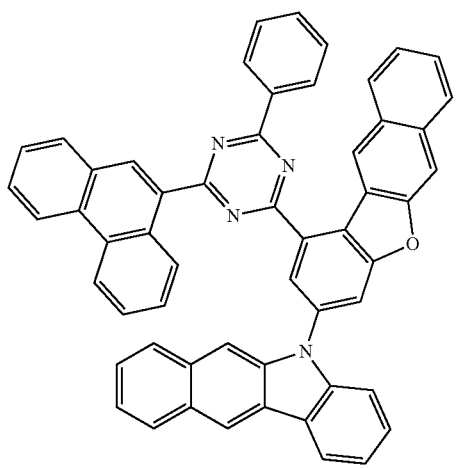
616
-continued
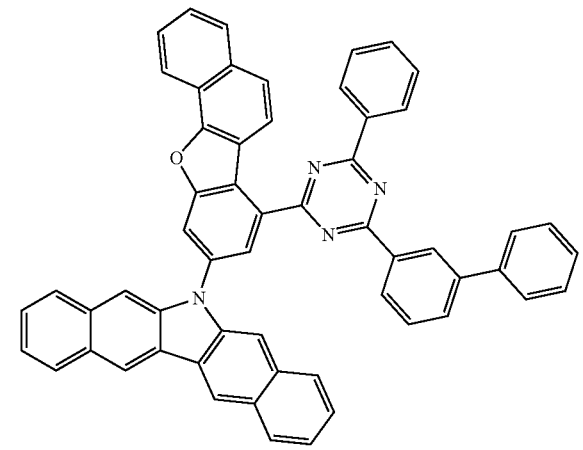
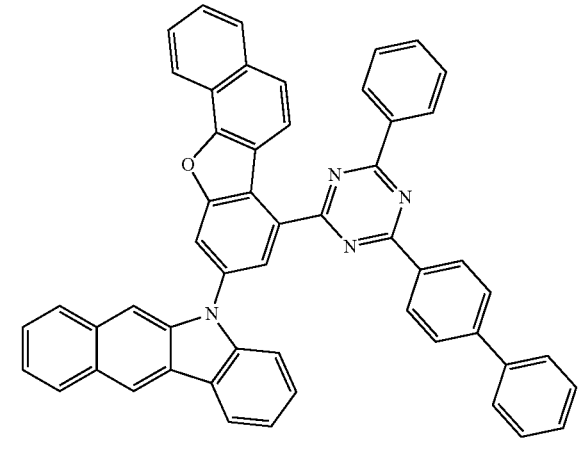
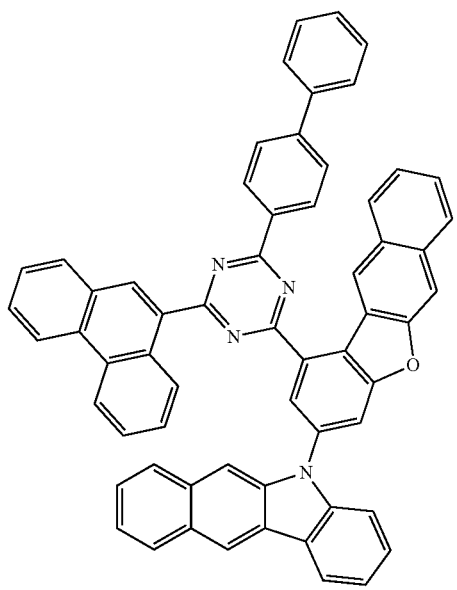

617
-continued
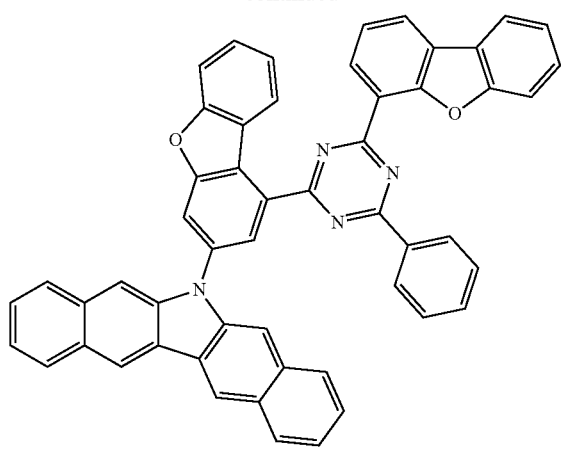
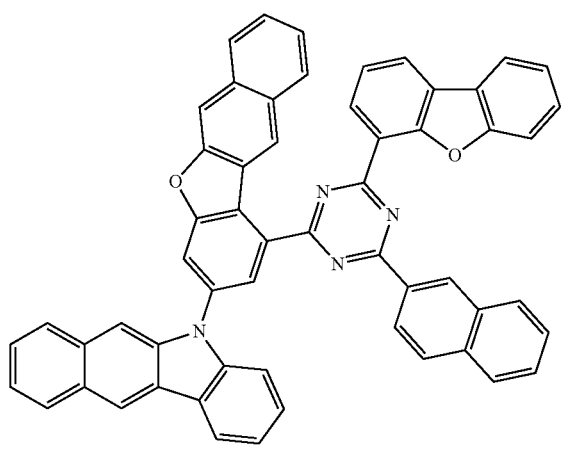
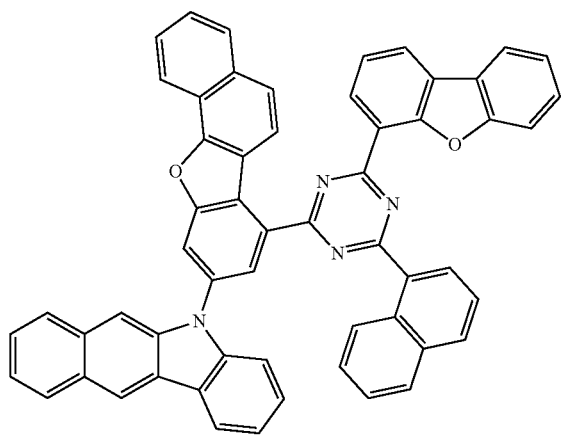
618
-continued
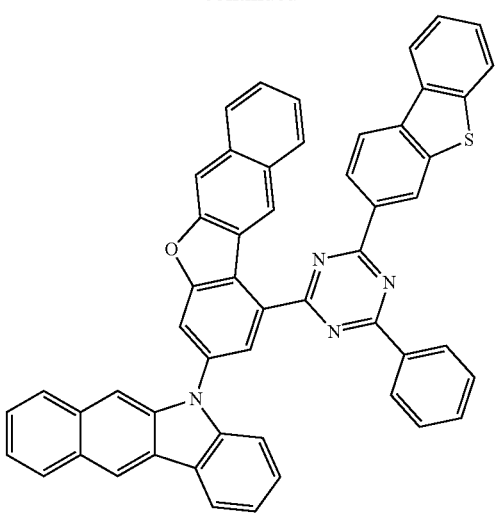
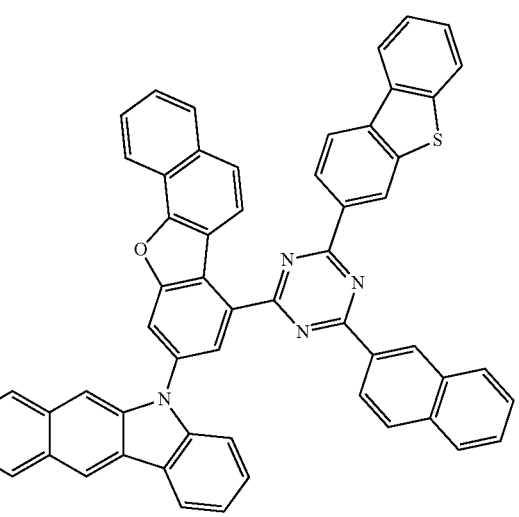
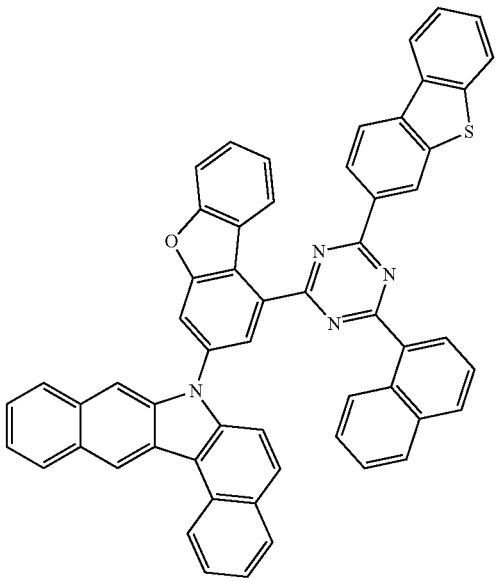

619
-continued
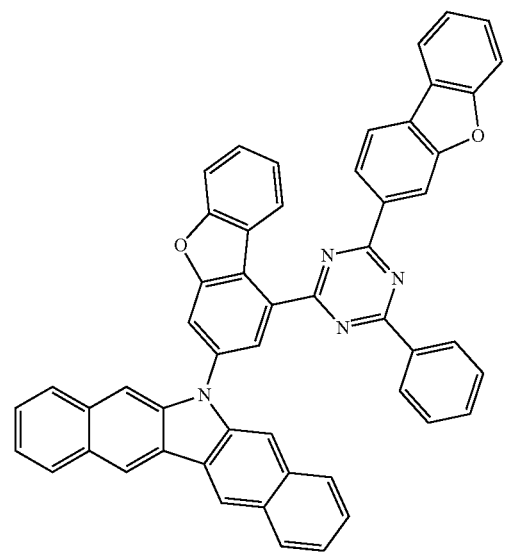
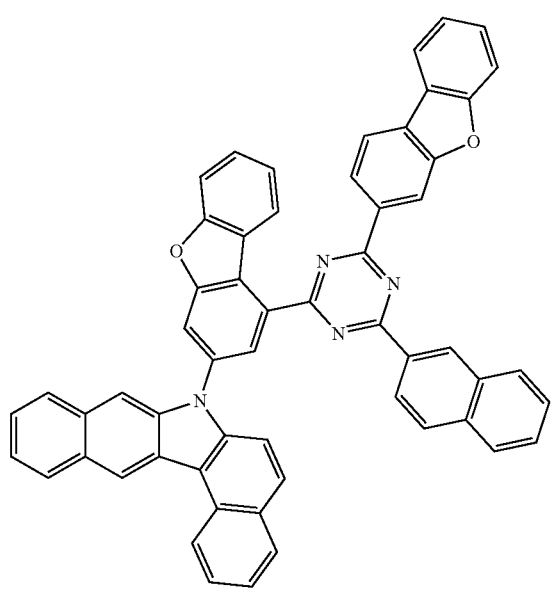
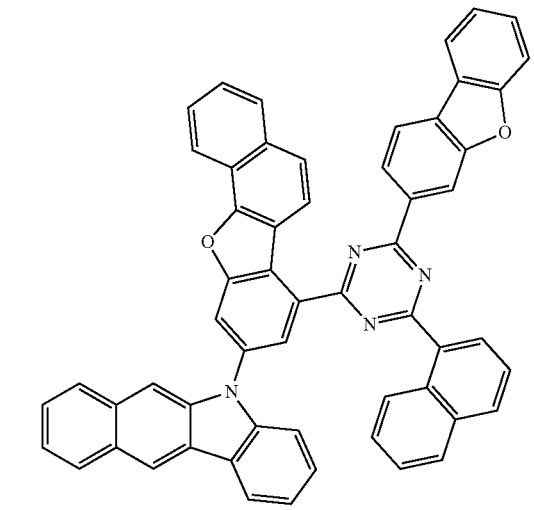
620
-continued
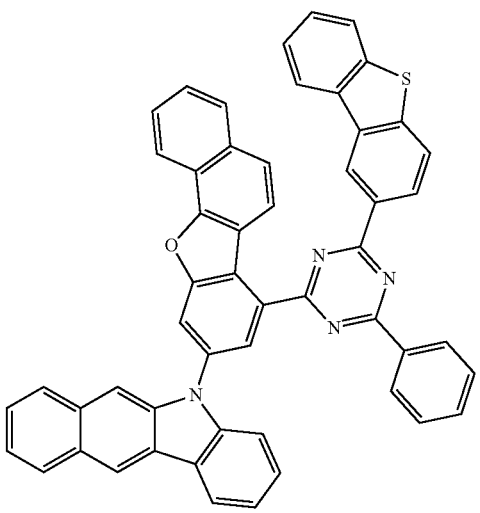
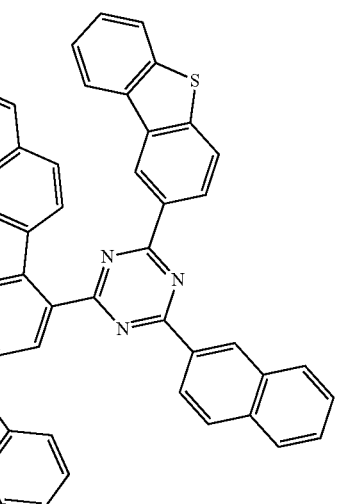

621
-continued
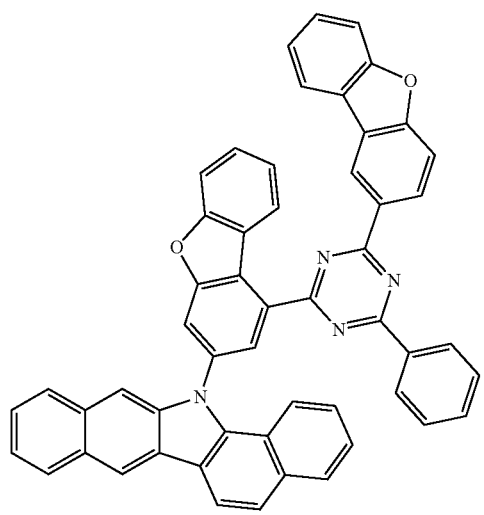
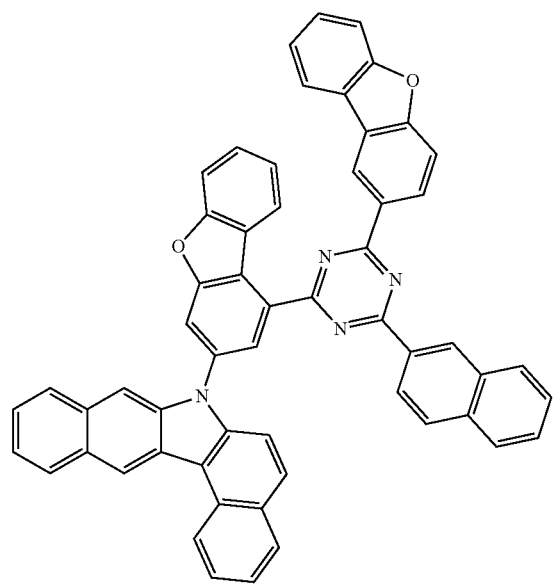
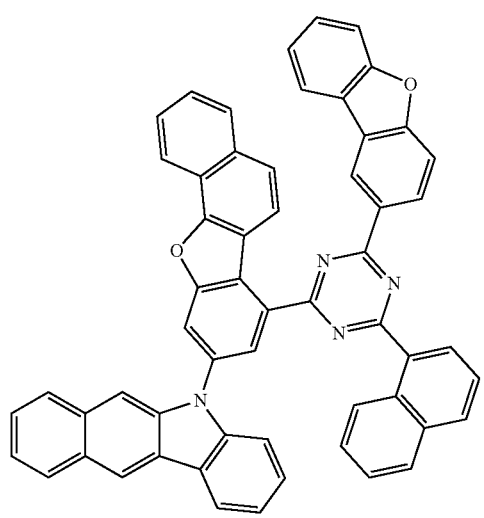
622
-continued
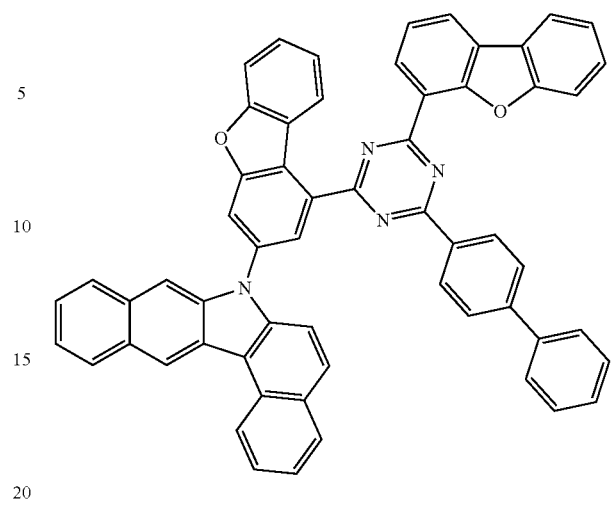
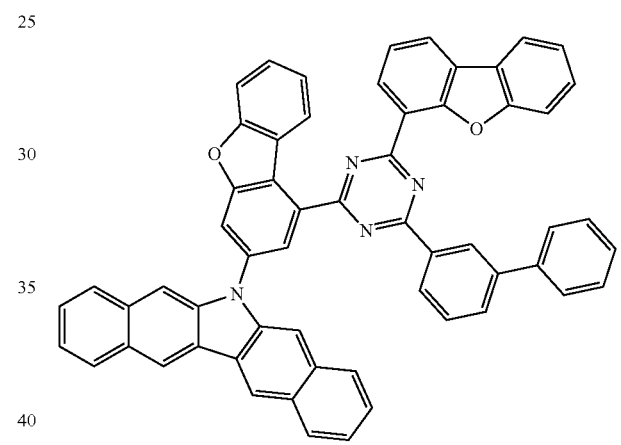
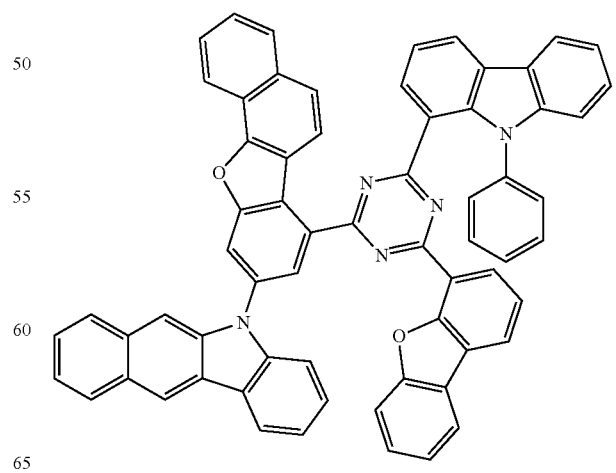

623
-continued
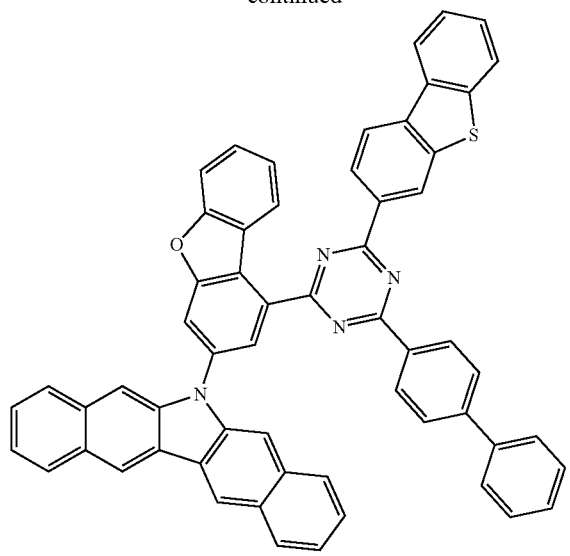
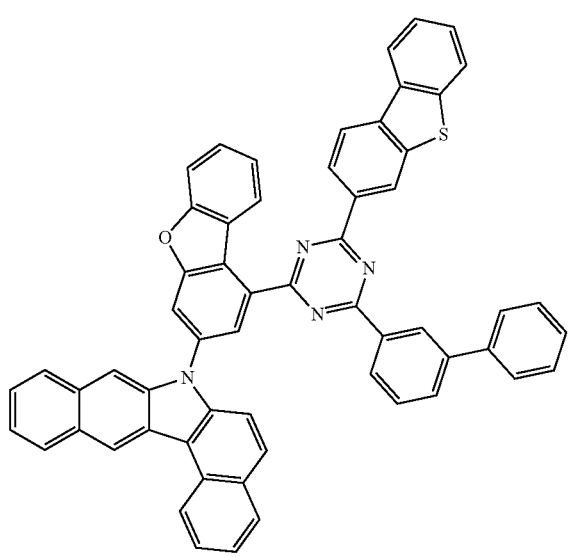
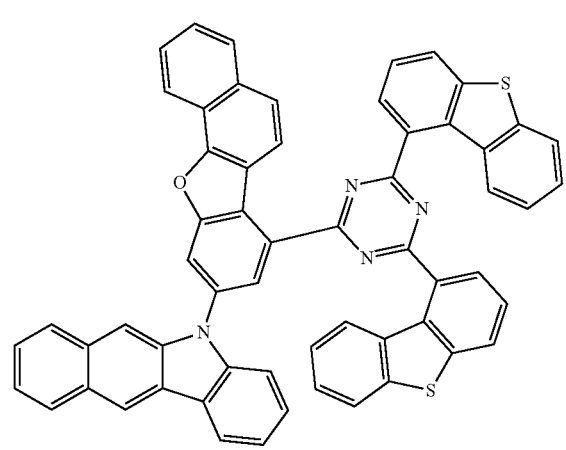
624
-continued
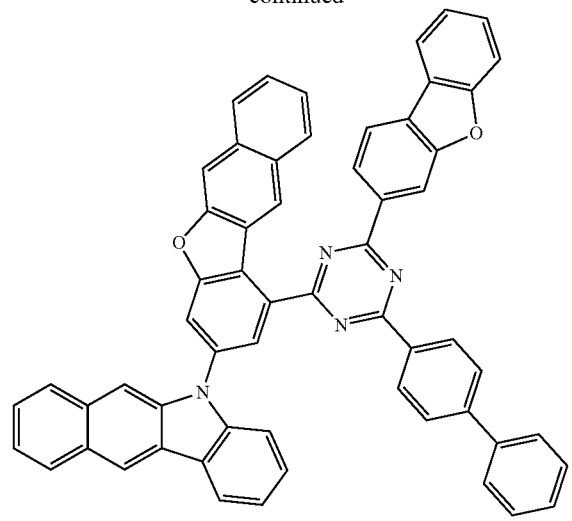
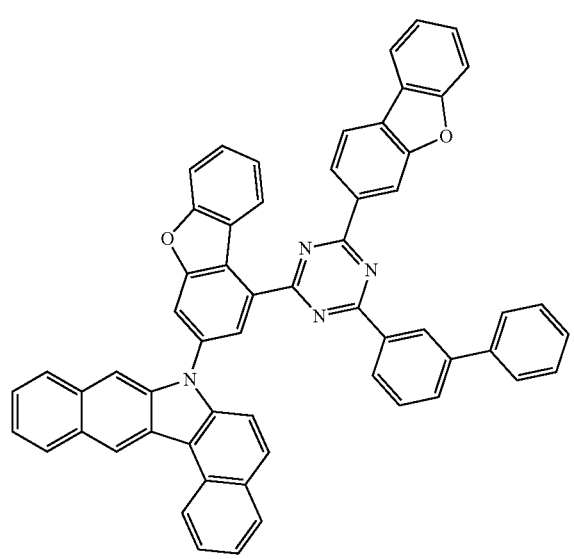

625
-continued
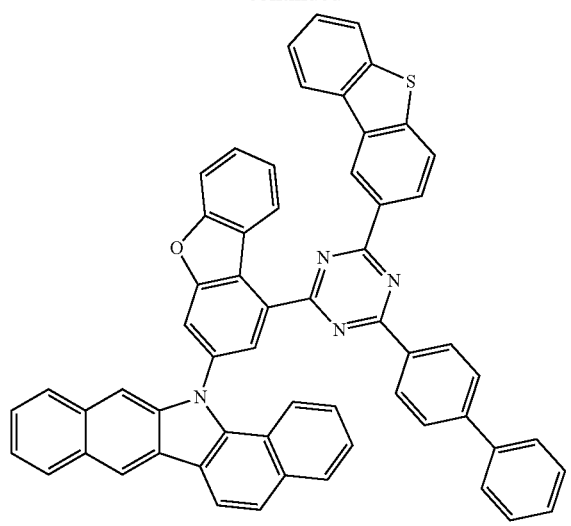
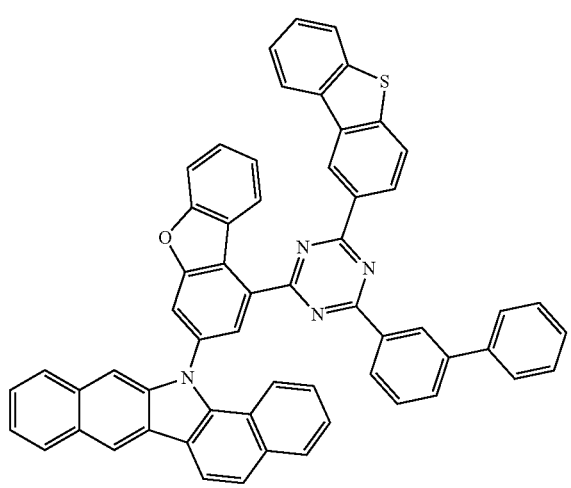
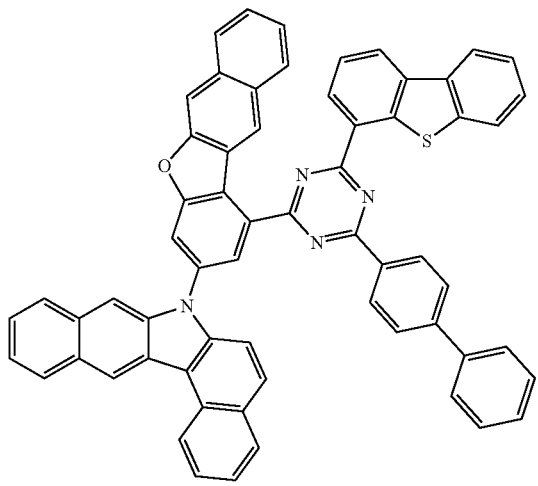
626
-continued
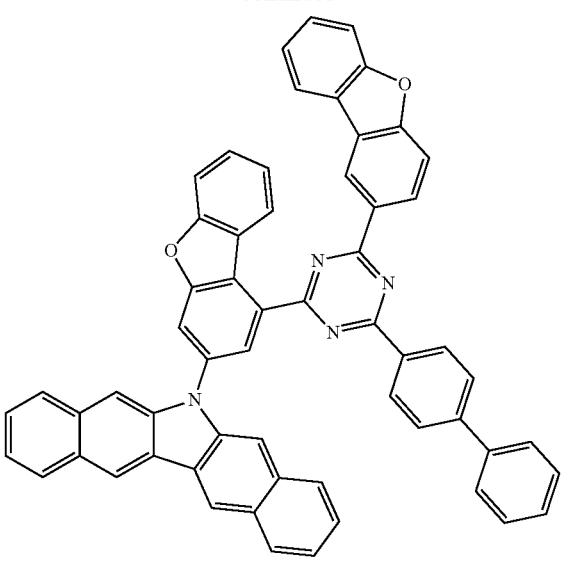
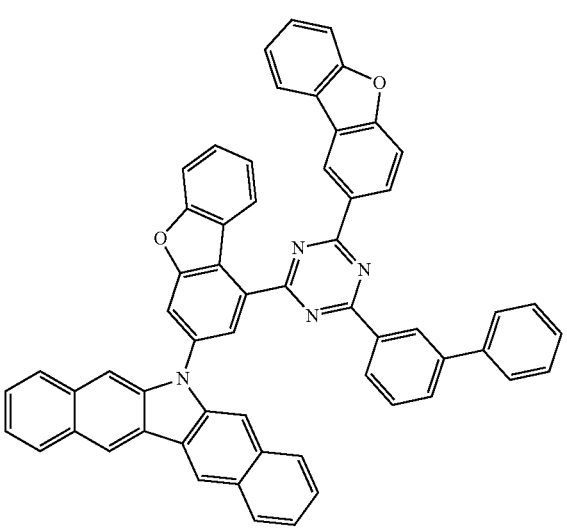
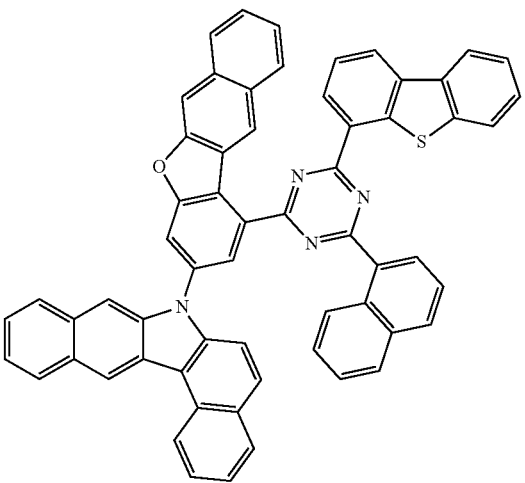

627
-continued
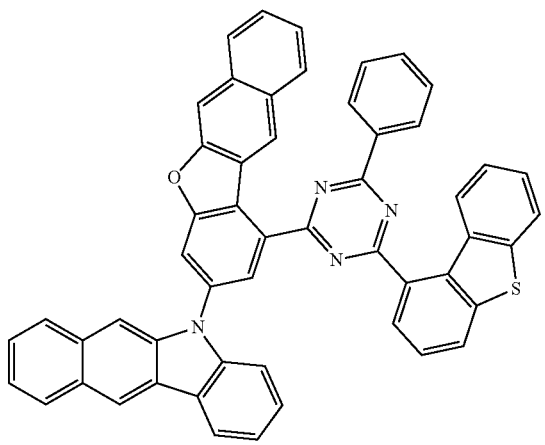
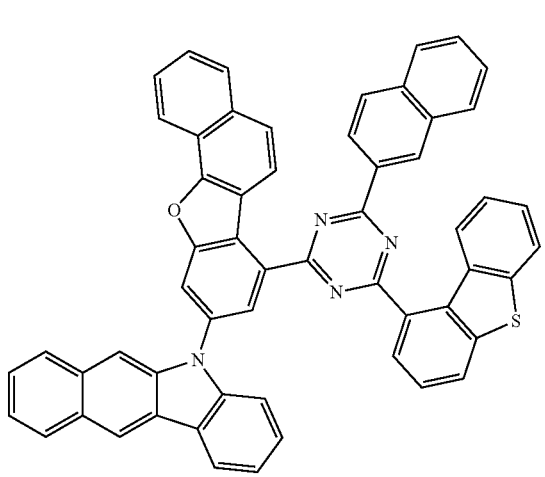
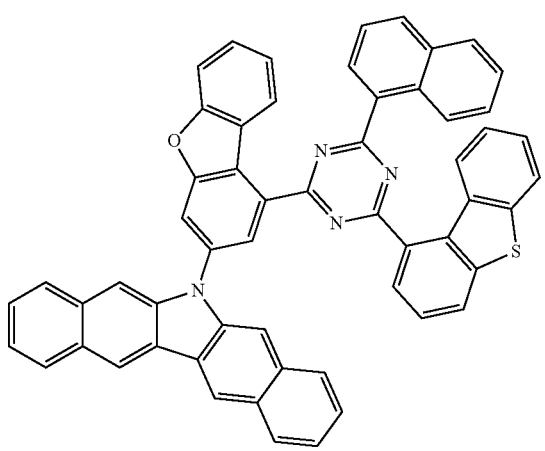
628
-continued
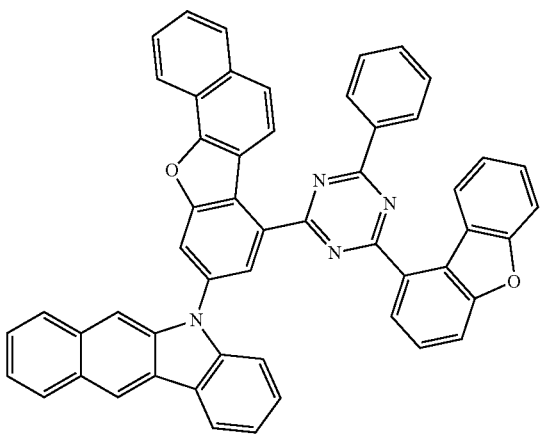
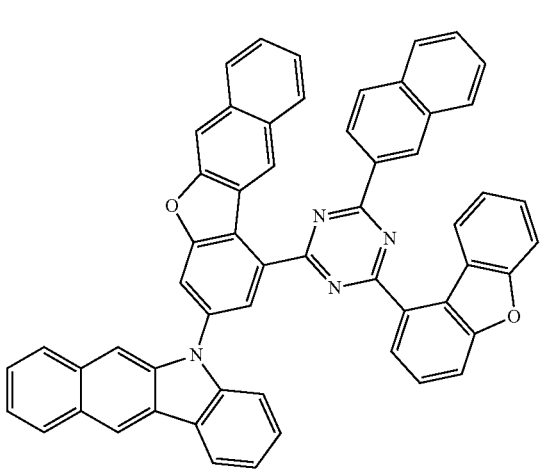
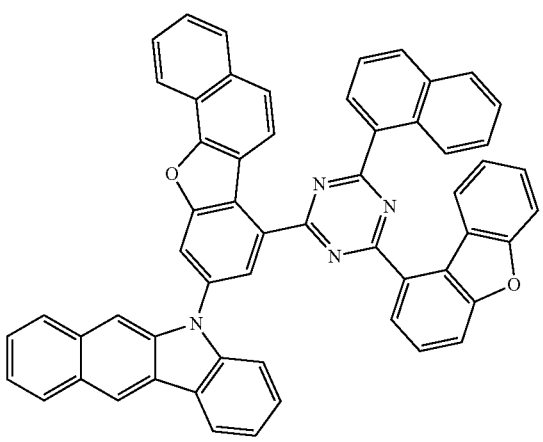

629
-continued
630
-continued
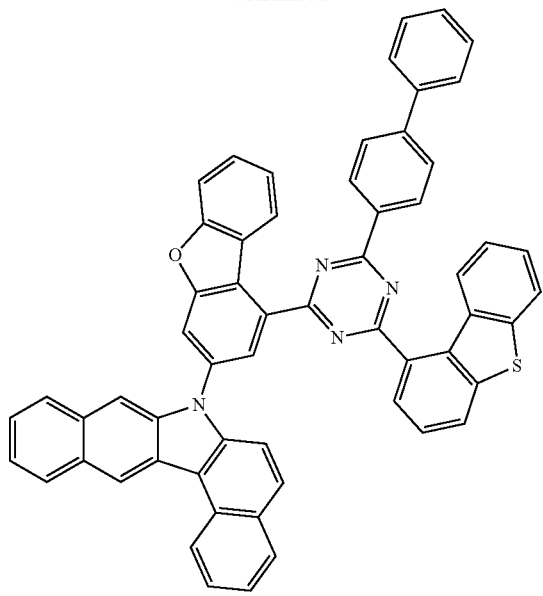
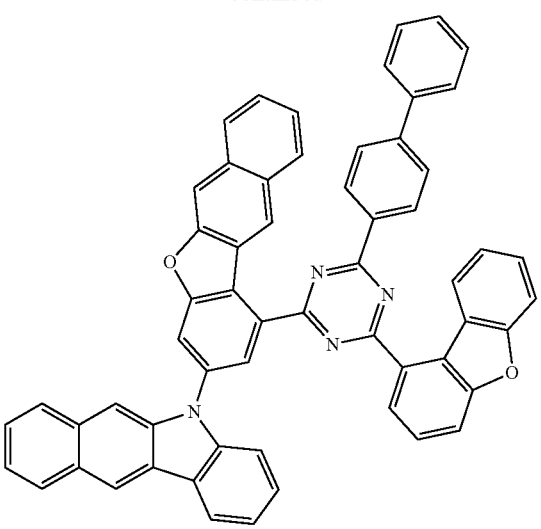
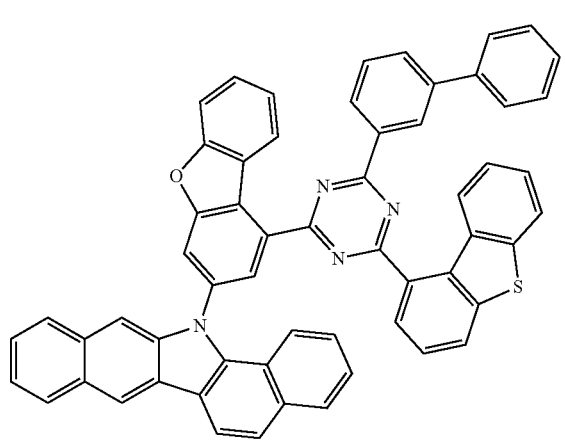
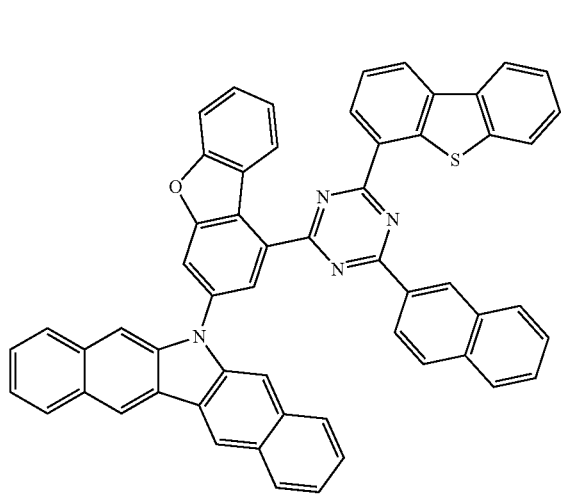
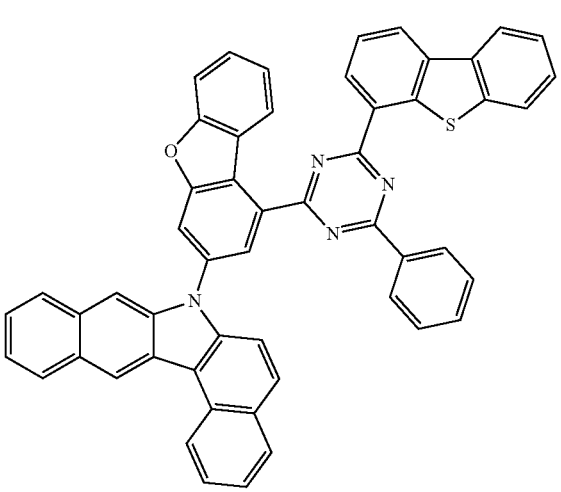

631
-continued
632
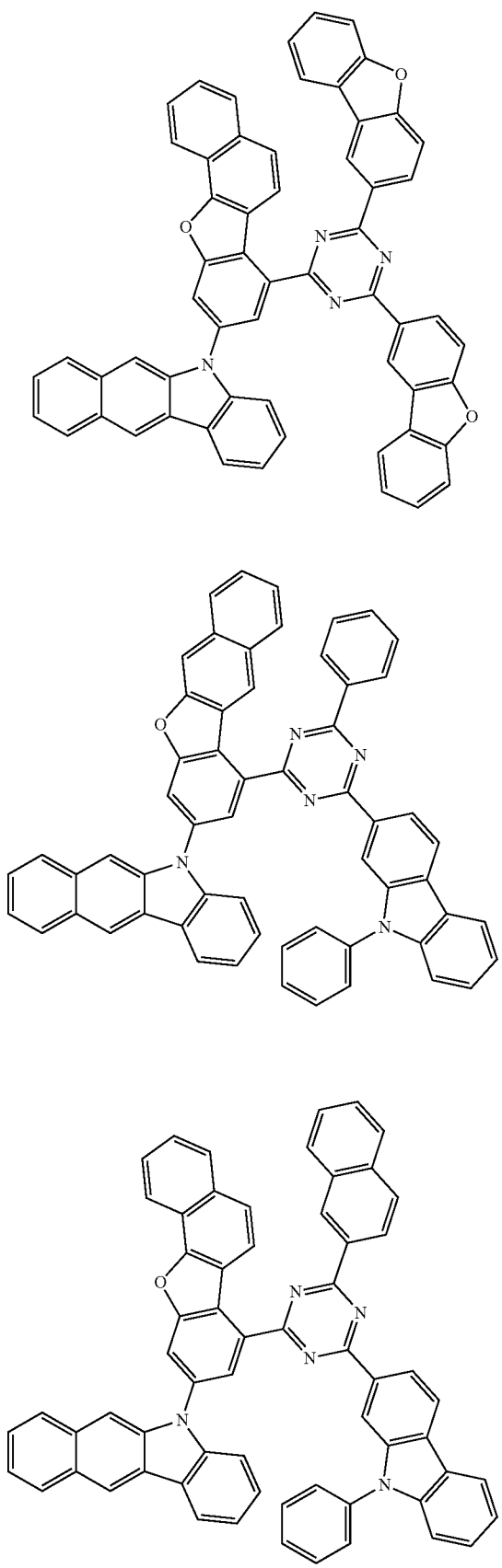
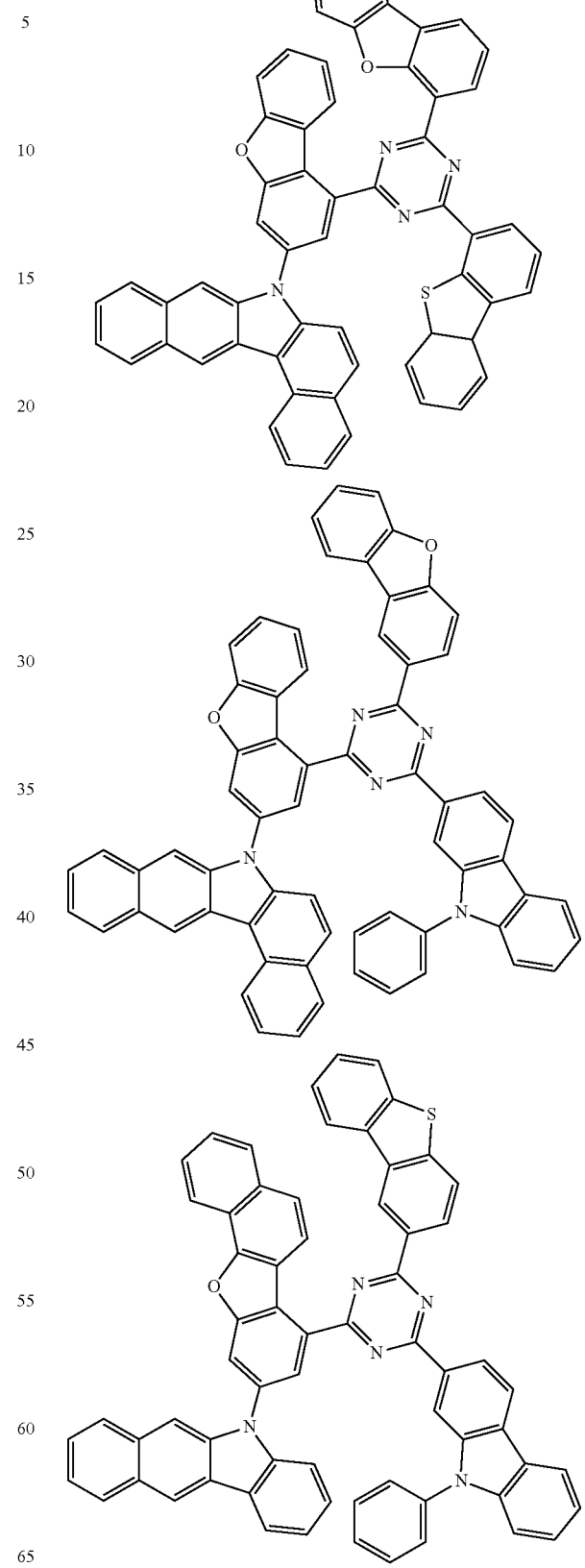

633
-continued
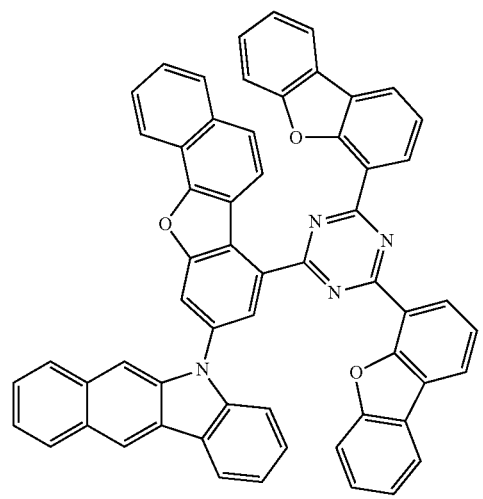
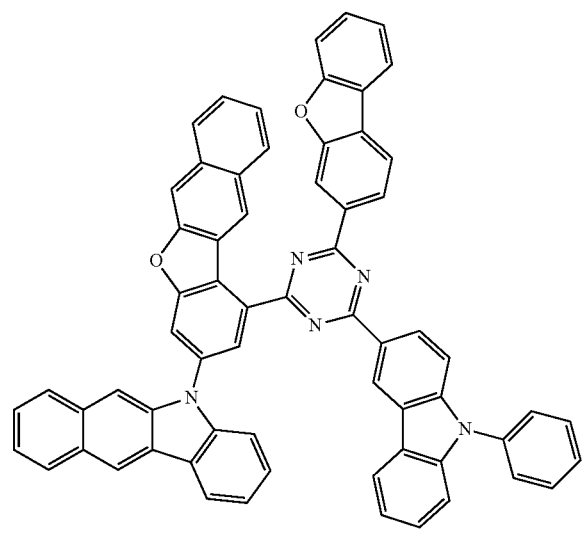
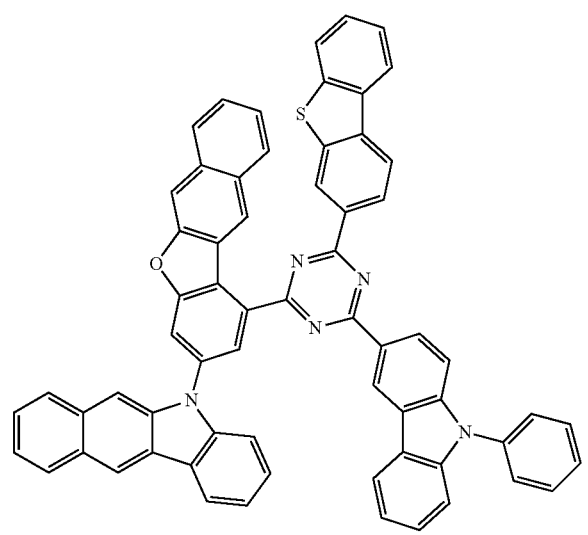
634
-continued
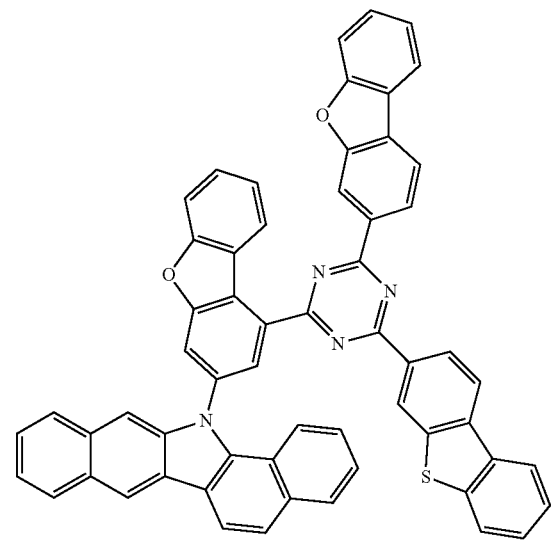
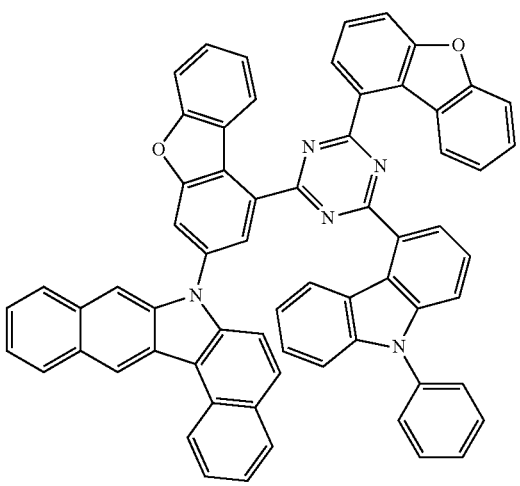
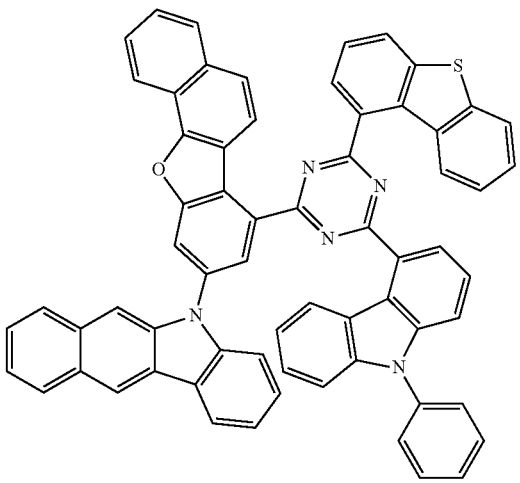

635
-continued
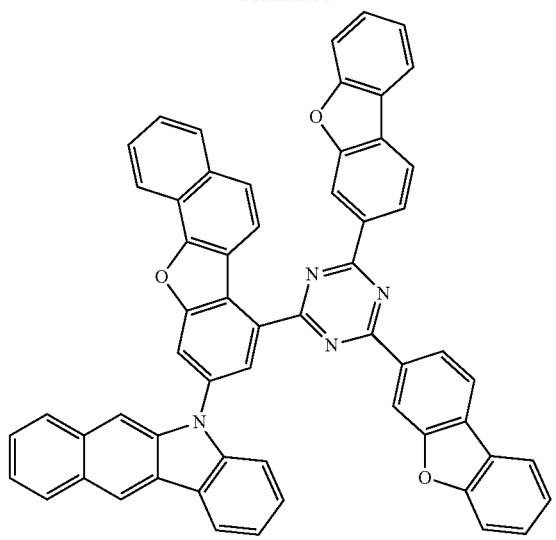
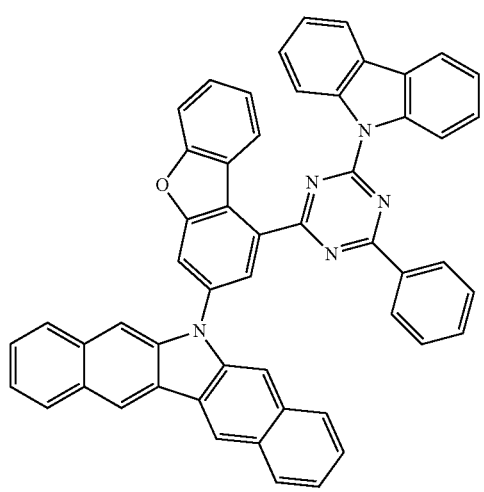
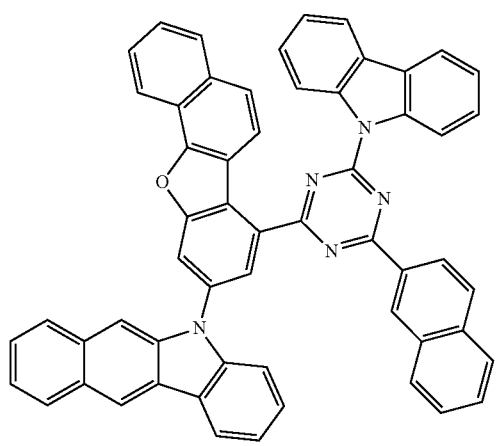
636
-continued
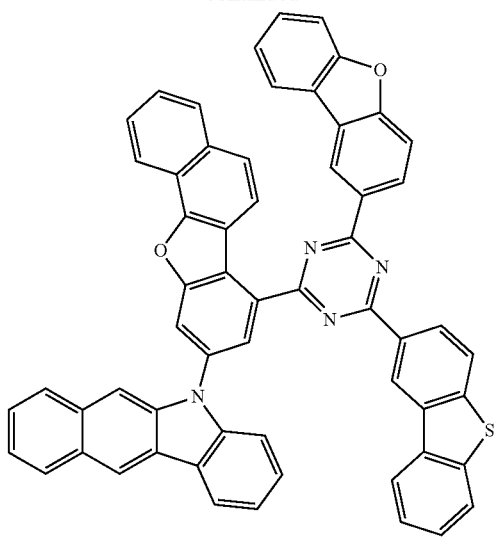
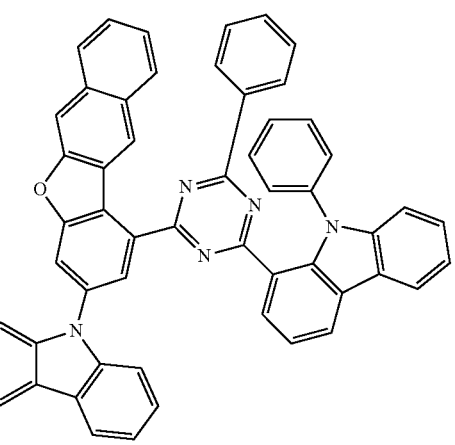
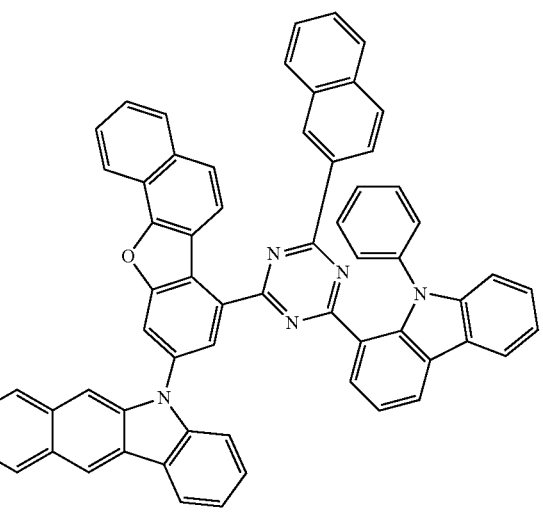

637
-continued
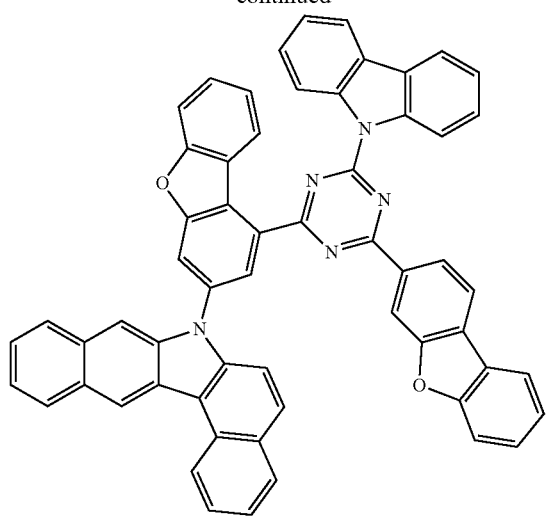
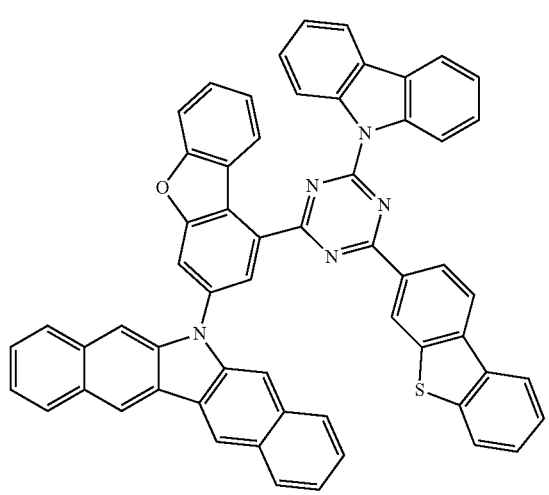
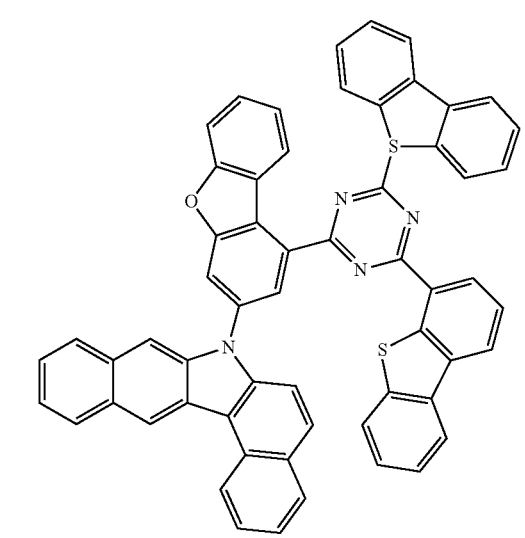
638
-continued
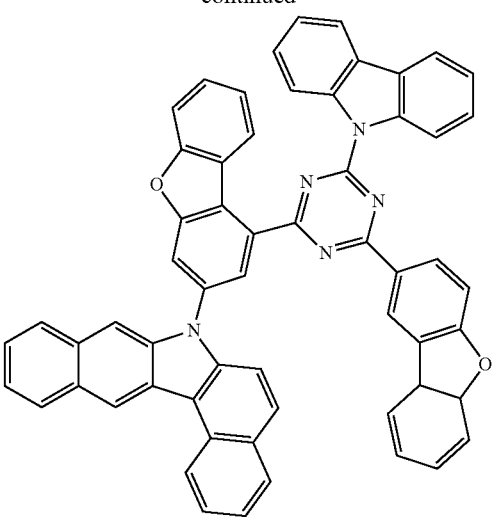
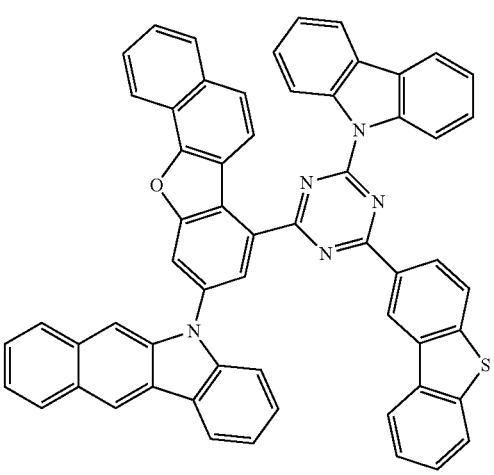
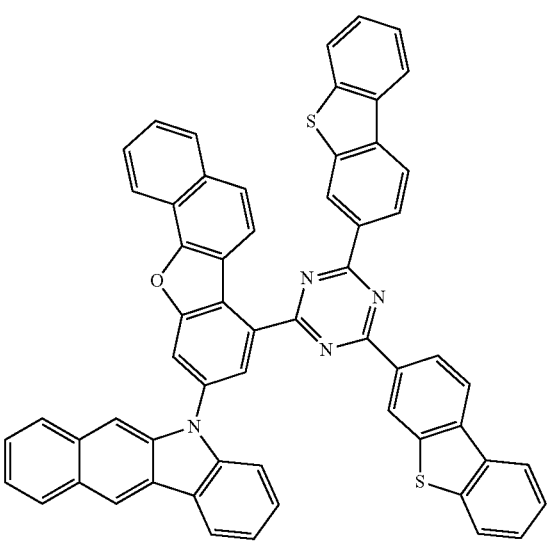

639
-continued
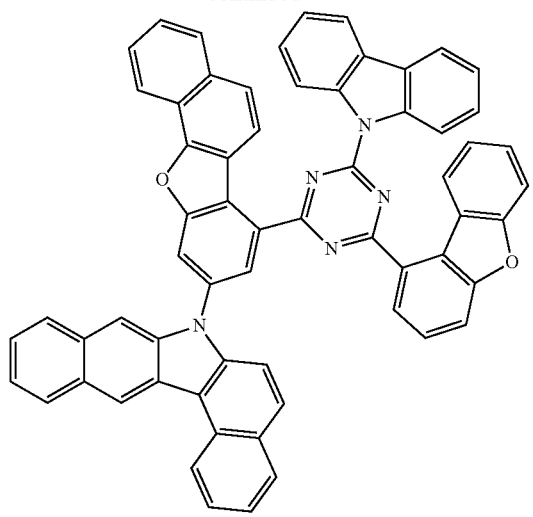
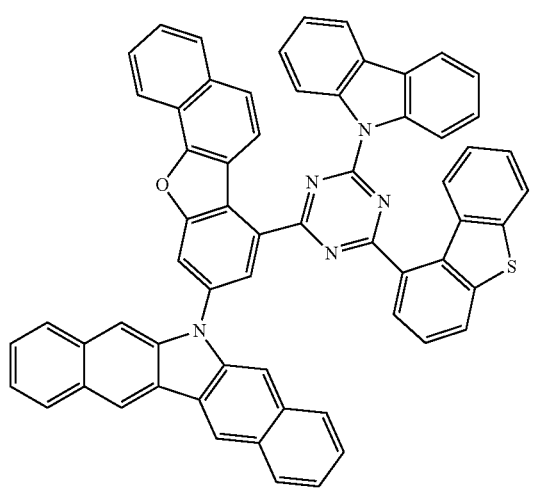
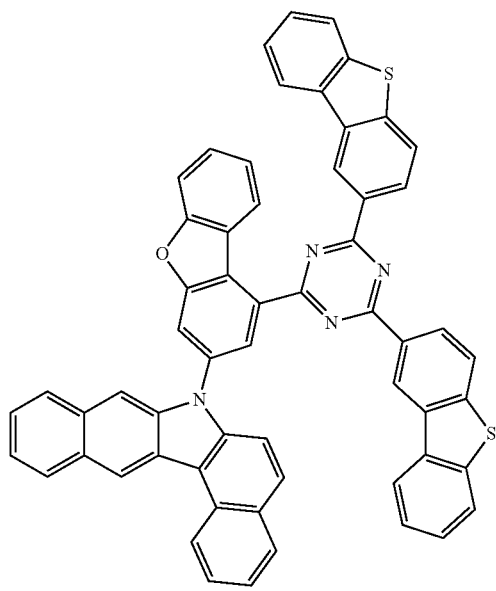
640
-continued
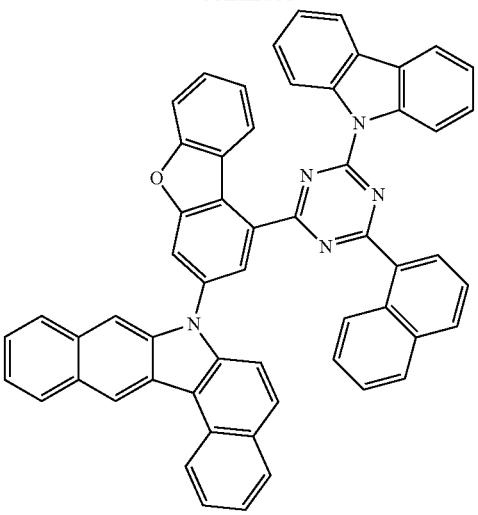
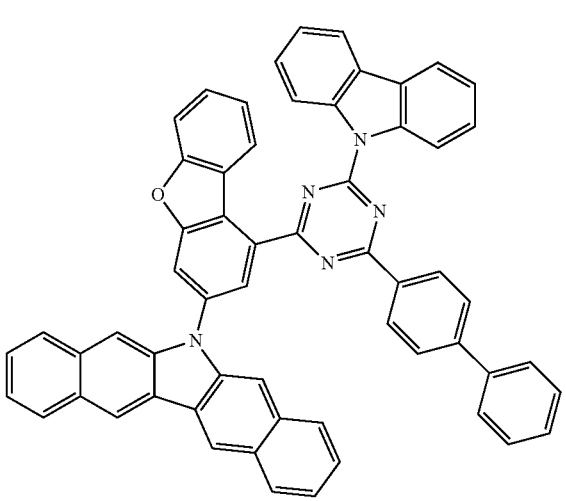
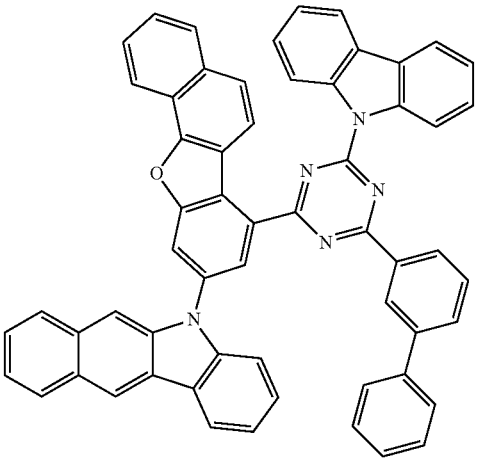

641
-continued
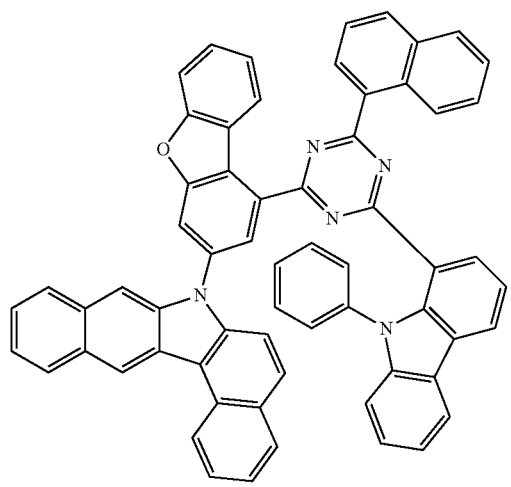
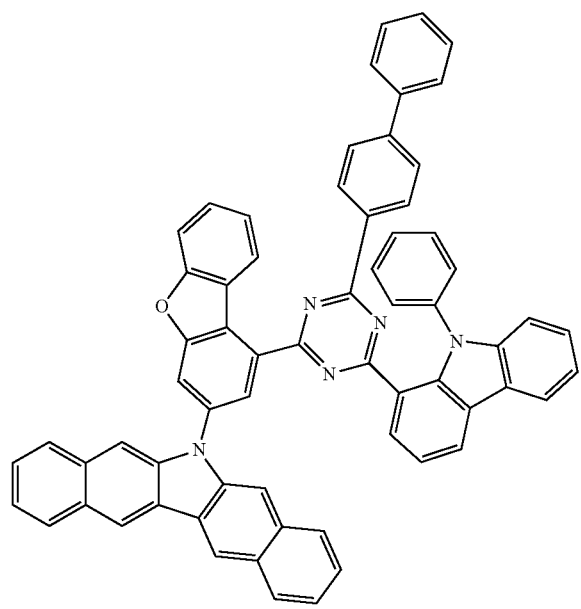
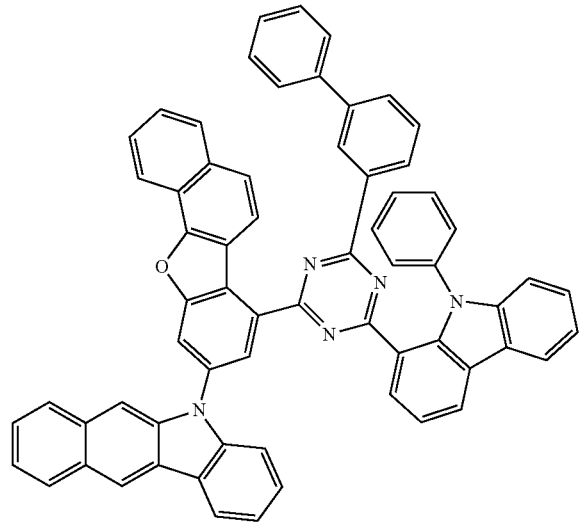
642
-continued
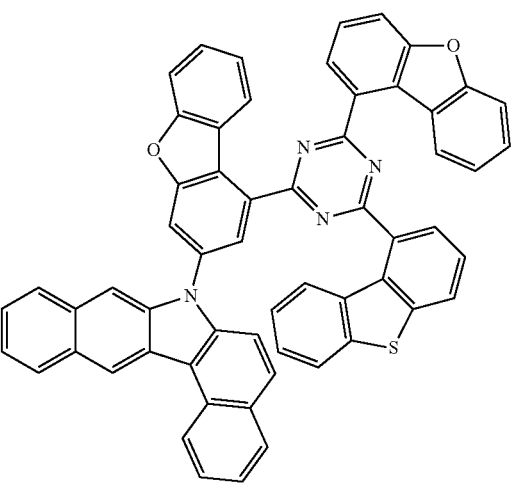
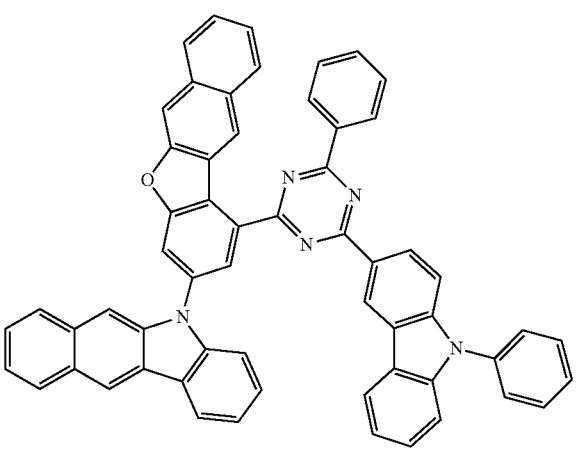
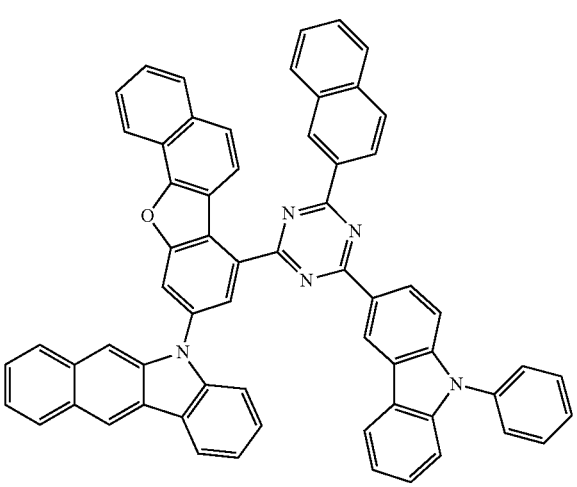

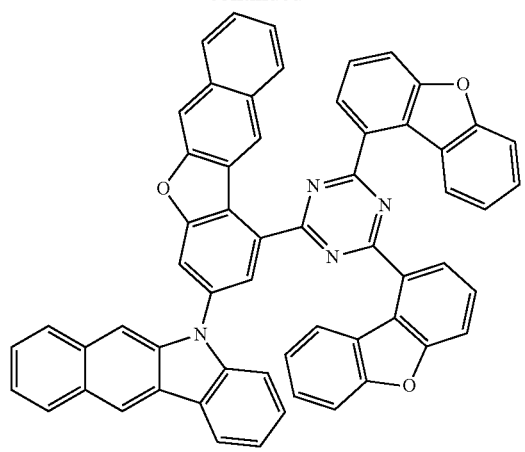
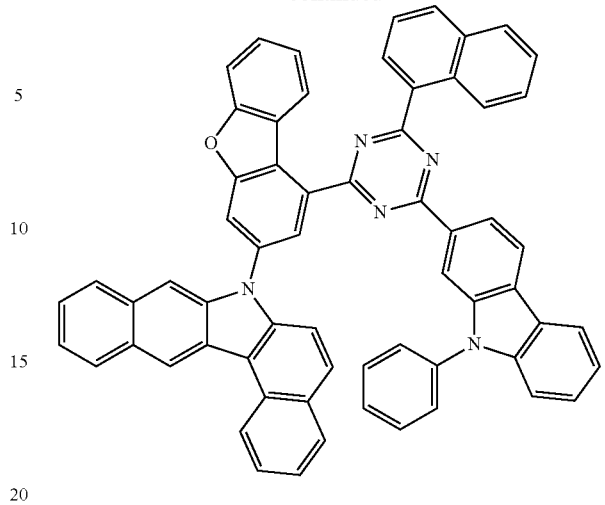

645
-continued
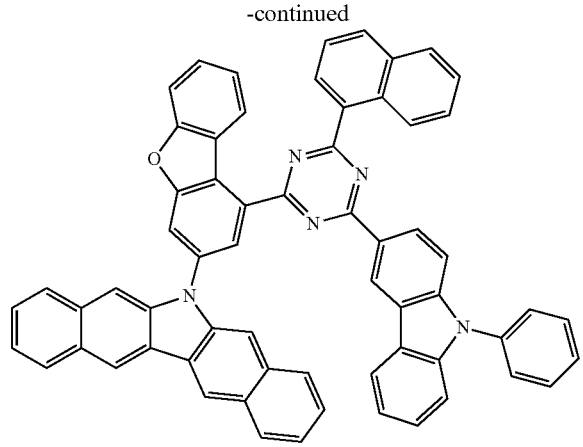
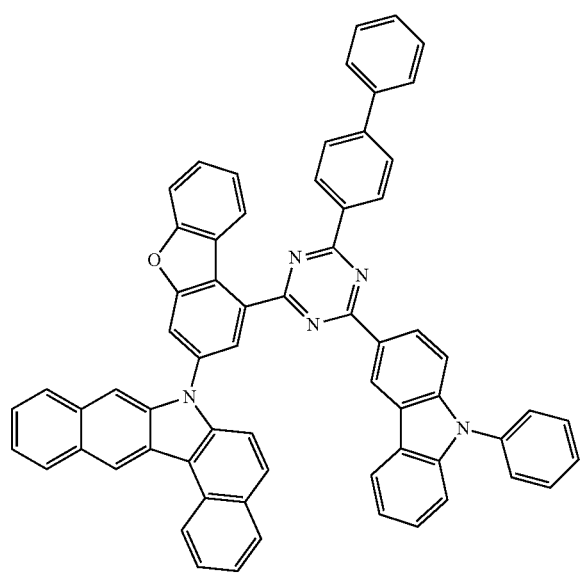
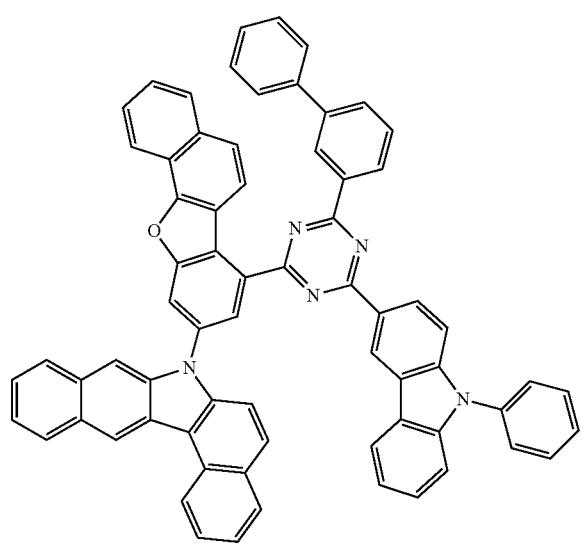
646
-continued
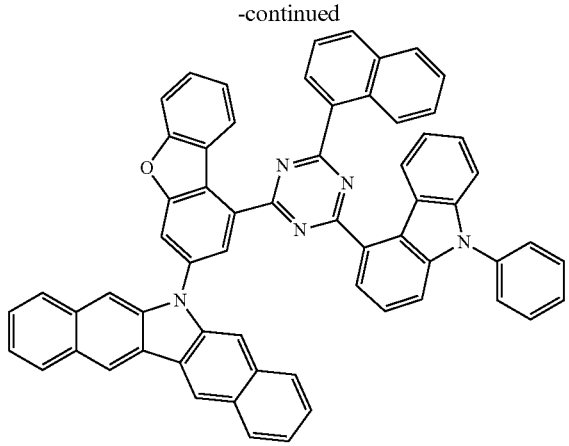
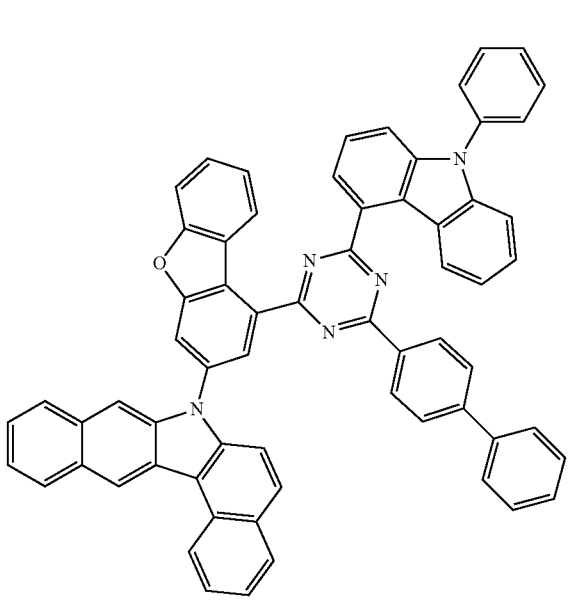
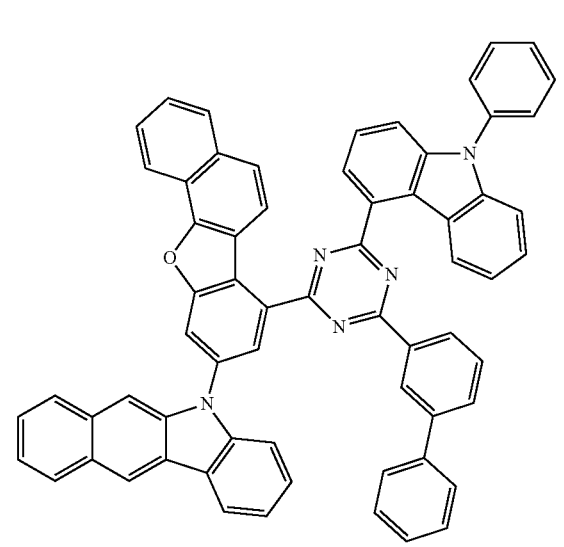

647
-continued
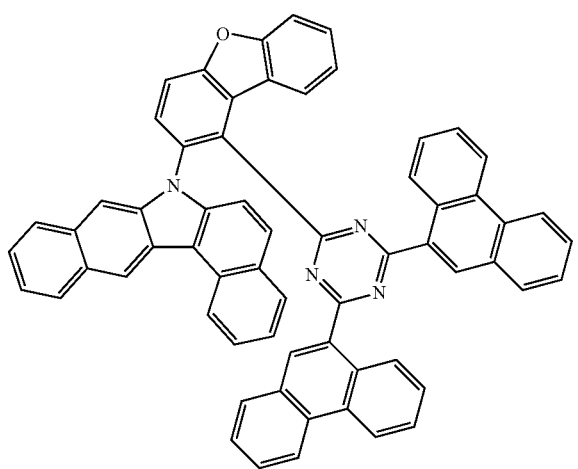
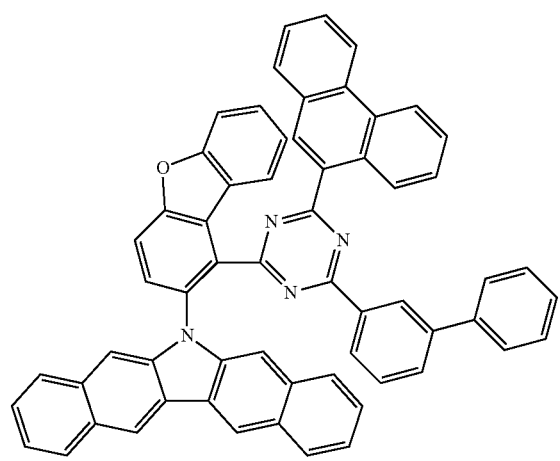
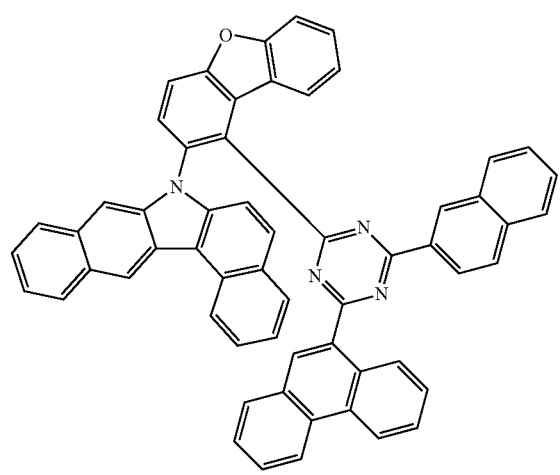
648
-continued
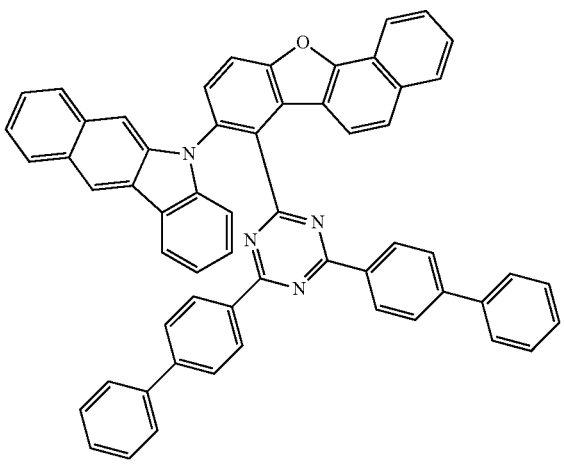
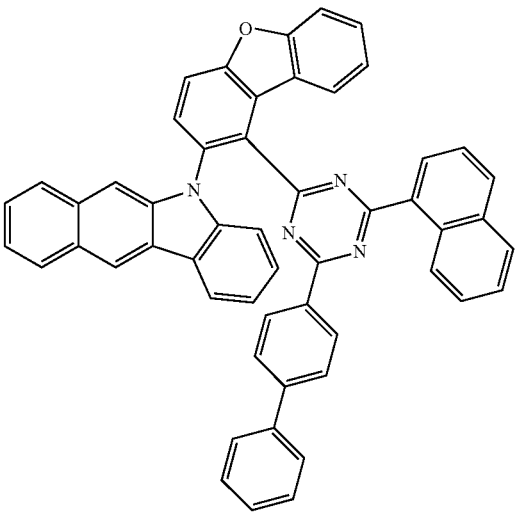
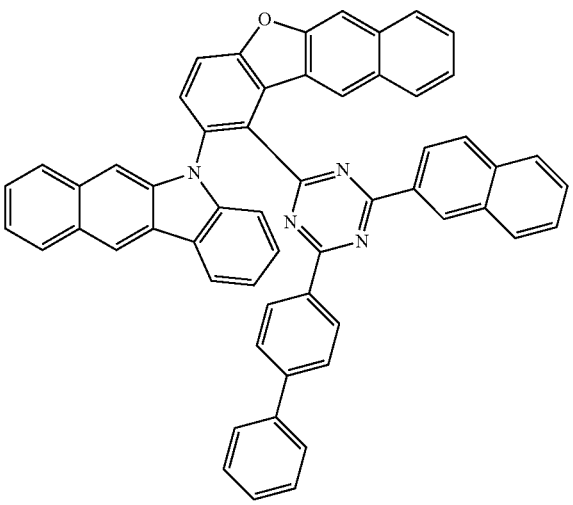

649
-continued
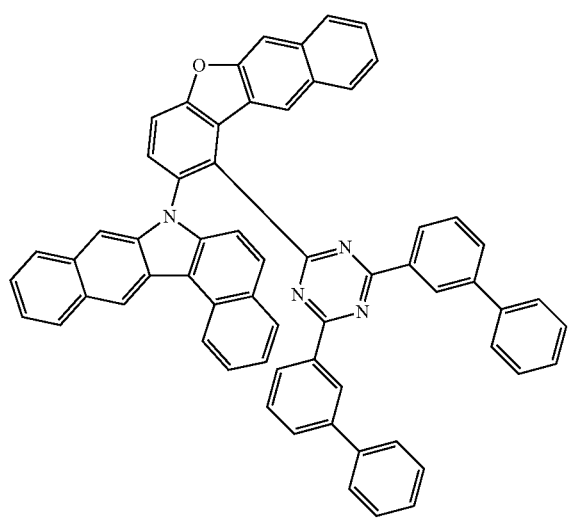
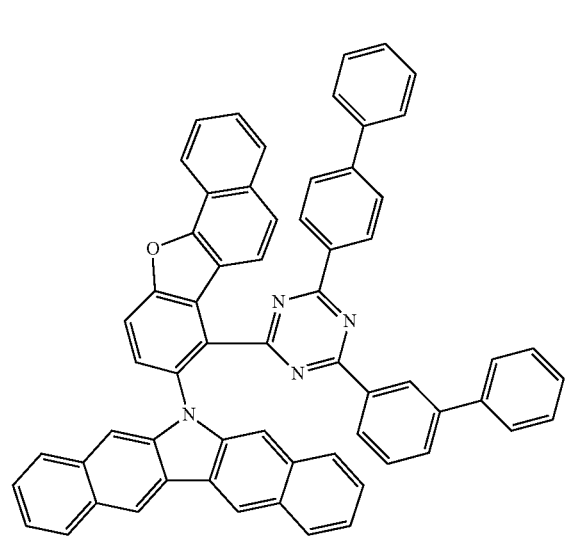
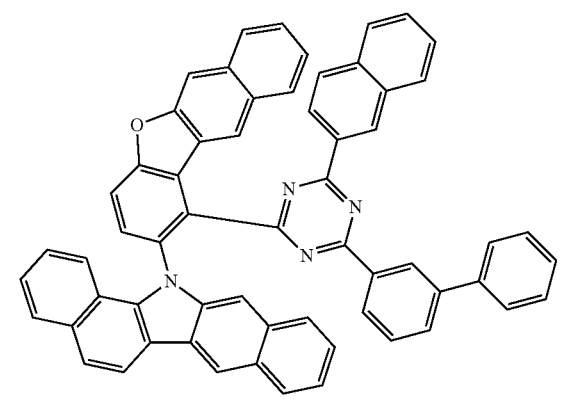
650
-continued
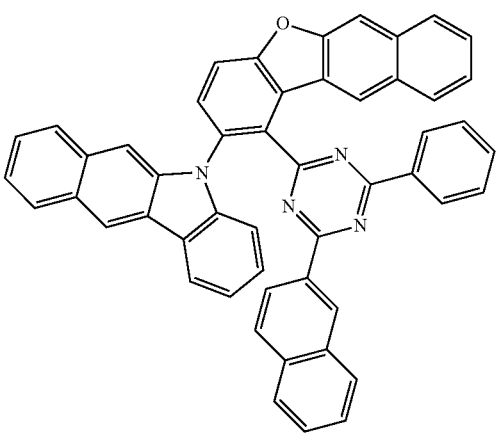
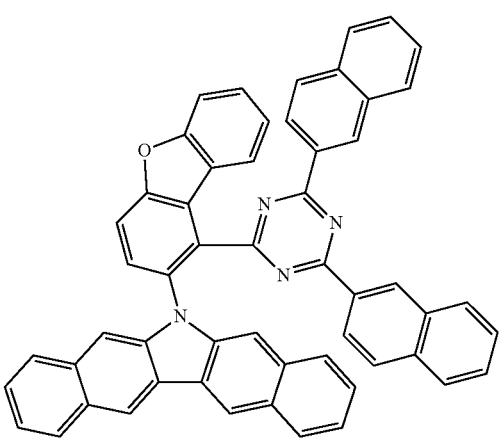
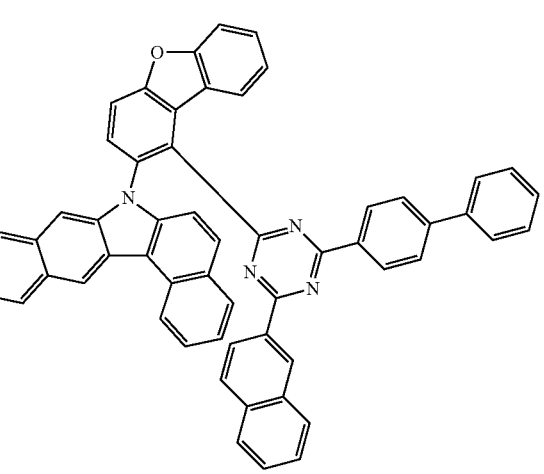

651
-continued
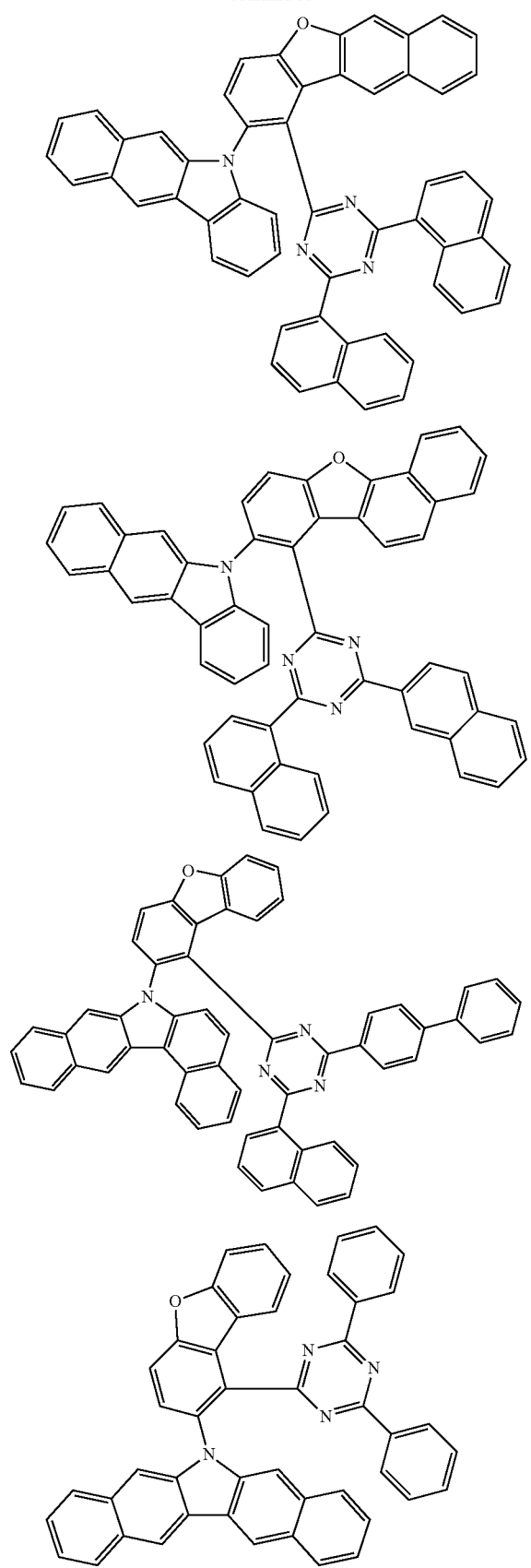
652
-continued
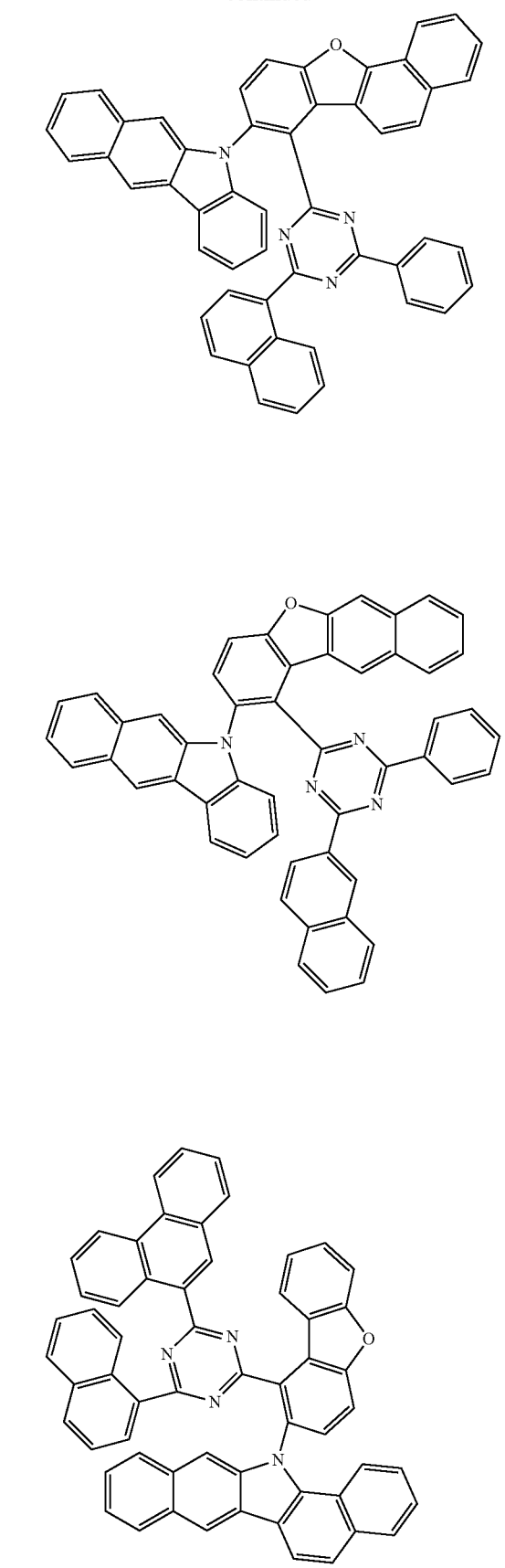

653
-continued
654
-continued
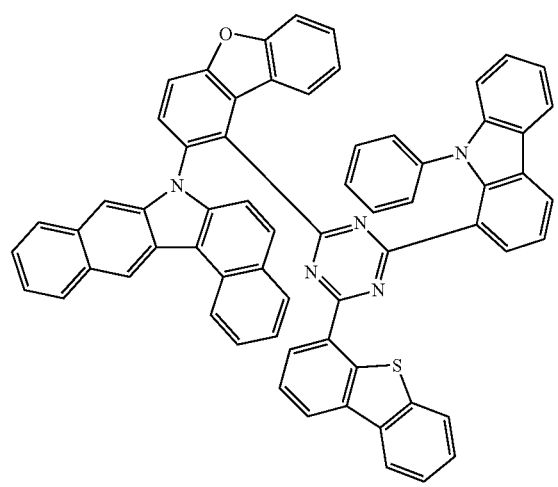
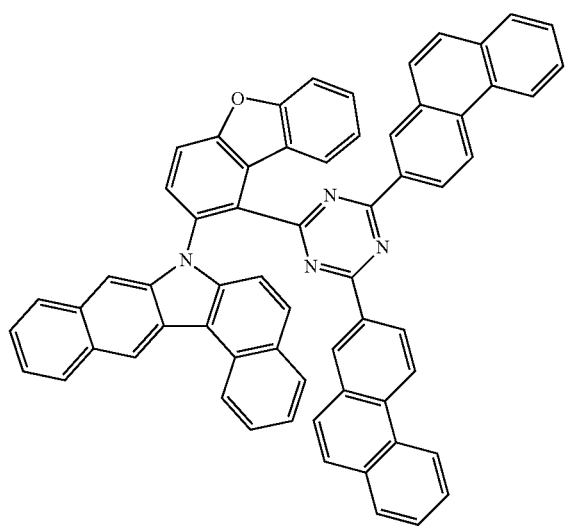
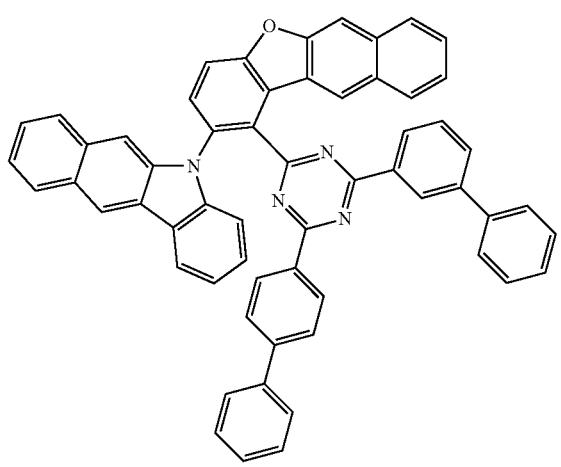
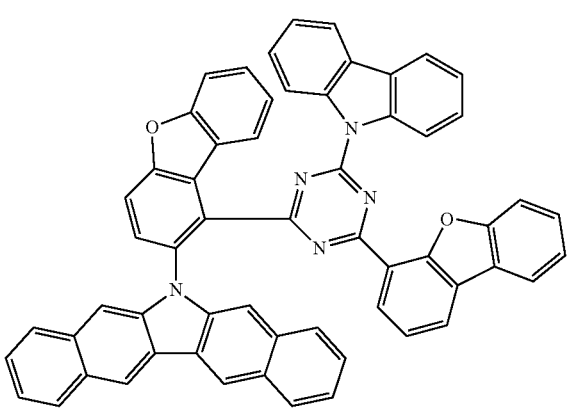

655
-continued
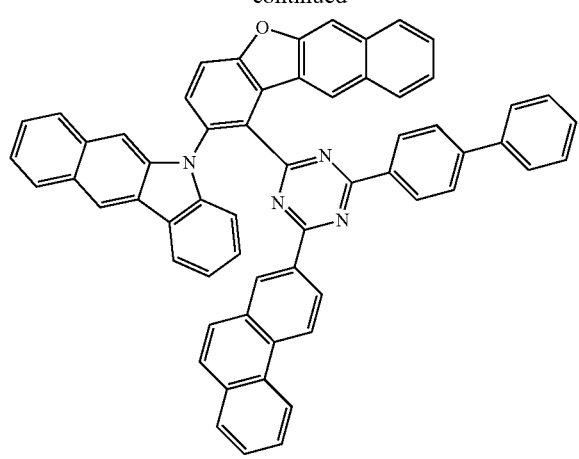
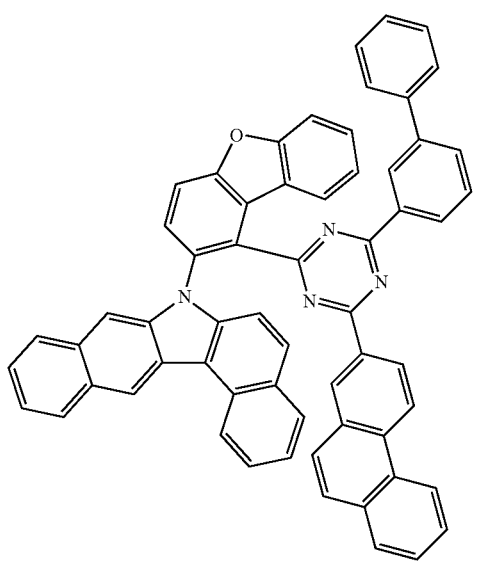
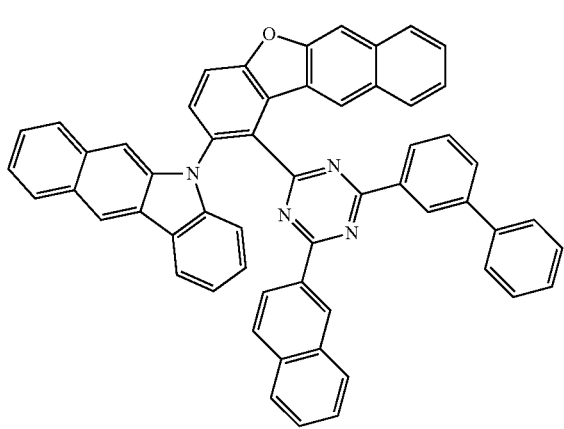
656
-continued
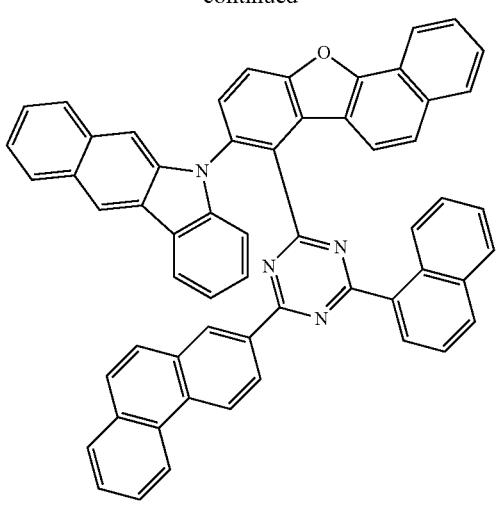
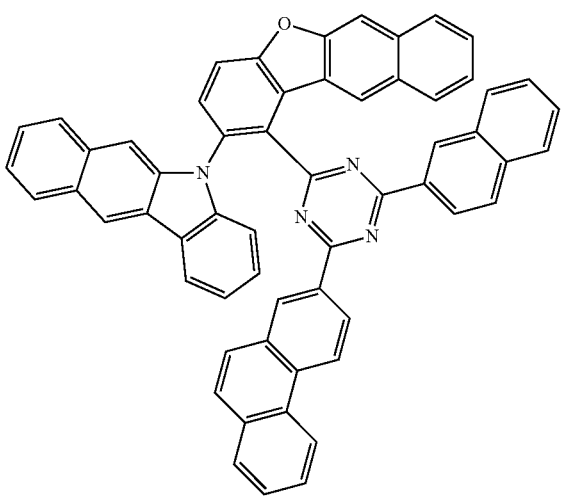
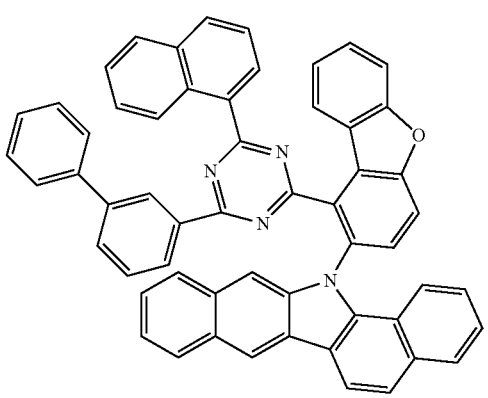

657
-continued
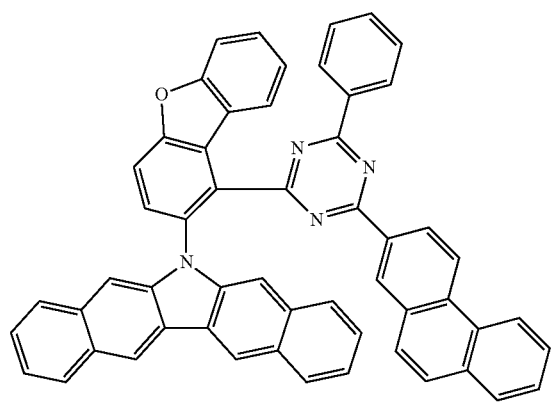
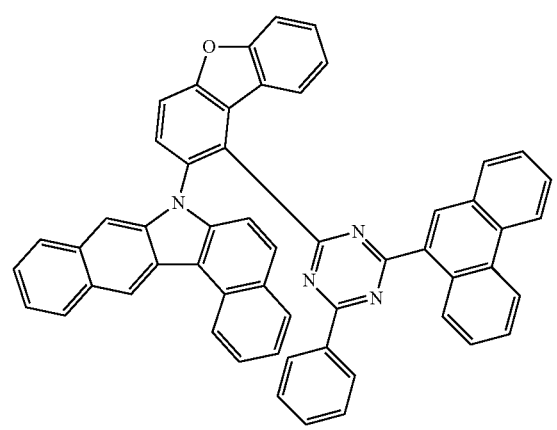
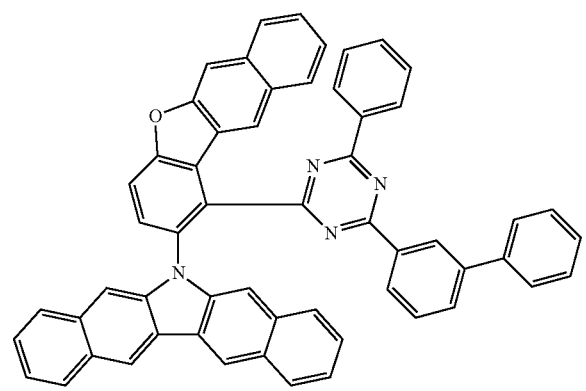
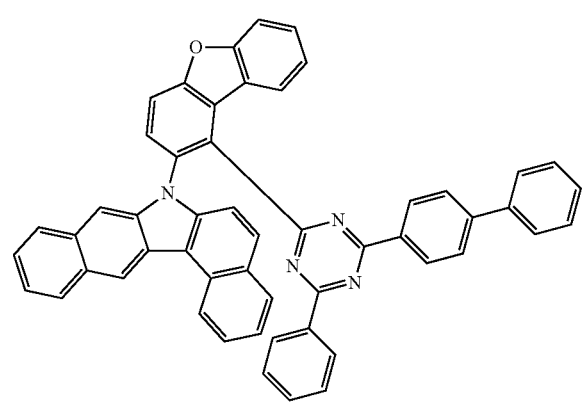
658
-continued
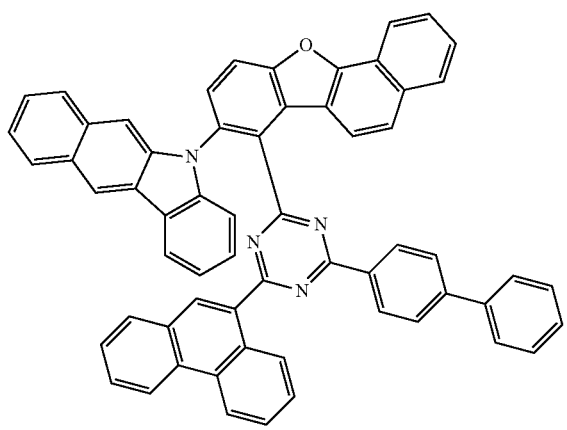
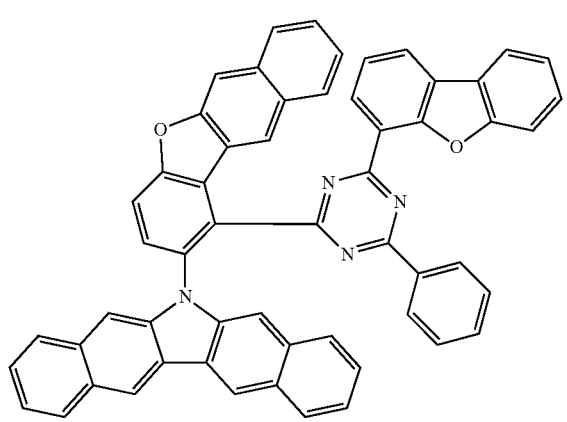
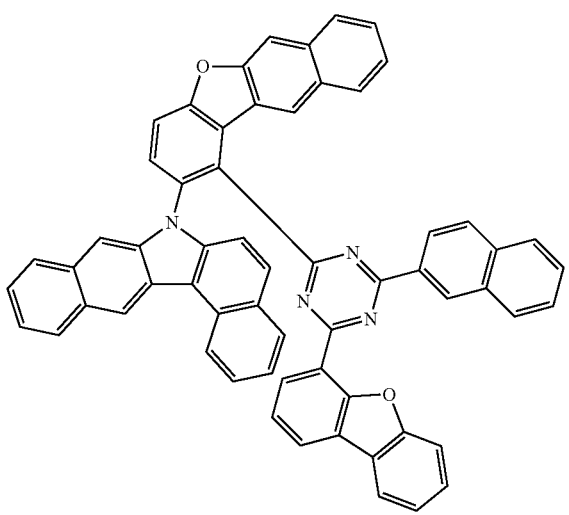

659
-continued
660
-continued
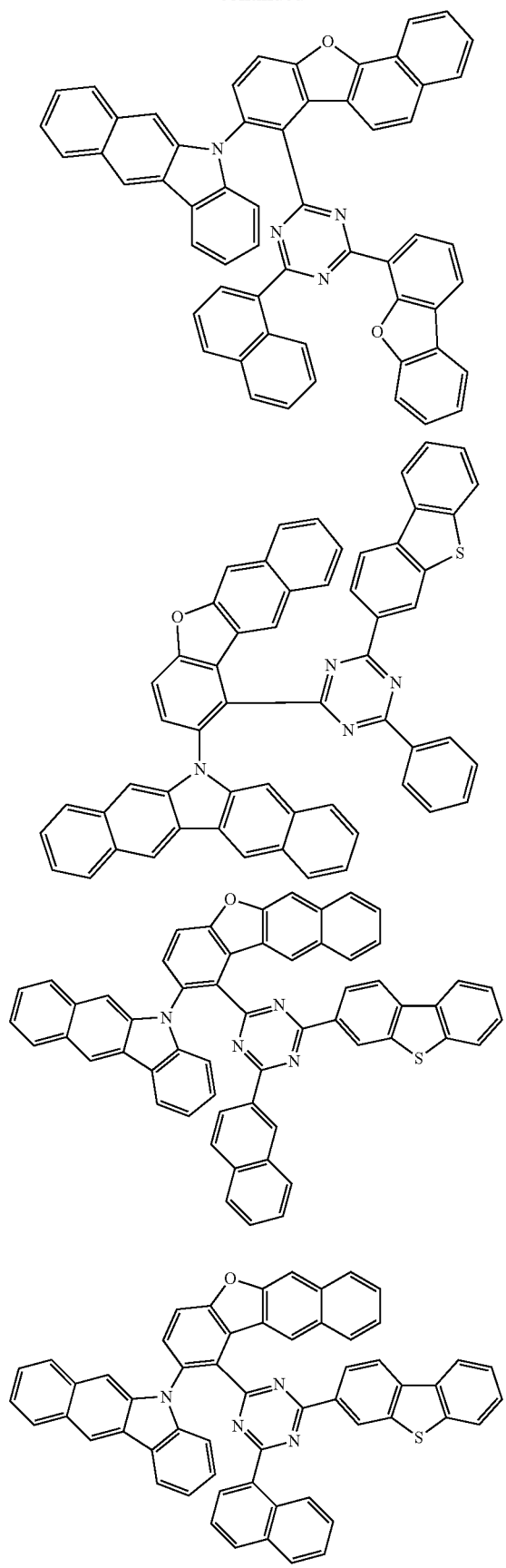
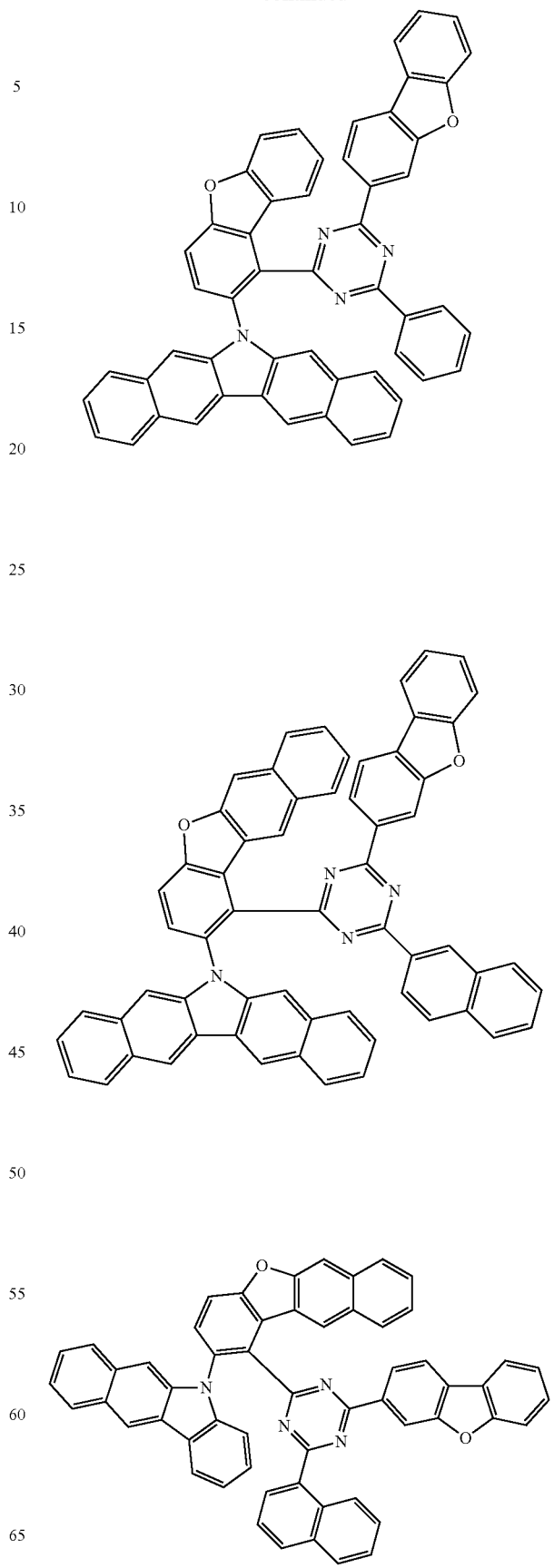

661
-continued
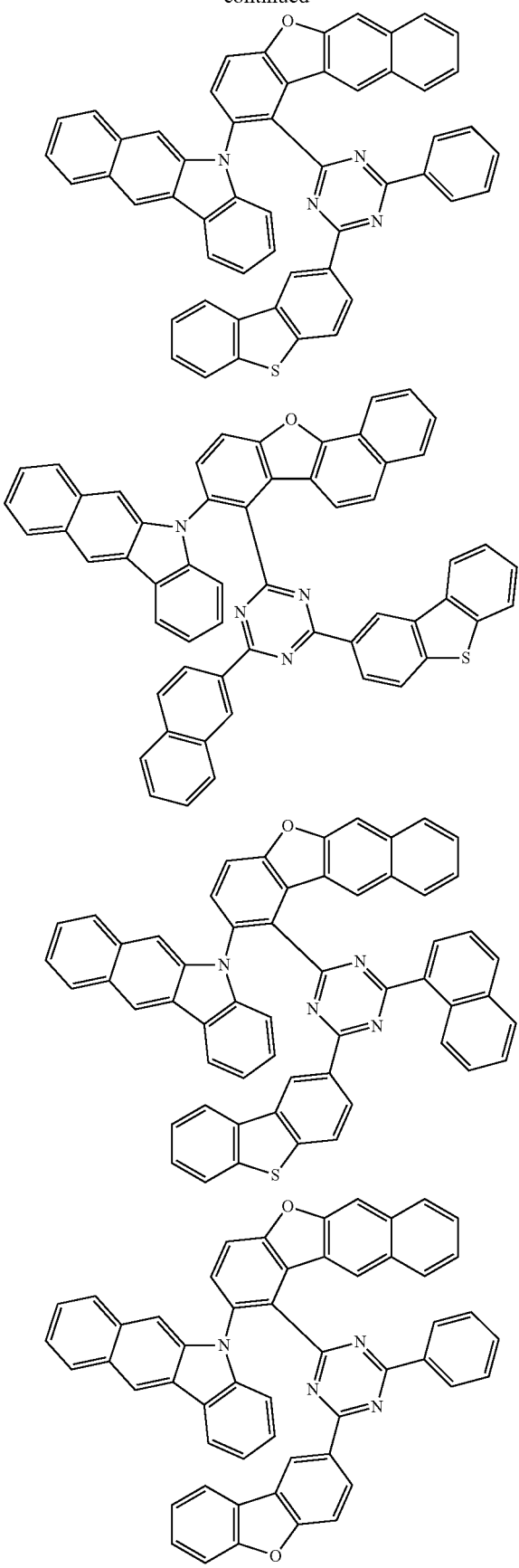
662
-continued
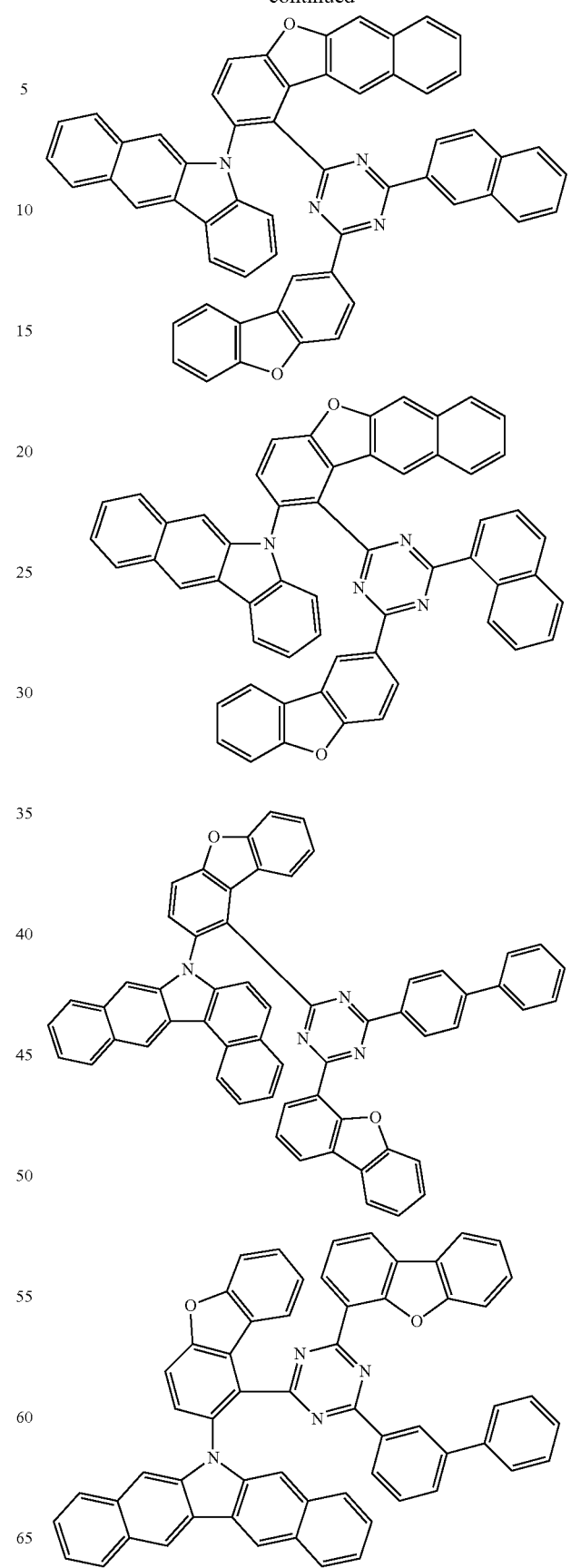

663
-continued
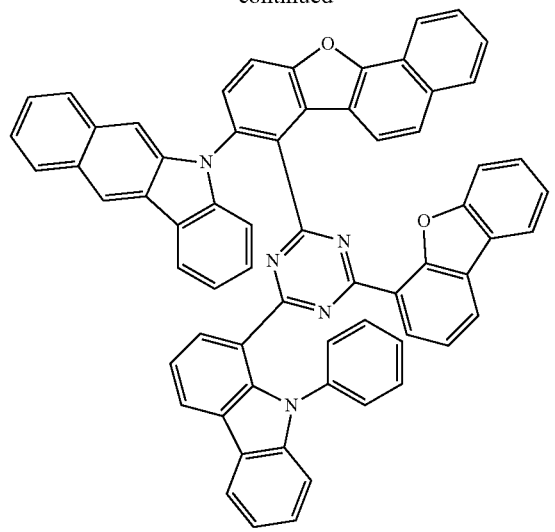
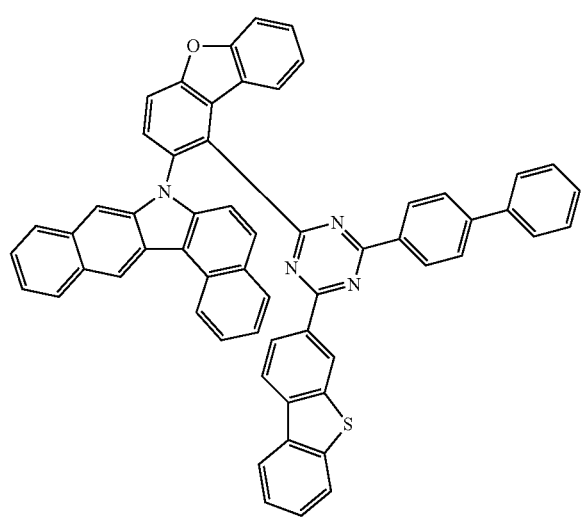
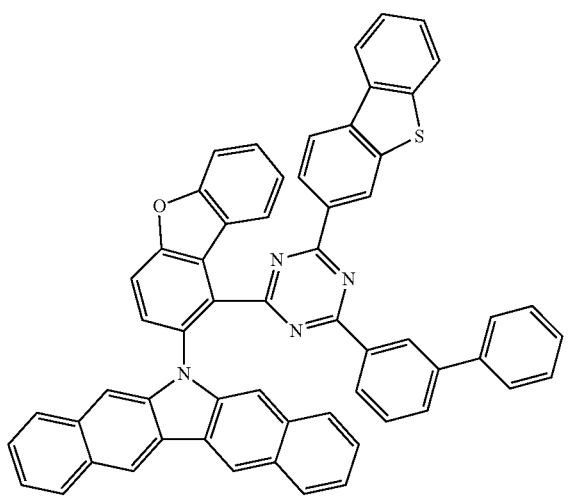
664
-continued
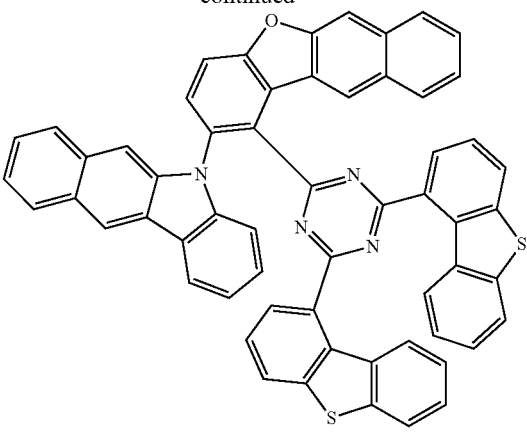
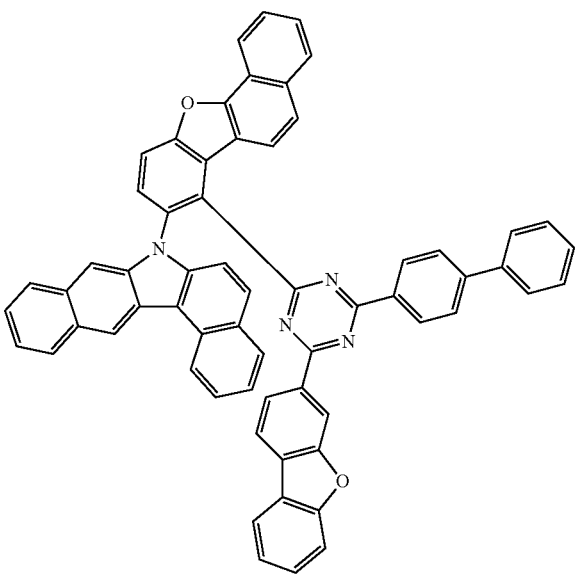
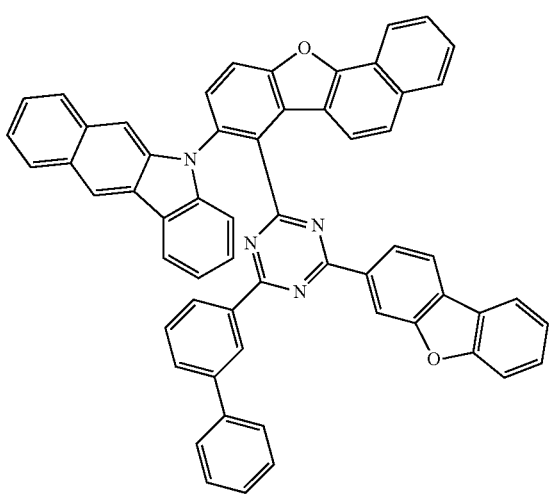

665
-continued
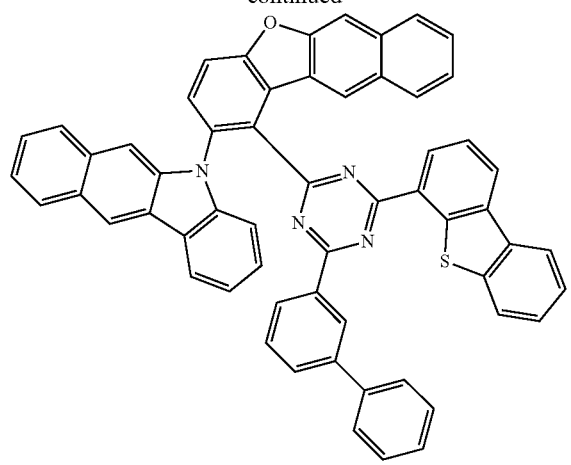
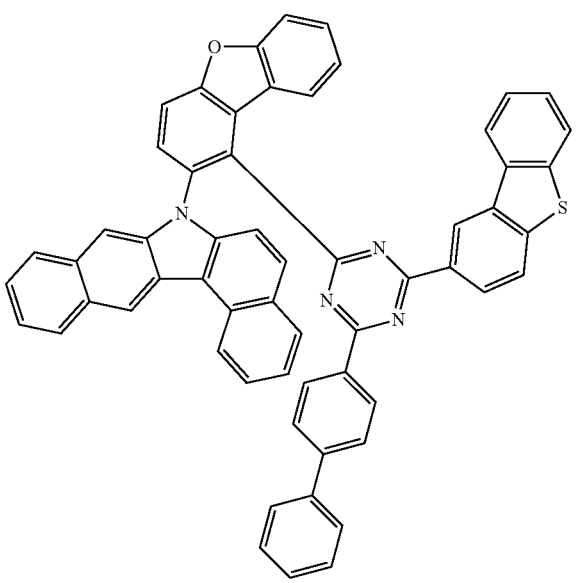
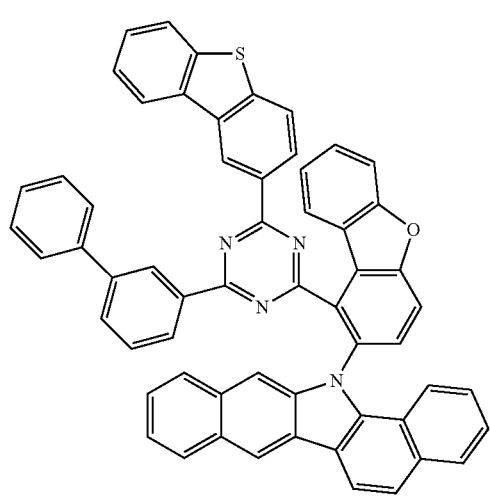
666
-continued
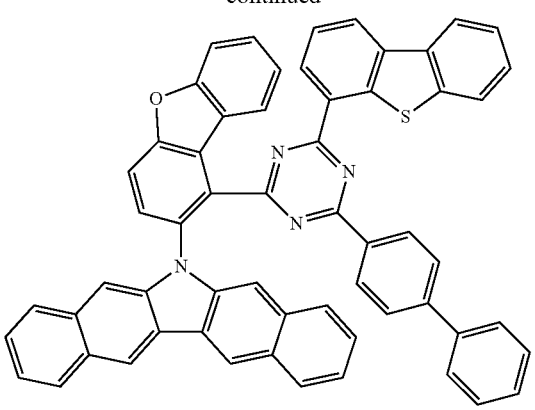
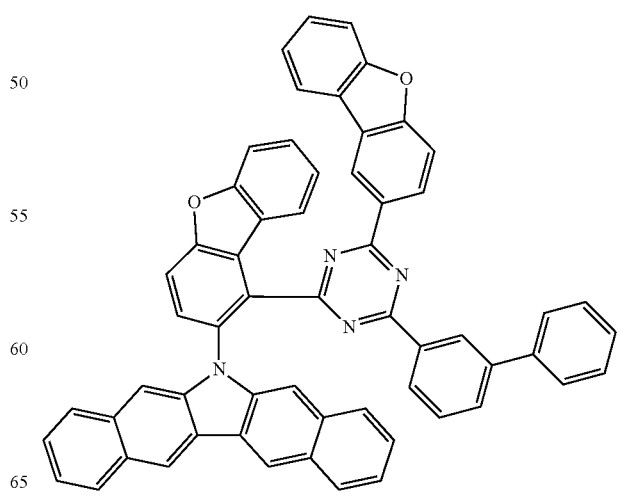

667
-continued
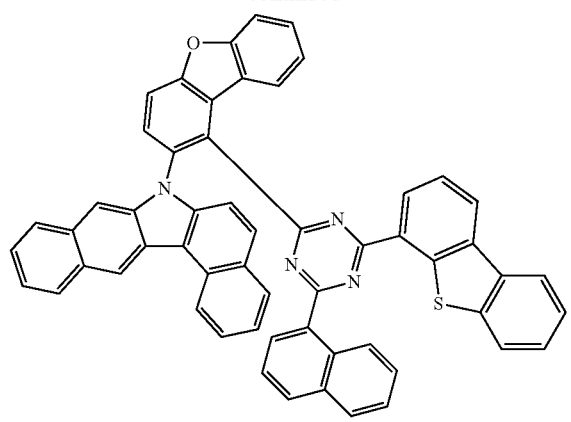
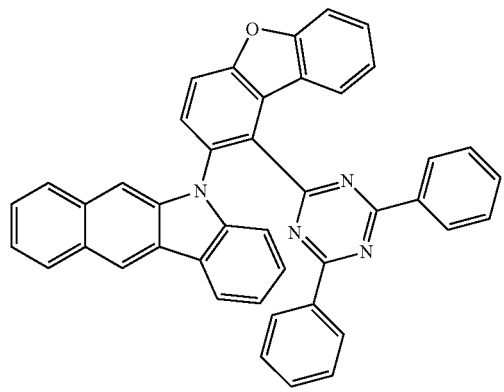
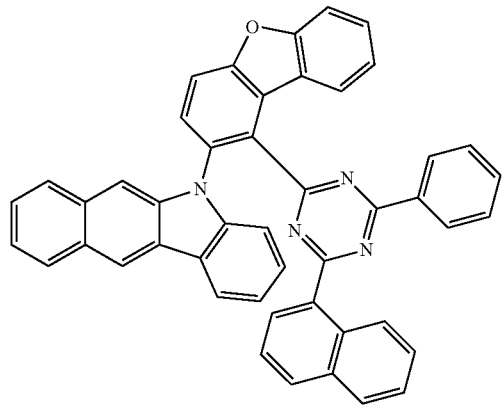
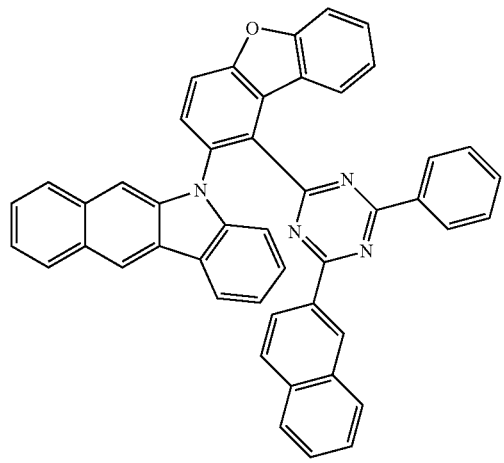
668
-continued
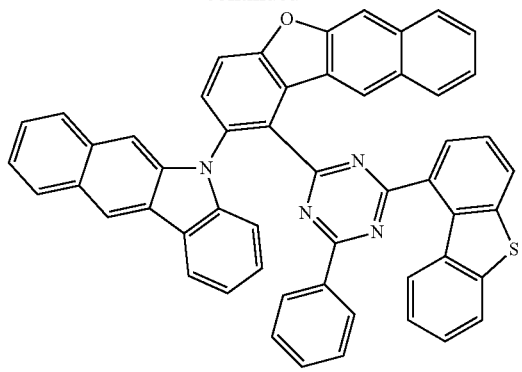
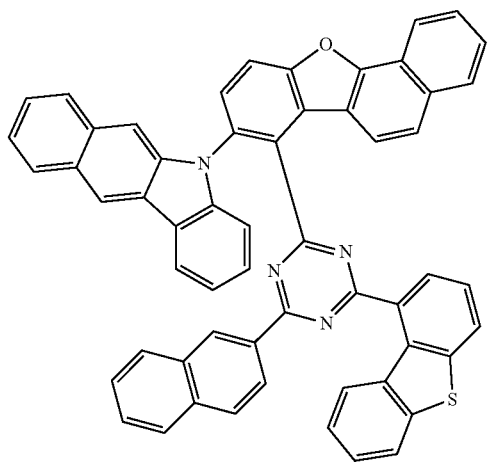
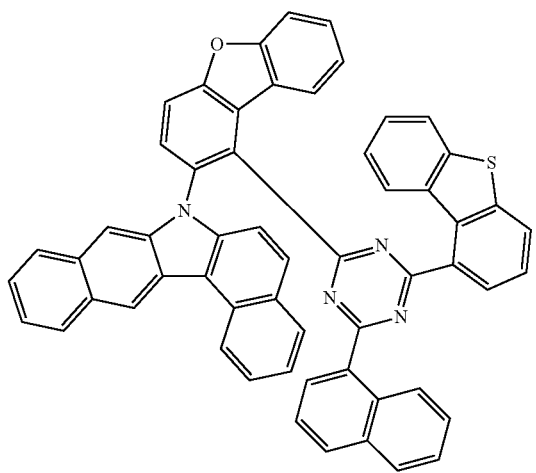

669
-continued
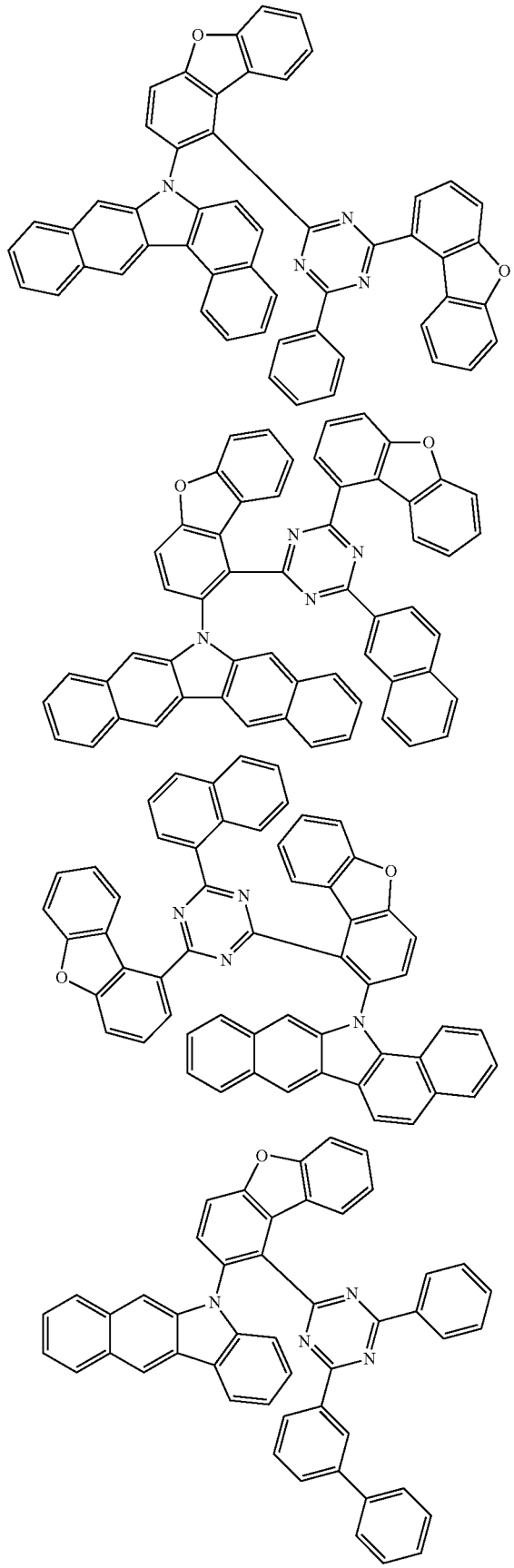
670
-continued
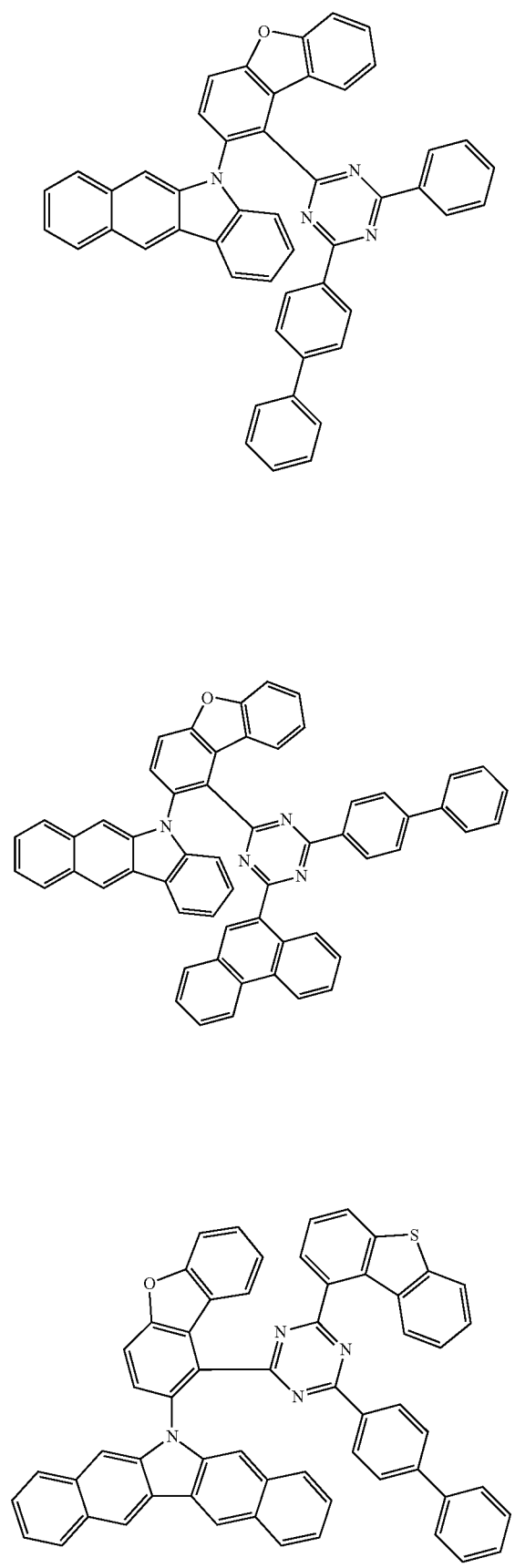

671
-continued
672
-continued
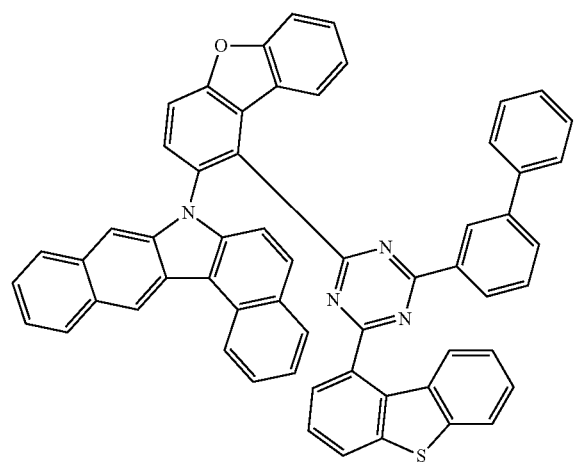
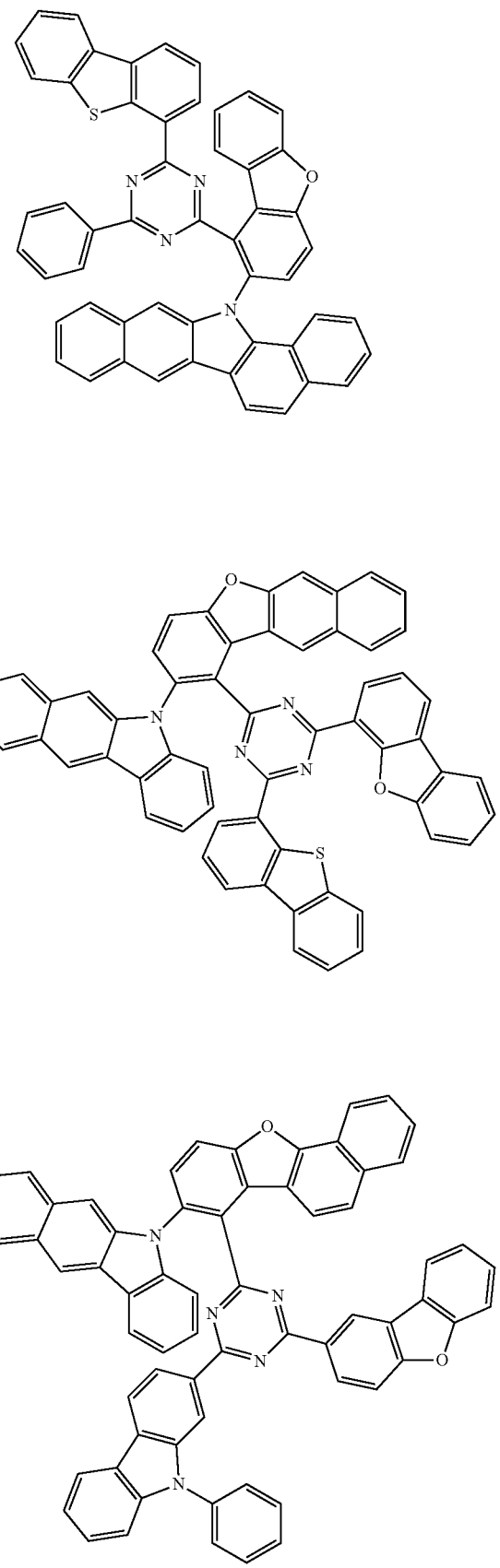

673
-continued
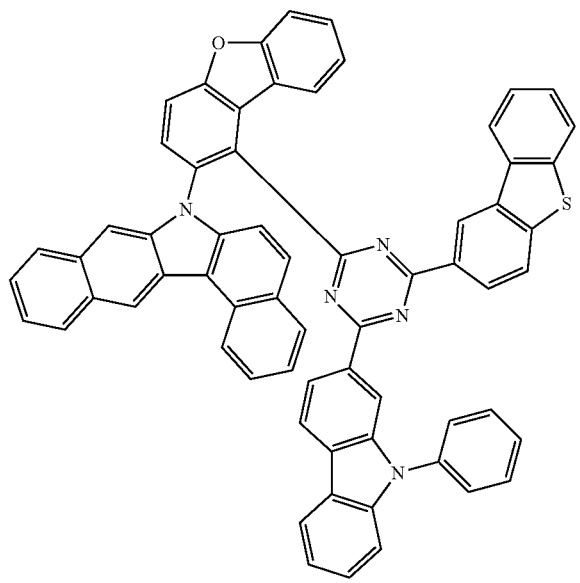
674
-continued
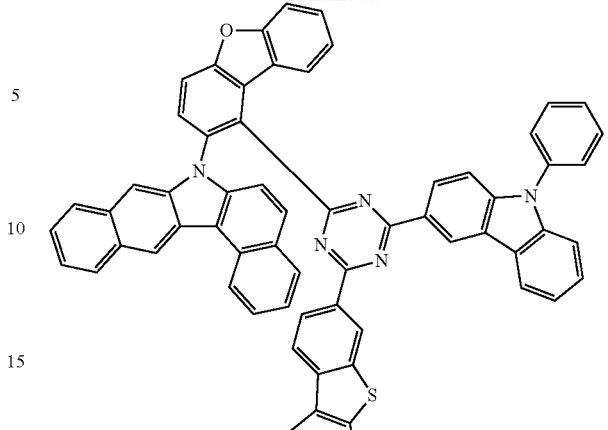
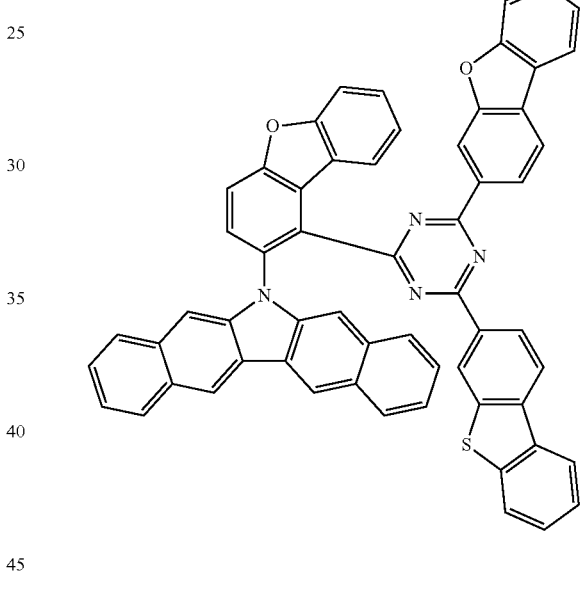
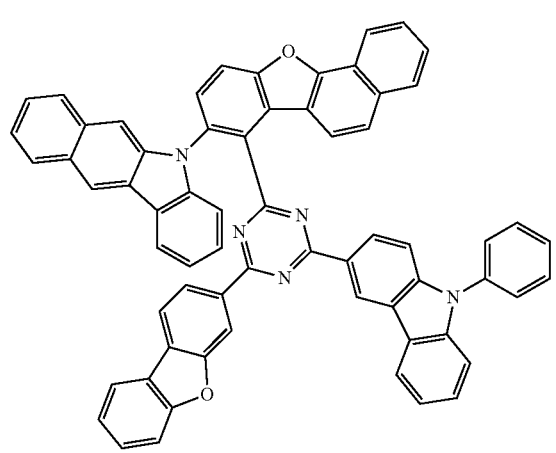
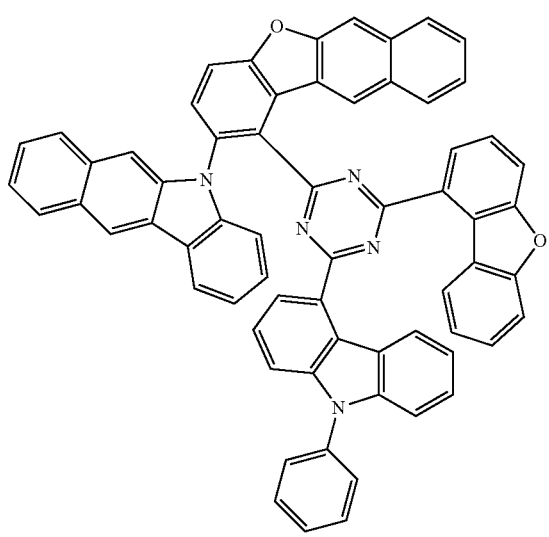

675
-continued
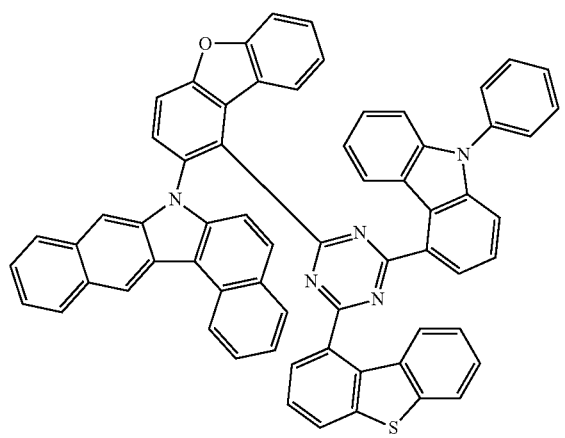
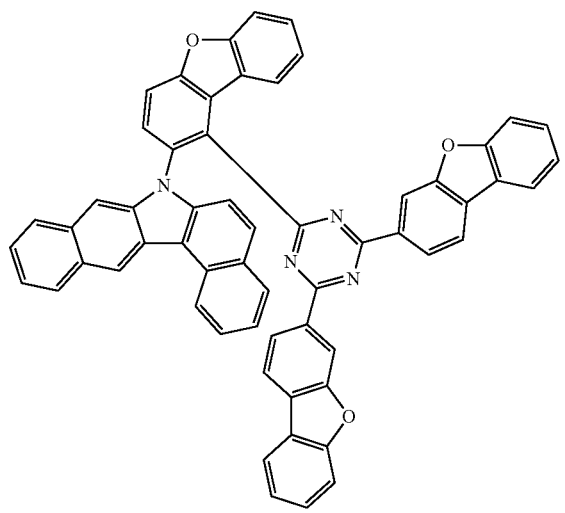
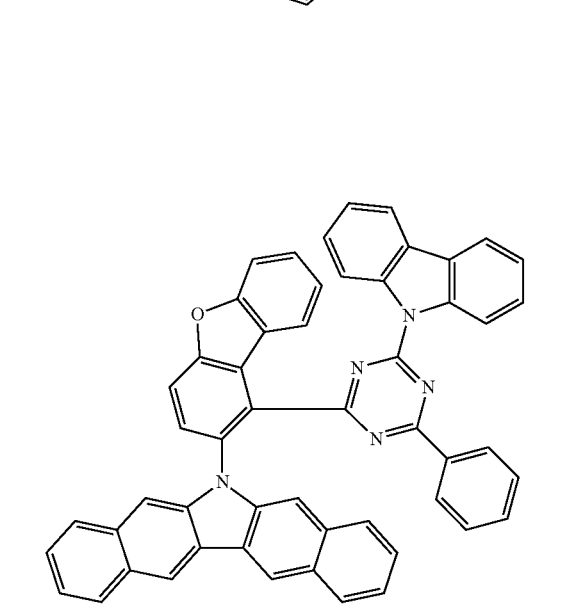
676
-continued
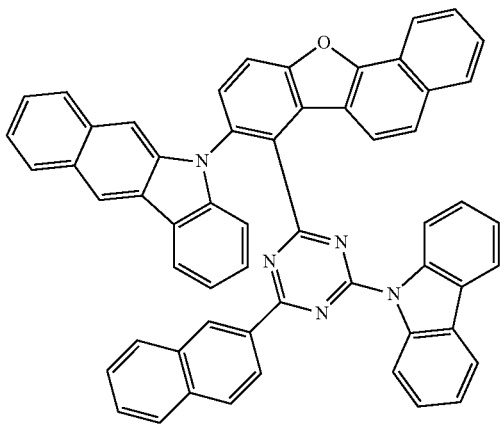
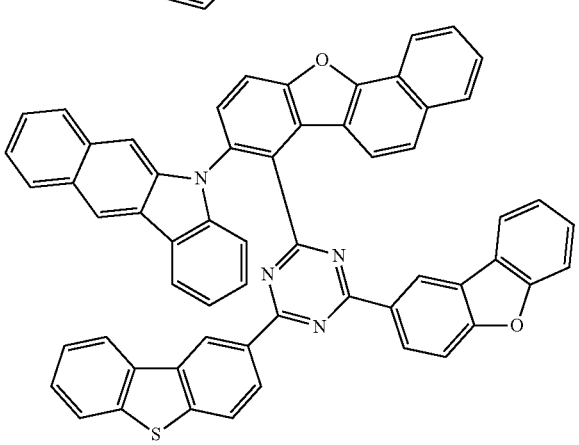
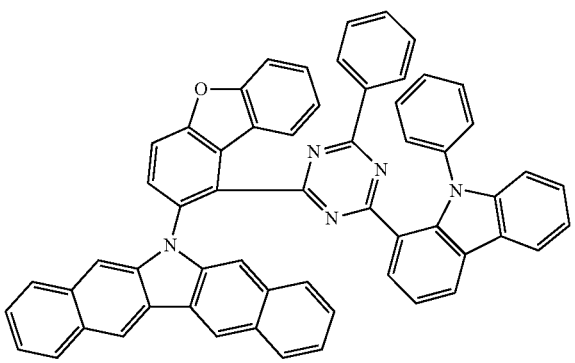
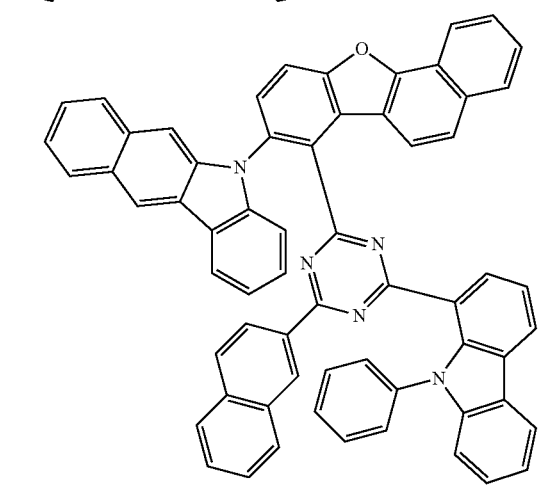

677
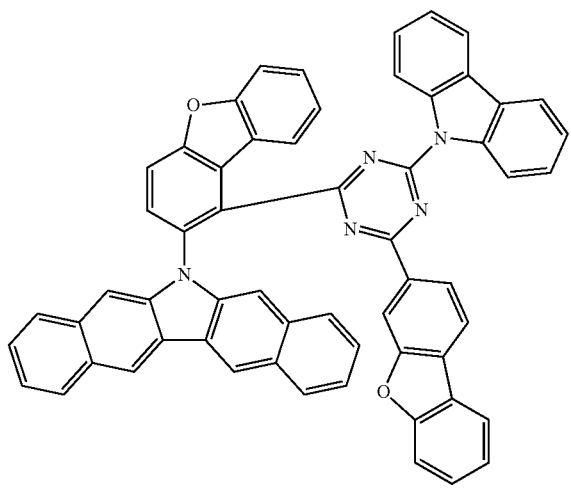
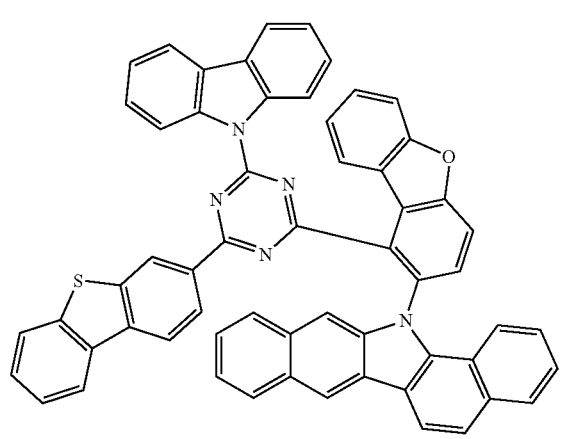
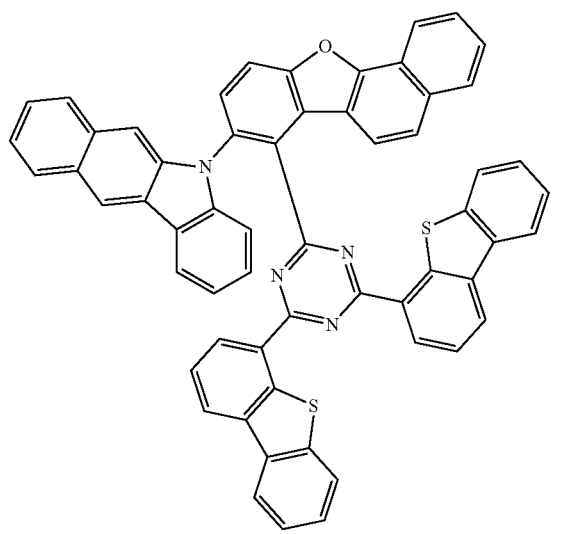
678
-continued
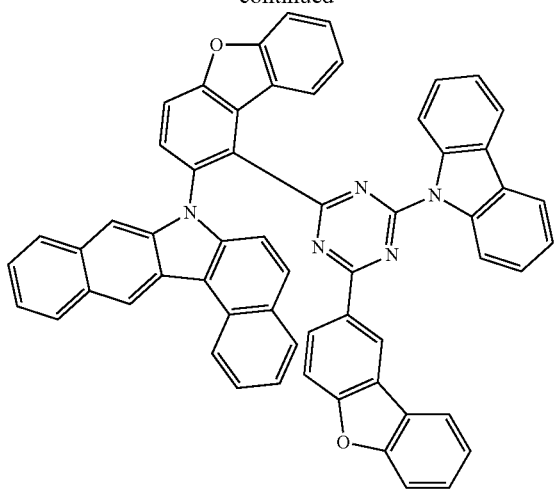
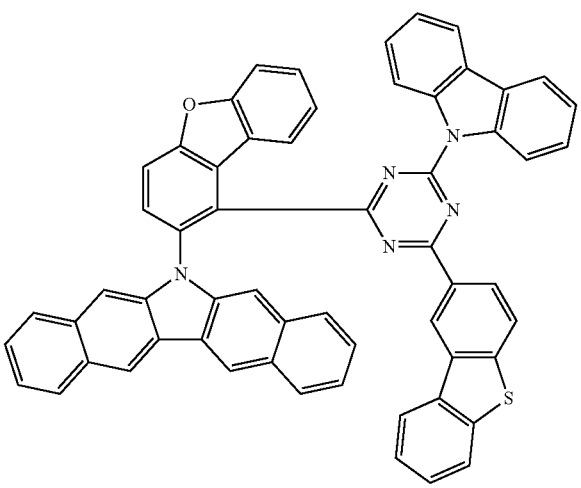
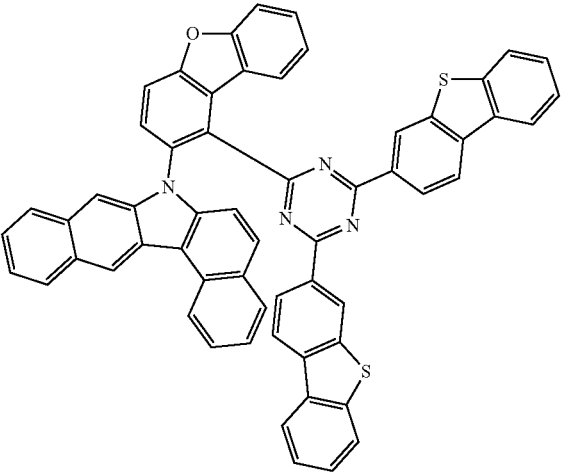

679
-continued
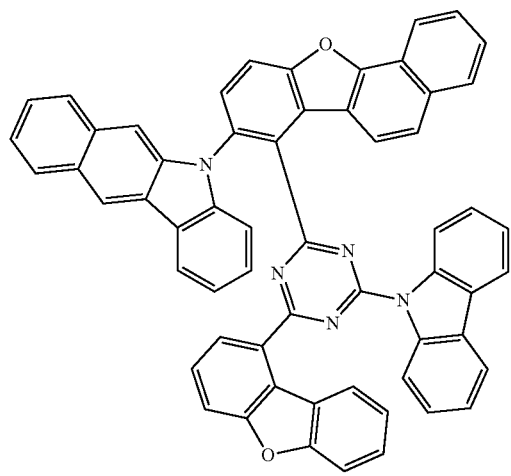
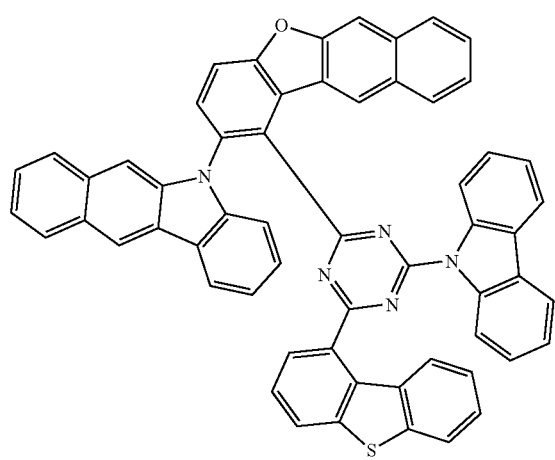
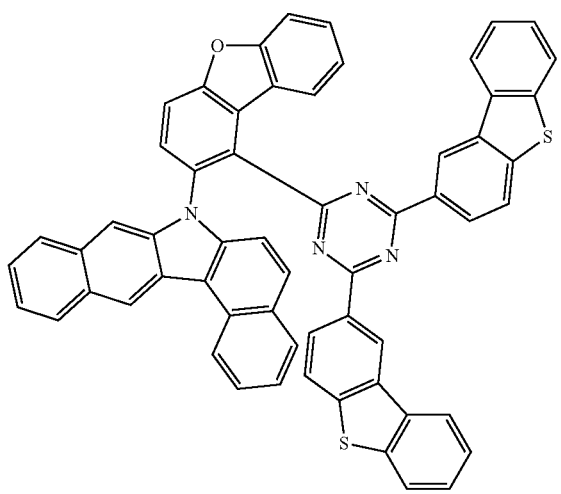
680
-continued
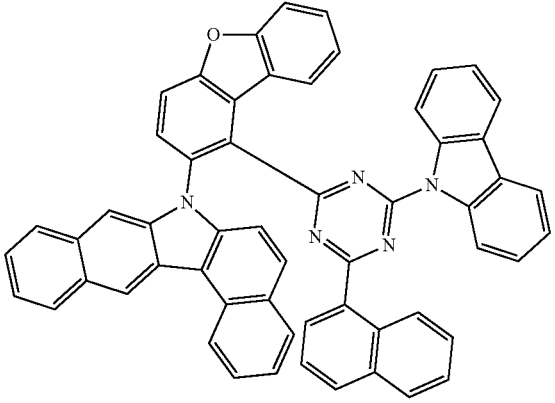
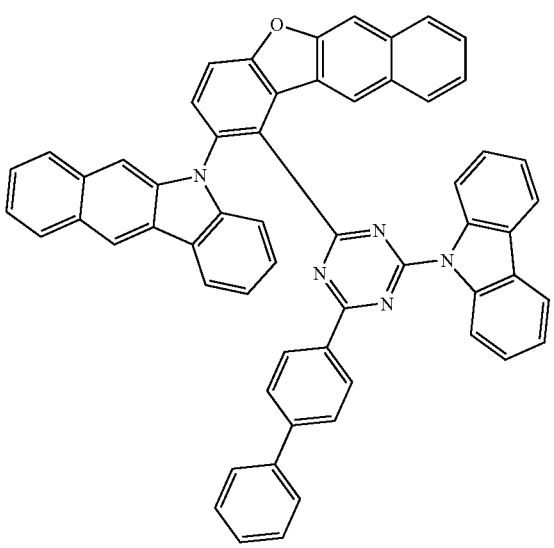
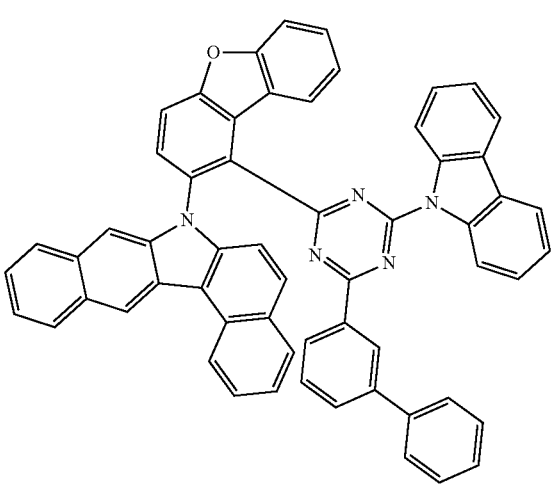

681
-continued
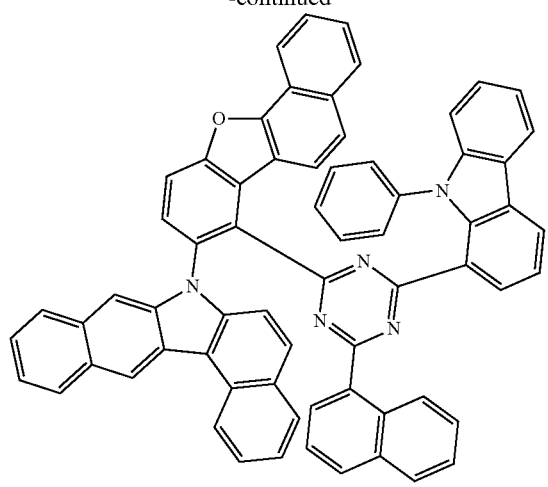
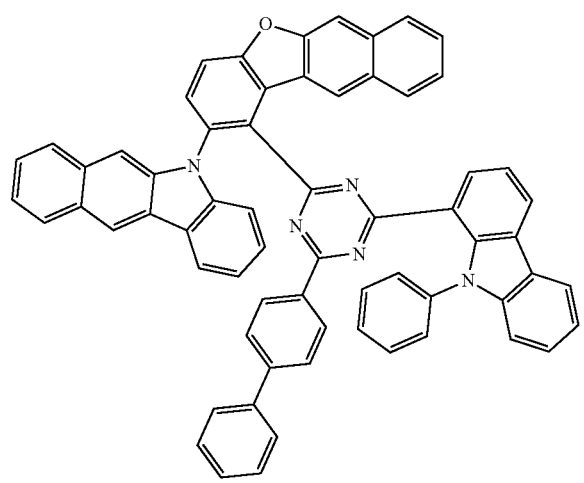
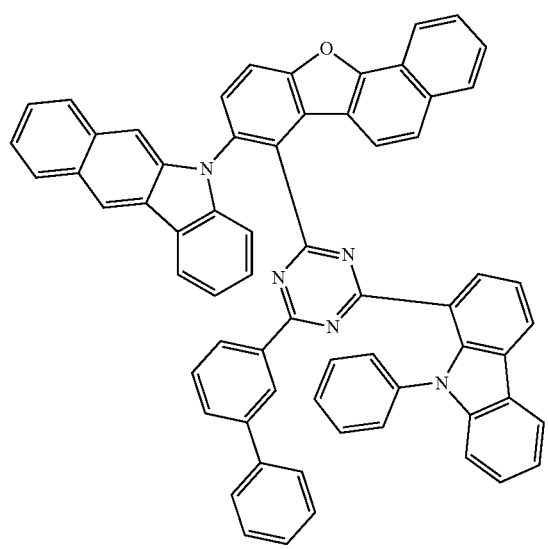
682
-continued
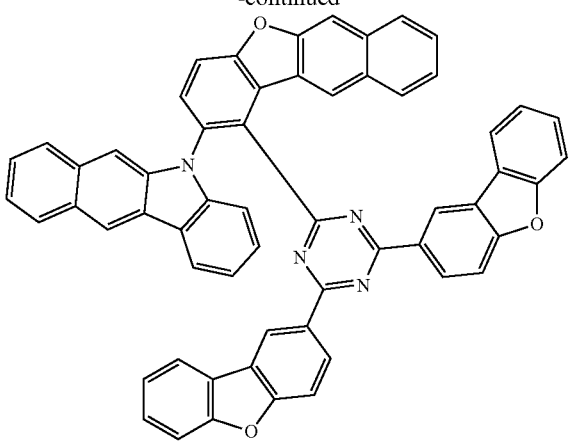
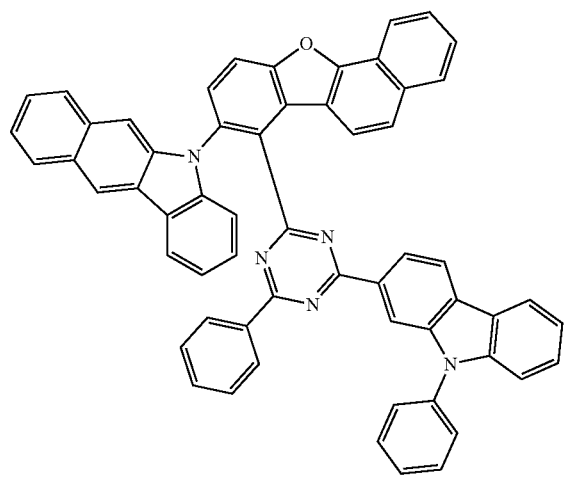
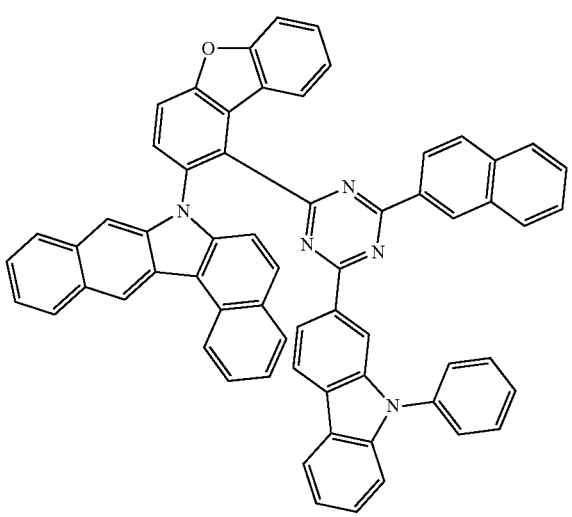

683
-continued
684
-continued
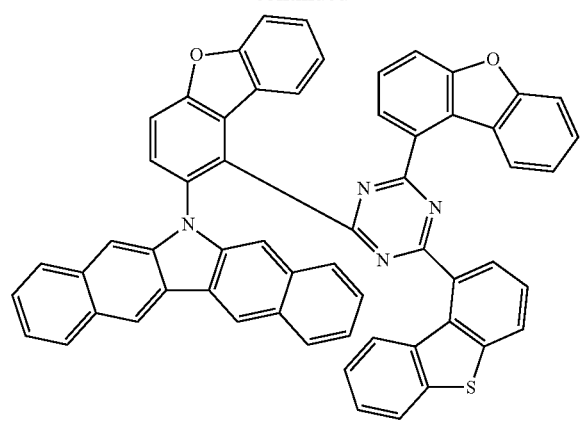
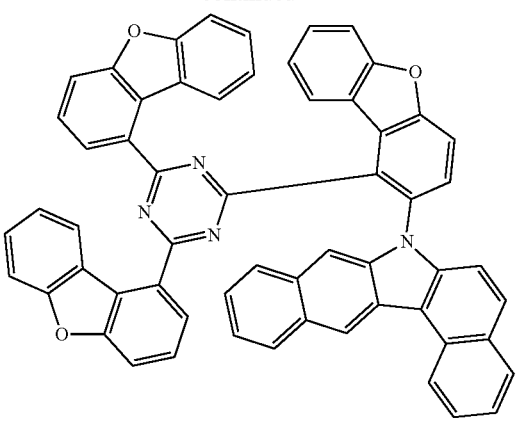
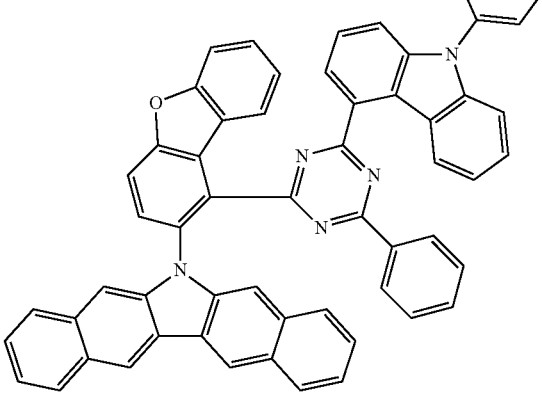
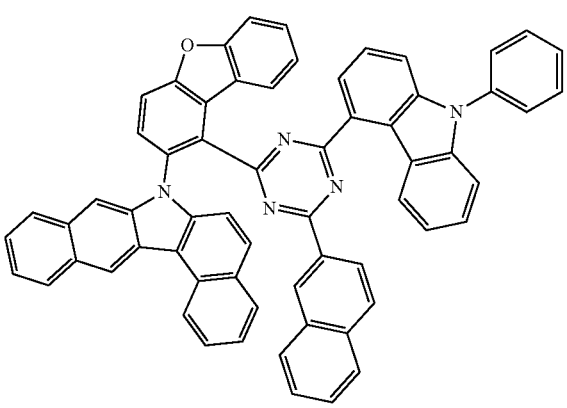
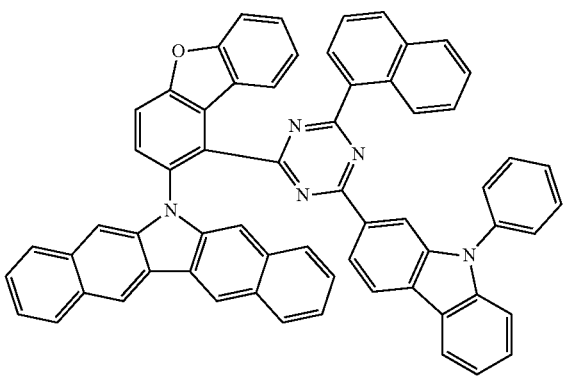

685
-continued
686
-continued
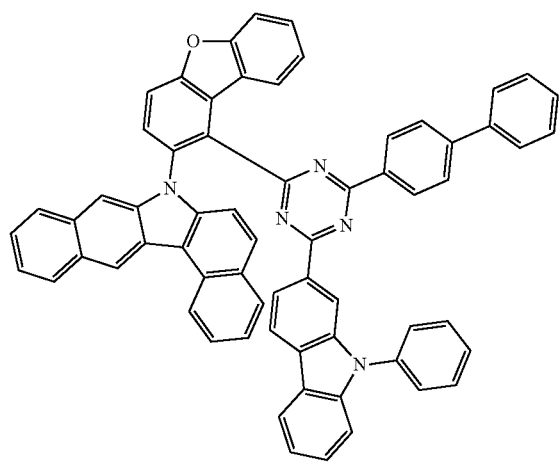
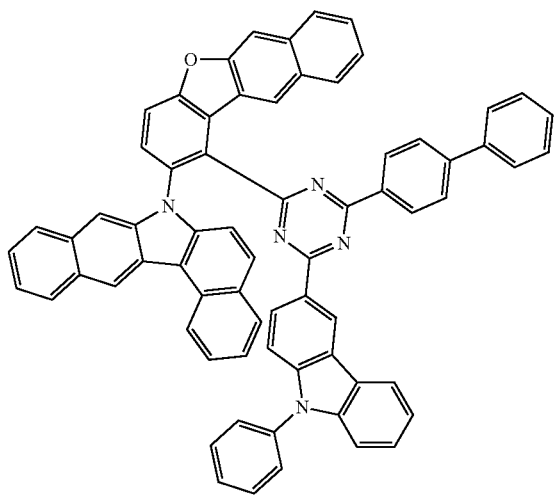
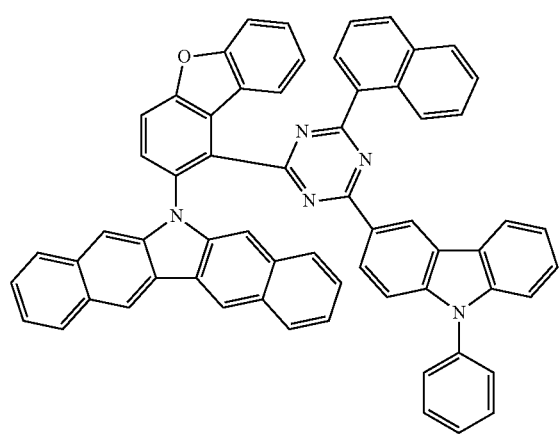
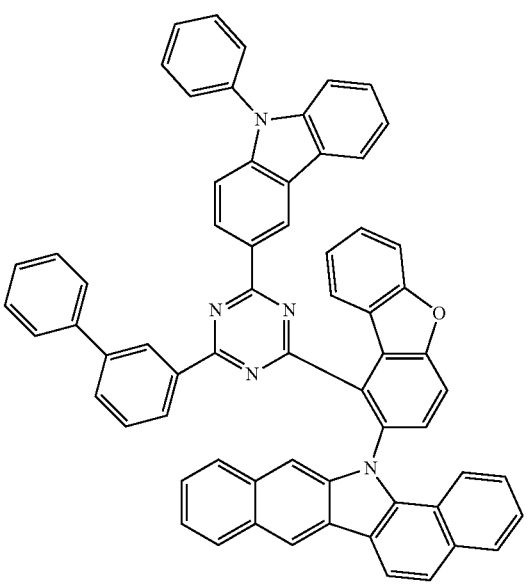
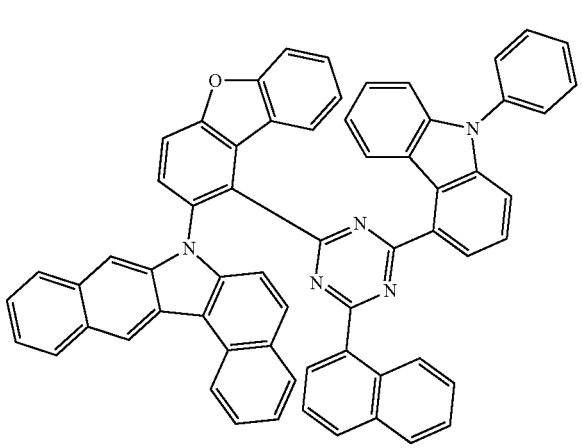

-continued

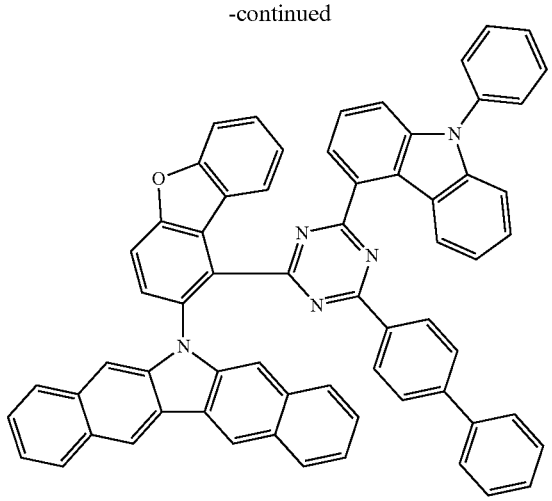

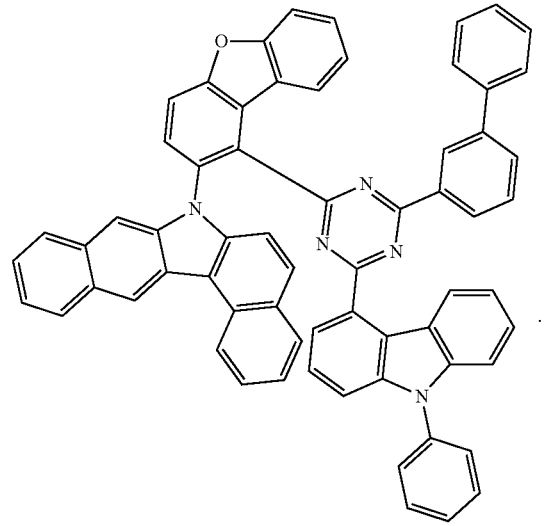

7. An organic light emitting device comprising:
a first electrode;
a second electrode provided to face the first electrode; and
an organic material layer having one or more layers provided between the first electrode and the second electrode,
wherein one or more layers of the organic material layer comprise the compound according to claim 1.

8. The organic light emitting device of claim 7, wherein the organic material layer comprises a light emitting layer, and
the light emitting layer comprises the compound of Formula 1.

9. The organic light emitting device of claim 7, wherein the organic material layer comprises a light emitting layer, and
the light emitting layer comprises the compound of Formula 1 as a host.

10. The organic light emitting device of claim 7, wherein the organic material layer comprises a hole injection layer or a hole transport layer, and
the hole injection layer or the hole transport layer comprises the compound of Formula 1.

11. The organic light emitting device of claim 7, wherein the organic material layer comprises an electron transport layer or an electron injection layer, and
the electron transport layer or the electron injection layer comprises the compound of Formula 1.

12. The organic light emitting device of claim 7, wherein the organic light emitting device further comprises one or two or more layers selected from the group consisting of a hole injection layer, a hole transport layer, an electron transport layer, an electron injection layer, an electron blocking layer, and a hole blocking layer.

13. The organic light emitting device of claim 7, wherein the organic material layer comprises a light emitting layer, and
the light emitting layer comprises the compound of Formula 1 as a first host, and further comprises a second host of the following Formula H:

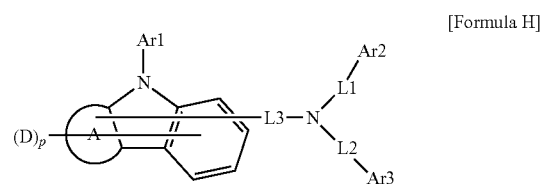

[Formula H]

wherein, in Formula H,

A is a substituted or unsubstituted naphthalene ring,

D is deuterium,

Ar1 is a substituted or unsubstituted aryl group having 6 to 60 carbon atoms,

L1 to L3 are each independently a single bond; or a substituted or unsubstituted arylene group having 6 to 60 carbon atoms, Ar2 and Ar3 are each independently a substituted or unsubstituted aryl group having 6 to 60 carbon atoms; or a substituted or unsubstituted heteroaryl group having 2 to 60 carbon atoms, comprising one or more heteroatoms selected from N, O, and S, and p is an integer from 0 to 9.

14. The organic light emitting device of claim 13, wherein the second host of Formula H is of any one selected from the following compounds:

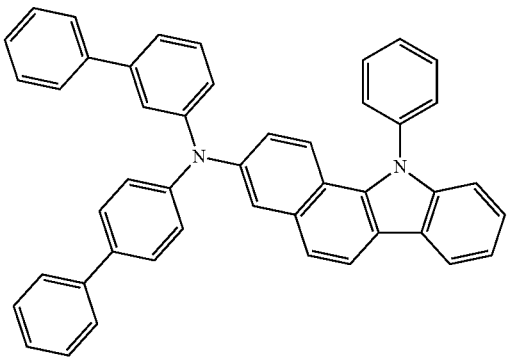

689
-continued
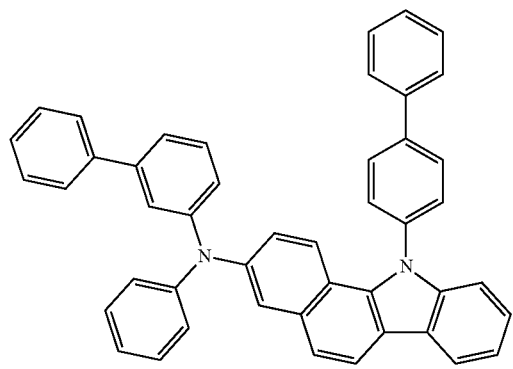
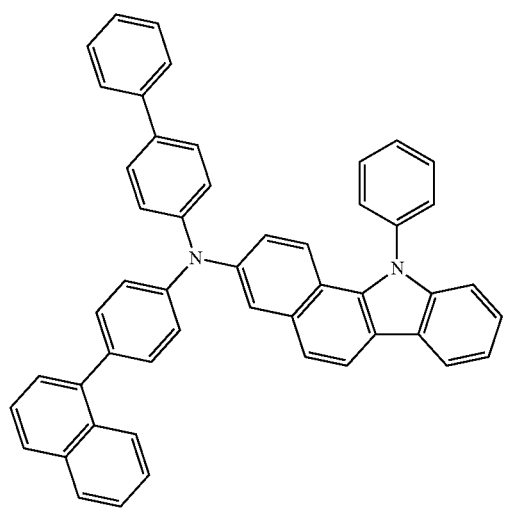
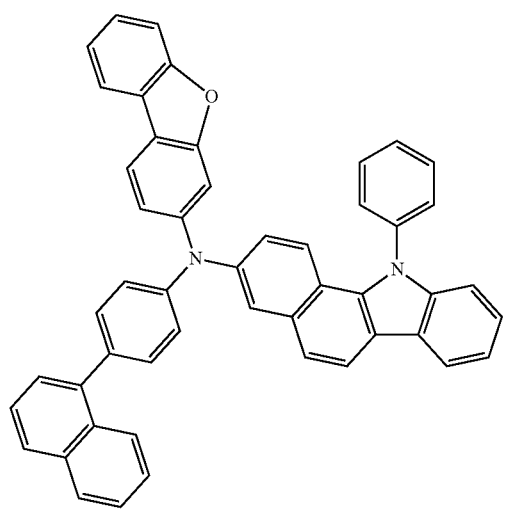
690
-continued
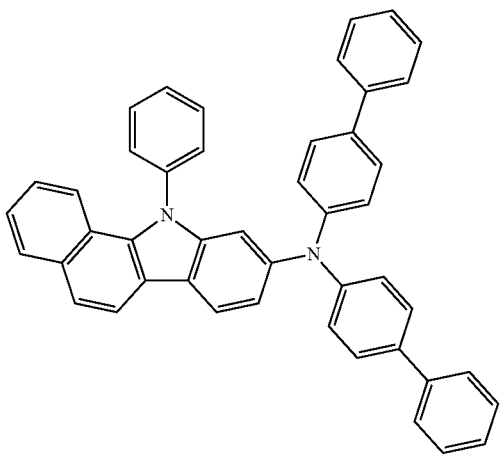
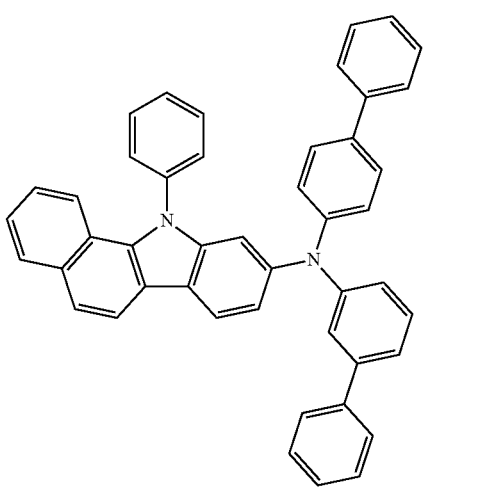
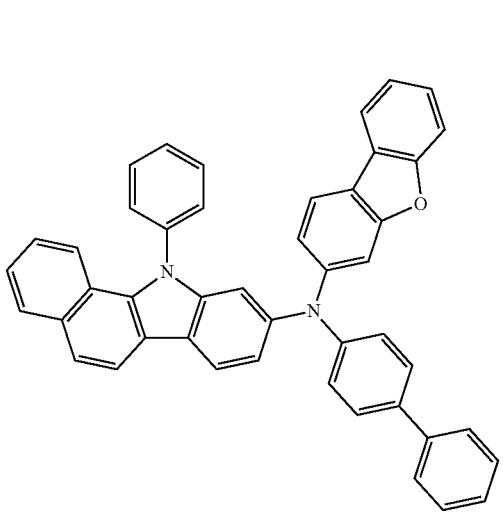

691
-continued
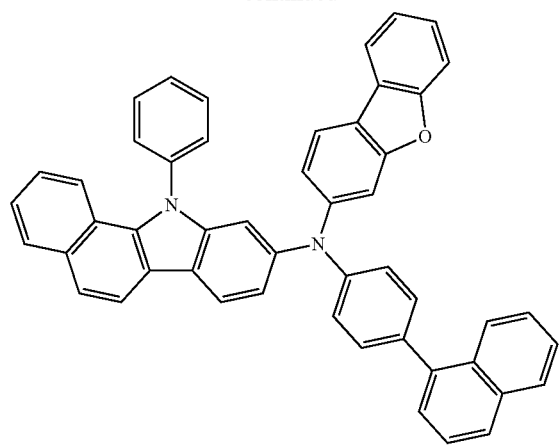
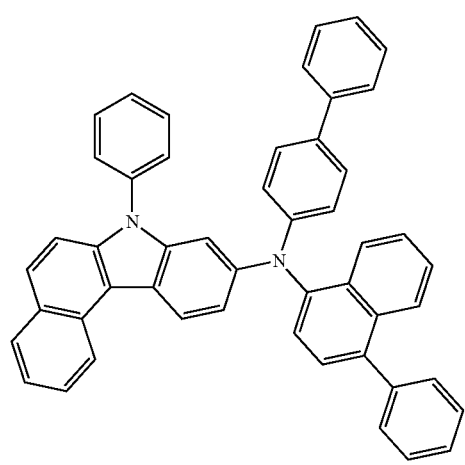
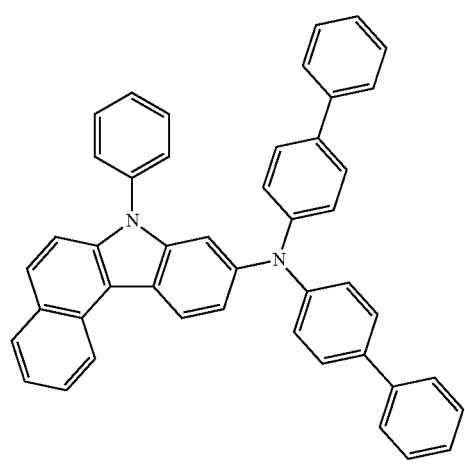
692
-continued
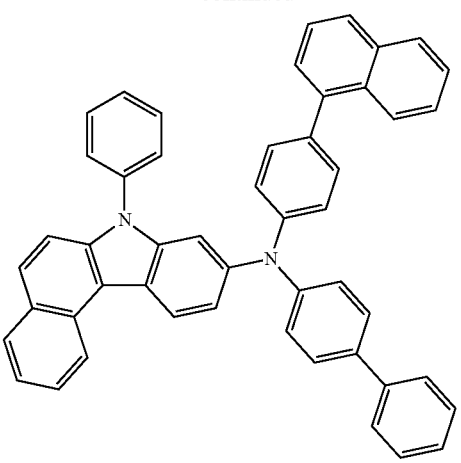
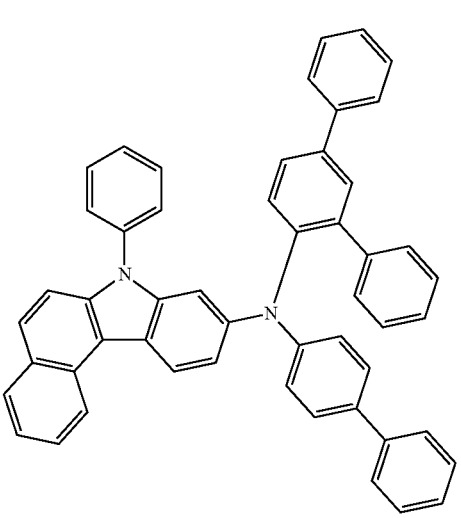
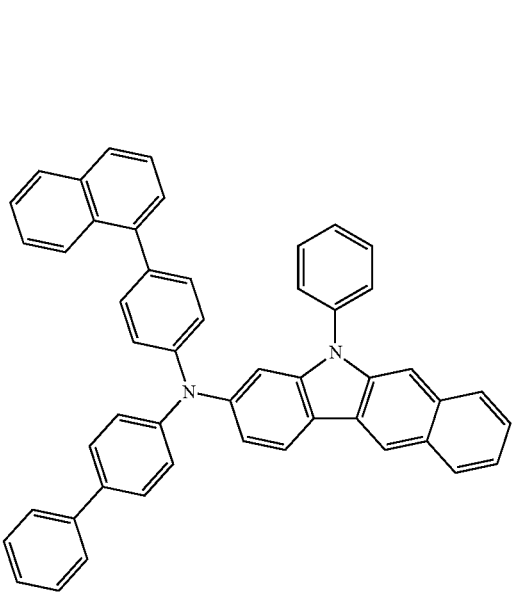

693
-continued
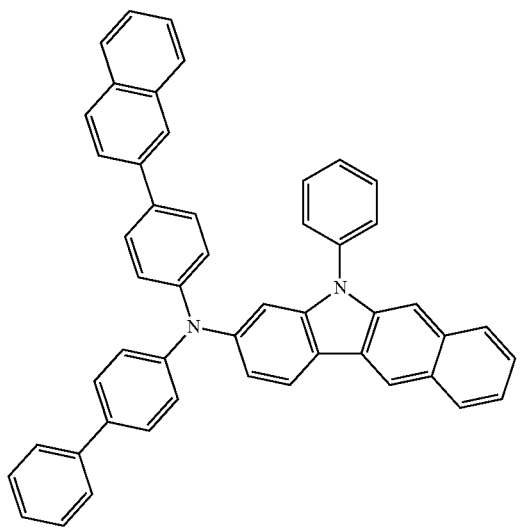
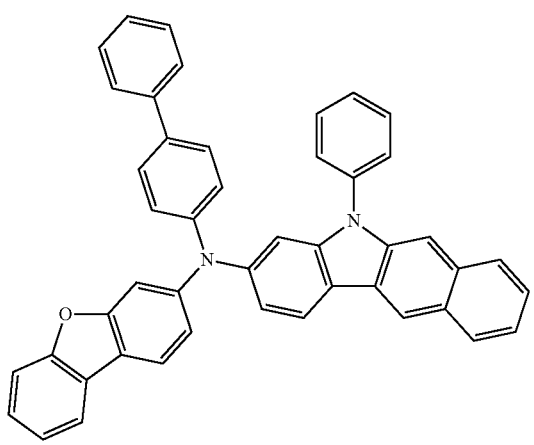
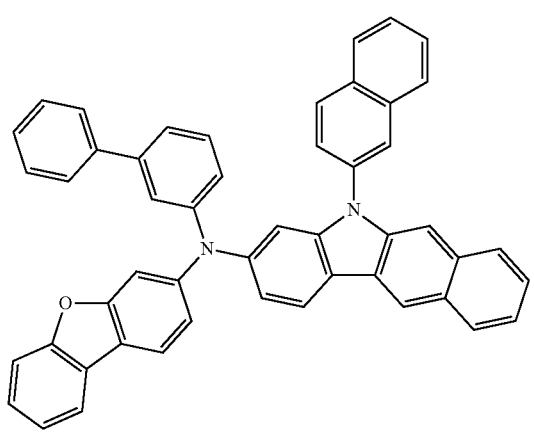
694
-continued
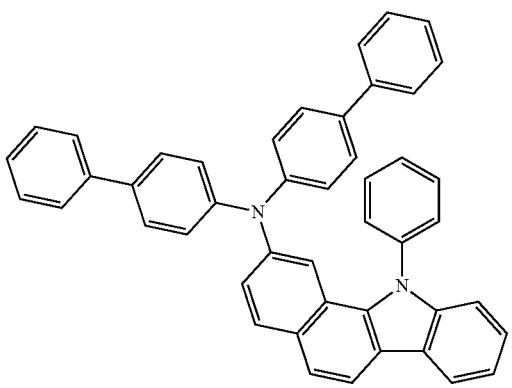
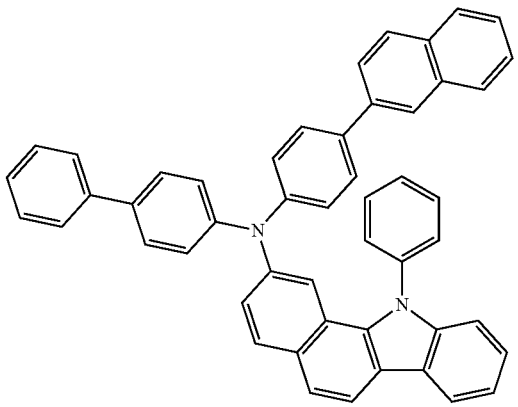
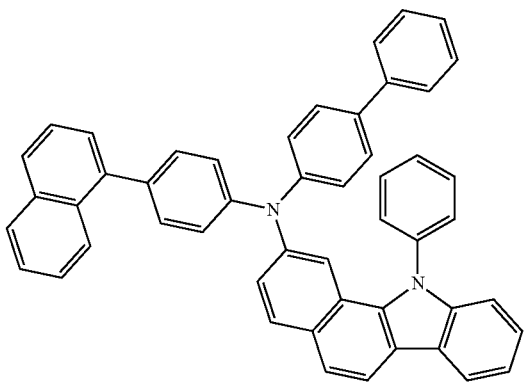
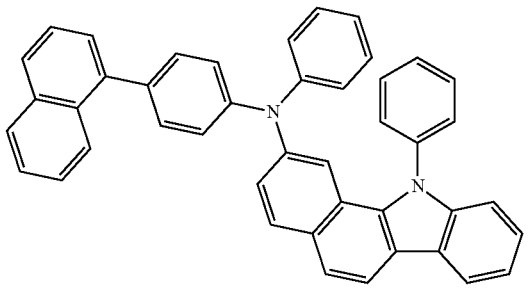

695
-continued
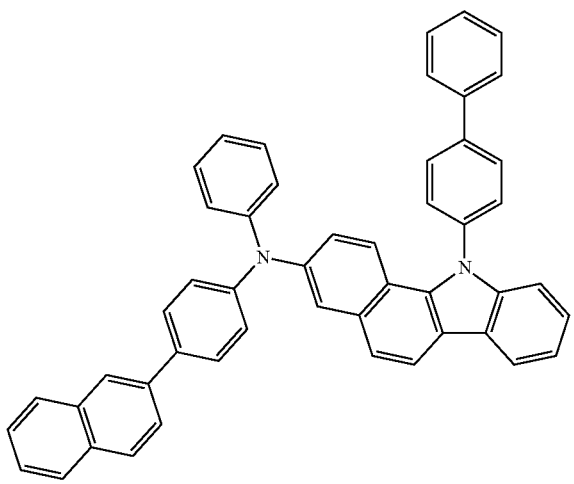
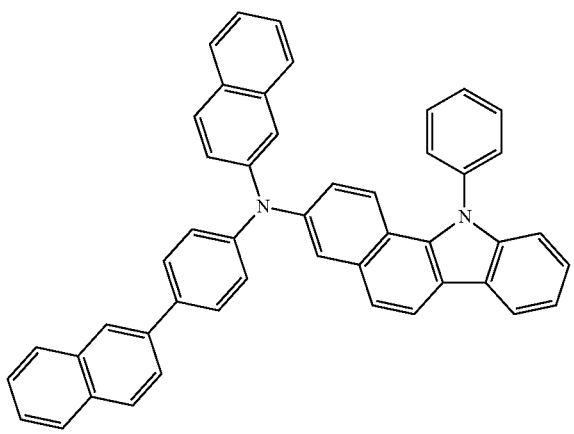
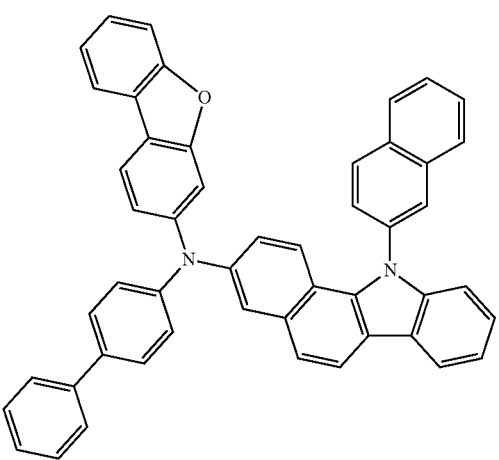
696
-continued
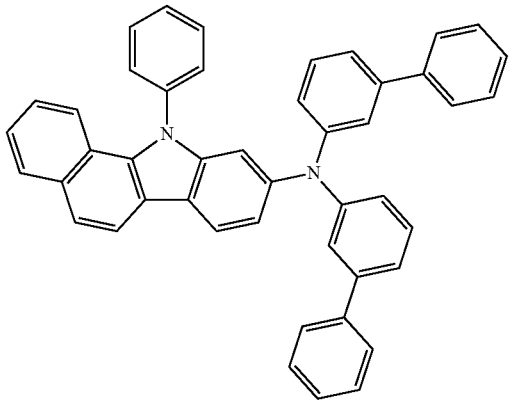
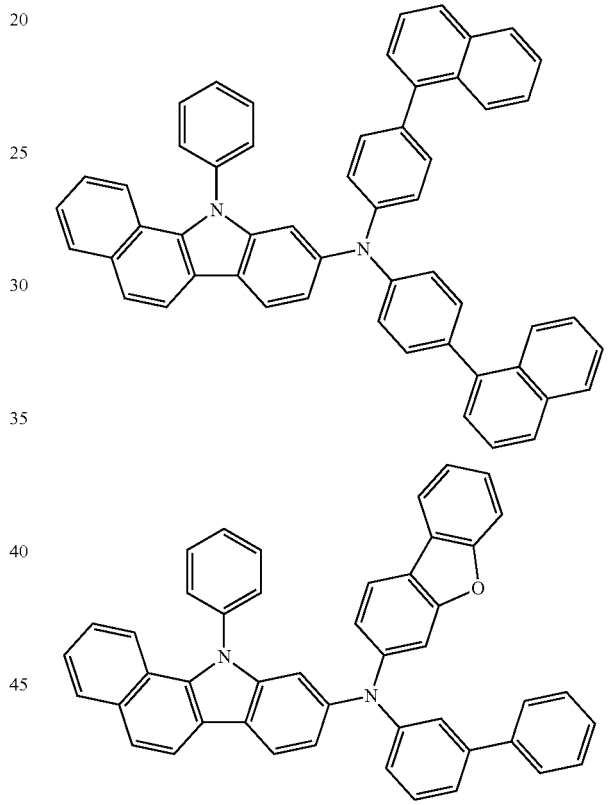
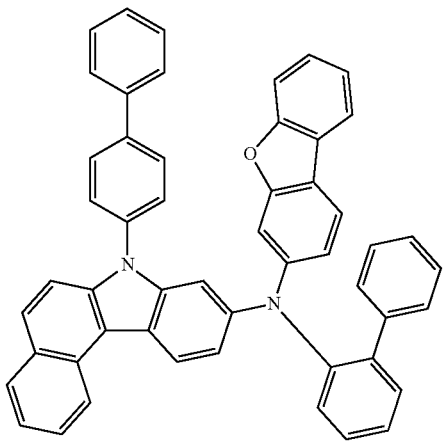

697
-continued
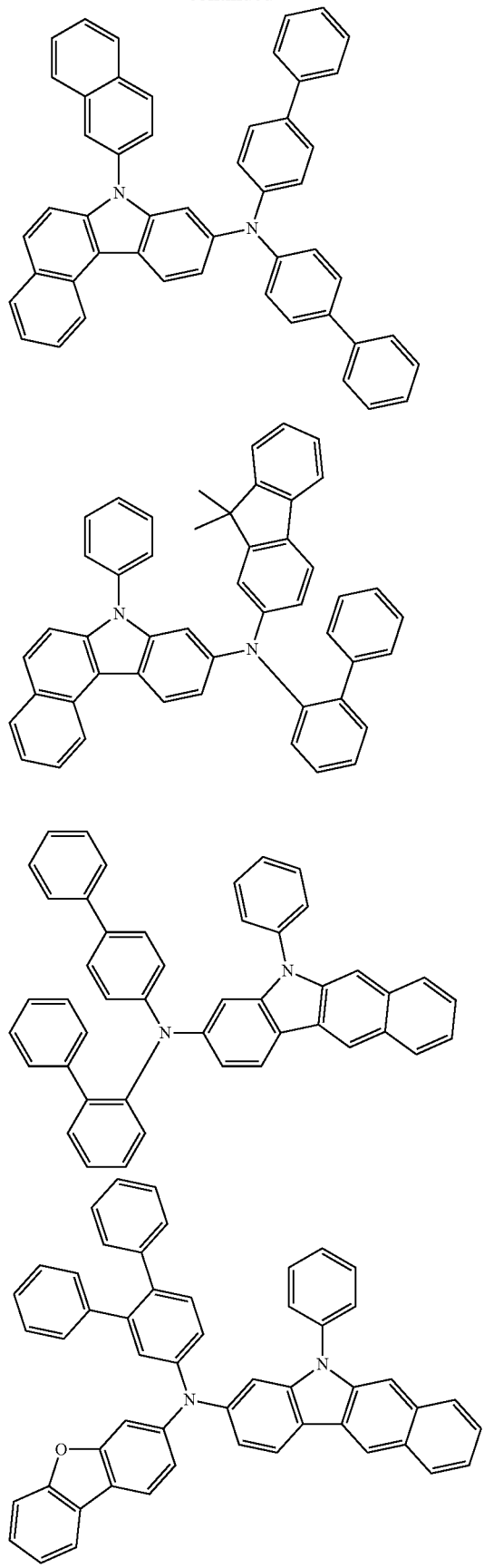
698
-continued
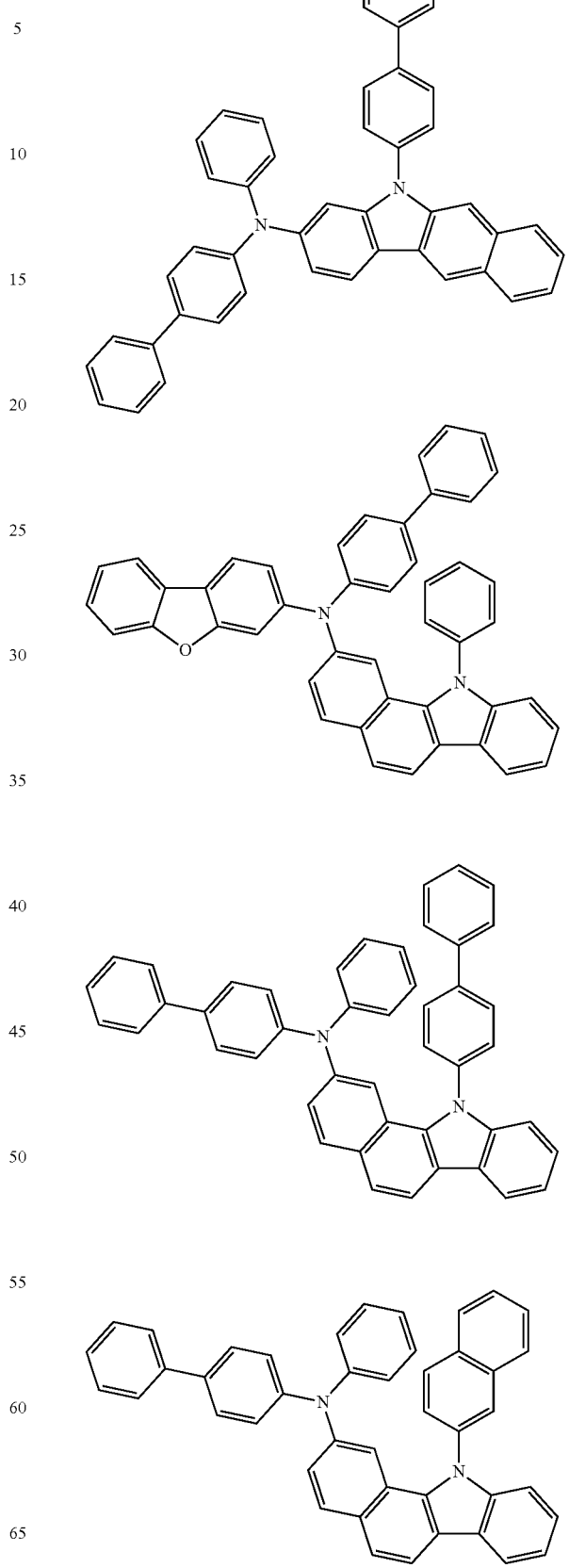

| 699 -continued | 700 -continued |
|---|---|
| 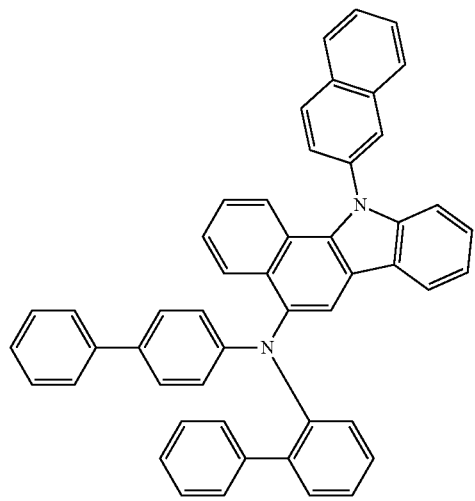 | 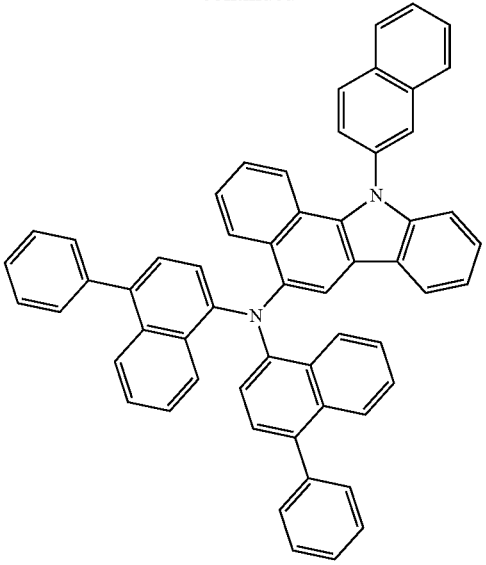 |
| 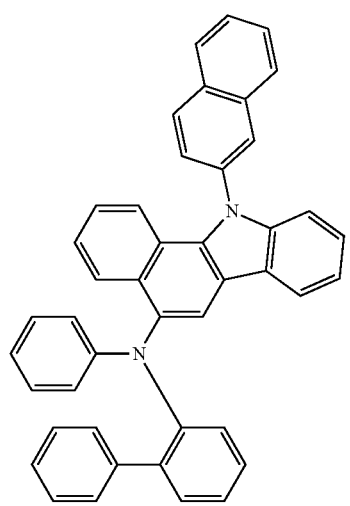 | 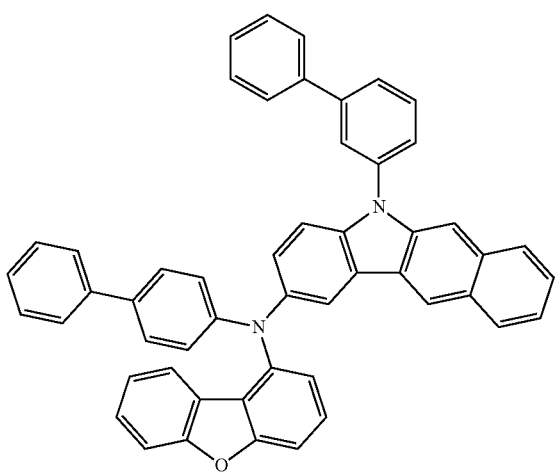 |
| 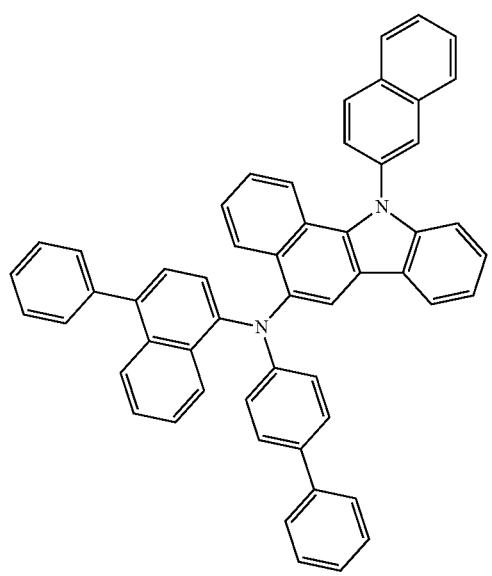 | 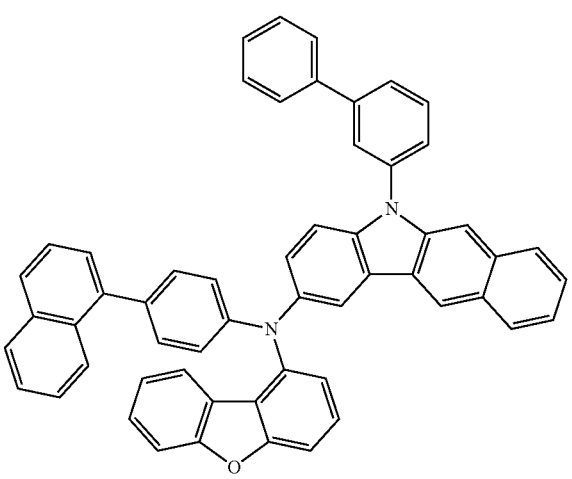 |

701
-continued
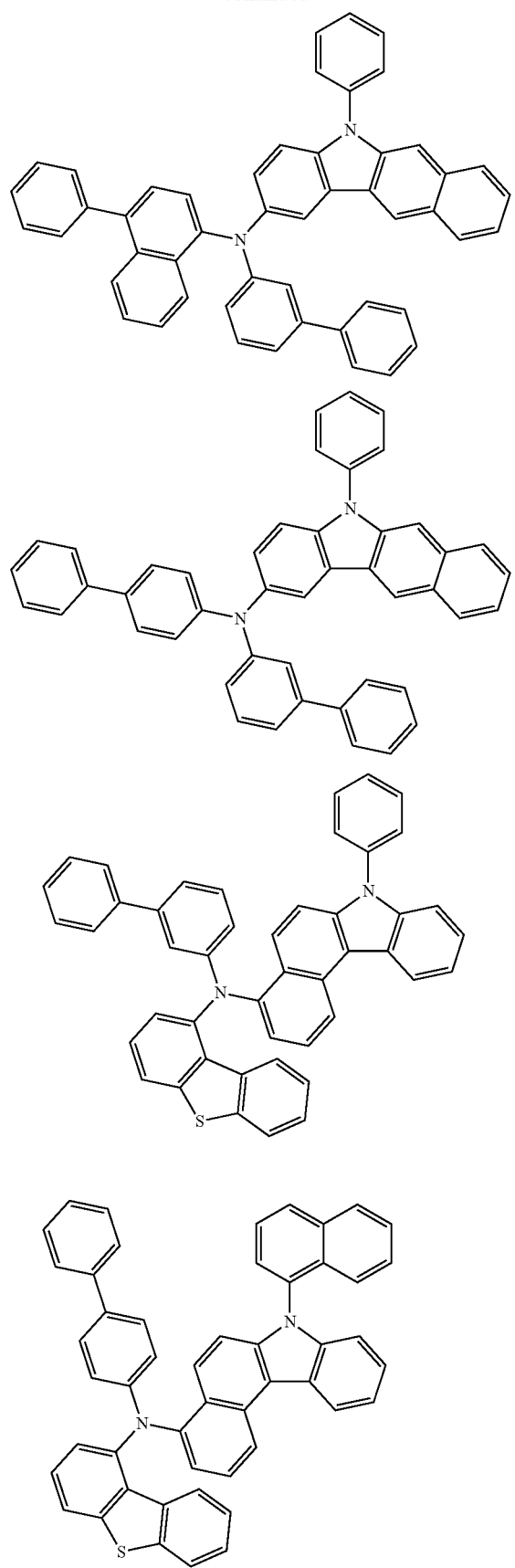
702
-continued
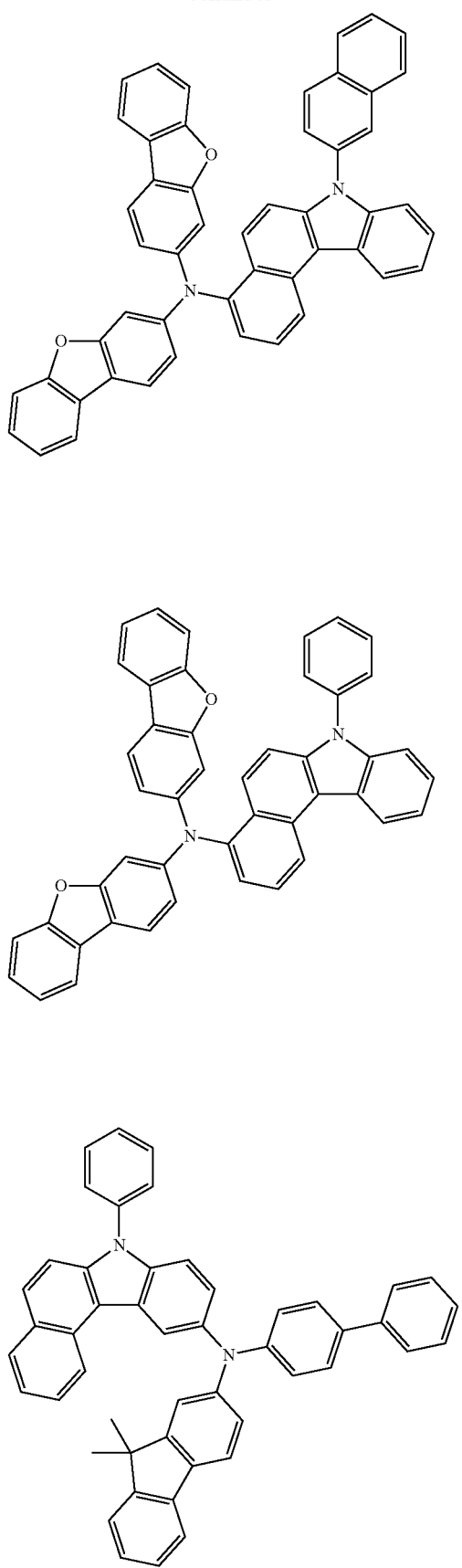

703
-continued
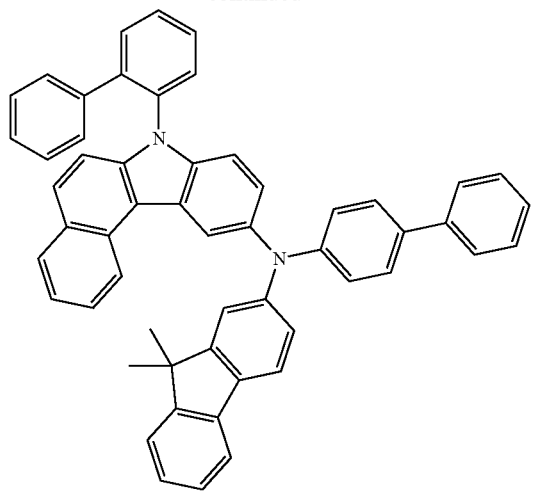
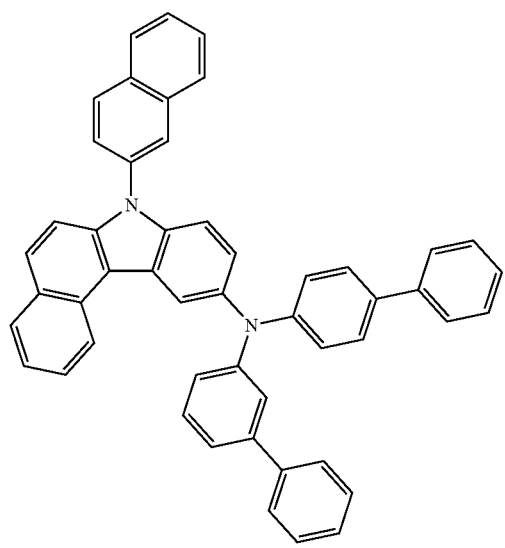
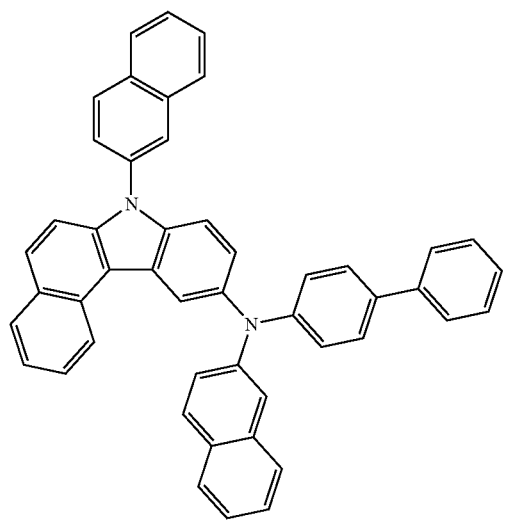
704
-continued
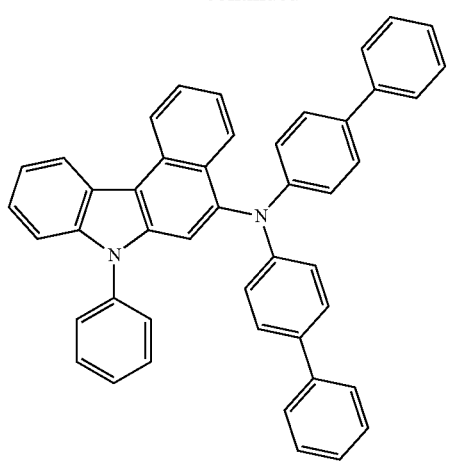
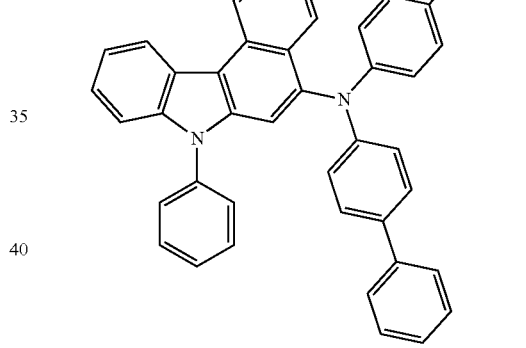
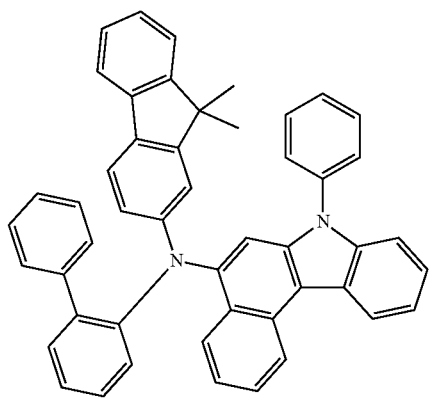

| 705 -continued | 706 -continued |
|---|---|
| 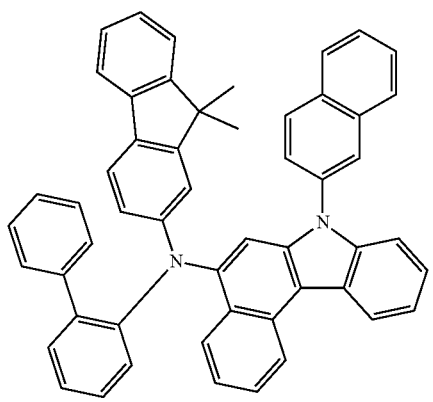 | 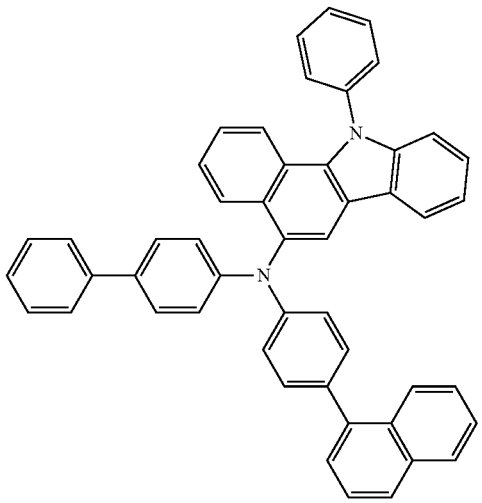 |
| 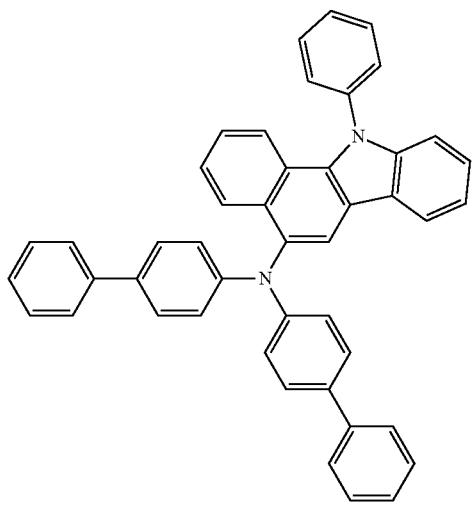 | 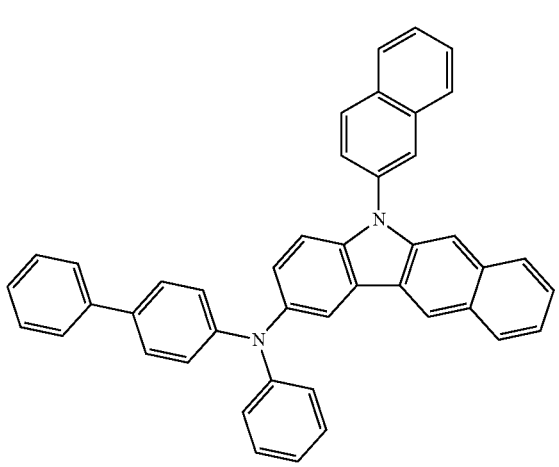 |
| 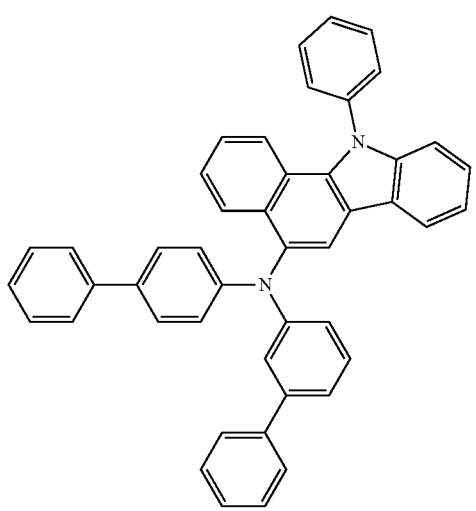 | 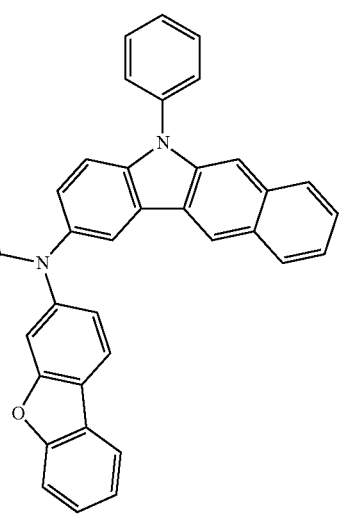 |

| 707 -continued | 708 -continued |
|---|---|
| 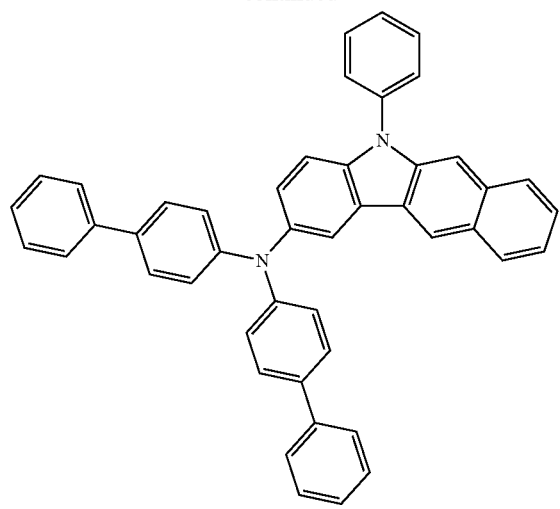 | 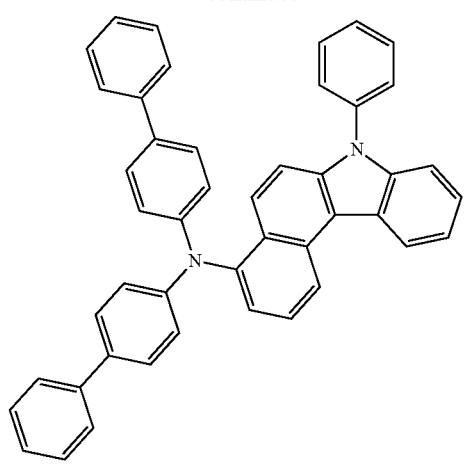 |
| 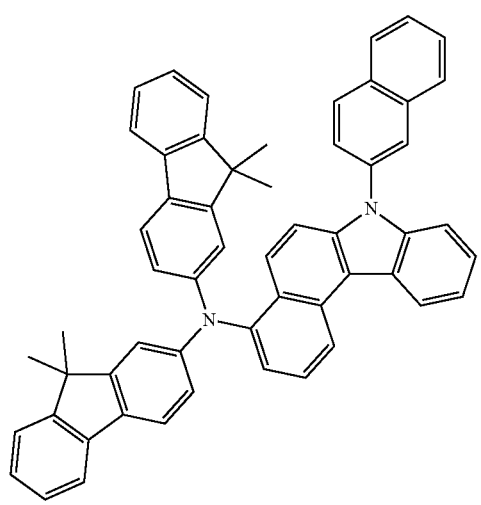 | 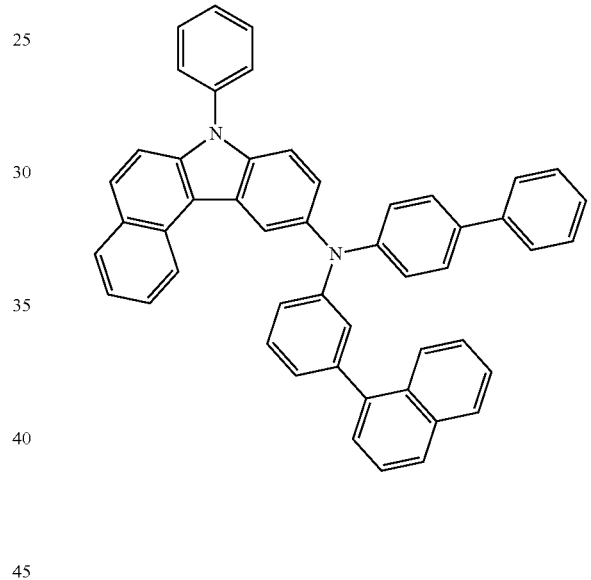 |
| 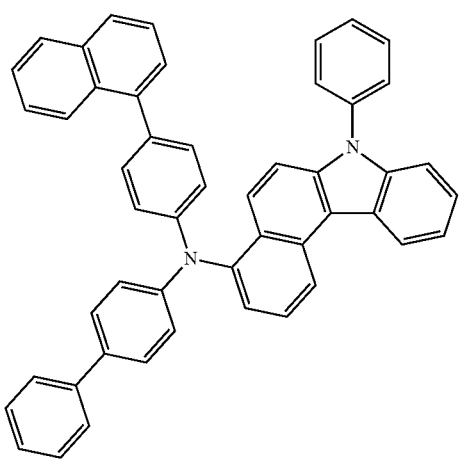 | 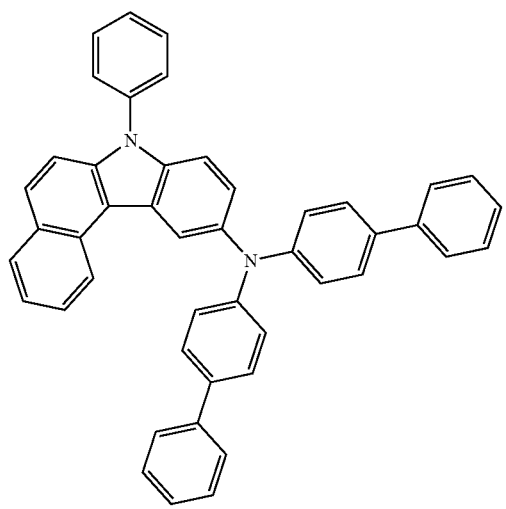 |

709
-continued
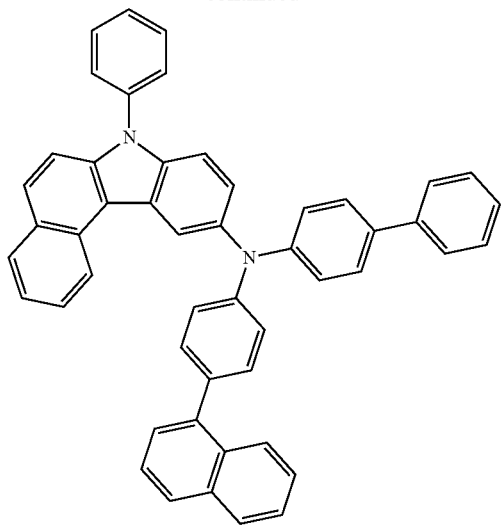
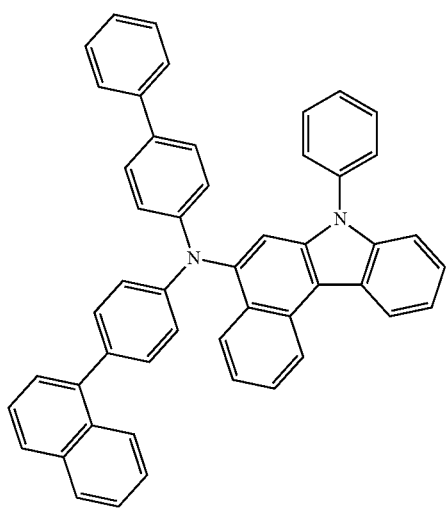
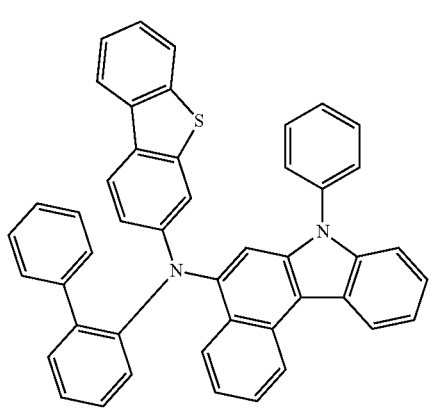
710
-continued
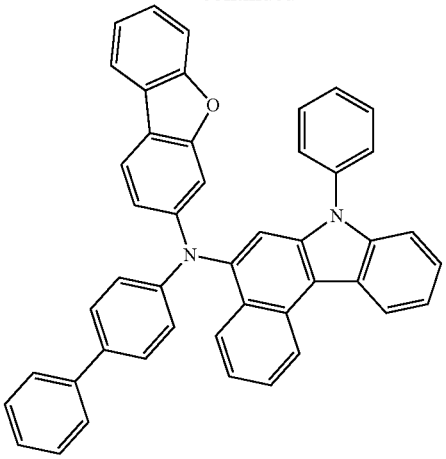
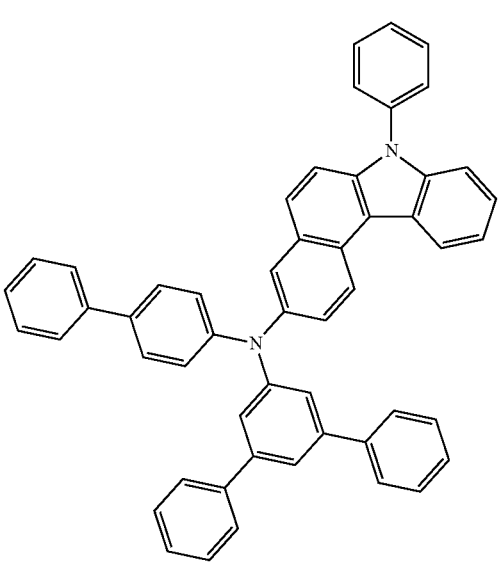
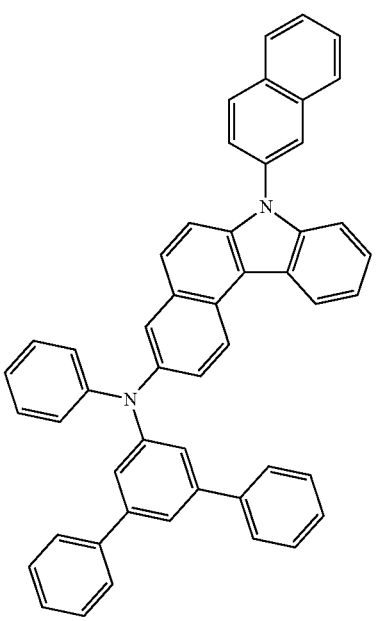

711
-continued
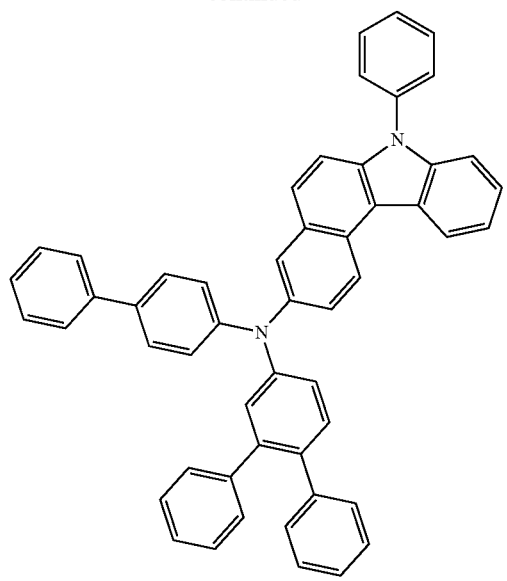
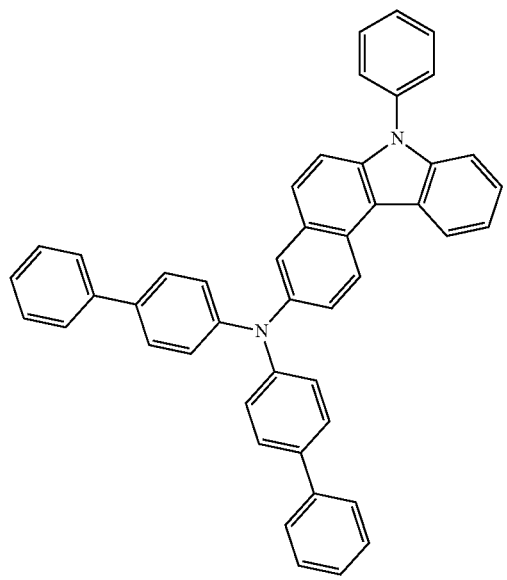
712
-continued
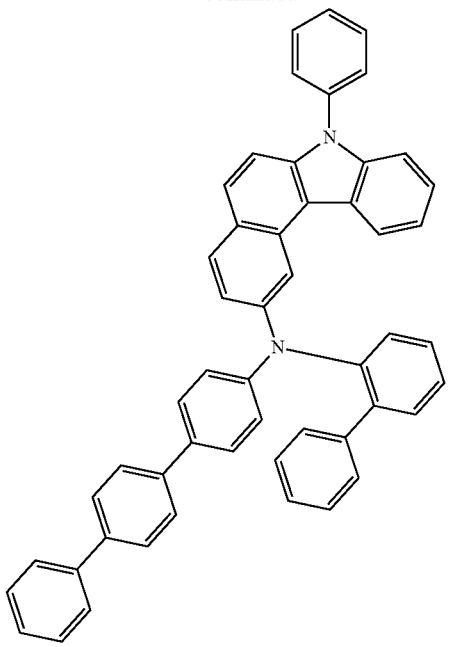
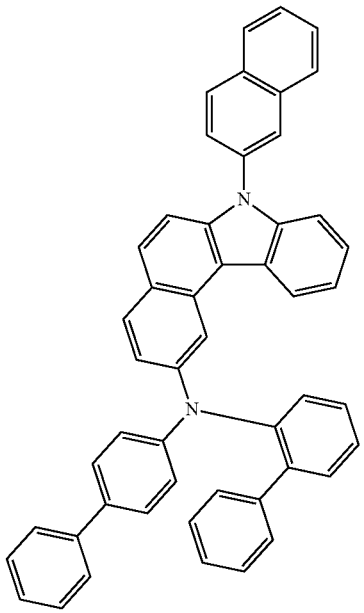

713
-continued
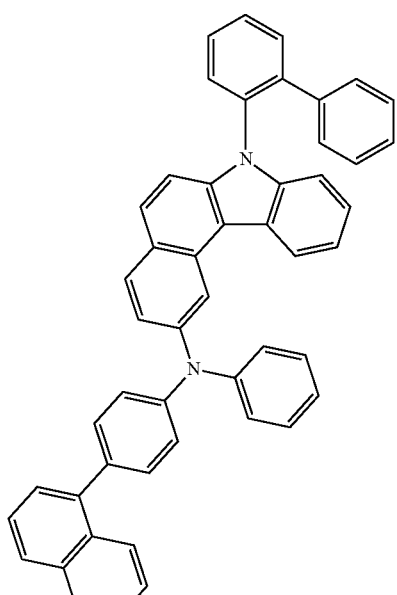
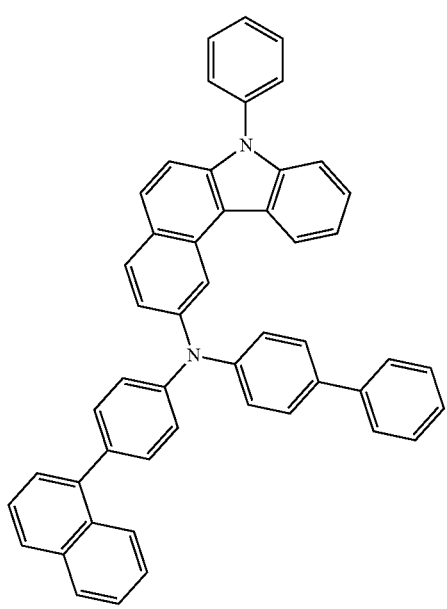
714
-continued
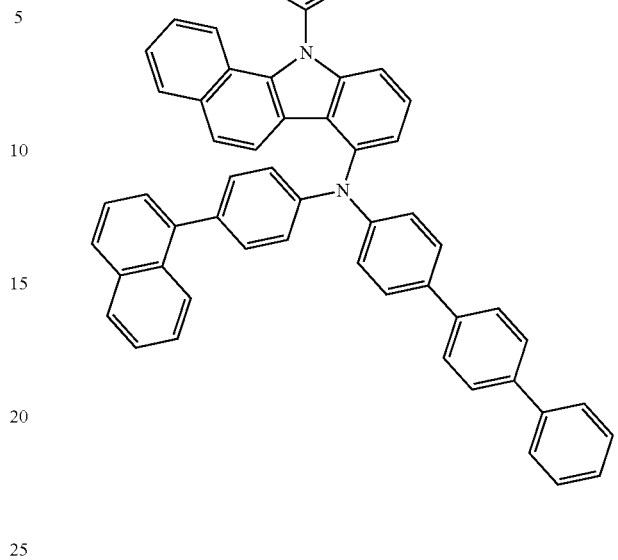
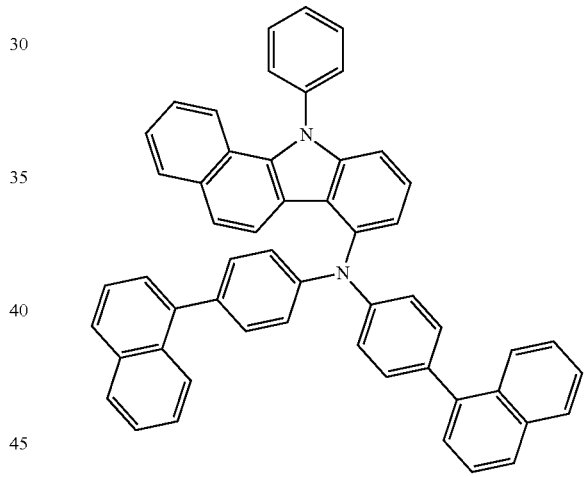
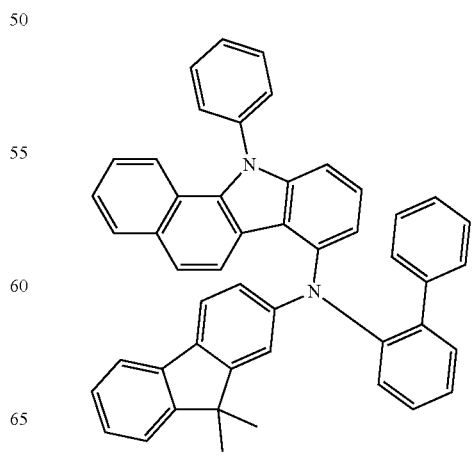

715
-continued
716
-continued
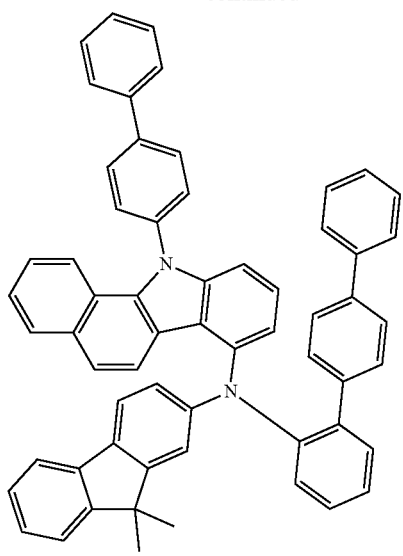
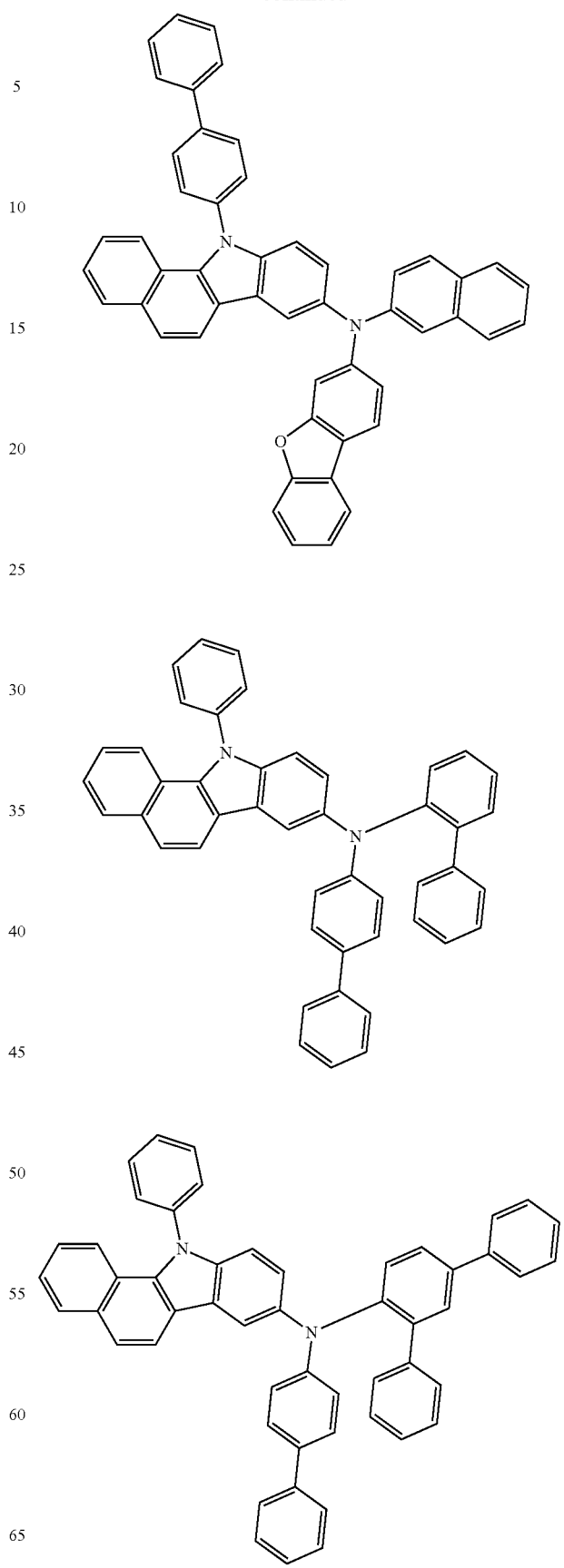

717
-continued
718
-continued
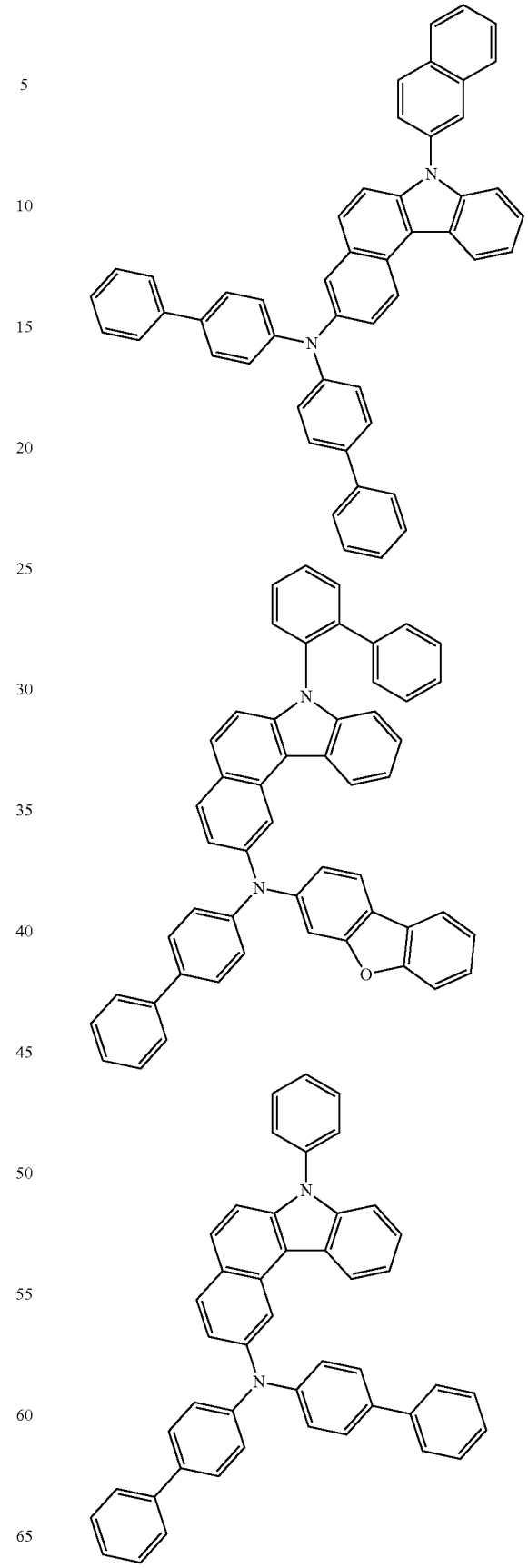

719
-continued
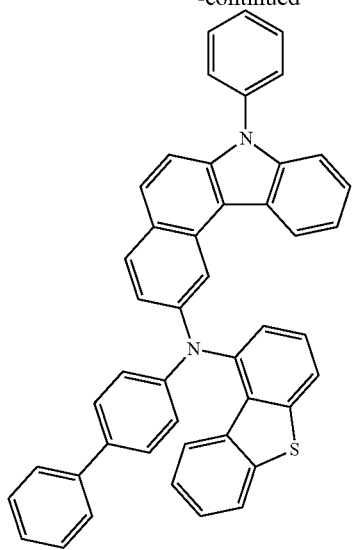
720
-continued
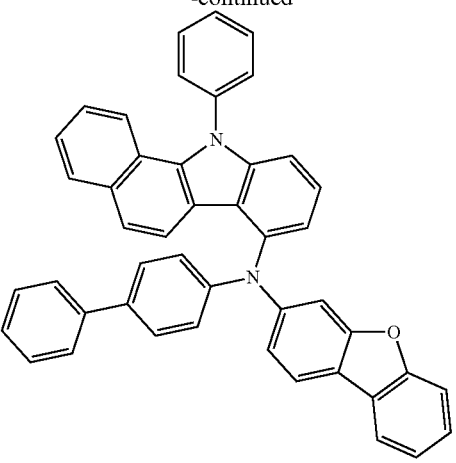
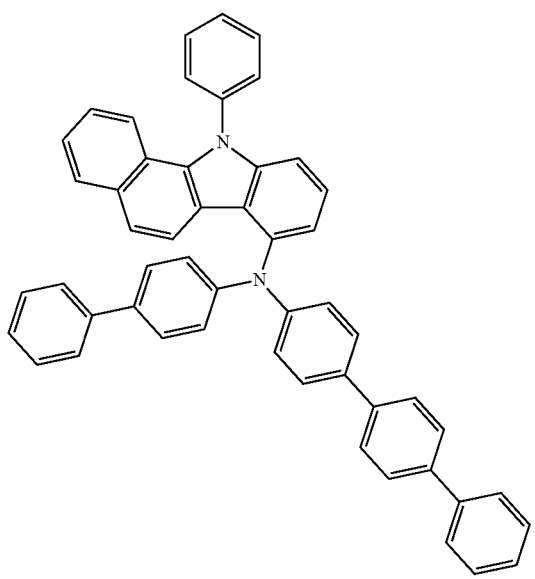
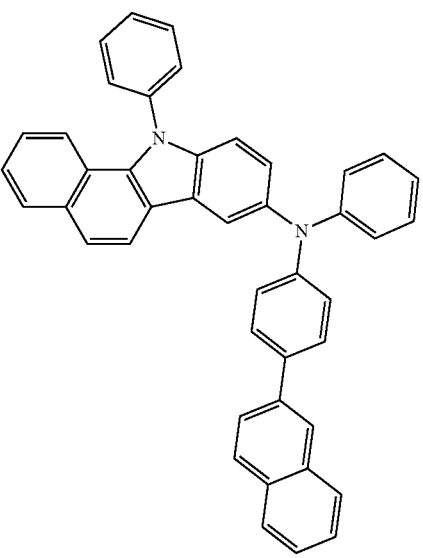
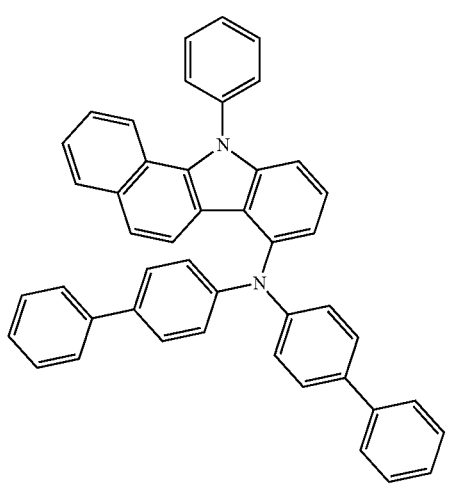
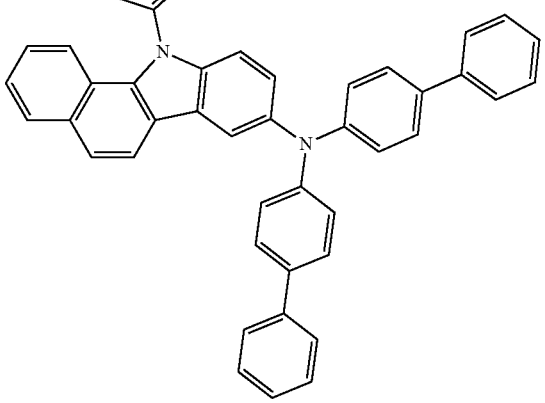

721
-continued
722
-continued
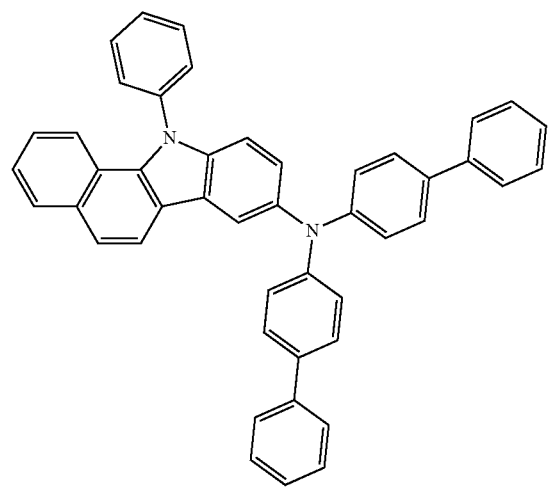
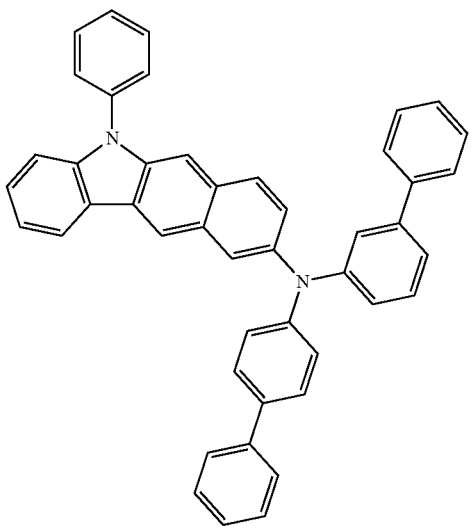
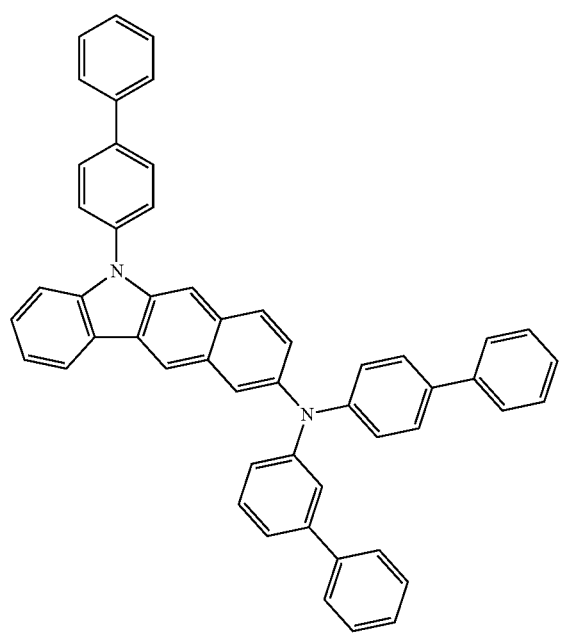
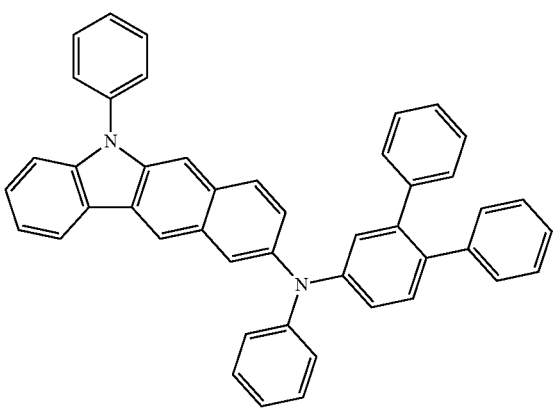
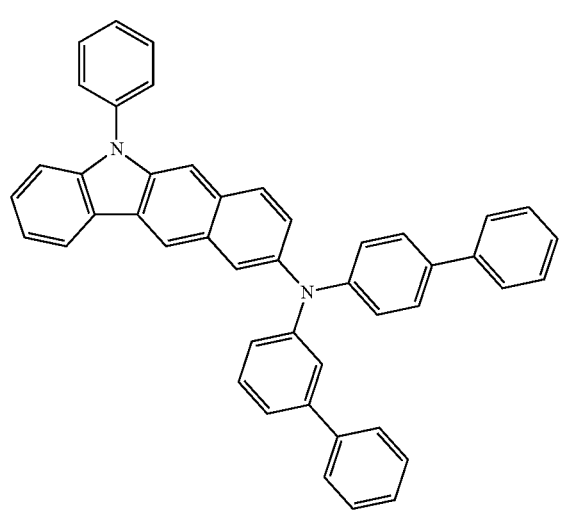

723
-continued
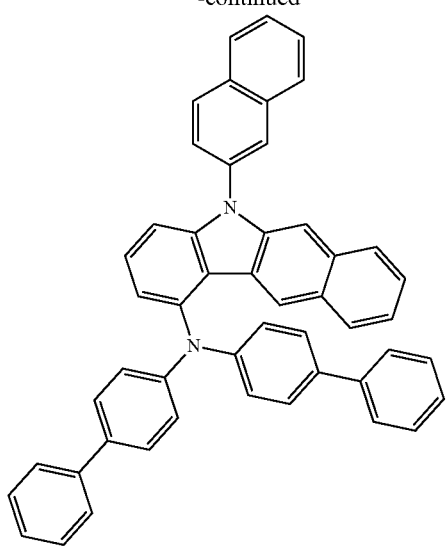
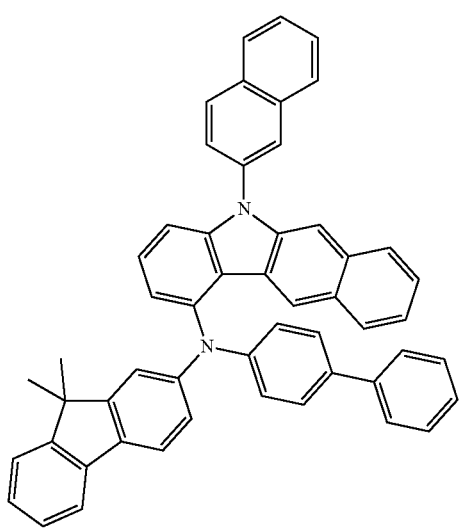
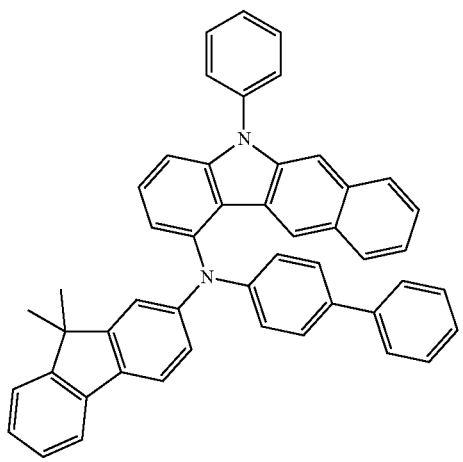
724
-continued
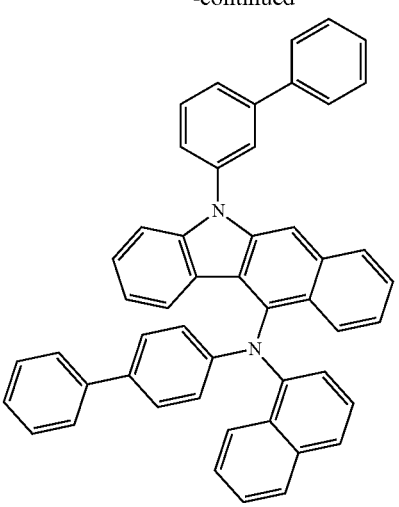
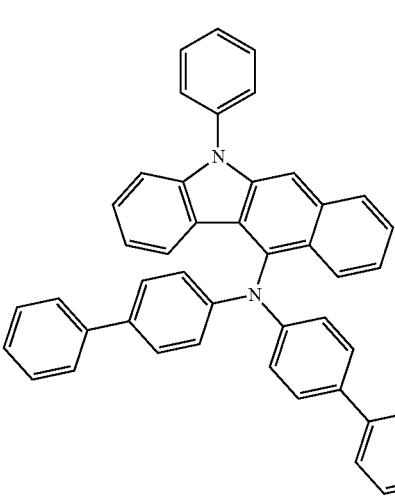
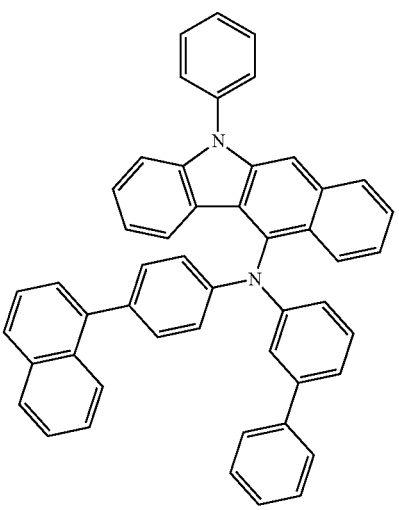

725
-continued
726
-continued
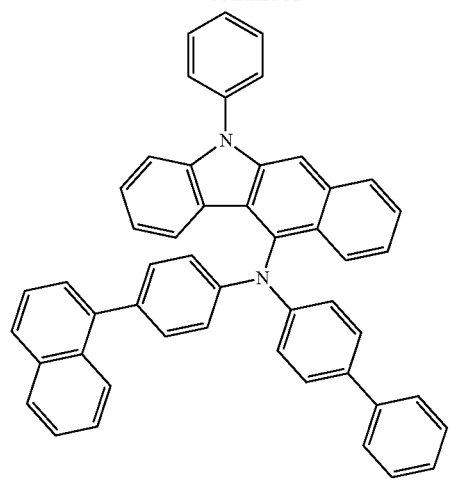
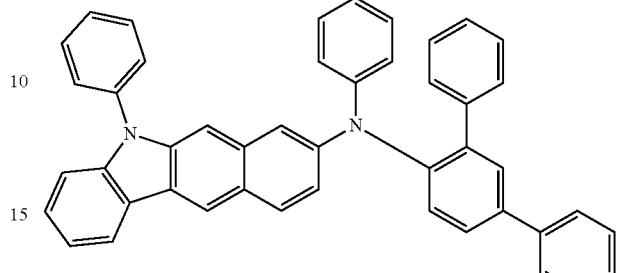
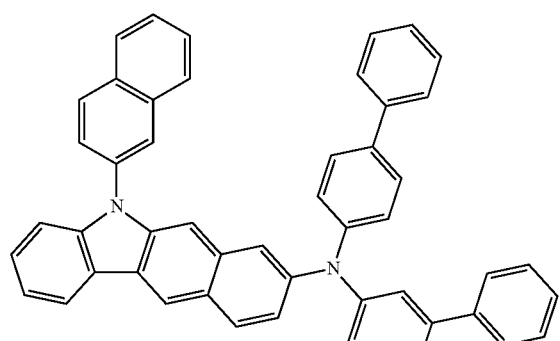
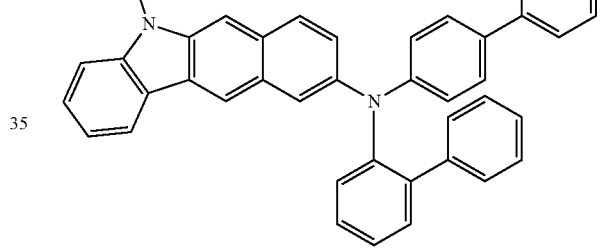
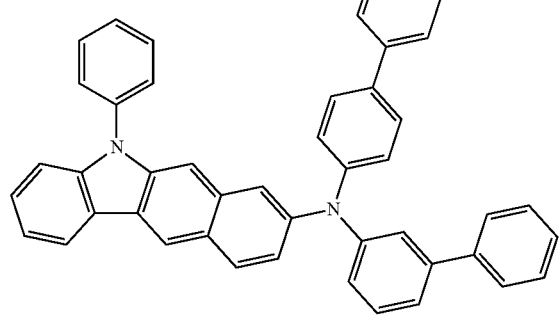
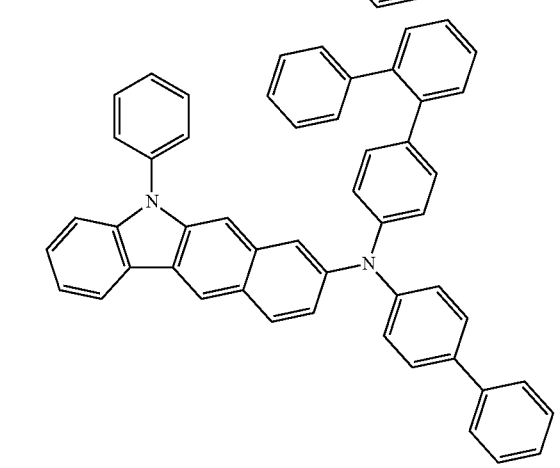
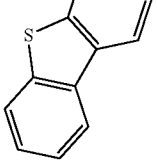

727
-continued
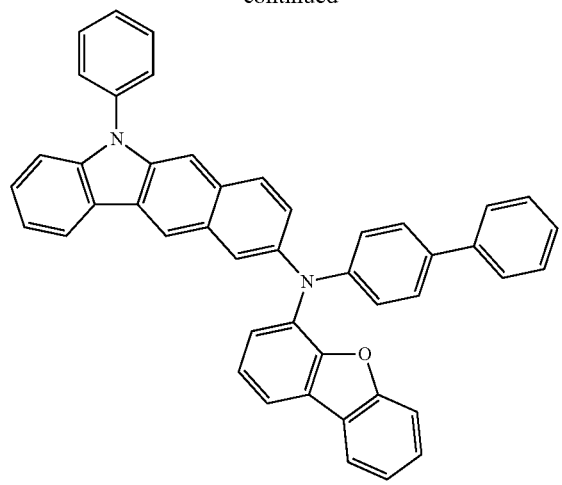
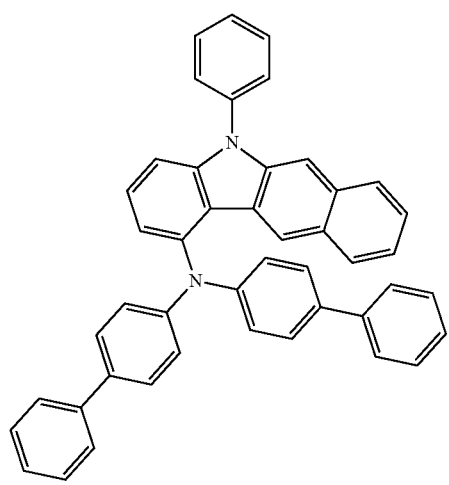
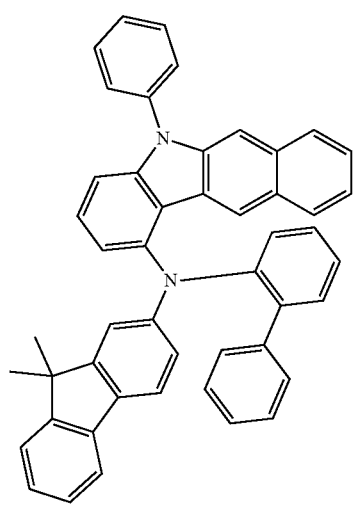
728
-continued
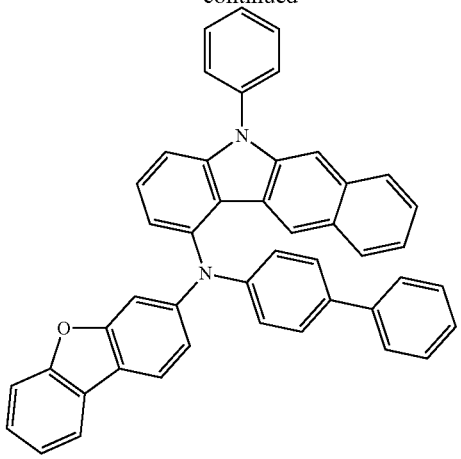
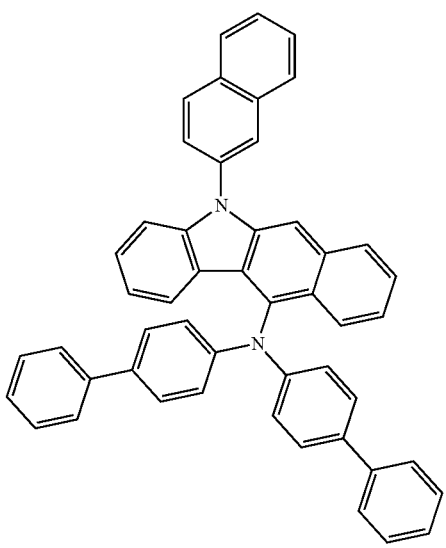
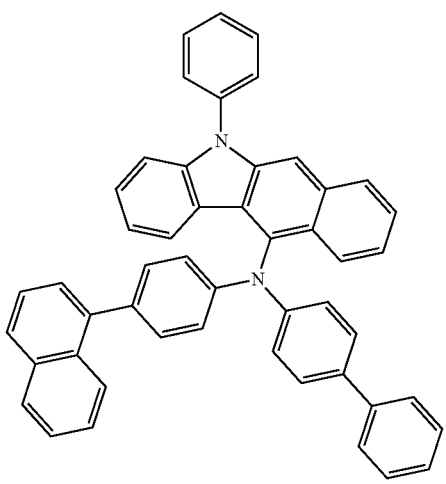

729
-continued
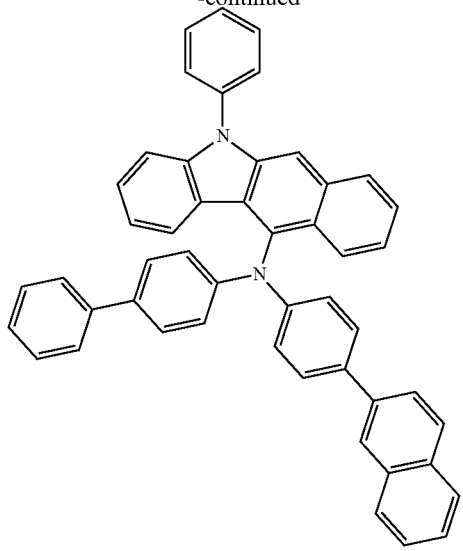
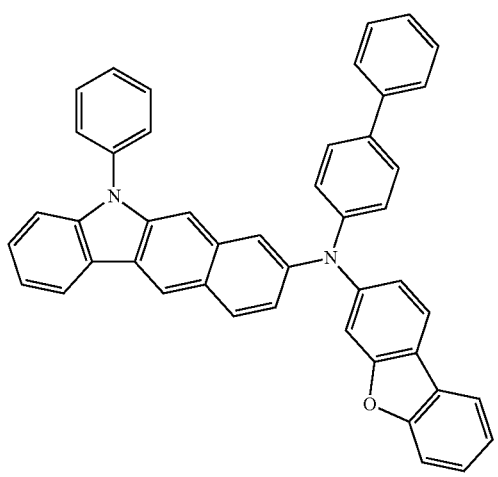
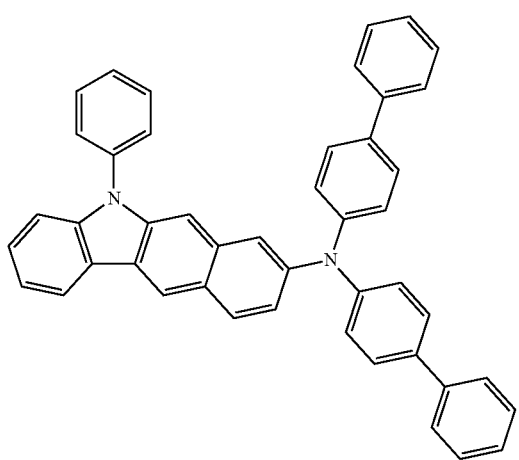
730
-continued
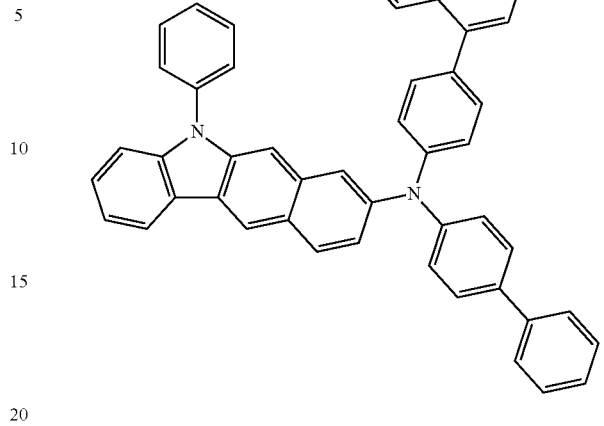
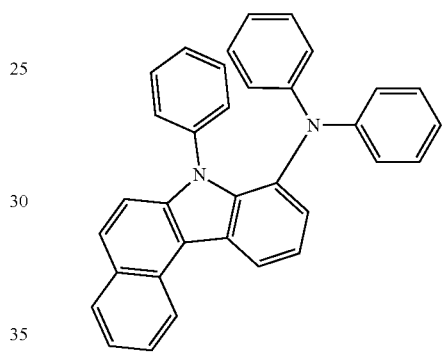
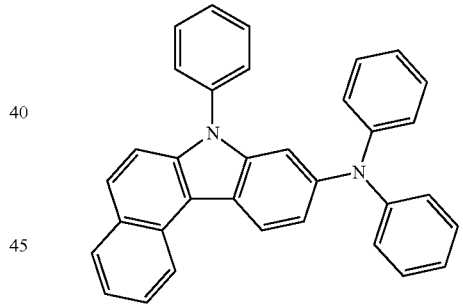
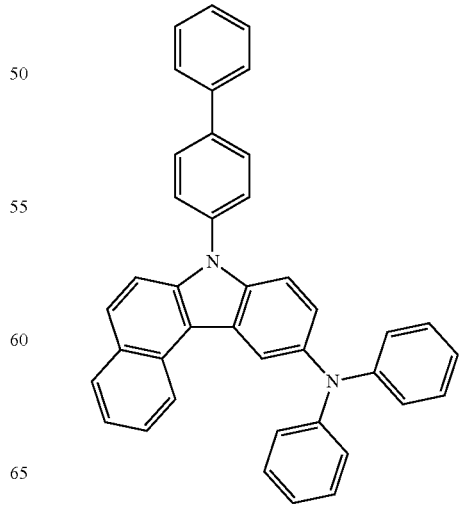

731
-continued
732
-continued
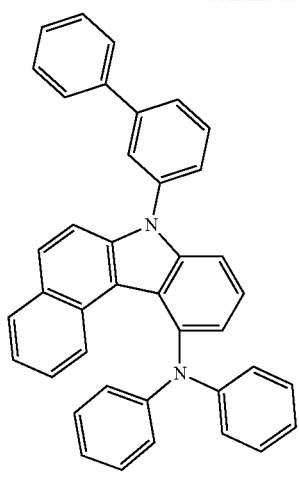
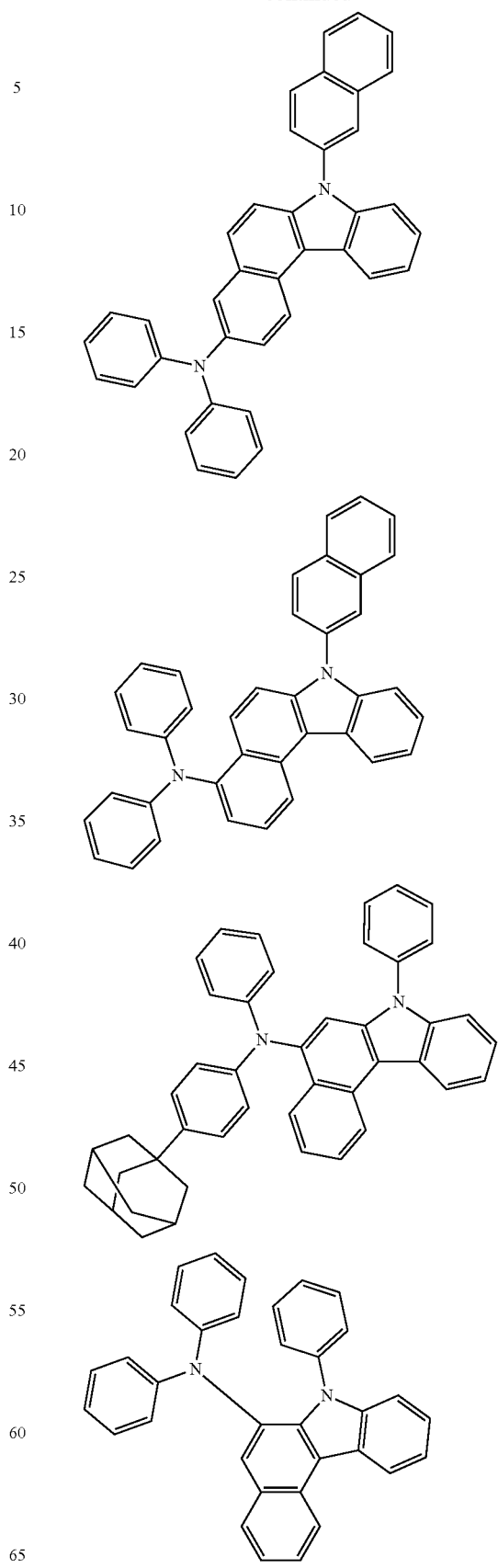

733
-continued
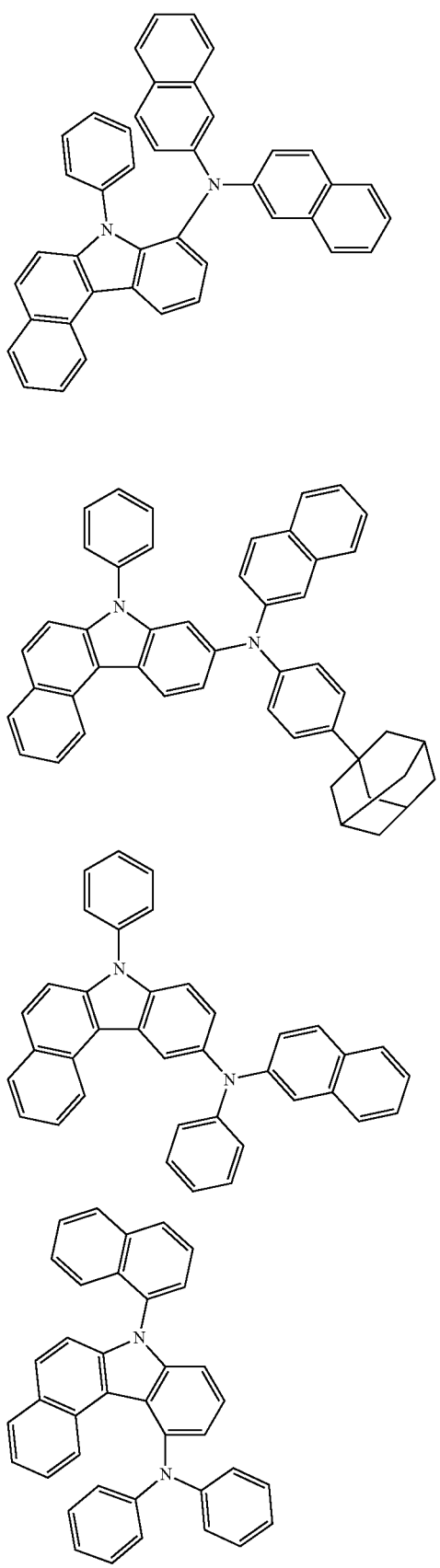
734
-continued
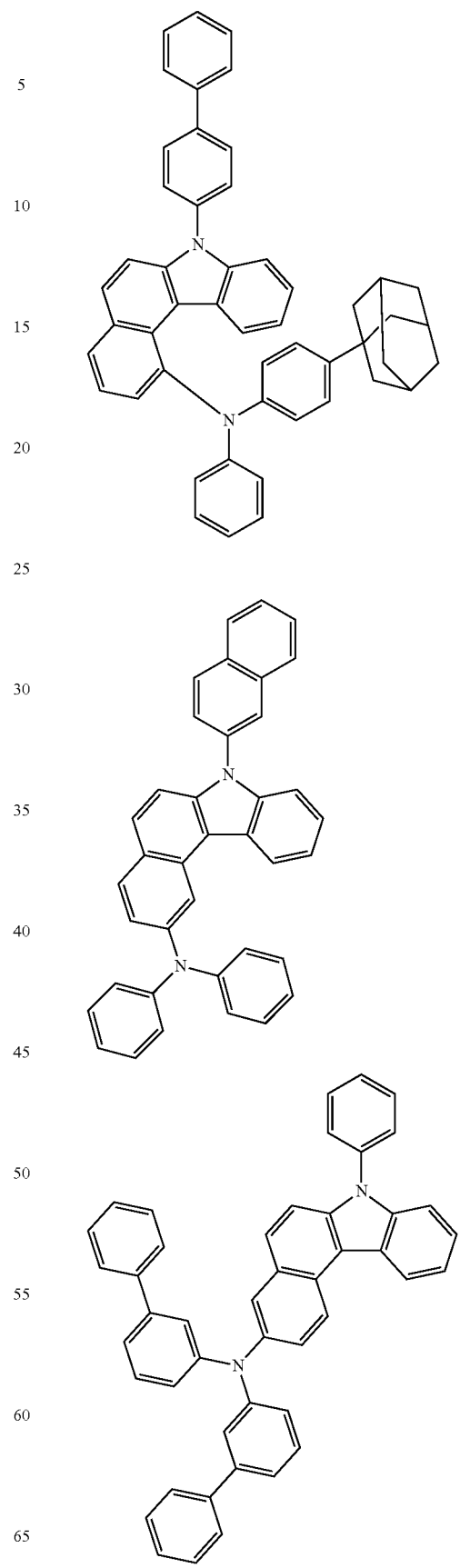

735
-continued
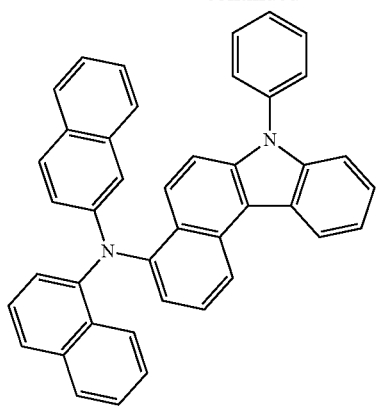
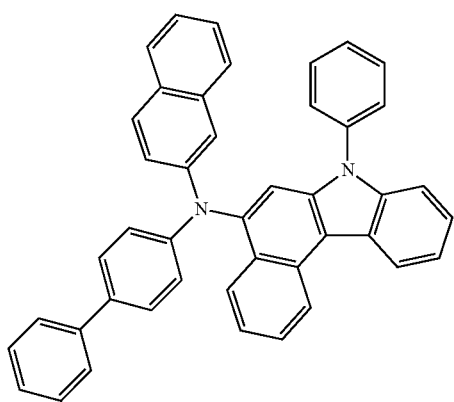
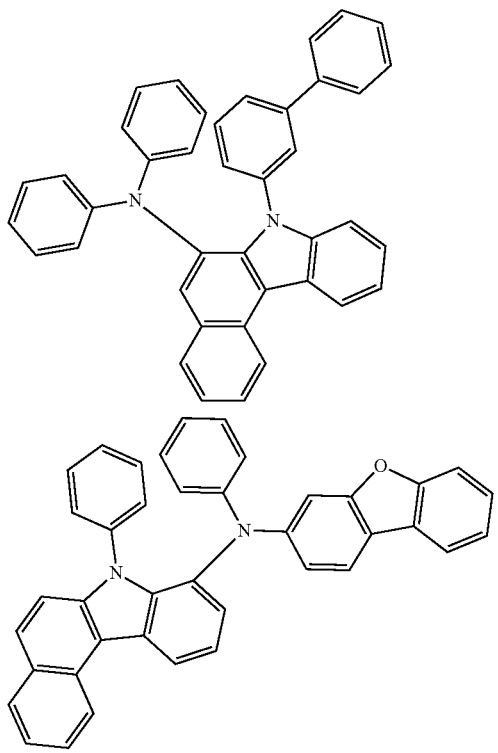
736
-continued
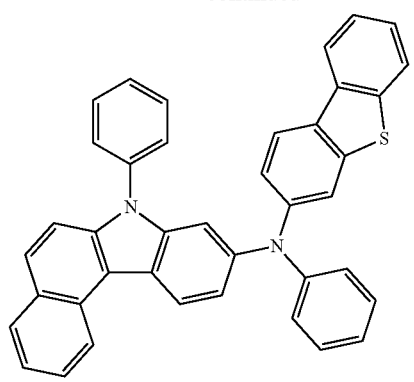
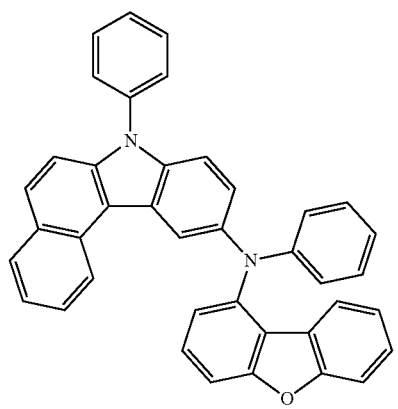
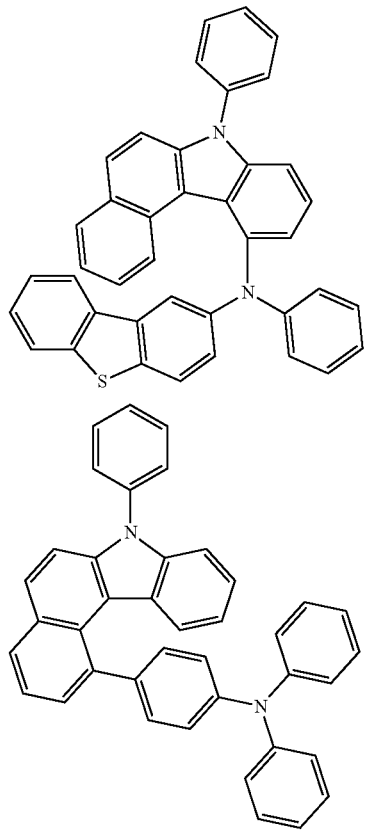

737
-continued
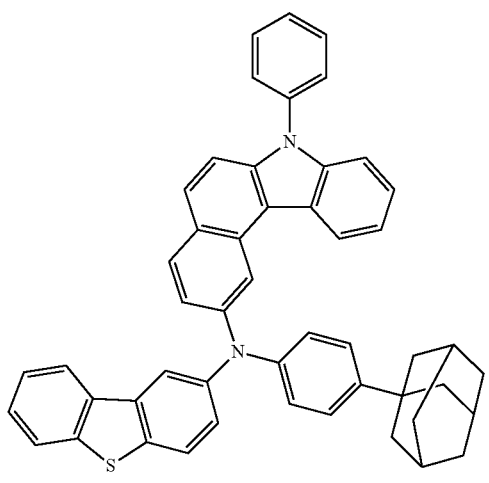
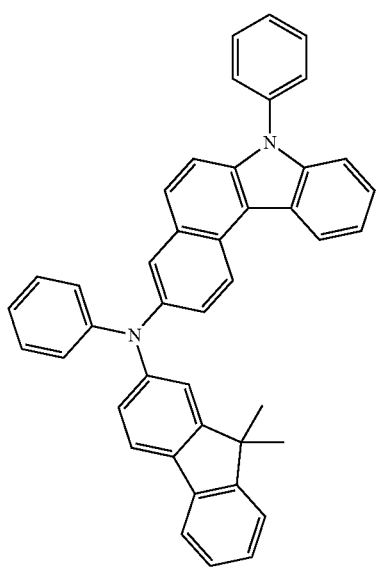
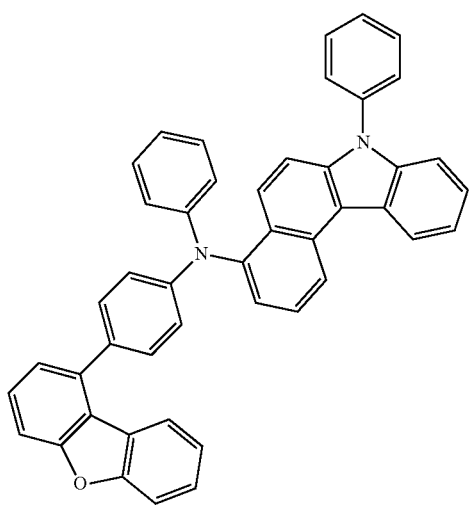
738
-continued
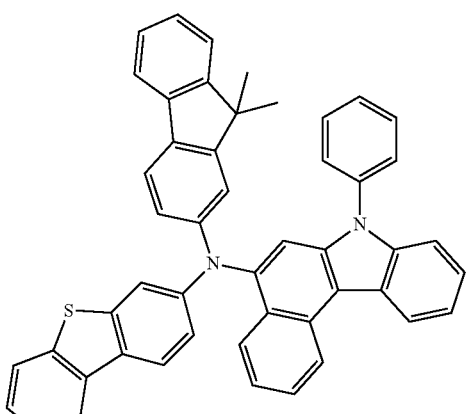
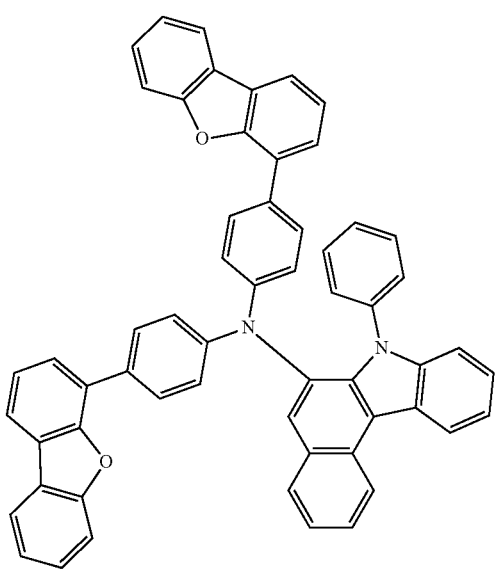
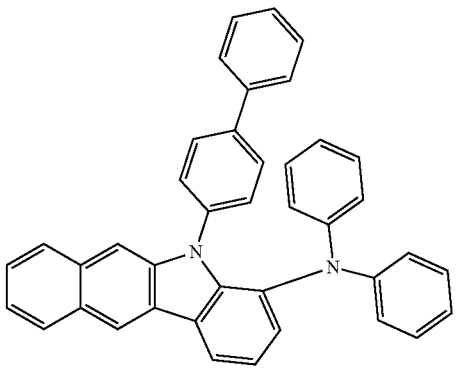

739
-continued
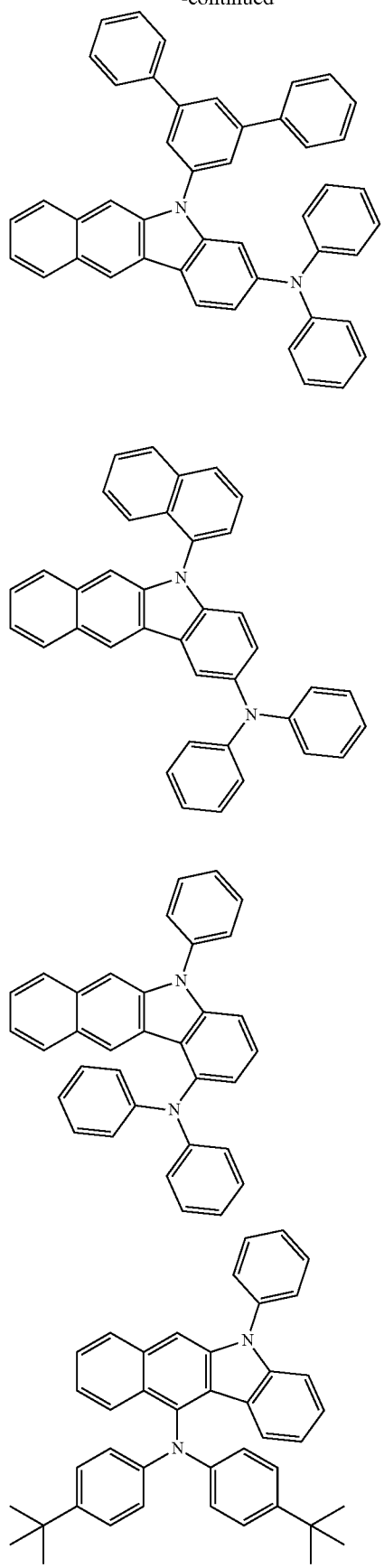
740
-continued
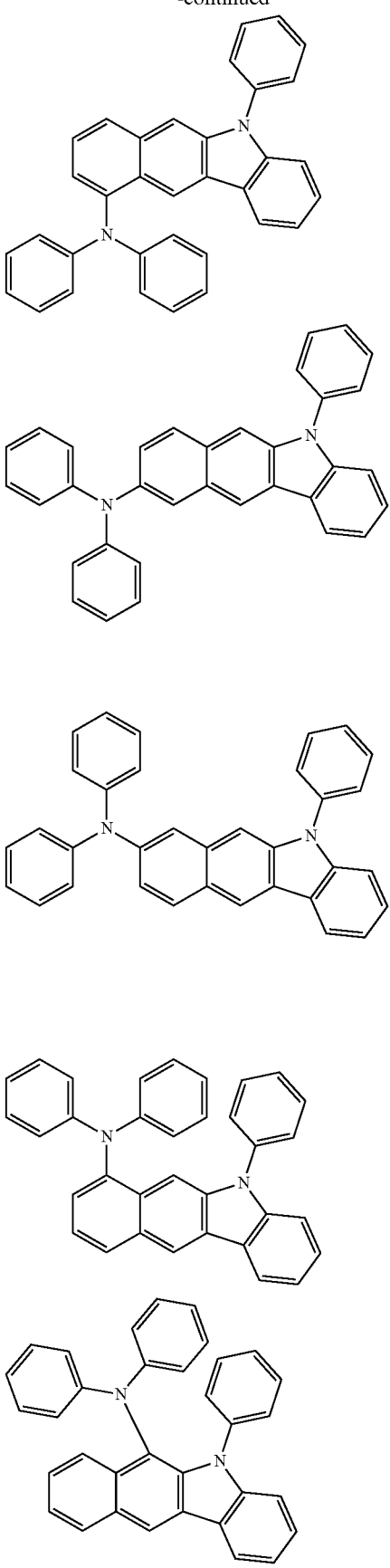

741
-continued
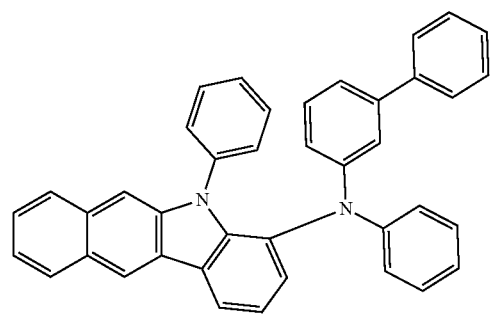
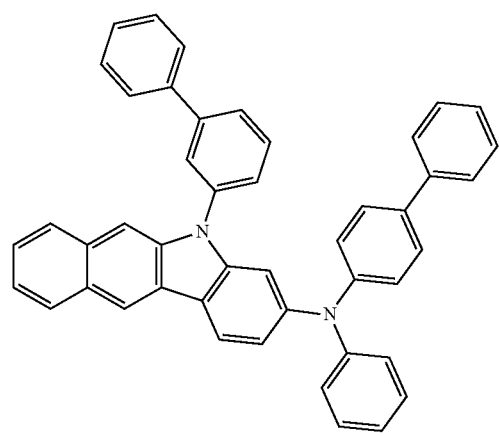
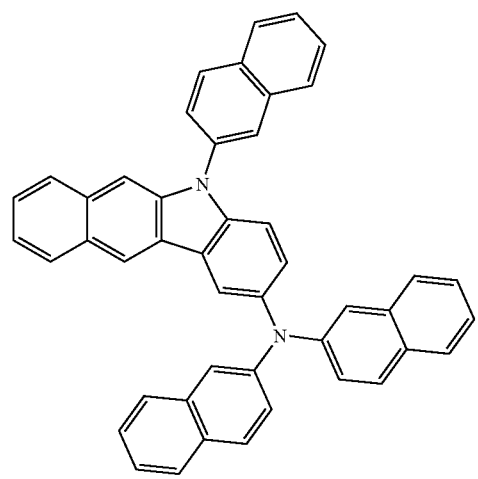
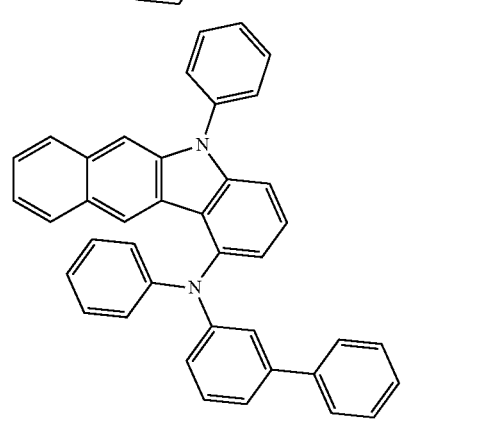
742
-continued
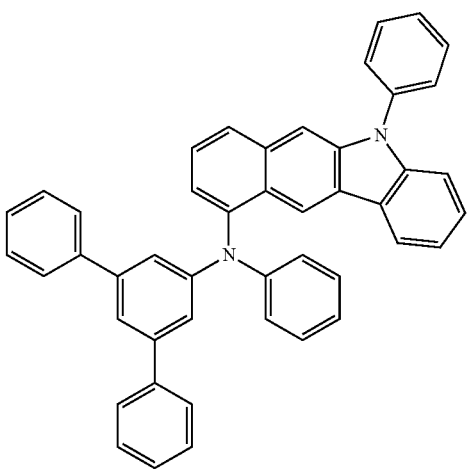
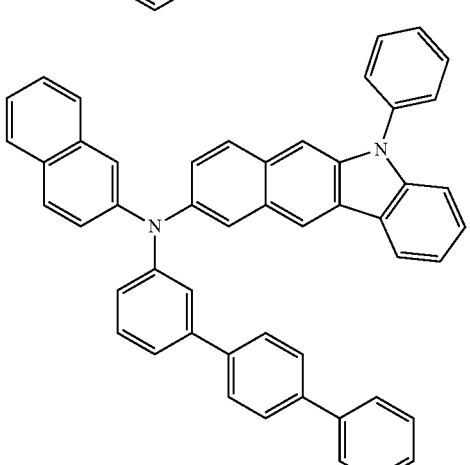
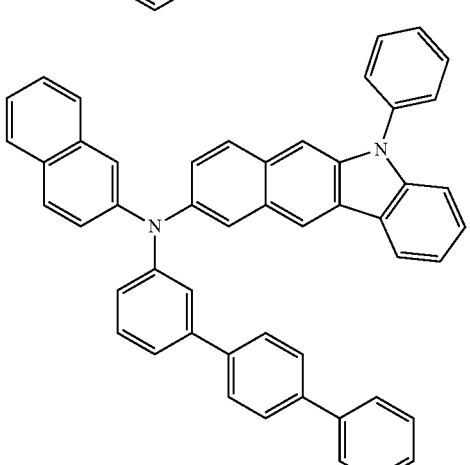
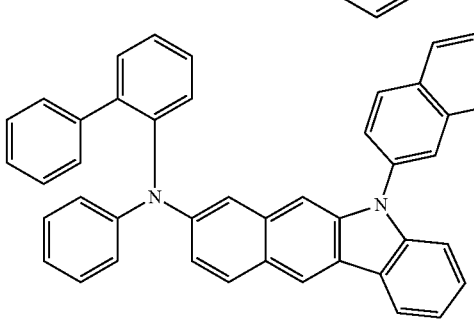

743
-continued
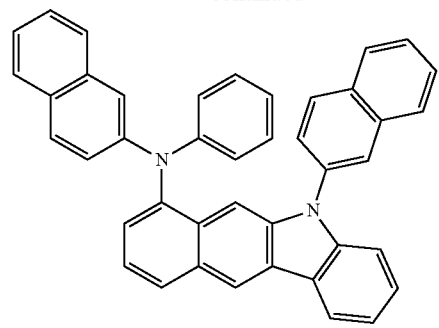
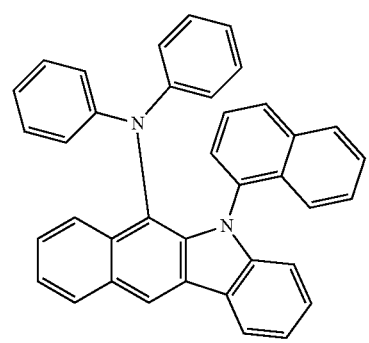
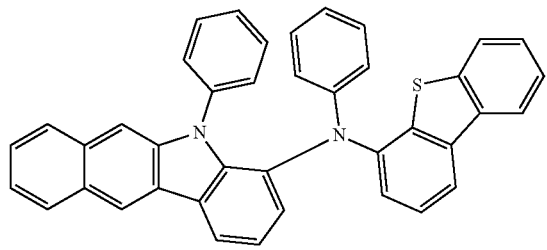
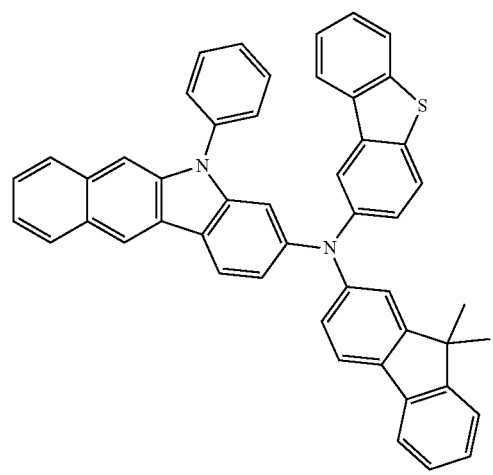
744
-continued
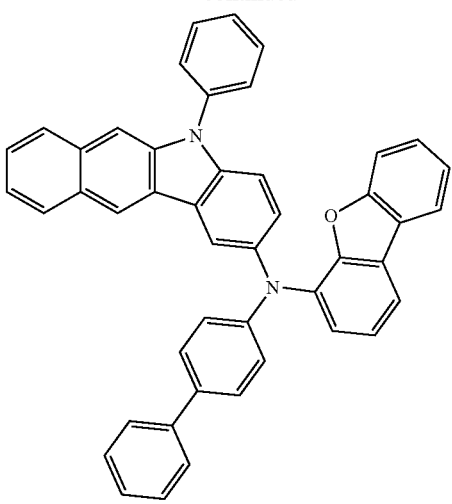
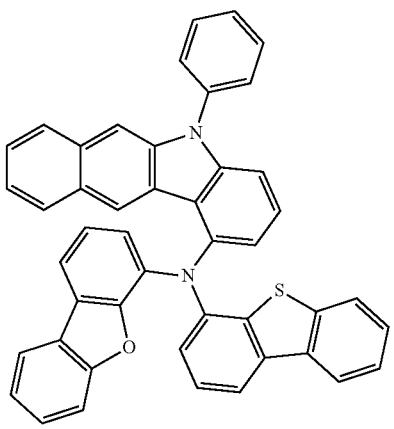
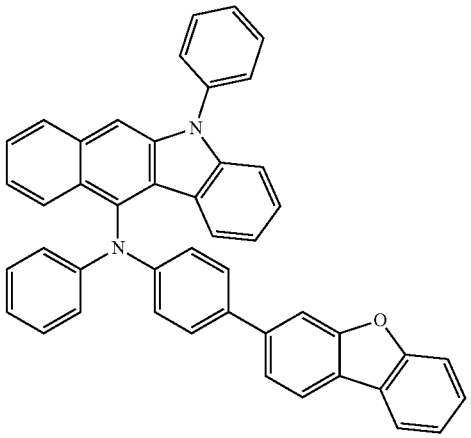

745
-continued
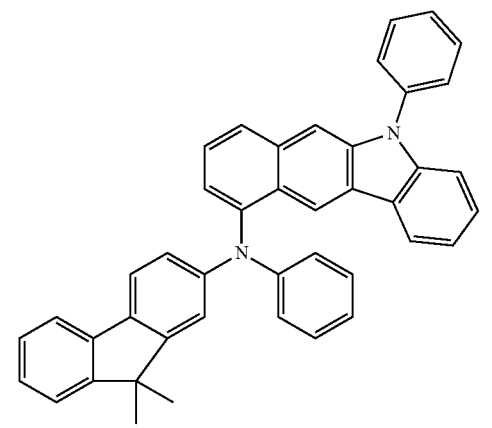
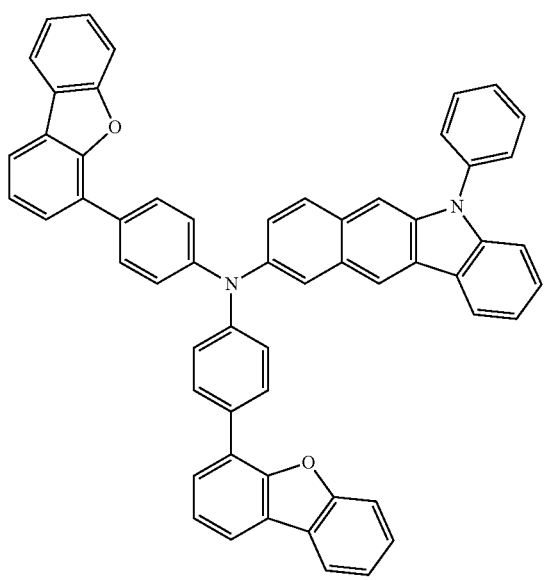
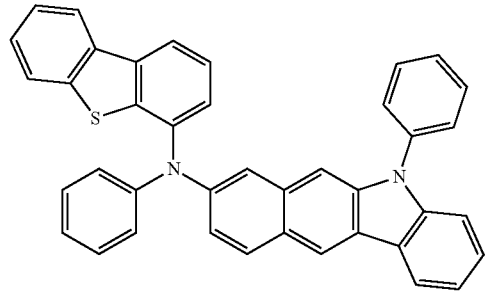
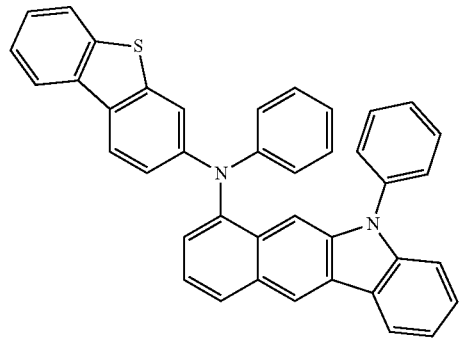
746
-continued
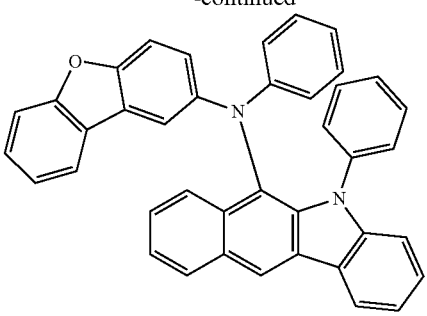
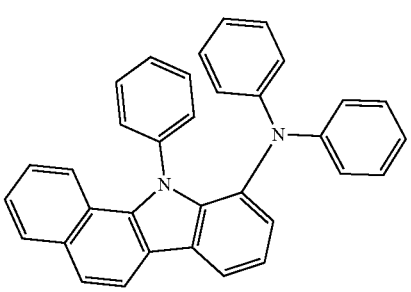
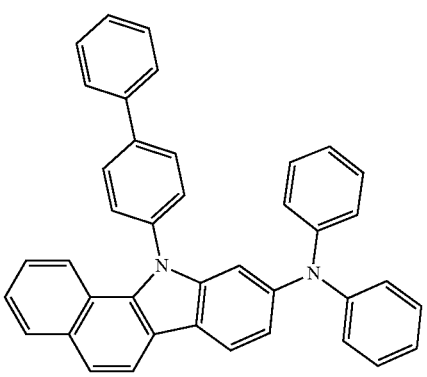
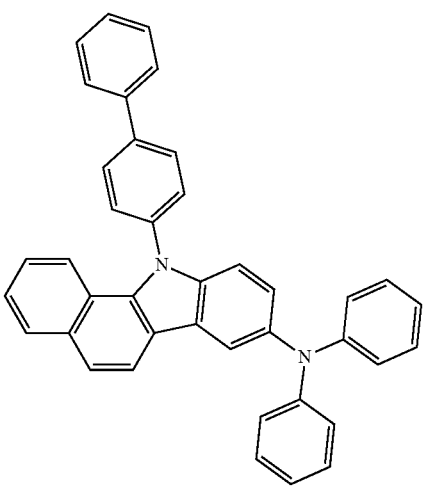

747
-continued
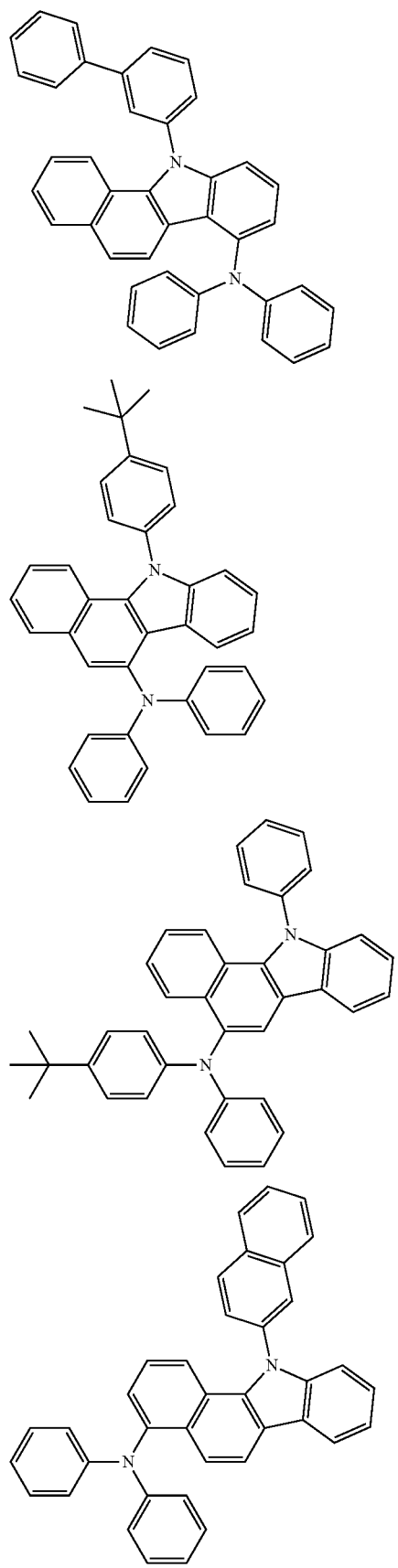
748
-continued
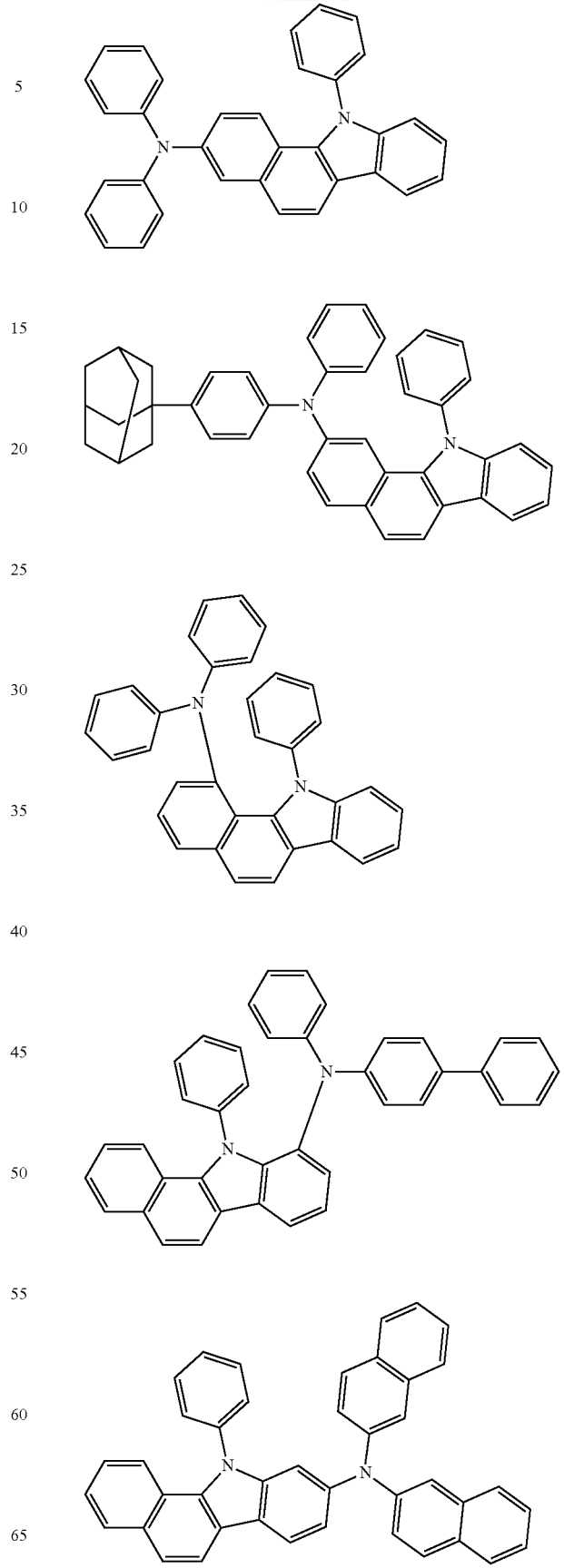

749
-continued
750
-continued
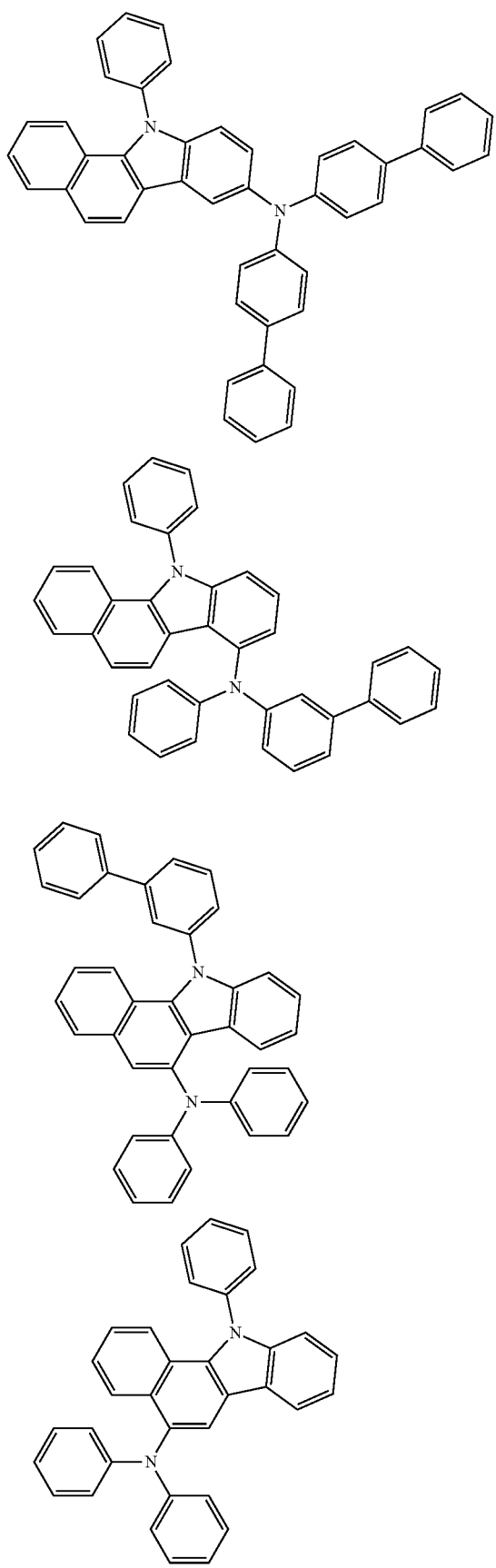
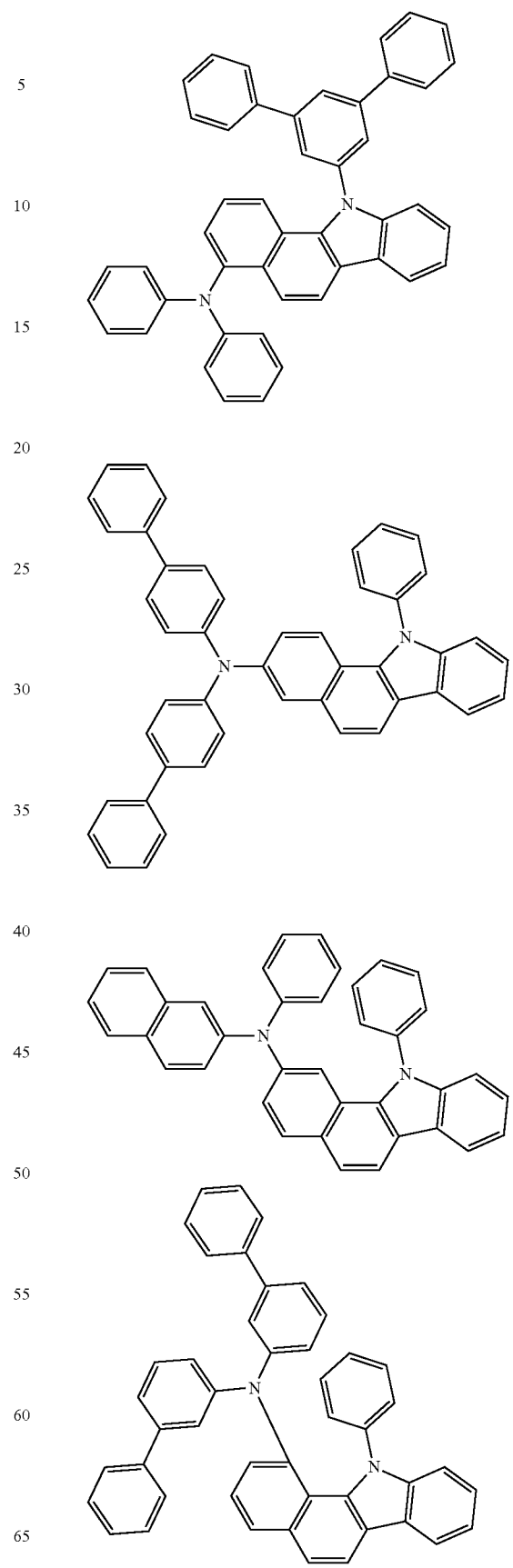

751
-continued
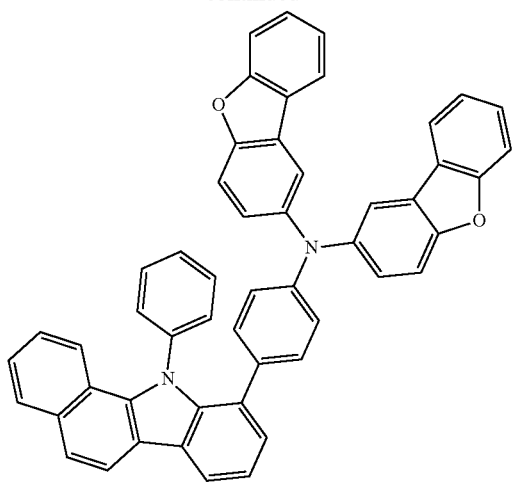
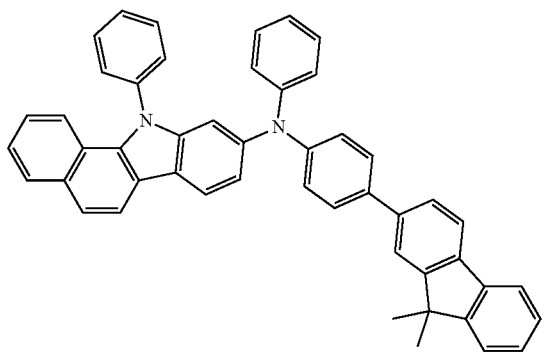
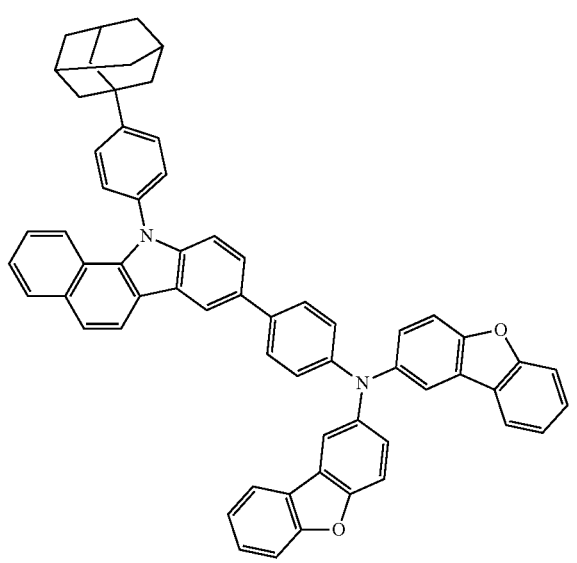
752
-continued
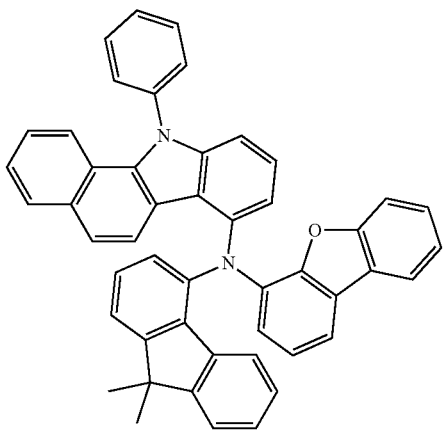
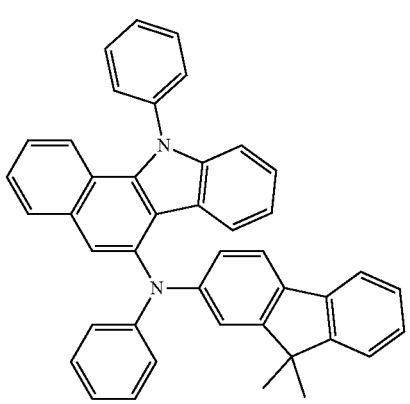
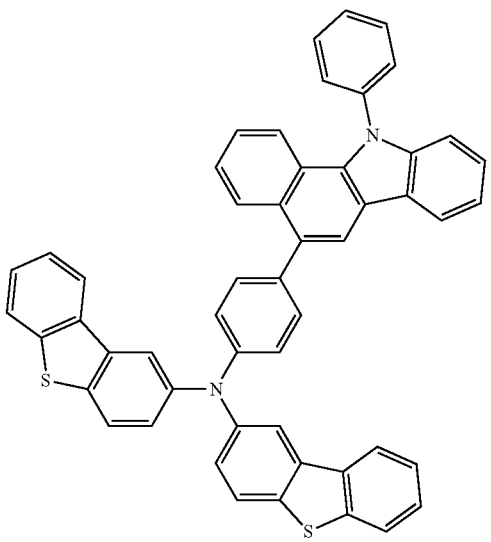

753
-continued
754
-continued
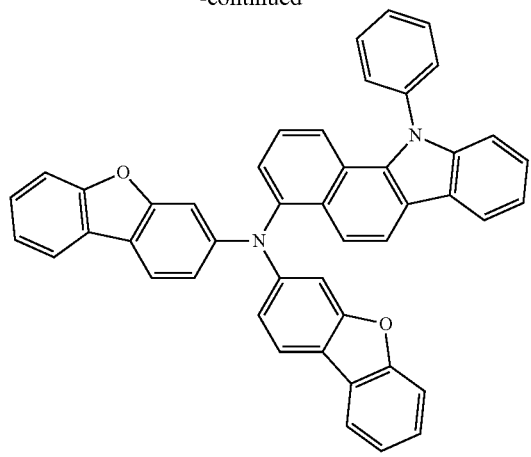
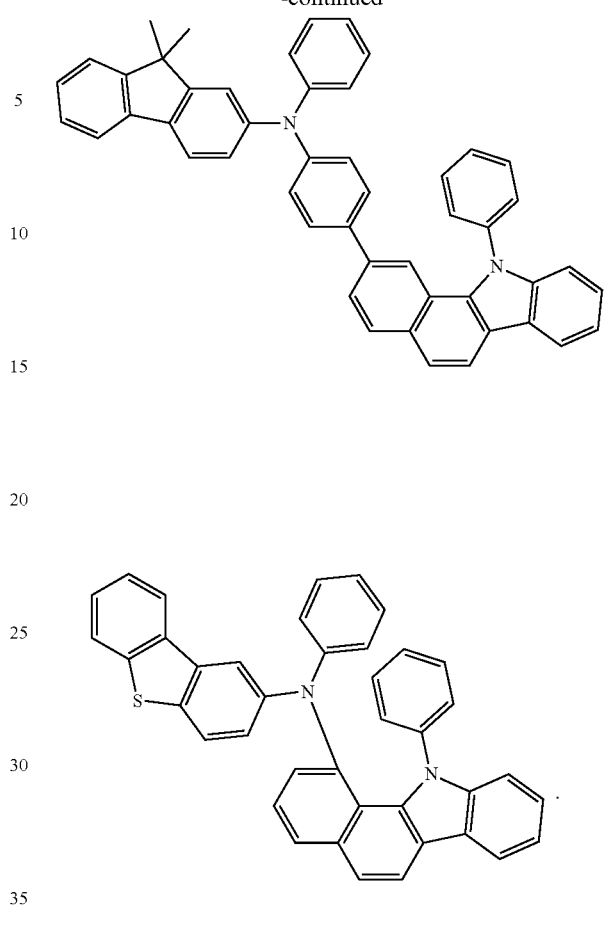
* * * * *